United States Patent
Pincetic et al.

(10) Patent No.: US 12,110,327 B2
(45) Date of Patent: Oct. 8, 2024

(54) ANTI-TREM1 ANTIBODIES AND METHODS OF USE THEREOF

(71) Applicant: Alector LLC, South San Francisco, CA (US)

(72) Inventors: Andrew Pincetic, San Francisco, CA (US); Arnon Rosenthal, Woodside, CA (US); Helen Lam, South San Francisco, CA (US); Francesca Avogadri-Connors, South Hamilton, MA (US); Seung-Joo Lee, Benicia, CA (US)

(73) Assignee: Alector LLC, South San Francisco, CA (US)

( * ) Notice: Subject to any disclaimer, the term of this patent is extended or adjusted under 35 U.S.C. 154(b) by 0 days.

(21) Appl. No.: 17/931,757

(22) Filed: Sep. 13, 2022

(65) Prior Publication Data

US 2023/0121869 A1   Apr. 20, 2023

Related U.S. Application Data

(62) Division of application No. 16/078,965, filed as application No. PCT/US2017/020745 on Mar. 3, 2017, now Pat. No. 11,472,877.

(60) Provisional application No. 62/304,018, filed on Mar. 4, 2016.

(51) Int. Cl.
C07K 16/28   (2006.01)

(52) U.S. Cl.
CPC ...... *C07K 16/2803* (2013.01); *C07K 2317/33* (2013.01); *C07K 2317/34* (2013.01); *C07K 2317/55* (2013.01); *C07K 2317/73* (2013.01); *C07K 2317/75* (2013.01); *C07K 2317/76* (2013.01); *C07K 2317/77* (2013.01); *C07K 2317/80* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,013,116 | B2 | 9/2011 | Faure et al. |
| 8,513,185 | B2 | 8/2013 | Sigalov |
| 8,981,061 | B2 | 3/2015 | Colonna et al. |
| 9,000,127 | B2 | 4/2015 | Stennicke et al. |
| 9,273,111 | B2 | 3/2016 | Faure et al. |
| 9,550,830 | B2 | 1/2017 | Stennicke et al. |
| 9,657,081 | B2 | 5/2017 | Gibot et al. |
| 10,179,814 | B2 | 1/2019 | Henriksen et al. |
| 10,189,904 | B2 | 1/2019 | Stennicke et al. |
| 10,711,062 | B2 * | 7/2020 | Culp ............ C07K 16/468 |
| 2013/0309239 | A1 | 11/2013 | Stennicke et al. |
| 2015/0175692 | A1 | 6/2015 | Padova et al. |

FOREIGN PATENT DOCUMENTS

| | | |
|---|---|---|
| JP | 2015508762 A | 3/2015 |
| WO | 2010132370 A2 | 11/2010 |

OTHER PUBLICATIONS

Amatngalim et al., Cathelicidin Peptide LL-37 Modulates TREM-1 Expression and Inflammatory Responses to Microbial Compounds, Inflammation, vol. 34, No. 5, Oct. 2011, pp. 412-425.
Arts, Joosten et al., "TREM-1 interaction with the LPS/TLR4 receptor complex," Eur. Cytokine Netw. vol. 22, No. 1, Mar. 2011, pp. 11-14.
Barthelemy, et al., "Comprehensive Analysis of the Factors Contributing to the Stability and Solubility of Autonomous Human VH Domains", Journal of Biological Chemistry, 2008, vol. 283, pp. 3639-3654.
Beiboer, et al., "Guided Selection of a Pan Carcinoma Specific Antibody Reveals Similar Binding Characteristics yet Structural Divergence Between the Original Murine Antibody and its Human Equivalent", Journal of Molecular Biology, 2000, vol. 296, pp. 833-849.
Bouchon et al., "Cutting Edge: Inflammatory Responses Can Be Triggered by TREM-1, a Novel Receptor Expressed on Neutrophils and Monocytes," J Immunol 2000; 164:4991-4995.
Bouchon et al., "TREM-1 amplifies inflammation and is a crucial mediator of septic shock," Nature, vol. 410, pp. 1103-1107 (Apr. 26, 2001).
Chao-Chi Ho et al: 11 TREM-I Expression in Tumor-associated Macrophages and Clinical Outcome in Lung Cancer American Journal of Respiratory and Critical Care Medicine, vol. 177, No. 7, Apr. 1, 2008, pp. 763-770.
Choi, et al., "Predicting antibody complementarity determining region structures without classification", Molecular BioSystems, 2011, vol. 7, pp. 3327-3334.
DeGenst, et al., "Antibody repertoire developments in camelids", Developmental and Comparative Immunology, 2006, vol. 30, pp. 187-198.
Fortin, C. F., et al., "Effects of TREM-1 activation in human neutrophils: activation of signaling pathways, recruitment into lipid rafts and association with TLR4", International Immunology, 19:1, pp. 41-50, Nov. 13, 2006.
Gibot et al., "A soluble form of the triggering receptor expressed on myeloid cells-1 modulates the inflammatory response in murine sepsis," The Journal of Experimental Medicine, vol. 200, No. 11,Dec. 6, 2004 (Dec. 6, 2004), pp. 1419-1426.
Griffiths, et al., "Human anti-self antibodies with high specificity from phage display libraries", The EMBO Journal, 1993, vol. 12, pp. 725-734.

(Continued)

*Primary Examiner* — Meera Natarajan
*Assistant Examiner* — Cheom-Gil Cheong
(74) *Attorney, Agent, or Firm* — McNeill PLLC

(57) ABSTRACT

The present disclosure is generally directed to compositions that include antibodies, e.g., monoclonal, chimeric, humanized antibodies, antibody fragments, etc., that specifically bind a TREM1 protein, e.g., a mammalian TREM1 or human TREM1, and use of such compositions in preventing, reducing risk, or treating an individual in need thereof.

22 Claims, 93 Drawing Sheets

Specification includes a Sequence Listing.

(56) References Cited

OTHER PUBLICATIONS

International Search Report and Written Opinion of International Application No. PCT/US2017/020745, dated Sep. 9, 2017 (26 pages).
Klimka, et al., "Human anti-CD30 recombinant antibodies by guided phage antibody selection using cell panning", British Journal of Cancer, 2000, vol. 83, pp. 252-260.
Lee et al., "TREM-I, a negative regulator of human osteoclastogenesis," Immunology Letters, vol. 171, Feb. 4, 2016, pp. 50-59 and Supplementary Figure 2.
Malia, et al., "Epitope mapping and structural basis for the recognition of phosphorylated tau by the anti-tau antibody AT8", Proteins, 2016, vol. 84, pp. 427-434.
Murakami et al. "Triggering receptor expressed on myeloid cells-1 as an inflammation amplifier," Japanese Journal of Clinical Immunology, vol. 32, No. 4, Aug. 2009, pp. 242-248.
R & D Systems, "Human TREM-1 Antibody", Internet Citation, Oct. 26, 2010.
Radsak et al., "Triggering receptor expressed on myeloid cells-1 in neutrophil inflammatory responses: differential regulation of activation and survival," J Immunol. Apr. 15, 2004;172(8):4956-63.
Ward, et al., "Binding activities of a repertoire of single immunoglobulin variable domains secreted from *Escherichia coli*", Nature, 1989, vol. 341, pp. 544-546.

\* cited by examiner

```
Q9NP99 TREM1_HUMAN      34  GQTLDVKCDYTLEKFASSQKAWQIIRDGEMPKTLACTE---RPSKNSHPVQVGRIILEDYH  91
                            GQTL V+C Y           +K W      +     L C           SK    R  + D
O95944-2 NCTR2_HUMAN    33  GQTLTVRCQYPPTGSLYEKKGWC-----KEASALVCIRLVTSSKPRTMAWTSRFTIWDDP  87

Q9NP99 TREM1_HUMAN      92  DHGLLRVRMVNLQVEDSGLYQCVIYQPPKEPHMLFDRIRLVVTKGFSGTPGS------NE  145
                            D G   V M +L+ EDSG Y C IY+P       R    LVV+    +   T   S
O95944-2 NCTR2_HUMAN    88  DAGFFTVTMTDLREEDSGHYWCRIYRPSDNSVSKSVRFYLVVSPASASTQTSWTPRDLVS  147

Q9NP99 TREM1_HUMAN      146 NSTQNVYKIPPTTKALCPLYTSPRTV--TQAPPKSTADVSTPDSEINLT----NVIDIIR  200
                            + TQ   +PPT    P     SP T+     P     S   V P   N T       I
O95944-2 NCTR2_HUMAN    148 SQTQTQSCVPPTAGARQAP--ESPSTIPVPSHPSSPLPVPLPSRPQNSTLRPGPAAPIAL  205

Q9NP99 TREM1_HUMAN      201 VPVFNIVILLAGGFLSKSLVFSVL                                     224
                            VPVF       G     ++KSIV S L
O95944-2 NCTR2_HUMAN    206 VPVF-------CGLIVAKSLVLSAL                                    223
```

FIG. 1A

```
Q9NP99 TREM1_HUMAN    1   MRKTRLWGLLWMLFVSELRAATKLTEEKYELKEGQTLDVKCDYTLEKFASSQKAWQIIRD    60
                          MRK  LWGLL + FVSE++AA   L EE+Y+L EGQTL VKC + + K+A+SQKAWQ + D
Q9JKE2 TREM1_MOUSE    1   MRKAGLWGLLCVFFVSEVKAAIVLEEERYDLVEGQTLTVKCPFNIMKYANSQKAWQRLPD    60

Q9NP99 TREM1_HUMAN   61   GEMPKTLACTERPSKNSHPVQVGRIILEDYHDGLLRVMVNLQVEDSGLYQCVIYQPPK    120
                          G+  P  TL    T+RP        V  +G+    L+     +L+V+M  +LQV DSGLY+CVIY PP
Q9JKE2 TREM1_MOUSE   61   GKEPLTLVVTQRPFTRPSEVHMGKFTLKHDPSEAMLQVQMTDLQVTDSGLYRCVIYHPPN    120

Q9NP99 TREM1_HUMAN  121   EPHMLFDRIRLVVTKGFSGTPGSNENSTQNVYKIPPTTKALCPLYTSPRTVTQAPPKST    180
                          +P  +LF          +RLVVTKG  S              + +   P  T    P     S    T  T++   PK T
Q9JKE2 TREM1_MOUSE  121   DPVVLFHPVRLVVTKGSSDVFTPVIIPITRLTERPILITTKYSP---SDTTTTRSLPKPT    177

Q9NP99 TREM1_HUMAN  181   ADVSTPDSEINLTNVTDIIRVPVFNIVILLAGGFLSKSLVFSVLFAVTLRSF          232
                          A  VS+P    + + N TD   V       ++   I  +    G  LSKSLVF  +LF VT  R+F
Q9JKE2 TREM1_MOUSE  178   AVVSSPGLGVTIINGTDADSVSTSSVTISVICGLLSKSLVFIILFIVTKRTF          229
```

FIG. 1B

```
Q9NP99 TREM1_HUMAN    9  LLWMLFVSELRAATKLTEEKYELKEGQTLDVKCDYTLEKFASSQKAW--QIIRDGEMPKT  66
                         LL +LFV+EL  A   T  ++   GQ+L V C Y   K   +KAW  Q+   G   +
Q9NZC2-2 TREM2_HUMAN  6  LLILLFVTELSGAHNTTV--FQGVAGQSLQVSCPYDSMKHWGRRKAWCRQLGEKGPCQRV 63

Q9NP99 TREM1_HUMAN   67  LACTERPSKNSHPVQVGRIILEDYHDGLLRVRMVNLQVEDSGLYQC 113
                         ++                G   +D    G L ++ NLQ  D+GLYQC
Q9NZC2-2 TREM2_HUMAN 64  VSTHNLWLLSFLRRWNGSTAITDDTLGGTLTITLRNLQPHDAGLYQC 110
```

FIG. 2

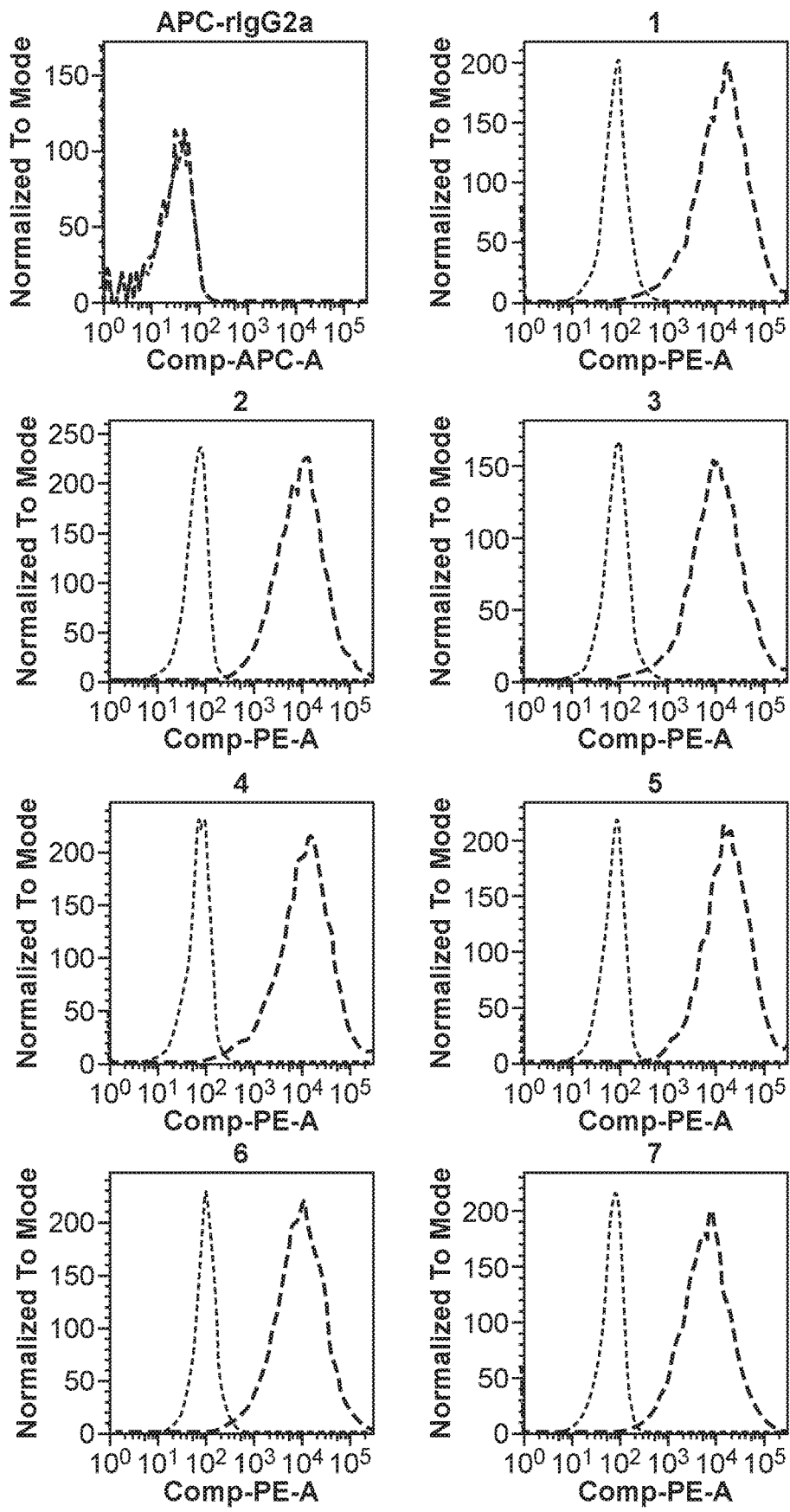
FIG. 3A (Cont. 1)

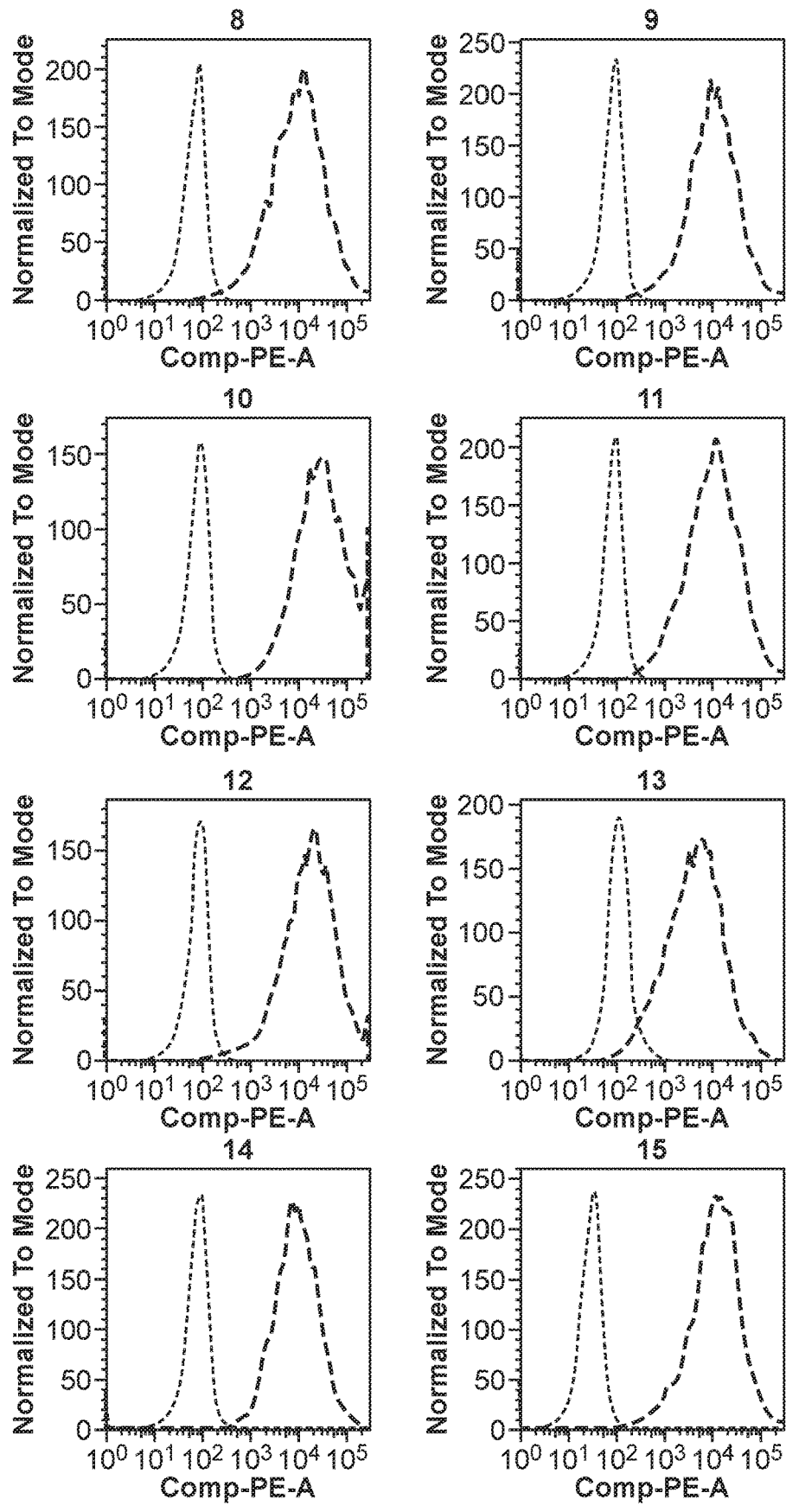
FIG. 3A (Cont. 2)

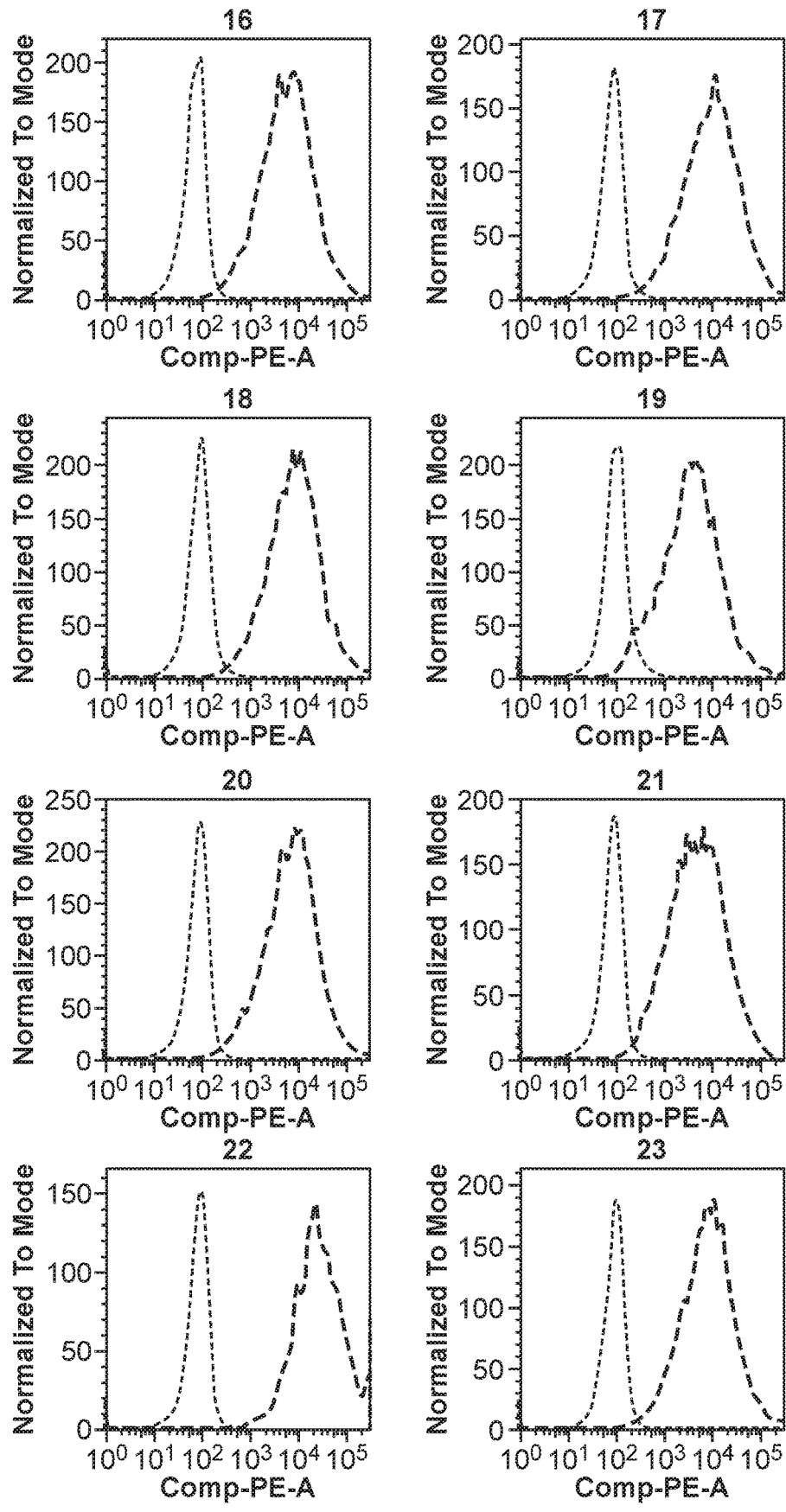
FIG. 3A (Cont. 3)

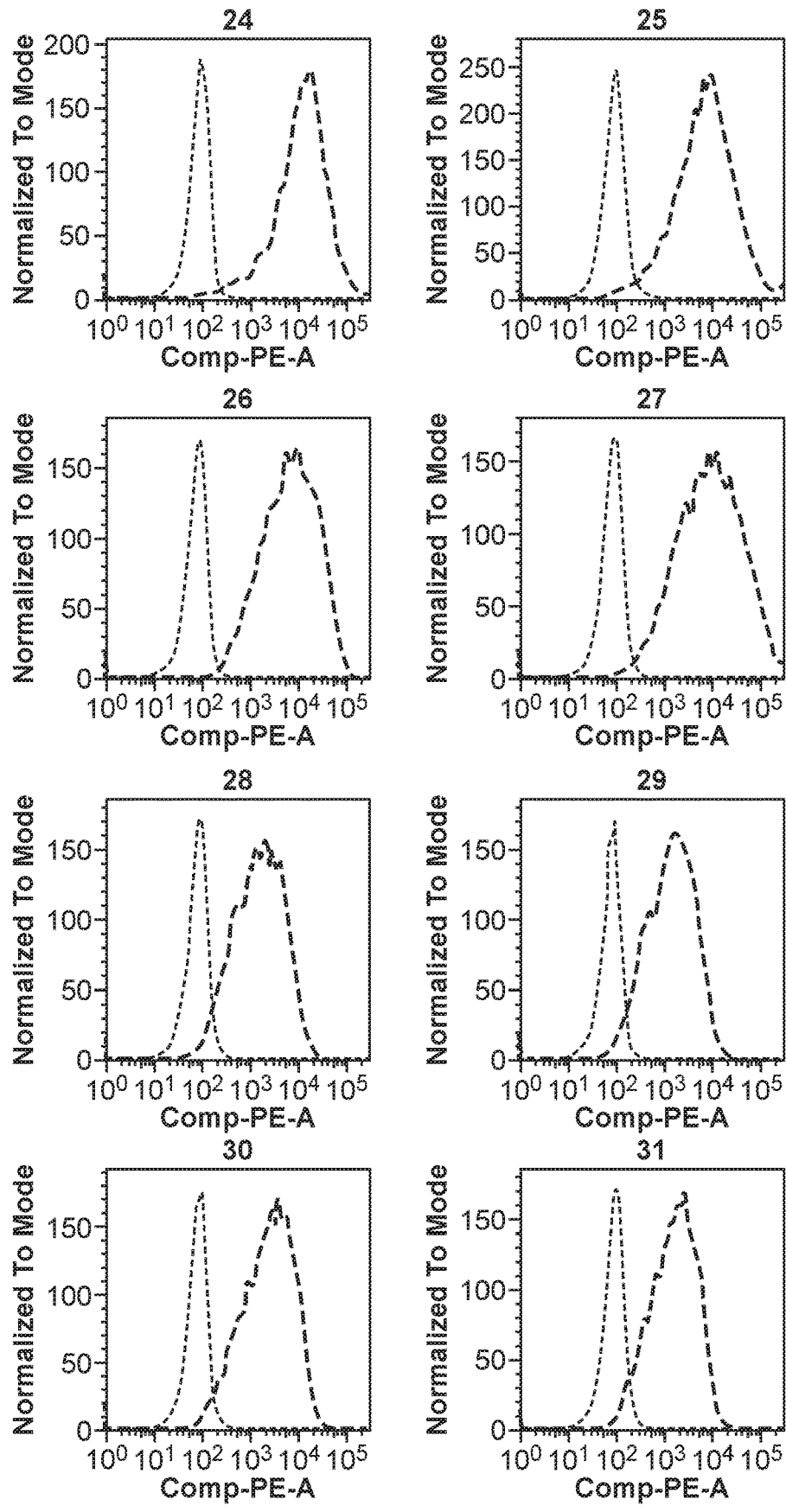
FIG. 3A (Cont. 4)

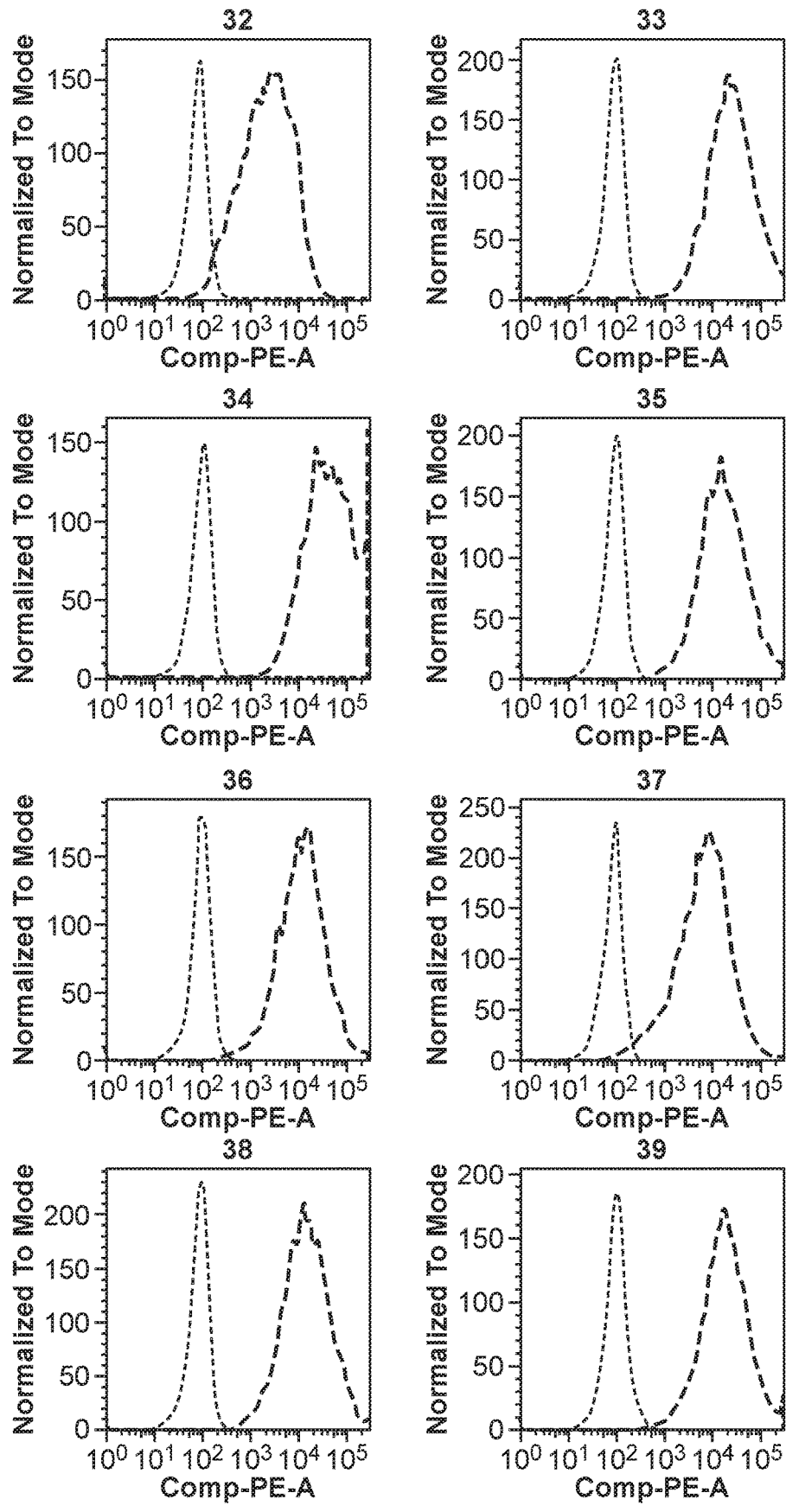
FIG. 3A (Cont. 5)

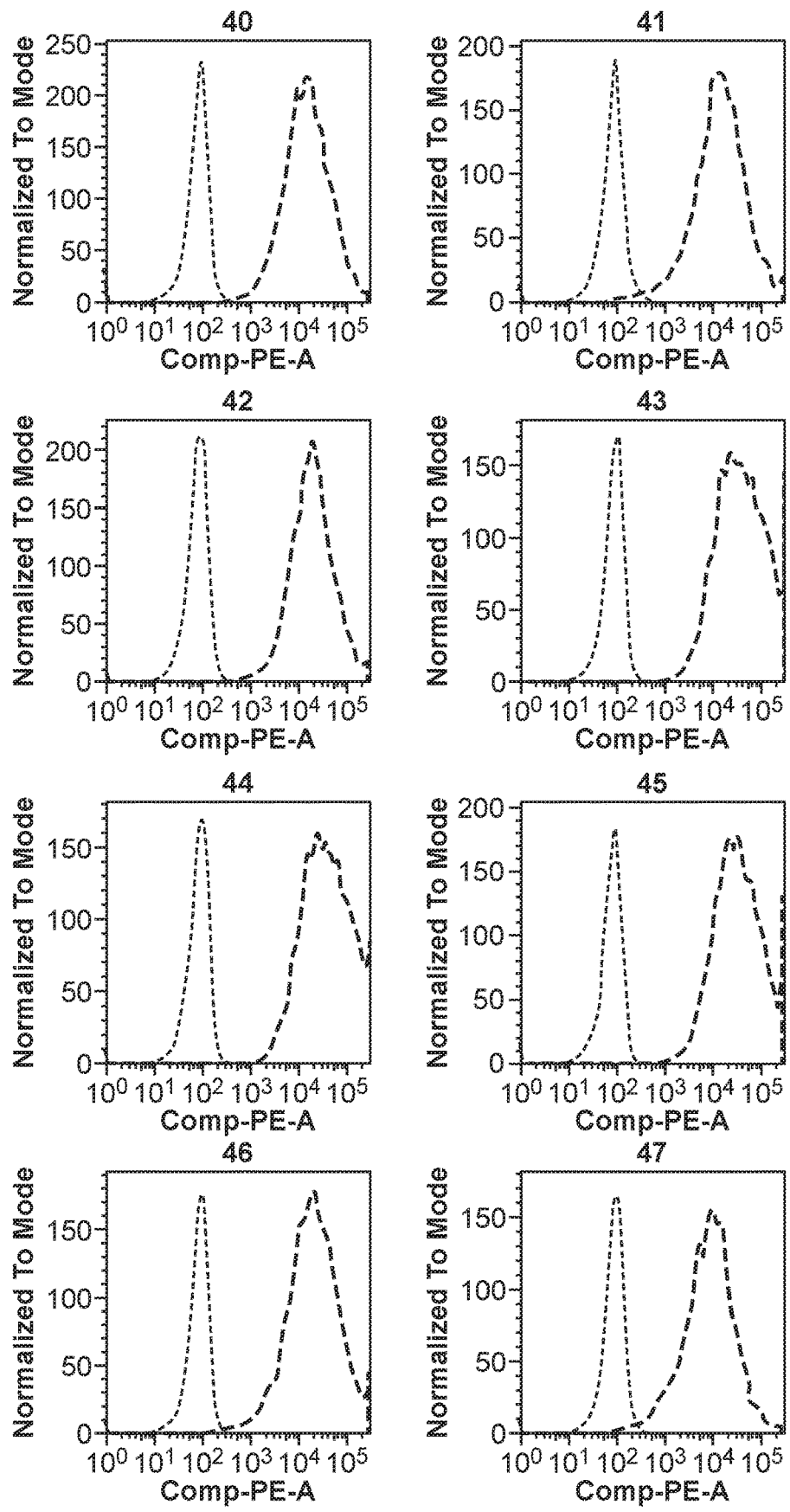
FIG. 3A (Cont. 6)

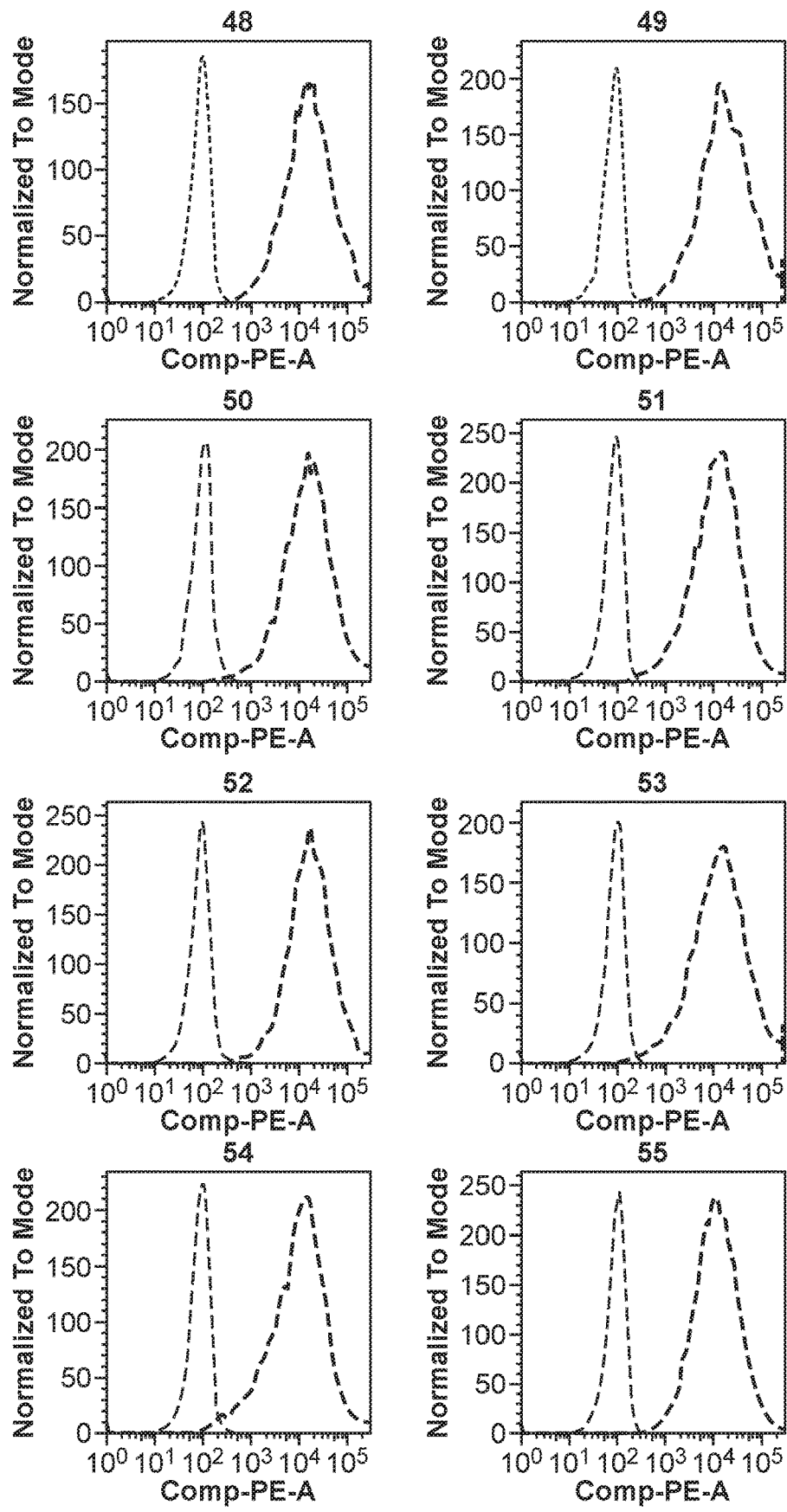
FIG. 3A (Cont. 7)

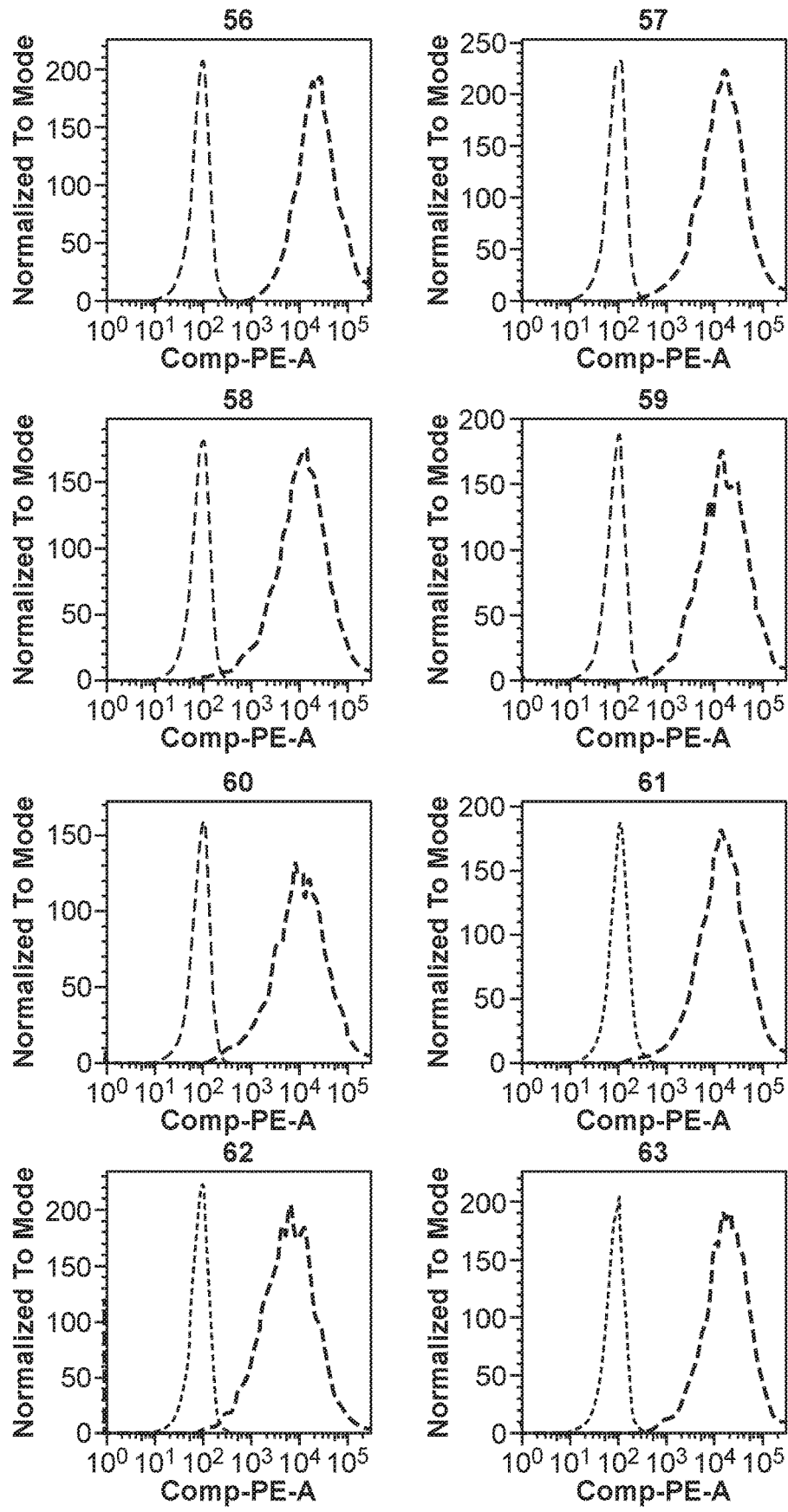
FIG. 3A (Cont. 8)

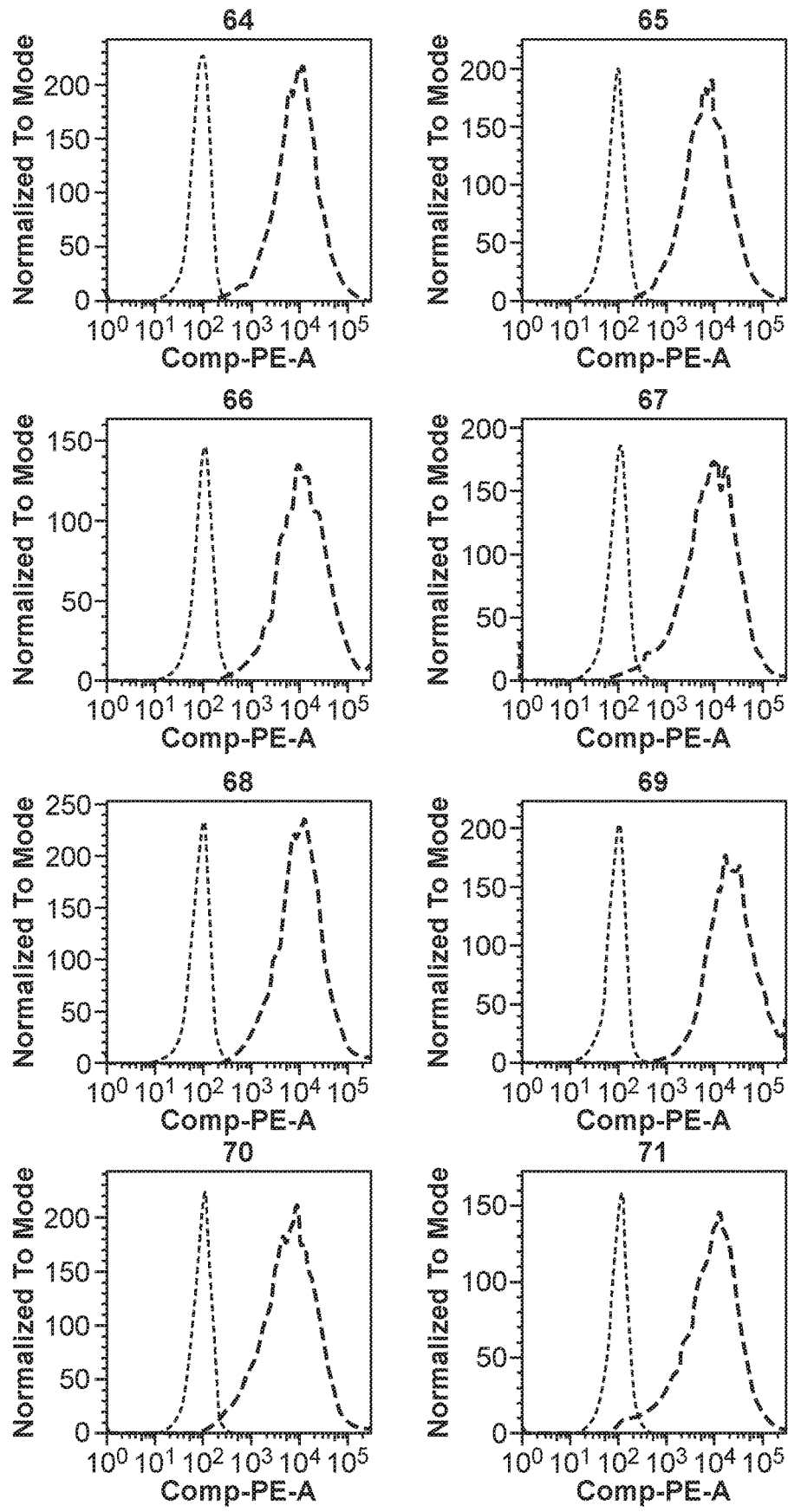
FIG. 3A (Cont. 9)

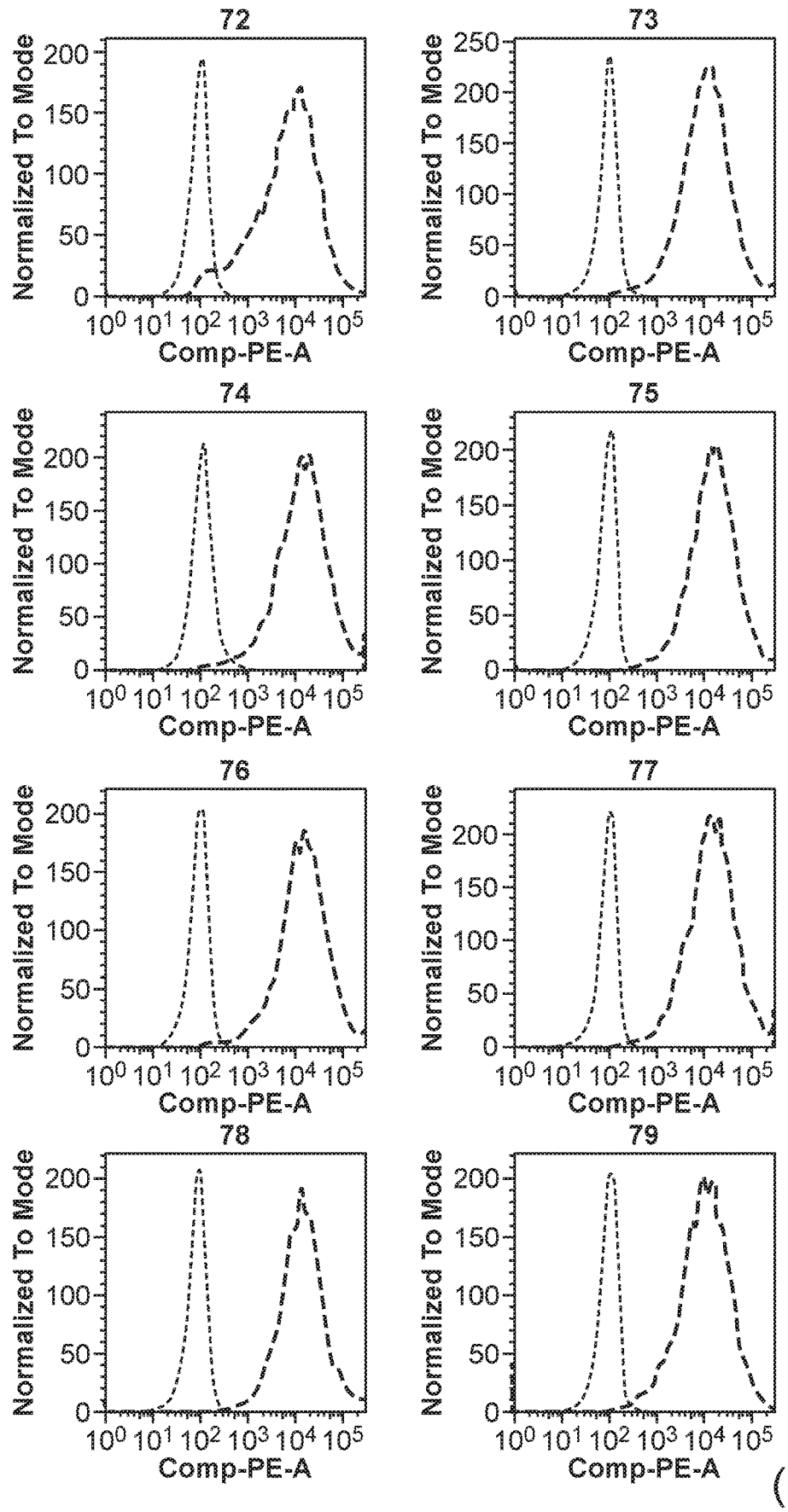
FIG. 3A (Cont. 10)

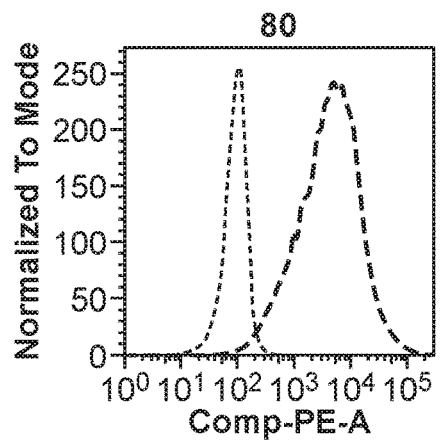
FIG. 3A (Cont. 11)
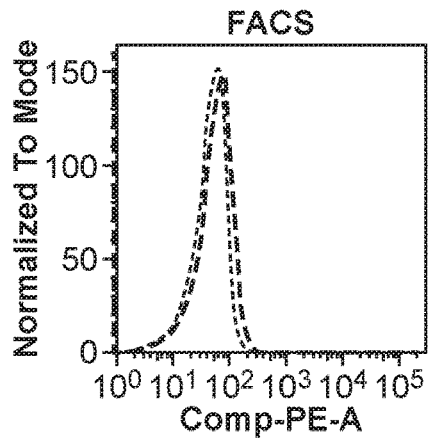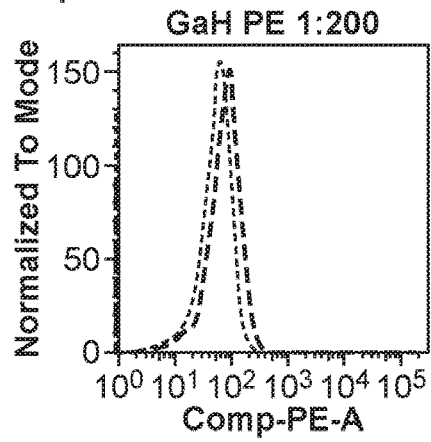
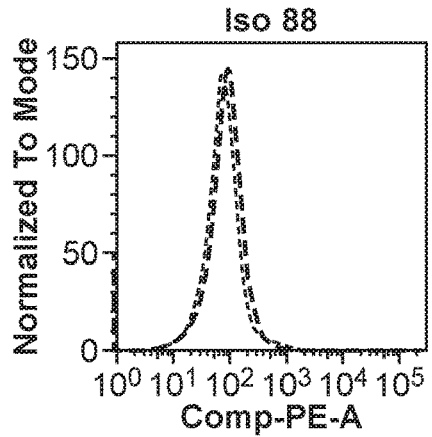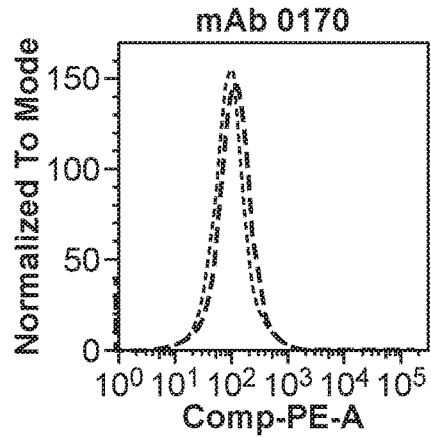
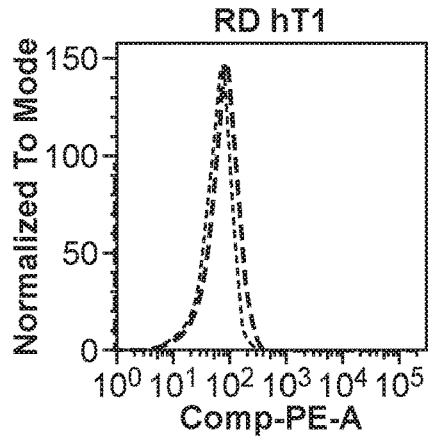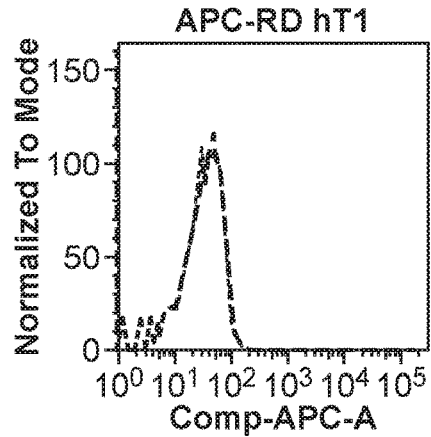
FIG. 3B

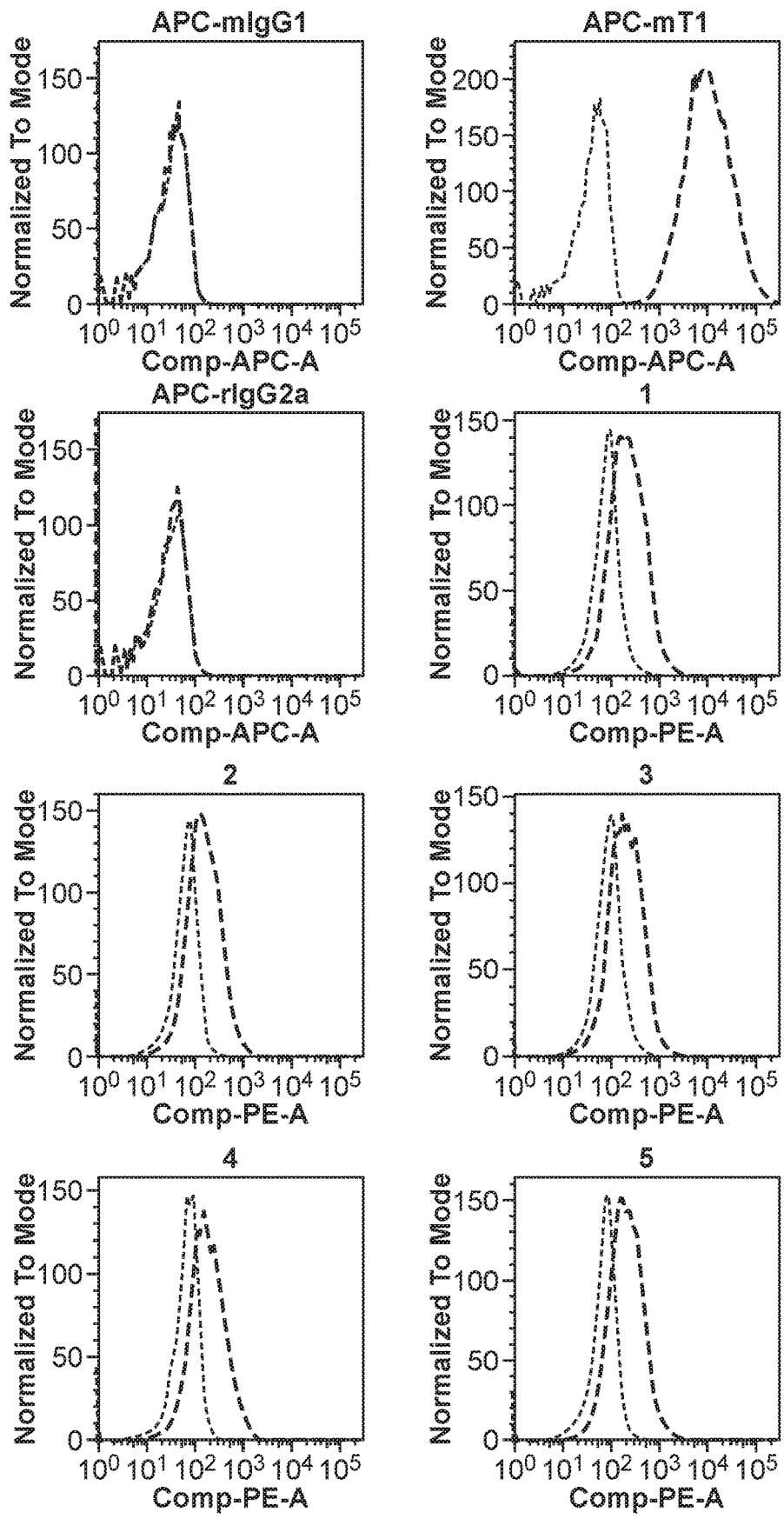
FIG. 3B (Cont. 1)

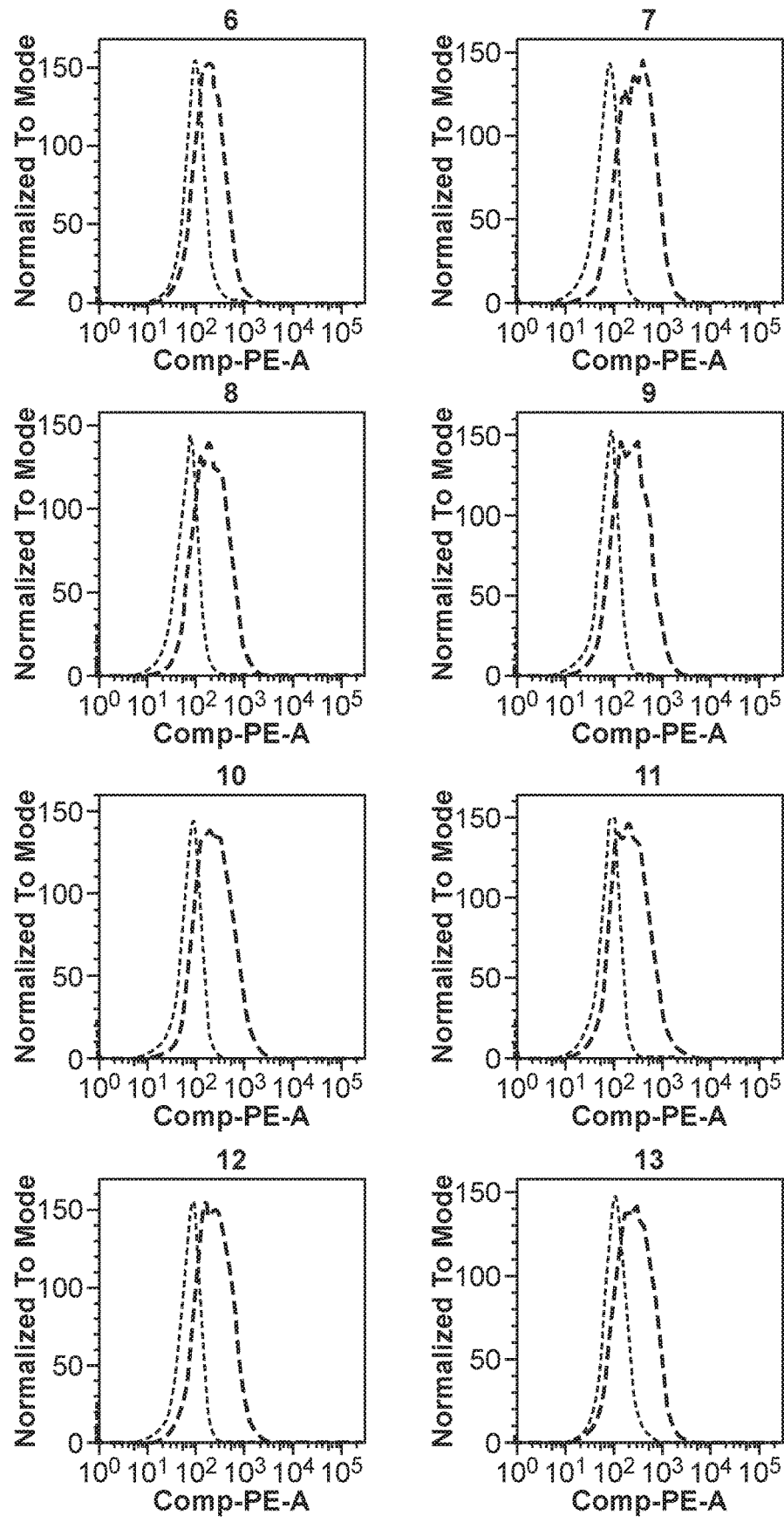
FIG. 3B (Cont. 2)

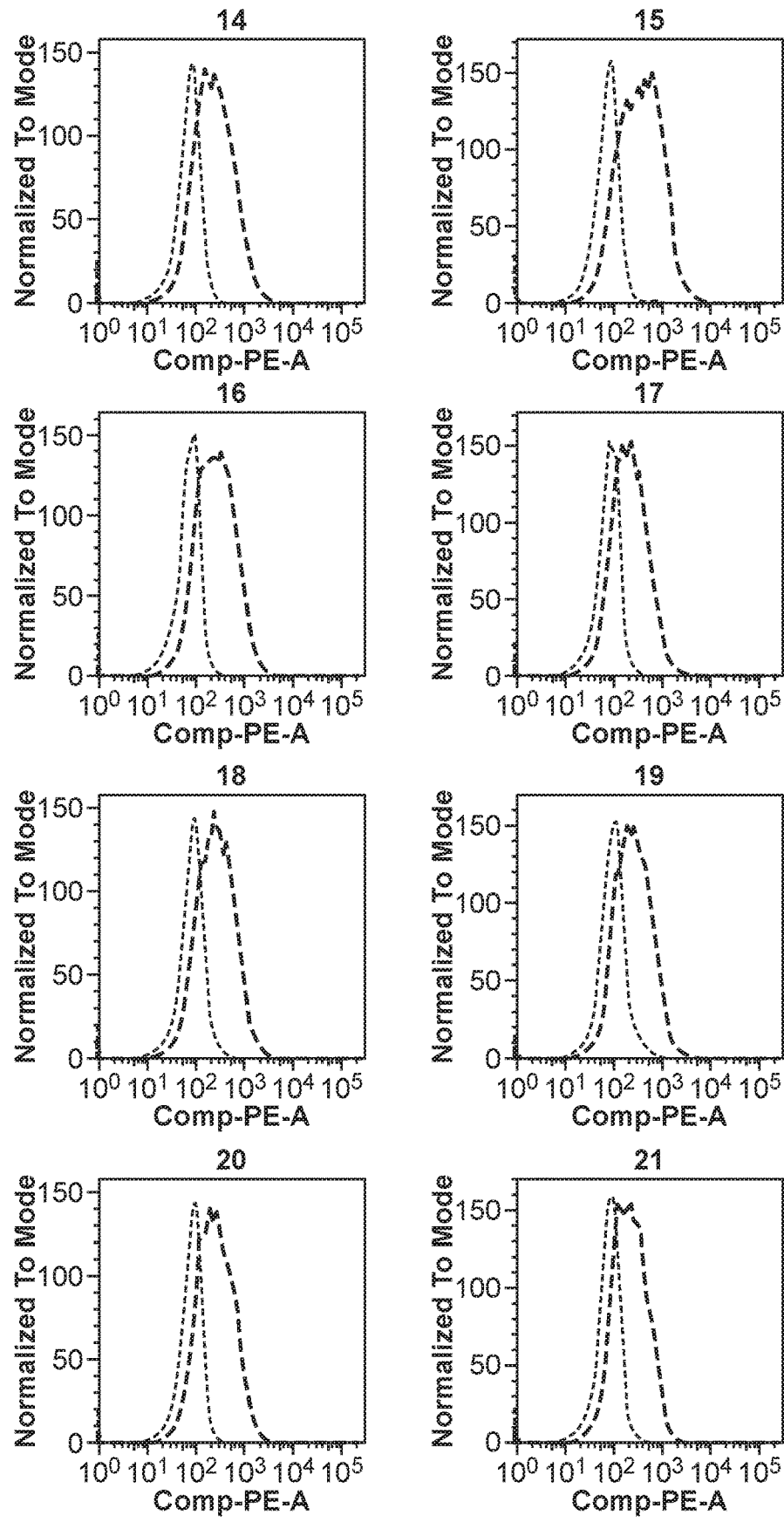
FIG. 3B (Cont. 3)

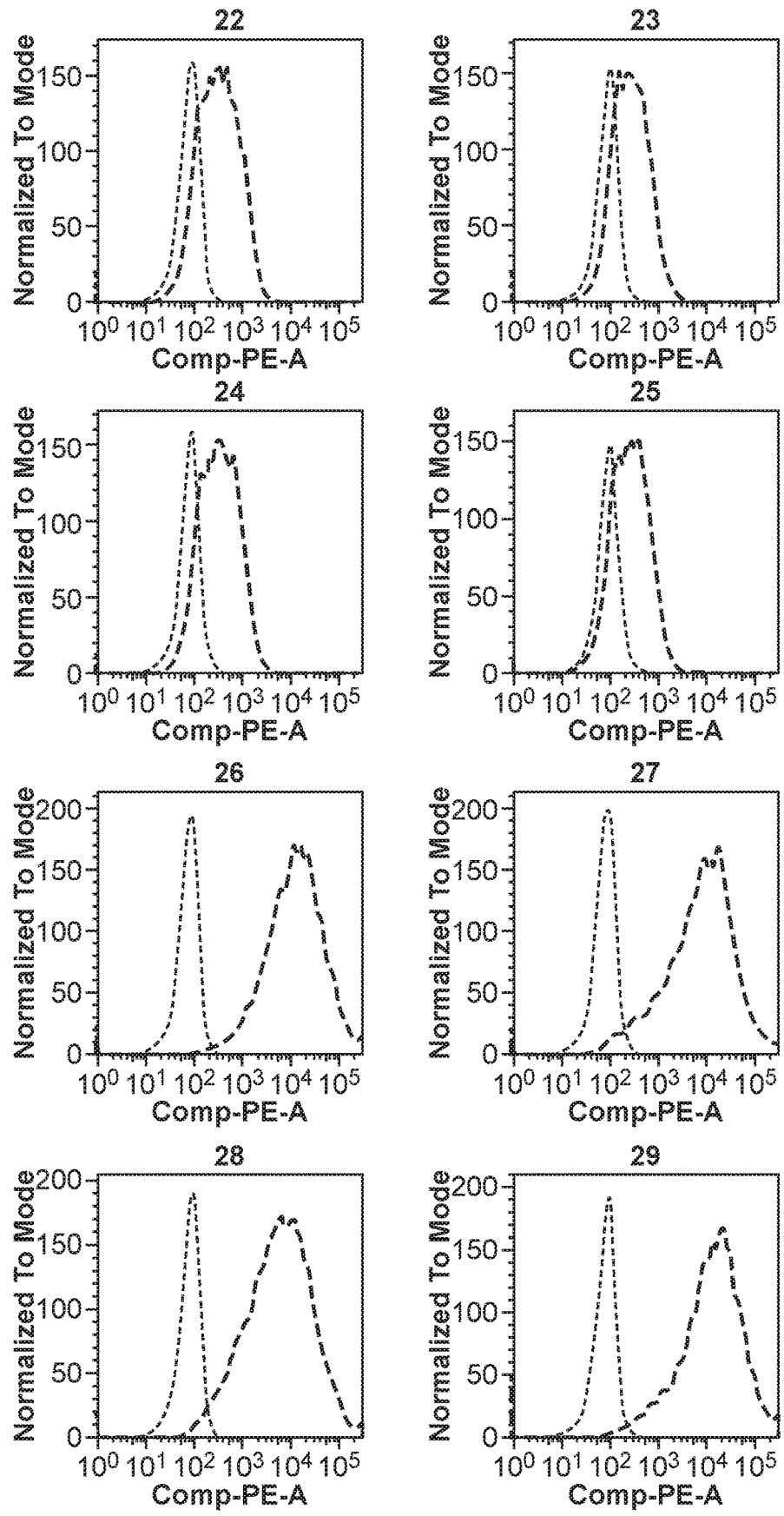
FIG. 3B (Cont. 4)

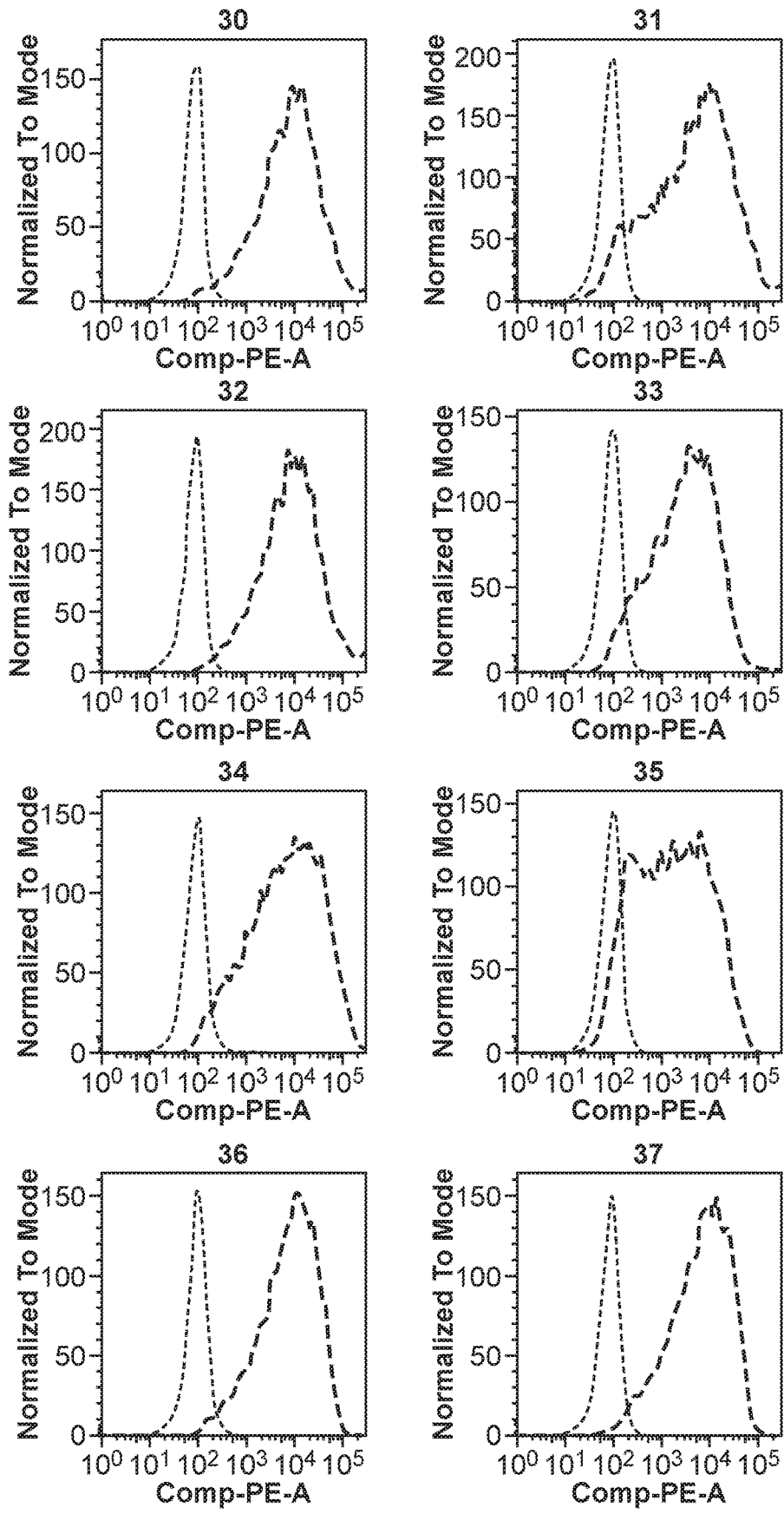
FIG. 3B (Cont. 5)

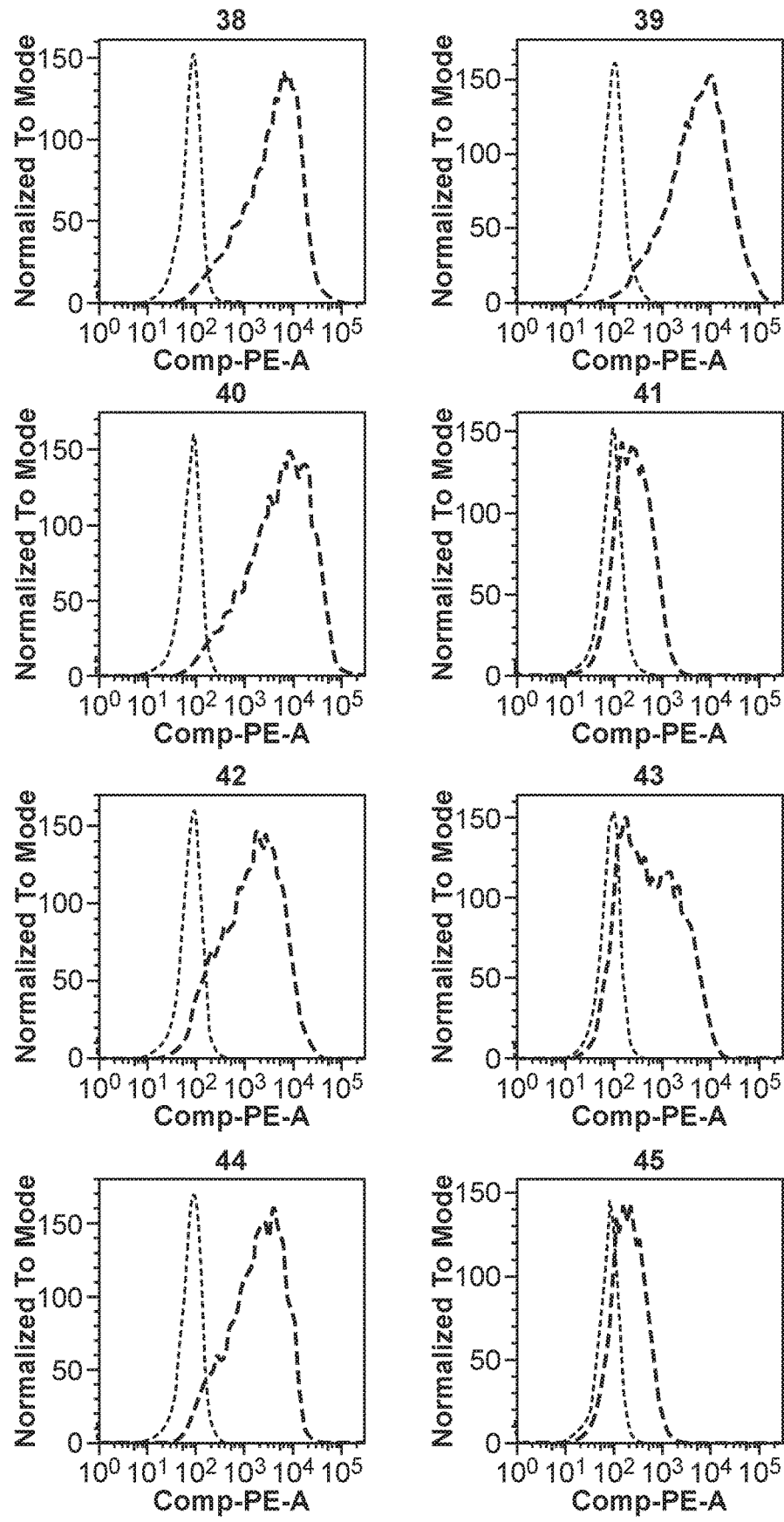
FIG. 3B (Cont. 6)

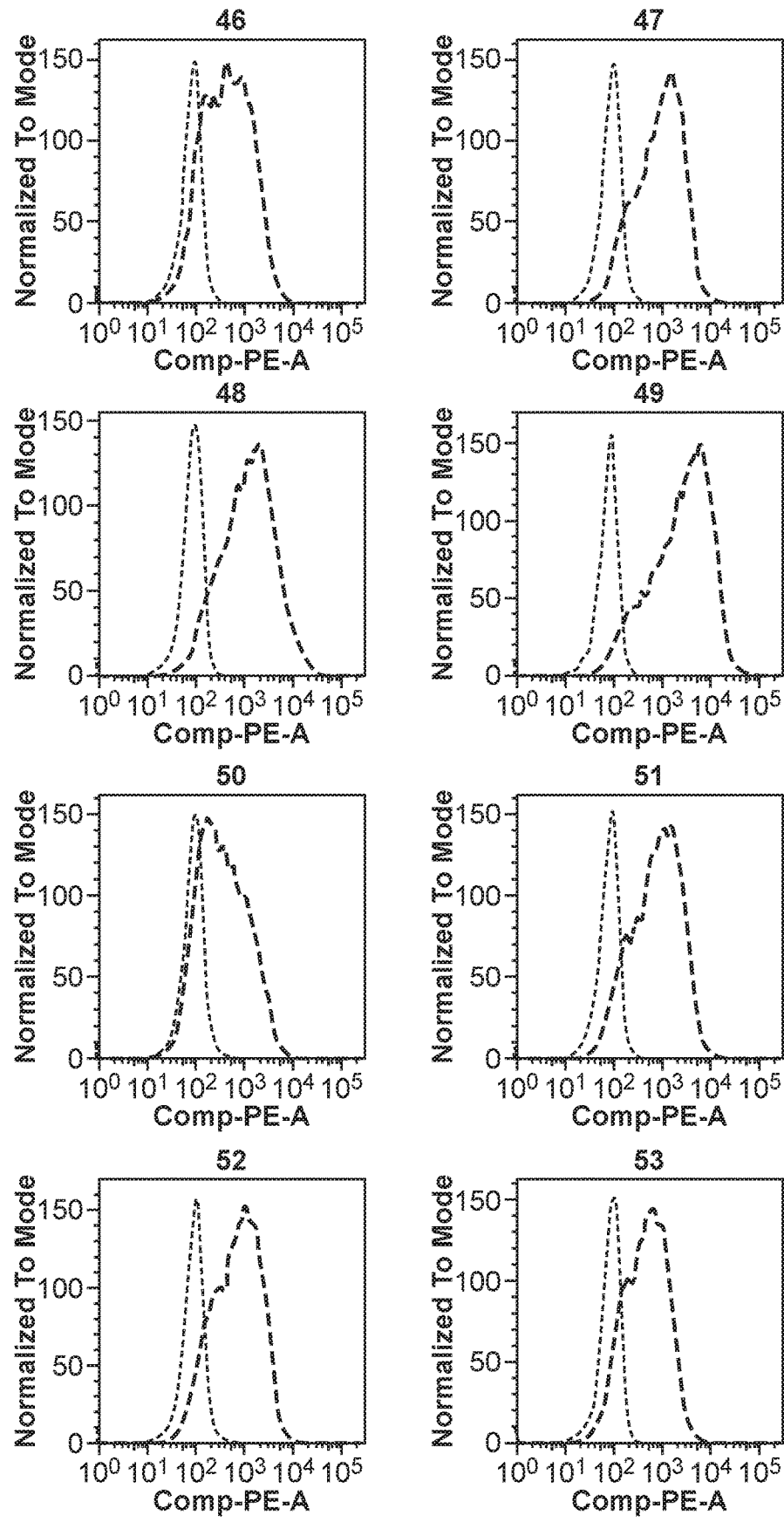
FIG. 3B (Cont. 7)

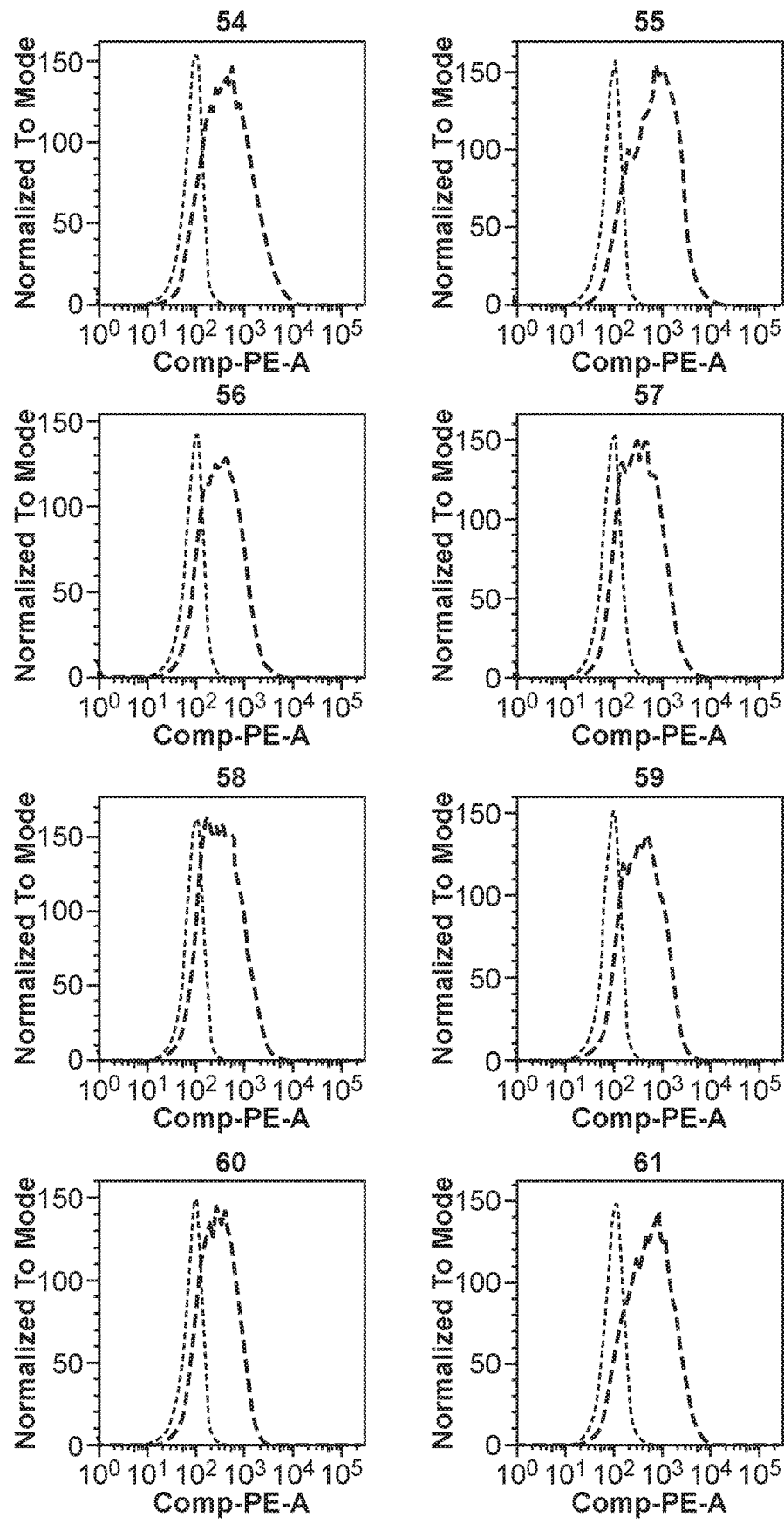
FIG. 3B (Cont. 8)

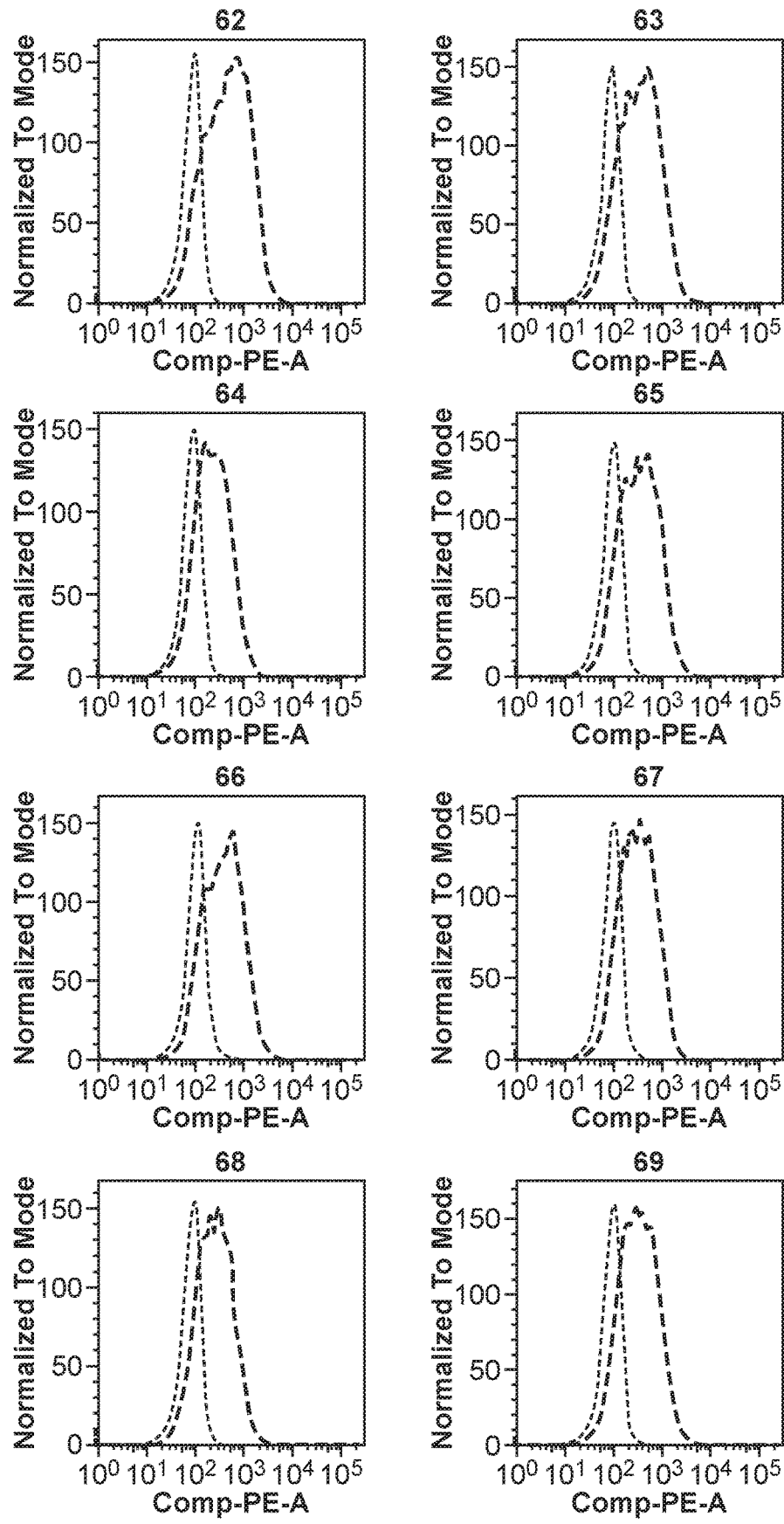
FIG. 3B (Cont. 9)

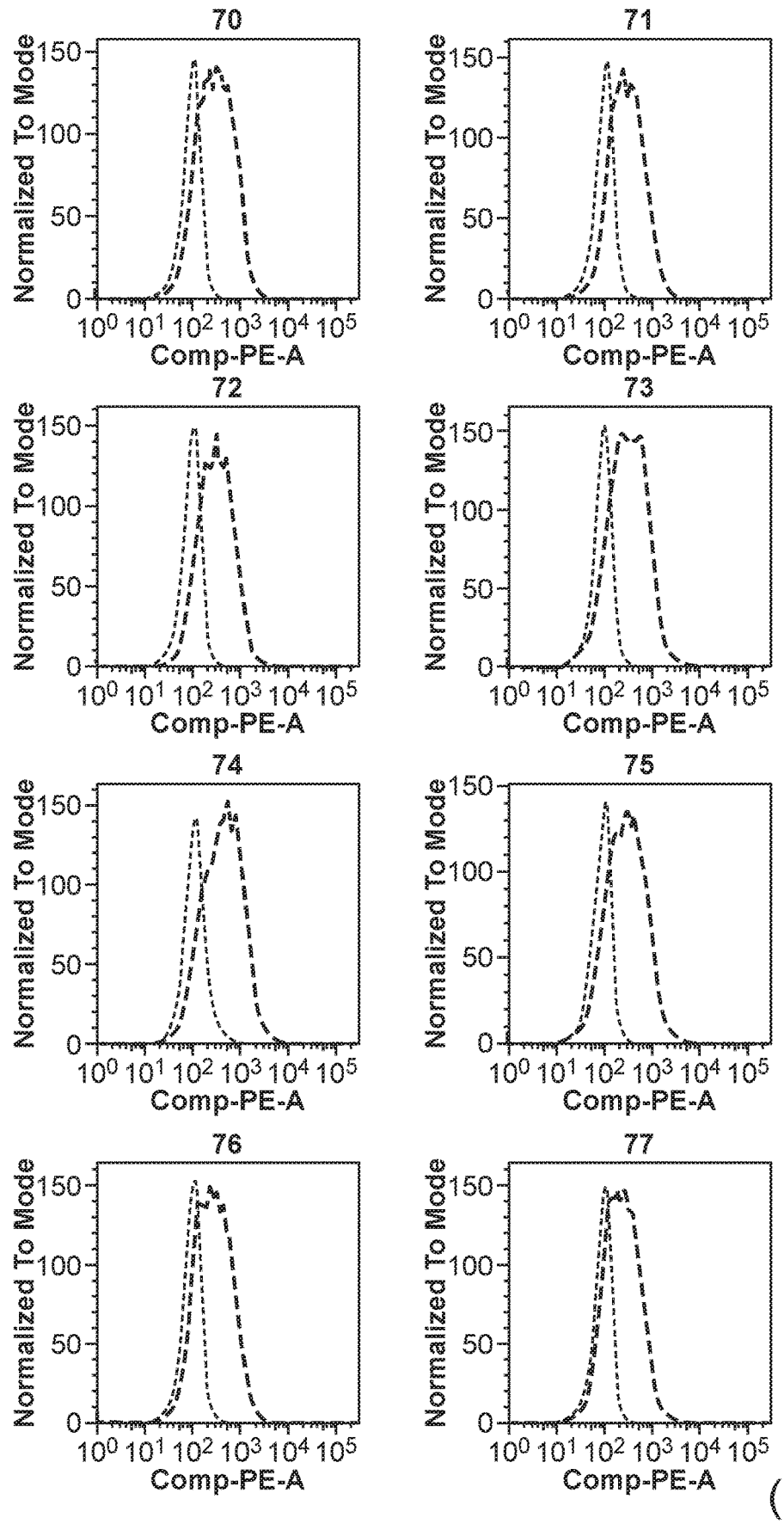
FIG. 3B (Cont. 10)

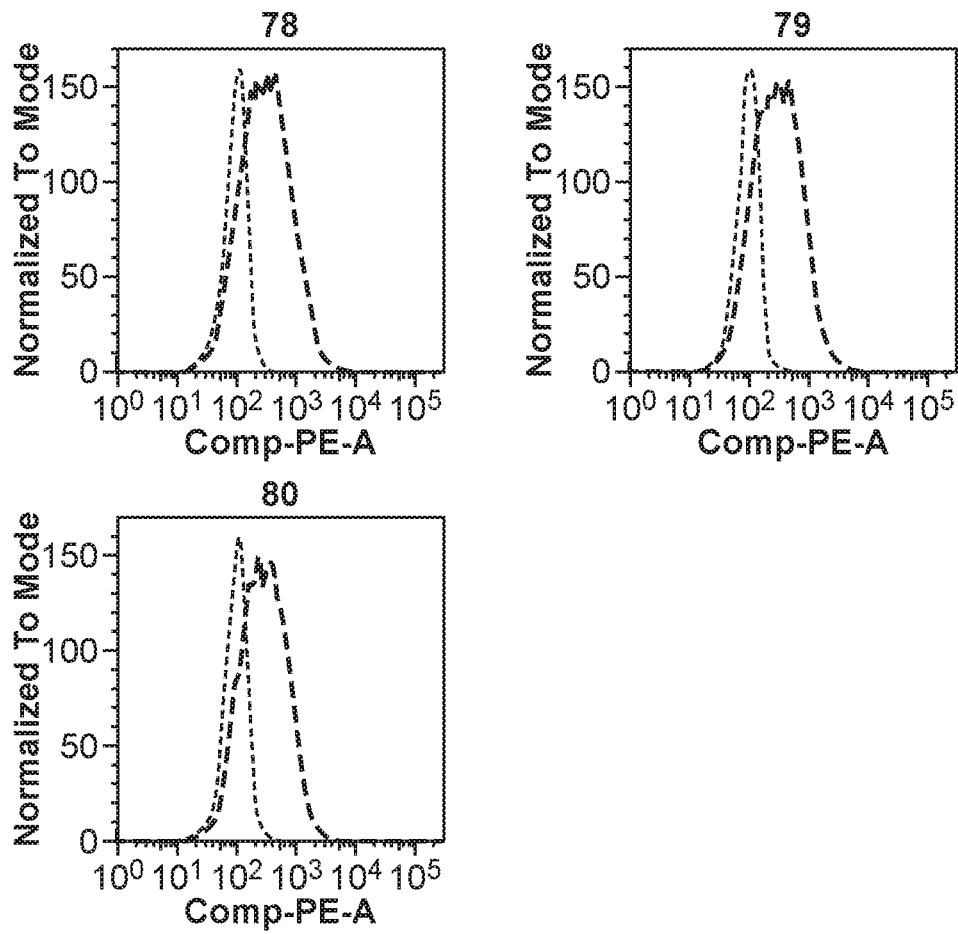
FIG. 3B (Cont. 11)

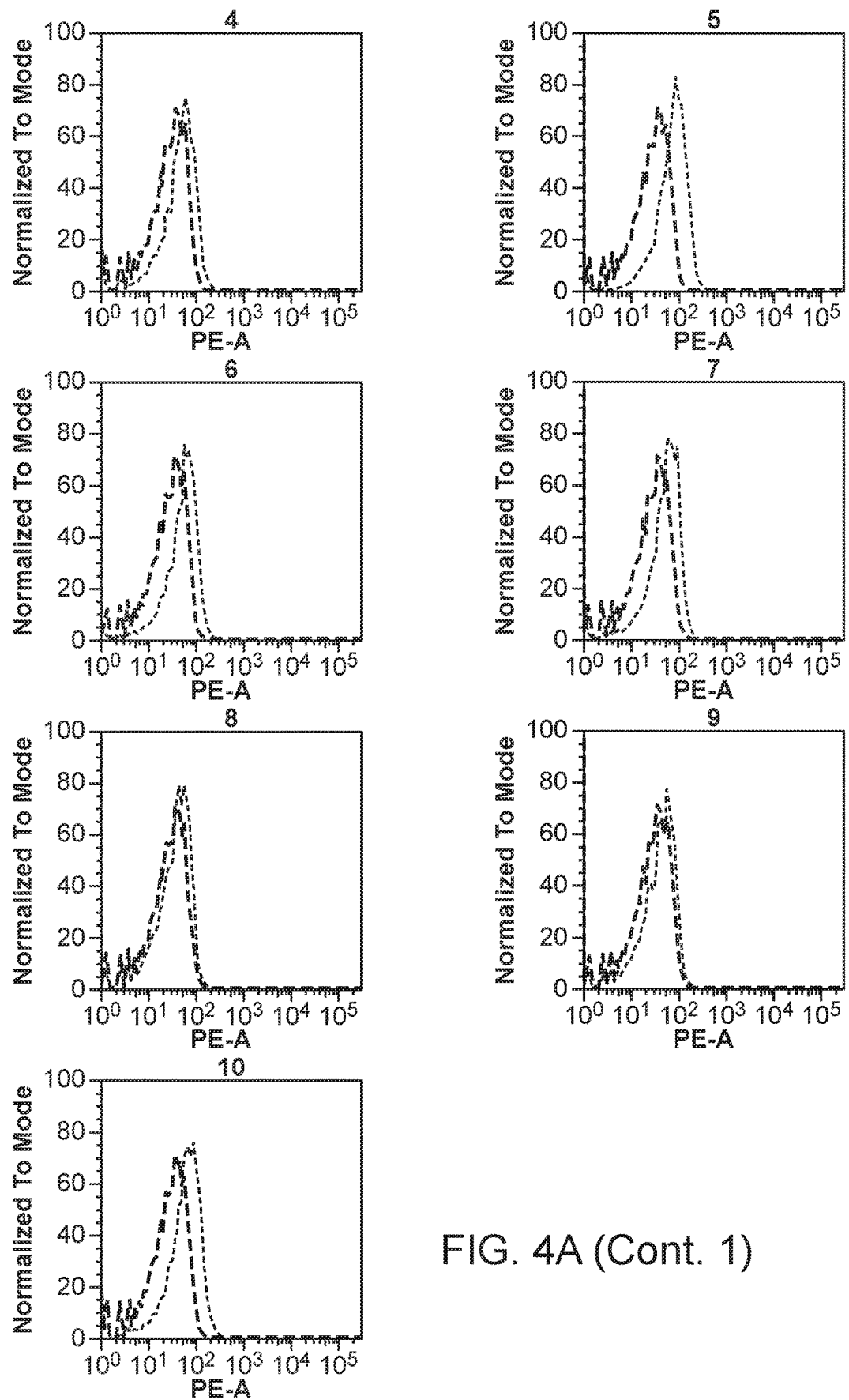
FIG. 4A (Cont. 1)

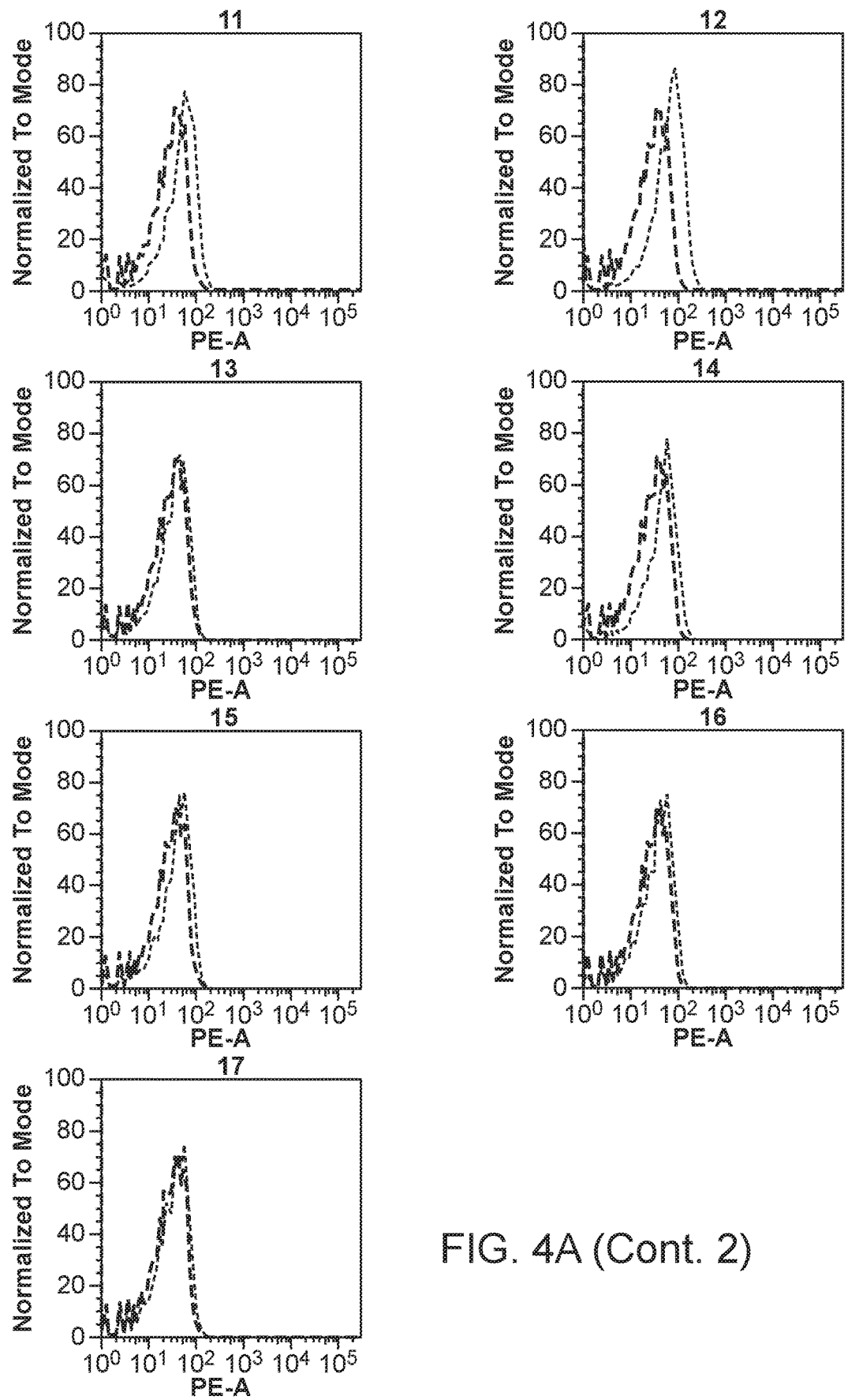
FIG. 4A (Cont. 2)

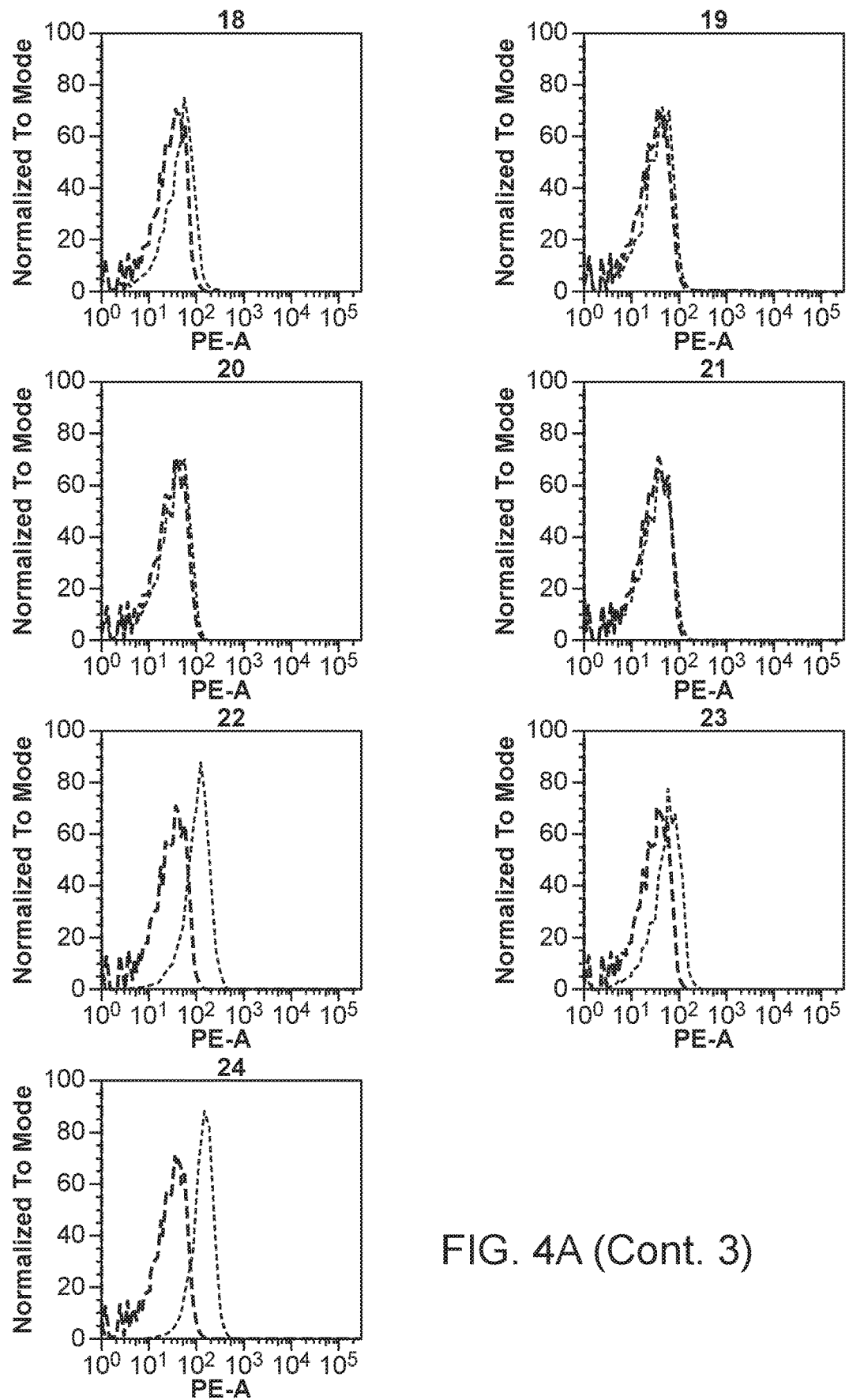
FIG. 4A (Cont. 3)

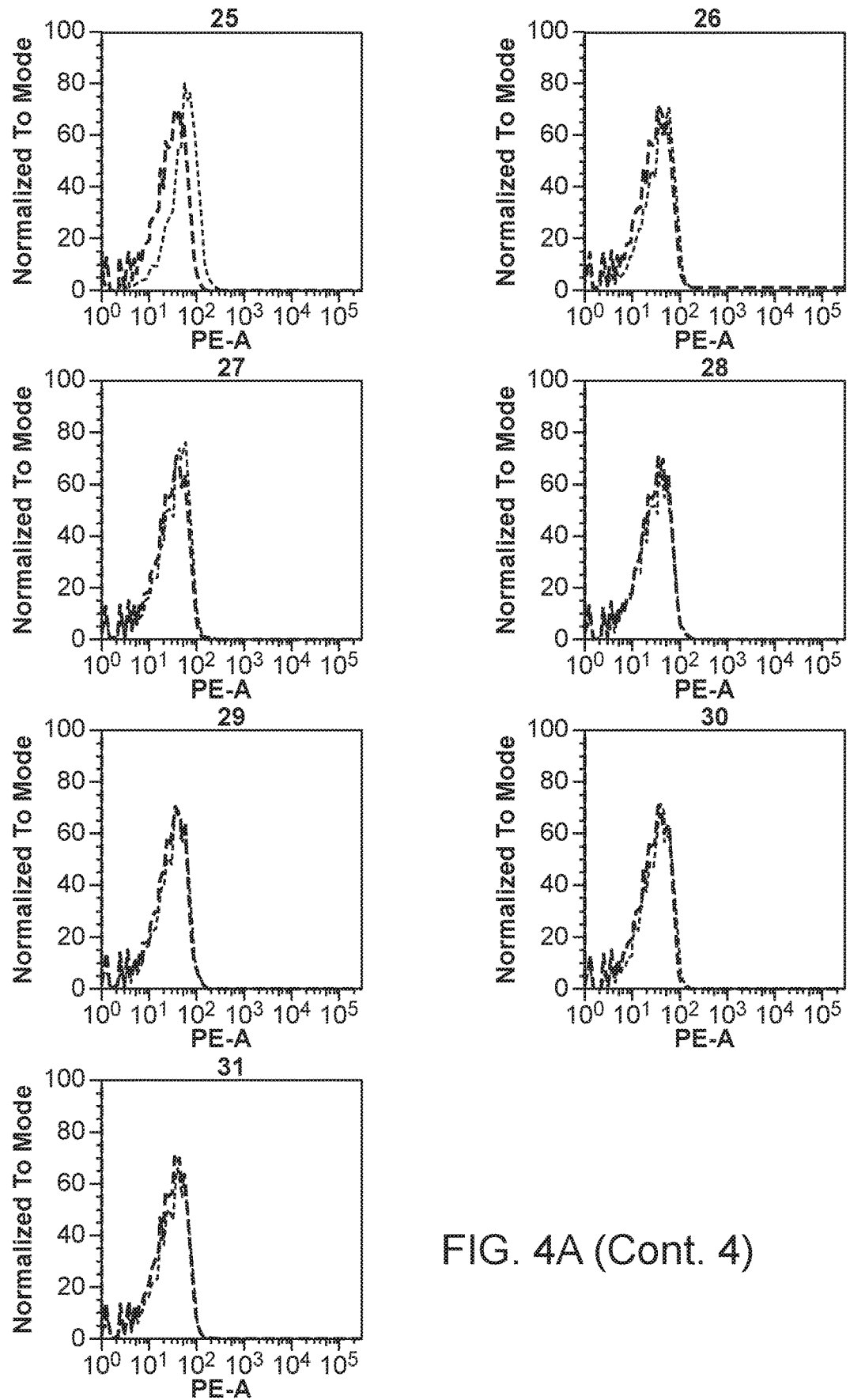
FIG. 4A (Cont. 4)

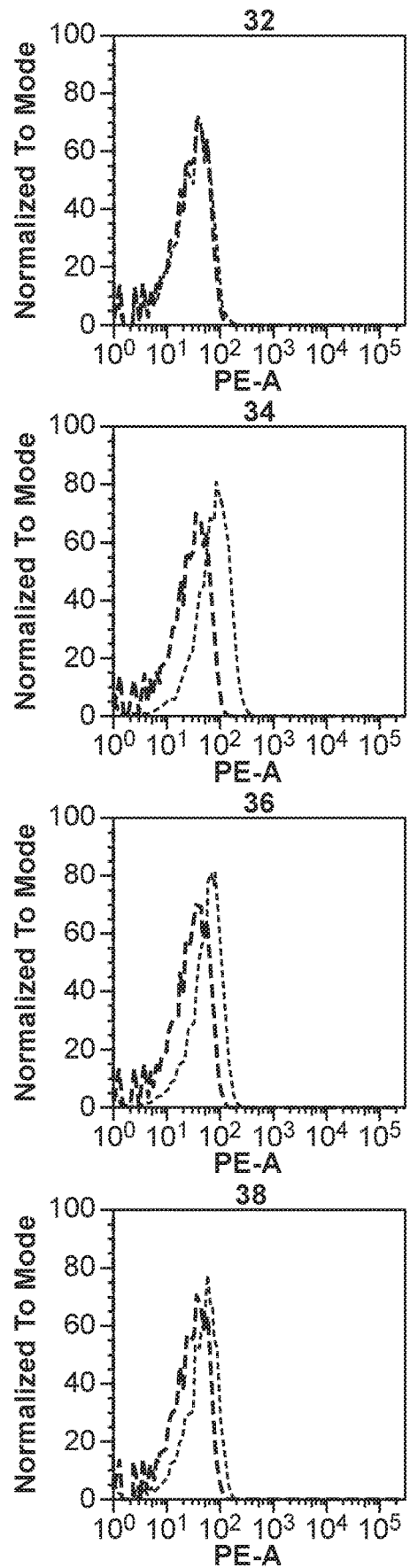
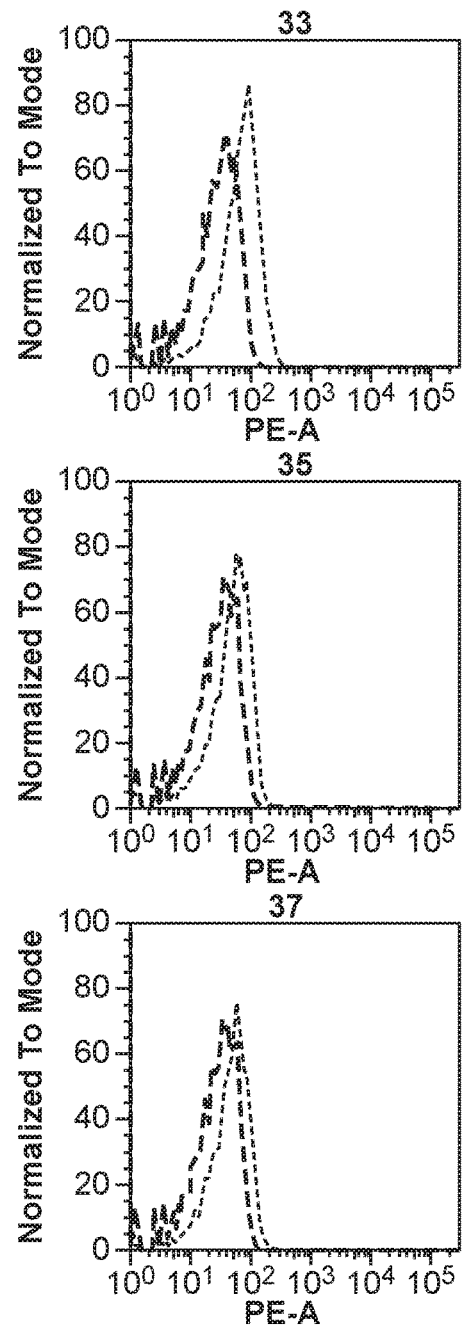
FIG. 4A (Cont. 5)

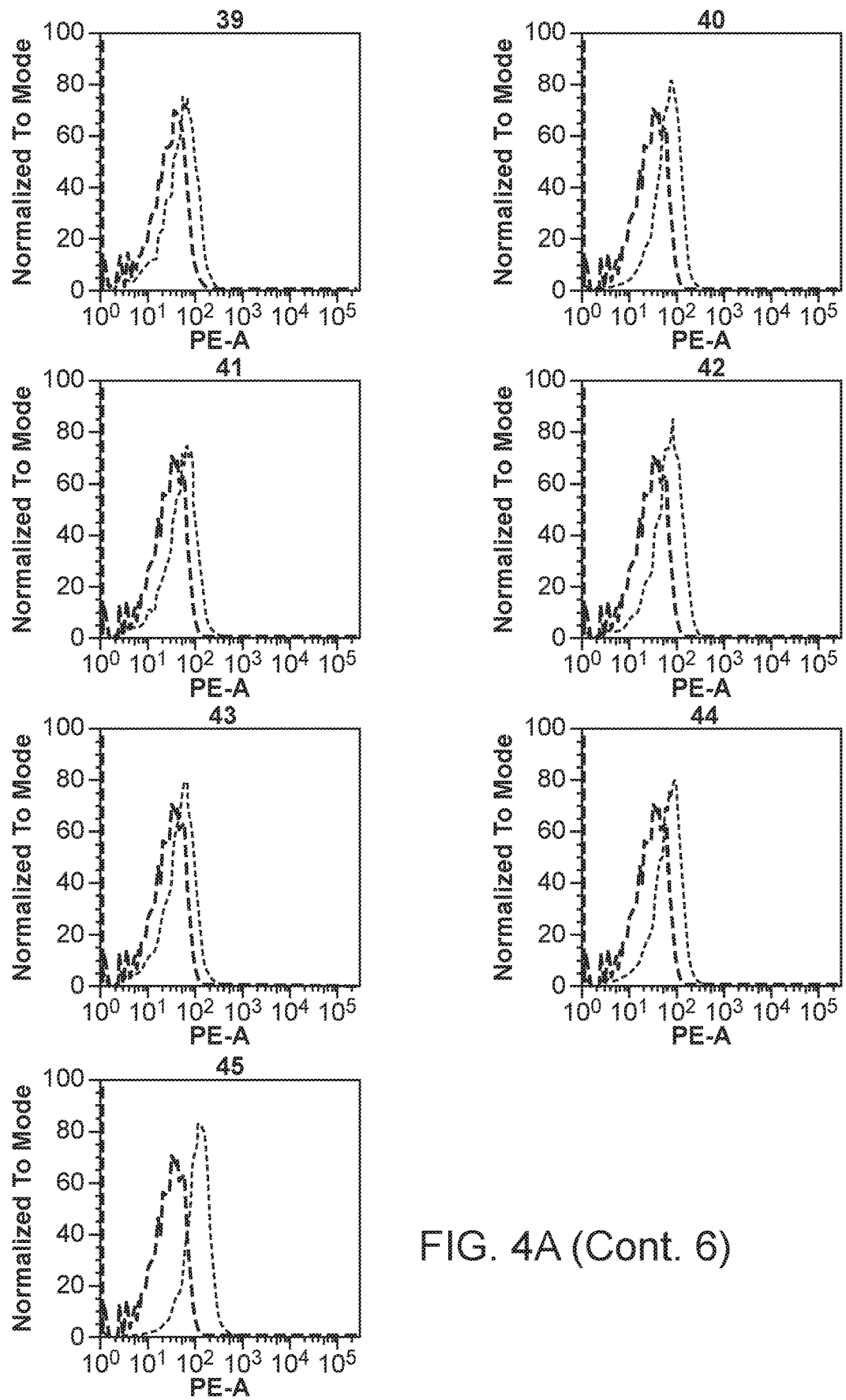
FIG. 4A (Cont. 6)

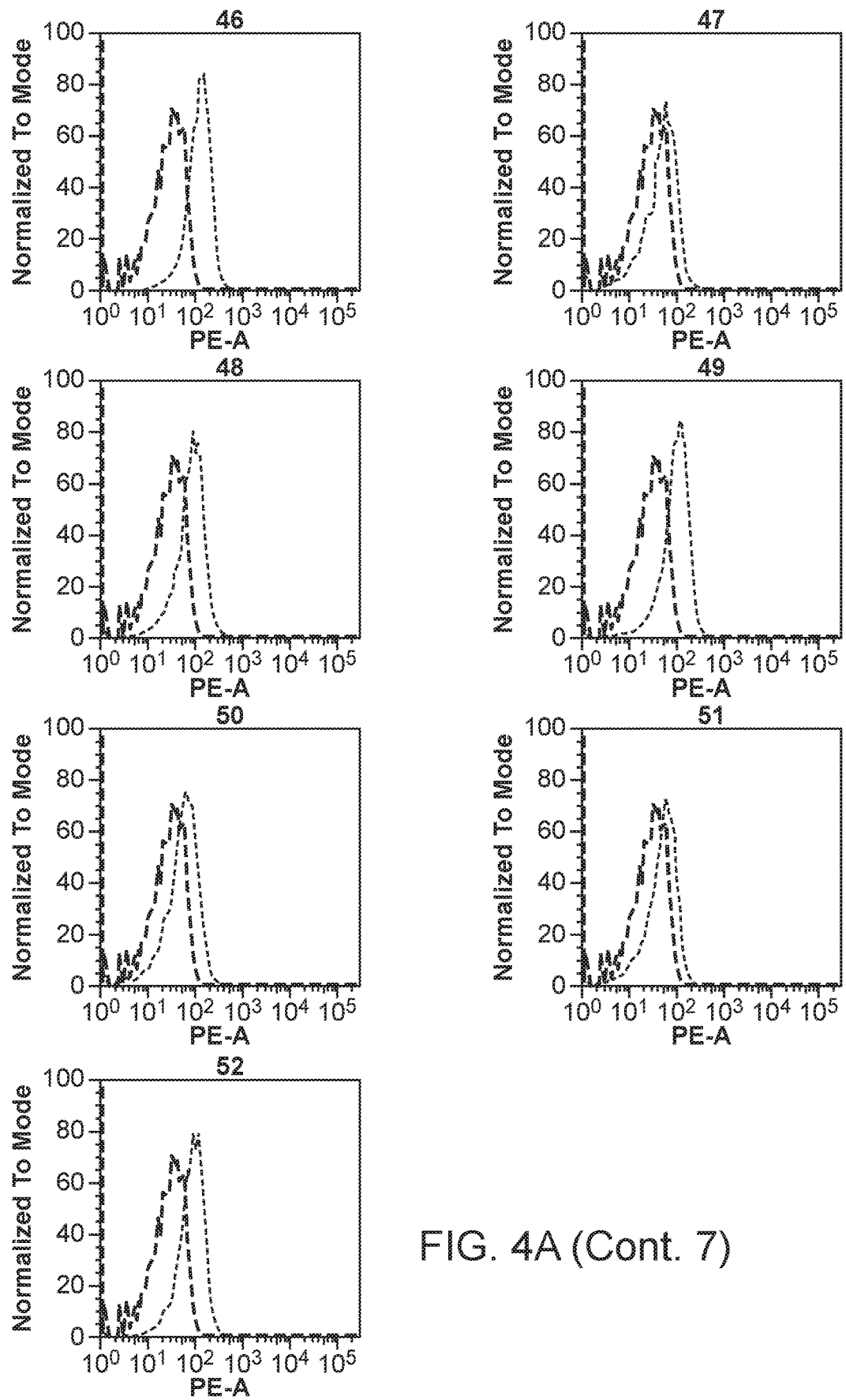
FIG. 4A (Cont. 7)

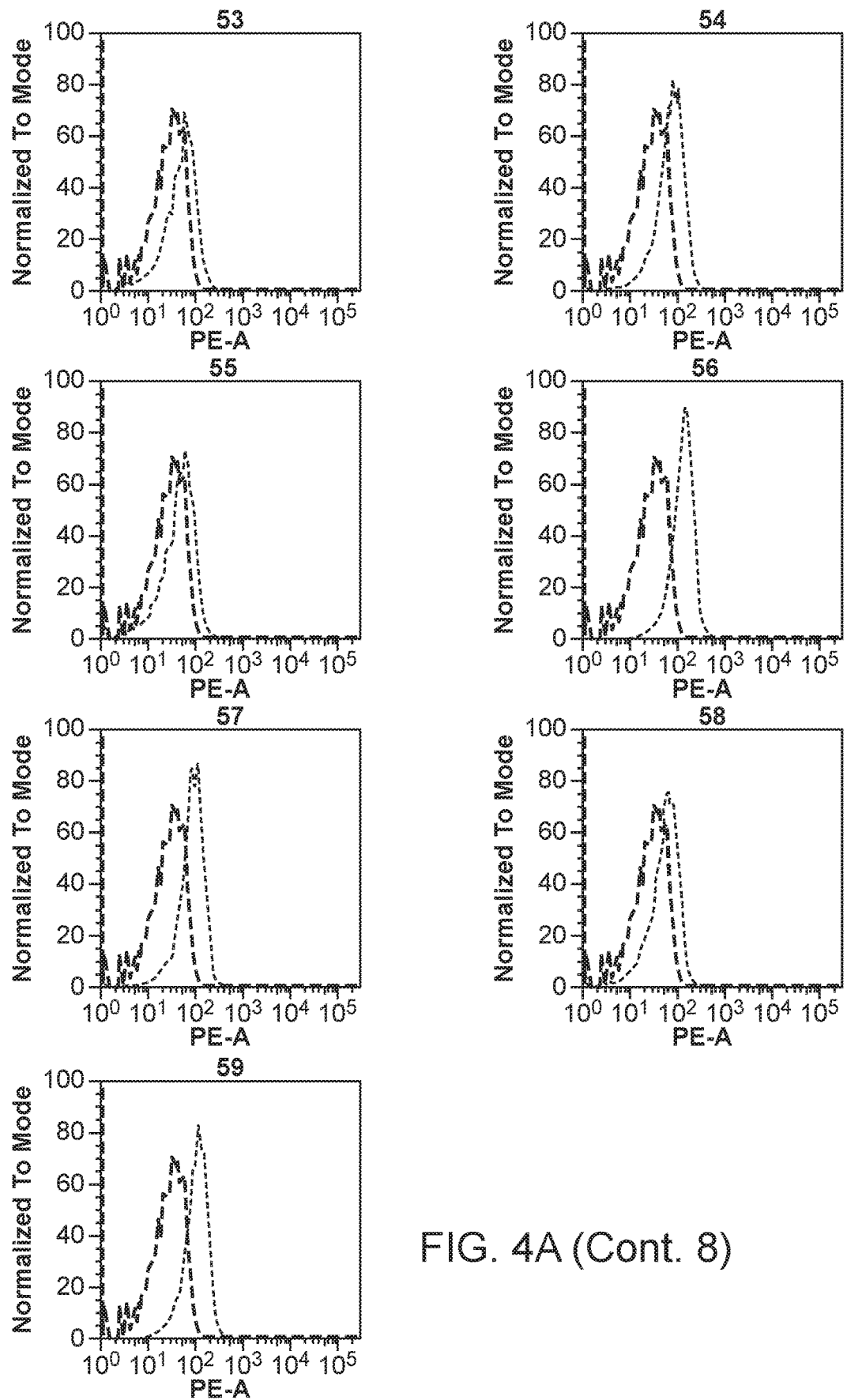
FIG. 4A (Cont. 8)

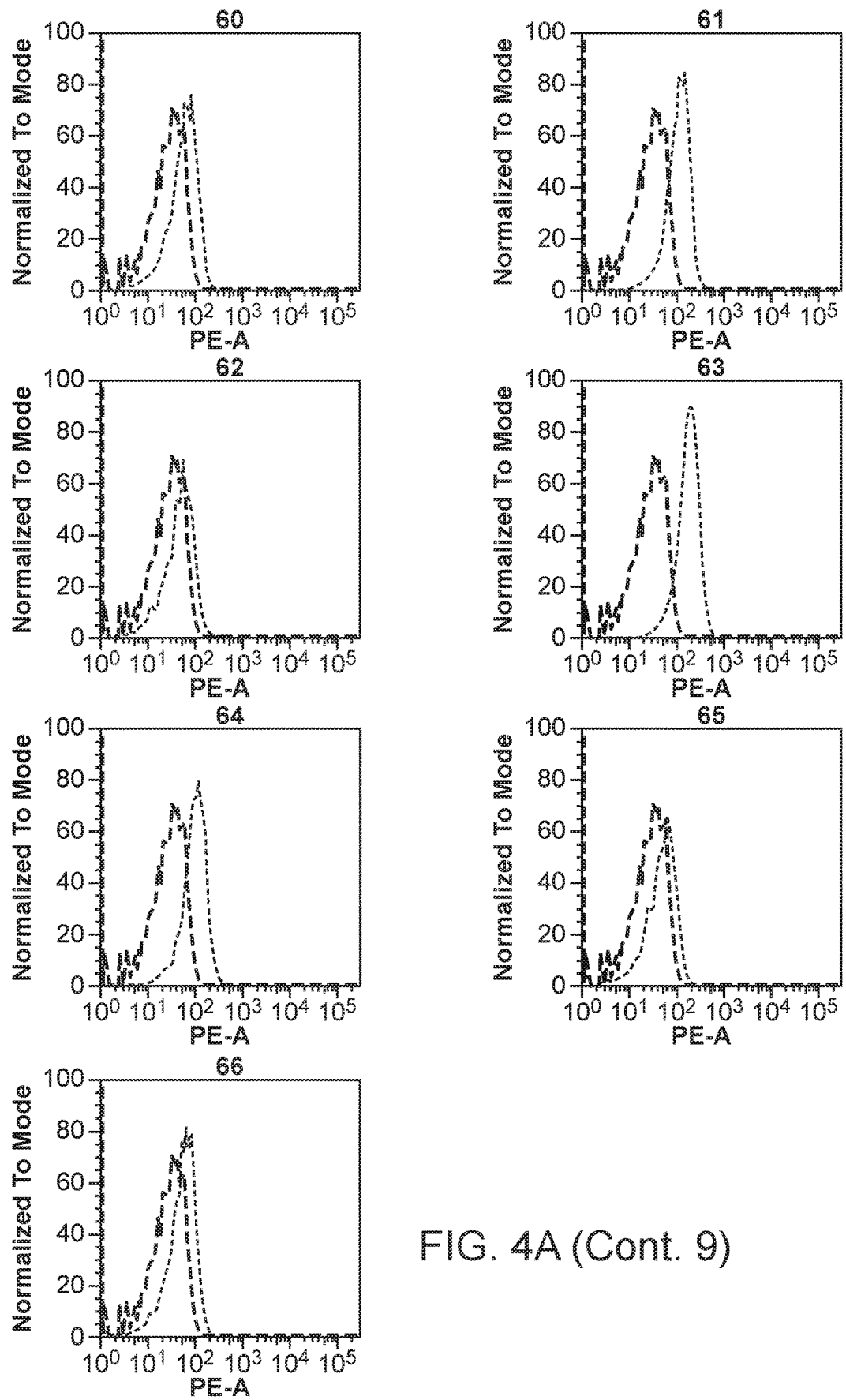
FIG. 4A (Cont. 9)

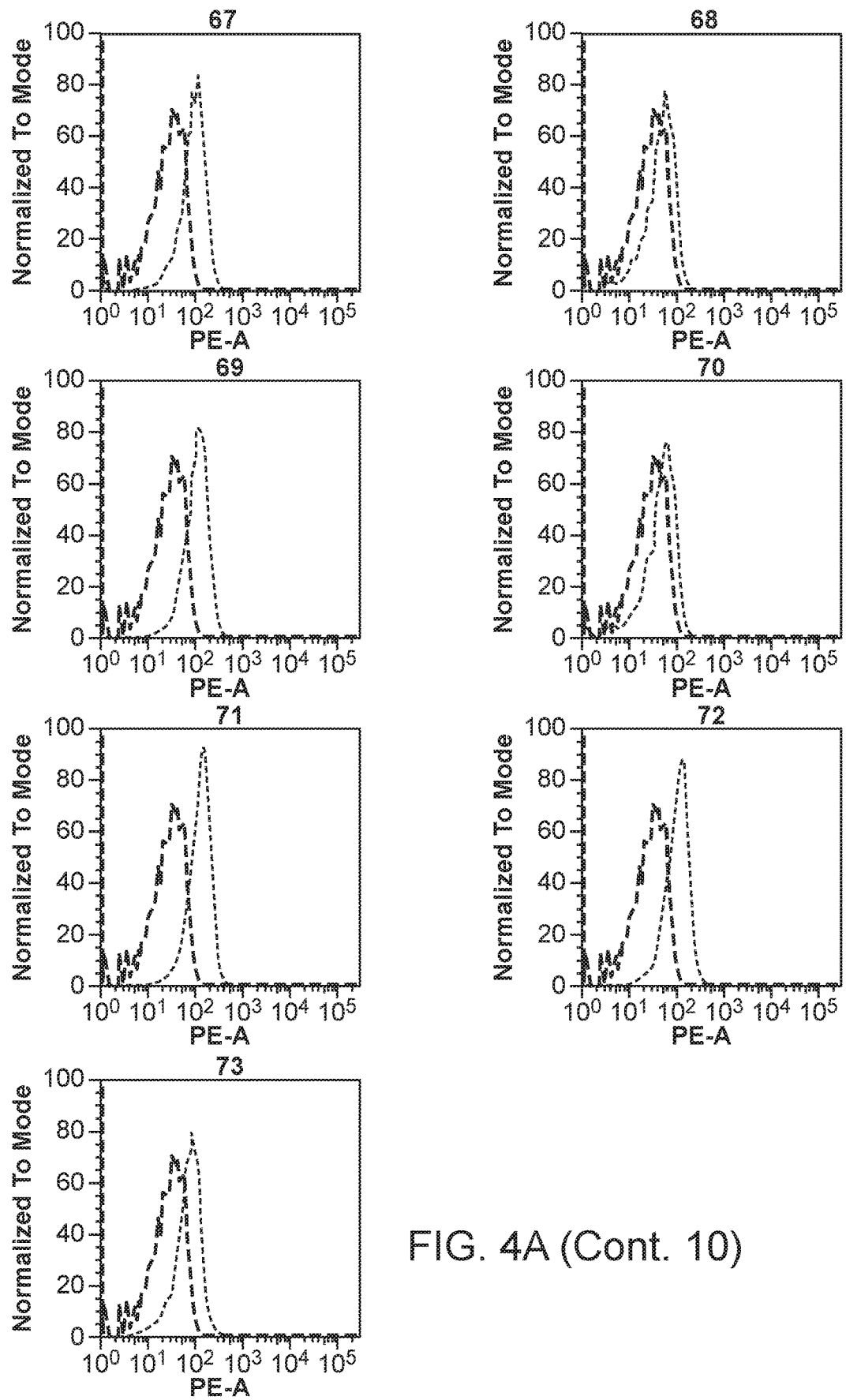
FIG. 4A (Cont. 10)

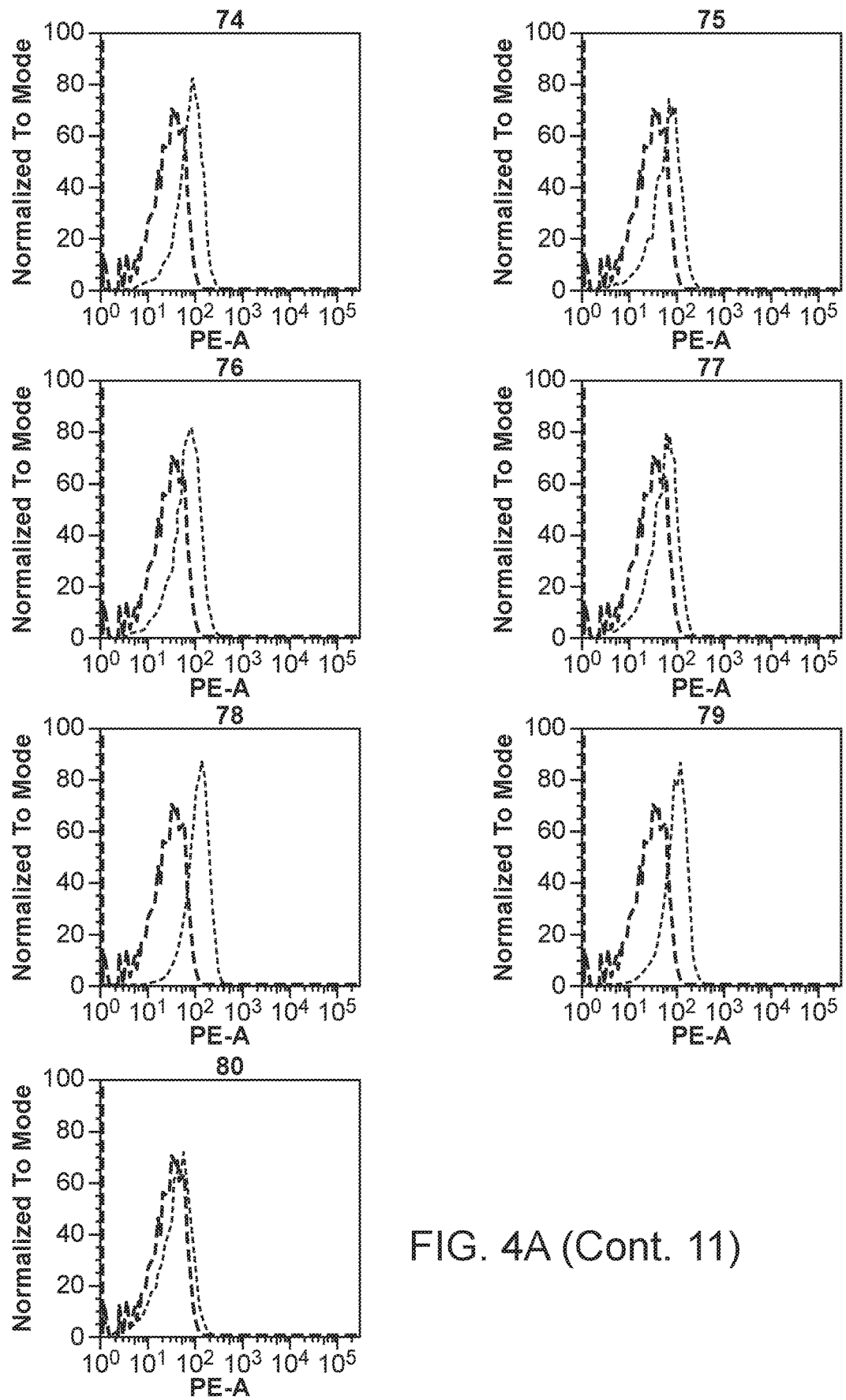
FIG. 4A (Cont. 11)

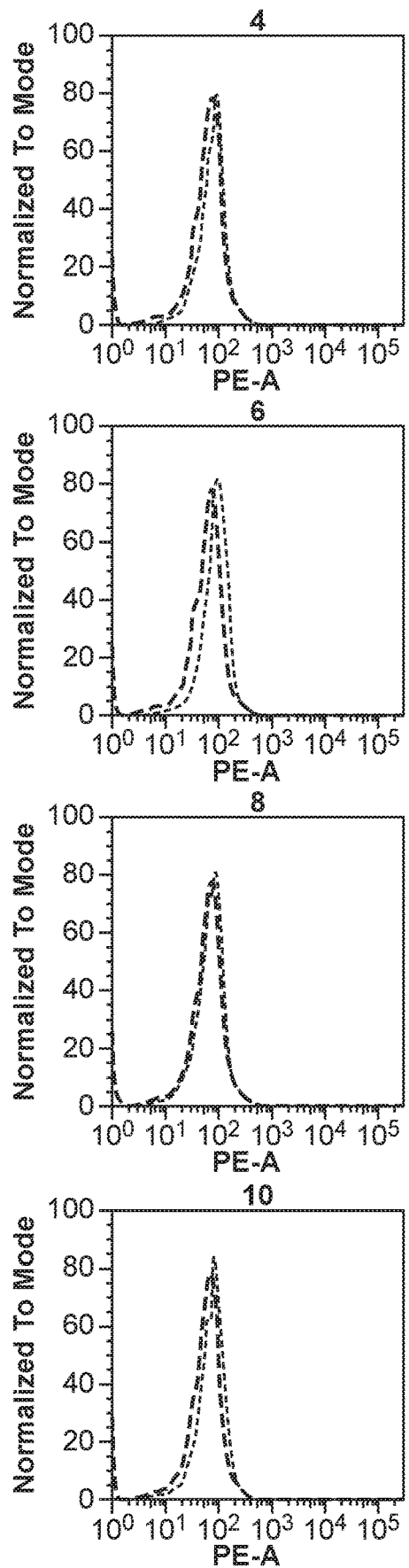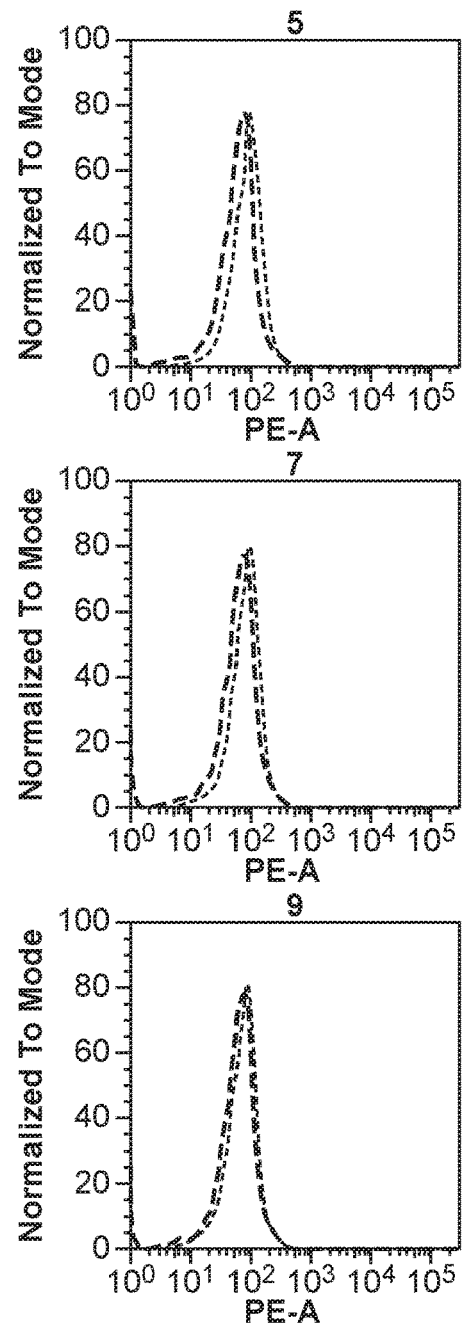
FIG. 4B (Cont. 1)

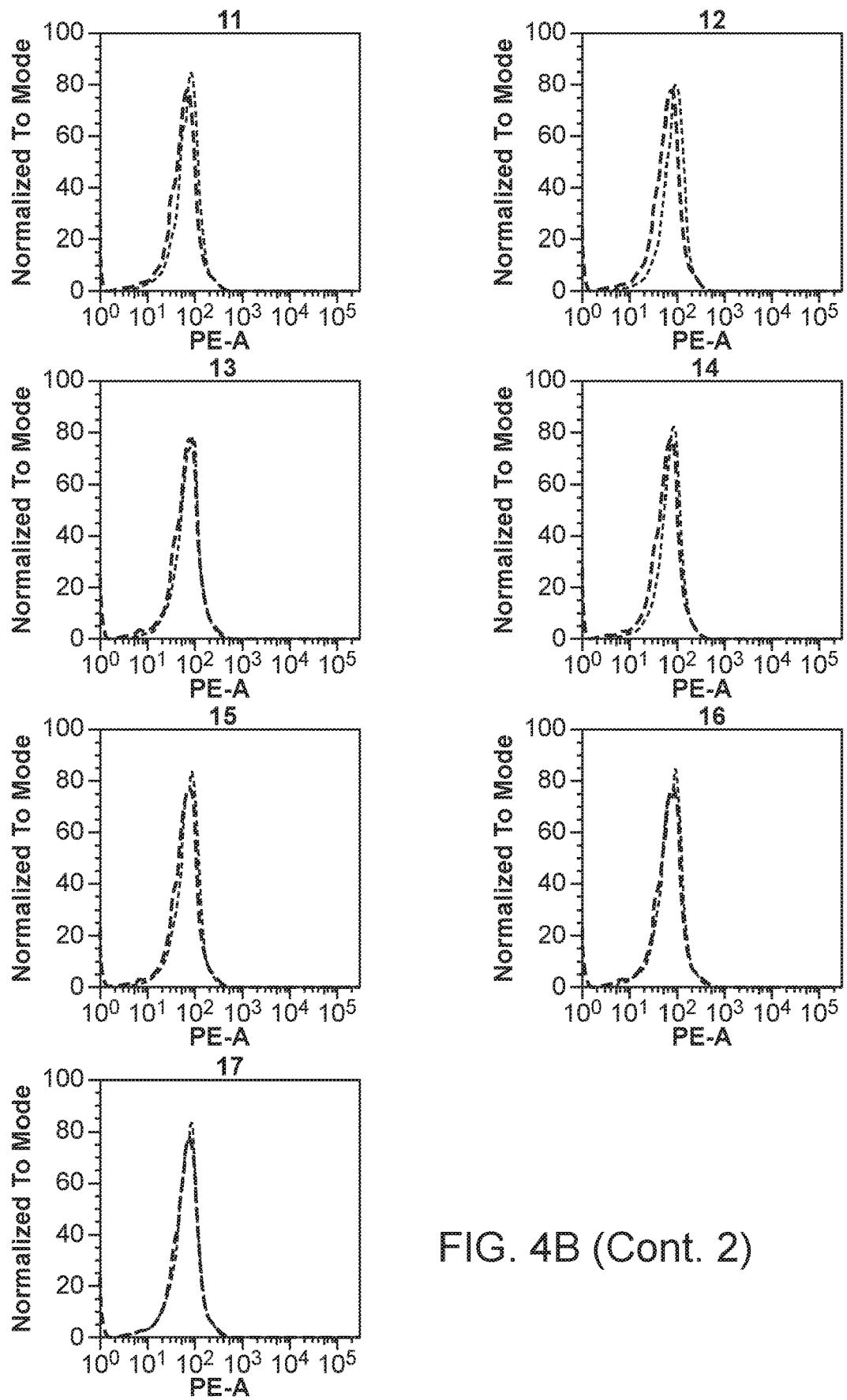
FIG. 4B (Cont. 2)

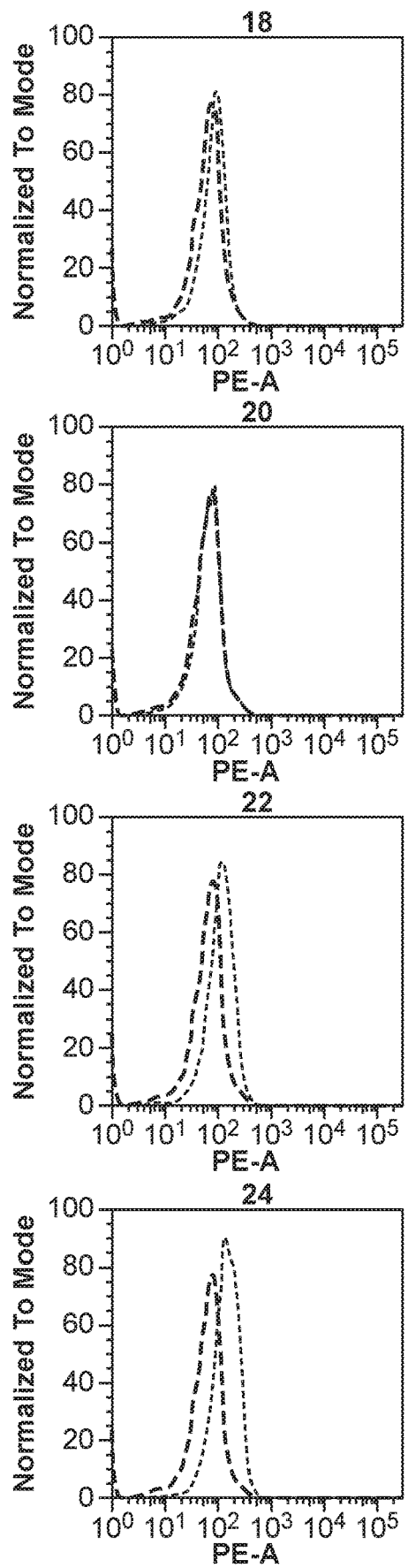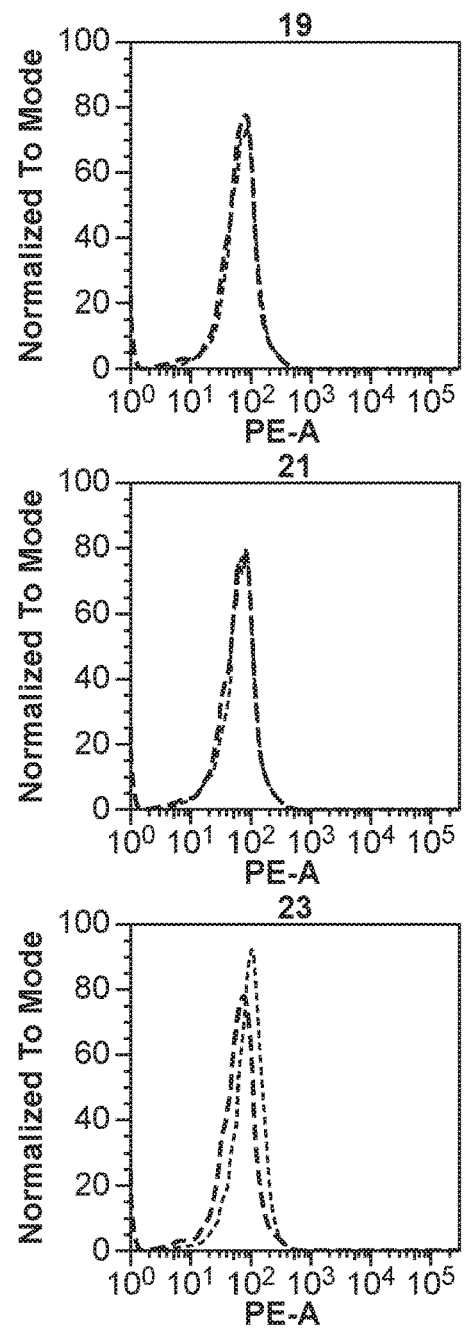
FIG. 4B (Cont. 3)

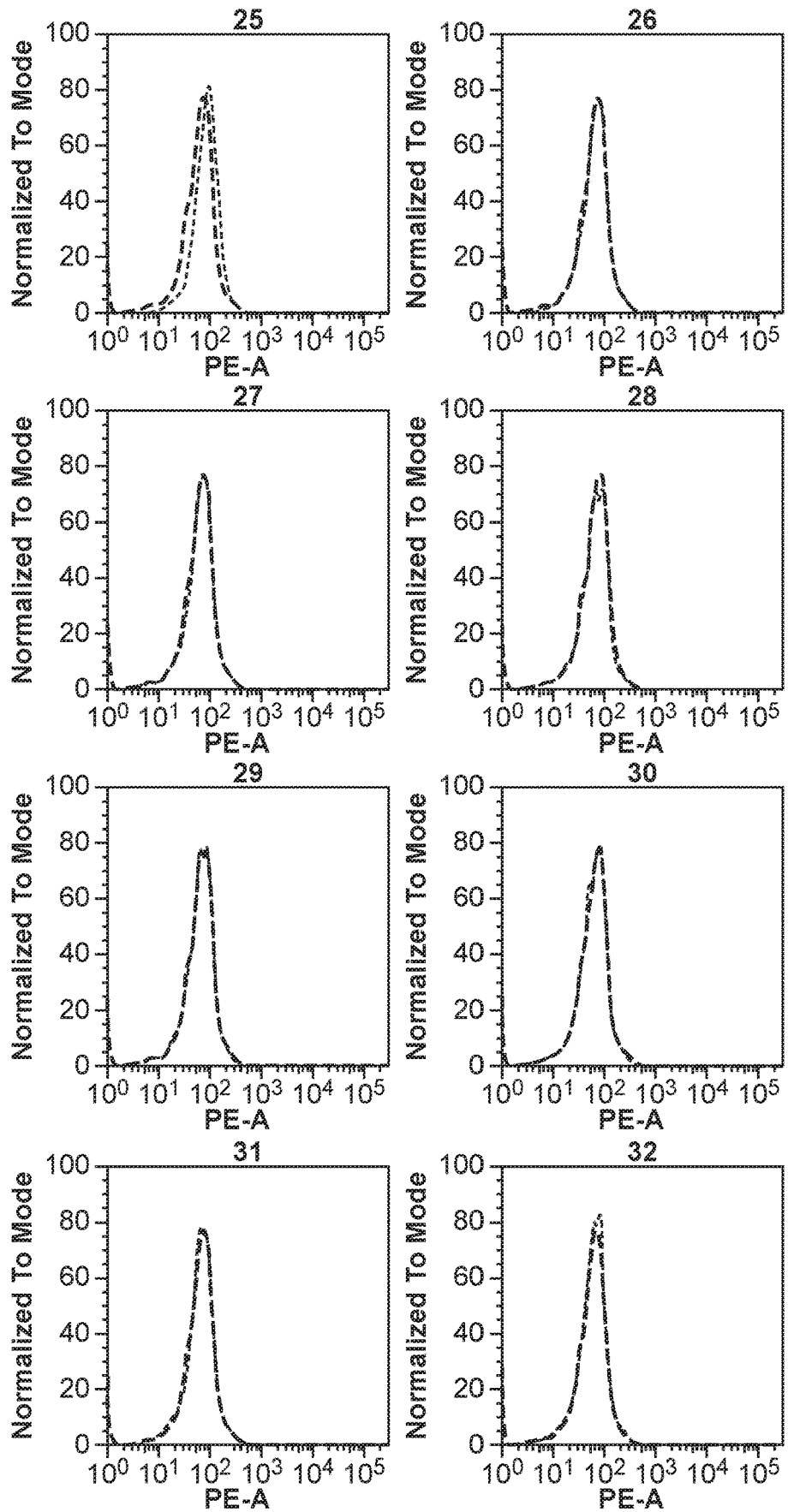
FIG. 4B (Cont. 4)

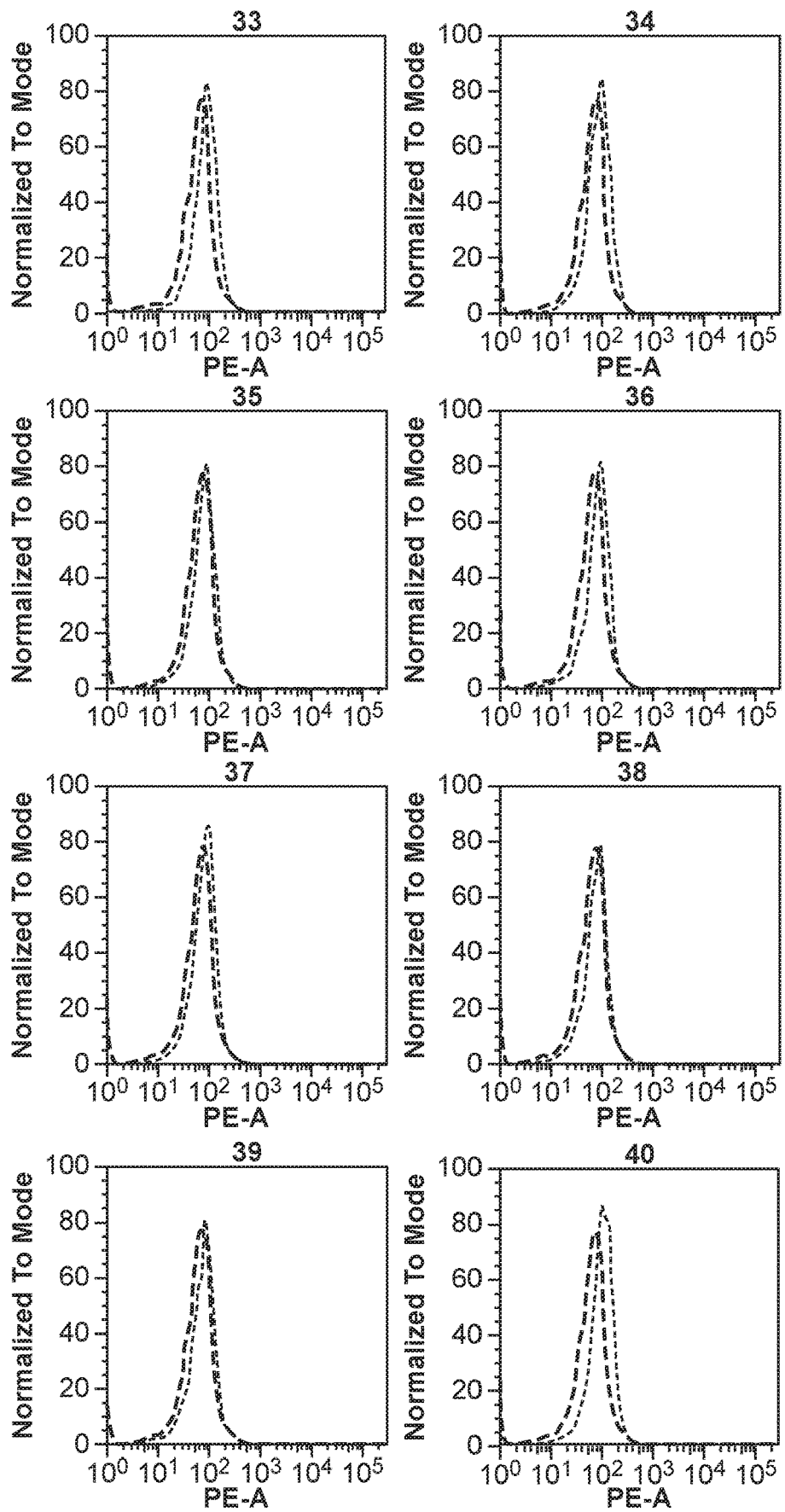
FIG. 4B (Cont. 5)

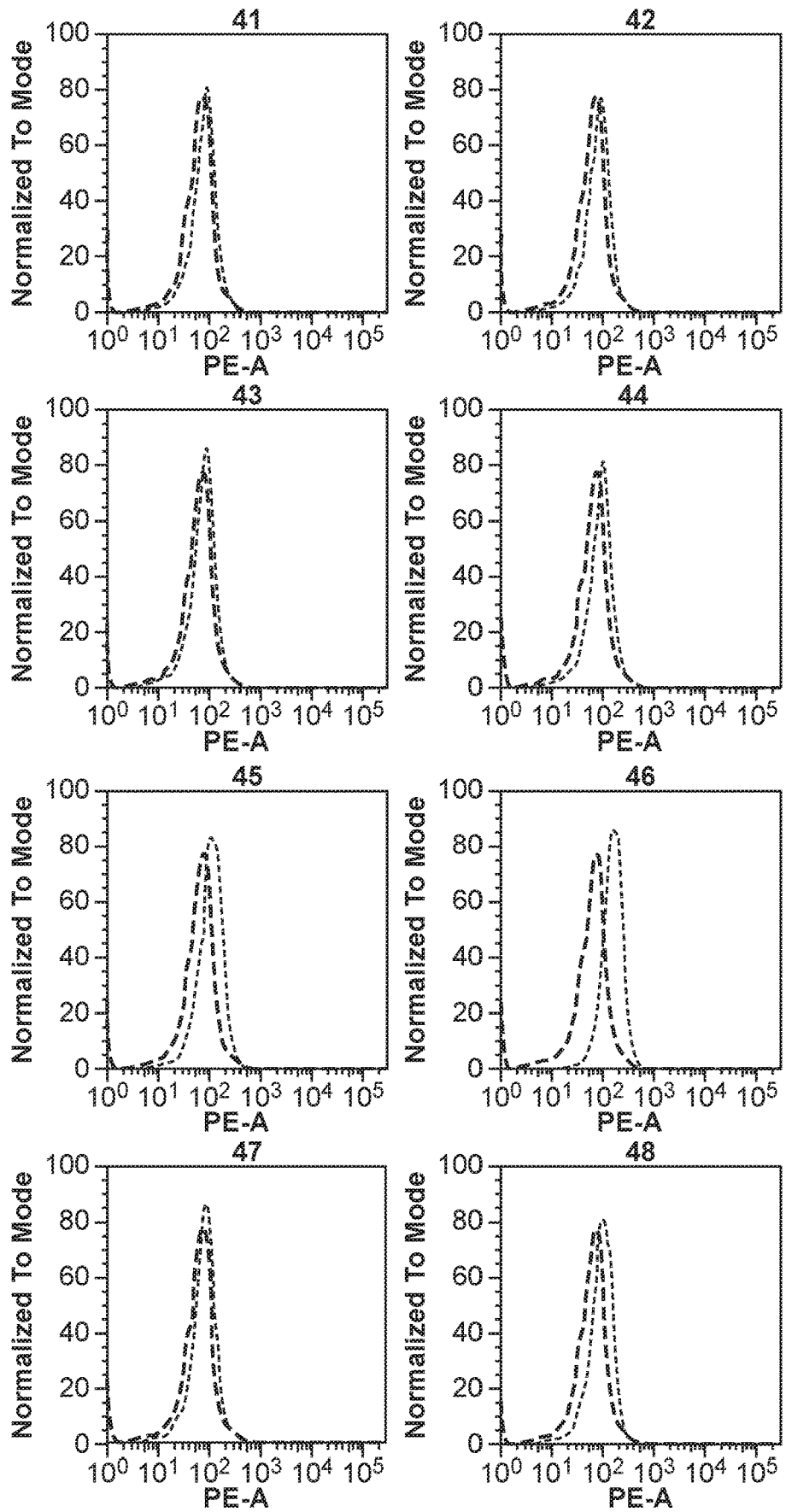
FIG. 4B (Cont. 6)

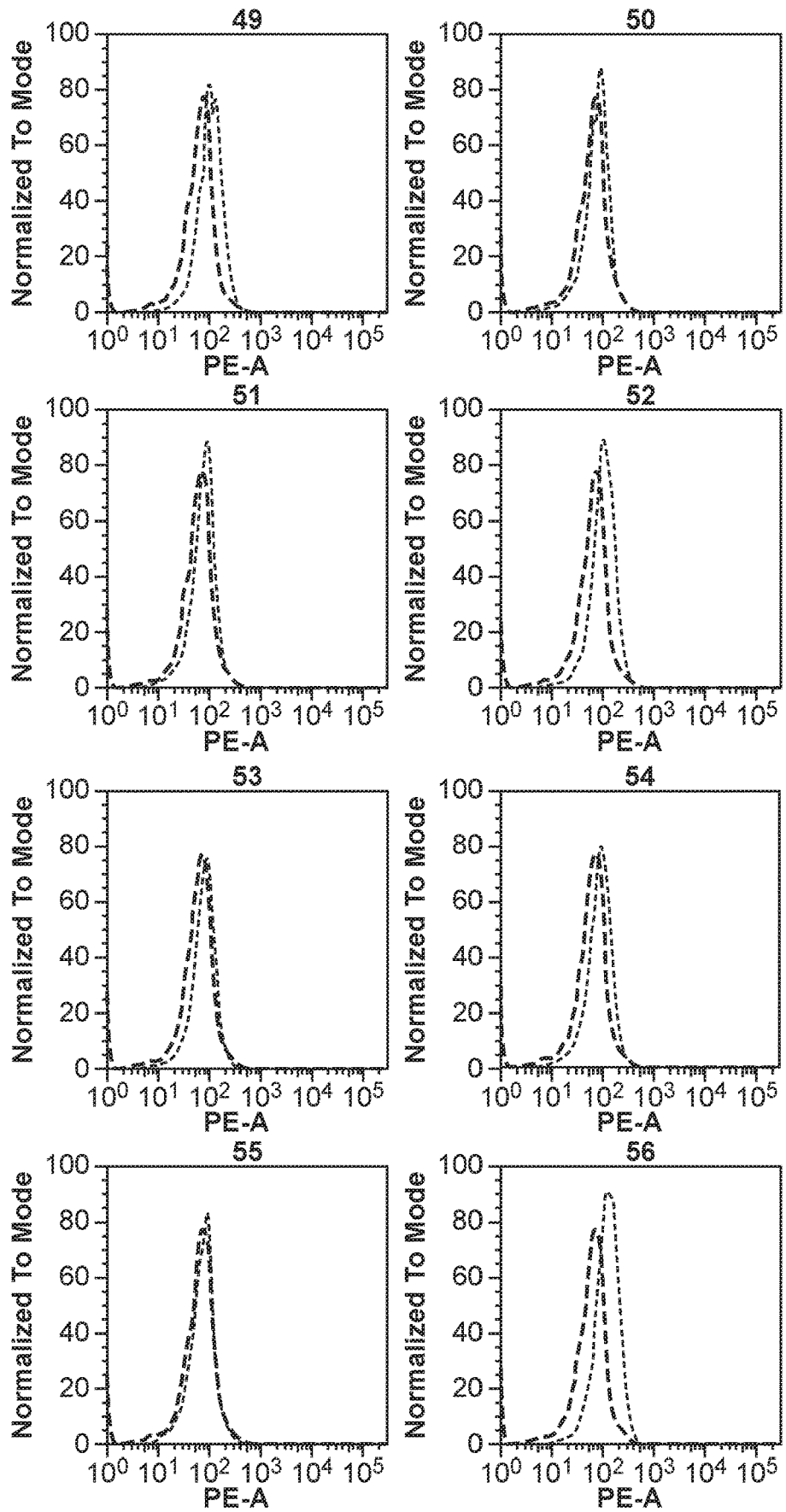
FIG. 4B (Cont. 7)

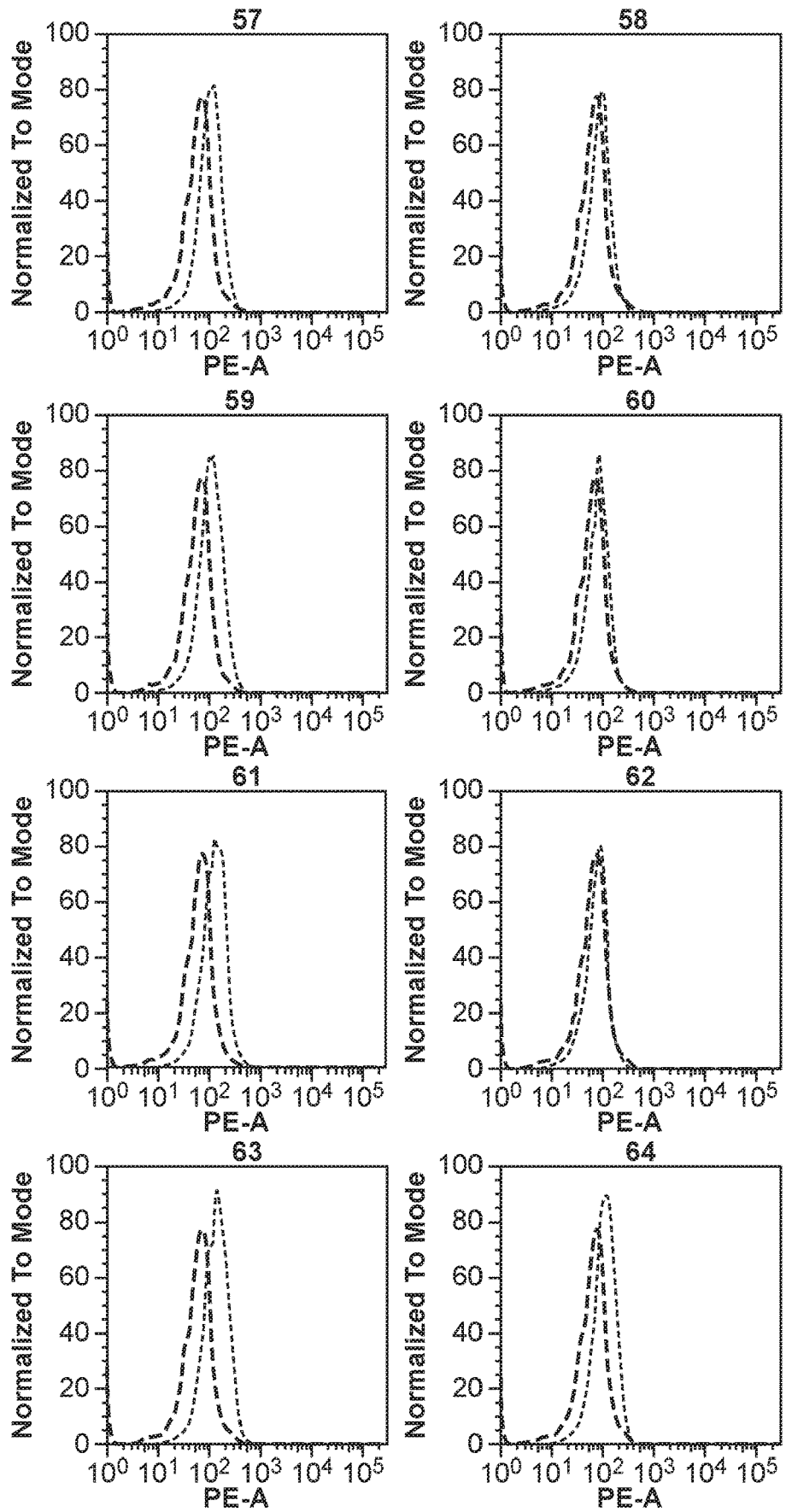
FIG. 4B (Cont. 8)

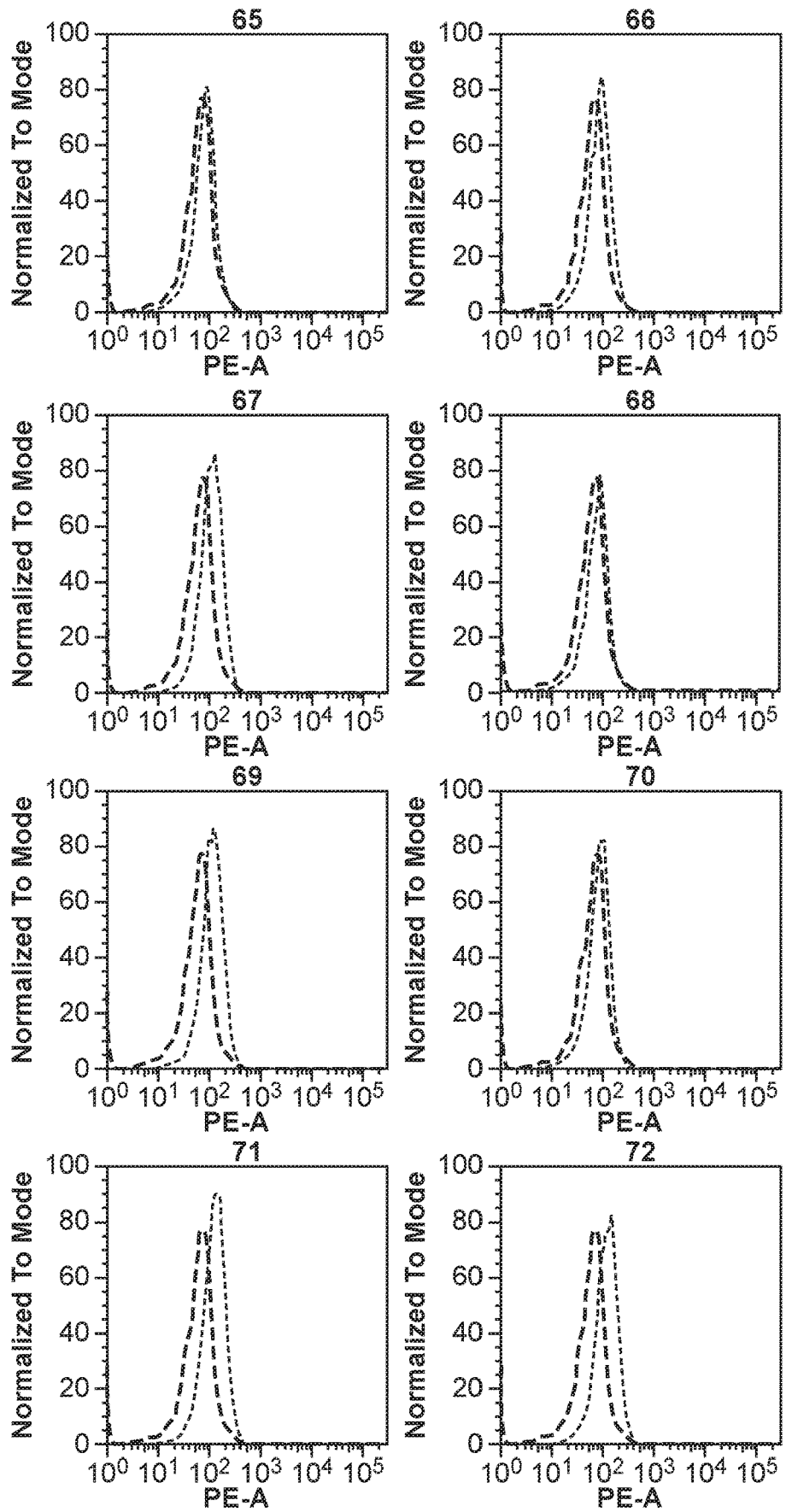
FIG. 4B (Cont. 9)

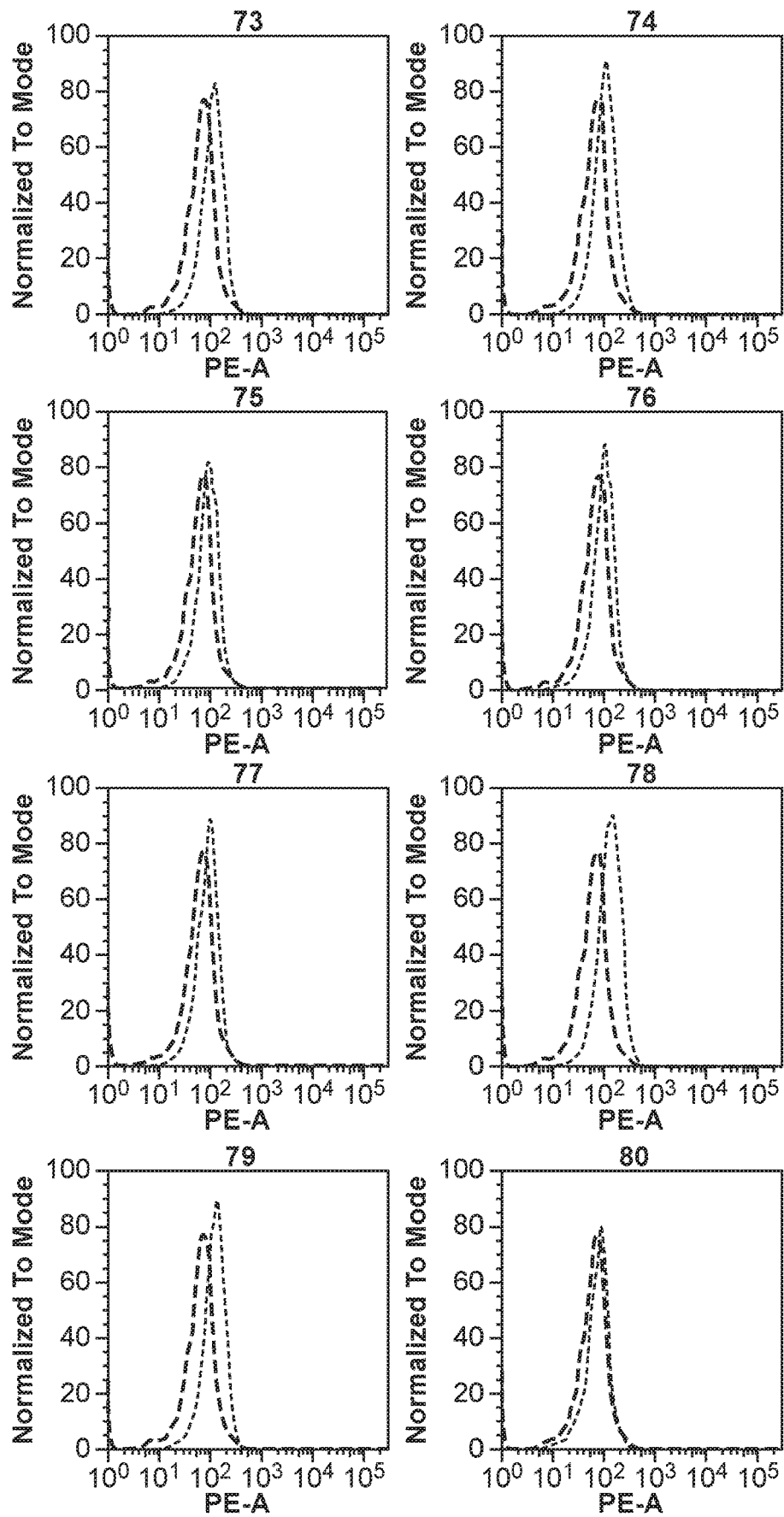
FIG. 4B (Cont. 10)

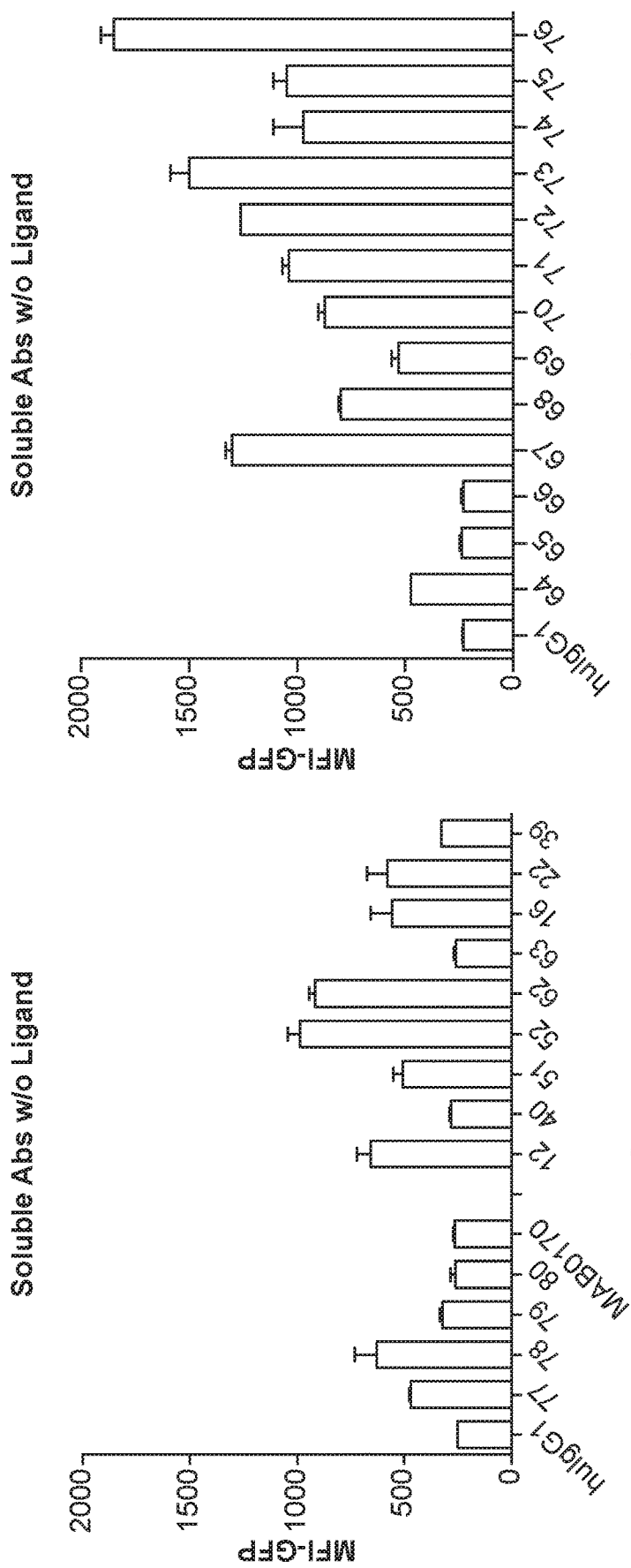

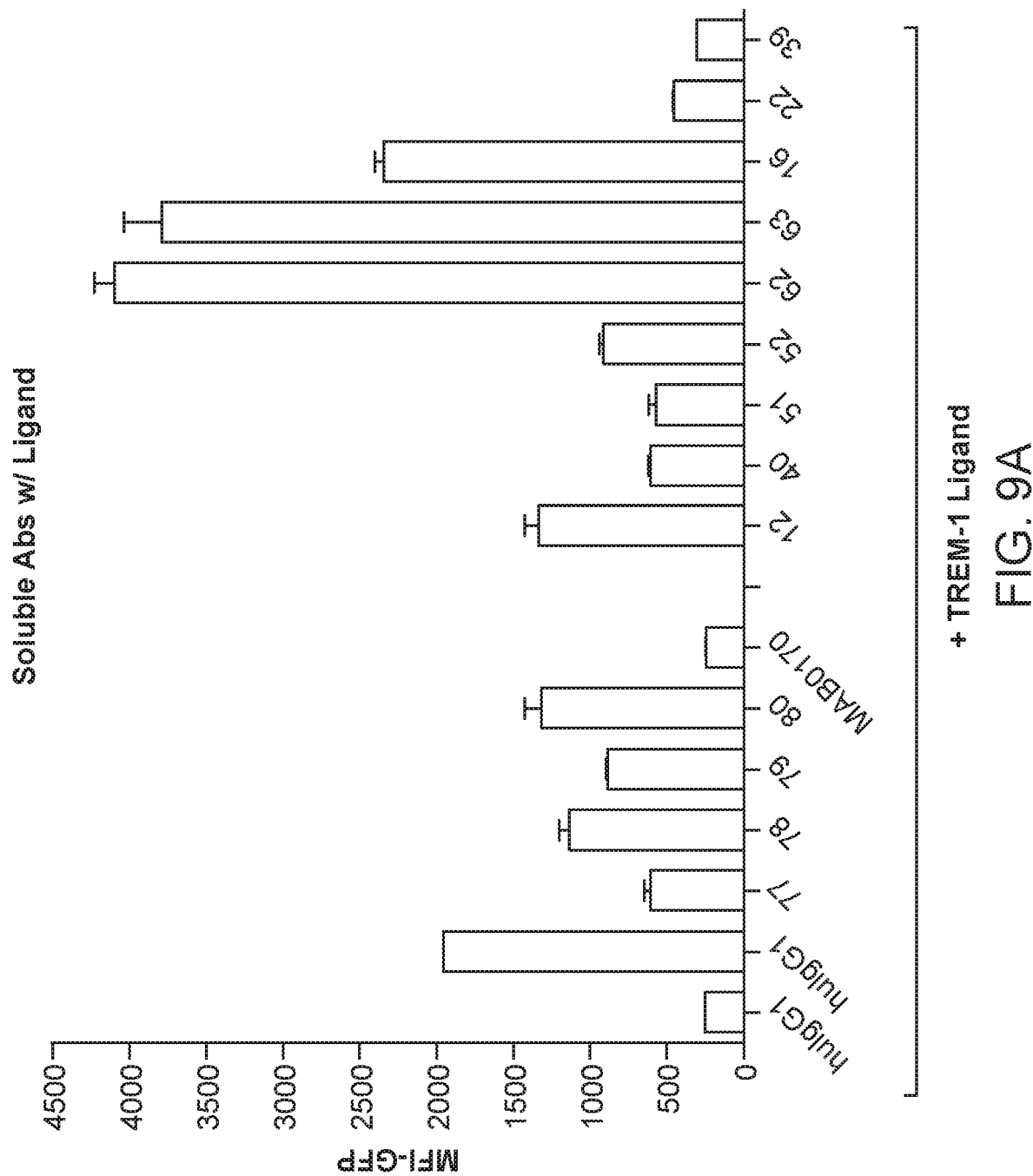

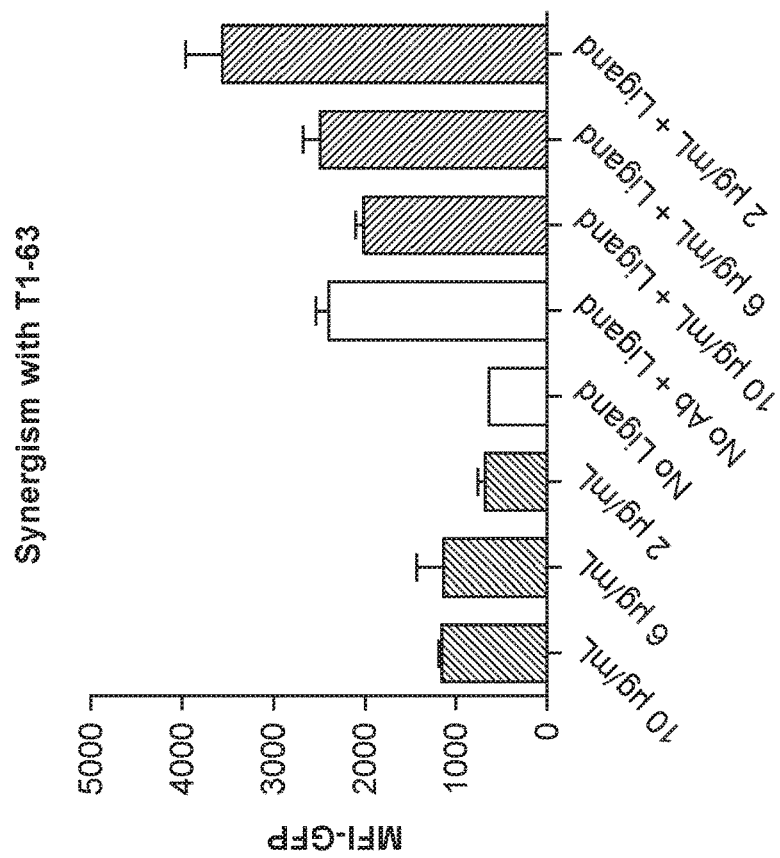
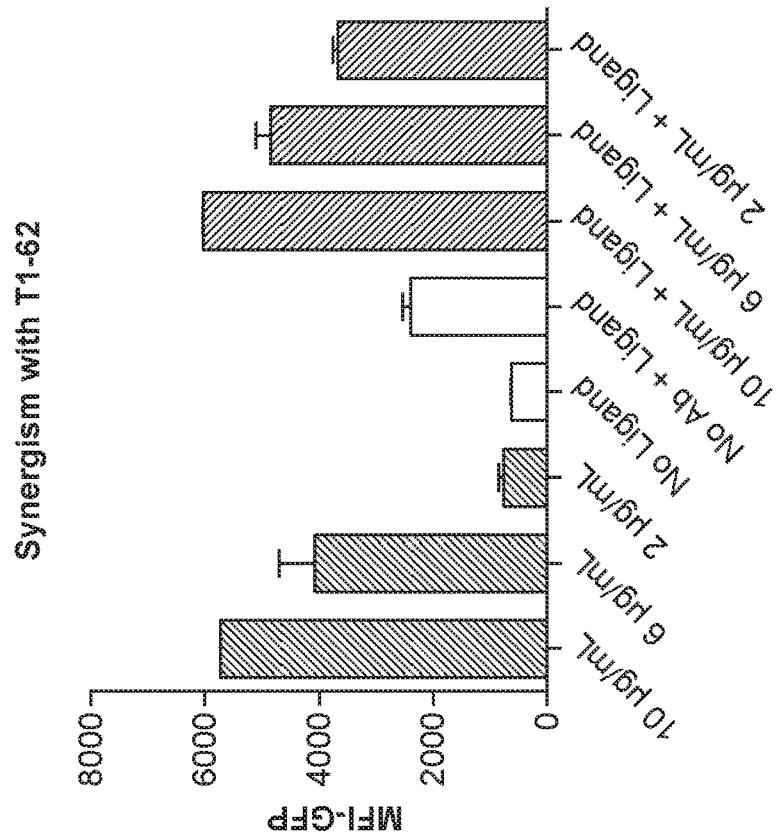
FIG. 9B

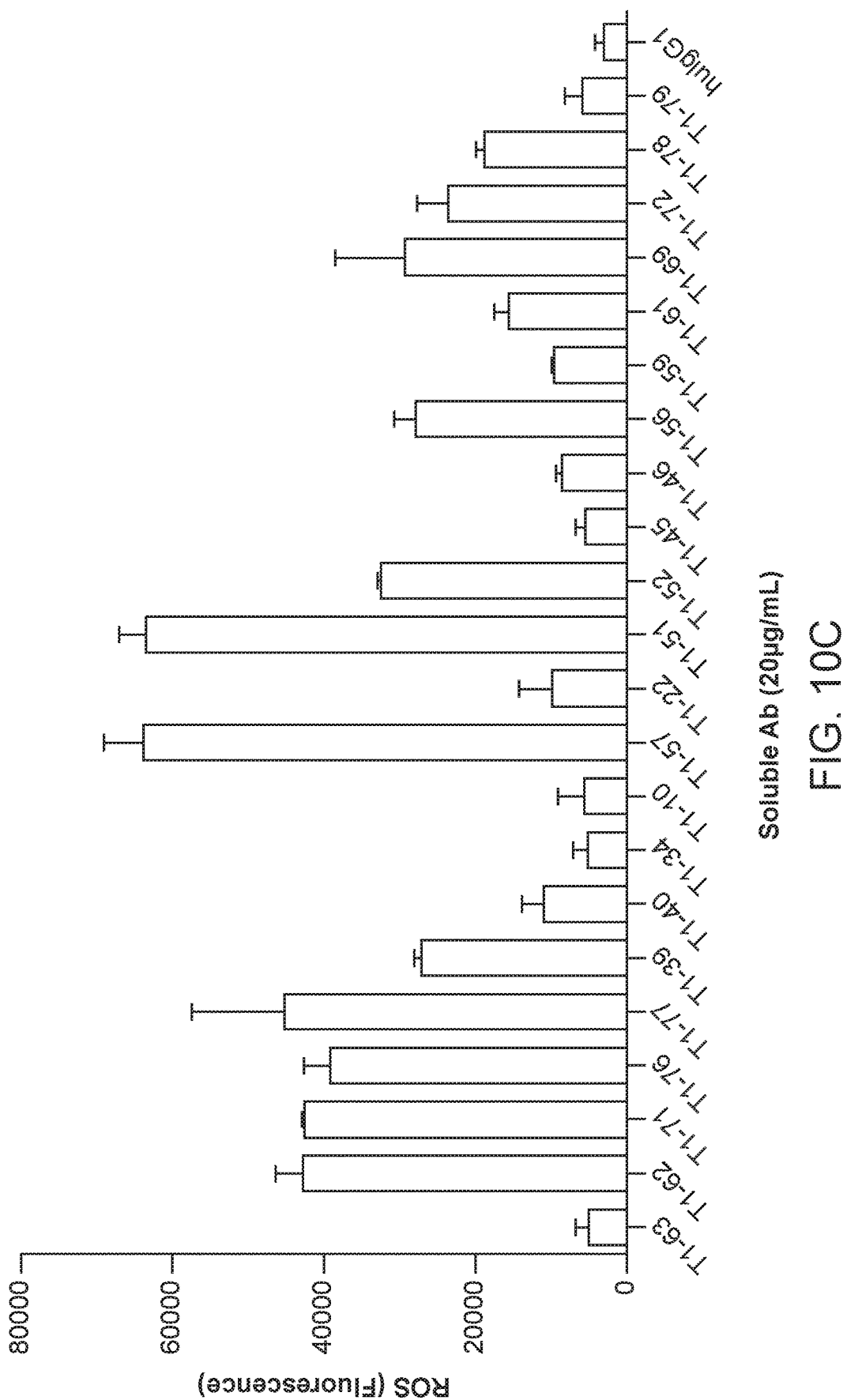

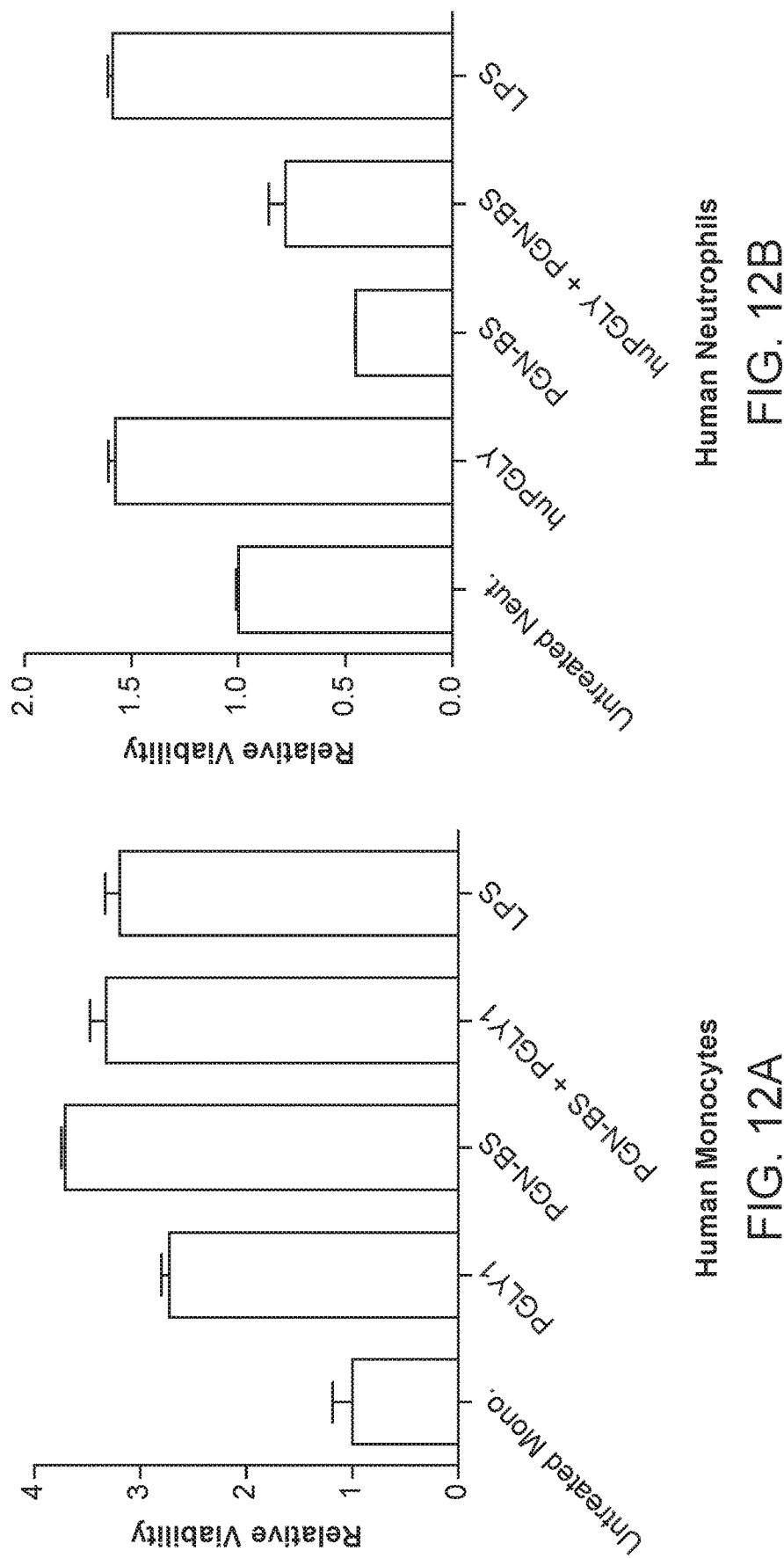

ILLUSTRATIVE ANTAGONIST ANTIBODIES
T1-39 (ADI-19113), T1-34 (ADI-19108), T1-40 (ADI-19114)

```
VH3-21*01   EVQLVESGGGLVKPGGSLRLSCAAS GFTFS--SYSMN WVRQAPGKGLEWVS SISSSSSYIY
ADI-19082   EVQLVESGGGLVKPGGSLRLSCAAS GFTFS--SYSMN WVRQAPGKGLEWVS SISSSSSYIY
ADI-19113   EVQLVESGGGLVKPGGSLRLSCAAS GFTFS--SYSMN WVRQAPGKGLEWVS SISSSSNYIY
ADI-19108   EVQLVESGGGLVKPGGSLRLSCAAS GFTFS--SYSMN WVRQAPGKGLEWVS SISSSSNYIY
ADI-19101   EVQLVESGGGLVKPGGSLRLSCAAS GFTFS--SYSMN WVRQAPGKGLEWVS SISSSSNYIY
ADI-19080   EVQLVESGGGLVKPGGSLRLSCAAS GFTFS--SYSMN WVRQAPGKGLEWVS SISSSSNYIY
ADI-19114   EVQLVESGGGLVKPGGSLRLSCAAS GFTFS--SYSMN WVRQAPGKGLEWVS SISSSSSYIY
                                                                    x
                                                                    x=S,N

VH3-21*01   YADSVKGRFTISRDNAKNSLYLQMNSLRAEDTAVYYCAR
ADI-19082   YADSVKGRFTISRDNAKNSLYLQMNSLRAEDTAVYYCAR RGGSYD------AFQH
ADI-19113   YADSVKGRFTISRDNAKNSLYLQMNSLRAEDTAVYYCAR RGGSST------GLLY
ADI-19108   YADSVKGRFTISRDNAKNSLYLQMNSLRAEDTAVYYCAR RPDDRRG-----LFQH
ADI-19101   YADSVKGRFTISRDNAKNSLYLKAEDTAVYYCAR      GPSQYYDSSAIE-AFDI
ADI-19080   YADSVKGRFTISRDNAKNSLYLQMNSLRAEDTAVYYCAR GRYRRTG-----SLDV
ADI-19114   YADSVKGRFTISRDNAKNSLYLQMNSLRAEDTAVYYCAR TRIDD-------SFDI
```

FIG. 14A

ILLUSTRATIVE LIGAND-ENHANCING ANTIBODIES: T1-63, T1-62
T1-63 (ADI-19139), T1-59 (ADI-19135), T1-60 (ADI-19136), T1-61 (ADI-19137), T1-77 (ADI-19154)

```
VH4-0B*01   QVQLQESGPGLVKPSETLSLTCAVS GYSISS-GYYWG WIRQPPGKGLEWIG SIYHS-GSTY
ADI-19139   QVQLQESGPGLVKPSETLSLTCAVS GYSISS-GYYWG WIRQPPGKGLEWIG SIYHS-GSTY
ADI-19135   QVQLQESGPGLVKPSETLSLTCAVS GYSISS-GYYWA WIRQPPGKGLEWIG SIYHS-GSTY
ADI-19136   QVQLQESGPGLVKPSETLSLTCAVS GYSISS-GYYWA WIRQPPGKGLEWIG SIYHS-GSTY
ADI-19137   QVQLQESGPGLVKPSETLSLTCAVS GYSISS-GYYWG WIRQPPGKGLEWIG SIYHS-GSTY
ADI-19154   QVQLQESGPGLVKPSETLSLTCAVS GYSISS-GYYWA WIRQPPGKGLEWIG SIYHS-GNTY
                                                x                                  x
                                              x=G,A                              x=S,N

VH4-0B*01   YNPSLKSRVTISVDTSKNQFSLKLSSVTAADTAVYYCAR
ADI-19139   YNPSLKSRVTISVDTSKNQFSLKLSSVTAADTAVYYCAR ELYAYSSP----MFYGMDV
ADI-19135   YNPSLKSRVTISVDTSKNQFSLKLSSVTAADTAVYYCAR DLGGYEG-------AFDP
ADI-19136   YNPSLKSRVTISVDTSKNQFSLKLSSVTAADTAVYYCAR DLGGYEG-------AFDP
ADI-19137   YNPSLKSRVTISVDTSKNQFSLKLSSVTAADTAVYYCAR HDDYLS--------SFDP
ADI-19154   YNPSLKSRVTISVDTSKNQFSLKLSSVTAADTAVYYCAR GGPYPWSG------WFDP
                                                                 FDP

T1-62 (ADI-19138)
VH4-31*01   QVQLQESGPGLVKPSQTLSLTCTVS GGSISSGGYYWS WIRQHPGKGLEWIG YIYYS-GSTY
ADI-19098   QVQLQESGPGLVKPSQTLSLTCTVS GGSISSGGYYWS WIRQHPGKGLEWIG YIYYS-GSTY
ADI-19138   QVQLQESGPGLVKPSQTLSLTCTVS GGSISSGGYYWS WIRQHPGKGLEWIG YIYYS-GSTY

VH4-31*01   YNPSLKSLVTISVDTSKNQFSLKLSSVTAADTAVYYCAR
ADI-19098   YNPSLKSRVTISVDTSKNQFSLKLSSVTAADTAVYYCAR DSSIAGRATL----SFDY
ADI-19138   YNPSLKSRVTISVDTSKNQFSLKLSSVTAADTAVYYCAR GPS-----------WIDV
```

FIG. 14B

ILLUSTRATIVE TREM1-ACTIVATING ANTIBODIES (LIGAND-MIMETICS)

```
VH3-09*01    EVQLVESGGGLVQPGRSLRLSCAAS GFTFD--DYAMH WVRQAPGKGLEWVS GISWNSGSIG
ADI-19092    EVQLVESGGGLVQPGRSLRLSCAAS GFTFD--DYAMH WVRQAPGKGLEWVS GISWNSGSIG
ADI-19085    EVQLVESGGGLVQPGRSLRLSCAAS GFTFD--DYAMH WVRQAPGKGLEWVS GISWNSGSIG
ADI-19090    EVQLVESGGGLVQPGRSLRLSCAAS GFTFD--DYAMH WVRQAPGKGLEWVS GISWNSGDIG
ADI-19150    EVQLVESGGGLVQPGRSLRLSCAAS GFTFD--DYAMH WVRQAPGKGLEWVS GITWNSGSIG
ADI-19147    EVQLVESGGGLVQPGRSLRLSCAAS GFTFG--DYAMH WVRQAPGKGLEWVS GITWNSGSIG
ADI-19152    QVQLVESGGGLVQPGRSLRLSCAAS GFTFD--DYAMH WVRQAPGKGLEWVS GISWNSGDIG
ADI-19132    EVQLVESGGGLVQPGRSLRLSCAAS GFTFD--DYAMH WVRQAPGKGLEWVS GITWNSGSIG
ADI-19083    EVQLVESGGGLVQPGRSLRLSCAAS GFTFD--DYAMH WVRQAPGKGLEWVS GISWNSGSIG
ADI-19148    EVQLVESGGGLVQPGRSLRLSCAAS GFTFD--DYAMH WVRQAPGKGLEWVS GISWNSGSIG
ADI-19131    EVQLVESGGGLVQPGRSLRLSCAAS GFTFD--DYAMH WVRQAPGKGLEWVS GISWNSGSIG
ADI-19151    EVQLVESGGGLVQPGRSLRLSCAAS GFTFD--DYAMH WVRQAPGKGLEWVS GISWNSGSIG
ADI-19149    EVQLVESGGGLVQPGRSLRLSCAAS GFTFD--DYAMH WVRQAPGKGLEWVS GISWNSGSIG
                                                                       x         z
                                                                    x=S,T      z=S,D

VH3-09*01    YADSVKGRFTISRDNAKNSLYLQMNSLRAEDTALYYCAK
ADI-19092    YADSVKGRFTISRDNAKNSLYLQMNSLRAEDTALYYCAK GGSRYS-------HFDY
ADI-19085    YADSVKGRFTISRDNAKNTLYLQMNSLRAEDTALYYCAK GPRMVT-------HLDV
ADI-19090    YADSVKGRFTISRDNAKNSLYLQMNSLRAEDTALYYCAK GPRLLS-------ALDV
ADI-19150    YADSVKGRFTISRDNAKNSLYLQMNSLRAEDTALYYCAK GPRLLS-------ALDV
ADI-19147    YADSVKGRFTISRDNAKNSLYLQMNSLRAEDTALYYCAK GPRRTS-------HLDI
ADI-19152    YADSVKGRFTISRDNAKNSLYLQMNSLRAEDTALYYCAK APRTRWT------YFDY
ADI-19132    YADSVKGRFTISRDNAKNSLYLQMNSLRAEDTALYYCAK GPRYSKP------YFDY
ADI-19083    YADSVKGRFTISRDNAKNSLYLQMNSLRAEDTALYYCAK GPRMSG-------WWAD
ADI-19148    YADSVKGRFTISRDNAKNSLYLQMNSLRAEDTALYYCAK GPRMTHS------YFDL
ADI-19131    YADSVKGRFTISRDNAKNSLYLQMNSLRAEDTALYYCAK GPRLLG-------YFDL
ADI-19151    YADSVKGRFTISRDNAKNSLYLQMNSLRAEDTALYYCAK GPRTRG-------YFDL
ADI-19149    YADSVKGRFTISRDNAKNSLYLQMNSLRAEDTALYYCAK APRMYG-------YFDL
                                                    GPR
```

FIG. 14C anti-TREM1 VH Sequences

|  | | CDR-H1 | | CDR-H2 |
|---|---|---|---|---|
| VH5-51*01 | EVQLVQSGAEVKKPGESLKISCKGS | GYSFT---SYWIG | WVRQMPGKGLEWMG | IIYPGDSDTR |
| ADI-19144 | EVQLVQSGAEVKKPGESLKISCKGS | GYSFT---TYWIG | WVRQMPGKGLEWMG | IIYPGDSDTR |
| | | | | |
| VH1-69*01 | QVQLVQSGAEVKKPGSSVKVSCKAS | GGTFS---SYAIS | WVRQAPGQGLEWMG | GIIPIFGTAN |
| ADI-19070 | QVQLVQSGAEVKKPGSSVKVSCKAS | GGTFS---SYAIS | WVRQAPGQGLEWMG | GIIPIFGTAN |
| ADI-19068 | QVQLVQSGAEVKKPGSSVKVSCKAS | GGTFS---SYAIS | WVRQAPGQGLEWMG | GIIPIFGTAN |
| ADI-19129 | QVQLVQSGAEVKKPGSSVKVSCKAS | GGTFS---SYAIS | WVRQAPGQGLEWMG | GIIPIFGTAN |
| ADI-19069 | QVQLVQSGAEVKKPGSSVKVSCKAS | GGTFS---SYAIS | WVRQAPGQGLEWMG | GIIPIFGTAN |
| ADI-19120 | QVQLVQSGAEVKKPGSSVKVSCKAS | GGTFS---NYAIS | WVRQAPGQGLEWMG | GIIPIFGTAN |
| ADI-19126 | QVQLVQSGAEVKKPGSSVKVSCKAS | GGTFS---SYAIS | WVRQAPGQGLEWMG | SIIPIFGTAN |
| ADI-19067 | QVQLVQSGAEVKKPGSSVKVSCKAS | GGTFS---SYAIS | WVRQAPGQGLEWMG | GIIPIFGTAN |
| ADI-19127 | QVQLVQSGAEVKKPGSSVKVSCKAS | GGTFS---SYAIS | WVRQAPGQGLEWMG | SIIPIFGTAN |
| | | x | | x |
| | | x=S,N | | x=S,G |
| | | | | |
| VH1-18*01 | QVQLVQSGAEVKKPGASVKVSCKAS | GYTFT---SYGIS | WVRQAPGQGLEWMG | WISAYNGNTN |
| ADI-19145 | QVQLVQSGAEVKKPGASVKVSCKAS | GYTFT---SYGIS | WVRQAPGQGLEWMG | WISAYNGNTN |
| ADI-19143 | QVQLVQSGAEVKKPGASVKVSCKAS | GYTFT---SYGIH | WVRQAPGQGLEWMG | WISAYNGNTN |
| ADI-19146 | QVQLVQSGAEVKKPGASVKVSCKAS | GYTFT---SYGIH | WVRQAPGQGLEWMG | WISAYNGNTN |
| | | x | | |
| | | x=S,H | | |
| | | | | |
| VH1-02*02 | QVQLVQSGAEVKKPGASVKVSCKAS | GYTFT---GYYMH | WVRQAPGQGLEWMG | WINPNSGGTN |
| ADI-19142 | QVQLVQSGAEVKKPGASVKVSCKAS | GYTFT---GYYMH | WVRQAPGQGLEWMG | WINPNSGGTK |

FIG. 15A

| | | | | | |
|---|---|---|---|---|---|
| VH1-46*01 | QVQLVQSGAEVKKPGASVKVSCKAS | GYTFT---SYYMH | WVRQAPGQGLEWMG | IINPSGGSTS |
| ADI-19097 | QVQLVQSGAEVKKPGASVKVSCKAS | GYTFT---SYY[H] | WVRQAPGQGLEWMG | IINPSGGSTS |
| ADI-19072 | QVQLVQSGAEVKKPGASVKVSCKAS | GYTFT---SYYMH | WVRQAPGQGLEWMG | [V]INPSGGSTS |
| ADI-19121 | QVQLVQSGAEVKKPGASVKVSCKAS | GYTFT---SYYMH | WVRQAPGQGLEWMG | [V]INPSGGSTS |
| ADI-19125 | QVQLVQSGAEVKKPGASVKVSCKAS | GYTFT---SYYMH | WVRQAPGQGLEWMG | IINPSGGSTS |
| ADI-19122 | QVQLVQSGAEVKKPGASVKVSCKAS | GYTFT---SYYMH | WVRQAPGQGLEWMG | IINPSGGSTS |
| ADI-19128 | QVQLVQSGAEVKKPGASVKVSCKAS | GYTFT---SYYMH | WVRQAPGQGLEWMG | IINPSGGSTS |
| ADI-19076 | QVQLVQSGAEVKKPGASVKVSCKAS | GYTFT---SYYMH | WVRQAPGQGLEWMG | IINPSGGSTS |
| ADI-19117 | QVQLVQSGAEVKKPGASVKVSCKAS | GYTFT---SYY[L]H | WVRQAPGQGLEWMG | IINPSGGSTS |
| ADI-19073 | QVQLVQSGAEVKKPGASVKVSCKAS | GYTFT---SYYMH | WVRQAPGQGLEWMG | IINPSGGSTS |
| ADI-19130 | QVQLVQSGAEVKKPGASVKVSCKAS | GYTFT---SYYMH | WVRQAPGQGLEWMG | [V]INPSGGSTS |
| ADI-19071 | QVQLVQSGAEVKKPGASVKVSCKAS | GYTFT---SYYMH | WVRQAPGQGLEWMG | [V]INPSGGSTS |
| ADI-19119 | QVQLVQSGAEVKKPGASVKVSCKAS | GYTFT---SYYMH | WVRQAPGQGLEWMG | [V]INPSGGSTS |
| ADI-19123 | QVQLVQSGAEVKKPGASVKVSCKAS | GYTFT---SYYMH | WVRQAPGQGLEWMG | IINPSGGSTS |
| ADI-19124 | QVQLVQSGAEVKKPGASVKVSCKAS | GYTFT---SYYMH | WVRQAPGQGLEWMG | IINPSGGSTS |
| ADI-19074 | QVQLVQSGAEVKKPGASVKVSCKAS | GYTFT---SYYMH | WVRQAPGQGLEWMG | IINPSGGSTS |
| ADI-19077 | QVQLVQSGAEVKKPGASVKVSCKAS | GYTFT---SYYMH | WVRQAPGQGLEWMG | IINPSGGSTS |
| | | x | | x |
| | | x=M,I | | x=I,V |

| | | | | | |
|---|---|---|---|---|---|
| VH4-0B*01 | QVQLQESGPGLVKPSETLSLTCAVS | GYSISS-GYYWG | WIRQPPGKGLEWIG | SIYHS-GSTY |
| ADI-19139 | QVQLQESGPGLVKPSETLSLTCAVS | GYSISS-GYYWG | WIRQPPGKGLEWIG | SIYHS-GSTY |
| ADI-19135 | QVQLQESGPGLVKPSETLSLTCAVS | GYSISS-GYY[A] | WIRQPPGKGLEWIG | SIYHS-G[N]TY |
| ADI-19136 | QVQLQESGPGLVKPSETLSLTCAVS | GYSISS-GYY[A] | WIRQPPGKGLEWIG | SIYHS-GSTY |
| ADI-19137 | QVQLQESGPGLVKPSETLSLTCAVS | GYSISS-GYYWG | WIRQPPGKGLEWIG | SIYHS-GSTY |
| ADI-19154 | QVQLQESGPGLVKPSETLSLTCAVS | GYSISS-GYYWG | WIRQPPGKGLEWIG | SIYHS-GSTY |
| | | x | | x |
| | | x=G,A | | x=S,N |

FIG. 15B

| | | | | |
|---|---|---|---|---|
| VH4-59*01 | QVQLQESGPGLVKPSETLSLTCTVS | GGSIS--SYYWS | WIRQPPGKGLEWIG | YIYYS-GSTN |
| ADI-19084 | QVQLQESGPGLVKPSETLSLTCTVS | GGSIS--SYYWS | WIRQPPGKGLEWIG | S̲I̲YYS-GSTN |
| ADI-19089 | QVQLQESGPGLVKPSETLSLTCTVS | GGSIS--SYYWS | WIRQPPGKGLEWIG | H̲I̲YYS-GSTN |
| | | | | |
| VH4-31*01 | QVQLQESGPGLVKPSQTLSLTCTVS | GGSISSGGYYWS | WIRQHPGKGLEWIG | YIYYS-GSTY |
| ADI-19098 | QVQLQESGPGLVKPSQTLSLTCTVS | GGSISSGGYYWS | WIRQHPGKGLEWIG | YIYYS-GSTY |
| ADI-19138 | QVQLQESGPGLVKPSQTLSLTCTVS | GGSISSGGYYWS | WIRQHPGKGLEWIG | YIYYS-GSTY |
| | | | | |
| VH4-39*01 | QLQLQESGPGLVKPSETLSLTCTVS | GGSISSSSYYWG | WIRQPPGKGLEWIG | SIYYS-GSTY |
| ADI-19102 | QLQLQESGPGLVKPSETLSLTCTVS | GGSISSSSYYWG | WIRQPPGKGLEWIG | SIYYS-GSTY |
| ADI-19104 | QLQLQESGPGLVKPSETLSLTCTVS | GGSISSSSYYWG | WIRQPPGKGLEWIG | SIYYS-GSTY |
| ADI-19140 | QLQLQESGPGLVKPSETLSLTCTVS | GGSISSSSYYWG | WIRQPPGKGLEWIG | SIS̲YS-GSTY |
| ADI-19105 | QLQLQESGPGLVKPSETLSLTCTVS | GGSISSSSYYWG | WIRQPPGKGLEWIG | SIYYS-GSTY |
| ADI-19103 | QLQLQESGPGLVKPSETLSLTCTVS | GGSISSSSYYWG | WIRQPPGKGLEWIG | SIYYS-GSTY |
| ADI-19156 | QLQLQESGPGLVKPSETLSLTCTVS | GGSISSSSYYWG | WIRQPPGKGLEWIG | SIYYS-GSTY |
| ADI-19079 | QLQLQESGPGLVKPSETLSLTCTVS | GGSISSSSYYWG | WIRQPPGKGLEWIG | SIYYS-GSTY |
| ADI-19141 | QLQLQESGPGLVKPSETLSLTCTVS | GGSISSSSYYWG | WIRQPPGKGLEWIG | SIYYS-GSTY |
| ADI-19155 | QLQLQESGPGLVKPSETLSLTCTVS | GGSISSSD̲YYWG | WIRQPPGKGLEWIG | SIYYS-GSTY |
| ADI-19078 | QLQLQESGPGLVKPSETLSLTCTVS | GGSISSSSYYWG | WIRQPPGKGLEWIG | SIYYS-GSTY |
| ADI-19133 | QLQLQESGPGLVKPSETLSLTCTVS | GGSISSSSYYWG | WIRQPPGKGLEWIG | SIYYS-GSTY |
| | | x | | x |
| | | x=S,D | | x=Y,S |
| | | | | |
| VH3-72*01 | EVQLVESGGGLVQPGGSLRLSCAAS | GFTFS--DHYMD | WVRQAPGKGLEWVG | RTRNKANSYTTE |
| ADI-19086 | EVQLVESGGGLVQPGGSLRLSCAAS | GFTFS--DHI̲MD | WVRQAPGKGLEWVG | RTRNKANSYTTE |
| | | | | |
| VH3-07*01 | EVQLVESGGGLVQPGGSLRLSCAAS | GFTFS--SYWMS | WVRQAPGKGLEWVA | NIKQDGSEKY |
| ADI-19087 | EVQLVESGGGLVQPGGSLRLSCAAS | GFTFS--SYWMS | WVRQAPGKGLEWVA | NIKQDGSEKY |

FIG. 15C

```
VH3-33*01    QVQLVESGGGVVQPGRSLRLSCAAS  GFTFS--SYGMH  WVRQAPGKGLEWVA  VIWYDGSNKY
ADI-19107    QVQLVESGGGVVQPGRSLRLSCAAS  GFTFS--NYGMH  WVRQAPGKGLEWVA  VIWYDGSNKY
ADI-19116    QVQLVESGGGVVQPGRSLRLSCAAS  GFTFS--SYGMH  WVRQAPGKGLEWVA  VIWYDGSNKY
ADI-19159    QVQLVESGGGVVQPGRSLRLSCAAS  GFTFS--SYGMH  WVRQAPGKGLEWVA  VIWYDGSNKG
ADI-19111    QVQLVESGGGVVQPGRSLRLSCAAS  GFTFS--SYGMH  WVRQAPGKGLEWVA  LIWYDGSNKY
                                                    x                           x    z
                                                  x=S,N                      x=V,L  z=Y,G

VH3-30*03    QVQLVESGGGVVQPGRSLRLSCAAS  GFTFS--SYGMH  WVRQAPGKGLEWVA  VISYDGSNKY
ADI-19112    QVQLVESGGGVVQPGRSLRLSCAAS  GITFS--SYGMH  WVRQAPGKGLEWVA  VISYDGSNKY
ADI-19081    QVQLVESGGGVVQPGRSLRLSCAAS  GFTFS--SYGMH  WVRQAPGKGLEWVA  VISYDGSNKY
ADI-19109    QVQLVESGGGVVQPGRSLRLSCAAS  GFTFS--SYGMH  WVRQAPGKGLEWVA  VISYDGSNKY
ADI-19110    QVQLVESGGGVVQPGRSLRLSCAAS  GFTFS--SYGMH  WVRQAPGKGLEWVA  VISYDGSNKY
                                             x
                                           x=F,L

VH3-09*01    EVQLVESGGGLVQPGRSLRLSCAAS  GFTFD---DYAMH  WVRQAPGKGLEWVS  GISWNSGSIG
ADI-19092    EVQLVESGGGLVQPGRSLRLSCAAS  GFTFD---DYAMH  WVRQAPGKGLEWVS  GISWNSGSIG
ADI-19085    EVQLVESGGGLVQPGRSLRLSCAAS  GFTFD---DYAMH  WVRQAPGKGLEWVS  GISWNSGSIG
ADI-19090    EVQLVESGGGLVQPGRSLRLSCAAS  GFTFD---DYAMH  WVRQAPGKGLEWVS  GISWNSGDIG
ADI-19150    EVQLVESGGGLVQPGRSLRLSCAAS  GFTFD---DYAMH  WVRQAPGKGLEWVS  GITWNSGSIG
ADI-19147    EVQLVESGGGLVQPGRSLRLSCAAS  GFTFD---DYAMH  WVRQAPGKGLEWVS  GITWNSGSIG
ADI-19152    QVQLVESGGGLVQPGRSLRLSCAAS  GFTFG---DYAMH  WVRQAPGKGLEWVS  GISWNSGSIG
ADI-19132    EVQLVESGGGLVQPGRSLRLSCAAS  GFTFD---DYAMH  WVRQAPGKGLEWVS  GISWNSGDIG
ADI-19083    EVQLVESGGGLVQPGRSLRLSCAAS  GFTFD---DYAMH  WVRQAPGKGLEWVS  GITWNSGSIG
ADI-19148    EVQLVESGGGLVQPGRSLRLSCAAS  GFTFD---DYAMH  WVRQAPGKGLEWVS  GISWNSGSIG
ADI-19131    EVQLVESGGGLVQPGRSLRLSCAAS  GFTFD---DYAMH  WVRQAPGKGLEWVS  GISWNSGDIG
ADI-19151    EVQLVESGGGLVQPGRSLRLSCAAS  GFTFD---DYAMH  WVRQAPGKGLEWVS  GISWNSGSIG
ADI-19149    EVQLVESGGGLVQPGRSLRLSCAAS  GFTFD---DYAMH  WVRQAPGKGLEWVS  GISWNSGSIG
                                                                         x       z
                                                                      x=S,T   z=S,D
```

FIG. 15D

| | | | | |
|---|---|---|---|---|
| VH3-48*01 | EVQLVESGGGLVQPGGSLRLSCAAS | GFTFS--SYSMN | WVRQAPGKGLEWVS | YISSSSSTIY |
| ADI-19088 | EVQLVESGGGLVQPGGSLRLSCAAS | GFTFS--SYSMN | WVRQAPGKGLEWVS | YISSSSSTIY |
| | | | | |
| VH3-21*01 | EVQLVESGGGLVKPGGSLRLSCAAS | GFTFS--SYSMN | WVRQAPGKGLEWVS | SISSSSSYIY |
| ADI-19082 | EVQLVESGGGLVKPGGSLRLSCAAS | GFTFS--SYSMN | WVRQAPGKGLEWVS | SISSSSSYIY |
| ADI-19113 | EVQLVESGGGLVKPGGSLRLSCAAS | GFTFS--SYSMN | WVRQAPGKGLEWVS | SISSSSNYIY |
| ADI-19108 | EVQLVESGGGLVKPGGSLRLSCAAS | GFTFS--SYSMN | WVRQAPGKGLEWVS | SISSSSSYIY |
| ADI-19101 | EVQLVESGGGLVKPGGSLRLSCAAS | GFTFS--SYSMN | WVRQAPGKGLEWVS | SISSSSNYIY |
| ADI-19080 | EVQLVESGGGLVKPGGSLRLSCAAS | GFTFS--SYSMN | WVRQAPGKGLEWVS | SISSSSNYIY |
| ADI-19114 | EVQLVESGGGLVKPGGSLRLSCAAS | GFTFS--SYSMN | WVRQAPGKGLEWVS | SISSSSSYIY |
| | | | | x |
| | | | | x=S, N |
| | | | | |
| VH3-23*01 | EVQLLESGGGLVQPGGSLRLSCAAS | GFTFS--SYAMS | WVRQAPGKGLEWVS | AISGGGSTY |
| ADI-19115 | EVQLLESGGGLVQPGGSLRLSCAAS | GFTFS--TYAMS | WVRQAPGKGLEWVS | AISGGGSTY |
| ADI-19153 | EVQLLESGGGLVQPGGSLRLSCAAS | GFTFS--SYAMS | WVRQAPGKGLEWVS | AISGGGSTY |
| | | x | | |
| | | x=S, T | | |

FIG. 15E

|  |  | CDR-H3 |  |
|---|---|---|---|
| VH5-51*01 | YSPSFQGQVTISADKSISTAYLQWSSLKASDTAMYYCAR | ------ | ---- WGQGTMVTVSS |
| ADI-19144 | YSPSFQGQVTISADKSISTAYLQWSSLKASDTAMYYCAR | GSPWDGR | LFDI WGQGTMVTVSS |
|  |  |  |  |
| VH1-69*01 | YAQKFQGRVTITADESTSTAYMELSSLRSEDTAVYYCAR | ------ | ---- WGRGTLVTVSS |
| ADI-19070 | YAQKFQGRVTITADESTSTAYMELSSLRSEDTAVYYCAR | HYYYGYA | YFDL WGQGTLVTVSS |
| ADI-19068 | YAQKFQGRVTITADESTSTAYMELSSLRSEDTAVYYCAR | EGGPRGASFN | WFDP WGQGTLVTVSS |
| ADI-19129 | YAQKFQGRVTITADESTSTAYMELSSLRSEDTAVYYCAR | HWYALG | SFDI WGQGTMVTVSS |
| ADI-19069 | YAQKFQGRVTITADESTSTAYMELSSLRSEDTAVYYCAR | DVGSM | YFDI WGQGTMVTVSS |
| ADI-19120 | YAQKFQGRVTITADESTSTAYMELSSLRSEDTAVYYCAR | GRGI | AFDI WGQGTMVTVSS |
| ADI-19126 | YAQKFQGRVTITADESTSTAYMELSSLRSEDTAVYYCAR | SGGYSSSWYGT | GYDY WGQGTLVTVSS |
| ADI-19067 | YAQKFQGRVTITADESTSTAYMELSSLRSEDTAVYYCAR | GQGSDH | YYYGMDV WGQGTLVTVSS |
| ADI-19127 | YAQKFQGRVTITADESTSTAYMELSSLRSEDTAVYYCAR | DRGQYSSSWYG | RMDV WGQGTTVTVSS |
|  |  |  |  |
| VH1-18*01 | YAQKLQGRVTMTTDTSTSTAYMELRSLRSDDTAVYYCAR | ------ | ---- WGQGTTVTVSS |
| ADI-19145 | YAQKLQGRVTMTTDTSTSTAYMELRSLRSDDTAVYYCAR | GAGMYDGSPL | GMDV WGQGTTVTVSS |
| ADI-19143 | YAQKLQGRVTMTTDTSTSTAYMELRSLRSDDTAVYYCAR | GRPSSSWGN | WFDP WGQGTTVTVSS |
| ADI-19146 | YAQKLQGRVTMTTDTSTSTAYMELRSLRSDDTAVYYCAR | AGTIYG | RLDL WGRGTLVTVSS |
|  |  |  |  |
| VH1-02*02 | YAQKFQGRVTMTRDTSISTAYMELSRLRSDDTAVYYCAR | ------ | ---- WGQGTLVTVSS |
| ADI-19142 | YAQKFQGRVTMTRDTSISTAYMELSRLRSDDTAVYYCAR | ERHSSL | GYAY WGQGTLVTVSS |

```
VH1-46*01    YAQKFQGRVTMTRDTSTSTVYMELSSLRSEDTAVYYCAR
ADI-19097    YAQKFQGRVTMTRDTSTSTVYMELSSLRSEDTAVYYCAR DSAQET------YYYGMDV  WGQGTTVTVSS
ADI-19072    YAQKFQGRVTMTRDTSTSTVYMELSSLRSEDTAVYYCAR ESGHSYVS-------SFDP  WGQGTLVTVSS
ADI-19121    YAQKFQGRVTMTRDTSTSTVYMELSSLRSEDTAVYYCAR EAGQTSS--------ALDV  WGQGTMVTVSS
ADI-19125    YAQKFQGRVTMTRDTSTSTVYMELSSLRSEDTAVYYCAR EAGTMSS--------AFDI  WGQGTMVTVSS
ADI-19122    YAQKFQGRVTMTRDTSTSTVYMELSSLRSEDTAVYYCAR EAGSWL-------ISTAFDI WGQGTMVTVSS
ADI-19128    YAQKFQGRVTMTRDTSTSTVYMELSSLRSEDTAVYYCAR ESGYH--------VSTAFDI WGQGTMVTVSS
ADI-19076    YAQKFQGRVTMTRDTSTSTVYMELSSLRSEDTAVYYCAR EAGYD--------ISSAFDI WGQGTMVTVSS
ADI-19117    YAQKFQGRVTMTRDTSTSTVYMELSSLRSEDTAVYYCAR EAGNYID------IESAFDI WGQGTMVTVSS
                                                     ExG          AFDI
                                                     x=A,G

ADI-19073    YAQKFQGRVTMTRDTSTSTVYMELSSLRSEDTAVYYCAR GLI----------YGDAFDY WGQGTLVTVSS
ADI-19130    YAQKFQGRVTMTRDTSTSTVYMELSSLRSEDTAVYYCAR GAD----------YYAGFDY WGQGTLVTVSS
ADI-19071    YAQKFQGRVTMTRDTSTSTVYMELSSLRSEDTAVYYCAR ESDG---------IDSYFDY WGQGTMVTVSS
ADI-19119    YAQKFQGRVTMTRDTSTSTVYMELSSLRSEDTAVYYCAR EGSG---------YDESMDV WGQGTTVTVSS
ADI-19123    YAQKFQGRVTMTRDTSTSTVYMELSSLRSEDTAVYYCAR EGSG---------YDESMDV WGQGTTVTVSS
ADI-19124    YAQKFQGRVTMTRDTSTSTVYMELSSLRSEDTAVYYCAR EGSG---------YDESMDV WGQGTMVTVSS
ADI-19074    YAQKFQGRVTMTRDTSTSTVYMELSSLRSEDTAVYYCAR EVSM---------TAASLDV WGQGTMVTVSS
ADI-19077    YAQKFQGRVTMTRDTSTSTVYMELSSLRSEDTAVYYCAR EGSG---------SWETLDV WGQGTMVTVSS
                                                     ExSG
                                                     x=G,V

VH4-0B*01    YNPSLKSRVTISVDTSKNQFSLKLSSVTAADTAVYYCAR
ADI-19139    YNPSLKSRVTISVDTSKNQFSLKLSSVTAADTAVYYCAR ELYAYSSP-----MFYGMDV WGRGTTVTVSS
ADI-19135    YNPSLKSRVTISVDTSKNQFSLKLSSVTAADTAVYYCAR DLGGYEG--------AFDP  WGQGTLVTVSS
ADI-19136    YNPSLKSRVTISVDTSKNQFSLKLSSVTAADTAVYYCAR DLGGYEG--------AFDP  WGQGTLVTVSS
ADI-19137    YNPSLKSRVTISVDTSKNQFSLKLSSVTAADTAVYYCAR HDDYLS---------SFDP  WGQGTLVTVSS
ADI-19154    YNPSLKSRVTISVDTSKNQFSLKLSSVTAADTAVYYCAR GGPYPWSG-------WFDP  WGQGTLVTVSS
                                                                    FDP
```

| | | | |
|---|---|---|---|
| VH4-59*01 | YNPSLKSRVTISVDTSKNQFSLKLSSVTAADTAVYYCAR | GAPGGRHN------WFDP | WGQGTLVTVSS |
| ADI-19084 | YNPSLKSRVTISVDTSKNQFSLKLSSVTAADTAVYYCAR | ------- | WGRGTLVTVSS |
| ADI-19089 | YNPSLKSRVTISVDTSKNQFSLKLSSVTAADTAVYYCAR | DAGRYGSSSSW—YFDL | WGRGTLVTVSS |
| | | | |
| VH4-31*01 | YNPSLKSLVTISVDTSKNQFSLKLSSVTAADTAVYYCAR | DSSIAGRATL-----SFDY | WGQGTLVTVSS |
| ADI-19098 | YNPSLKSRVTISVDTSKNQFSLKLSSVTAADTAVYYCAR | GPS----------WIDV | WGQGTMVTVSS |
| ADI-19138 | YNPSLKSRVTISVDTSKNQFSLKLSSVTAADTAVYYCAR | | |
| | | | |
| VH4-39*01 | YNPSLKSRVTISVDTSKNQFSLKLSSVTAADTAVYYCAR | DGGGTAQADGAYYYGMDV | WGQGTTVTVSS |
| ADI-19102 | YNPSLKSRVTISVDTSKNQFSLKLSSVTAADTAVYYCAR | DRRMWDP-------YGMDV | WGQGTTVTVSS |
| ADI-19104 | YNPSLKSRVTISVDTSKNQFSLKLSSVTAADTAVYYCAR | YYSP---------YGMDV | WGQGTTVTVSS |
| ADI-19140 | YNPSLKSRVTISVDTSKNQFSLKLSSVTAADTAVYYCAR | DAPAVVGESP-----AFDI | WGQGTMVTVSS |
| ADI-19105 | YNPSLKSRVTISVDTSKNQFSLKLSSVTAADTAVYYCAR | GRKAAAGIDEAE—YFQH | WGQGTLVTVSS |
| ADI-19103 | YNPSLKSRVTISVDTSKNQFSLKLSSVTAADTAVYYCAR | LGDGYRI--------WADY | WGQGTLVTVSS |
| ADI-19156 | YNPSLKSRVTISVDTSKNQFSLKLSSVTAADTAVYYCAR | GGGYPWE---------AFDY | WGKGTTVTVSS |
| ADI-19079 | YNPSLKSRVTISVDTSKNQFSLKLSSVTAADTAVYYCAR | DSGQYTG---------SLDV | WGQGTMVTVSS |
| ADI-19141 | YNPSLKSRVTISVDTSKNQFSLKLSSVTAADTAVYYCAR | DLGQYEG---------YFDL | WGRGTLVTVSS |
| ADI-19155 | YNPSLKSRVTISVDTSKNQFSLKLSSVTAADTAVYYCAR | SGEY-----------GFDL | WGRGTLVTVSS |
| ADI-19078 | YNPSLKSRVTISVDTSKNQFSLKLSSVTAADTAVYYCAR | QEYGDG----------YFDL | WGRGTLVTVSS |
| ADI-19133 | | | |
| | | | |
| VH3-72*01 | YAASVKGRFTISRDDSKNSLYLQMNSLKTEDTAVYYCAR | | |
| ADI-19086 | YAASVKGRFTISRDDSKNSLYLQMNSLKTEDTAVYYCAR | GPL-------------GYKL | WGQGTLVTVSS |
| | | | |
| VH3-07*01 | YVDSVKGRFTISRDNAKNSLYLQMNSLRAEDTAVYYCAR | | |
| ADI-19087 | YVDSVKGRFTISRDNAKNSLYLQMNSLRAEDTAVYYCAR | DAPQL-----------GLDV | WGQGTMVTVSS |

FIG. 15H

```
VH3-33*01    YADSVKGRFTISRDNSKNTLYLQMNSLRAEDTAVYYCAR
ADI-19107    YADSVKGRFTISRDNSKNTLYLQMNSLRAEDTAVYYCAR GSTHRGSA------YGMDV WGQGTTVTVSS
ADI-19116    YADSVKGRFTISRDNSKNTLYLQMNSLRAEDTAVYYCAR ELMVTSGGWL----YGMDV WGQGTTVTVSS
ADI-19159    YADSVKGRFTISRDNSKNTLYLQMNSLRAEDTAVYYCAR ELIVGATGGLTYYGMDV   WGQGTTVTVSS
ADI-19111    YADSVKGRFTISRDNSKNTLYLQMNSLRAEDTAVYYCAR GDYLDP--------LFDY  WGQGTLVTVSS

VH3-30*03    YADSVKGRFTISRDNSKNTLYLQMNSLRAEDTAVYYCAR
ADI-19112    YADSVKGRFTISRDNSKNTLYLQMNSLRAEDTAVYYCAR ERGTYYYAS-----GWAN  WGQGTLVTVSS
ADI-19081    YADSVKGRFTISRDNSKNTLYLQMNSLRAEDTAVYYCAR RSSGD---------YLDV  WGQGTMVTVSS
ADI-19109    YADSVKGRFTISRDNSKNTLYLQMNSLRAEDTAVYYCAR PDYYSSRG------VFDI  WGQGTMVTVSS
ADI-19110    YADSVKGRFTISRDNSKNTLYLQMNSLRAEDTAVYYCAR PDYYSSRG------VFDI  WGQGTMVTVSS

VH3-09*01    YADSVKGRFTISRDNAKNSLYLQMNSLRAEDTALYYCAK
ADI-19092    YADSVKGRFTISRDNAKNSLYLQMNSLRAEDTALYYCAK GGSRYS--------HFDY  WGQGTLVTVSS
ADI-19085    YADSVKGRFTISRDNAKNTLYLQMNSLRAEDTALYYCAK GPRMVT--------HLDV  WGQGTLVTVSS
ADI-19090    YADSVKGRFTISRDNAKNSLYLQMNSLRAEDTALYYCAK GPRLLS--------ALDV  WGQGTMVTVSS
ADI-19150    YADSVKGRFTISRDNAKNSLYLQMNSLRAEDTALYYCAK GPRLLS--------ALDV  WGQGTMVTVSS
ADI-19147    YADSVKGRFTISRDNAKNSLYLQMNSLRAEDTALYYCAK GPRRTS--------HLDI  WGQGTMVTVSS
ADI-19152    YADSVKGRFTISRDNAKNSLYLQMNSLRAEDTALYYCAK APRTRWT-------YFDY  WGQGTLVTVSS
ADI-19132    YADSVKGRFTISRDNAKNSLYLQMNSLRAEDTALYYCAK GPRYSKP-------YFDY  WGQGTLVTVSS
ADI-19083    YADSVKGRFTISRDNAKNSLYLQMNSLRAEDTALYYCAK GPRMSG--------WWAD  WGQGTLVTVSS
ADI-19148    YADSVKGRFTISRDNAKNSLYLQMNSLRAEDTALYYCAK GPRMTHS-------YFDL  WGRGTLVTVSS
ADI-19131    YADSVKGRFTISRDNAKNSLYLQMNSLRAEDTALYYCAK GPRLLG--------YFDL  WGRGTLVTVSS
ADI-19151    YADSVKGRFTISRDNAKNSLYLQMNSLRAEDTALYYCAK GPRTRG--------YFDL  WGRGTLVTVSS
ADI-19149    YADSVKGRFTISRDNAKNSLYLQMNSLRAEDTALYYCAK APRMYG--------YFDL  WGRGTSVTVSS
                                                GPR
```

FIG. 15I

| | | | |
|---|---|---|---|
| VH3-48*01 | YADSVKGRFTISRDNAKNSLYLQMNSLRAEDTAVYYCAR | | |
| ADI-19088 | YADSVKGRFTISRDNAKNSLYLQMNSLRAEDTAVYYCAR | GGPLGYGDYK----GMDV | WGQGTTVTVSS |
| | | | |
| VH3-21*01 | YADSVKGRFTISRDNAKNSLYLQMNSLRAEDTAVYYCAR | | |
| ADI-19082 | YADSVKGRFTISRDNAKNSLYLQMNSLRAEDTAVYYCAR | RGGSYD---------AFQH | WGQGTLVTVSS |
| ADI-19113 | YADSVKGRFTISRDNAKNSLYLQMNSLRAEDTAVYYCAR | RGGSSST--------GLLY | WGQGTLVTVSS |
| ADI-19108 | YADSVKGRFTISRDNAKNSLYLQMNSLRAEDTAVYYCAR | RPDDRRG--------LFQH | WGQGTLVTVSS |
| ADI-19101 | YADSVKGRFTISRDNAKNSLYLQMNSLRAEDTAVYYCAR | GPSQYYDSSAIE--AFDI | WGQGTMVTVSS |
| ADI-19080 | YADSVKGRFTISRDNAKNSLYLQMNSLRAEDTAVYYCAR | GRYRRTG--------SLDV | WGQGTMVTVSS |
| ADI-19114 | YADSVKGRFTISRDNAKNSLYLQMNSLRAEDTAVYYCAR | TRIDD----------SFDI | WGQGTMVTVSS |
| | | | |
| VH3-23*01 | YADSVKGRFTISRDNSKNTLYLQMNSLRAEDTAVYYCAK | | |
| ADI-19115 | YADSVKGRFTISRDNSKNTLYLQMNSLRAEDTAVYYCAK | SKHSTT---------SLDV | WGQGTMVTVSS |
| ADI-19153 | YADSVKGRFTISRDNSKNTLYLQMNSLRAEDTAVYYCAK | ARRGALA--------GMDV | WGQGTTVTVSS |

FIG. 15J anti-TREM1 VL

```
                                              CDR-L1                              CDR-L2
VK2-28*01    DIVMTQSPLSLPVTPGEPASISC RSSQSLL-HSNGYNYLD WYLQKPGQSPQLLIY LGSNRAS
ADI-19131    DIVMTQSPLSLPVTPGEPASISC RSSQSLL-HSNGYNYLD WYLQKPGQSPQLLIY LGSNRAS
ADI-19121    DIVMTQSPLSLPVTPGEPASISC RSSQSLL-HSNGYNYLD WYLQKPGQSPQLLIY LGS[H]RAS
ADI-19123    DIVMTQSPLSLPVTPGEPASISC RSSQSLL-HSNGYNYLD WYLQKPGQSPQLLIY LGSNRAS
ADI-19071    DIVMTQSPLSLPVTPGEPASISC RSSQSLL-HSNGYNYLD WYLQKPGQSPQLLIY LGSNRAS
ADI-19074    DIVMTQSPLSLPVTPGEPASISC RSSQSLL-HSNGYNYLD WYLQKPGQSPQLLIY LGSNRAS
ADI-19122    DIVMTQSPLSLPVTPGEPASISC RSSQSLL-HSNGYNYLD WYLQKPGQSPQLLIY LGSNRAS
ADI-19117    DIVMTQSPLSLPVTPGEPASISC RSSQSLL-HSNGYNYLD WYLQKPGQSPQLLIY LGSNRAS
ADI-19128    DIVMTQSPLSLPVTPGEPASISC RSSQSLL-HSNGYNYLD WYLQKPGQSPQLLIY LGSNRAS
ADI-19072    DIVMTQSPLSLPVTPGEPASISC RSSQSLL-HSNGYNYLD WYLQKPGQSPQLLIY LGSNRAS
ADI-19076    DIVMTQSPLSLPVTPGEPASISC RSSQSLL-HSNGYNYLD WYLQKPGQSPQLLIY LGSNRAS
ADI-19125    DIVMTQSPLSLPVTPGEPASISC RSSQSLL-HSNGYNYLD WYLQKPGQSPQLLIY LGSNRAS
ADI-19077    DIVMTQSPLSLPVTPGEPASISC RSSQSLL-HSNGYNYLD WYLQKPGQSPQLLIY LGSNRAS
ADI-19124    DIVMTQSPLSLPVTPGEPASISC RSSQSLL-H[R]NGYNYLD WYLQKPGQSPQLLIY LGSNRAS
ADI-19148    DIVMTQSPLSLPVTPGEPASISC RSSQSLL-HSNGYNYLD WYLQKPGQSPQLLIY LGSNRAS
ADI-19130    DIVMTQSPLSLPVTPGEPASISC RSSQSLL-HSNGYNYLD WYLQKPGQSPQLLI[E] LGSNRAS
ADI-19078    DIVMTQSPLSLPVTPGEPASISC RSSQSLL-HSNGYNYLD WYLQKPGQSPQLLIY LGSNRAS
ADI-19119    DIVMTQSPLSLPVTPGEPASISC RSSQSLL-HSNGYNYLD WYLQKPGQSPQ[V]LIY LGSNRAS
                                              x                                    x
                                              x=S,R                                x=N,H

VK1-33*01    DIQMTQSPSSLSASVGDRVTITC QASQDIS------NYLN WYQQKPGKAPKLLIY DASNLET
ADI-19067    DIQMTQSPSSLSASVGDRVTITC QASQDIS------NYLN WYQQKPGKAPKLLIY DASNLET
ADI-19084    DIQMTQSPSSLSASVGDRVTITC QASQDIS------NYLN WYQQKPGKAPKLLIY DASNL[A]T
ADI-19104    DIQMTQSPSSLSASVGDRVTITC QASQDIS------NYLN WYQQKPGKAPKLLIY DASNLET
                                                                                   x
                                                                                   x=E,A
```

FIG. 16A

| | | | | |
|---|---|---|---|---|
| VK1-05*01 | DIQMTQSPSTLSASVGDRVTITC | RASQSIS-----SWLA | WYQQKPGKAPKLLIY | DASSLES |
| ADI-19108 | DIQMTQSPSTLSASVGDRVTITC | RASQSIN-----SWLA | WYQQKPGKAPKLLIY | DASSLES |
| ADI-19153 | DIQMTQSPSTLSASVGDRVTITC | RASQSIS-----SWLA | WYQQKPGKAPKLLIS | DASSLES |
| | | x<br>x=S,N | x<br>x=Y,S | |
| VK1-05*03 | DIQMTQSPSTLSASVGDRVTITC | RASQSIS-----SWLA | WYQQKPGKAPKLLIY | KASSLES |
| ADI-19087 | DIQMTQSPSTLSASVGDRVTITC | RASQSIS-----SWLA | WYQQKPGKAPKLLIY | KASSLES |
| ADI-19127 | DIQMTQSPSTLSASVGDRVTITC | RASQSIS-----SWLA | WYQQKPGKAPKLLIY | KASSLES |
| ADI-19149 | DIQMTQSPSTLSASVGDRVTITC | RASQSIS-----SWLA | WYQQKPGKAPKLLIY | KASSLES |
| ADI-19090 | DIQMTQSPSTLSASVGDRVTITC | RASQSIG-----SWLA | WYQQKPGKAPKLLIY | KASSLES |
| ADI-19151 | DIQMTQSPSTLSASVGDRVTITC | RASQSIS-----SWLA | WYQQKPGKAPKLLIY | KASSLES |
| ADI-19085 | DIQMTQSPSTLSASVGDRVTITC | RASQSIS-----SWLA | WYQQKPGKAPKLLIY | KASSLES |
| ADI-19150 | DIQMTQSPSTLSASVGDRVTITC | RASQSIS-----SWLA | WYQQKPGKAPKLLIY | KASSLES |
| ADI-19126 | DIQMTQSPSTLSASVGDRVTITC | RASQSIS-----SWLA | WYQQKPGKAPKLLIY | KASSLES |
| | | x<br>x=S,G | | |
| VK1-12*01 | DIQMTQSPSSVSASVGDRVTITC | RASQGIS-----SWLA | WYQQKPGKAPKLLIY | AASSLQS |
| ADI-19115 | DIQTQSPSSVSASVGDRVTITC | RASQDIS-----SWLA | WYQQKPGKAPKLLIY | AASSLQS |
| ADI-19146 | DIQLQSPSSVSASVGDRVTITC | RASQDIS-----SWLA | WYQQKPGKAPKLLIY | AASSLQS |
| ADI-19113 | DIQLTQSPSSVSASVGDRVTITC | RASQDIS-----SWLA | WYQQKPGKAPKLLIY | AASSLQS |
| ADI-19103 | DIQMTQSPSSVSASVGDRVTITC | RASQGIS-----SWLA | WYQQKPGKAPKLLIY | AASSLQS |
| ADI-19132 | DIQMTQSPSSVSASVGDRVTITC | RASQGID-----SWLA | WYQQKPGKAPKLLIY | AASSLQS |
| ADI-19107 | DIQMTQSPSSVSASVGDRVTITC | RASQGIS-----SWLA | WYQQKPGKAPKLLIY | AASSLQS |
| ADI-19083 | DIQMTQSPSSVSASVGDRVTITC | RASQGIS-----SWLA | WYQQKPGKAPKLLIY | AASSLQS |
| ADI-19147 | DIQMTQSPSSVSASVGDRVTITC | RASQGID-----SWLA | WYQQKPGKAPKLLIY | AASSLQS |
| ADI-19086 | DIQMTQSPSSVSASVGDRVTITC | RASQGIS-----SWLA | WYQQKPGKAPKLLIY | AASNLQS |
| ADI-19145 | DIQMTQSPSSVSASVGDRVTITC | RASQGIS-----SWLA | WYQQKPGKAPKLLIY | AASNLQS |
| | | x  z<br>x=G,D  z=S,D | | x<br>x=S,N |

FIG. 16B

| VK1-39*01 | DIQMTQSPSSLSASVGDRVTITC | RASQSIS------SYLN | WYQQKPGKAPKLLIY | AASSLQS |
|---|---|---|---|---|
| ADI-19088 | DIQ[L]TQSPSSLSASVGDRVTITC | RASQSIS------S[E]LN | WYQQKPGKAPKLLIY | AASSLQS |
| ADI-19139 | DIQMTQSPSSLSASVGDRVTITC | RASQSIS------[R]YLN | WYQQKPGKAPKLLIY | AASSLQS |
| ADI-19105 | DIQMTQSPSSLSASVGDRVTITC | RASQSIS------[R]YLN | WYQQKPGKAPKLLIY | AASSLQS |
| ADI-19097 | DIQMTQSPSSLSASVGDRVTITC | RASQSIS------SYLN | WYQQKPGKAPKLLIY | AASSLQS |
| ADI-19098 | DIQMTQSPSSLSASVGDRVTITC | RASQSIS------SYLN | WYQQKPGKAPKLLIY | AASSLQS | xz
x=S, R  z=Y, F

| VK4-01*01 | DIVMTQSPDSLAVSLGERATINC | KSSQSVLYSSNNKNYLA | WYQQKPGQPPKLLIY | WASTRES |
|---|---|---|---|---|
| ADI-19133 | DIVMTQSPDSLAVSLGERATINC | KSSQSVL[F]SSNNKNYLA | WYQQKPGQPPKLLIY | WASTRES |
| ADI-19137 | DIVMTQSPDSLAVSLGERATINC | KSSQSVL[F]SSNNKNYLA | WYQQKPGQPPKLLIY | WASTRES |
| ADI-19081 | DIVMTQSPDSLAVSLGERATINC | KSSQSVLYSSNNKNYLA | WYQQKPGQPPKLLIY | WASTRES |
| ADI-19156 | DIVMTQSPDSLAVSLGERATINC | KSSQSVLYSSNNKNYLA | WYQQKPGQPPKLLIY | WASTRES |
| ADI-19141 | DIVMTQSPDSLAVSLGERATINC | KSSQSVLYSSNNKNYLA | WYQQKPGQPPKLLIY | WASTRES |
| ADI-19069 | DIVMTQSPDSLAVSLGERATINC | KSSQSVLYSSNNKNYLA | WYQQKPGQPPKLLIY | WASTRES |
| ADI-19109 | DIVMTQSPDSLAVSLGERATINC | KSSQSVLYSSNNKNYLA | WYQQKPGQPPKLLIY | WASTRES |
| ADI-19140 | DIVMTQSPDSLAVSLGERATINC | KSSQSVL[F]SSNNKNYLA | WYQQKPGQPPKLLIY | WASTRES |
| ADI-19136 | DIVMTQSPDSLAVSLGERATINC | KSSQSVL[F]SSNNKNYLA | WYQQKPGQPPKLLIY | WASTRES |
| ADI-19120 | DIVMTQSPDSLAVSLGERATINC | KSSQSVL[F]SSNNKNYLA | WYQQKPGQPPKLLIY | WASTRES |
| ADI-19114 | DIVMTQSPDSLAVSLGERATINC | KSSQSVLYSSNNKNYLA | WYQQKPGQPPKLLIY | WASTRES |
| ADI-19112 | DIVMTQSPDSLAVSLGERATINC | KSSQSVLYSSNNKNYLA | WYQQKPGQPPKLLIY | WASTRES |
| ADI-19073 | DIVMTQSPDSLAVSLGERATINC | KSSQSVLYSSNNKNYLA | WYQQKPGQPPKLLIY | WASTRES |
| ADI-19110 | DIVMTQSPDSLAVSLGERATINC | KSSQSVLYSSNNKNYLA | WYQQKPGQPPKLLIY | WASTRES |
| ADI-19135 | DIVMTQSPDSLAVSLGERATINC | KSSQSVLYSSNNKNYLA | WYQQKPGQPPKLLIY | WASTRES |
| ADI-19142 | DIVMTQSPDSLAVSLGERATINC | KSSQSVL[F]SSNNKNYLA | WYQQKPGQPPKLLIY | WASTRES |
| ADI-19155 | DIVMTQSPDSLAVSLGERATINC | KSSQSVLYSSNNKNYLA | WYQQKPGQPPKLLIY | WASTRES | x
x=Y, F

FIG. 16C

| | | | | |
|---|---|---|---|---|
| VK3-20*01 | EIVLTQSPGTLSLSPGERATLSC | RASQSVS------ | -SSYLA | WYQQKPGQAPRLLIY GASSRAT |
| ADI-19138 | EIVLTQSPGTLSLSPGERATLSC | RASQSVS------ | -SSYLA | WYQQKPGQAPRLLIY GASSRAT |
| ADI-19068 | EIVLTQSPGTLSLSPGERATLSC | RASQSVS------ | -SSYLA | WYQQKPGQAPRLLIY GASSRAT |
| ADI-19089 | EIVLTQSPGTLSLSPGERATLSC | RASQSVS------ | -SSYLA | WYQQKPGQAPRLLIY GASSRAT |
| ADI-19082 | EIVLTQSPGTLSLSPGERATLSC | RASQSVS------ | -SSYLA | WYQQKPGQAPRLLIY GASSRAT |
| ADI-19080 | EIVLTQSPGTLSLSPGERATLSC | RASQSVS------ | -SSFLA | WYQQKPGQAPRLLIY GASSRAT |
| ADI-19143 | EIVLTQSPGTLSLSPGERATLSC | RASQSVS------ | -SSFLA | WYQQKPGQAPRLLIY GASSRAT | x
x=Y,F

| | | | | |
|---|---|---|---|---|
| VK3-15*01 | EIVMTQSPATLSVSPGERATLSC | RASQSVS------ | -SNLA | WYQQKPGQAPRLLIY GASTRAT |
| ADI-19116 | EIVMTQSPATLSVSPGERATLSC | RASQSVS------ | -SNLA | WYQQKPGQAPRLLIY GASTRAT |
| ADI-19159 | EIVMTQSPATLSVSPGERATLSC | RASQSVG------ | -SNLA | WYQQKPGQAPRLLIY GASTRAT |
| ADI-19154 | EIVMTQSPATLSVSPGERATLSC | RASQSVS------ | -SNLA | WYQQKPGQAPRLLIY GASTRAT |
| ADI-19070 | EIVMTQSPATLSVSPGERATLSC | RASQSVG------ | -SNLA | WYQQKPGQAPRLLIY GASTRAT |
| ADI-19101 | EILTQSPATLSVSPGERATLSC | RASQSVG------ | -SNLA | WYQQKPGQAPRLLIY GASTRAT |
| ADI-19111 | EIVMTQSPATLSVSPGERATLSC | RASQSVS------ | -SNLA | WYQQKPGQAPRLLIY GASTRAT | x
x=S,G

| | | | | |
|---|---|---|---|---|
| VK3-11*01 | EIVLTQSPATLSLSPGERATLSC | RASQSVS------ | --SYLA | WYQQKPGQAPRLLIY DASNRAT |
| ADI-19152 | EIVLTQSPATLSLSPGERATLSC | RASQSVS------ | --SYLA | WYQQKPGQAPRLLIY DASNRAT |
| ADI-19129 | EIVMTQSPATLSLSPGERATLSC | RASQSVS------ | --SYLA | WYQQKPGQAPRLLIY DSSNRAT |
| ADI-19079 | EIVLTQSPATLSLSPGERATLSC | RASQSVS------ | --SYLA | WYQQKPGQAPRLLIY DASNRAT |
| ADI-19092 | EIVLTQSPATLSLSPGERATLSC | RASQSVS------ | --SYLA | WYQQKPGQAPRLLIY DASNRAT |
| ADI-19102 | EIVLTQSPATLSLSPGERATLSC | RASQSVS------ | --SYLA | WYQQKPGQAPRLLIY DASNRAT |
| ADI-19144 | EIVLTQSPATLSLSPGERATLSC | RASQSVS------ | --SYLA | WYQQKPGQAPRLLIY DASNRAT | x
x=A,S

FIG. 16D

| | | | CDR-L3 | |
|---|---|---|---|---|
| VK2-28*01 | GVPDRFSGSGSGTDFTLKISRVEAEDVGVYYC | MQALQTPP | | |
| ADI-19131 | GVPDRFSGSGSGTDFTLKISRVEAEDVGVYYC | MQDFARPP | -T | FGGGTKVEIK |
| ADI-19121 | GVPDRFSGSGSGTDFTLKISRVEAEDVGVYYC | MQGRQVPF | -T | FGGGTKVEIK |
| ADI-19123 | GVPDRFSGSGSGTDFTLKISRVEAEDVGVYYC | MQAREVPF | -T | FGGGTKVEIK |
| ADI-19071 | GVPDRFSGSGSGTDFTLKISRVEAEDVGVYYC | MQARQTPL | -T | FGGGTKVEIK |
| ADI-19074 | GVPDRFSGSGSGTDFTLKISRVEAEDVGVYYC | VQARQTPL | -T | FGGGTKVEIK |
| ADI-19122 | GVPDRFSGSGSGTDFTLKISRVEAEDVGVYYC | MQARQTPF | -T | FGGGTKVEIK |
| ADI-19117 | GVPDRFSGSGSGTDFTLKISRVEAEDVGVYYC | MQARGTPW | -T | FGGGTKVEIK |
| ADI-19128 | GVPDRFSGSGSGTDFTLKISRVEAEDVGVYYC | MQSRNAPW | -T | FGGGTKVEIK |
| ADI-19072 | GVPDRFSGSGSGTDFTLKISRVEAEDVGVYYC | MQARQLPW | -T | FGGGTKVEIK |
| ADI-19076 | GVPDRFSGSGSGTDFTLKISRVEAEDVGVYYC | MQARDAPW | -T | FGGGTKVEIK |
| ADI-19125 | GVPDRFSGSGSGTDFTLKISRVEAEDVGVYYC | MQARQAPW | -T | FGGGTKVEIK |
| ADI-19077 | GVPDRFSGSGSGTDFTLKISRVEAEDVGVYYC | MQSRRAPPWT | | FGGGTKVEIK |
| ADI-19124 | GVPDRFSGSGSGTDFTLKISRVEAEDVGVYYC | MQARQVPPWT | | FGGGTKVEIK |
| ADI-19148 | GVPDRFSGSGSGTDFTLKISRVEAEDVGVYYC | MQARHVPPLT | | FGGGTKVEIK |
| ADI-19130 | GVPDRFSGSGSGTDFTLKISRVEAEDVGVYYC | MQRLQAW-- | -T | FGGGTKVEIK |
| ADI-19078 | GVPDRFSGSGSGTDFTLKISRVEAEDVGVYYC | MQTRHTP-- | -T | FGGGTKVEIK |
| ADI-19119 | GVPDRFSGSGSGTDFTLKISRVEAEDVGVYYC | MQARQAF-- | -T | FGGGTKVEIK |
| | GVPDRFSGSGSGTDFTLKISRVEAEDVGVYYC | MQARHGF-- | -T | FGGGTKVEIK |
| VK1-33*01 | GVPSRFSGSGSGTDFTFTISSLQPEDIATYYC | QQYDNLPP | | |
| ADI-19067 | GVPSRFSGSGSGTDFTFTISSLQPEDIATYYC | QQVVLPF | -T | FGGGTKVEIK |
| ADI-19084 | GVPSRFSGSGSGTDFTFTISSLQPEDIATYYC | QQSDIHPR | -T | FGGGTKVEIK |
| ADI-19104 | GVPSRFSGSGSGTDFTFTISSLQPEDIATYYC | QQYDDFPPIT | | FGGGTKVEIK |
| VK1-05*01 | GVPSRFSGSGSGTEFTLTISSLQPDDFATYYC | QQYNSYSP | | |
| ADI-19108 | GVPSRFSGSGSGTEFTLTISSLQPDDFATYYC | QQYGPY-PYT | | FGGGTKVEIK |
| ADI-19153 | GVPSRFSGSGSGTEFTLTISSLQPDDFATYYC | QQHSTYSW | -T | FGGGTKVEIK |

FIG. 16E

| | | | |
|---|---|---|---|
| VK1-05*03 | GVPSRFSGSGSGTEFTLTISSLQPDDFATYYC | QQYNSYSP | |
| ADI-19087 | GVPSRFSGSGSGTEFTLTISSLQPDDFATYYC | QQYKSFSPFT | FGGGTKVEIK |
| ADI-19127 | GVPSRFSGSGSGTEFTLTISSLQPDDFATYYC | QQSSADSPFT | FGGGTKVEIK |
| ADI-19149 | GVPSRFSGSGSGTEFTLTISSLQPDDFATYYC | QQYRTY-P-T | FGGGTKVEIK |
| ADI-19090 | GVPSRFSGSGSGTEFTLTISSLQPDDFATYYC | QQHQSFSP-T | FGGGTKVEIK |
| ADI-19151 | GVPSRFSGSGSGTEFTLTISSLQPDDFATYYC | QQHSLLSI-T | FGGGTKVEIK |
| ADI-19085 | GVPSRFSGSGSGTEFTLTISSLQPDDFATYYC | QQDSIYPI-T | FGGGTKVEIK |
| ADI-19150 | GVPSRFSGSGSGTEFTLTISSLQPDDFATYYC | QQDSIYPI-T | FGGGTKVEIK |
| ADI-19126 | GVPSRFSGSGSGTEFTLTISSLQPDDFATYYC | QQFQSYPF-T | FGGGTKVEIK |
| | | | |
| VK1-12*01 | GVPSRFSGSGSGTDFTLTISSLQPEDFATYYC | QQANSFPP | |
| ADI-19115 | GVPSRFSGSGSGTDFTLTISSLQPEDFATYYC | QQAVIHPPYT | FGGGTKVEIK |
| ADI-19146 | GVPSRFSGSGSGTDFTLTISSLQPEDFATYYC | QQAVSH-PLT | FGGGTKVEIK |
| ADI-19113 | GVPSRFSGSGSGTDFTLTISSLQPEDFATYYC | QQSLTH-P-T | FGGGTKVEIK |
| ADI-19103 | GVPSRFSGSGSGTDFTLTISSLQPEDFATYYC | QQVISF-P-T | FGGGTKVEIK |
| ADI-19132 | GVPSRFSGSGSGTDFTLTISSLQPEDFATYYC | QQRAVFPP-T | FGGGTKVEIK |
| ADI-19107 | GVPSRFSGSGSGTDFTLTISSLQPEDFATYYC | QQINDHPF-T | FGGGTKVEIK |
| ADI-19083 | GVPSRFSGSGSGTDFTLTISSLQPEDFATYYC | QQADTLPI-T | FGGGTKVEIK |
| ADI-19147 | GVPSRFSGSGSGTDFTLTISSLQPEDFATYYC | QQATSLPL-T | FGGGTKVEIK |
| ADI-19086 | GVPSRFSGSGSGTDFTLTISSLQPEDFATYYC | QQANSFPL-T | FGGGTKVEIK |
| ADI-19145 | GVPSRFSGSGSGTDFTLTISSLQPEDFATYYC | QQATAHPP-T | FGGGTKVEIK |
| | | | |
| VK1-39*01 | GVPSRFSGSGSGTDFTLTISSLQPEDFATYYC | QQSYSTPP | |
| ADI-19088 | GVPSRFSGSGSGTDFTLTISSLQPEDFATYYC | QQSYSDL--T | FGGGTKVEIK |
| ADI-19139 | GVPSRFSGSGSGTDFTLTISSLQPEDFATYYC | QQLYHAPPIT | FGGGTKVEIK |
| ADI-19105 | GVPSRFSGSGSGTDFTLTISSLQPEDFATYYC | QQSLD-LPFT | FGGGTKVEIK |
| ADI-19097 | GVPSRFSGSGSGTDFTLTISSLQPEDFATYYC | QQIFS-TPLT | FGGGTKVEIK |
| ADI-19098 | GVPSRFSGSGSGTDFTLTISSLQPEDFATYYC | QQSFY-DPIT | FGGGTKVEIK |

FIG. 16F

| | | | |
|---|---|---|---|
| VK4-01*01 | GVPDRFSGSGSGTDFTLTISSLQAEDVAVYYC | QQYYSTPP- | FGGGTKVEIK |
| ADI-19133 | GVPDRFSGSGSGTDFTLTISSLQAEDVAVYYC | QQDATGI--T | FGGGTKVEIK |
| ADI-19137 | GVPDRFSGSGSGTDFTLTISSLQAEDVAVYYC | QQDHSFI--T | FGGGTKVEIK |
| ADI-19081 | GVPDRFSGSGSGTDFTLTISSLQAEDVAVYYC | QQYDVD-PLT | FGGGTKVEIK |
| ADI-19156 | GVPDRFSGSGSGTDFTLTISSLQAEDVAVYYC | QQYALT-PYT | FGGGTKVEIK |
| ADI-19141 | GVPDRFSGSGSGTDFTLTISSLQAEDVAVYYC | QQVYLF-PWT | FGGGTKVEIK |
| ADI-19069 | GVPDRFSGSGSGTDFTLTISSLQAEDVAVYYC | QQSFLT-PWT | FGGGTKVEIK |
| ADI-19109 | GVPDRFSGSGSGTDFTLTISSLQAEDVAVYYC | QQSHST-PLT | FGGGTKVEIK |
| ADI-19140 | GVPDRFSGSGSGTDFTLTISSLEPEDVAVYYC | QQYDSL-PFT | FGGGTKVEIK |
| ADI-19136 | GVPDRFSGSGSGTDFTLTISSLQAEDVAVYYC | QQLAFT-PWT | FGGGTKVEIK |
| ADI-19120 | GVPDRFSGSGSGTDFTLTISSLQAEDVAVYYC | QQHDSA-PYT | FGGGTKVEIK |
| ADI-19114 | GVPDRFSGSGSGTDFTLTISSLQAEDVAVYYC | QQYDLL-PYT | FGGGTKVEIK |
| ADI-19112 | GVPDRFSGSGSGTDFTLTISSLQAEDVAVYYC | QQDFSL-PYT | FGGGTKVEIK |
| ADI-19073 | GVPDRFSGSGSGTDFTLTISSLQAEDVAVYYC | QQLASY-PYT | FGGGTKVEIK |
| ADI-19110 | GVPDRFSGSGSGTDFTLTISSLQAEDVAVYYC | QQLASQ-PPT | FGGGTKVEIK |
| ADI-19135 | GVPDRFSGSGSGTDFTLTISSLQAEDVAVYYC | QQLASF-PWT | FGGGTKVEIK |
| ADI-19142 | GVPDRFSGSGSGTDFTLTISSLQAEDVAVYYC | QQFFLA-PPT | FGGGTKVEIK |
| ADI-19155 | GVPDRFSGSGSGTDFTLTISSLQAEDVAVYYC | QQYFST-PPT | FGGGTKVEIK |
| | | | |
| VK3-20*01 | GIPDRFSGSGSGTDFTLTISRLEPEDFAVYYC | QQYGSSPP- | FGGGTKVEIK |
| ADI-19138 | GIPDRFSGSGSGTDFTLTISRLEPEDFAVYYC | QQDVSDF--T | FGGGTKVEIK |
| ADI-19068 | GIPDRFSGSGSGTDFTLTISRLEPEDFAVYYC | QQYLGFP-PT | FGGGTKVEIK |
| ADI-19089 | GIPDRFSGSGSGTDFTLTISRLEPEDFAVYYC | QQYLI-PPIT | FGGGTKVEIK |
| ADI-19082 | GIPDRFSGSGSGTDFTLTISRLEPEDFAVYYC | QQAFIS-PPT | FGGGTKVEIK |
| ADI-19080 | GIPDRFSGSGSGTDFTLTISRLEPEDFAVYYC | QQLDSH-PPT | FGGGTKVEIK |
| ADI-19143 | GIPDRFSGSGSGTDFTLTISRLEPEDFAVYYC | QQAVSL-PWT | FGGGTKVEIK |

FIG. 16G

| | | | |
|---|---|---|---|
| VK3-15*01 | GIPARFSGSGSGTEFTLTISSLQSEDFAVYYC | QQYNNWPP | |
| ADI-19116 | GIPARFSGSGSGTEFTLTISSLQSEDFAVYYC | QQYNVHPPRT | FGGGTKVEIK |
| ADI-19159 | GIPARFSGSGSGTEFTLTISSLQSEDFAVYYC | QQDHDR-PLT | FGGGTKVEIK |
| ADI-19154 | GIPARFSGSGSGTEFTLTISSLQSEDFAVYYC | QQHDVW-PYT | FGGGTKVEIK |
| ADI-19070 | GIPARFSGSGSGTEFTLTISSLQSEDFAVYYC | QQFNNH-PIT | FGGGTKVEIK |
| ADI-19101 | GIPARFSGSGSGTEFTLTISSLQSEDFAVYYC | QQYLYF-PLT | FGGGTKVEIK |
| ADI-19111 | GIPARFSGSGSGTEFTLTISSLQSEDFAVYYC | QQYAYW-PLT | FGGGTKVEIK |
| | | | |
| VK3-11*01 | GIPARFSGSGSGTDFTLTISSLEPEDFAVYYC | QQRSNWPP | |
| ADI-19152 | GIPARFSGSGSGTDFTLTISSLEPEDFAVYYC | QHYNLWR---T | FGGGTKVEIK |
| ADI-19129 | GIPARFSGSGSGTDFTLTISSLEPEDFAVYYC | QQHDVW-PIT | FGGGTKVEIK |
| ADI-19079 | GIPARFSGSGSGTDFTLTISSLEPEDFAVYYC | QQYTSW-PLT | FGGGTKVEIK |
| ADI-19092 | GIPARFSGSGSGTDFTLTISSLEPEDFAVYYC | QQRSVL-PLT | FGGGTKVEIK |
| ADI-19102 | GIPARFSGSGSGTDFTLTISSLEPEDFAVYYC | QQGVNY-PFT | FGGGTKVEIK |
| ADI-19144 | GIPARFSGSGSGTDFTLTISSLEPEDFAVYYC | QQFDNL-PYT | FGGGTKVEIK |

FIG. 16H

ANTI-TREM1 ANTIBODIES AND METHODS OF USE THEREOF

CROSS-REFERENCE TO RELATED APPLICATIONS

This application is a division of U.S. patent application Ser. No. 16/078,965, filed Aug. 22, 2018, which is a U.S. national phase entry pursuant to 35 U.S.C. § 371 of International Application No. PCT/US2017/020745, filed Mar. 3, 2017, which claims benefit of priority of U.S. Provisional Application No. 62/304,018, filed Mar. 4, 2016, each of which is incorporated by reference herein in its entirety for all purposes.

SEQUENCE LISTING

The instant application contains a Sequence Listing which has been submitted electronically in XML format and is hereby incorporated by reference in its entirety for all purposes. The XML copy, created on Sep. 8, 2022, is named "2022-09-08_01209-0002-01US_ST26", and is 720,896 bytes in size.

BACKGROUND OF THE PRESENT DISCLOSURE

The innate immune system consists of a diverse set of cell types including neutrophils, tissue macrophages, monocytes, dendritic cells, and CNS microglia. These cells are best known for their role as a relatively primitive immune system, as opposed to the adaptive immune cells, T and B cells. Innate immune cells, and in particular the neutrophils, are typically the first cells to arrive at an infectious or inflammatory site. Another key aspect of the innate immune cells, such as tissue macrophages, dendritic cells, and CNS microglia, is to serve as sentinals for pathogens and danger, secondarily recruiting additional innate immune cells such as neutrophils, as well as adaptive immune cells. A third critical function of the innate immune system cells, especially dendritic cells, is to regulate the adaptive immune system, in part as professional antigen presenting cells, and in part through mediators including cytokines and chemokines. Innate immune cells also play key roles, through these factors and cell surface signals, in driving tissue towards either repair and healing, or towards inflammation and destruction. Innate immune cells such as macrophage are often described as polarized towards either an M1 like pro-inflammatory or M2-like pro-repair phenotype, but there is increasing recognition that these cells show a greater degree of diversity.

Innate immune cells express a multitude of cell surface receptors and intracellular sensing molecules that allow for autonomous recognition of pathogen- or danger-associated molecular patterns (PAMPs or DAMPs) and initiation of pro-inflammatory anti-microbial reponses when needed. A family of evolutionary conserved innate immune receptors has been identified and characterized, the so-called triggering receptors expressed on myeloid cells (TREMs). TREMs belong to the immunoglobulin (Ig) superfamily of receptors and contain both inhibitory and activating receptor family members (Allcock, Barrow et al., European Journal of Immunology, 567-577; 2003) (Ford and McVicar, Current Opinion in Immunology, 38-46; 2009) (Klesney-Tait, Turnbull et al., Nat Immunol, 1266-1273; 2006). In contrast to the fairly ubiquitously expressed TLRs and NOD-like receptors, expression of TREMs appears restricted to cells of the myeloid lineage (Bouchon, Dietrich et al., J Immunol, 4991-4995; 2000). Moreover, based on their capacity to integrate and potently modulate TLR- and NOD-induced signals, TREMs appear to mainly act as fine-tuners rather than initiators of inflammatory responses (Arts, Joosten et al., Journal of Leukocyte Biology, 209-215; 2012).

Triggering receptor expressed on myeloid cells-1 (TREM-1, also referred to herein as TREM1) is the first identified and best characterized receptor of the TREM family and harbors primarily activating functions ((Weber, Schuster et al., PLoS Pathog, e1003900; 2014). TREM-1 consists of an ectodomain, composed of a single Ig V-type domain, a transmembrane region and a short cytoplasmic tail that recruits DNAX-activation protein 12 (DAP12) for signaling (Bouchon, Dietrich et al., J Immunol, 4991-4995; 2000, Bouchon, Facchetti et al., Nature, 1103-1107; 2001). TREM-1 is constitutively expressed on neutrophils and on subsets of monocytes and macrophages, and TREM-1 expression is further upregulated upon exposure of cells to microbial products (Bouchon, Dietrich et al., J Immunol, 4991-4995; 2000). Whereas crosslinking of TREM-1 with agonistic antibodies alone induces only modest cellular activation, TREM-1 potently synergizes with distinct TLR ligands for a substantial amplification of oxidative burst and production of pro-inflammatory mediators such as TNF, IL-1β, IL-6, IL-8, MCP-1 and Mip-1α (Bouchon, Dietrich et al., J Immunol, 4991-4995; 2000) (Bouchon, Facchetti et al., Nature, 1103-1107; 2001) (Radsak, Salih et al., The Journal of Immunology, 4956-4963; 2004). Human genetic evidence and disease model studies, as detailed below, specifically implicate TREM-1 in human diseases.

In vivo, the role of TREM-1 has been mostly characterized in experimental models of endotoxin-induced shock or microbial sepsis where blockade of TREM-1 signaling conferred significant protection (Bouchon, Facchetti et al., Nature, 1103-1107; 2001) (Gibot, Journal of Experimental Medicine, 1419-1426; 2004, Gibot, Annals of Internal Medicine, 9; 2004). Soluble forms of the TREM-1 molecule, a small putative peptide blocker (LP17), or siRNA to inhibit expression of TREM-1 all have been used in animal studies to reduce TREM-1 signaling. All 3 methods applied to studies of lipopolysaccharide-induced endotoxemia were reported to decrease TREM-1 signaling and systemic cytokine production resulting in improved survival of animals (Wu, Li et al., Cancer Research, 3977-3986; 2012) (Gibot, Journal of Experimental Medicine, 1419-1426; 2004) (Bouchon, Facchetti et al., Nature, 1103-1107; 2001).

In order to investigate the role of TREM-1 in inflammation, homeostasis and disease, Weber et al. (Weber, Schuster et al., PLoS Pathog, e1003900; 2014) generated a TREM-1 deficient (TREM1$^{-/-}$) mouse by targeted deletion of exon 2. Employing distinct inflammation and infection models ranging from experimental colitis to infections with *Leishmania major*, influenza virus and *Legionella pneumophila*, they show that complete absence of TREM-1 significantly attenuates morbidity and immune-mediated pathologies while microbial control in the models tested remains unimpaired. These findings demonstrate a clear role for TREM-1 in chronic inflammatory disorders, and suggest limited roles in infection. However, these findings are contradicted by other published studies that show deficits in certain forms of microbial control (Lin, Tseng et al., Infect Immun, 1335-1342; 2014) including through the formation of Neutrophil extracellular trap (NET) (Barletta, Cagnina et al., American Journal of Respiratory and Critical Care Medicine, 1044-1050; 2012).

TREM-1 may additionally play roles in non-infectious inflammatory conditions. Thus, expression of TREM-1 can also be induced by the non-microbial agent monosodium urate monohydrate crystals (MSU) as seen in gaut, or by hypoxic cell culture conditions in vitro (Bosco, Pierobon et al., Blood, 2625-2639; 2010) (Murakami, Akahoshi et al., Arthritis & Rheumatism, 455-462; 2006). Augmented sTREM-1 levels have been reported for patients with rheumatoid arthritis, acute pancreatitis, chronic obstructive pulmonary disease, and cardiac arrest (Radsak, Taube et al., Clinical and Developmental Immunology, 1-7; 2007) Yasuda, 2008 #29}(Adib-Conquy, Monchi et al., Shock, 406-410; 2007, Collins, La et al., Annals of the Rheumatic Diseases, 1768-1774; 2008). Furthermore, Weber et al. (Weber, Saurer et al., European Journal of Immunology, 773-779; 2011) have described an involvement of TREM-1 in human inflammatory bowel diseases (IBD) and in animal models of colitis (Schenk, Bouchon et al., Journal of Clinical Investigation, 3097-3106; 2007, Weber, Saurer et al., European Journal of Immunology, 773-779; 2011, Saurer, Rihs et al., Journal of Crohn's and Colitis, 913-923; 2012).

Studies addressing the impact of TREM-1 in disease have so far mostly relied on the use of TREM-1/Ig fusion proteins or synthetic peptides mimicking part of the extracellular domain of TREM-1, as competitive inhibitors of the pathway. These inhibitory agents have been reported to afford protection from endotoxin-induced shock, microbial sepsis and experimental colitis in animal models (Schenk, Bouchon et al., Journal of Clinical Investigation, 3097-3106; 2007) (Bouchon, Facchetti et al., Nature, 1103-1107; 2001). However, some of the findings with respect to the impact of TREM-1 inhibitors on microbial control appear controversial (Klesney-Tait, Keck et al., Journal of Clinical Investigation, 138-149; 2012) (Gibot, Massin et al., European Journal of Immunology, 456-466; 2007) (Gibot, Alauzet et al., The Journal of Infectious Diseases, 975-983; 2006) (Bouchon, Facchetti et al., Nature, 1103-1107; 2001).

Investigations on the precise physiological functions of TREM-1 and roles in diseases have often been limited by the lack of definitive substrates. Putative ligands for TREM-1 have been described on the surface of human platelets and on murine granulocytes during experimental peritonitis and endotoxaemia (Haselmayer, Grosse-Hovest et al., Blood, 1029-1035; 2007, Zanzinger, Schellack et al., Immunology, 185-195; 2009) (Gibot, Alauzet et al., The Journal of Infectious Diseases, 975-983; 2006). In addition, necrotic cell lysates also appear to stimulate pro-inflammatory responses in a TREM-1-dependent manner, which may relate to association of TREM-1 with the High Mobility Group Box 1 (HMGB1) protein (El Mezayen, El Gazzar et al., Immunology Letters, 36-44; 2007) (Wu, Li et al., Cancer Res, 3977-3986; 2012)

The substances released by necrotic cells that are thought to trigger an inflammatory signal transduction cascade and cytokine/chemokine production by myeloid cells include TREM-1 potential ligands such as High Mobility Group Box 1 (HMGB1) and heat shock protein 70 (HSP70) (El Mezayen, El Gazzar et al., Immunology Letters, 36-44; 2007). The binding between TREM-1 and HMGB1 molecules has been analyzed by SPR by Wu et al. (Wu, Li et al., Cancer Res, 3977-3986; 2012). The BlAcore sensograms of the 2 proteins showed a rapid increase of response units (RU) indicating binding of these proteins to the immobilized HMGB1 on the chip followed by a decrease of RU resulting from a loss of the binding molecules upon washing(Wu, Li et al., Cancer Research, 3977-3986; 2012). Binding of RAGE and TREM-1 to HMGB1 was concentration dependent. The affinity constants, Kd, were determined by SPR technique and found to be Kd 0.2 mmol/L for RAGE and HMGB1 and Kd 35.4 mmol/L for TREM-1 and HMGB1, respectively (Wu, Li et al., Cancer Research, 3977-3986; 2012). Thus, binding to this ligand candidate appears of relatively low affinity.

Another molecular ligand implicated in TREM-1 signaling was described by Read et al. (Read, Kuijper et al., J Immunol, 1417-1421; 2015), based on previous studies by Gibot et al. (Gibot, Buonsanti et al., Infect Immun, 2823-2830; 2006) that suggested an endogenous ligand for TREM-1 existed on neutrophils activated by bacteria or TLR ligands (TLRL). The relationship between cancer and inflammation appears multifaceted. Thus, inflammation can promote initiation of tumors, but inflammation can also promote anti-tumor checkpoint immune responses to established tumors. Some innate immune myeloid cells, when polarized to an anti-inflammatory phenotype such as myeloid-derived suppressor cells, are thought to support tumor growth, whereas other myeloid cells, such as dendritic cells, play a critical role in presenting tumor antigens to T cells in the context of anti-tumor immune responses by cytotoxic T lymphocytes (CTLs). Experimental and clinical evidence suggests that chronic inflammation can promote multiple aspects of carcinogenesis, favoring the initial genetic alterations that give rise to tumor cells, and acting as a tumor promoter by establishing a tissue microenvironment that allows the tumor to progress and metastasize (From Wu, (Wu, Li et al., Cancer Research, 3977-3986; 2012)) (Trinchieri, F1000Med Rep, 2011, Trinchieri, Annual Review of Immunology, 677-706; 2012) (Borrello, Degl'Innocenti et al., Cancer Letters, 262-270; 2008) (Kuraishy, Karin et al., Immunity, 467-477; 2011). Deletion of the murine homolog of TREM1 in mice attenuated hepatocellular carcinogenesis triggered by diethylnitrosamine (DEN). A single injection of DEN to 2-week-old WT male mice resulted within 8 months in the induction of α-fetoprotein (AFP)-expressing hepatocellular carcinomas (HCCs) (Wu, Li et al., Cancer Research, 3977-3986; 2012), many of which were large with evident neovascularization. Unlike WT mice, TREM1 −/− male mice given DEN at the same age were tumor free at 8 months. At 14 months, only 4% of TREM1 −/− mice developed small HCCs, whereas all WT mice at that time had developed a large numbers of typical HCCs (Wu, Li et al., Cancer Research, 3977-3986; 2012). These data indicate that efficient HCC induction in response to DEN administration requires TREM1.

TREM-1 was found to be essential for the initiation of liver damage by DEN and TREM1-deficient mice exhibited less liver damage than WT mice during the early stage of HCC development. Taken together, the data suggest that TREM1 normally plays a role in DEN-mediated inflammatory activation of Kupfer cells leading to tumorigenesis (Wu, Li et al., Cancer Research, 3977-3986; 2012). It has been shown that cancer cells can directly upregulate TREM-1 expression in patient macrophages, and TREM-1 expression in tumor-associated macrophages was linked with cancer recurrence and poor survival of patients with non-small cell lung cancer (Ho, Liao et al., Am J Respir Crit Care Med, 763-770; 2008) Yuan et al. (Yuan, Mehta et al., PLoS One, e94241; 2014) TREM1 antibodies have been described (U.S. Pat. No. 9,000,127 B2) (Arts, Joosten et al., Eur Cytokine Netw, 11-14; 2011). However, no agonistic antibodies that activate TREM1 in solution and/or antibodies that synergize with TREM1 ligands have been described. Such antibodies can be used to treat cancer, where increased myeloid cell promotion of an inflammatory polarization is predicted to be beneficial, as well as diseases such as Frontotemporal dementia and Alzheimer's disease, where insufficient TREM1 and/or DAP12 signaling is implicated.

In addition, no antagonistic antibodies that block TREM1 function non-competitively, independent of ligand blocking, and no antagonstic antibodies that block TREM1 function by binding to multiple sites on TREM1 have been reported. Such antibodies can be used to treat multiple inflammatory disorders where excessive myeloid cell activation or survival is pathogenic, such as sepsis, rheumatoid- or osteoarthritis, Crohn's disease, inflammatory bowel disease, ulcerative colitis, Multiple Sclerosis, or others. Furthermore, neurodegenerative diseases at an inflammatory stage are paradoxically be predicted to benefit from reduced TREM-1 signaling, despite the protective role of TREM-1. Finally in some contexts such as TREM-1 expressing tumors, or with tumors infiltrated by myeloid-derived suppressor cells, blocking TREM-1 may be protective by reducing tumor survival and potentiating anti-tumor immunity All references cited herein, including patent applications and publications, are hereby incorporated by reference in their entirety.

SUMMARY OF ASPECTS OF THE PRESENT DISCLOSURE

This section provides a summary of certain aspects of the present disclosure. The invention is not limited to the specific aspects or specific embodiments described in this summary.

The present disclosure is generally directed to compositions that include antibodies, e.g., monoclonal, chimeric, humanized antibodies, antibody fragments, etc., that specifically bind a TREM1 protein, e.g., a mammalian TREM1 or human TREM1, and to methods of using such compositions. The antibodies of the present disclosure may include agonist, antagonist, or inert antibodies. The methods provided herein find use in preventing, reducing risk, or treating an individual having a disorder or disease described herein. The methods provided herein also find use in inducing or promoting the survival, maturation, functionality, migration, or proliferation of one or more immune cells in an individual in need thereof. The methods provided herein find further use in decreasing the activity, functionality, or survival of regulatory T cells, tumor-imbedded immunosuppressor dendritic cells, tumor-imbedded immunosuppressor macrophages, neutrophils, natural killer (NK) cells, myeloid-derived suppressor cells, tumor-associated macrophages, NK cells, acute myeloid leukemia (AML) cells, chronic lymphocytic leukemia (CLL) cell, or chronic myeloid leukemia (CML) cell in an individual in need thereof.

In instances in which tumor cells, such as AML cells, express TREM1, anti-TREM1 antibodies of the present disclosure also find use in treating cancers. In some embodiments, anti-TREM1 antibodies, including antibodies that display antibody-dependent cell-mediated cytotoxicity (ADCC) and/or TREM1 antibody drug conjugates, can be used to target and inhibit cancer, such as AML.

One class of anti-TREM1 antibodies of the present disclosure relates to agonist antibodies that induce one or more TREM1 activities on, for example, human primary immune cells and TREM1-expressing cell lines. In some embodiments, an anti-TREM1 antibody of the present disclosure, when combined with one or more TREM1 ligands, enhances one or more TREM1 activities induced by binding of the one or more TREM1 ligands to the TREM1 protein. In some embodiments, such agonist anti-TREM1 antibodies can, advantageously, enhance ligand-induced TREM1 activity without competing with or otherwise blocking binding of the one or more TREM1 ligands to the TREM1 protein. In some embodiments, the agonist antibodies can activate and/or enhance one or more TREM1 activities regardless of whether the antibodies are clustered or in solution. In some embodiments, the agonist antibodies can activate TREM1 in solution without the need to be clustered by secondary antibodies, by Fc receptors, or by binding to plates. In some embodiments, the agonist antibodies may activate TREM1 regardless of whether the mechanism for antibody clustering are present at the therapeutic site of action in vivo. In some embodiments, the agonist antibodies can ensure that immune cells that express TREM1 will act primarily in the location where they are required for therapeutic efficacy and will be able to interact with their physiological targets. In some embodiments, the agonist antibodies do not block TREM1 activity that leads to increased disease risks similar to those observed with genetic mutations that reduce TREM1 activity.

In certain aspects, the present disclosure relates to an isolated antibody that binds to a TREM1 protein, wherein the antibody induces one or more TREM1 activities. In some embodiments, the antibody enhances one or more TREM1 activities induced by binding of one or more TREM1 ligands to the TREM1 protein, as compared to the one or more TREM1 activities induced by binding of the one or more TREM1 ligands to the TREM1 protein in the absence of the isolated antibody. In some embodiments that may be combined with any of the preceding embodiments, the antibody enhances the one or more TREM1 activities without blocking binding of the one or more TREM1 ligands to the TREM1 protein. In some embodiments that may be combined with any of the preceding embodiments, the antibody does not compete with the one or more TREM1 ligands for binding to the TREM1 protein. In some embodiments that may be combined with any of the preceding embodiments, the antibody enhances binding of the one or more TREM1 ligands to the TREM1 protein.

In some embodiments that may be combined with any of the preceding embodiments, the antibody competes with one or more TREM1 ligands for binding to the TREM1 protein. In some embodiments that may be combined with any of the preceding embodiments, the antibody induces one or more TREM1 activities as described herein and enhances one or more TREM1 activities induced by binding of one or more TREM1 ligands to the TREM1 protein.

In some embodiments that may be combined with any of the preceding embodiments, the antibody synergizes with the one or more TREM1 ligands to enhance the one or more TREM1 activities as described herein. In some embodiments that may be combined with any of the preceding embodiments, the antibody enhances the one or more TREM1 activities in the absence of cell surface clustering of TREM1. In some embodiments that may be combined with any of the preceding embodiments, the antibody enhances the one or more TREM1 activities by inducing or retaining cell surface clustering of TREM1. In some embodiments that may be combined with any of the preceding embodiments, the antibody is clustered by an Fc-gamma receptor expressed on one or more immune cells. In some embodiments, the antibody has an Fc region as described herein, e.g., that has a substitution or modification as described herein. In some embodiments that may be combined with any of the preceding embodiments, the one or more immune cells are B cells or microglial cells. In some embodiments that may be combined with any of the preceding embodiments, the enhancement of the one or more TREM1 activities induced by binding of one or more TREM1 ligands to the TREM1 protein is measured on primary cells selected from the group consisting of dendritic cells, bone marrow-derived dendritic cells, monocytes, microglia, macrophages, neutrophils, NK cells, osteoclasts, Langerhans cells of skin, and Kupffer cells, or on cell lines, and wherein the enhancement of the one or more TREM1 activities induced by binding of one or more TREM1 ligands to the TREM1 protein is measured utilizing an in vitro cell assay. In some embodiments that may be combined with any of the preceding embodiments, the antibody increases levels of soluble TREM1, increases half-life of soluble TREM1, or both. In some embodiments that may be combined with any of the preceding embodiments, the levels of soluble TREM1 are selected from the group consisting of serum levels of TREM1, cerebral spinal fluid (CSF) levels of TREM1, tissue levels of TREM1, and any combination thereof. In some embodiments that may be combined with any of the preceding embodiments, the antibody decreases levels of TREM1 in one or more cells. In some embodiments that may be combined with any of the preceding embodiments, the antibody decreases cell surface levels of TREM1, decreases intracellular levels of TREM1, decreases total levels of TREM1, or any combination thereof. In some embodiments that may be combined with any of the preceding embodiments, the antibody induces TREM1 degradation, TREM1 cleavage, TREM1 internalization, TREM1 shedding, downregulation of TREM1 expression, or any combination thereof. In some embodiments that may be combined with any of the preceding embodiments, the levels of TREM1 in one or more cells are measured in primary cells selected from the group consisting of dendritic cells, bone marrow-derived dendritic cells, monocytes, microglia, macrophages, neutrophils, NK cells, osteoclasts, Langerhans cells of skin, and Kupffer cells, or on cell lines, and wherein the cellular levels of TREM1 are measured utilizing an in vitro cell assay.

An additional class of antibodies relates to antagonist antibodies that specifically bind to and inhibit TREM1, and do not activate TREM1 regardless of their configuration or their ability to cluster. In some embodiments, anti-TREM1 antagonist antibodies bind to TREM1 and decrease, inhibit, or otherwise reduce one or more TREM1 activities. In some embodiments, antagonist anti-TREM1 antibodies of the present disclosure block or otherwise inhibit ligand binding to TREM1 expressed on a cell surface.

A further class of antibodies relates to an inert antibody that specifically bind to TREM1, but do not modulate (e.g., decrease/inhibit or activate/induce) TREM1 function.

In some embodiments that may be combined with any of the preceding embodiments, the antibody inhibits one or more TREM1 activities as described herein. In some embodiments that may be combined with any of the preceding embodiments, the antibody inhibits interaction between TREM1 and one or more TREM1 ligands, inhibits TREM1 signal transduction, or both.

In some embodiments that may be combined with any of the preceding embodiments, the antibody is incapable of binding an Fc-gamma receptor (FcγR). In some embodiments that may be combined with any of the preceding embodiments, the antibody has an IgG1, IgG2, IgG3, or IgG4 isotype. In some embodiments that may be combined with any of the preceding embodiments: (a) the antibody has a human or mouse IgG1 isotype and comprises one or more amino acid substitutions in the Fc region at a residue position selected from the group consisting of: N297A, N297Q, D270A, D265A, L234A, L235A, C226S, C229S, P238S, E233P, L234V, P238A, A327Q, A327G, P329A, K322A, L234F, L235E, P331S, T394D, A330L, M252Y, S254T, T256E, L328E, P238D, S267E, L328F, E233D, G237D, H268D, P271G, A330R, and any combination thereof, wherein the numbering of the residues is according to EU or Kabat numbering, or comprises an amino acid deletion in the Fc region at a position corresponding to glycine 236; (b) the antibody has an IgG2 isotype and comprises one or more amino acid substitutions in the Fc region at a residue position selected from the group consisting of: P238S, V234A, G237A, H268A, H268Q, H268E, V309L, N297A, N297Q, A330S, P331S, C232S, C233S, M252Y, S254T, T256E, and any combination thereof, wherein the numbering of the residues is according to EU or Kabat numbering; or (c) the antibody has an IgG4 isotype and comprises one or more amino acid substitutions in the Fc region at a residue position selected from the group consisting of: E233P, F234V, L234A/F234A, L235A, G237A, E318A, S228P, L236E, S241P, L248E, T394D, M252Y, S254T, T256E, N297A, N297Q, and any combination thereof, wherein the numbering of the residues is according to EU or Kabat numbering. In some embodiments that may be combined with any of the preceding embodiments: (a) the Fc region further comprises one or more additional amino acid substitutions at a position selected from the group consisting of A330L, L234F; L235E, P331S, and any combination thereof, wherein the numbering of the residues is according to EU or Kabat numbering; (b) the Fc region further comprises one or more additional amino acid substitutions at a position selected from the group consisting of M252Y, S254T,T256E, and any combination thereof, wherein the numbering of the residues is according to EU or Kabat numbering; or (c) the Fc region further comprises a S228P amino acid substitution according to EU or Kabat numbering.

Other aspects of the present disclosure, embodiments of which may be combined with any of the preceding embodiments, relate to an isolated antibody that binds to a TREM1 protein, wherein the antibody binds to one or more amino acids within amino acid residues selected from the group consisting of: i. amino acid residues 21-205 of SEQ ID NO: 1, or amino acid residues on a TREM1 protein corresponding to amino acid residues 21-205 of SEQ ID NO: 1; ii. amino acid residues 26-134 of SEQ ID NO: 1, or amino acid residues on a TREM1 protein corresponding to amino acid residues 26-134 of SEQ ID NO: 1; iii. amino acid residues 45-54 of SEQ ID NO: 1, or amino acid residues on a TREM1 protein corresponding to amino acid residues 45-54 of SEQ ID NO: 1; iv. amino acid residues 70-79 of SEQ ID NO: 1, or amino acid residues on a TREM1 protein corresponding to amino acid residues 70-79 of SEQ ID NO: 1; v. amino acid residues 89-97 of SEQ ID NO: 1, or amino acid residues on a TREM1 protein corresponding to amino acid residues 89-97 of SEQ ID NO: 1; vi. amino acid residues 119-125 of SEQ ID NO: 1, or amino acid residues on a TREM1 protein corresponding to amino acid residues 119-125 of SEQ ID NO: 1; vii. amino acid residues 83-90 of SEQ ID NO: 1, or amino acid residues on a TREM1 protein corresponding to amino acid residues 83-90 of SEQ ID NO: 1; viii. amino acid residues 191-201 of SEQ ID NO: 1, or amino acid residues on a TREM1 protein corresponding to amino acid residues 191-201 of SEQ ID NO: 1; ix. amino acid residues 116-125 of SEQ ID NO: 1, or amino acid residues on a TREM1 protein corresponding to amino acid residues 116-125 of SEQ ID NO: 1.

Other aspects of the present disclosure relate to an isolated antibody that binds to a TREM1 protein, wherein the antibody competes with one or more antibodies selected from the group consisting of T1-1-T1-80 or selected from the group consisting of T1-1-T1-25 or T1-33-T1-80.

Other aspects of the present disclosure, embodiments of which may be combined with any relate to an isolated antibody that binds to a TREM1 protein, wherein the antibody comprises a light chain variable domain and a heavy chain variable domain, wherein the light chain variable domain, the heavy chain variable domain, or both comprise at least one, two, three, four, five, or six HVRs selected from HVR-L1, HVR-L2, HVR-L3, HVR-H1, HVR-H2, and HVR-H3 of a monoclonal antibody selected from the group consisting of T1-1-T1-80 or selected from the group consisting of T1-1-T1-25 or T1-33-T1-80.

In some embodiments that may be combined with any of the preceding embodiments: (a) the HVR-L1 comprises an amino acid sequence selected from the group consisting of SEQ ID NOs: 9-27; (b) the HVR-L2 comprises an amino acid sequence selected from the group consisting of SEQ ID NOs: 28-40; (c) the HVR-L3 comprises an amino acid sequence selected from the group consisting of SEQ ID NOs: 41-119; (d) the HVR-H1 comprises an amino acid sequence selected from the group consisting of SEQ ID NOs: 120-143; (e) the HVR-H2 comprises an amino acid sequence selected from the group consisting of SEQ ID NOs: 144-172; or (f) the HVR-H3 comprises an amino acid sequence selected from the group consisting of SEQ ID NOs: 173-247. In some embodiments that may be combined with any of the preceding embodiments, the light chain variable domain comprises: (a) an HVR-L1 comprising an amino acid sequence selected from the group consisting of SEQ ID NOs: 9-27, or an amino acid sequence with at least about 90% identity to an amino acid sequence selected from the group consisting of SEQ ID NOs: 9-27; (b) an HVR-L2 comprising an amino acid sequence selected from the group consisting of SEQ ID NOs: 28-40, or an amino acid sequence with at least about 90% identity to an amino acid sequence selected from the group consisting of SEQ ID NOs: 28-40; and (c) an HVR-L3 comprising an amino acid sequence selected from the group consisting of SEQ ID NOs: 41-119, or an amino acid sequence with at least about 90% identity to an amino acid sequence selected from the group consisting of SEQ ID NOs: 41-119 and wherein the heavy chain variable domain comprises: (a) an HVR-H1 comprising an amino acid sequence selected from the group consisting of SEQ ID NOs: 120-143, or an amino acid sequence with at least about 90% identity to an amino acid sequence selected from the group consisting of SEQ ID NOs: 120-143; (b) an HVR-H2 comprising an amino acid sequence selected from the group consisting of SEQ ID NOs: 144-172, or an amino acid sequence with at least about 90% identity to an amino acid sequence selected from the group consisting of SEQ ID NOs: 144-172; and (c) an HVR-H3 comprising an amino acid sequence selected from the group consisting of SEQ ID NOs: 173-247, or an amino acid sequence with at least about 90% identity to an amino acid sequence selected from the group consisting of SEQ ID NOs: 173-247.

Other aspects of the present disclosure relate to an isolated antibody that binds to a TREM1 protein, wherein the antibody comprises a light chain variable domain comprising an amino acid sequence selected from the group consisting of SEQ ID NOs: 316-395; and/or a heavy chain variable domain comprising an amino acid sequence selected from the group consisting of SEQ ID NOs: 396-475.

Other aspects of the present disclosure relate to an isolated antibody that binds to a TREM1 protein, wherein the antibody comprises a light chain variable domain of a monoclonal antibody selected from the group consisting of T1-1-T1-80 or selected from the group consisting of T1-1-T1-25 or T1-33-T1-80; and/or a heavy chain variable domain of a monoclonal antibody selected from the group consisting of T1-1-T1-80 or selected from the group consisting of T1-1-T1-25 or T1-33-T1-80.

Other aspects of the present disclosure relate to an isolated antibody that binds to a TREM1 protein, wherein the antibody binds essentially the same TREM1 epitope as a monoclonal antibody selected from the group consisting of T1-1-T1-80 or selected from the group consisting of T1-1-T1-25 or T1-33-T1-80.

Other aspects of the present disclosure relate to an isolated antibody that binds to a TREM1 protein, wherein the antibody comprises a light chain variable domain and a heavy chain variable domain, wherein the light chain variable domain comprises: (a) an HVR-H1 comprising an amino acid sequence selected from the group consisting of SEQ ID NOs: 120-143, or an amino acid sequence with at least about 90% identity to an amino acid sequence selected from the group consisting of SEQ ID NOs: 120-143; (b) an HVR-H2 comprising an amino acid sequence selected from the group consisting of SEQ ID NOs: 144-172, or an amino acid sequence with at least about 90% identity to an amino acid sequence selected from the group consisting of SEQ ID NOs: 144-172; and (c) an HVR-H3 comprising an amino acid sequence selected from the group consisting of SEQ ID NOs: 173-247, or an amino acid sequence with at least about 90% identity to an amino acid sequence selected from the group consisting of SEQ ID NOs: 173-247.

In some embodiments that may be combined with any of the preceding embodiments, the TREM1 protein is a mammalian protein or a human protein. In some embodiments that may be combined with any of the preceding embodiments, the TREM1 protein is a wild-type protein. In some embodiments that may be combined with any of the preceding embodiments, the TREM1 protein is a naturally occurring variant. In some embodiments that may be combined with any of the preceding embodiments, the TREM1 protein is a disease variant. In some embodiments that may be combined with any of the preceding embodiments, the TREM1 protein is expressed on human dendritic cells, human macrophages, human monocytes, human osteoclasts, human Langerhans cells of skin, human Kupffer cells, human microglia, or any combination thereof.

In some embodiments that may be combined with any of the preceding embodiments, the antibody is an antibody fragment that binds to one or more human proteins selected from the group consisting of human TREM1, a naturally occurring variant of human TREM1, and a disease variant of human TREM1, and optionally wherein the antibody fragment is cross-linked to a second antibody fragment that binds to one or more human proteins selected from the group consisting of human TREM1, a naturally occurring variant of human TREM1, and a disease variant of human TREM1. In some embodiments that may be combined with any of the preceding embodiments, the fragment is an Fab, Fab', Fab'-SH, F(ab')2, Fv or scFv fragment. In some embodiments that may be combined with any of the preceding embodiments, the antibody is a murine antibody. In some embodiments that may be combined with any of the preceding embodiments, the antibody is a humanized antibody, a bispecific antibody, a multivalent antibody, a conjugated antibody, or a chimeric antibody. In some embodiments that may be combined with any of the preceding embodiments, the antibody is a monoclonal antibody. In some embodiments that may be combined with any of the preceding embodiments, the antibody is a bispecific antibody recognizing a first antigen and a second antigen. In some embodiments that may be combined with any of the preceding embodiments, the first antigen is human TREM1 or a naturally occurring variant thereof, and the second antigen is: (a) an antigen facilitating transport across the blood-brain-barrier; (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005; (c) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading flame 72) c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from the group consisting of CD40, OX40, ICOS, CD28, CD137/4-1BB, CD27, GITR, PD-L1, CTLA4, PD-L2, PD-1, B7-H3, B7-H4, HVEM, BTLA, KIR, GAL9, TIM3, A2AR, LAG, and phosphatidylserine; and (e) a protein, lipid, polysaccharide, or glycolipid expressed on one or more tumor cells. In some embodiments that may be combined with any of the preceding embodiments, the antibody is used in combination with one or more antibodies that specifically bind a disease-causing agent selected from the group consisting of disease-causing peptides, disease-causing proteins, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, TREM1, TREM1, CD33, Siglec-5, Siglec-9, Siglec-11, phosphatidylserine, disease-causing nucleic acids, antisense GGCCCC (G2C4) repeat-expansion RNA, and any combination thereof. In some embodiments that may be combined with any of the preceding embodiments, when administered to an individual increases memory, reduces cognitive deficit, or both. In some embodiments that may be combined with any of the preceding embodiments, the antibody binds specifically to both human TREM1 and mouse TREM1. In some embodiments that may be combined with any of the preceding embodiments, the antibody has dissociation constant ($K_D$) for human TREM1 and mouseTREM1 that ranges from about 12.8 nM to about 1.2 nM, or less than 1.2 nM. In some embodiments that may be combined with any of the preceding embodiments, the antibody has dissociation constant ($K_D$) for human TREM1 that ranges from about 12.8 nM to about 2.9 nM, or less than 2.9 nM. In some embodiments that may be combined with any of the preceding embodiments, the antibody has dissociation constant ($K_D$) for mouse TREM1 that ranges from about 10.4 nM to about 1.2 nM, or less than 1.2 nM.

Other aspects of the present disclosure relate to an isolated nucleic acid comprising a nucleic acid sequence encoding the antibody of any one of the preceding claims. Other aspects of the present disclosure relate to a vector comprising the nucleic acid of any of the preceding embodiments. Other aspects of the present disclosure relate to an isolated host cell comprising the vector of any of the preceding embodiments. Other aspects of the present disclosure relate to a method of producing an antibody that binds to TREM1, comprising culturing the host cell of any of the preceding embodiments so that the antibody is produced. In some embodiments, the method further comprising recovering the antibody produced by the cell. Other aspects of the present disclosure relate to an isolated antibody that binds to TREM1 produced by the method of any of the preceding embodiments. Other aspects of the present disclosure relate to a pharmaceutical composition comprising the antibody of any of the preceding embodiments and a pharmaceutically acceptable carrier.

Other aspects of the present disclosure relate to a method of preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, atherosclerosis, Paget's disease of bone, bladder cancer, brain cancer, e.g., glioma, such as low-grade glioma, and glioblastoma; cervical cancer, breast cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and Haemophilus influenza, comprising administering to an individual in need thereof a therapeutically effective amount of an isolated antibody that binds to a TREM1 protein as decribed herein. In some embodiments, the isolated antibody is the antibody of any of the preceding embodiments.

Other aspects of the present disclosure relate to an isolated antibody that binds to a TREM1 protein as described herein for use in preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, cognitive deficit, memory loss, lupus, acute and chronic colitis, rheumatoid arthritis, atherosclerosis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, bladder cancer, brain cancer, e.g., glioma such as low-grad glioma, or glioblastoma; breast cancer, cervical cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and Haemophilus influenza. In some embodiments, the isolated antibody is the antibody of any of the preceding embodiments.

Other aspects of the present disclosure relate to use of an isolated antibody that binds to a TREM1 protein in the manufacture of a medicament for preventing, reducing risk, or treating an individual having a disease, disorder, or injury selected from the group consisting of dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, bladder cancer, brain cancer, e.g., glioma such as low grade glioma, or glioblastoma; breast cancer, cervical cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and Haemophilus influenza. In some embodiments, the isolated antibody is the antibody of any of the preceding embodiments.

In some embodiments that may be combined with any of the preceding embodiments, the method further comprising administering to the individual at least one antibody that specifically binds to an inhibitory checkpoint molecule, and/or another standard or investigational anti-cancer therapy. In some embodiments that may be combined with any of the preceding embodiments, the at least one antibody that specifically binds to an inhibitory checkpoint molecule is administered in combination with the isolated antibody. In some embodiments that may be combined with any of the preceding embodiments, the at least one antibody that specifically binds to an inhibitory checkpoint molecule is selected from the group consisting of an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments that may be combined with any of the preceding embodiments, the standard or investigational anti-cancer therapy is one or more therapies selected from the group consisting of radiotherapy, cytotoxic chemotherapy, targeted therapy, hormonal therapy, imatinib (Gleevec®), trastuzumab (Herceptin®), bevacizumab (Avastin®), Ofatumumab (Arzerra®), Rituximab (Rituxan®, MabThera®, Zytux®), cryotherapy, ablation, radiofrequency ablation, adoptive cell transfer (ACT), chimeric antigen receptor T cell transfer (CAR-T), vaccine therapy, and cytokine therapy. In some embodiments that may be combined with any of the preceding embodiments, the method further comprising administering to the individual at least one antibody that specifically binds to an inhibitory cytokine. In some embodiments that may be combined with any of the preceding embodiments, the at least one antibody that specifically binds to an inhibitory cytokine is administered in combination with the isolated antibody. In some embodiments that may be combined with any of the preceding embodiments, the at least one antibody that specifically binds to an inhibitory cytokine is selected from the group consisting of an anti-CCL2 antibody, an anti-CSF-1 antibody, an anti-IL-2 antibody, and any combination thereof. In some embodiments that may be combined with any of the preceding embodiments, the method further comprising administering to the individual at least one agonistic antibody that specifically binds to a stimulatory checkpoint protein. In some embodiments that may be combined with any of the preceding embodiments, the at least one agonistic antibody that specifically binds to a stimulatory checkpoint protein is administered in combination with the isolated antibody. In some embodiments that may be combined with any of the preceding embodiments, the at least one agonistic antibody that specifically binds to a stimulatory checkpoint protein is selected from the group consisting of an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof. In some embodiments that may be combined with any of the preceding embodiments, the method further comprising administering to the individual at least one stimulatory cytokine. In some embodiments that may be combined with any of the preceding embodiments, the at least one stimulatory cytokine is administered in combination with the isolated antibody. In some embodiments that may be combined with any of the preceding embodiments, the at least one stimulatory cytokine is selected from the group consisting of TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, IL-23, IFN-α, IFN-β, IL-2, IL-18, GM-CSF, G-CSF, and any combination thereof.

Other aspects of the present disclosure relate to a method of enhancing one or more TREM1 activities induced by binding of one or more TREM1 ligands to a TREM1 protein in an individual in need thereof, comprising administering to the individual a therapeutically effective amount of an isolated antibody that binds to a TREM1 protein. Other aspects of the present disclosure relate to an isolated antibody that binds to a TREM1 protein for use in enhancing one or more TREM1 activities induced by binding of one or more TREM1 ligands to a TREM1 protein in an individual in need thereof. Other aspects of the present disclosure relate to use of an isolated antibody that binds to a TREM1 protein in the manufacture of a medicament for enhancing one or more TREM1 activities induced by binding of one or more TREM1 ligands to a TREM1 protein in an individual in need thereof. In some embodiments, the isolated antibody is the antibody of any of the preceding embodiments.

Other aspects of the present disclosure relate to a method of inducing one or more TREM1 activities in an individual in need thereof, comprising administering to the individual a therapeutically effective amount of an isolated antibody that binds to a TREM1 protein. Other aspects of the present disclosure relate to an isolated antibody that binds to a TREM1 protein for use in inducing one or more TREM1 activities in an individual in need thereof. Other aspects of the present disclosure relate to use of an isolated antibody that binds to a TREM1 protein in the manufacture of a medicament for inducing one or more TREM1 activities in an individual in need thereof. In some embodiments, the isolated antibody is the antibody of any of the preceding embodiments.

Other aspects of the present disclosure relate to a method of inducing one or more TREM1 activities and enhancing one or more TREM1 activities induced by binding of one or more TREM1 ligands to a TREM1 protein in an individual in need thereof, comprising administering to the individual a therapeutically effective amount of an isolated antibody that binds to a TREM1 protein. Other aspects of the present disclosure relate to an isolated antibody that binds to a TREM1 protein for use in inducing one or more TREM1 activities and enhancing one or more TREM1 activities induced by binding of one or more TREM1 ligands to a TREM1 protein in an individual in need thereof. Other aspects of the present disclosure relate to use of an isolated antibody that binds to a TREM1 protein in the manufacture of a medicament for inducing one or more TREM1 activities and enhancing one or more TREM1 activities induced by binding of one or more TREM1 ligands to a TREM1 protein in an individual in need thereof. In some embodiments, the isolated antibody is the antibody of any of the preceding embodiments.

Other aspects of the present disclosure relate to a method of decreasing levels of TREM1 in one or more cells in an individual in need thereof, comprising administering to the individual a therapeutically effective amount of an isolated antibody that binds to a TREM1 protein. Other aspects of the present disclosure relate to an isolated antibody that binds to a TREM1 protein for use in decreasing levels of TREM1 in one or more cells in an individual in need thereof. Other aspects of the present disclosure relate to use of an isolated antibody that binds to a TREM1 protein in the manufacture of a medicament for decreasing levels of TREM1 in one or more cells in an individual in need thereof. In some embodiments, the isolated antibody is the antibody of any of the preceding embodiments.

Other aspects of the present disclosure relate to a method of inducing or promoting innate immune cell survival or wound healing an individual in need thereof, comprising administering to the individual a therapeutically effective amount of an isolated agonist antibody that binds to a TREM1 protein. Other aspects of the present disclosure relate to an isolated agonist antibody that binds to a TREM1 protein for use in inducing or promoting innate immune cell survival or wound healing an individual in need thereof. Other aspects of the present disclosure relate to use of an isolated agonist antibody that binds to a TREM1 protein in the manufacture of a medicament for inducing or promoting innate immune cell survival or wound healing an individual in need thereof. In some embodiments, the isolated agonist antibody is the agonist antibody of any of the preceding embodiments.

Other aspects of the present disclosure relate to a method of increasing memory, reducing cognitive deficit, or both in an individual in need thereof, comprising administering to the individual a therapeutically effective amount of an isolated agonist antibody that binds to a TREM1 protein. Other aspects of the present disclosure relate to an isolated agonist antibody that binds to a TREM1 protein for use in increasing memory, reducing cognitive deficit, or both in an individual in need thereof. Other aspects of the present disclosure relate to use of an isolated agonist antibody that binds to a TREM1 protein in the manufacture of a medicament for increasing memory, reducing cognitive deficit, or both in an individual in need thereof. In some embodiments, the isolated agonist antibody is the agonist antibody of any of the preceding embodiments.

BRIEF DESCRIPTION OF THE DRAWINGS

FIG. 1A shows an amino acid sequence alignment between the human TREM1 protein (SEQ ID NO: 498) and the human NCTR2 protein (SEQ ID NO: 499), depicting the homology between the two proteins.

FIG. 1B shows an amino acid sequence alignment between the human TREM1 protein (SEQ ID NO: 500) and the mouse TREM1 protein (SEQ ID NO: 501), depicting the homology between the two proteins.

FIG. 2 shows an amino acid sequence alignment between the human TREM1 protein protein (SEQ ID NO: 502) and the human TREM2 protein protein (SEQ ID NO: 503), depicting the homology between the two proteins.

FIG. 3B shows FACS histograms of TREM1 antibodies T1-1 through T1-80 binding to CHO cells expressing mouse TREM1. Shaded histograms represent the parental TREM1-negative CHO cells. Black outlined histograms represent the TREM1 positive cell population Antibodies mIgG1, mIgG2A, and ISO88 represent negative isotype control. Antibodies MAB0170, RD hT1, and RD mT1 represent positive controls.

FIG. 5A shows the amino acid region D38-F48 in black as the predicted epitope for MAB0170, a positive control antibody for human TREM1. FIG. 5B shows the amino acid region L45-A54, T70-P79, D89-R97, and P119-L125 in black as the predicted epitope for T1-53 and T1-63. FIG. 5C shows the amino acid region L45-A54 and Y116-L125 in black as the predicted epitope for T1-10 and T1-61. FIG. 5D shows the amino acid region G83-Y90 in black as the predicted epitope for T1-34, -39, -62, -71, and -76.

FIG. 8A shows induction of human TREM1-dependent GFP reporter in a cell-based assay. Cells were either treated with soluble full-length isotype control or soluble full-length anti-TREM1 antibodies T1-77, -78, -79, -80, -12, -40, -51, -52, -62, -63, -16, -22, and -39. Antibody huIgG1 is the isotype negative control. FIG. 8B shows induction of human TREM1-dependent GFP reporter in a cell-based assay. Cells were either treated with soluble full-length isotype control or soluble full-length anti-TREM1 antibodies T1-64 through T1-76. Results are representative of the entire set of TREM1 antibodies available and are depicted as absolute MFI values.

FIG. 9A shows induction of human TREM1-dependent GFP reporter in a cell-based assay. Cells were either treated with soluble full-length isotype control or soluble full-length anti-TREM1 antibodies T1-77, -78, -79, -80, -12, -40, -51, -52, -62, -63, -16, -22, and -39 in the presence of soluble TREM1 ligand complex. TREM1 ligand consists of 50 nM human PGLYRP1 complexed with 10 µg/mL PGN-BS (Invivogen). Antibody huIgG1 is the isotype negative control. Antibody Mab0170 represents the positive control. Results are representative of the entire set of TREM1 antibodies available and are depicted as absolute MFI values. FIG. 9B shows the capacity of agonistic TREM1 antibodies to enhance TREM1 ligand-induced GFP expression in reporter cell-based assays. Cells were treated with decreasing concentrations of anti-TREM1 antibodies T1-62 or T1-63 in the presence or absence of the soluble TREM1 ligand complex consisting of recombinant human PGLYRP1 and PGN-BS. 'No Ligand' samples represent basal GFP expression in cells not stimulated with antibodies or ligand. Results are depicted as absolute MFI values.

FIG. 10C shows TREM1-mediated respiratory burst from primary human neutrophils. Cells were stimulated with soluble full-length human IgG1 isotype control or the anti-TREM1 antibodies T1-63, -62, -71, -76, -77, -39, -40, -34, -10, -57, -22, -51, -52, -45, -46, -56, -59, -61, -69, -72, -78, and -79. Antibody huIgG1 is the isotype negative control. In all experiments, production of reactive oxygen species (ROS) was monitored by labeling cells with 2 μM of the fluorescent indicator, CM-H2DCFDA.

FIG. 12A shows the relative viability of primary human monocytes cultured for 20 hours in the absence or presence of TREM1 ligand and Toll-like receptor ligands. FIG. 12B shows the relative viability of primary human neutrophils cultured for 20 hours in the absence or presence of TREM1 ligand and Toll-like receptor ligands. Cells were treated with either 500 nM human PGLYRP1, 10 μg/mL PGN-BS, soluble TREM1 ligand complex (500 nM PGLYRP1+10 μg/mL PGN-BS), or 1 μg/mL LPS. Cell viability was determined by quantitation of ATP using a luciferase-based assay kit (CellTiter-Glo; Promega) according to the manufacturer's instructions.

FIG. 14A-14C shows alignments of heavy chain sequences of illustrative antagonist, enhancing and mimetic anti-TREM1 antibodies of the present disclosure. (VH3-21*01=SEQ ID NO:504); (ADI-19082=SEQ ID NO:505); (ADI-19113=SEQ ID NO:506); (ADI-19108=SEQ ID NO:507); (ADI-19101=SEQ ID NO:508); (ADI-19080=SEQ ID NO:509); (ADI-19114=SEQ ID NO:510); (VH4-0B*01=SEQ ID NO:511); (ADI-19139=SEQ ID NO:512); (ADI-19135=SEQ ID NO:513); (ADI-19136=SEQ ID NO:514); (ADI-19137=SEQ ID NO:515); (ADI-19154=SEQ ID NO:516); (VH4-31*01=SEQ ID NO:517); (ADI-19098=SEQ ID NO:518); (ADI-19138=SEQ ID NO:519); (VH3-09*01=SEQ ID NO:520); (ADI-19092=SEQ ID NO:521); (ADI-19085=SEQ ID NO:522); (ADI-19090=SEQ ID NO:523); (ADI-19150=SEQ ID NO:524); (ADI-19147=SEQ ID NO:525); (ADI-19152=SEQ ID NO:526); (ADI-19132=SEQ ID NO:527); (ADI-19083=SEQ ID NO:528); (ADI-19148=SEQ ID NO:529); (ADI-19131=SEQ ID NO:530); (ADI-19151=SEQ ID NO:531); and (ADI-19149=SEQ ID NO:532).

FIG. 15A-15J show alignments of heavy chain variable region sequences of various anti-TREM1 antibodies of the present disclosure. FIG. 15A-15E show the heavy chain sequences through the CDR2 sequence; FIG. 15F-15J show the remainder of the heavy chain sequences through FR4. (VH5-51*01=SEQ ID NO:533); (ADI-19144=SEQ ID NO:463); (VH1-69*01=SEQ ID NO:534); (ADI-19070=SEQ ID NO:399); (ADI-19068=SEQ ID NO:397); (ADI-19129=SEQ ID NO:449); (ADI-19069=SEQ ID NO:398); (ADI-19120=SEQ ID NO:442); (ADI-19126=SEQ ID NO:446); (ADI-19067=SEQ ID NO:396); (ADI-19127=SEQ ID NO:447); (VH1-18*01=SEQ ID NO:535); (ADI-19145=SEQ ID NO:464); (ADI-19143=SEQ ID NO:462); (ADI-19146=SEQ ID NO:465); (VH1-02*02=SEQ ID NO:536); (ADI-19142=SEQ ID NO:461); (VH1-46*01=SEQ ID NO:537); (ADI-19097=SEQ ID NO:421); (ADI-19072=SEQ ID NO:401);

Figure 3A:
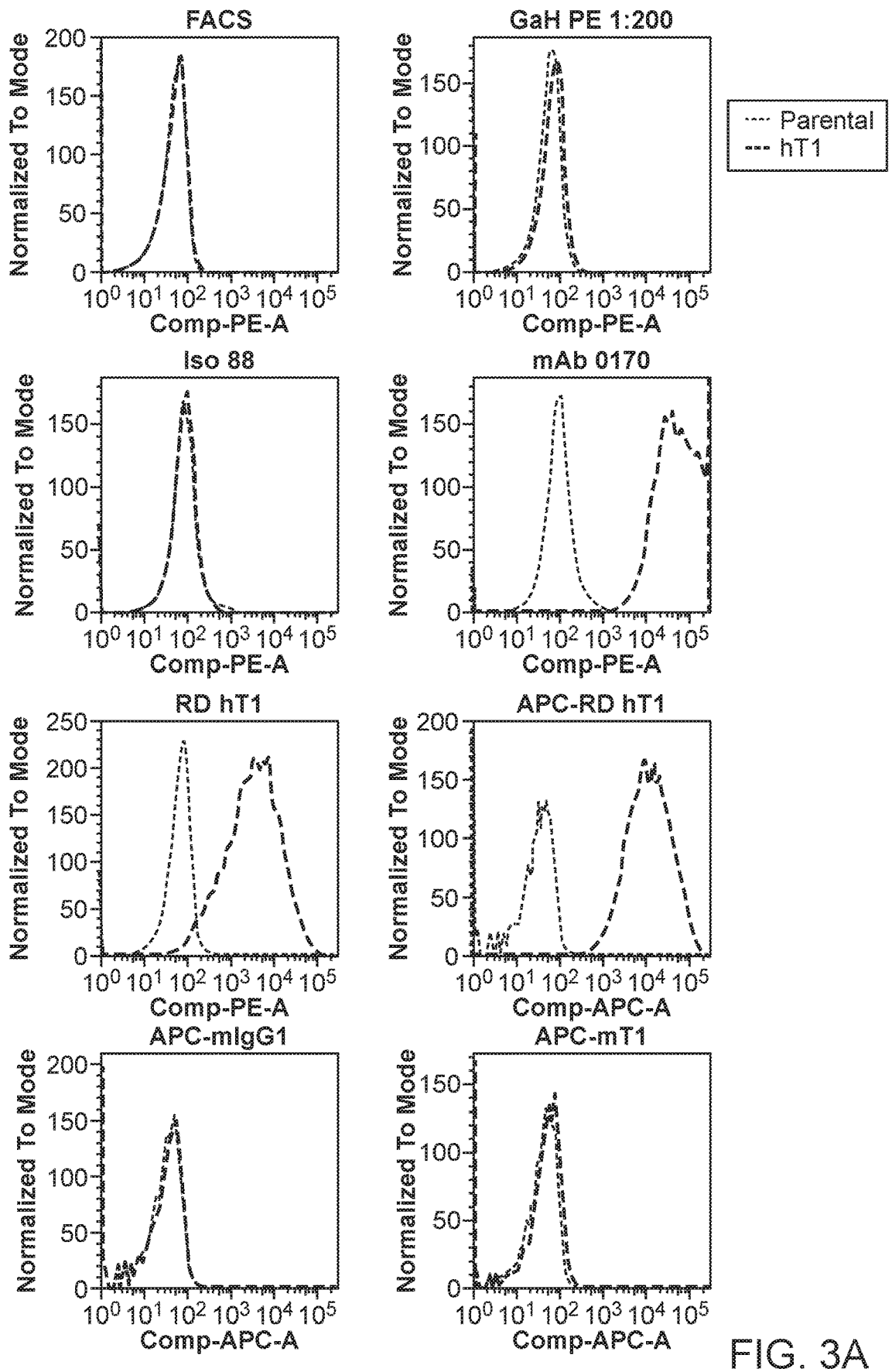
FIG. 3A shows FACS histograms of TREM1 antibodies T1-1 through T1-80 binding to the rodent Chinese hamster ovary cell line (CHO) expressing recombinant human TREM1.

(ADI-19121=SEQ ID NO:443); (ADI-19125=SEQ ID NO:445); (ADI-19122=SEQ ID NO:444); (ADI-19128=SEQ ID NO:448); (ADI-19076=SEQ ID NO:404); (ADI-19117=SEQ ID NO:438); (ADI-19073=SEQ ID NO:402); (ADI-19130=SEQ ID NO:450); (ADI-19071=SEQ ID NO:400); (ADI-19119=SEQ ID NO:439); (ADI-19123=SEQ ID NO:440); (ADI-19124=SEQ ID NO:441); (ADI-19074=SEQ ID NO:403); (ADI-19077=SEQ ID NO:405); (VH4-0B*01=SEQ ID NO:538); (ADI-19139=SEQ ID NO:458); (ADI-19135=SEQ ID NO:454); (ADI-19136=SEQ ID NO:455); (ADI-19137=SEQ ID NO:456); (ADI-19154=SEQ ID NO:472); (VH4-59*01=SEQ ID NO:539); (ADI-19084=SEQ ID NO:412); (ADI-19089=SEQ ID NO:417); (VH4-31*01=SEQ ID NO:540); (ADI-19098=SEQ ID NO:422); (ADI-19138=SEQ ID NO:457); (VH4-39*01=SEQ ID NO:541); (ADI-19102=SEQ ID NO:424); (ADI-19104=SEQ ID NO:426); (ADI-19140=SEQ ID NO:459); (ADI-19105=SEQ ID NO:427); (ADI-19103=SEQ ID NO:425); (ADI-19156=SEQ ID NO:474); (ADI-19079=SEQ ID NO:407); (ADI-19141=SEQ ID NO:460); (ADI-19155=SEQ ID NO:473); (ADI-19078=SEQ ID NO:406); (ADI-19133=SEQ ID NO:453); (VH3-72*01=SEQ ID NO:542); (ADI-19086=SEQ ID NO:414); (VH3-07*01=SEQ ID NO:543); (ADI-19087=SEQ ID NO:415); (VH3-33*01=SEQ ID NO:544); (ADI-19107=SEQ ID NO:428); (ADI-19116=SEQ ID NO:437); (ADI-19159=SEQ ID NO:475); (ADI-19111=SEQ ID NO:432); (VH3-30*03=SEQ ID NO:545); (ADI-19112=SEQ ID NO:433); (ADI-19081=SEQ ID NO:409); (ADI-19109=SEQ ID NO:430); (ADI-19110=SEQ ID NO:431); (VH3-09*01=SEQ ID NO:546); (ADI-19092=SEQ ID NO:420); (ADI-19085=SEQ ID NO:413); (ADI-19090=SEQ ID NO:418); (ADI-19150=SEQ ID NO:419); (ADI-19147=SEQ ID NO:466); (ADI-19152=SEQ ID NO:470); (ADI-19132=SEQ ID NO:452); (ADI-19083=SEQ ID NO:411); (ADI-19148=SEQ ID NO:467); (ADI-19131=SEQ ID NO:451); (ADI-19151=SEQ ID NO:469); (ADI-19149=SEQ ID NO:468); (VH3-48*01=SEQ ID NO:547); (ADI-19088=SEQ ID NO:416); (VH3-21*01=SEQ ID NO:548); (ADI-19082=SEQ ID NO:410); (ADI-19113=SEQ ID NO:434); (ADI-19108=SEQ ID NO:429); (ADI-19101=SEQ ID NO:423); (ADI-19080=SEQ ID NO:408); (ADI-19114=SEQ ID NO:435); (VH3-23*01=SEQ ID NO:549); (ADI-19115=SEQ ID NO:436); and (ADI-19153=SEQ ID NO:471).

FIG. 16A-16H show alignments of light chain variable region sequences of various anti-TREM1 antibodies of the present disclosure. FIG. 16A-16D show the light chain sequences through the CDR2 sequence; FIG. 16E-16H show the remainder of the light chain sequences through FR4. (VK2-28*01=SEQ ID NO:550); (ADI-19131=SEQ ID NO:371); (ADI-19121=SEQ ID NO:363); (ADI-19123=SEQ ID NO:360); (ADI-19071=SEQ ID NO:320); (ADI-19074=SEQ ID NO:323); (ADI-19122=SEQ ID NO:364); (ADI-19117=SEQ ID NO:358); (ADI-19128=SEQ ID NO:368); (ADI-19072=SEQ ID NO:321); (ADI-19076=SEQ ID NO:324); (ADI-19125=SEQ ID NO:365); (ADI-19077=SEQ ID NO:325); (ADI-19124=SEQ ID NO:361); (ADI-19148=SEQ ID NO:387); (ADI-19130=SEQ ID NO:370); (ADI-19078=SEQ ID NO:326); (ADI-19119=SEQ ID NO:359); (VK1-33*01=SEQ ID NO:551); (ADI-19068=SEQ ID NO:316); (ADI-19084=SEQ ID NO:332); (ADI-19104=SEQ ID NO:346); (VK1-05*01=SEQ ID NO:552); (ADI-19108=SEQ ID NO:349); (ADI-19153=SEQ ID NO:391); (VK1-05*03=SEQ ID NO:553); (ADI-19087=SEQ ID NO:335); (ADI-19127=SEQ ID NO:367); (ADI-19149=SEQ ID NO:388); (ADI-19090=SEQ ID NO:338); (ADI-19151=SEQ ID NO:389); (ADI-19085=SEQ ID NO:333); (ADI-19150=SEQ ID NO:339); (ADI-19126=SEQ ID NO:366); (VK1-12*03=SEQ ID NO:554); (ADI-19115=SEQ ID NO:356); (ADI-19146=SEQ ID NO:385); (ADI-19113=SEQ ID NO:354); (ADI-19103=SEQ ID NO:345); (ADI-19132=SEQ ID NO:372); (ADI-19107=SEQ ID NO:348); (ADI-19083=SEQ ID NO:331); (ADI-19147=SEQ ID NO:386); (ADI-19096=SEQ ID NO:334); (ADI-19145=SEQ ID NO:384); (VK1-39*01=SEQ ID NO:555); (ADI-19088=SEQ ID NO:336); (ADI-19139=SEQ ID NO:378); (ADI-19105=SEQ ID NO:347); (ADI-19097=SEQ ID NO:341); (ADI-19098=SEQ ID NO:342); (VK4-01*01=SEQ ID NO:556); (ADI-19133=SEQ ID NO:373); (ADI-19137=SEQ ID NO:376); (ADI-19081=SEQ ID NO:329); (ADI-19156=SEQ ID NO:394); (ADI-19141=SEQ ID NO:380); (ADI-19069=SEQ ID NO:318); (ADI-19109=SEQ ID NO:350); (ADI-19140=SEQ ID NO:379); (ADI-19136=SEQ ID NO:375); (ADI-19120=SEQ ID NO:362); (ADI-19114=SEQ ID NO:355); (ADI-19112=SEQ ID NO:353); (ADI-19073=SEQ ID NO:322); (ADI-19110=SEQ ID NO:351); (ADI-19135=SEQ ID NO:374); (ADI-19142=SEQ ID NO:381); (ADI-19155=SEQ ID NO:393); (VK3-20*01=SEQ ID NO:557); (ADI-19138=SEQ ID NO:377); (ADI-19068=SEQ ID NO:317); (ADI-19089=SEQ ID NO:337); (ADI-19082=SEQ ID NO:330); (ADI-19080=SEQ ID NO:328); (ADI-19143=SEQ ID NO:382); (VK3-15*01=SEQ ID NO:558); (ADI-19116=SEQ ID NO:357); (ADI-19159=SEQ ID NO:395); (ADI-19154=SEQ ID NO:392); (ADI-19070=SEQ ID NO:319); (ADI-19101=SEQ ID NO:343); (ADI-19111=SEQ ID NO:352); (VK3-11*01=SEQ ID NO:559); (ADI-19152=SEQ ID NO:390); (ADI-19129=SEQ ID NO:369); (ADI-19079=SEQ ID NO:327); (ADI-19092=SEQ ID NO:340); (ADI-19092=SEQ ID NO:344); and (ADI-1944=SEQ ID NO:383).

Figure 17:
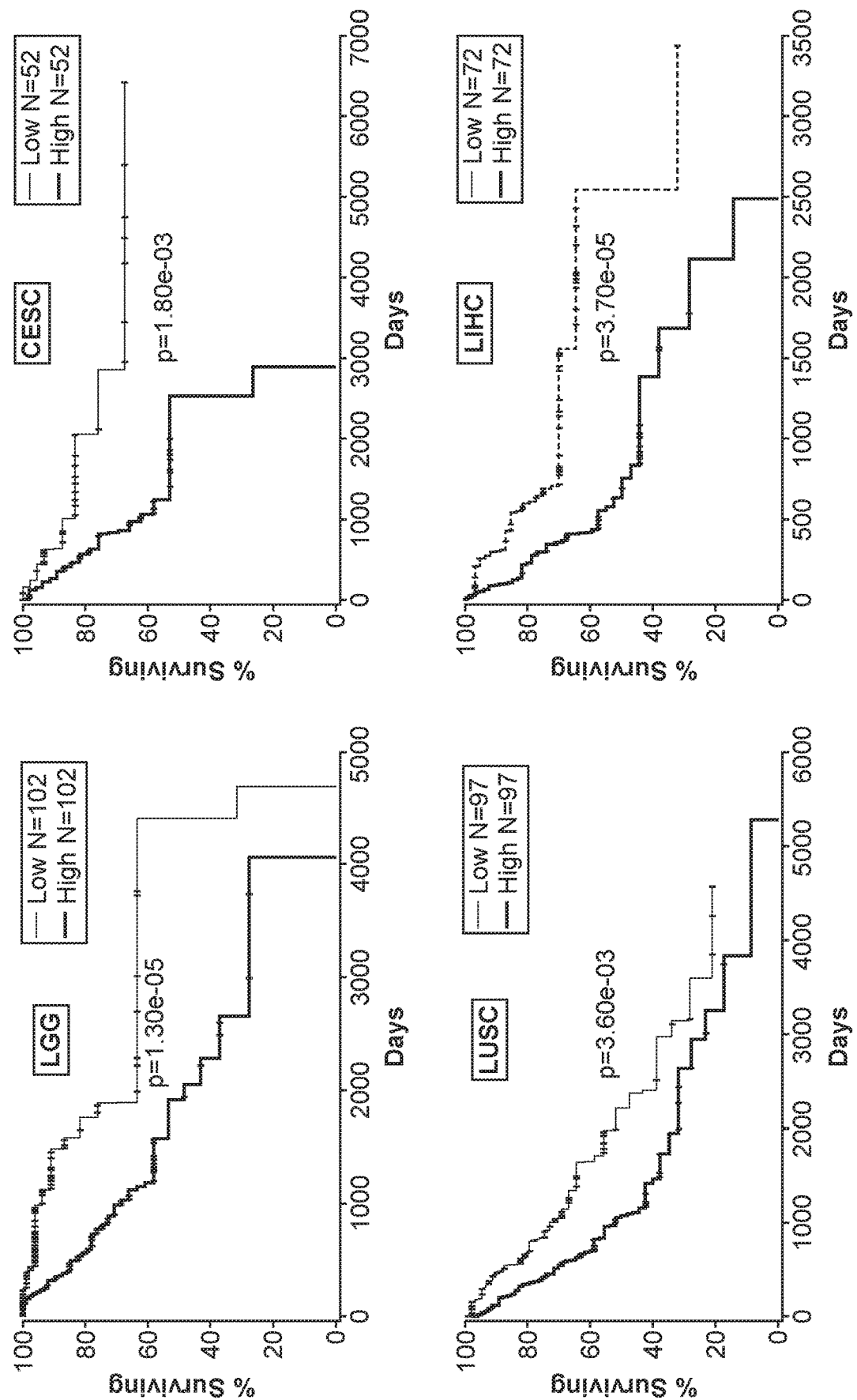

FIG. 17 provides data illustrating identification of tumor types in humans likely to respond to Treml antibodies. CESC: Cervical squamous cell carcinoma and endocervical adenocarcinoma; LGG: Brain Lower Grade Glioma; LIHC: Liver hepatocellular carcinoma; LUSC: Lung squamous cell carcinoma.

DETAILED DESCRIPTION OF THE PRESENT DISCLOSURE

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Labo-* ratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "therapeutically effective amount" is at least the minimum concentration required to effect a measurable improvement of a particular disease, disorder, or condition. A therapeutically effective amount herein may vary according to factors such as the disease state, age, sex, and weight of the patient, and the ability of the anti-TREM1 antibody to elicit a desired response in the individual. A therapeutically effective amount is also one in which any toxic or detrimental effects of the anti-TREM1 antibody are outweighed by the therapeutically beneficial effects.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., Basic and Clinical Immunology, 8th Ed., Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, 4$^{th}$ ed. (W. B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an isolated anti-TREM1 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody, such as an anti-TREM1 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-TREM1 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs), both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "hypervariable region," "HVR," or "HV," when used herein, refers to the regions of an antibody-variable domain, such as that of an anti-TREM1 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, NJ, 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
| --- | --- | --- | --- | --- |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3)

in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or, Kabat numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. References to residue numbers in the variable domain of antibodies means residue numbering by the Kabat numbering system. References to residue numbers in the constant domain of antibodies means residue numbering by the EU or, Kabat numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, MD (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

The term "monoclonal antibody" as used herein refers to an antibody, such as a monoclonal anti-TREM1 antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256: 495-97 (1975); Hongo et al., *Hybridoma,* 14 (3):253-260 (1995), Harlow et al., *Antibodies: A Laboratory Manual,* (Cold Spring Harbor Laboratory Press, 2d ed. 1988); Hamerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-TREM1 antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-TREM1 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate the six HVRs (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding. For a review of the sFv, see Pluckthun in *The Pharmacology of Monoclonal Antibodies*, vol. 113, Rosenburg and Moore eds., Springer-VerLAG-3, New York, pp. 269-315 (1994).

"Functional fragments" of antibodies, such as anti-TREM1 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as a chimeric anti-TREM1 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA*, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-TREM1 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-TREM1 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA,* 103:3557-3562 (2006) regarding human antibodies generated via a human B-cell hybridoma technology.

An "amino-acid modification" at a specified position, e.g., of an anti-TREM1 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-TREM1 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as between an anti-TREM1 antibody and TREM1 that is determinative of the presence of the target in the presence of a heterogeneous population of molecules including biological molecules. For example, an antibody, such as an anti-TREM1 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a TREM1 protein, or DAP12 protein, and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-TREM1 antibody of the present disclosure, that induces (e.g., increases) one or more activities or functions of the antigen after the antibody binds the antigen.

An "antagonist" antibody or a "blocking" antibody is an antibody, such as an antagonist anti-TREM1 antibody of the present disclosure, that reduces or eliminates (e.g., decreases) antigen binding to one or more ligand after the antibody binds the antigen, and/or that reduces or eliminates (e.g., decreases) one or more activities or functions of the antigen after the antibody binds the antigen. In some embodiments, antagonist antibodie, or blocking antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or, Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% identity with a native sequence Fc region and/or with an Fc region of a parent polypeptide, and most preferably at least about 90% identity therewith, more preferably at least about 95% identity therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared. An amino acid residue "corresponds to" another amino acid acid residue present in a reference sequence when the sequence of interest and reference sequence are maximally aligned.

An "isolated" nucleic acid molecule encoding an antibody, such as an anti-TREM1 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates to anti-TREM1 antibodies with one or more agonist or antagonist activities; methods of making and using such antibodies; pharmaceutical compositions containing such antibodies; nucleic acids encoding such antibodies; and host cells containing nucleic acids encoding such antibodies.

In some embodiments, the agonistic activities of the anti-TREM1 antibodies of the present disclosure are due, at least in part, to the ability of the antibodies to enhance one or more TREM1 activities induced by binding of one or more TREM1 ligands to the TREM1 protein without competing with or otherwise blocking binding of the one or more TREM1 ligands to the TREM1 protein. In some embodiments, the enhancement of the one or more TREM1 activities by the anti-TREM1 antibodies is compared to the one or more TREM1 activities induced by binding of the one or more TREM1 ligands to the TREM1 protein in the absence of the anti-TREM1 antibodies. In some embodiments, enhancement of one or more TREM1 activities can be determined or tested in vitro or in vivo by any of several techniques disclosed herein (see, e.g., Table 1B).

Accordingly, certain aspects of the present disclosure are based, at least in part, on the identification of anti-TREM1 antibodies that are capable of binding to human TREM1 with high affinity (see, e.g., Table 1A); that can activate and enhance (e.g., by synergizing with TREM1 ligands) TREM1 activities (see, e.g., Table 1B).

Further aspects of the present disclosure are based, at least in part, on the surprising discovery that the anti-TREM1 antibodies of the present disclosure can also induce antagonistic activities when the antibody is produced or otherwise formatted such that it is incapable of inducing or retaining TREM1 receptor clustering. In some embodiments, anti-TREM1 antibodies of the present disclosure exhibit one or more antagonistic TREM1 activities, including, without limitation, inhibition of TREM1-dependent gene activation (see, e.g., Table 1B).

TREM1 Proteins

In one aspect, the present disclosure provides antibodies that bind to a TREM1 protein of the present disclosure and induce one or more TREM1 activities and/or enhance one or more TREM1 activities after binding to a TREM1 protein expressed in a cell. TREM1 is a 234 amino acid immunoglobulin-like receptor membrane protein primarily expressed on myeloid lineage cells, including without limitation, macrophages, dendritic cells, monocytes, Langerhans cells of skin, Kupffer cells, osteoclasts, neutrophils and microglia. In some instances, TREM1 forms a receptor signaling complex with DAP12. In some instances, TREM1 may phosphorylate and signal through DAP12 (an ITAM domain adaptor protein). TREM1 signaling may result in the downstream activation of PI3K or other intracellular signals. On myeloid cells, Toll-like receptor (TLR) signals are important for the activation of TREM1 activities, e.g., in the context of an infection response. TLRs also play a key role in the pathological inflammatory response, e.g., TLRs expressed in macrophages and dendritic cells.

TREM1 proteins of the present disclosure include, without limitation, a mammalian TREM1 protein, human TREM1 protein (Uniprot Accession No. Q9NP99; SEQ ID NO: 1), mouse TREM1 protein (Uniprot Accession No. Q9JKE2; SEQ ID NO: 2), rat TREM1 protein (Uniprot Accession No. D4ABU7; SEQ ID NO: 3), Rhesus monkey TREM1 protein (Uniprot Accession No. F6TBB4; SEQ ID NO: 4), bovine TREM1 protein (Uniprot Accession No. Q6QUN5; SEQ ID NO: 5), equine TREM1 protein (Uniprot Accession No. F6PSF7; SEQ ID NO: 6), pig TREM1 protein (Uniprot Accession No. R4SEY7; SEQ ID NO: 7), Chimpanzee TREM1 protein (Uniprot Accession No. H2QSZ3; SEQ ID NO: 561) and dog TREM1 protein (Uniprot Accession No. E2RP37; SEQ ID NO: 8). As used herein "TREM1 protein" refers to both wild-type sequences and naturally occurring variant sequences.

An example of a human TREM1 amino acid sequence is set forth below as SEQ ID NO: 1:

```
         10         20         30         40
MRKTRLWGLL WMLFVSELRA ATKLTEEKYE LKEGQTLDVK 50         60         70         80
CDYTLEKFAS SQKAWQIIRD GEMPKTLACT ERPSKNSHPV 90        100        110        120
QVGRIILEDY HDHGLLRVRM VNLQVEDSGL YQCVIYQPPK 130        140        150        160
EPHMLFDRIR LVVTKGFSGT PGSNENSTQN VYKIPPTTTK 170        180        190        200
ALCPLYTSPR TVTQAPPKST ADVSTPDSEI NLTNVTDIIR 210        220        230
VPVFNIVILL AGGELSKSLV FSVLFAVTLR SFVP
```

A human TREM1 may be a preprotein form that includes a signal peptide. In some embodiments, the human TREM1 is a mature protein that does not include a signal peptide. In some embodiments, the mature TREM1 protein is expressed on a cell. An illustrative human TREM1 portein may contain a signal peptide located at amino acid residues 1-25 of human TREM1 (SEQ ID NO: 1); an extracellular immunoglobulin-like variable-type (IgV) domain located at amino acid residues 26-134 of human TREM1 (SEQ ID NO: 1); additional extracellular sequences located at amino acid residues 135-205 of human TREM1 (SEQ ID NO: 1); a transmembrane domain located at amino acid residues 227-234 of human TREM1 (SEQ ID NO: 1); and an intracellular domain located at amino acid residues 227-234 of human TREM1 (SEQ ID NO: 1).

The transmembrane domain of human TREM1 contains a lysine at amino acid residue 217 that can interact with an aspartic acid in DAP12, which is a key adaptor protein that transduces signaling from TREM2, TREM1, and other related IgV family members.

Homologues of human TREM1 include, without limitation, the natural killer (NK) cell receptor NK-p44 (NCTR2), the polymeric immunoglobulin receptor (pIgR), CD300E, CD300A, CD300C, and TREML1/TLT1. In some embodiments, NCTR2 has similarity with TREM1 within the IgV domain.

DAP12 Proteins

In one aspect, the present disclosure provides anti-TREM1 antibodies that may further modulate one or more DAP12 activities of a DAP12 protein expressed in a cell. In some signaling pathways, an aspartic acid residue in DAP12 interacts with the transmembrane domain of human TREM1 containing a lysine at amino acid residue 217, and transduces signaling from TREM2, TREM1, and other related IgV family member proteins.

DAP12 is variously referred to as Killer-activating receptor-associated protein, KAR-associated protein (KARAP), PLOSL, PLO-SL, TYRO protein, and tyrosine kinase-binding protein. DAP12 is a single-pass type I membrane. It may associate with the killer-cell inhibitory receptor (KIR) family of membrane glycoproteins and may act as an activating signal transduction element. In other embodiments, the DAP12 protein may bind zeta-chain (TCR) associated protein kinase 70 kDa (ZAP-70) and spleen tyrosine kinase (SYK), and play a role in signal transduction, bone modeling, brain myelination, and inflammation.

Human DAP12 is 113 amino acids in length. It is a homodimer; disulfide-linked protein. DAP12 contains an extracellular domain located at amino acid residues 22-40 of human; a transmembrane domain located at amino acid residues 41-61 of human DAP12; and an intracellular domain located at amino acid residues 62-113 of human DAP12. The immunoreceptor tyrosine-based activation motif (ITAM) domain is located at amino acid residues 80-113 of human DAP12.

An example of a human DAP12 amino acid sequence is set forth below as SEQ ID NO:560:

```
MGGLEPCSRL LLLPLLLAVS GLRPVQAQAQ SDCSCSTVSP

GVLAGIVMGD LVLTVLIALA VYFLGRLVPR GRGAAEAATR

KQRITEIESP YQELQGQRSD VYSDLNTQRP YYK
```

An illustrative human DAP12 may be a preprotein that includes a signal peptide. In some embodiments, the human DAP12 is a mature protein that does not include a signal peptide. In some embodiments, the mature DAP12 protein is expressed on a cell.

Mutations within the DAP12-encoding gene have been associated with polycystic lipomembranous osteodysplasia with sclerosing leukoencephalopathy (PLOSL), also known as Nasu-Hakola disease.

Multiple alternative transcript variants encoding distinct isoforms of DAP12 have been identified. DAP12 non-covalently associates with activating receptors of the CD300 family. Cross-linking of CD300-TYROBP/DAP12 complexes results in cellular activation, such as neutrophil activation mediated by integrin. In some embodiments, DAP12 interacts with SIRPB1, TREM2, CLECSF5, SIGLEC14, CD300LB, CD300E, and CD300D by similarity and via ITAM domain, as well as with SYK via SH2 domain. In other embodiments, DAP12 activates SYK, which mediates neutrophils and macrophages integrin-mediated activation. In other embodiments, DAP12 interacts with KLRC2 and KIR2DS3.

DAP12 proteins include, without limitation, a mammalian DAP12 protein, human DAP12 protein (Uniprot Accession No. O43914), mouse DAP12 protein (Uniprot Accession No. O54885), rat DAP12 protein (Uniprot Accession No. Q6X9T7), Rhesus monkey DAP12 protein (Uniprot Accession No. Q8WNQ8), bovine DAP12 protein (Uniprot Accession No. Q95J80), and pig DAP12 protein (Uniprot Accession No. Q9TU45). As used herein "DAP12 protein" refers to both wild-type sequences and naturally occurring variant sequences.

Anti-TREM1 Antibodies

Certain aspects of the present disclosure relate to antibodies that specifically bind to TREM1. In some embodiments, antibodies of the present disclosure bind a mature TREM1 protein. In some embodiments, antibodies of the present disclosure bind a mature TREM1 protein expressed on a cell. In some embodiments, antibodies of the present disclosure bind a TREM1 protein expressed on one or more human cells selected from human dendritic cells, human macrophages, human monocytes, human neutrophils, human osteoclasts, human Langerhans cells of skin, human Kupffer cells, human microglia, and any combinations thereof. In some embodiments, antibodies of the present disclosure are agonist antibodies. In some embodiments, antibodies of the present disclosure are inert antibodies. In some embodiments, antibodies of the present disclosure are antagonist antibodies.

In some embodiments, anti-TREM1 antibodies of the present disclosure bind to a TREM1 protein without competing with, inhibiting, or otherwise blocking one or more TREM1 ligands from binding to the TREM1 protein. Examples of suitable TREM1 ligands include, without limitation, TREM1 ligands expressed by E. coli cells, apoptotic cells, nucleic acids, anionic lipids, anionic APOE2, anionic APOE3, anionic APOE4, lipidated APOE2, lipidated APOE3, lipidated APOE4, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide. Accordingly, in certain embodiments, the one or more TREM1 ligands comprise E. coli cells, apoptotic cells, nucleic acids, anionic lipids, zwitterionic lipids, negatively charged phospholipids, phosphatidylserine (PS), sulfatides, phosphatidylcholin, sphingomyelin (SM), phospholipids, lipidated proteins, proteolipids, lipidated peptides, and lipidated amyloid beta peptide.

Agonist Anti-TREM1 Antibodies

One class of anti-TREM1 antibodies of the invention is agonist antibodies. For example, as the TREM1 receptor is thought to require clustering on the cell surface in order to transduce a signal, agonist antibodies may have unique features to stimulate, for example, the TREM1 receptor. By way of illustration, an agonist anti-TREM1 antibody may have the correct epitope specificity that is compatible with receptor activation, as well as the ability to induce or retain receptor clustering on the cell surface. In addition, agonist anti-TREM1 antibodies of the present disclosure may display the ability to bind TREM1 without blocking simultaneous binding of one or more TREM1 ligands. The anti-TREM1 antibodies of the present disclosure may further display additive and/or synergistic functional interactions with one or more TREM1 ligands. Thus, in some embodiments, the maximal activity of TREM1 when bound to anti-TREM1 antibodies of the present disclosure in combination with one or more TREM1 ligands of the present disclosure may be greater (e.g., enhanced) than the maximal activity of TREM1 when exposed to saturating concentrations of ligand alone or to saturating concentrations of the antibody alone. In addition, the activity of TREM1 at a given concentration of TREM1 ligand may be greater (e.g., enhanced) in the presence of the antibody. Accordingly, in some embodiments, anti-TREM1 antibodies of the present disclosure have an additive effect with the one or more TREM1 ligands to enhance the one or more TREM1 activities when bound to the TREM1 protein. In some embodiments, anti-TREM1 antibodies of the present disclosure synergize with the one or more TREM1 ligands to enhance the one or more TREM1 activities. In some embodiments, anti-TREM1 antibodies of the present disclosure increase the potency of the one or more TREM1 ligands to induce the one or more TRENT1 activities, as compared to the potency of the one or more TREM1 ligands to induce the one or more TREM1 activities in the absence of the antibody. In some embodiments, anti-TREM1 antibodies of the present disclosure enhance the one or more TREM1 activities in the absence of cell surface clustering of TREM1. In some embodiments, anti-TREM1 antibodies of the present disclosure enhance the one or more TREM1 activities by inducing or retaining cell surface clustering of TREM1. In some embodiments, anti-TREM1 antibodies of the present disclosure are clustered by one or more Fc-gamma receptors expressed on one or more immune cells, including without limitation, B cells and microglial cells. In some embodiments, enhancement of the one or more TREM1 activities induced by binding of one or more TREM1 ligands to the TREM1 protein is measured on primary cells, including without limitation, dendritic cells, bone marrow-derived dendritic cells, monocytes, microglia, macrophages, neutrophils, NK cells, osteoclasts, Langerhans cells of skin, and Kupffer cells, or on cell lines, and the enhancement of the one or more TREM1 activities induced by binding of one or more TREM1 ligands to the TREM1 protein is measured, for example, utilizing an in vitro cell assay.

In vivo, anti-TREM1 antibodies of the present disclosure may activate receptors by multiple potential mechanisms. In some embodiments, agonistic anti-TREM1 antibodies of the present disclosure, have, due to the correct epitope specificity, the ability to activate TREM1 in solution without having to be clustered with a secondary antibody, bound on plates, or clustered through Fcγ receptors. In some embodiments, anti-TREM1 antibodies of the present disclosure have isotypes of human antibodies, such as IgG2, that have, due to their unique structure, an intrinsic ability to cluster receptors or retain receptors in a clustered configuration, thereby activating receptors such as TREM1 without binding to an Fc receptor (e.g., White et al., (2015) Cancer Cell 27, 138-148).

In some embodiments, anti-TREM1 antibodies of the present disclosure cluster receptors (e.g., TREM1) by binding to Fcγ receptors on adjacent cells. Binding of the constant IgG Fc part of the antibody to Fcγ receptors leads to aggregation of the antibodies, and the antibodies in turn aggregate the receptors to which they bind through their variable region (Chu et al (2008) Mol Immunol, 45:3926-3933; and Wilson et al., (2011) Cancer Cell 19, 101-113). Binding to the inhibitory Fcγ receptor FcγR (FcγRIIB) that does not elicit cytokine secretion, oxidative burst, increased phagocytosis, and enhanced antibody-dependent, cell-mediated cytotoxicity (ADCC) is often a preferred way to cluster antibodies in vivo, since binding to FcγRIIB is not associated with immune adverse effects.

Other mechanisms may also be used to cluster receptors, including TREM1 receptors. For example, in some embodiments, antibody fragments (e.g., Fab fragments) that are cross-linked together may be used to cluster receptors (e.g., TREM1) in a manner similar to antibodies with Fc regions that bind Fcγ receptors, as described above. In some embodiments, cross-linked antibody fragments (e.g., Fab fragments) may function as agonist antibodies if they induce receptor clustering on the cell surface and bind an appropriate epitope on the target, such as TREM1.

In some embodiments, antibodies of the present disclosure that bind a TREM1 protein may include agonist antibodies that due to their epitope specificity bind TREM1 and activate one or more TREM1 activities. In some embodiments, such antibodies may bind to the ligand-binding site on TREM1 and mimic the action of one or more TREM1 ligands, or stimulate the target antigen to transduce signal by binding to one or more domains that are not the ligand-binding sites. In some embodiments, the antibodies do not compete with or otherwise block ligand binding to TREM1. In some embodiments, the antibodies, act additively or synergistically with one or more TREM1 ligands to activate and/or enhance one more TREM1 activities.

As used herein, an agonist anti-TREM1 antibody of the present disclosure enhances one or more TREM1 activities induced by binding of one or more TREM1 ligands to the TREM1 protein if it induces at least a 2-fold, at least a 3-fold, at least a 4-fold, at least a 5-fold, at least a 6-fold, at least a 7-fold, at least a 8-fold, at least a 9-fold, at least a 10-fold, at least an 11-fold, at least a 12-fold, at least a 13-fold, at least a 14-fold, at least a 15-fold, at least a 16-fold, at least a 17-fold, at least an 18-fold, at least a 19-fold, at least a 20-fold or greater increase in the one or more TREM1 activities as compared to levels of the one or more TREM1 activities induced by binding of one or more TREM1 ligands to the TREM1 protein in the absence of the anti-TREM1 antibody. In some embodiments, the increase in one more TEM1 activities is measured by any suitable in vitro cell-based assays or suitable in vivo model, see, e.g., the Examples section or assays known in the art, for example, by utilizing a luciferase-based reporter assay to measure TREM1-dependent gene expression, using Western blot analysis to measure increase in TREM1-induced phosphorylation of downstream signaling partners, such as Syk, or by utilizing flow cytometry, such as fluorescence-activated cell sorting (FACS) to measure changes in cell surface levels of markers of TREM1 activation. Any in vitro cell-based assays or suitable in vivo model described herein or known in the art may be used to measure interaction (e.g., binding) between TREM1 and one or more TREM1 ligands.

As used herein, an anti-TREM1 antibody of the present disclosure is considered to not compete with, inhibit, or otherwise block the interaction (e.g., binding) between one or more TREM1 ligands and TREM1 if it decreases ligand binding to TREM1 by less than 20% at saturating antibody concentrations utilizing any in vitro assay or cell-based culture assay described herein or known in the art. In some embodiments, anti-TREM1 antibodies of the present disclosure inhibit interaction (e.g., binding) between one or more TREM1 ligands and TREM1 by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% at saturating antibody concentrations utilizing any in vitro assay or cell-based culture assay described herein or known in the art.

In some embodiments, an agonist anti-TREM1 antibody of the present disclosure induces one or more activities of TREM1 after binding to a TREM1 protein that is expressed on a cell. In some embodiments, the antibody induces one or more activities of TREM1 after binding to a soluble TREM1 protein that is not bound to the cell membrane. In certain embodiments, soluble TREM1 protein (sTREM1) is non-cellular. In certain embodiments, soluble TREM1 protein (sTREM1) may be found, without limitation, in extracellular milieu, in blood serum, in cerebrospinal fluid (CSF), and in the interstitial space within tissues. In some embodiments, anti-TREM1 antibodies of the present disclosure increase levels of soluble TREM1 protein (sTREM1) and/or increase the half-life of soluble TREM1 (sTREM1) protein.

The TREM1 activities induced or enhanced by anti-TREM1 agonist antibodies of the present disclosure and/or one or more TREM1 ligands of the present disclosure include, without limitation, TREM1 binding to DAP12; TREM1 phosphorylation and/or DAP12 phosphoryation; activation of one or more tyrosine kinases, e.g., a SRC tyrosine kinase, such as a Syk kinase, or ZAP70 kinase, or both; activation of phosphatidylinositol 3-kinase (PI3K); activation of protein kinase B (Akt); recruitment of phospholipase C-gamma (PLC-gamma) to a cellular plasma membrane, activation of PLC-gamma, or both; recruitment of TEC-family kinase dVav to a cellular plasma membrane; inhibition of MAPK signaling; phosphorylation of linker for activation of T cells (LAT), linker for activation of B cells (LAB), or both; or activation of IL-2-induced tyrosine kinase (Itk). Additoinal TREM1 activites induced or enhanced by anti-TREM1 agonist antibodies include (a) modulating expression and/or activity of one or more anti-inflammatory cytokines, optionally wherein the one or more anti-inflammatory cytokines are selected from IL-4, IL-10 TGF-β, IL-13, IL-35 IL-16, IFN-alpha, IL-1Rα, VEGF, G-CSF, and soluble receptors for TNF or IL-6; (b) modulating expression and/or activity of one or more anti-inflammatory cytokines in one or more cells selected from macrophages, e.g., M1 macrophages, activated M1 macrophages, and/or M2 macrophages; dendritic cells, bone marrow-derived dendritic cells, monocytes, osteoclasts, Langerhans cells of skin, Kupffer cells, and microglial cells; (c) modulating expression and/or activity of one or more pro-inflammatory cytokines, optionally wherein the one or more pro-inflammatory cytokines are selected from IFN-β, IL-1α, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, and MCP-1; (d) modulating expression and/or activity of one or more pro-inflammatory cytokines in one or more cells selected from macrophages, M1 macrophages, activated M1 macrophages, M2 macrophages; dendritic cells, bone marrow-derived dendritic cells, monocytes, osteoclasts, Langerhans cells of skin, Kupffer cells, and microglial cells; (e) activating extracellular signal-regulated kinase (ERK) phosphorylation; (f) activating tyrosine phosphorylation on multiple cellular proteins; (g) modulating expression of C-C chemokine receptor 7 (CCR7); (h) activating microglial cell chemotaxis toward CCL19 and CCL21 expressing cells; (i) increasing priming and/or modulating function of one or moreT cells, such as CD8+ T cells, CD4+ T cells and/or regulatory T cell by one or more cells selected from dendritic cells, bone marrow-derived dendritic cells, monocytes, microglia, M1 microglia, activated M1 microglia, M2 microglia, macrophages, M1 macrophages, activated M1 macrophages, and M2 macrophages; (j) activating osteoclast production, increasing rate of osteoclastogenesis, or both; (k) increasing survival of one or more cells selected from dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (j) increasingproliferation of one or more cells selected from dendritic cells, bone marrow-derived dendritic cells, macrophages, M1 macrophages, activated M1 macrophages, or M2 macrophages, monocytes, osteoclasts, T cells, T helper cells, cytotoxic T cells, granulocytes, neutrophils, microglia, M1 microglia, activated M1 microglia, and M2 microglia; (m) activating migration of one or more cells selected from dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (n) activating one or more functions of one or more cells selected from t dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (o) activating maturation of one or more cells selected from dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (p) activating one or more types of clearance selected from apoptotic neuron clearance, nerve tissue debris clearance, non-nerve tissue debris clearance, bacteria clearance, other foreign body clearance, disease-causing protein clearance, disease-causing peptide clearance, and tumor cell clearance; optionally wherein the disease-causing protein is selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and optionally where the tumor cell is from a cancer selected from bladder cancer, brain cancer, e.g., glioma such as low-grade glioma, or glioblastoma; breast cancer, cervical cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, and thyroid cancer; (q) inhibiting phagocytosis of one or more of apoptotic neurons, nerve tissue debris, non-nerve tissue debris, bacteria, other foreign bodies, disease-causing proteins, disease-causing peptides, disease-causing nucleic acids, or tumor cells; optionally wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and optionally where the tumor cells are from a cancer selected from bladder cancer, brain cancer, e.g., glioma such as low-grade glioma, or glioblastoma; breast cancer, cervical cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, or thyroid cancer; (r) binding to TREM1 ligand on tumor cells; (s) binding to TREM1 ligand on cells selected from neutrophils, dendritic cells, bone marrow-derived dendritic cells, monocytes, microglia, and macrophages; (t) activating tumor cell killing by one or more of microglia, macrophages, dendritic cells, bone marrow-derived dendritic cells, neutrophils, T cells, T helper cells, or cytotoxic T cells; (u) activating anti-tumor cell proliferation activity of one or more of microglia, macrophages, dendritic cells, bone marrow-derived dendritic cells, neutrophils, T cells, T helper cells, or cytotoxic T cells; (v) activating anti-tumor cell metastasis activity of one or more of microglia, macrophages, dendritic cells, bone marrow-derived dendritic cells, neutrophils, T cells, T helper cells, or cytotoxic T cells; (w) activating one or more ITAM motif containing receptors, optionally wherein the one or more ITAM motif containing receptors are selected from TREM1, TREM1, FcγR, DAP10, and DAP12; (x) activating signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; (y) activating one or more receptors comprising the motif D/Ex$_{0-2}$YxxL/IX$_{6-8}$YxxL/I; (z) activating signaling by one or more Toll-like receptors; (aa) activating the JAK-STAT signaling pathway; (bb) activating nuclear factor kappa-light-chain-enhancer of activated B cells (NFκB); (cc) phosphorylating an ITAM motif containing receptor; (dd) modulating expression of one or more inflammatory receptors, optionally wherein the one or more inflammatory receptors comprise CD86 and the one or more inflammatory receptors are expressed on one or more of microglia, macrophages, dendritic cells, bone marrow-derived dendritic cells, neutrophils, T cells, T helper cells, or cytotoxic T cells; (ee) increasing expression of one or more TREM1-dependent genes; (gg) normalizing disrupted TREM1-dependent gene expression; (ff) increasing expression of one or more ITAM-dependent genes, optionally wherein the one more ITAM-dependent genes are activated by nuclear factor of activated T cells (NFAT) transcription factors; (gg) inhibiting differentiation of one or more of immunosuppressor dendritic cells, immunosuppressor macrophages, myeloid derived suppressor cells, tumor-associated macrophages, immunosuppressor neutrophils, and regulatory T cells; (hh) inhibiting functionality of one or more of immunosuppressor dendritic cells, immunosuppressor macrophages, myeloid-derived suppressor cells, tumor-associated macrophages, immunosuppressor neutrophils, and regulatory T cells; (ii) decreasing infiltration of one or more of immunosuppressor dendritic cells, immunosuppressor macrophages, myeloid derived suppressor cells, tumor-associated macrophages, immunosuppressor neutrophils, and regulatory T cells into tumors; (jj) decreasing number of tumor-promoting myeloid/granulocytic immune-suppressive cells in a tumor, in peripheral blood, or other lymphoid organ; (kk) inhibiting tumor-promoting activity of myeloid-derived suppressor cells; (ll) decreasing expression of tumor-promoting cytokines in a tumor or in peripheral blood, optionally wherein the tumor-promoting cytokines are TGF-beta or IL-10; (mm)

decreasing tumor infiltration of tumor-promoting FoxP3+ regulatory T lymphocytes; (nn) increasing activation of tumor-specific T lymphocytes with tumor killing potential; (oo) decreasing tumor volume; (pp) decreasing tumor growth rate; (qq) increasing efficacy of one or more immune-therapies that modulate anti-tumor T cell responses, optionally wherein the one or more immune-therapies are selected from f PD1/PDL1 blockade, CTLA-4 blockade, and cancer vaccines; (rr) inhibiting PLCγ/PKC/calcium mobilization; (uu) inhibiting PI3K/Akt, Ras/MAPK signaling; (ss) increasing phagocytosis by dendritic cells, macrophages, monocytes, and/or microglia (tt) inducing or maintaining TREM1 clustering on a cell surface; (yy) increasing memory; and (zz) reducing cognitive deficit.

In some embodiments, antibody cross-linking is required for agonist antibody function. Antibody cross-linking can occur through binding to a secondary antibody in vitro or through binding to Fc receptors in vivo. For example, antagonistic antibodies can be converted to agonistic antibodies via biotin/streptavidin cross-linking or secondary antibody binding in vitro (see for example Gravestein et al., (1996) J. Exp. Med. 184:675-685; Gravestein et al., (1994) International Immunol. 7:551-557). Agonistic antibodies may exert their activity by mimicking the biological activity of the receptor ligand or by enhancing receptor aggregation, thereby activating receptor signaling.

An antibody dependent on binding to FcγR receptor to activate targeted receptors may lose its activity if engineered to eliminate FcγR binding (see, e.g., Wilson et al., (2011) Cancer Cell 19, 101-113; Armour at al., (2003) Immunology 40 (2003) 585-593); and White et al., (2015) Cancer Cell 27, 138-148). As such, it is thought that an anti-TREM1 antibody of the present disclosure with the correct epitope specificity can be an agonist antibody and activate the target antigen, with minimal adverse effects, when the antibody has an Fc domain from a human IgG2 isotype (CH1 and hinge region) or another type of Fc domain that is capable of preferentially binding the inhibitory FcγRIIB receptors, or a variation thereof.

Exemplary agonist antibody Fc isotypes and modifications are provided in Table A below. In some embodiments, the agonist antibody has an Fc isotype listed in Table A below.

TABLE A

Exemplary anti-TREM1 antibody Fc isotypes

| Fc Isotype | Mutation (EU or Kabat numbering scheme) |
|---|---|
| IgG1 | N297A |
| IgG1 | D265A and N297A |
| IgG1 | D270A |
| IgG1 | L234A and L235A<br>L234A and G237A<br>L234A and L235A and G237A |
| IgG1 | P238D and/or L328E and/or S267E/L328F and/or E233 and or/ G237D and/or H268D and/or P271G and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |
| IgG1 | P238D and S267E and L328F and G237D and H268D and P271G and A330R |
| IgG2 | V234A and G237A |
| IgG4 | L235A and G237A and E318A |
| IgG4 | S228P and L236E |
| IgG2/4 hybrid | IgG2 aa 118 to 260 and IgG4 aa 261 to 447<br>H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E, and L328F<br>S267E alone |
| IgG2 | S267E and L328F |

TABLE A-continued

Exemplary anti-TREM1 antibody Fc isotypes

| Fc Isotype | Mutation (EU or Kabat numbering scheme) |
|---|---|
| IgG4 | S267E and L328F |
| IgG2 | WT HC with Kappa (light chain) LC<br>HC C127S with Kappa LC<br>Kappa LC C214S<br>Kappa LC C214S and HC C233S<br>Kappa LC C214S and HC C232S<br>Any of the above listed mutations together with P330S and P331S mutations<br>F(ab')2 fragment of WT IgG1 and any of the above listed mutations |
| IgG1 | Substitute the Constant Heavy 1 (CH1) and hinge region of IgG1 With CH1 and hinge region of IGg2<br>ASTKGPSVFP LAPCSRSTSE STAALGCLVK<br>DYFPEPVTVS WNSGALTSGV HTFPAVLQSS<br>GLYSLSSVVT VPSSNFGTQT YTCNVDHKPS<br>NTKVDKTVER KCCVECPPCP (SEQ ID NO: 476)<br>With a Kappa LC |
| IgG1 | Any of the above listed mutations together with A330L and/ or L234F and/or L235E and/or P331S |
| IgG1, IgG2, or IgG4 | Any of the above listed mutations together with M252Y and/or 5254T and/or T256E |
| Mouse IgG1 | For mouse disease models |
| IgG4 | WT |

In addition to the isotypes described in Table A, and without wishing to be bound to theory, it is thought that antibodies with human IgG1 or IgG3 isotypes and mutants thereof (e.g. Strohl (2009) Current Opinion in Biotechnology 2009, 20:685-691) that bind the activating Fcγ Receptors I, IIA, IIC, IIIA, IIIB in human and/or Fcγ Receptors I, III and IV in mouse, may also act as agonist antibodies in vivo but may be associated with adverse effects related to ADCC. However, such Fcγ receptors appear to be less available for antibody binding in vivo, as compared to the Inhibitory Fcγ receptor FcγRIIB (see, e.g., White, et al., (2013) Cancer Immunol. Immunother. 62, 941-948; and Li et al., (2011) Science 333(6045):1030-1034.).

In some embodiments, the agonist antibody is of the IgG class, the IgM class, or the IgA class. In some embodiments, the agonist antibody has an IgG1, IgG2, IgG3, or IgG4 isotype.

In certain embodiments, the agonist antibody has an IgG2 isotype. In some embodiments, the agonist antibody contains a human IgG2 constant region. In some embodiments, the human IgG2 constant region includes an Fc region. In some embodiments, the agonist antibody induces the one or more TREM1 activities, the DAP12 activities, or both independently of binding to an Fc receptor. In some embodiments, the agonist antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) *Transplantation* 57:1537-1543. 31; Xu et al., (2000) *Cell Immunol*, 200:16-26), G237A (Cole et al. (1999) *Transplantation*, 68:563-571), H268Q, V309L, A330S, P331S (US 2007/0148167; Armour et al. (1999) *Eur J Immunol* 29: 2613-2624; Armour et al. (2000) *The Haematology Journal* 1(Suppl.1):27; Armour et al. (2000) *The Haematology Journal* 1(Suppl.1):27), C232S, and/or C233S (White et al.(2015) *Cancer Cell* 27, 138-148), S267E, L328F (Chu et al., (2008) *Mol Immunol,* 45:3926-3933), M252Y, S254T, and/or T256E, where the amino acid position is according to the EU or, Kabat numbering convention.

In some embodiments, the agonist antibody has an IgG2 isotype with a heavy chain constant domain that contains a C127S amino acid substitution, where the amino acid position is according to the EU or, Kabat numbering convention (White et al., (2015) *Cancer Cell* 27, 138-148; Lightle et al., (2010) *PROTEIN SCIENCE* 19:753-762; and WO2008079246).

In some embodiments, the agonist antibody has an IgG2 isotype with a Kappa light chain constant domain that contains a C214S amino acid substitution, where the amino acid position is according to the EU or, Kabat numbering convention (White et al., (2015) *Cancer Cell* 27, 138-148; Lightle et al., (2010) *PROTEIN SCIENCE* 19:753-762; and WO2008079246).

In certain embodiments, the agonist antibody has an IgG1 isotype. In some embodiments, the agonist antibody contains a mouse IgG1 constant region. In some embodiments, the agonist antibody contains a human IgG1 constant region. In some embodiments, the human IgG1 constant region includes an Fc region. In some embodiments, the agonist antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU or, Kabat numbering convention.

In some embodiments, the antibody includes an IgG2 isotype heavy chain constant domain 1 (CH1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYF-PEPVTVSWNSGALTSGVHTFPAVLQSSGLYS-LSSVVTVPSSNFGTQTYTCNVDHKPSNTKVDKTVER KCCVECPPCP (SEQ ID NO: 476). In some embodiments, the antibody Fc region contains a S267E amino acid substitution, a L328F amino acid substitution, or both, and/or a N297A or N297Q amino acid substitution, where the amino acid position is according to the EU or, Kabat numbering convention.

In certain embodiments, the agonist antibody has an IgG4 isotype. In some embodiments, the agonist antibody contains a human IgG4 constant region. In some embodiments, the human IgG4 constant region includes an Fc region. In some embodiments, the agonist antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) *J Immunol,* 164:1925-1933), S267E, E318A, L328F, M252Y, S254T, and/or T256E, where the amino acid position is according to the EU or, Kabat numbering convention.

In certain embodiments, the agonist antibody has a hybrid IgG2/4 isotype. In some embodiments, the agonist antibody includes an amino acid sequence containing amino acids 118 to 260 according to EU or, Kabat numbering of human IgG2 and amino acids 261-447 according to EU or, Kabat numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from A330L, L234F; L235E, or P331S according to EU or, Kabat numbering; and any combination thereof.

Inert Antibodies

Another class of antibodies of the present disclosure includes inert antibodies. As used herein, "inert" antibodies refer to antibodies that specifically bind their target antigen but do not modulate (e.g., decrease/inhibit or activate/induce) antigen function. For example, in the case of TREM1, inert antibodies do not modulate ligand binding and/or TREM1 activities. Without wishing to be bound to theory, it is thought that antibodies that do not have the ability to cluster TREM1 on the cell surface may be inert antibodies even if they have an epitope specificity that is compatible with receptor activation.

In some embodiments, antibodies that bind a TREM1 protein may include antibodies that bind TREM1 but, due to their epitope specificity, do not modulate protein function. Such functionally inert antibodies can be used as cargo to transport toxins or to tumor cells as described for the CD33 antibody Gemtuzumab zogamicin, (marketed as Mylotarg) which is conjugated to the cytotoxic agent from the class of calicheamicins and is used to target and kill acute myelogenous leukemia tumors (Naito et al., (2000), Leukemia, 14, 1436-1443; Ricart (2011) Clin Cancer Res 17; 6417-6436; Hamann et al., (2002) Journal: Bioconjugate Chemistry, 13, 47-58; and Beitz et al., (2001) Clin Cancer Res 7; 1490-6.). Therefore, in some embodiments, antibodies of the present disclosure are inert antibodies that bind TREM1 but are incapable of inducing one or more TREM1 activities (e.g., a TREM1 activity described herein).

Exemplary inert antibody Fc isotypes and modifications are provided in Table B below. In some embodiments, the inert antibody has an Fc isotype listed in Table B below.

Antagonistic Anti-TREM1 Antibodies

Another class of antibodies is antagonistic antibodies. In some embodiments, antibodies that bind a TREM1 protein may include antagonist antibodies that bind TREM1 and inhibit one or more TREM1 activities, either by preventing interaction between TREM1 and one or more TREM1 ligands, or by preventing the transduction of signal from the extracellular domain of TREM1 into the cell cytoplasm in the presence of ligand.

TREM1 receptor is thought to require clustering on the cell surface in order to transduce a signal. Thus, in some embodiments, antagonist antibodies may have unique features to inhibit TREM1 receptor clustering on the cell surface. For example, such antibodies may have the correct epitope specificity that is compatible with receptor inhibition, as well as the ability to block or reverse receptor clustering on the cell surface. In some embodiments, antagonist antibodies of the present disclosure may have the epitope specificity of an agonist antibody of the present disclosure, but have an Fc domain that is not capable of binding Fcγ receptors and thus is unable to cluster the TREM1 receptor.

In some embodiments, the antagonist antibody decreases activity of one or more TREM1-dependent genes. In some embodiments, the anti-TREM1 antibody decreases levels of TREM1 in one or more cells (e.g., cell surface levels, intracellular levels, or total levels). In some embodiments, the anti-TREM1 antibody induces degradation of TREM1. In some embodiments, the anti-TREM1 antibody induces cleavage of TREM1. In some embodiments, the anti-TREM1 antibody induces internalization of TREM1. In some embodiments, the anti-TREM1 antibody induces shedding of TREM1. In some embodiments, the anti-TREM1 antibody induces downregulation of TREM1 expression. In some embodiments, the anti-TREM1 antibody inhibits interaction (e.g., binding) between TREM1 and one or more TREM1 ligands. In some embodiments, the anti-TREM1 antibody transiently activates and then induces degradation of TREM1. In some embodiments, the anti-TREM1 antibody transiently activates and then induces cleavage of TREM1. In some embodiments, the anti-TREM1 antibody transiently activates and then induces internalization of TREM1. In some embodiments, the anti-TREM1 antibody transiently activates and then induces shedding of TREM1.

In some embodiments, the anti-TREM1 antibody transiently activates and then induces downregulation of TREM1 expression. In some embodiments, the anti-TREM1 antibody transiently activates and then induces decreased expression of TREM1. In certain embodiments, the individual has a TREM1 variant allele. In some embodiments, the anti-TREM1 antibody acts in solution.

In some instances, antagonist-TREM1 antibodies of the present disclosure may bind TREM1 and block the binding of one or more TREM1 ligands. The anti-TREM1 antibodies of the present disclosure may further exhibit inhibitory interactions with one or more TREM1 ligands. Thus, in some embodiments, the maximal activity of TREM1 when bound to anti-TREM1 antibodies as described herein in combination with one or more TREM1 ligands of the present disclosure may be lower (e.g., reduced) than the maximal activity of TREM1 when exposed to saturating concentrations of ligand. In addition, the activity of TREM1 at a given concentration of TREM1 ligand may be smaller (e.g., reduced) in the presence of the antibody. Accordingly, in some embodiments, anti-TREM1 antibodies of the present disclosure have an disruptive effect with the one or more TREM1 ligands to inhibit the one or more TREM1 activities when bound to the TREM1 protein. In some embodiments, anti-TREM1 antibodies of the present disclosure decrease the potency of the one or more TREM1 ligands to induce the one or more TREM1 activities, as compared to the potency of the one or more TREM1 ligands to induce the one or more TREM1 activities in the absence of the antibody. In some embodiments, anti-TREM1 antibodies of the present disclosure inhibit the one or more TREM1 activities in the presence of cell surface clustering of TREM1. In some embodiments, anti-TREM1 antibodies of the present disclosure inhibit the one or more TREM1 activities by blocking or reducing cell surface clustering of TREM1. In some embodiments, anti-TREM1 antibodies of the present disclosure are clustered by one or more Fc-gamma receptors expressed on one or more immune cells, including without limitation, B cells and microglial cells. In some embodiments, inhibition of the one or more TREM1 activities induced by binding of one or more TREM1 ligands to the TREM1 protein is measured on primary cells, including without limitation, dendritic cells, bone marrow-derived dendritic cells, monocytes, microglia, macrophages, neutrophils, NK cells, osteoclasts, Langerhans cells of skin, and Kupffer cells, or on cell lines, and the inhibition of the one or more TREM1 activities induced by binding of one or more TREM1 ligands to the TREM1 protein is measured, for example, utilizing an in vitro cell assay.

In some embodiments the antibody inhibits one or more activities of TREM1 after binding to a soluble TREM1 protein that is not bound to the cell membrane. In certain embodiments, soluble TREM1 protein (sTREM1) may be found, without limitation, in extracellular milieu, in blood serum, in cerebrospinal fluid (CSF), and in the interstitial space within tissues. In certain embodiments, soluble TREM1 protein (sTREM1) is non-cellular. In some embodiments, anti-TREM1 antibodies of the present disclosure increase levels of soluble TREM1 protein (sTREM1) and/or increase the half-life of soluble TREM1 protein (sTREM1).

The TREM1 activities inhibited by anti-TREM1 antibodies of the present disclosure may include one or more of the following, (a) modulating expression of one or more anti-inflammatory cytokines, optionally wherein the one or more anti-inflammatory cytokines are selected from IL-4, IL-10 TGF-β, IL-13, IL-35 IL-16, IFN-alpha, IL-1Ra, VEGF, G-CSF, and soluble receptors for TNF or IL-6; (b) modulating expression of one or more anti-inflammatory cytokines in one or more cells selected from macrophages, dendritic cells, bone marrow-derived dendritic cells, monocytes, osteoclasts, and microglial cells; (c) modulating expression of one or more pro-inflammatory cytokines, optionally wherein the one or more pro-inflammatory cytokines are selected from IFN-β, IL-1α, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, and MCP-1; (d) modulating expression of one or more pro-inflammatory cytokines in one or more cells selected from macrophages, dendritic cells, bone marrow-derived dendritic cells, monocytes, osteoclasts, and microglial cells; (e) activating extracellular signal-regulated kinase (ERK) phosphorylation; (f) activating tyrosine phosphorylation on multiple cellular proteins; (g) modulating expression of C-C chemokine receptor 7 (CCR7); (h) activating microglial cell chemotaxis toward CCL19 and CCL21 expressing cells; (i) increasing priming and/or modulating function of one or more T cells, such as CD8+ T cells, CD4+ T cells and/or regulatory T cell by one or more cells selected from dendritic cells, bone marrow-derived dendritic cells, monocytes, microglia, M1 microglia, activated M1 microglia, M2 microglia, macrophages, M1 macrophages, activated M1 macrophages, and M2 macrophages; (j) activating osteoclast production, increased rate of osteoclastogenesis, or both; (k) increasing survival of one or more cells selected from dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1; microglia, Myeloid-Derived Suppressor Cells, Gr-1$^+$CD11$^+$ myeloid cells, and M2 microglia (1) increasing proliferation of one or more cells selected from dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, Myeloid-Derived Suppressor Celts, Gr-1$^+$CD11b$^+$ myeloid cells, microglia, M1 microglia, activated M1 microglia, and M2 microglia; (m) activating migration of one or more cells selected from dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (n) activating one or more functions of one or more cells selected from t dendritic cells, Myeloid-Derived Suppressor Cells, Gr-1$^+$CD11b$^+$ myeloid cells, bone marrow-derived dendritic cells, macrophages, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (o) activating maturation of one or more cells selected from dendritic cells, bone marrow-derived dendritic cells, macrophages, Myeloid-Derived Suppressor Cells, Gr-1$^+$CD11b$^+$ myeloid cells, M1 macrophages, activated M1 macrophages, M2 macrophages, monocytes, osteoclasts, T cells, T helper cells, cytotoxic T cells, granulocytes, neutrophils, microglia, M1 microglia, activated M1 microglia, and M2 microglia; (p) binding to TREM1 ligand on tumor cells; (q) binding to TREM1 ligand on cells selected from neutrophils, dendritic cells, bone marrow-derived dendritic cells, monocytes, microglia, and macrophages; (r) activating of one or more ITAM motif containing receptors, optionally wherein the one or more ITAM motif containing receptors are selected from TREM1, TREM1, FcγR, DAP10, and DAP12; (x) activating of signaling by one or more pattern recognition receptors (PRRs), optionally wherein the one or more PRRs are selected from receptors that identify pathogen-associated molecular patterns (PAMPs), receptors that identify damage-associated molecular patterns (DAMPs), and any combination thereof; (y) activating of one or more receptors comprising the motif $D/Ex_{0-2}YxxL/IX_{6-8}YxxL/I$; (z) activating of signaling by one or more Toll-like receptors; (aa) activating of the JAK-STAT signaling pathway; (bb) activating of nuclear factor kappa-light-chain-enhancer of activated B cells (NFκB); (cc) phosphorylation of an ITAM motif containing receptor; (dd) modulated expression of one or more inflammatory receptors, optionally wherein the one or more inflammatory receptors comprise CD86 and the one or more inflammatory receptors are expressed on one or more of microglia, macrophages, dendritic cells, bone marrow-derived dendritic cells, neutrophils, T cells, T helper cells, or cytotoxic T cells; (ee) increasing expression of one or more TREM1-dependent genes; (gg) normalization of disrupted TREM1-dependent gene expression; (ff) increasing expression of one or more ITAM-dependent genes, optionally wherein the one more ITAM-dependent genes are activated by nuclear factor of activated T cells (NFAT) transcription factors; (gg) activating differentiation of one or more of immunosuppressor dendritic cells, immunosuppressor macrophages, myeloid derived suppressor cells, tumor-associated macrophages, immunosuppressor neutrophils, and regulatory T cells; (hh) activating functionality of one or more of immunosuppressor dendritic cells, immunosuppressor macrophages, myeloid-derived suppressor cells, tumor-associated macrophages, immunosuppressor neutrophils, and regulatory T cells; (ii) increasing infiltration of one or more of immunosuppressor dendritic cells, immunosuppressor macrophages, myeloid derived suppressor cells, tumor-associated macrophages, immunosuppressor neutrophils, and regulatory T cells into tumors; (jj) increasing number of tumor-promoting myeloid/granulocytic immune-suppressive cells in a tumor, in peripheral blood, or other lymphoid organ; (kk) stimulating tumor-promoting activity of myeloid-derived suppressor cells; (ll) increasing expression of tumor-promoting cytokines in a tumor or in peripheral blood, optionally wherein the tumor-promoting cytokines are TGF-beta or IL-10; (mm) decreasing tumor infiltration of tumor-promoting FoxP3+ regulatory T lymphocytes; (nn) decreasing activation of tumor-specific T lymphocytes with tumor killing potential; (oo) increasing tumor volume; (pp) increasing tumor growth rate; (qq) decreasing efficacy of one or more immune-therapies that modulate anti-tumor T cell responses, optionally wherein the one or more immune-therapies are selected from f PD1/PDL1 blockade, CTLA-4 blockade, and cancer vaccines; (rr) inhibition of PLCγ/PKC/calcium mobilization; and (uu) inhibition of PI3K/Akt, Ras/MAPK signaling. (ss) induction or retaintion of TREM1 clustering on a cell surface; (xx) TREM1 binding to DAP12; (uu) TREM1 phosphorylation; (vv) DAP12 phosphorylation; (ww) TREM1 phosphorylation; (xx) activation of one or more SRC family tyrosine kinases including Syk kinase; yy) modulating expression of one or more proteins selected from the group consisting of C1qa, C1qB, C1qC, C1s, C1R, C4, C2, C3, ITGB2, HMOX1, LAT2. CASP1, CSTA, VSIG4, MS4A4A, C3AR1, GPX1, TyroBP, ALOX5AP, ITGAM, SLC7A7, CD4, ITGAX, PYCARD, and VEGF1 (zz) increasing memory; and (aaa) reducing cognitive deficit.

In some embodiments, the antagonist antibody decreases the survival of macrophages, microglial cells, M1 macrophages, M1 microglial cells, M2 macrophages, M2 microglial cells, osteoclasts, Langerhans cells of skin, Kupffer cells, and/or dendritic cells. In some embodiments, the antagonist antibody inhibits interaction between TREM1 and one or more TREM1 ligands. In some embodiments, the antagonist antibody inhibits TREM1 signal transduction. In some embodiments, the antagonist antibody inhibits interaction between TREM1 and one or more TREM1 ligands and inhibits TREM1 signal transduction. In some embodiments, the antagonist antibody inhibits TREM1 interaction with DAP12.

As explained above, in some embodiments, TREM1 antagonist antibodies may inhibit expression of one or more TREM1-dependent genes, including, without limitation, one or more nuclear factor of activated T-cells (NFAT) transcription factors.

Levels of TREM1 in one or more cells (e.g., cellular levels) may refer to, without limitation, cell surface levels of TREM1, intracellular levels of TREM1, and total levels of TREM1. In some embodiments, a decrease in cellular levels of TREM1 comprises decrease in cell surface levels of TREM1. As used herein, cell surface levels of TREM1 may be measured by any in vitro cell-based assays or suitable in vivo model described herein or known in the art, for example, utilizing flow cytometry, such as fluorescence-activated cell sorting (FACS), to measure cell surface levels of TREM1. In some embodiments, a decrease in levels of TREM1 in cells comprises a decrease in intracellular levels of TREM1. As used herein intracellular levels of TREM1 may be measured by any in vitro cell-based assays or suitable in vivo model described herein or known in the art, for example immunostaining, Western blot analysis, co-immunoprecipitation, and cell cytometry. In some embodiments, a decrease in cellular levels of TREM1 comprises a decrease in total levels of TREM1. As used herein, total levels of TREM1 may be measured by any in vitro cell-based assays or suitable in vivo model described herein or known in the art, for example immunostaining, Western blot analysis, co-immunoprecipitation, and cell cytometry. In some embodiments, the anti-TREM1 antibodies induce TREM1 degradation, TREM1 cleavage, TREM1 internalization, TREM1 shedding, and/or downregulation of TREM1 expression. In some embodiments, levels of TREM1 in one or more cells (e.g., cellular levels) are measured on primary cells (e.g., dendritic cells, bone marrow-derived dendritic cells, monocytes, microglia, and macrophages) or on cell lines utilizing an in vitro cell assay. In some embodiments, anti-TREM1 antibodies of the present disclosure decrease cellular levels of TREM1 by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or more as compared to cellular levels of TREM1 in the absence of the anti-TREM1 antibody. Any in vitro cell-based assays or suitable in vivo model described herein or known in the art may be used to measure inhibition of interaction (e.g., binding) between TREM1 and one or more TREM1 ligands. In some embodiments, anti-TREM1 antibodies of the present disclosure inhibit interaction (e.g., binding) between TREM1 and one or more TREM1 ligands by a at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or more at saturating antibody concentrations utilizing any in vitro assay or cell-based culture assay described herein or known in the art.

In some embodiments, the absence of antibody cross-linking is required for antagonistic activity. In some embodiments, the antibody will act as antagonistic when presented as monomer and as an agonist when presented as a dimer or a multimer. Antagonistic antibodies may exert their activity by blocking receptor-ligand interactions.

Exemplary antagonist antibody Fc isotypes and modifications are provided in Table B below. In some embodiments, the antagonist antibody has an Fc isotype listed in Table B below.

Exemplary Fc Isotypes of Inert and Antagonist Antibodies

In some embodiments, inert and/or antagonist anti-TREM antibodies have an Fc isotype listed in Table B below.

TABLE B

Exemplary anti-TREM1 antibody Fc isotypes with reduced binding to Fc gamma receptor

| Fc Isotype | Mutation (EU or Kabat numbering scheme) |
| --- | --- |
| IgG1 | N297A or N297Q |
| IgG1 | D265A and N297A |
| IgG1 | L234A and L235A |
| IgG2 | V234A and G237A |
| IgG4 | F235A and G237A and E318A |
|  | E233P and/or F234V |
|  | N297A or N297Q |
| IgG4 | S228P and L236E |
|  | S241P |
|  | S241P and L248E |
|  | S228P and F234A and L235A |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
|  | P238A |
|  | D265A |
|  | N297A |
|  | A327Q or A327G |
|  | P329A |
| IgG1 | K322A and L234A and L235A |
| IgG1 | L234F and L235E and P331S |
| IgG1 or IgG4 | T394D |
| IgG2 | C232S or C233S |
|  | N297A or N297Q |
| IgG2 | V234A and G237A and P238S and H268A and V309L and A330S and P331S |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A, N297Q (Bolt S et al. (1993) Eur J Immunol 23:403-411), D265A, L234A, L235A (McEarchern et al., (2007) Blood, 109:1185-1192), C226S, C229S (McEarchern et al., (2007) Blood, 109:1185-1192), P238S (Davis et al., (2007) J Rheumatol, 34:2204-2210), E233P, L234V (McEarchern et al., (2007) Blood, 109:1185-1192), P238A, A327Q, A327G, P329A (Shields R L. et al., (2001) J Biol Chem. 276(9):6591-604), K322A, L234F, L235E (Hezareh, et al., (2001) J Virol 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU or, Kabat numbering convention. In certain embodiments, the Fc region further includes an amino acid deletion at a position corresponding to glycine 236 according to the EU or, Kabat numbering convention.

In some embodiments, the antibody has an IgG1 isotype with a heavy chain constant region that contains a C220S amino acid substitution according to the EU or, Kabat numbering convention.

In some embodiments, the Fc region further contains one or more additional amino acid substitutions selected from t A330L, L234F; L235E, and/or P331S according to EU or, Kabat numbering convention.

In certain embodiments, the antibody has an IgG2 isotype. In some embodiments, the antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A, G237A, H268E, V309L, N297A, N297Q, A330S, P331S, C232S, C233S, M252Y, S254T, and/or T256E, where the amino acid position is according to the EU or, Kabat numbering convention.

In certain embodiments, the antibody has an IgG4 isotype. In some embodiments, the antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) Proc Natl Acad Sci USA, 92:11980-11984), S228P, L236E, S241P, L248E (Reddy et al., (2000) J Immunol, 164:1925-1933; Angal et al., (1993) Mol Immunol. 30(1): 105-8; U.S. Pat. No. 8,614,299 B2), T394D, M252Y, S254T, T256E, and/or N297A, N297Q, where the amino acid position is according to the EU or, Kabat numbering convention.

In some embodiments, the Fc region further contains one or more additional amino acid substitutions selected from a M252Y, S254T, and/or T256E, where the amino acid position is according to the EU or, Kabat numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU or, Kabat numbering convention, to eliminate complement activation. In some embodiments, the IgG variants described herein may be combined with one or more mutations to enhance the antibody half-life in human serum (e.g. M252Y, S254T,T256E mutations according to the EU or, Kabat numbering convention) (Dall'Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU or, Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

Exemplary Anti-TREM1 Antibodies

Anti-TREM1 antibodies of the present disclosure may be tested for inducing or blocking one or more TREM1 activities as described in the above sections.

In some embodiments, the anti-TREM1 antibodies of the present disclosure are monoclonal antibodies.

In some embodiments, an isolated anti-TREM1 antibody of the present disclosure enhances one or more TREM1 activities induced by binding of one or more TREM1 ligands to the TREM1 protein, as compared to the one or more TREM1 activities induced by binding of the one or more TREM1 ligands to the TREM1 protein in the absence of the isolated antibody. In some embodiments, the anti-TREM1 antibody enhances one or more TREM1 activities without competing with or otherwise blocking binding of the one or more TREM1 ligands to the TREM1 protein. In some embodiments, the antibody is a human antibody, a humanized antibody, a bispecific antibody, a multivalent antibody, or a chimeric antibody. Exemplary descriptions of such antibodies are found throughout the present disclosure. In some embodiments, the antibody is a bispecific antibody recognizing a first antigen and a second antigen.

In some embodiments, anti-TREM1 antibodies of the present disclosure bind to a human TREM1, or a homolog thereof, including without limitation a mammalian TREM1 protein human TREM1 protein (Uniprot Accession No. Q9NP99; SEQ ID NO: 1), mouse TREM1 protein (Uniprot Accession No. Q9JKE2; SEQ ID NO: 2), rat TREM1 protein (Uniprot Accession No. D4ABU7; SEQ ID NO: 3), Rhesus monkey TREM1 protein (Uniprot Accession No. F6TBB4; SEQ ID NO: 4), bovine TREM1 protein (Uniprot Accession No. Q6QUN5; SEQ ID NO: 5), equine TREM1 protein (Uniprot Accession No. F6PSF7; SEQ ID NO: 6), pig TREM1 protein (Uniprot Accession No. R4SEY7; SEQ ID NO: 7), Chimpanzee TREM1 protein (Uniprot Accession No. H2QSZ3; SEQ ID NO:561) and dog TREM1 protein (Uniprot Accession No. E2RP37; SEQ ID NO: 8). In some embodiments, anti-TREM1 antibodies of the present disclosure specifically bind to human TREM1. In some embodiments, anti-TREM1 antibodies of the present disclosure specifically bind to mouse TREM1. In some embodiments, anti-TREM1 antibodies of the present disclosure specifically bind to both human TREM1 and mouse TREM1. In some embodiments, anti-TREM1 antibodies of the present disclosure modulate (e.g., induce or inhibit) at least one TREM1 activity as described herein In some embodiments, anti-TREM1 antibodies of the present disclosure bind to membrane bound or soluble form of a TREM1 protein of the present disclosure and/or naturally occurring variants. In certain preferred embodiments, the anti-TREM1 antibodies bind to human TREM1.

In some embodiments, anti-TREM1 antibodies of the present disclosure are agonist antibodies or antagonist antibodies that bind to a TREM1 protein of the present disclosure expressed on the surface of a cell and modulate (e.g., induce or inhibit) at least one TREM1 activity of the present disclosure after binding to the surface-expressed TREM1 protein. In some embodiments, anti-TREM1 antibodies of the present disclosure are inert antibodies.

Illustrative assays for assessing antibody binding to TREM1 and the effects of an anti-TREM1 antibody on TREM1-mediated activity are provided in the Examples section.

Anti-TREM1 Antibody-Binding Regions

Certain aspects of the present disclosure provide anti-TREM1 antibodies that bind to one or more amino acids within amino acid residues 21-205 of human TREM1 (SEQ ID NO: 1), or within amino acid residues on a TREM1 homolog or ortholog corresponding to amino acid residues 21-205 of SEQ ID NO: 1. In some embodiments, the anti-TREM1 antibody binds to one or more amino acids within amino acid residues 26-134 of human TREM1 (SEQ ID NO: 1), or within amino acid residues on a TREM1 homolog or ortholog corresponding to amino acid residues 26-134 of SEQ ID NO: 1. In some embodiments, the anti-TREM1 antibody binds to one or more amino acids within amino acid residues 45-54 of human TREM1 (SEQ ID NO: 1), or within amino acid residues on a TREM1 homolog or ortholog corresponding to amino acid residues 45-54 of SEQ ID NO: 1. In some embodiments, the anti-TREM1 antibody binds to one or more amino acids within amino acid residues 70-79 of human TREM1 (SEQ ID NO: 1), or within amino acid residues on a TREM1 homolog or ortholog corresponding to amino acid residues 70-79 of SEQ ID NO: 1. In some embodiments, the anti-TREM1 antibody binds to one or more amino acids within amino acid residues 89-97 of human TREM1 (SEQ ID NO: 1), or within amino acid residues on a TREM1 homolog or ortholog corresponding to amino acid residues 89-97 of SEQ ID NO: 1. In some embodiments, the anti-TREM1 antibody binds to one or more amino acids within amino acid residues 119-125 of human TREM1 (SEQ ID NO: 1), or within amino acid residues on a TREM1 homolog or ortholog corresponding to amino acid residues 119-125 of SEQ ID NO: 1. In some embodiments, the anti-TREM1 antibody binds to one or more amino acids within amino acid residues 83-90 of human TREM1 (SEQ ID NO: 1), or within amino acid residues on a TREM1 homolog or ortholog corresponding to amino acid residues 83-90 of SEQ ID NO: 1. In some embodiments, the anti-TREM1 antibody binds to one or more amino acids within amino acid residues 191-201 of human TREM1 (SEQ ID NO: 1), or within amino acid residues on a TREM1 homolog or ortholog corresponding to amino acid residues 191-201 of SEQ ID NO: 1. In some embodiments, the anti-TREM1 antibody binds to one or more amino acids within amino acid residues 116-125 of human TREM1 (SEQ ID NO: 1), or within amino acid residues on a TREM1 homolog or ortholog corresponding to amino acid residues 116-125 of SEQ ID NO: 1.

In some embodiments, anti-TREM1 antibodies of the present disclosure competitively inhibit binding of at least one antibody selected from any of the antibodies listed in Tables 2-5. In some embodiments, anti-TREM1 antibodies of the present disclosure competitively inhibit binding of at least one antibody selected from T1-1-T1-80 or at least one antibody selected from T1-1-T1-25 and T1-33 and -T1-80.

In some embodiments, anti-TREM1 antibodies of the present disclosure bind to an epitope of human TREM1 that is the same as or overlaps with the TREM1 epitope bound by at least one antibody selected from any of the antibodies listed in Tables 2-5. In some embodiments, anti-TREM1 antibodies of the present disclosure bind to an epitope of human TREM1 that is the same as or overlaps with the TREM1 epitope bound by at least one antibody selected from T1-1-T1-80 or at least one antibody selected from T1-1-T1-25 and T1-33 and -T1-80.

In some embodiments, anti-TREM1 antibodies of the present disclosure bind essentially the same TREM1 epitope bound by at least one antibody selected from any of the antibodies listed in Tables 2-5. In some embodiments, anti-TREM1 antibodies of the present disclosure bind essentially the same TREM1 epitope bound by at least one antibody selected from T1-1-T1-80 or at least one antibody selected from T1-1-T1-25 and T1-33 and -T1-80. Detailed exemplary methods for mapping an epitope to which an antibody binds are provided in Morris (1996) "Epitope Mapping Protocols," in *Methods in Molecular Biology* vol. 66 (Humana Press, Totowa, NJ) and in Example 2 of the present disclosure. In some embodiments, an anti-TREM1 antibody of the present disclosure binds essentially the same epitope as T1-62 or essentially the same epitope as T1-63. In some embodiments, an anti-TREM1 antibody of the present disclosures binds essentially the same epitope as T1-34, essentially the same epitope as T1-39, or essentially the same epitope as T1-40. In some embodiments, an anti-TREM1 antibody of the present disclosure binds to an epitope comprising amino acids 83-90 and 191-201 of SEQ ID NO:1. In some embodiments, an anti-TREM1 antibody binds to an epitope comprising amino acids 45-54, 70-79, 89-97, and 119-125 of SEQ ID NO:1

In some embodiments, anti-TREM1 antibodies of the present disclosure compete with one or more antibodies selected from T1-1-T1-80 for binding to TREM1. In some embodiments, anti-TREM1 antibodies of the present disclosure compete with one or more antibodies selected from T1-1-T1-25 and T1-33-T1-80 for binding to TREM1. In some embodiments, an anti-TREM1 antibody of the present disclosure competes with T1-62 for binding to TREM1. In some embodiments, an anti-TREM1 antibody of the present disclosure competes with T1-63 for binding to TREM1. In some embodiments, an anti-TREM1 antibody of the present disclosure competes with T1-34 for binding to TREM1. In some embodiments, an anti-TREM1 antibody of the present disclosure competes with T1-39 for binding to TREM1. In some embodiments, an anti-TREM1 antibody of the present disclosure competes with T1-40 for binding to TREM1.

In an exemplary competition assay, immobilized TREM1 or cells expressing TREM1 on the cell surface are incubated in a solution comprising a first labeled antibody that binds to TREM1 (e.g., human or non-human primate) and a second unlabeled antibody that is being tested for its ability to compete with the first antibody for binding to TREM1. The second antibody may be present in a hybridoma supernatant. As a control, immobilized TREM1 or cells expressing TREM1 is incubated in a solution comprising the first labeled antibody but not the second unlabeled antibody. After incubation under conditions permissive for binding of the first antibody to TREM1, excess unbound antibody is removed, and the amount of label associated with immobilized TREM1 or cells expressing TREM1 is measured. If the amount of label associated with immobilized TREM1 or cells expressing TREM1 is substantially reduced in the test sample relative to the control sample, then that indicates that the second antibody is competing with the first antibody for binding to TREM1. See, Harlow and Lane (1988) *Antibodies: A Laboratory Manual* ch. 14 (Cold Spring Harbor Laboratory, Cold Spring Harbor, NY).

Anti-TREM1 Antibody Light Chain and Heavy Chain Variable Regions

In some embodiments, anti-TREM1 antibodies of the present disclosure comprise (a) a light chain variable region comprising at least one, two, or three HVRs selected from HVR-L1, HVR-L2, and HVR-L3 of any one of the antibodies listed in Tables 2-5, or selected from T1-1-T1-80; or selected from T1-1-T1-25 and T1-33-T1-80, and any combination thereof; and/or (b) a heavy chain variable region comprising at least one, two, or three HVRs selected from HVR-H1, HVR-H2, and HVR-H3 of any one of the antibodies listed in Tables 2-5, or selected from T1-1-T1-80 and any combination thereof. In some embodiments, the HVR-L1, HVR-L2, HVR-L3, HVR-H1, HVR-H2, and HVR-H3 comprise EU or Kabat HVR, Chothia HVR, or Contact HVR sequences as shown in Tables 2-5, or from an antibody selected from T1-1-T1-80 and any combination thereof; or selected from T1-1-T1-25 and T1-33-T1-80, and any combination thereof.

In some embodiments, anti-TREM1 antibodies of the present disclosure comprise at least one, two, three, four, five, or six HVRs selected from (i) HVR-L1 comprising the amino acid sequence of any of the HVR-L1 sequences listed in Tables 2-5, or from an antibody selected from T1-1-T1-80 or selected from T1-1-T1-25 and T1-33-T1-80; (ii) HVR-L2 comprising the amino acid sequence of any of the HVR-L2 sequences listed in Tables 2-5, or from an antibody selected from T1-1-T1-80 or selected from T1-1-T1-25 and T1-33-T1-80; (iii) HVR-L3 comprising the amino acid sequence of any of the HVR-L3 sequences listed in Tables2-5, or from an antibody selected from T1-1-T1-80 or selected from T1-1-T1-25 and T1-33-T1-80; (iv) HVR-H1 comprising the amino acid sequence of any of the HVR-H1 sequences listed in Tables 2-5, or from an antibody selected from T1-1-T1-80 or selected from T1-1-T1-25 and T1-33-T1-80; (v) HVR-H2 comprising the amino acid sequence of any of the HVR-H2 sequences listed in Tables 2-5, or from an antibody selected from T1-1-T1-80 or selected from T1-1-T1-25 and T1-33-T1-80; and (vi) HVR-H3 comprising the amino acid sequence of any of the HVR-H3 sequences listed in Tables 2-5, or from an antibody selected from T1-1-T1-80 or selected from T1-1-T1-25 and T1-33-T1-80.

In some embodiments, anti-TREM1 antibodies of the present disclosure comprise a light chain variable domain and a heavy chain variable domain, wherein the light chain variable domain comprises one or more of: (a) an HVR-L1 comprising an amino acid sequence selected from SEQ ID NOs: 9-27, or an amino acid sequence with at least about 90% identity to an amino acid sequence selected from SEQ ID NOs: 9-27; (b) an HVR-L2 comprising an amino acid sequence selected from SEQ ID NOs: 28-40, or an amino acid sequence with at least about 90% identity to an amino acid sequence selected from SEQ ID NOs: 28-40; and (c) an HVR-L3 comprising an amino acid sequence selected from SEQ ID NOs: 41-119, or an amino acid sequence with at least about 90% identity to an amino acid sequence selected from SEQ ID NOs: 41-119; and/or wherein the heavy chain variable domain comprises one or more of: (a) an HVR-H1 comprising an amino acid sequence selected from SEQ ID NOs: 120-143, or an amino acid sequence with at least about 90% identity to an amino acid sequence selected from SEQ ID NOs: 120-143; (b) an HVR-H2 comprising an amino acid sequence selected from SEQ ID NOs: 144-172, or an amino acid sequence with at least about 90% identity to an amino acid sequence selected from SEQ ID NOs: 144-172; and (c) an HVR-H3 comprising an amino acid sequence selected from SEQ ID NOs: 173-247, or an amino acid sequence with at least about 90% identity to an amino acid sequence selected from SEQ ID NOs: 173-247.

In some embodiments, anti-TREM1 antibodies of the present disclosure comprise a light chain variable region of any one of the antibodies listed in Tables 2-5, or selected from T1-1-T1-80, or selected from T1-1-T1-25 and T1-33-T1-80; and/or a heavy chain variable region of any one of the antibodies listed in Tables 2-5, or selected from T1-1-T1-80, or selected from T1-1-T1-25 and T1-33-T1-80. In some embodiments, anti-TREM1 antibodies of the present disclosure comprise a light chain variable region comprising an amino acid sequence selected from any of SEQ ID NOs: 316-395; and/or a heavy chain variable domain comprising an amino acid sequence selected from any of SEQ ID NOs: 396-475.

In some embodiments, an anti-TREM1 antibody of the disclosure that enhances a TREM1 activity comprises: a heavy chain HVR3 comprising a sequence ARGPSWIDV (SEQ ID NO: 477), a heavy chain HVR1 comprising a consensus sequence SISS-GYYW (SEQ ID NO: 478), and/or a heavy chain HVR2 antigen contact region comprising a consensus sequence WIG(S/Y)IYxSGxTYY (SEQ ID NO: 479), where "WIG" is the c-terminal amino acid sequence of the heavy chain FR2. In some embodiments, an anti-TREM1 antibody of the disclosure that enhances a TREM1 acivity comprises: a heavy chain HVR3 comprising a sequence ARELYAYSSPMFYGMDV (SEQ ID NO: 480), a heavy chain HVR1 comprising a consensus sequence SISS-GYYW (SEQ ID NO: 478), and/or a heavy chain HVR2 antigen contact region comprising a consensus sequence WIG(S/Y)IYxSGxTYY (SEQ ID NO: 479), where "WIG" is the c-terminal amino acid sequence of the heavy chain FR2. In some embodiments, an anti-TREM1 antibody of the disclosure that enhances TREM1 activity comprises: a light chain HVR3 comprising a sequence QQDVSDFT (SEQ ID NO: 481), a light chain HVR1 comprising a consensus sequence QS(I/V)S (SEQ ID NO: 482), and/or a light chain HVR2 antigen contact region comprising a consensus sequence LLIY(G/A)ASS (SEQ ID NO: 483), where "LLIY" (SEQ ID NO: 484) is the c-terminal amino acid sequence of the light chain FR2. In some embodiments, an anti-TREM1 antibody of the disclosure that enhances TREM1 activity comprises: a light chain HVR3 comprising a sequence QQLYHAPPIT (SEQ ID NO: 485), a light chain HVR1 comprising a consensus sequence QS(IN) S (SEQ ID NO: 482) and/or a light chain HVR2 antigen contact region comprising a consensus sequence LLIY(G/A)ASS (SEQ ID NO: 483), where "LLIY" (SEQ ID NO: 484) is the c-terminal amino acid sequence of the light chain FR2. In some embodiments, an antibody that enhances TREM1 activity comprises: a heavy chain HVR3 comprising a sequence ARGPSWIDV (SEQ ID NO: 477) or ARELYAYSSPM-FYGMDV (SEQ ID NO: 481), a heavy chain HVR1 comprising a consensus sequence SISS-GYYW (SEQ ID NO: 478), a heavy chain HVR2 antigen contact region comprising a consensus sequence WIG(S/Y)IYxSGxTYY (SEQ ID NO: 479), where "WIG" is the c-terminal amino acid sequence of the heavy chain FR2, a light chain HVR3 comprising a sequence QQDVSDFT (SEQ ID NO: 481) or QQLYHAPPIT (SEQ ID NO: 485), a light chain HVR1 sequence comprising a consensus sequence QS(I/V)S (SEQ ID NO: 482), and a light chain HVR2 antigen contact region comprising a consensus sequence LLIY(G/A)ASS (SEQ ID NO: 483), where "LLIY" (SEQ ID NO: 484) is the c-terminal amino acid sequence of the light chain FR2.

In some embodiments, an anti-TREM1 antibody that enhances a TREM1 activity has the six HVRs of T1-62 or T1-63. Accordingly, in some embodiments, the antibody has a light chain HVR1 comprising SEQ ID NO:10, a light chain HVR2 comprising SEQ ID NO:29, a light chain HVR3 comprising SEQ ID NO:101, a heavy chain HVR1 comprising SEQ ID NO:130, a heavy chain HVR2 comprising SEQ ID NO:159; and a heavy chain HVR3 comprising SEQ ID NO:229. In some embodiments, the antibody has a light chain HVR1 comprising SEQ ID NO:23, a light chain HVR2 comprising SEQ ID NO:34, a light chain HVR3 comprising SEQ ID NO:102, a heavy chain HVR1 comprising SEQ ID NO:136, a heavy chain HVR2 comprising SEQ ID NO:168; and a heavy chain HVR3 comprising SEQ ID NO:230.

In some embodiments, an anti-TREM1 antibody that antagonizes a TREM1 activity comprises: a heavy chain HVR3 comprising a sequence ARRPDDRRGLFQH (SEQ ID NO: 486); a heavy chain HVR1 comprising a consensus sequence FTFS(S/T)YSMN (SEQ ID NO: 487) and/or a heavy chain HVR2 antigen contact region comprising a consensus sequence WVSSISSSSxYIYY (SEQ ID NO: 488), wherein "WV" is the c-terminal amino acid sequence of the heavy chain FR2. In some embodiments, an an anti-TREM1 antibody that antagonizes a TREM1 activity comprises: a heavy chain HVR3 comprising a sequence ARRGGSSSTGLLY (SEQ ID NO: 489); a heavy chain HVR1 comprising a consensus sequence FTFS(S/T)YSMN (SEQ ID NO: 487) and/or a heavy chain HVR2 antigen contact region comprising a consensus sequence WVSSIS-SSSxYIYY (SEQ ID NO: 488), wherein "WV" is the c-terminal amino acid sequence of the heavy chain FR2. In some embodiments, an an anti-TREM1 antibody that antagonizes a TREM1 activity comprises: a heavy chain HVR3 comprising a sequence ARTRIDDSFDI (SEQ ID NO: 490); a heavy chain HVR1 comprising a consensus sequence FTFS(S/T)YSMN (SEQ ID NO: 488) and/or a heavy chain HVR2 antigen contact region comprising a consensus sequence WVSSISSSSxYIYY (SEQ ID NO: 488), wherein "WV" is the c-terminal amino acid sequence of the heavy chain FR2.

In some embodiments, an anti-TREM1 antibody that antagonizes a TREM1 activity comprises: a light chain HVR3 comprising QQYGPYPYT (SEQ ID NO: 491); a light chain HVR1 comprising a consensus sequence Q(S/D)ISSWLA (SEQ ID NO: 492); and/or a light chain HVR2 antigen contact region comprising a consensus sequence LLIY(D/A)ASSL(E/Q)S (SEQ ID NO: 493), where "LLIY" (SEQ ID NO: 484) is the c-terminal amino acid sequence of the light chain FR2. In some embodiments, an anti-TREM1 antibody that antagonizes a TREM1 activity comprises: a light chain HVR3 comprising QQSLTHPT (SEQ ID NO: 494); a light chain HVR1 comprising a consensus sequence Q(S/D)ISSWLA (SEQ ID NO: 492); and/or a light chain HVR2 antigen contact region comprising a consensus sequence LLIY(D/A)ASSL(E/Q)S (SEQ ID NO: 493), where "LLIY" (SEQ ID NO: 484) is the c-terminal amino acid sequence of the light chain FR2. In some embodiments, an anti-TREM1 antibody that antagonizes a TREM1 activity comprises: a light chain HVR3 comprising AAQDLLPYT (SEQ ID NO: 495); a light chain HVR1 comprising a consensus sequence Q(S/D)ISSWLA (SEQ ID NO: 492); and/or a light chain HVR2 antigen contact region comprising a consensus sequence LLIY(D/A)ASSL(E/Q)S (SEQ ID NO: 493), where "LLIY" (SEQ ID NO: 484) is the c-terminal amino acid sequence of the light chain FR2.

In some embodiments, an anti-TREM1 antibody that antagonizes a TREM1 activity comprises a heavy chain HVR3 comprising a sequence ARRPDDRRGLFQH (SEQ ID NO: 496) or ARRGGSSSTGLLY (SEQ ID NO: 489); a heavy chain HVR1 comprising a consensus sequence FTFS (S/T)YSMN (SEQ ID NO: 487); a heavy chain HVR2 antigen contact region comprising a consensus sequence WVSSISSSSxYIYY (SEQ ID NO: 488), wherein "WV" is the c-terminal amino acid sequence of the heavy chain FR2; a light chain HVR3 comprising QQYGPYPYT (SEQ ID NO: 491), QQSLTHPT (SEQ ID NO: 494), or AAQDLLPYT (SEQ ID NO: 495); a light chain HVR1 comprising a consensus sequence Q(S/D)ISSWLA (SEQ ID NO: 492); and a light chain HVR2 antigen contact region comprising a consensus sequence LLIY(D/A)ASSL(E/Q)S (SEQ ID NO: 493), where "LLIY" (SEQ ID NO: 484) is the c-terminal amino acid sequence of the light chain FR2.

In some embodiments, an anti-TREM1 antibody that antagonizes a TREM1 activity has the six HVRs of T1-34, T1-39, or T1-40. Accordingly, in some embodiments, the antibody has a light chain HVR1 comprising SEQ ID NO:24, a light chain HVR2 comprising SEQ ID NO:38, a light chain HVR3 comprising SEQ ID NO:73, a heavy chain HVR1 comprising SEQ ID NO:123, a heavy chain HVR2 comprising SEQ ID NO:148; and a heavy chain HVR3 comprising SEQ ID NO:205. In some embodiments, the antibody has a light chain HVR1 comprising SEQ ID NO:25, a light chain HVR2 comprising SEQ ID NO:34, a light chain HVR3 comprising SEQ ID NO:78, a heavy chain HVR1 comprising SEQ ID NO:123, a heavy chain HVR2 comprising SEQ ID NO:148; and a heavy chain HVR3 comprising SEQ ID NO:209. In some embodiments, the antibody has a light chain HVR1 comprising SEQ ID NO:14, a light chain HVR2 comprising SEQ ID NO:30, a light chain HVR3 comprising SEQ ID NO:79, a heavy chain HVR1 comprising SEQ ID NO:123, a heavy chain HVR2 comprising SEQ ID NO:50 and a heavy chain HVR3 comprising SEQ ID NO:210.

In some embodiments, an anti-TREM1 antibody of the present disclosure has a heavy chain CDR1 sequence in which position X of the CDR1 as shown in the heavy chain sequences for ligand-enhancing antibodies in FIG. 14 is G or A. In some embodiments, the antibody has a heavy chain CDR2 sequence in which position X of the CDR2 as shown in the heavy chain sequences for ligand enhancing antibodies in FIG. 14 is S or N. In some embodiments, the heavy chain variable region comprises an FR1 through FR3 sequence of a ligand-enhancing antibody as shown in FIG. 14. In some embodiments, an anti-TREM1 antibody of the present disclosure has a heavy chain variable region sequence comprising an FR1 through CDR3 sequence of a ligand-enhancing antibody as shown in FIG. 14. In some embodiments, an anti-TREM1 antibody comprises a heavy chain variable region comprising a VH4-0B*01 or VH4-31*01 sequence as shown in FIG. 14.

In some embodiments, an anti-TREM1 antibody of the present disclosure has a heavy chain CDR2 sequence in which position X of the CDR2 as shown in the heavy chain sequences for antagonist antibodies in FIG. 14 is S or N. In some embodiments, the heavy chain variable region comprises an FR1 through FR3 sequence of an antagonist antibody as shown in FIG. 14. In some embodiments, an anti-TREM1 antibody of the present disclosure has a heavy chain variable region sequence comprising an FR1 through CDR3 sequence of an antagonist antibody as shown in FIG. 14. In some embodiments, an anti-TREM1 antibody comprises a heavy chain variable region comprising a VH3-21*01 sequence as shown in FIG. 14.

In some embodidments, an anti-TREM1 antibody of the present disclosure has a heavy chain CDR2 sequence in which position X of the CDR2 as shown in the heavy chain sequences for ligand mimetic antibodies in FIG. 14 is S or T and position Z of the CDR2 as shown in the heavy chain sequences for ligand mimetic antibodies in FIG. 14 is S or D. In some embodiments, the heavy chain variable region comprises an FR1 through FR3 sequence of a ligand mimetic antibody as shown in FIG. 14. In some embodiments, an anti-TREM1 antibody of the present disclosure has a heavy chain variable region sequence comprising an FR1 through CDR3 sequence of a ligand mimetic antibody as shown in FIG. 14. In some embodiments, an anti-TREM1 antibody comprises a heavy chain variable region comprising a VH3-09*01 sequence as shown in FIG. 14.

In some embodiments, an anti-TREM1 antibody of the present disclosure has a heavy chain CDR1 sequence in which position X of the CDR1 as shown in the heavy chain sequences in the section for VH1-69*01 in FIG. 15 is S or N and position X of the CDR2 as shown in the heavy chain sequences in the section for VH1-69*01 in FIG. 15 is S or N. In some embodiments, an anti-TREM1 antibody of the present disclosure has a heavy chain CDR1 sequence in which position X of the CDR1 as shown in the heavy chain sequences in the section for VH1-18*01 in FIG. 15 is S or H. In some embodiments, an anti-TREM1 antibody of the present disclosure has a heavy chain CDR1 sequence in which position X of the CDR1 as shown in the heavy chain sequences in the section for VH1-02*02 in FIG. 15 is M or I and position X of the CDR2 as shown in the heavy chain sequences in the section for VH1-02*02 in FIG. 15 is I or V. In some embodiments, an anti-TREM1 antibody of the present disclosure has a heavy chain CDR1 sequence in which position X of the CDR1 as shown in the heavy chain sequences in the section for VH4-0B*01 in FIG. 15 is G or A and position X of the CDR2 as shown in the heavy chain sequences in the section for VH4-0B*01 in FIG. 15 is S or N. In some embodiments, an anti-TREM1 antibody of the present disclosure has a heavy chain CDR1 sequence in which position X of the CDR1 as shown in the heavy chain sequences in the section for VH4-39*01 in FIG. 15 is S or D and position X of the CDR2 as shown in the heavy chain sequences in the section for VH4-39*01 in FIG. 15 is Y or S. In some embodiments, an anti-TREM1 antibody of the present disclosure has a heavy chain CDR1 sequence in which position X of the CDR1 as shown in the heavy chain sequences in the section for VH3-33*01 in FIG. 15 is S or N, position X of the CDR2 as shown in the heavy chain sequences in the section for VH3-33*01 in FIG. 15 is V or L, and position Z of the CDR2 as shown in the heavy chain sequences in the section for VH3-33*01 in FIG. 15 is Y or G. In some embodiments, an anti-TREM1 antibody of the present disclosure has a heavy chain CDR1 sequence in which position X of the CDR1 as shown in the heavy chain sequences in the section for VH3-30*03 in FIG. 15 is F or L. In some embodiments, an anti-TREM1 antibody of the present disclosure has a heavy chain CDR2 sequence in which position X of the CDR2 as shown in the heavy chain sequences in the section for VH3-09*01 in FIG. 15 is S or T and position Z is S or D. In some embodiments, an anti-TREM1 antibody of the present disclosure has a heavy chain CDR2 sequence in which position X of the CDR2 as shown in the heavy chain sequences in the section for VH3-21*01 in FIG. 15 is S or N. In some embodiments, an anti-TREM1 antibody of the present disclosure has a heavy chain CDR1 sequence in which position X of the CDR1 as shown in the heavy chain sequences in the section for VH3-23*01 in Figure S or T. In some embodiments, the heavy chain variable region comprises an FR1 through FR3 sequence as shown in FIG. 15. In some embodiments, an anti-TREM1 antibody of the present disclosure has a heavy chain variable region sequence comprising an FR1 through CDR3 sequence as shown in FIG. 15.

In some embodiments, an anti-TREM1 antibody of the present disclosure has a light chain CDR1 sequence in which position X of the CDR1 as shown in the light chain sequences in the section for VK2-28*01 in FIG. 16 is S or R and position X of the CDR2 as shown in the light chain sequences in the section for VK2-28*01 in FIG. 16 is N or H. In some embodiments, an anti-TREM1 antibody of the present disclosure has a light chain CDR2 sequence in which position X of the CDR2 as shown in the light chain sequences in the section for VK1-33*01 in FIG. 16 is E or A. In some embodiments, an anti-TREM1 antibody of the present disclosure has a light chain CDR1 sequence in which position X of the CDR1 as shown in the light chain sequences in the section for VK1-05*01 in FIG. 16 is S or N and position X of the CDR2 as shown in the light chain sequences in the section for VK1-05*01 is Y or S. In some embodiments, an anti-TREM1 antibody of the present disclosure has a light chain CDR1 sequence in which position X of the CDR1 as shown in the light chain sequences in the section for VK1-05*0 in FIG. 16 is S or G. In some embodiments, an anti-TREM1 antibody of the present disclosure has a light chain CDR1 sequence in which position X of the CDR1 as shown in the light chain sequences in the section for VK1-12*01 in FIG. 16 is G or D, position z is S or D, and position X of the CDR2 as shown in the light chain sequences in the section for VK1-12*01 in FIG. 16 is S or N. In some embodiments, an anti-TREM1 antibody of the present disclosure has a light chain CDR1 sequence in which position X of the CDR1 as shown in the light chain sequences in the section for VK1-39*01 in FIG. 16 is S or R and position z is Y or F. In some embodiments, an anti-TREM1 antibody of the present disclosure has a light chain CDR1 sequence in which position X of the CDR1 as shown in the light chain sequences in the section for VK4-01*01 in FIG. 16 is Y or F. In some embodiments, an anti-TREM1 antibody of the present disclosure has a light chain CDR1 sequence in which position X of the CDR1 as shown in the light chain sequences in the section for VK3-20*01 in FIG. 16 is Y or F. In some embodiments, an anti-TREM1 antibody of the present disclosure has a light chain CDR1 sequence in which position X of the CDR1 as shown in the light chain sequences in the section for VK3-15*01 in FIG. 16 is S or G. In some embodiments, an anti-TREM1 antibody of the present disclosure has a light chain CDR2 sequence in which position X of the CDR2 as shown in the light chain sequences in the section for VK3-11*01 in FIG. 16 is A or S. In some embodiments, the light chain variable region comprises an FR1 through FR3 sequence as shown in FIG. 16. In some embodiments, an anti-TREM1 antibody of the present disclosure has a light chain variable region sequence comprising an FR1 through CDR3 sequence as shown in FIG. 16.

Any of the antibodies of the present disclosure may be produced by a cell line. In some embodiments, the cell line may be a mammalian cell line. In certain embodiments, the cell line may be a hybridoma cell line. In other embodiments, the cell line may be a yeast cell line. Any cell line known in the art suitable for antibody production may be used to produce an antibody of the present disclosure. Exemplary cell lines for antibody production are described throughout the present disclosure.

In some embodiments, the anti-TREM1 antibody is an anti-TREM1 monoclonal antibody selected from T1-1-T1-80, and humanized variants thereof. In certain embodiments, the anti-TREM1 antibody is an agonist antibody. In certain embodiments, the anti-TREM1 antibody is an inert antibody. In certain embodiments, the anti-TREM1 antibody is an antagonist antibody.

In some embodiments, the anti-TREM1 antibody is one or more anti-TREM1 monoclonal antibody listed in Table 1A, Table 1B, or Tables 2-5. In some embodiments, the anti-TREM1 antibody is an isolated antibody that binds essentially the same TREM1 epitope as one or more anti-TREM1 monoclonal antibody listed in Table 1A, Table 1B, or Tables 2-5. In some embodiments, the anti-TREM1 antibody is an isolated antibody comprising the HVR-H1, HVR-H2, and HVR-H3 of the heavy chain variable domain of monoclonal antibody T1-1-T1-80. In some embodiments, the anti-TREM1 antibody is an isolated antibody comprising the HVR-L1, HVR-L2, and HVR-L3 of the light chain variable domain of monoclonal antibody T1-1-T1-80. In some embodiments, the anti-TREM1 antibody is an isolated antibody comprising the HVR-H1, HVR-H2, and HVR-H3 of the heavy chain variable domain and the HVR-L1, HVR-L2, and HVR-L3 of the light chain variable domain of at least one of the monoclonal antibodies T1-1-T1-80.

In some embodiments, the anti-TREM1 antibody is an isolated antibody which binds essentially the same TREM1 epitope as at least one of the monoclonal antibodies T1-1-T1-80.

In some embodiments, anti-TREM1 antibodies of the present disclosure do not compete with one or more TREM1 ligands for binding to TREM1. In some embodiments, anti-TREM1 antibodies of the present disclosure are capable of binding TREM1 without blocking simultaneous binding of one or moreTREM1 ligands to TREM1. In some embodiments anti-TREM1 antibodies of the present disclosure are capable of additive and/or synergistic functional interactions with one or more TREM1 ligands. In some embodiments, anti-TREM1 antibodies of the present disclosure increase the maximal activity of TREM1 exposed to saturating concentrations of one or more TREM1 ligands. In some embodiments, anti-TREM1 antibodies of the present disclosure increase the activity of TREM1 obtained at any concentration of one or more TREM1 ligands.

Anti-TREM1 Antibody Binding Affinity

The dissociation constants ($K_D$) of anti-TREM1 antibodies for human TREM1 and mouse TREM1 may be less than 15 nM, less than 14.5 nM, less than 14 nM, less than 13.5 nM, less than 13 nM, less than 12.9 nM, less than 12.8 nM, less than 12.7 nM, less than 12.6 nM, less than 12.5 nM, less than 12.4 nM, less than 12.3 nM, less than 12.2 nM, less than 12.1 nM, less than 12 nM, less than 11.5 nM, less than 11 nM, less than 10.9 nM, less than 10.8 nM, less than 10.7 nM, less than 10.6 nM, less than 10.5 nM, less than 10.4 nM, less than 10.3 nM, less than 10.2 nM, less than 10.1 nM, less than 10 nM, less than 9.5 nM, less than 9 nM, less than 8.5 nM, less than 8 nM, less than 7.5 nM, less than 7 nM, less than 6.9 nM, less than 6.8 nM, less than 6.7 nM, less than 6.6 nM, less than 6.5 nM, less than 6.4 nM, less than 6.3 nM, less than 6.2 nM, less than 6.1 nM, less than 6 nM, less than 5.5 nM, less than 5 nM, less than 4.5 nM, less than 4 nM, less than 3.5 nM, less than 3.4 nM, less than 3.3 nM, less than 3.2 nM, less than 3.1 nM, less than 3 nM, less than 2.9 nM, less than 2.8 nM, less than 2.7 nM, less than 2.6 nM, less than 2.5 nM, less than 2.4 nM, less than 2.3 nM, less than 2.2 nM, less than 2.1 nM, less than 2 nM, less than 1.9 nM, less than 1.8 nM, less than 1.7 nM, less than 1.6 nM, less than 1.5 nM, less than 1.4 nM, less than 1.3 nM, less than 1.2 nM, less than 1.1 nM, less than 1 nM, less than 0.95 nM, or less than 0.9 nM. In some embodiments, dissociation constants range from about 12.8 nM to about 1.2 nM, or less than 1.2 nM. In some embodiments, dissociation constants of anti-TREM1 antibodies for human TREM1 range from about 12.8 nM to about 2.9 nM, or less than 2.9 nM. In some embodiments, dissociation constants of anti-TREM1 antibodies for mouse TREM1 range from about 10.4 nM to about 1.2 nM, or less than 1.2 nM. Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses.

Additional anti-TREM1 antibodies, e.g., antibodies that specifically bind to a TREM1 protein of the present disclosure, may be identified, screened, and/or characterized for their physical/chemical properties and/or biological activities by various assays known in the art.

Bispecific Antibodies

Certain aspects of the present disclosure relate to bispecific antibodies that bind to a TREM1 protein of the present disclosure and a second antigen. Methods of generating bispecific antibodies are well known in the art and described herein. In some embodiments, bispecific antibodies of the present disclosure bind to one or more amino acid residues of human TREM1 (SEQ ID NO: 1), or amino acid residues on a TREM1 protein corresponding to amino acid residues of SEQ ID NO: 1. In other embodiments, bispecific antibodies of the present disclosure also bind to one or more amino acid residues of human DAP12 (SEQ ID NO:560), or amino acid residues on a DAP12 protein corresponding to amino acid residues of SEQ ID NO:560).

In some embodiments, bispecific antibodies of the present disclosure recognize a first antigen and a second antigen. In some embodiments, the first antigen is human TREM1 or a naturally occurring variant thereof, or human DAP12 or a naturally occurring variant thereof. In some embodiments, the second antigen is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; and (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (e) a protein, lipid, polysaccharide, or glycolipid expressed on one or more tumor cells and any combination thereof.

Antibody Fragments

Certain aspects of the present disclosure relate to antibody fragments that bind to one or more of human TREM1, a naturally occurring variant of human TREM1, and a disease variant of human TREM1. In some embodiments, the antibody fragment is an Fab, Fab', Fab'-SH, F(ab')$_2$, Fv or scFv fragment. In some embodiments, the antibody fragment is used in combination with one or more antibodies that specifically bind a disease-causing protein selected from: a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; and (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (e) a protein, lipid, polysaccharide, or glycolipid expressed on one or more tumor cells, and any combination thereof.

Antibody Frameworks

Any of the antibodies described herein further include a framework, such as a human immunoglobulin framework. For example, in some embodiments, an antibody (e.g., an anti-TREM1 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633

(2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, an antibody comprises a light chain variable region comprising an HVR-L1, an HVR-L2, and an HVR-L3 of the present disclosure and one, two, three or four of the light chain framework regions as shown in Table 4. In some embodiments, an antibody comprises a heavy chain variable region comprising an HVR-H1, an HVR-H2, and an HVR-H3 of the present disclosure and one, two, three or four of the heavy chain framework regions as shown in Table 5. In some embodiments, an antibody comprises a light chain variable region comprising an HVR-L1, an HVR-L2, and an HVR-L3 of the present disclosure and one, two, three or four of the light chain framework regions as shown in Table 4 and further comprises a heavy chain variable region comprising an HVR-H1, an HVR-H2, and an HVR-H3 of the present disclosure and one, two, three or four of the heavy chain framework regions as shown in Table 5.

PI3K Activation

In some embodiments, the anti-TREM1 antibodies of the present disclosure may induce PI3K activation after binding to a TREM1 protein expressed in a cell.

PI3Ks are a family of related intracellular signal transducer kinases capable of phosphorylating the 3-position hydroxyl group of the inositol ring of phosphatidylinositol (PtdIns). The PI3K family is divided into three different classes (Class I, Class II, and Class III) based on primary structure, regulation, and in vitro lipid substrate specificity.

Activated PI3K produces various 3-phosphorylated phosphoinositides, including without limitation, PtdIns3P, PtdIns(3,4)P2, PtdIns(3,5)P2, and PtdIns(3,4,5)P3. These 3-phosphorylated phosphoinositides function in a mechanism by which signaling proteins are recruited to various cellular membranes. These signaling proteins contain phosphoinositide-binding domains, including without limitation, PX domains, pleckstrin homology domains (PH domains), and FYVE domains. Any method known in the art for determining PI3K activation may be used.

In some embodiments, anti-TREM1 antibodies of the present disclosure may be beneficial for preventing, lowering the risk of, or treating conditions and/or diseases associated with decreased levels of PI3K activity.

Modulated Expression of Cytokines

In some embodiments, the anti-TREM1 antibodies of the present disclosure modulate (e.g., increase or decrease) pro-inflammatory mediators in the brain after binding to a TREM1 protein expressed on a cell surface. The anti-TREM1 antibodies of the present disclosure modulate the expression of cytokines (e.g., anti-inflammatory mediators) and/or modulate the expression of pro-inflammatory mediators after binding to a TREM1 protein expressed in a cell. Once the cells are dying due to deficiency in TREM1 signaling they induce a pro inflammatory response.

Inflammation is part of a complex biological response of vascular tissues to harmful stimuli, such as pathogens, damaged cells, and irritants. The classical signs of acute inflammation are pain, heat, redness, swelling, and loss of function. Inflammation is a protective attempt by an organism to remove the injurious stimuli and to initiate the healing process. Inflammation can be classified as either acute inflammation or chronic inflammation. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Chronic inflammation is prolonged inflammation that leads to a progressive shift in the type of cells present at the site of inflammation and is characterized by simultaneous destruction and healing of the tissue from the inflammatory process.

As used herein, anti-inflammatory mediators are proteins involved either directly or indirectly (e.g., by way of an anti-inflammatory signaling pathway) in a mechanism that reduces, inhibits, or inactivates an inflammatory response. Any method known in the art for identifying and characterizing anti-inflammatory mediators may be used. Examples of anti-inflammatory mediators include, without limitation, cytokines, such as IL-4, IL-10 TGF-β, IL-13, IL-35 IL-16, IFN-alpha, IL-1Ra, VEGF, G-CSF, and soluble receptors for TNF or IL-6

In some embodiments, the anti-TREM1 antibodies of the present disclosure may modulate expression of cytokines, such as IL-12p70, IL-6, and IL-10. In certain embodiments, modulated expression of the cytokines occurs in macrophages, dendritic cells, monocytes, osteoclasts, Langerhans cells of skin, Kupffer cells, and/or microglial cells. Modulated expression may include, without limitation, modulated gene expression, modulated transcriptional expression, or modulated protein expression. Any method known in the art for determining gene, transcript (e.g., mRNA), and/or protein expression may be used. For example, Northern blot analysis may be used to determine cytokine gene expression levels, RT-PCR may be used to determine the level of cytokine transcription, and Western blot analysis may be used to determine cytokine protein levels.

As used herein, a cytokine may have modulated (e.g., increased or decreased) expression if its expression in one or more cells of a subject treated with an anti-TREM1 antibody of the present disclosure is modulated as compared to the expression of the same cytokine expressed in one or more cells of a corresponding subject that is not treated with the anti-TREM1 antibody. In some embodiments, an anti-TREM1 antibody of the present disclosure may modulate cytokine expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to cytokine expression in one or more cells of a corresponding subject that is not treated with the anti-TREM1 antibody. In other embodiments, an anti-TREM1 antibody of the present disclosure modulate cytokine expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to cytokine expression in one or more cells of a corresponding subject that is not treated with the anti-TREM1 antibody.

In some embodiments, anti-TREM1 antibodies of the present disclosure may be useful for preventing, lowering the risk of, or treating conditions and/or diseases associated with abnormal levels of one or more anti-inflammatory mediators.

Modulated Expression of Pro-Inflammatory Mediators

In some embodiments, the anti-TREM1 antibodies of the present disclosure may modulate (e.g., increase or decrease) the expression of pro-inflammatory mediators after binding to a TREM1 protein expressed in a cell.

As used herein, pro-inflammatory mediators are proteins involved either directly or indirectly (e.g., by way of pro-inflammatory signaling pathways) in a mechanism that induces, activates, promotes, or otherwise increases an inflammatory response. Any method known in the art for identifying and characterizing pro-inflammatory mediators may be used. Examples of pro-inflammatory mediators include, without limitation, cytokines such as FN-☐, IL-1☐, IL-1β, TNF-α, IL-6, IL-8, CRP, IL-20 family members, IL-33, LIF, IFN-gamma, OSM, CNTF, GM-CSF, IL-11, IL-12, IL-17, IL-18, IL-23, CXCL10, and MCP-1.

In some embodiments, the anti-TREM1 antibodies of the present disclosure may modulate functional expression and/or secretion of pro-inflammatory mediators, such as IFN-a4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, GM-CSF, IL-11, IL-12, IL-23, MCP-1, CXCL10, VEGF, IL-17, IL-18, and CRP. In certain embodiments, modulated expression of the pro-inflammatory mediators occurs in macrophages, dendritic cells, monocytes, osteoclasts, Langerhans cells of skin, Kupffer cells, and/or microglial cells. Modulated expression may include, without limitation, modulated gene expression, modulated transcriptional expression, or modulated protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

In certain embodiments, pro-inflammatory mediators include inflammatory cytokines. Accordingly, in certain embodiments, the anti-TREM1 antibodies of the present disclosure may modulate secretion of one or more inflammatory cytokines. Examples of inflammatory cytokines whose secretion may be reduced by the anti-TREM1 antibodies of the present disclosure include, without limitation, IFN-a4, IFN-b, IL-1β, TNF-α, IL-10, IL-6, IL-8, CRP, TGF-beta, members of the chemokine protein families, IL-20 family members, IL-33, LIF, IFN-gamma, OSM, CNTF, GM-CSF, IL-11, IL-12, IL-23, MCP-1, CXCL10, VEGF, IL-17, IL-18, CRP, and MCP-1.

In certain embodiments, pro-inflammatory mediators include inflammatory receptors. Accordingly, in certain embodiments, the anti-TREM1 antibodies of the present disclosure may modulate expression of one or more inflammatory receptors. Examples of inflammatory receptors whose expression may be reduced by the anti-TREM1 antibodies of the present disclosure include, without limitation, CD86.

As used herein, a pro-inflammatory mediator may have modulated expression if its expression in one or more cells of a subject treated with an agonist anti-TREM1 antibody of the present disclosure is modulated (e.g., increased or deacreased) as compared to the expression of the same pro-inflammatory mediator expressed in one or more cells of a corresponding subject that is not treated with the agonist anti-TREM1 antibody. In some embodiments, the agonist anti-TREM1 antibody of the present disclosure may modulate pro-inflammatory mediator expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the agonist anti-TREM1 antibody. In other embodiments, the agonist anti-TREM1 antibody may modulate pro-inflammatory mediator expression in one or more cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-TREM1 antibody.

In some embodiments, anti-TREM1 antibodies of the present disclosure may be useful for preventing, lowering the risk of, or treating conditions and/or diseases associated with abnormal levels of one or more pro-inflammatory mediators.

ERK Phosphorylation

In some embodiments, the anti-TREM1 antibodies of the present disclosure may induce extracellular signal-regulated kinase (ERK) phosphorylation after binding to a TREM1 protein expressed in a cell.

Extracellular-signal-regulated kinases (ERKs) are widely expressed protein kinase intracellular signaling kinases that are involved in, for example, the regulation of meiosis, mitosis, and postmitotic functions in differentiated cells. Various stimuli, such as growth factors, cytokines, virus infection, ligands for heterotrimeric G protein-coupled receptors, transforming agents, and carcinogens, activate ERK pathways. Phosphorylation of ERKs leads to the activation of their kinase activity.

In some embodiments, anti-TREM1 antibodies of the present disclosure may be beneficial for preventing, lowering the risk of, or treating conditions and/or diseases associated with decreased levels of ERK phosphorylation.

Syk Phosphorylation

In some embodiments, the anti-TREM1 antibodies of the present disclosure may induce spleen tyrosine kinase (Syk) phosphorylation after binding to a TREM1 protein expressed in a cell.

Spleen tyrosine kinase (Syk) is an intracellular signaling molecule that functions downstream of TREM1 by phosphorylating several substrates, thereby facilitating the formation of a signaling complex leading to cellular activation and inflammatory processes.

In some embodiments, anti-TREM1 antibodies of the present disclosure may be beneficial for preventing, lowering the risk of, or treating conditions and/or diseases associated with decreased levels of Syk phosphorylation.

TREM1 Autophosphorylation

In some embodiments, the anti-TREM1 a antibodies of the present disclosure may induce TREM1 autophosphorylation after binding to a TREM1 protein expressed in a cell.

In some embodiments, anti-TREM1 antibodies of the present disclosure may be beneficial for preventing, lowering the risk of, or treating conditions and/or diseases associated with decreased levels of TREM1 phosphorylation.

DAP12 Binding and Phosphorylation

In some embodiments, the anti-TREM1 antibodies of the present disclosure may induce binding of TREM1 to DAP12. In other embodiments, the anti-TREM1 antibodies of the present disclosure may induce DAP12 phosphorylation after binding to a TREM1 protein expressed in a cell. In other embodiments, TREM1-mediated DAP12 phosphorylation is induced by one or more SRC family tyrosine kinases. Examples of Src family tyrosine kinases include, without limitation, Src, Syk, Yes, Fyn, Fgr, Lck, Hck, Blk, Lyn, and Frk.

DAP12 is variously referred to as TYRO protein tyrosine kinase-binding protein, TYROBP, KARAP, and PLOSL. DAP12 is a transmembrane signaling protein that contains an immunoreceptor tyrosine-based activation motif (ITAM) in its cytoplasmic domain. In certain embodiments, the anti-TREM1 and/or anti-DAP12 antibody may induce DAP12 phosphorylation in its ITAM motif. Any method known in the art for determining protein phosphorylation, such as DAP12 phosphorylation, may be used.

In some embodiments, DAP12 is phosphorylated by SRC family kinases, resulting in the recruitment and activation of the Syk kinase, ZAP70 kinase, or both, to a DAP12/TREM1 complex. Thus, in certain embodiments, the anti-TREM1 antibodies of the present disclosure may recruit Syk, ZAP70, or both to a DAP12/TREM1 complex. Without wishing to be bound by theory, it is believed that anti-TREM1 a antibodies of the present disclosure are useful for preventing, lowering the risk of, or treating conditions and/or diseases associated with decreased levels of DAP12 activity, DAP12 phosphorylation, or recruitment of Syk, ZAP70, or both to a DAP12/TREM1 complex.

Modulated Expression of C-C Chemokine Receptor 7

In some embodiments, the anti-TREM1 antibodies of the present disclosure may modulate (e.g., increase or deacrease) expression of C-C chemokine receptor 7 (CCR7) after binding to a TREM1 protein expressed in a cell. Modulated expression may include, without limitation, modulatation in gene expression, modulatation in transcriptional expression, or modulatation in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

C-C chemokine receptor 7 (CCR7) is a member of the G protein-coupled receptor family. CCR7 is expressed in various lymphoid tissues and can activate B-cells and T-cells. In some embodiments, CCR7 may modulate the migration of memory T-cells to secondary lymphoid organs, such as lymph nodes. In other embodiments, CCR7 may stimulate dendritic cell maturation. CCR7 is a receptor protein that can bind the chemokine (C-C motif) ligands CCL19/ELC and CCL21.

As used herein, CCR7 may have modulated (e.g., increased or decreased) expression if its expression in one or more cells of a subject treated with an anti-TREM1 antibody of the present disclosure is modulated as compared to the expression of CCR7 expressed in one or more cells of a corresponding subject that is not treated with the anti-TREM1 antibody. In some embodiments, an anti-TREM1 antibody of the present disclosure may modulate CCR7 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to CCR7 expression in one or more cells of a corresponding subject that is not treated with the anti-TREM1 antibody. In other embodiments, an anti-TREM1 antibody of the present disclosure modulates CCR7 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to CCR7 expression in one or more cells of a corresponding subject that is not treated with the anti-TREM1 antibody.

In some embodiments, modulated expression of CCR7 occurs in macrophages, dendritic cells, and/or microglial cells. Increased expression of CCR7 may induce microglial cell chemotaxis toward cells expressing the chemokines CCL19 and CCL21. Accordingly, in certain embodiments, anti-TREM1 antibodies of the present disclosure may induce microglial cell chemotaxis toward CCL19 and CCL21 expressing cells.

In some embodiments, anti-TREM1 antibodies of the present disclosure may be useful for preventing, lowering the risk of, or treating conditions and/or diseases associated with abnormal levels of CCR7, including dementia, frontotemporal dementia, Alzheimer's disease, Nasu-Hakola disease, Parkinson's disease, Amyotrophic lateral sclerosis, Huntington's disease, Taupathy disease.

Enhancement or Normalization of the Ability of Bone Marrow-Derived Dendritic Cells to Prime or Modulate Function of Antigen-Specific T-cells In some embodiments, the anti-TREM1 antibodies of the present disclosure may enhance and/or normalize the ability of bone marrow-derived dendritic cells to prime or modulate function of antigen-specific T cells, including of CD8+ T cells, CD4+ T cells, and/or regulatory T cells, after binding to a TREM1 protein expressed in a cell.

In some embodiments, agonist anti-TREM1 antibodies of the present disclosure may enhance and/or normalize the ability of bone marrow-derived dendritic cells to prime or modulate function of one or more antigen-specific T cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the ability of bone marrow-derived dendritic cells to prime or modulate function of one or more antigen-specific T cells in a corresponding subject that is not treated with the agonist anti-TREM1 antibody. In other embodiments, the agonist anti-TREM1 antibody may enhance and/or normalize the ability of bone marrow-derived dendritic cells to prime or modulate function of antigen-specific T cells in a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to prime or modulate function of antigen-specific T cells in a corresponding subject that is not treated with the agonist anti-TREM1 antibody.

In some embodiments, anti-TREM1 antibodies of the present disclosure may be beneficial for preventing, lowering the risk of, or treating conditions and/or diseases associated with a decreased or disregulated ability of bone marrow-derived dendritic cells to prime or modulate function of antigen-specific T cells.

Osteoclast Production

In some embodiments, the anti-TREM1 antibodies of the present disclosure may induce osteoclast production and/or increase the rate of osteoclastogenesis after binding to a TREM1 protein expressed in a cell.

As used herein, an osteoclast is a type of bone cell that can remove bone tissue by removing its mineralized matrix and breaking up the organic bone (e.g., bone resorption). Osteoclasts can be formed by the fusion of cells of the monocyte-macrophage cell line. In some embodiments, osteoclasts may be characterized by high expression of tartrate resistant acid phosphatase (TRAP) and cathepsin K.

As used herein, the rate of osteoclastogenesis may be increased if the rate of osteoclastogenesis in a subject treated with an agonist anti-TREM1 antibody of the present disclosure is greater than the rate of osteoclastogenesis in a corresponding subject that is not treated with the agonist anti-TREM1 antibody. In some embodiments, an agonist anti-TREM1 antibody of the present disclosure may increase the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the agonist anti-TREM1 antibody. In other embodiments, an agonist anti-TREM1 antibody of the present disclosure may increase the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the agonist anti-TREM1 antibody.

As used herein, the rate of osteoclastogenesis may be decreased if the rate of osteoclastogenesis in a subject treated with an antagonist anti-TREM1 antibody of the present disclosure is smaller than the rate of osteoclastogenesis in a corresponding subject that is not treated with the antagonist anti-TREM1 antibody. In some embodiments, an antagonist anti-TREM1 antibody of the present disclosure may decrease the rate of osteoclastogenesis in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to rate of osteoclastogenesis in a corresponding subject that is not treated with the antagonist anti-TREM1 antibody. In other embodiments, an antagonist anti-TREM1 antibody of the present disclosure may decrease the rate of osteoclastogenesis in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to rate of osteoclastogenesis in a corresponding subject that is not treated with the antagonist anti-TREM1 antibody.

In some embodiments, anti-TREM1 antibodies of the present disclosure may be beneficial for preventing, lowering the risk of, or treating conditions and/or diseases associated with abnormal bone formation and maintenance including osteoporosis, which is associated with pathological decrease in bone density and osteoporotic diseases which are associated with pathological increase in bone density.

Proliferation, Survival and Functionality of TREM1-Expressing Cells

In some embodiments, the anti-TREM1 antibodies of the present disclosure may increase the proliferation, survival, and/or function of dendritic cells, macrophages, monocytes, osteoclasts, Langerhans cells of skin, Kupffer cells, and microglial cells (microglia) after binding to TREM1 protein expressed in a cell.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most infections from reaching the vulnerable nervous tissue. In the case where infectious agents are directly introduced to the brain or cross the blood-brain barrier, microglial cells must react quickly to decrease inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T-cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial cells. In some embodiments, anti-TREM1 antibodies of the present disclosure may be beneficial for, lowering the risk of, or treating conditions and/or diseases associated with decreased proliferation or survival, of immune cells.

In some embodiments, anti-TREM1 antibodies of the present disclosure may increase the expression of CD83 and/or CD86 on dendritic cells, monocytes, and/or macrophages.

As used herein, the rate of proliferation, survival, and/or function of macrophages, dendritic cells, monocytes, and/or microglia may include increased expression if the rate of proliferation, survival, and/or function of dendritic cells, macrophages, monocytes, osteoclasts, Langerhans cells of skin, Kupffer cells, and/or microglia in a subject treated with an anti-TREM1 antibody of the present disclosure is greater than the rate of proliferation, survival, and/or function of dendritic cells, macrophages, monocytes, osteoclasts, Langerhans cells of skin, Kupffer cells, and/or microglia in a corresponding subject that is not treated with the anti-TREM1 antibody. In some embodiments, an anti-TREM1 antibody of the present disclosure may increase the rate of proliferation, survival, and/or function of dendritic cells, macrophages, monocytes, osteoclasts, Langerhans cells of skin, Kupffer cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, monocytes, osteoclasts, Langerhans cells of skin, Kupffer cells, and/or microglia in a corresponding subject that is not treated with the anti-TREM1 antibody. In other embodiments, an anti-TREM1 antibody of the present disclosure may increase the rate of proliferation, survival, and/or function of dendritic cells, macrophages, monocytes, osteoclasts, Langerhans cells of skin, Kupffer cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, monocytes, osteoclasts, Langerhans cells of skin, Kupffer cells, and/or microglia in a corresponding subject that is not treated with the anti-TREM1 antibody.

In some embodiments, anti-TREM1 antibodies of the present disclosure may be beneficial for preventing, lowering the risk of, or treating conditions and/or diseases associated with a reduction in function of dendritic cells, macrophages, monocytes, osteoclasts, Langerhans cells of skin, Kupffer cells, and/or microglia.

Clearance and Phagocytosis

In some embodiments, the anti-TREM1 antibodies of the present disclosure may induce clearance and/or phagocytosis after binding to a TREM1 protein expressed in a cell of one or more of apoptotic neurons, nerve tissue debris of the nervous system, non-nerve tissue debris of the nervous system, bacteria, other foreign bodies, disease-causing proteins, disease-causing peptides, disease-causing nucleic acid, or tumor cells. In certain embodiments, disease-causing proteins include, without limitation, amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, and Repeat-associated non-ATG (RAN) translation products including DiPeptide Repeats, (DPRs peptides) composed of glycine-alanine (GA), glycine-proline (GP), glycine-arginine (GR), proline-alanine (PA), or proline-arginine (PR). In certain embodiments, disease-causing nucleic acids include, without limitation, antisense GGCCCC (G2C4) repeat-expansion RNA.

In some embodiments, the anti-TREM1 antibodies of the present disclosure may induce of one or more types of clearance, including without limitation, apoptotic neuron clearance, nerve tissue debris clearance, non-nerve tissue debris clearance, bacteria or other foreign body clearance, disease-causing protein clearance, disease-causing peptide clearance, disease-causing nucleic acid clearance, and tumor cell clearance.

In some embodiments, the anti-TREM1 antibodies of the present disclosure may induce phagocytosis of one or more of apoptotic neurons, nerve tissue debris, non-nerve tissue debris, bacteria, other foreign bodies, disease-causing proteins, disease-causing peptides, disease-causing nucleic acid, and/or tumor cells.

In some embodiments, the anti-TREM1 antibodies of the present disclosure may increase phagocytosis by macrophages, dendritic cells, monocytes, and/or microglia under conditions of reduced levels of macrophage colony-stimulating factor (MCSF). Alternatively, in some embodiments, the anti-TREM1 antibodies of the present disclosure may increase phagocytosis by macrophages, dendritic cells, monocytes, and/or microglia in the presence of normal levels of macrophage colony-stimulating factor (MCSF)

In some embodiments, anti-TREM1 antibodies of the present disclosure may be beneficial for preventing, lowering the risk of, or treating conditions and/or diseases associated with clearance and/or phagocytosis of apoptotic neurons, nerve tissue debris of the nervous system, non-nerve tissue debris of the nervous system, bacteria, other foreign bodies, disease-causing proteins, disease-causing peptides, disease-causing nucleic acid, or tumor cells.

TREM1-Dependent Gene Expression

In some embodiments, agonist anti-TREM1 antibodies of the present disclosure may increase the activity and/or expression of TREM1-dependent genes, such as one or more transcription factors of the nuclear factor of activated T-cells (NFAT) family of transcription factors. Alternatively, antagonistic anti-TREM1 antibodies of the present disclosure may inhibit the activity and/or expression of TREM1-dependent genes, such as one or more transcription factors of the NFAT family of transcription factors.

In some embodiments, anti-TREM1 antibodies of the present disclosure may be beneficial for preventing, lowering the risk of, or treating conditions and/or diseases associated with decreased levels of TREM1-dependent genes.

In some embodiments, anti-TREM1 antibodies of the present disclosure may be benficial for preventing, lowering the risk of, or treating conditions and/or diseases i dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, e.g., glioma or glioblastoma, breast cancer, cervical cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM1, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and Haemophilus influenza.

In some embodiments, a method of treating a disease or condition in accordance with the invention comprises administering to an individual in need thereof a therapeutically effective amount of an agent that does not inhibit interaction between TREM1 and one or more TREM1 ligands, and/or enhances one or more activities of at least one TREM1 ligand.

Other aspects of the present disclosure relate to an agent that does not inhibit interaction between TREM1 and one or more CD33 ligands for use in preventing, reducing risk of, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, e.g., glioma such as low-grade glioma or glioblastoma, breast cancer, cervical cancer, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM1, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and Haemophilus influenza.

Antibody Preparation

Anti-TREM1 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, library derived antibodies, antibodies having modified effector functions, fusion proteins containing an antibody portion, and any other modified configuration of the immunoglobulin molecule that includes an antigen recognition site, such as an epitope having amino acid residues of a TREM1 protein of the present disclosure, including glycosylation variants of antibodies, amino acid sequence variants of antibodies, and covalently modified antibodies. The anti-TREM1 antibodies may be human, murine, rat, or of any other origin (including chimeric or humanized antibodies).

(1) Polyclonal Antibodies

Polyclonal antibodies, such as anti-TREM1 polyclonal antibodies, are generally raised in animals by multiple subcutaneous (sc) or intraperitoneal (ip) injections of the relevant antigen and an adjuvant. It may be useful to conjugate the relevant antigen (e.g., a purified or recombinant TREM1 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 μg (for mice) of the protein or conjugate with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant-cell culture as protein fusions. Also, aggregating agents such as alum are suitable to enhance the immune response.

(2) Monoclonal Antibodies

Monoclonal antibodies, such as anti-TREM1 monoclonal antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the anti-TREM1 monoclonal antibodies may be made using the hybridoma method first described by Köhler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant TREM1 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The immunizing agent will typically include the antigenic protein (e.g., a purified or recombinant TREM1 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, California USA), as well as SP-2 cells and derivatives thereof (e.g., X63-Ag8-653) (available from the American Type Culture Collection, Manassas, Virginia USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a TREM1 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a TREM1 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-TREM1 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host-cells such as *E. coli* cells, simian COS cells, Chinese hamster ovary (CHO) cells, or myeloma cells that do not otherwise produce immunoglobulin protein, in order to synthesize monoclonal antibodies in such recombinant host-cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, anti-TREM1 antibodies can be isolated from antibody phage libraries generated using the techniques described in McCafferty et al., *Nature*, 348:552-

554 (1990). Clackson et al., *Nature,* 352:624-628 (1991) and Marks et al., *J. Mol. Biol.,* 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies of desired specificity (e.g., those that bind a TREM1 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-TREM1 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-TREM1 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-TREM1 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human anti-TREM1 antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332: 323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.,* 151:2296 (1993); Chothia et al., *J. Mol. Biol.,* 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., TREM1 proteins of the present disclosure), is achieved. In general, the CDR residues are directly and most substantially involved in influencing antigen binding.

Various forms of the humanized anti-TREM1 antibody are contemplated. For example, the humanized anti-TREM1 antibody may be an antibody fragment, such as an Fab, which is optionally conjugated with one or more TREM1 ligand, such as HSP60. Alternatively, the humanized anti-TREM1 antibody may be an intact antibody, such as an intact IgG1 antibody.

(4) Human Antibodies

Alternatively, human anti-TREM1 antibodies can be generated. For example, it is now possible to produce transgenic animals (e.g., mice) that are capable, upon immunization, of producing a full repertoire of human antibodies in the absence of endogenous immunoglobulin production. The homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Nat'l Acad. Sci. USA*, 90:2551 (1993); Jakobovits et al., *Nature*, 362:255-258 (1993); Bruggermann et al., *Year in Immunol.*, 7:33 (1993); U.S. Pat. No. 5,591,669 and WO 97/17852.

Alternatively, phage display technology can be used to produce human anti-TREM1 antibodies and antibody fragments in vitro, from immunoglobulin variable (V) domain gene repertoires from unimmunized donors. McCafferty et al., *Nature* 348:552-553 (1990); Hoogenboom and Winter, *J. Mol. Biol.* 227: 381 (1991). According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Curr. Opin Struct. Biol.* 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See also U.S. Pat. Nos. 5,565,332 and 5,573,905. Additionally, yeast display technology can be used to produce human anti-TREM1 antibodies and antibody fragments in vitro (e.g., WO 2009/036379; WO 2010/105256; WO 2012/009568; US 2009/0181855; US 2010/0056386; and Feldhaus and Siegel (2004) J. Immunological Methods 290:69-80). In other embodiments, ribosome display technology can be used to produce human anti-TREM1 antibodies and antibody fragments in vitro (e.g., Roberts and Szostak (1997) Proc Natl Acad Sci 94:12297-12302; Schaffitzel et al. (1999) J. Immunolical Methods 231:119-135; Lipovsek and Pluckthun (2004) J. Immunological Methods 290:51-67).

The techniques of Cole et al., and Boerner et al., are also available for the preparation of human anti-TREM1 monoclonal antibodies (Cole et al., Monoclonal Antibodies and Cancer Therapy, Alan R. Liss, p. 77 (1985) and Boerner et al., *J. Immunol.* 147(1): 86-95 (1991). Similarly, human anti-TREM1 antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., *Bio/Technology* 10: 779-783 (1992); Lonberg et al., *Nature* 368: 856-859 (1994); Morrison, *Nature* 368: 812-13 (1994), Fishwild et al., *Nature Biotechnology* 14: 845-51 (1996), Neuberger, *Nature Biotechnology* 14: 826 (1996) and Lonberg and Huszar, *Intern. Rev. Immunol.* 13: 65-93 (1995).

Finally, human anti-TREM1 antibodies may also be generated in vitro by activated B-cells (see U.S. Pat. Nos. 5,567,610 and 5,229,275).

(5) Antibody Fragments

In certain embodiments there are advantages to using anti-TREM1 antibody fragments, rather than whole anti-TREM1 antibodies. In some embodiments, smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host-cells, for example, using nucleic acids encoding anti-TREM1 antibodies of the present disclosure. Fab, Fv and scFv antibody fragments can all be expressed in and secreted from *E. coli*, thus allowing the straightforward production of large amounts of these fragments. Anti-TREM1 antibody fragments can also be isolated from the antibody phage libraries as discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host-cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-TREM1 antibody fragment may also be a "linear antibody," e.g., as described in U.S. Pat. No. 5,641,870. Such linear antibody fragments may be monospecific or bispecific.

(6) Bispecific and Polyspecific Antibodies

Bispecific antibodies (BsAbs) are antibodies that have binding specificities for at least two different epitopes, including those on the same or another protein (e.g., one or more TREM1 proteins of the present disclosure). Alternatively, one part of a BsAb can be armed to bind to the target TREM1 antigen, and another can be combined with an arm that binds to a second protein. Such antibodies can be derived from full-length antibodies or antibody fragments (e.g., F(ab')$_2$ bispecific antibodies).

Methods for making bispecific antibodies are known in the art. Traditional production of full-length bispecific antibodies is based on the coexpression of two immunoglobulin heavy-chain/light chain pairs, where the two chains have different specificities. Millstein et al., *Nature,* 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986); and Garber, *Nature Reviews Drug Discovery* 13, 799-801 (2014).

According to another approach described in WO 96/27011 or U.S. Pat. No. 5,731,168, the interface between a pair of antibody molecules can be engineered to maximize the percentage of heterodimers which are recovered from recombinant-cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA,* 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

Another method to generate bispecific antibodies is designated controlled Fab-arm exchange (cFAE), which is an easy-to-use method to generate bispecific IgG1 (bsIgG1). The protocol involves the following: (i) separate expression of two parental IgG1s containing single matching point mutations in the CH3 domain; (ii) mixing of parental IgG1s under permissive redox conditions in vitro to enable recombination of half-molecules; (iii) removal of the reductant to allow reoxidation of interchain disulfide bonds; and (iv) analysis of exchange efficiency and final product using chromatography-based or mass spectrometry (MS)-based methods. The protocol generates bsAbs with regular IgG architecture, characteristics and quality attributes both at bench scale (micrograms to milligrams) and at a mini-bioreactor scale (milligrams to grams) that is designed to model large-scale manufacturing (kilograms). Starting from good-quality purified proteins, exchange efficiencies of ≥95% can be obtained within 2-3 days (including quality control). See Labrijn et al., *Natur Protocols* 9, 2450-2463 (2014); and Garber, *Nature Reviews Drug Discovery* 13, 799-801 (2014).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a TREM1 protein of the present disclosure). In some embodiments a bispecific antibody binds to a first antigen, such as a TREM1 or DAP12 protein of the present disclosure, and a second antigen facilitating transport across the blood-brain barrier. Numerous antigens are known in the art that facilitate transport across the blood-brain barrier (see, e.g., Gabathuler R., Approaches to transport therapeutic drugs across the blood-brain barrier to treat brain diseases, Neurobiol. Dis. 37 (2010) 48-57). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10):e13741). In some embodiments, second antigens for an anti-TREM1 antibody may include, without limitation, a DAP12 antigen of the present disclosure. In other embodiments, second antigens for an anti-DAP12 antibody may include, without limitation, a TREM1 antigen of the present disclosure. In other embodiments, bispecific antibodies that bind to both TREM1 and DAP12 may facilitate and enhance one or more TREM1 activities. In other embodiments, second antigens for an anti-TREM1 antibody may include, without limitation, A beta peptide, antigen or an alpha synuclain protein antigene or, Tau protein antigen or, TDP-43 protein antigen or, prion protein antigen or, huntingtin protein antigen, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR).

(7) Multivalent Antibodies

A multivalent antibody may be internalized (and/or catabolized) faster than a bivalent antibody by a cell expressing an antigen to which the antibodies bind. The anti-TREM1 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The Multivalent antibodies may recognize the TREM1 angigen as well as without limitation additional antigens A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier.

(8) Effector Function Engineering

It may also be desirable to modify an anti-TREM1 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000). In other embodiments, it may also be desirable to modify an anti-TREM1 antibody of the present disclosure to modify effector function to increase finding selectivity toward the ITIM-containing FcgRIIb (CD32b) to increase clustering of TREM1 antibodies on adjacent cells without activating humoral responses inclsing Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(9) Other Amino Acid Sequence Modifications

Amino acid sequence modifications of anti-TREM1 antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a TREM1 protein of the present disclosure). The amino acid changes also may alter post-translational processes of the antibody, such as changing the number or position of glycosylation sites.

A useful method for identification of certain residues or regions of the anti-TREM1 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table C below under the heading of "preferred substitutions". If such substitutions result in a change in biological activity, then more substantial changes, denominated "exemplary substitutions" in Table C, or as further described below in reference to amino acid classes, may be introduced and the products screened.

TABLE C

Amino Acid Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |

TABLE C-continued

Amino Acid Substitutions

| Original Residue | Exemplary Substitutions | Preferred Substitutions |
| --- | --- | --- |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-TREM1 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a TREM1 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-TREM1 antibodies of the present disclosure) or antibody fragments.

(10) Other Antibody Modifications

Anti-TREM1 antibodies of the present disclosure, or antibody fragments thereof, can be further modified to contain additional non-proteinaceous moieties that are known in the art and readily available, or to contain different types of drug conjugates that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

Drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

Binding Assays and Other Assays

Anti-TREM1 antibodies of the present disclosure may be tested for antigen binding activity, e.g., by known methods such as ELISA, Western blot, etc.

In some embodiments, competition assays may be used to identify an antibody that competes with any of the antibodies listed in Tables 1-5, selected from T1-1-T1-80, and humanized variants thereof for binding to TREM1. In certain embodiments, such a competing antibody binds to the same epitope (e.g., a linear or a conformational epitope) that is bound by any of the antibodies listed in Tables 1-5, selected from T1-1-T1-80 and their humanized derivatives. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized TREM1 or cells expressing TREM1 on cell surface are incubated in a solution comprising a first labeled antibody that binds to TREM1 (e.g., human or non-human primate) and a second unlabeled antibody that is being tested for its ability to compete with the first antibody for binding to TREM1. The second antibody may be present in a hybridoma supernatant. As a control, immobilized TREM1 or cells expressing TREM1 is incubated in a solution comprising the first labeled antibody but not the second unlabeled antibody. After incubation under conditions permissive for binding of the first antibody to TREM1, excess unbound antibody is removed, and the amount of label associated with immobilized TREM1 or cells expressing TREM1 is measured. If the amount of label associated with immobilized TREM1 or cells expressing TREM1 is substantially reduced in the test sample relative to the control sample, then that indicates that the second antibody is competing with the first antibody for binding to TREM1. See Harlow and Lane (1988) *Antibodies: A Laboratory Manual* ch. 14 (Cold Spring Harbor Laboratory, Cold Spring Harbor, NY).

Nucleic Acids, Vectors, and Host Cells

Anti-TREM1 antibodies of the present disclosure may be produced using recombinant methods and compositions, e.g., as described in U.S. Pat. No. 4,816,567. In some embodiments, isolated nucleic acids having a nucleotide sequence encoding any of the anti-TREM1 antibodies of the present disclosure are provided. Such nucleic acids may encode an amino acid sequence containing the VL and/or an amino acid sequence containing the VH of the anti-TREM1 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-TREM1 antibody of the present disclosure are provided. In some embodiments, the method includes culturing a host cell of the present disclosure containing a nucleic acid encoding the anti-TREM1 antibody, under conditions suitable for expression of the antibody. In some embodiments, the antibody is subsequently recovered from the host cell (or host cell culture medium).

For recombinant production of an anti-TREM1 antibody of the present disclosure, a nucleic acid encoding the anti-TREM1 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-TREM1 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-TREM1 antibody of the present disclosure.

Suitable host cells for cloning or expression of antibody-encoding vectors include prokaryotic or eukaryotic cells. For example, anti-TREM1 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology, Vol.* 248 (B. K. C. Lo, ed., Humana Press, Totowa, NJ, 2003), pp. 245-254, describing expression of antibody fragments in *E. coli.*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TM cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Pharmaceutical Compositions

Anti-TREM1 antibodies can be incorporated into a variety of formulations for therapeutic administration by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, PA, 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-TREM1 antibody of the present disclosure, in a biodegradable or bio-erodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-TREM1 antibody of the present disclosure may be administered to an individual in need of treatment with the anti-TREM1 antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-TREM1 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-TREM1 antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-TREM1 antibody administered, can vary over time independently of the dose used.

Dosages for a particular anti-TREM1 antibody may be determined empirically in individuals who have been given one or more administrations of the anti-TREM1 antibody. Individuals are given incremental doses of an anti-TREM1 antibody. To assess efficacy of an anti-TREM1 antibody, a clinical symptom of ay of the diseases, disorders, or conditions of the present disclosure (e.g., dementia, frontotemporal dementia, Alzheimer's disease, Nasu-Hakola disease, and multiple sclerosis) can be monitored.

Administration of an anti-TREM1 antibody of the present disclosure can be continuous or intermittent, depending, for example, on the recipient's physiological condition, whether the purpose of the administration is therapeutic or prophylactic, and other factors known to skilled practitioners. The administration of an anti-TREM1 antibody may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

Further aspects of the present disclosure provide methods for modulating (e.g., activating or inhibiting) TREM1, modulating (e.g., activating or inhibiting) DAP12, modulating (e.g., activating or inhibiting) PI3K, modulating modulating (e.g., increasing or reducing) expression of one or more pro-and anti-inflammatory mediators (e.g., IFN-a4, IFN-b, IL-1β, TNF-α, IL-10, IL-6, IL-8, IL-23, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, IL-23, MCP-1, VEGF, CXCL10 and CRP) or, modulating (e.g., increasing or reducing) survival of one or more TREM1 expressing cells or, modulating (e.g., increasing or reducing) functionality of one or more TREM1 expressing cells, or, modulating (e.g., increasing or reducing) proliferation of one or more TREM1 expressing cells or, or, modulating (e.g., increasing or reducing) migration of one or more TREM1 expressing cells, or, modulating (e.g., increasing or reducing) interaction with other cells of one or more TREM1 expressing cells in an individual in need thereof, by administering to the individual a therapeutically effective amount of an anti-TREM1 antibody of the present disclosure to modulate (e.g., induce or inhibit) one or more TREM1 activities in the individual.

The anti-TREM1 antibodies provided by the disclosure also find use in inducing or promoting the survival, maturation, functionality, migration, or proliferation of one or more immune cells in an individual in need thereof. Anti-TREM1 antibodies provided herein find further use in decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cell in an individual in need thereof. Tumor-Anti-TREM1 antibodies additionally find further use in increasing memory and/or reducing cognitive deficit; and may also be used in advanced wound care.

As explained above, anti-TREM1 antibodies of the present disclosure can be used to prevent, reduce risk of, or treat any number of disorders, including, but not limited to, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, solid and blood cancer, bladder cancer, brain cancer, e.g., glioma such as low grade glioma, or glioblastoma; breast cancer, cervical cancer, glioma, glioblastoma, colon cancer, rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM1, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and Haemophilus influenza. The invention thus provides methods of preventing, reducing risk, or treating an individual having one or more such diseases or disorders by administering to the individual a therapeutically effective amount of an anti-TREM1 antibody of the present disclosure. In some embodiments, the anti-TREM1 antibody is an agonist antibody. In some embodiments, the anti-TREM1 antibody is an inert antibody. In some embodiments, the anti-TREM1 antibody is an antagonist antibody.

In some embodiments, the method further includes administering to the individual at least one antibody that specifically binds to an inhibitory checkpoint molecule, and/or another standard or investigational anti-cancer therapy. In some embodiments, the antibody that specifically binds to an inhibitory checkpoint molecule is administered in combination with the isolated antibody. In some embodiments, the at least one antibody that specifically binds to an inhibitory checkpoint molecule is selected from an anti-PD-L1 antibody, an anti-CTLA-4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, hormonal therapy, imatinib (Gleevec®), trastuzumab (Herceptin®), bevacizumab (Avastin®), Ofatumumab (Arzerra®), Rituximab (Rituxan®, MabThera®, Zytux®), cryotherapy, ablation, radiofrequency ablation, adoptive cell transfer (ACT), chimeric antigen receptor T cell transfer (CAR-T), vaccine therapy, and cytokine therapy. In some embodiments, the method further includes administering to the individual at least one antibody that specifically binds to an inhibitory cytokine. In some embodiments, the at least one antibody that specifically binds to an inhibitory cytokine is administered in combination with the isolated antibody. In some embodiments, the at least one antibody that specifically binds to an inhibitory cytokine is selected from an anti-CCL2 antibody, an anti-CSF-1 antibody, an anti-IL-2 antibody, and any combination thereof. In some embodiments, the method further includes administering to the individual at least one agonistic antibody that specifically binds to a stimulatory checkpoint protein. In some embodiments, the at least one agonistic antibody that specifically binds to a stimulatory checkpoint protein is administered in combination with the isolated antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof. In some embodiments, the method further includes administering to the individual at least one stimulatory cytokine. In some embodiments, the at least one stimulatory cytokine is administered in combination with the isolated antibody. In some embodiments, the at least one stimulatory cytokine is selected from TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, IL-23, IFN-α, IFN-β, IL-2, IL-18, GM-CSF, G-CSF, and any combination thereof.

Other aspects of the present disclosure relate to methods of enhancing one or more TREM1 activities induced by binding of one or more TREM1 ligands to a TREM1 protein in an individual in need thereof, by administering to the individual a therapeutically effective amount of an anti-TREM1 antibody of the present disclosure. Other aspects of the present disclosure relate to methods of inducing one or more TREM1 activities in an individual in need thereof, by administering to the individual a therapeutically effective amount of an anti-TREM1 antibody of the present disclosure. Any suitable method for measuring TREM1 activity, such as the in vitro cell-based assays or in vivo models of the present disclosure may be used.

As disclosed herein, anti-TREM1 antibodies of the present disclosure may be used for decreasing cellular levels of TREM1 on one or more cells, including without limitation, dendritic cells, bone marrow-derived dendritic cells, monocytes, microglia, macrophages, neutrophils, NK cells, osteoclasts, Langerhans cells of skin, and Kupffer cells and/or cell lines. In some embodiments, the present disclosure provides methods of decreasing cellular levels of TREM1 on one or more cells in an individual in need thereof, by administering to the individual a therapeutically effective amount of an anti-TREM1 antibody of the present disclosure. In some embodiments, the one or more cells are selected from dendritic cells, bone marrow-derived dendritic cells, monocytes, microglia, macrophages, neutrophils, NK cells, osteoclasts, Langerhans cells of skin, and Kupffer cells, and any combination thereof. Cellular levels of TREM1 may refer to, without limitation, cell surface levels of TREM1, intracellular levels of TREM1, and total levels of TREM1. In some embodiments, a decrease in cellular levels of TREM1 comprises decrease in cell surface levels of TREM1. As used herein, cell surface levels of TREM1 may be measured by any in vitro cell-based assays or suitable in vivo model described herein or known in the art. In some embodiments, a decrease in cellular levels of TREM1 comprises a decrease in intracellular levels of TREM1. As used herein, intracellular levels of TREM1 may be measured by any in vitro cell-based assays or suitable in vivo model described herein or known in the art. In some embodiments, a decrease in cellular levels of TREM1 comprises a decrease in total levels of TREM1. As used herein, total levels of TREM1 may be measured by any in vitro cell-based assays or suitable in vivo model described herein or known in the art. In some embodiments, the anti-TREM1 antibodies induce TREM1 degradation, TREM1 cleavage, TREM1 internalization, TREM1 shedding, and/or downregulation of TREM1 expression. In some embodiments, cellular levels of TREM1 are measured on primary cells (e.g., dendritic cells, bone marrow-derived dendritic cells, monocytes, microglia, and macrophages) or on cell lines utilizing an in vitro cell assay.

As disclosed herein, anti-TREM1 antibodies of the present disclosure may also be used for increasing memory and/or reducing cognitive deficit. In some embodiments, the present disclosure provides methods of increasing memory and/or reducing cognitive deficit in an individual in need thereof, by administering to the individual a therapeutically effective amount of an anti-TREM1 antibody of the present disclosure.

As disclosed herein, anti-TREM1 antibodies of the present disclosure may also be used for inducing and/or promoting innate immune cell survival. In some embodiments, the present disclosure provides methods of inducing or promoting innate immune cell survival in an individual in need thereof, by administering to the individual a therapeutically effective amount of an agonist anti-TREM1 antibody of the present disclosure.

As disclosed herein, anti-TREM1 antibodies of the present disclosure may also be used for inducing and/or promoting wound healing, such as after injury. In some embodiments, the wound healing may be colonic wound repair following injury. In some embodiments, the present disclosure provides methods of inducing or promoting wound healing an individual in need thereof, by administering to the individual a therapeutically effective amount of an agonist anti-TREM1 antibody of the present disclosure.

In some embodiments, the methods of the present disclosure may involve the coadministration of anti-TREM1 antibodies, or bispecific antibodies with TLR antagonists or with agents neutralizing TLR agonist (e.g., neutralizing cytokine or interleukin antibodies).

In some embodiments, the methods of the present disclosure may involve the administration of chimeric constructs, including an anti-TREM1 antibody of the present disclosure in conjunction with a TREM1 ligand, such as PGLYRP-1.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-TREM1 antibody of the present disclosure can prevent, reduce the risk, and/or treat dementia. In some embodiments, administering an anti-TREM1 antibody may induce one or more TREM1 activities in an individual having dementia (e.g., DAP12 phosphorylation, PI3K activation, increased expression of one or more anti-inflammatory mediators, or reduced expression of one or more pro-inflammatory mediators).

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the progranulin gene.

In some embodiments, administering an anti-TREM1 antibody of the present disclosure can prevent, reduce the risk, and/or treat FTD. In some embodiments, administering an anti-TREM1 antibody may induce one or more TREM1 activities in an individual having FTD (e.g., DAP12 phosphorylation, PI3K activation, increased expression of one or more anti-inflammatory mediators, or reduced expression of one or more pro-inflammatory mediators).

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering an anti-TREM1 antibody of the present disclosure can prevent, reduce the risk, and/or treat Alzheimer's disease. In some embodiments, administering an anti-TREM1 antibody may induce one or more TREM1 activities in an individual having Alzheimer's disease (e.g., DAP12 phosphorylation, PI3K activation, increased expression of one or more anti-inflammatory mediators, or reduced expression of one or more pro-inflammatory mediators).

Nasu-Hakola Disease

Nasu-Hakola disease (NHD), which may alternatively be referred to as polycystic lipomembranous osteodysplasia with sclerosing leukoencephalopathy (PLOSL), is a rare inherited leukodystrophy characterized by progressive presenile dementia associated with recurrent bone fractures due to polycystic osseous lesions of the lower and upper extremities. NHD disease course is generally divided into four stages: latent, osseous, early neurologic, and late neurologic. After a normal development during childhood (latent stage), NHD starts manifesting during adolescence or young adulthood (typical age of onset 20-30 years) with pain in the hands, wrists, ankles, and feet. Patients then start suffering from recurrent bone fractures due to polycystic osseous and osteoporotic lesions in the limb bones (osseous stage). During the third or fourth decade of life (early neurologic stage), patients present with pronounced personality changes (e.g., euphoria, lack of concentration, loss of judgment, and social inhibitions) characteristic of a frontal lobe syndrome. Patients also typically suffer from progressive memory disturbances. Epileptic seizures are also frequently observed. Finally (late neurologic stage), patients progress to a profound dementia, are unable to speak and move, and usually die by the age of 50.

In some embodiments, administering an anti-TREM1 antibody of the present disclosure can prevent, reduce the risk, and/or treat Nasu-Hakola disease (NHD). In some embodiments, administering an anti-TREM1 antibody may induce one or more TREM1 activities in an individual having NHD (e.g., DAP12 phosphorylation, PI3K activation, increased expression of one or more anti-inflammatory mediators, or reduced expression of one or more pro-inflammatory mediators).

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-TREM1 antibody of the present disclosure can prevent, reduce the risk, and/or treat Parkinson's disease. In some embodiments, administering an anti-TREM1 antibody may induce one or more TREM1 activities in an individual having Parkinson's disease (e.g., DAP12 phosphorylation, PI3K activation, increased expression of one or more anti-inflammatory mediators, or reduced expression of one or more pro-inflammatory mediators).

Amyotrophic Lateral Sclerosis

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that progranulin play a role in ALS (Schymick, J C et al., (2007) J Neurol Neurosurg Psychiatry.; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering an anti-TREM1 antibody of the present disclosure can prevent, reduce the risk, and/or treat ALS. In some embodiments, administering an anti-TREM1 antibody may induce one or more TREM1 activities in an individual having ALS (e.g., DAP12 phosphorylation, PI3K activation, increased expression of one or more anti-inflammatory mediators, or reduced expression of one or more pro-inflammatory mediators).

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering an anti-TREM1 antibody of the present disclosure can prevent, reduce the risk, and/or treat Huntington's disease (HD). In some embodiments, administering an anti-TREM1 antibody may induce one or more TREM1 activities in an individual having HD (e.g., DAP12 phosphorylation, PI3K activation, increased expression of one or more anti-inflammatory mediators, or reduced expression of one or more pro-inflammatory mediators).

Taupathy Disease

Taupathy diseases, or Tauopathies, are a class of neurodegenerative disease caused by aggregation of the microtubule-associated protein tau within the brain. Alzheimer's disease (AD) is the most well-known Taupathy disease, and involves an accumulation of tau protein within neurons in the form of insoluble neurofibrillary tangles (NFTs). Other Taupathy diseases and disorders include progressive supranuclear palsy, dementia pugilistica (chromic traumatic encephalopathy), Frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, frontotemporal dementia, and frontotemporal lobar degeneration.

In some embodiments, administering an anti-TREM1 antibody of the present disclosure can prevent, reduce the risk, and/or treat Taupathy disease. In some embodiments, administering an anti-TREM1 antibody may induce one or more TREM1 activities in an individual having Taupathy disease (e.g., DAP12 phosphorylation, PI3K activation, increased expression of one or more anti-inflammatory mediators, or reduced expression of one or more pro-inflammatory mediators).

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoff's phenomenon, which is an exacerbation of extant symptoms due to an exposure to higher than usual ambient temperatures; and Lhermitte's sign, which is an electrical sensation that runs down the back when bending the neck.

In some embodiments, administering an anti-TREM1 antibody of the present disclosure can prevent, reduce the risk, and/or treat multiple sclerosis. In some embodiments, administering an anti-TREM1 antibody may induce one or more TREM1 activities in an individual having multiple sclerosis (e.g., DAP12 phosphorylation, PI3K activation, increased expression of one or more anti-inflammatory mediators, and reduced expression of one or more pro-inflammatory mediators).

Cancer

Yet further aspects of the present disclosure provide methods for preventing, reducing risk, or treating an individual having cancer, comprising administering to the individual a therapeutically effective amount of an isolated anti-TREM1 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure.

As described above, the tumor microenvironment is known to contain a heterogeneous immune infiltrate, which includes T lymphocytes, macrophages and cells of myeloid/granulocytic lineage. In particular, the presence of M2-macrophages in tumors is associated with poor prognosis. Therapies that reduce the number of these cells in the tumor, such as CSF1R blocking agents, are showing beneficial effects in preclinical models and early stage clinical studies. It has been shown that TREM1 synergizes with CSF1 to promote survival of macrophages in vitro, and that this effect is particularly prominent in M2-type macrophages, compared to other types of phagocytic cells. A seminal preclinical study has also shown synergies between drugs that target tumor-associated macrophages (e.g., CSF1/CSF1R blocking antibodies) and checkpoint blocking antibodies that target T cells, indicating that manipulating both cell types shows efficacy in tumor models where individual therapies are poorly effective (Zhu Y; Cancer Res. 2014 Sep. 15; 74(18): 5057-69). Therefore, without wishing to be bound by theory, it is thought that blocking TREM1 signaling in tumor associated macrophages may inhibit suppression of the immune response in the tumor microenvironment, resulting in a therapeutic anti-tumor immune response.

Due to the synergies between TREM1 and CSF1, and between targeting tumor-associated macrophages and targeting T cells, in some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA-4 antibody, an anti-PD-L2 antibody, an anti-PD-1 antibody, an anti-B7-H3 antibody, an anti-B7-H4 antibody, and anti- HVEM antibody, an anti-BTLA antibody, an anti-GAL9 antibody, an anti-TIM3 antibody, an anti-A2AR antibody, an anti-LAG-3 antibody, an anti-phosphatidylserine antibody, and any combination thereof. In some embodiments, the at least one antibody that specifically binds to an inhibitory checkpoint molecule is administered in combination with an antagonist anti-TREM1 antibody of the present disclosure.

In some embodiments, a cancer to be prevented or treated by the methods of the present disclosure includes, but is not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, glioma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer is squamous non-small cell lung cancer, cervical cancer, e.g., cervical squamous cell carcinoma or endocervical adenocarcinoma; liver hepatocellular carcinoma, low grade glioma, glioblastoma, renal clear cell carcinoma, renal papillary cell carcinoma, chromophobe renal cell carcinoma, or pancreatic cancer. In some embodiments, the cancer is squamous non-small cell lung cancer, cervical squamous cell carcinoma or endocervical adenocarcinoma; liver hepatocellular carcinoma, or low grade glioma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, anti-TREM1 antibodies of the present disclosure may be used for preventing, reducing risk, or treating cancer, including, without limitation, bladder cancer, breast cancer, brain cancer, e.g., glioma such as low grade glioma, or glioblastoma; cervical cancer, colon and rectal cancer, endometrial cancer, kidney cancer, renal cell cancer, renal pelvis cancer, leukemia, lung cancer, e.g., non-small cell lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of an anti-TREM1 antibody of the present disclosure.

In some embodiments, the method further includes administering to the individual at least one antibody that specifically binds to an inhibitory checkpoint molecule, and/or another standard or investigational anti-cancer therapy. In some embodiments, the at least one antibody that specifically binds to an inhibitory checkpoint molecule is administered in combination with the isolated antibody. In some embodiments, the at least one antibody that specifically binds to an inhibitory checkpoint molecule is selected from an anti-PD-L1 antibody, an anti-CTLA-4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, hormonal therapy, bevacizumab (Avastin®), Ofatumumab (Arzerra®), Rituximab (Rituxan®, MabThera®, Zytux®), cryotherapy, ablation, radiofrequency ablation, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the isolated antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory checkpoint protein. In some embodiments, the at least one agonistic antibody that specifically binds to a stimulatory checkpoint protein is administered in combination with the isolated antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the isolated antibody. In some embodiments, the at least one stimulatory cytokine is selected from TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, CRP, IFN-α, IFN-β, IL-2, IL-18, IL-23, CXCL10, MCP-1, VEGF, GM-CSF, G-CSF, and any combination thereof.

Kits/Articles of Manufacture

The present disclosure also provides kits containing an isolated antibody of the present disclosure (e.g., an anti-TREM1 or anti-DAP12 antibody described herein), or a functional fragment thereof. Kits of the present disclosure may include one or more containers comprising a purified antibody of the present disclosure. In some embodiments, the kits further include instructions for use in accordance with the methods of this disclosure. In some embodiments, these instructions comprise a description of administration of the isolated antibody of the present disclosure (e.g., an anti-TREM1 or anti-DAP12 antibody described herein) to prevent, reduce risk, or treat an individual having a disease, disorder, or injury selected from dementia, frontotemporal dementia, Alzheimer's disease, Nasu-Hakola disease, multiple sclerosis, and cancer, according to any methods of this disclosure.

In some embodiments, the instructions comprise a description of how to detect TREM1 and/or DAP12, for example in an individual, in a tissue sample, or in a cell. The kit may further comprise a description of selecting an individual suitable for treatment based on identifying whether that individual has the disease and the stage of the disease.

In some embodiments, the kits may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits may further include instructions for using the antibody and/or stimulatory cytokine in combination with an isolated antibody of the present disclosure (e.g., an anti-TREM1 antagonist antibody described herein), instructions for using the isolated antibody of the present disclosure in combination with an antibody and/or stimulatory cytokine, or instructions for using an isolated antibody of the present disclosure and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an isolated antibody of the present disclosure (e.g., an anti-TREM1 or anti-DAP12 antibody described herein). The container may further comprise a second pharmaceutically active agent.

Kits may optionally provide additional components such as buffers and interpretive information. Normally, the kit comprises a container and a label or package insert(s) on or associated with the container.

Diagnostic Uses

The isolated antibodies of the present disclosure also have diagnostic utility. This disclosure therefore provides for methods of using the anti-TREM1 antibodies of this disclosure, or functional fragments thereof, for diagnostic purposes, such as the detection of TREM1 in an individual or in tissue samples derived from an individual.

In some embodiments, the individual is a human. In some embodiments, the individual is a human patient suffering from, or at risk for developing, cancer. In some embodiments, the diagnostic methods involve detecting TREM1 in a biological sample, such as a biopsy specimen, a tissue, or a cell. An isolated TREM1 antibody of the present disclosure is contacted with the biological sample and antigen-bound antibody is detected. For example, a tumor sample (e.g., a biopsy specimen) may be stained with an anti-TREM1 antibody described herein in order to detect and/or quantify tumor-associated macrophages (e.g., M2-type macrophages). The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radio-labeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated anti-TREM! antibody of the present disclosure may be used to detect and/or quantify, for example, microglia in a brain specimen taken from a preclinical disease model (e.g., a non-human disease model). As such, an isolated anti-TREM1 antibody of the present disclosure may be useful in evaluating therapeutic response after treatment in a model for a nervous system disease or injury such as dementia, frontotemporal dementia, Alzheimer's disease, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Production, Identification, and Characterization of Agonist Anti-TREM1 Antibodies Introduction The amino acid sequence of the human TREM1 preprotein is set forth below in SEQ ID NO: 1. Human TREM1 contains a signal peptide located at amino residues 1-20 of SEQ ID NO: 1. Human TREM1 contains an extracellular immunoglobulin-like variable-type (IgV) domain located at amino residues 26-134 of SEQ ID NO: 1; additional extracellular sequences located at amino residues 135-205 of SEQ ID NO: 1; a transmembrane domain located at amino residues 206-226 of SEQ ID NO: 1; and an intracellular domain located at amino residues 227-234 of SEQ ID NO: 1.

```
TREM1 amino acid sequence (SEQ ID NO: 1):
MRKTRLWGLL WMLFVSELRA ATKLTEEKYE LKEGQTLDVK

CDYTLEKFAS SQKAWQIIRD GEMPKTLACT ERPSKNSHPV

QVGRIILEDY HDHGLLRVRM VNLQVEDSGL YQCVIYQPPK

EPHMLFDRIR LVVTKGFSGT PGSNENSTQN VYKIPPTTTK

ALCPLYTSPR TVTQAPPKST ADVSTPDSEI NLTNVTDIIR

VPVFNIVILL AGGFLSKSLV FSVLFAVTLR SFVP
```

A known feature of human TREM1 is that the transmembrane domain contains a lysine (aa186) that can interact with an aspartic acid in DAP12, a key adaptor protein that transduces signaling from TREM1, TREM1, and other related IgV family members.

A BLAST analysis of human TREM1 identified 18 related homologues. These homologues included the Natural Killer (NK) cell receptor NK-p44 (NCTR2), the polymeric immunoglobulin receptor (pIgR), CD300E, CD300A, CD300C, and TREML1/TLT1. The closest homologue was identified as NCTR2, having similarity with TREM1 within the IgV domain (FIG. 1A). A BLAST analysis also compared TREM proteins with other IgV family proteins (FIG. 1B).

TREM1 is also related to TREM2. An alignment of the amino acid sequences of TREM1 and TREM2 was generated by 2-way blast (FIG. 2A). This is limited to the IgV domain as well.

Antibodies that bind the extracellular domain of TREM1, particularly the extra cellular domain (amino acid residues 21-205 of SEQ ID NO: 1) are generated using mouse hybridoma technology, phage display technology, and yeast display technology. Antibodies are then screened for their ability to bind cells that express TREM1 and for their ability to activate TREM1 signaling and functions in cells and in a whole animal in vivo as described in Examples 2-48 below. For example, agonist anti-TREM1 antibodies can be produced that target the IgV domain (amino acid residues 26-134). IgV domains bind to targets, and through multimerization of receptors, lead to activation. Thus these domains are rational targets for agonistic antibodies. They are also highly divergent.

Results

Anti-TREM1 Antibody Production

Immunization Procedure

Rapid prime method: Four 50-day old female BALB/c mice were immunized with using the following procedure. A series of subcutaneous aqueous injections containing human TREM1 antigen but no adjuvant were given over a period of 19 days. Mice were housed in a ventilated rack system from Lab Products. All four mice were euthanized on Day 19 and lymphocytes were harvested for hybridoma cell line generation.

Standard method: Four 50-day old female BALB/c or NZB/W mice were immunized using the following procedure. Mice were housed in a ventilated rack system from Lab Products. Mice were injected intraperitoneally every 3 weeks with a human TREM1 antigen mixed in CpG-ODN adjuvant at 25 µg protein antigen per mouse (total volume 125 µL per mouse). Test bleeds were done by saphenous vein lancing seven days after the second boost. The test bleed (immune sera) was tested by indirect ELISA assay to determine the best two responding mice for the fusion. The mice may require a 3rd and 4th boost and another test bleed 7 days after boost to assess titre before fusion. When the antibody titre is high enough the best two responding mice are given a final intravenous boost via lateral tail vein. Four days after the IV boost the mice were euthanized for fusion. The spleens were harvested and lymphocytes isolated from the spleen were used in the fusion process to produce hybridomas.

Hybridoma Development

Lymphocytes were isolated and fused with murine SP2/0 myeloma cells in the presence of poly-ethylene glycol (PEG 1500) as per standard Roche Protocol. Fused cells were cultured using a single-step cloning method (HAT selection). This method uses a semi-solid methylcellulose-based HAT selective medium to combine the hybridoma selection and cloning into one step. Single cell-derived hybridomas grow to form monoclonal colonies on the semi-solid media. Ten days after the fusion event, 948 of the resulting hybridoma clones were transferred to 96-well tissue culture plates and grown in HT containing medium until mid-log growth was reached (5 days).

Hybridoma Screening

Tissue culture supernatants from the 948 hybridomas were tested by indirect ELISA on screening antigen (Primary Screening) and probed for both IgG and IgM antibodies using a Goat anti-IgG/IgM(H&L)-HRP secondary and developed with TMB substrate. Clones>0.2 OD in this assay were taken to the next round of testing. Positive cultures were retested on screening antigen to confirm secretion and on an irrelevant antigen (Human Transferrin) to eliminate non-specific or "sticky" mAbs and rule out false positives. All clones of interest were isotyped by antibody trapping ELISA to determine if they are IgG or IgM isotype.

Hybridoma Cell Culture

The hybridoma cell lines of interest were maintained in culture in 24-well culture plates for 32 days post transfer to 96-well plates. This is referred to as the stability period and tests whether clones remain stable and secreting. During this stability period time temporary frozen cell line back up is made of all the clones of interest for −80° C. storage (viable 6 months). Hybridomas were periodically tested during this time period for secretion and specificity.

Subcloning

The top hybridoma cell lines (clones) were subcloned to ensure monoclonality. Subcloning was performed by plating parental clones out again using the single-step cloning system. Between 24 and 90 subclones were transferred to 96-well culture plates. Subclones were screened by indirect ELISA and antibody trapping ELISA. The top subclones for each parent were taken for expansion in culture. Any parental clones that were <50% clonal had a second round of subcloning performed.

The antibodies were then screened for TREM1 binding. Antibodies that were positive for binding to human TREM1 were tested for ability to block ligand binding and ability to induce, enhance, or otherwise increase ligand-induced TREM1 activity in multiple cell types. The isotype bin category, Kd and biological activities of each of the antibodies are listed in Table 1A and 1B. In Table 1A, "ND" refers to antibodies for which the Bin category has not been determined.; "NB" refers to antibodies with no binding activity against antigen; "PF" refers to antibodies whose kinetic constants cannot be calculated due to poor fit of binding curve. In Table 1B, "NA" refers to antibodies with no activity.

Table 1: Anti-TREM1 Antibodies

TABLE 1A

| | | | biochemical characterization | | | | | |
|---|---|---|---|---|---|---|---|---|
| Ab ID | Bin | Ab Isotype | Fab KD Human TREM1-Fc (M) Monovalent | kon (1/Ms) | koff (1/s) | IgG $K_D$ (M) mono-valent | kon (1/Ms) | koff (1/s) |
| T1-1 | 2 | huIgG1 | 3.85E−08 | 1.72E+05 | 6.64E−03 | 1.79E−07 | 9.36E+04 | 1.68E−02 |
| T1-2 | 1 | huIgG1 | 4.07E−08 | 9.54E+04 | 3.88E−03 | P.F. | | |
| T1-3 | 2 | huIgG1 | 6.31E−08 | 7.48E+04 | 4.72E−03 | 7.89E−08 | 4.70E+04 | 3.71E−03 |
| T1-4 | 1 | huIgG1 | 4.70E−08 | 1.81E+05 | 8.51E−03 | 1.11E−07 | 2.39E+05 | 2.64E−02 |
| T1-5 | 2 | huIgG1 | 1.48E−07 | 5.43E+04 | 8.02E−03 | 7.26E−08 | 1.58E+05 | 1.15E−02 |
| T1-6 | 2 | huIgG1 | 1.23E−07 | 1.06E+05 | 1.30E−02 | 2.03E−07 | 8.28E+04 | 1.68E−02 |
| T1-7 | 2 | huIgG1 | 3.19E−08 | 1.99E+05 | 6.36E−03 | 1.67E−07 | 1.24E+05 | 2.06E−02 |
| T1-8 | 2 | huIgG1 | 6.55E−08 | 1.18E+05 | 7.75E−03 | 1.77E−07 | 8.04E+04 | 1.42E−02 |
| T1-9 | 2 | huIgG1 | 5.96E−08 | 1.45E+05 | 8.61E−03 | 1.10E−07 | 7.81E+04 | 8.56E−03 |
| T1-10 | 2 | huIgG1 | 6.07E−09 | 1.04E+05 | 6.34E−04 | 8.45E−09 | 7.85E+04 | 6.63E−04 |
| T1-11 | 2 | huIgG1 | 7.04E−08 | 8.04E+04 | 5.66E−03 | P.F. | | |
| T1-12 | 1 | huIgG1 | 2.58E−08 | 1.24E+05 | 3.21E−03 | P.F. | | |
| T1-13 | 1 | huIgG1 | N.B. | | | N.B. | | |
| T1-14 | 2 | huIgG1 | 2.13E−07 | 4.06E+04 | 8.62E−03 | N.B. | | |
| T1-15 | 1 | huIgG1 | P.F. | | | 7.47E−08 | 2.44E+05 | 1.82E−02 |
| T1-16 | 1 | huIgG1 | P.F. | | | N.B. | | |
| T1-17 | 1 | huIgG1 | 9.14E−08 | 8.19E+04 | 7.48E−03 | N.B. | | |
| T1-18 | 1 | huIgG1 | 1.86E−07 | 7.88E+04 | 1.46E−02 | N.B. | | |
| T1-19 | 1 | huIgG1 | P.F. | | | N.B. | | |
| T1-20 | 1 | huIgG1 | P.F. | | | P.F. | | |
| T1-21 | 2 | huIgG1 | N.B. | | | N.B. | | |
| T1-22 | 1 | huIgG1 | 3.14E−08 | 8.98E+04 | 2.82E−03 | 3.46E−08 | 9.75E+04 | 3.38E−03 |
| T1-23 | 1 | huIgG1 | P.F. | | | P.F. | | |
| T1-24 | 1 | huIgG1 | P.F. | | | P.F. | | |
| T1-25 | 1 | huIgG1 | P.F. | | | P.F. | | |
| T1-26 | N.D | huIgG1 | N.B. | | | N.B. | | |
| T1-27 | N.D | huIgG1 | N.B. | | | N.B. | | |
| T1-28 | N.D | huIgG1 | N.B. | | | N.B. | | |
| T1-29 | N.D | huIgG1 | N.B. | | | N.B. | | |
| T1-30 | N.D | huIgG1 | N.B. | | | N.B. | | |
| T1-31 | N.D | huIgG1 | N.B. | | | N.B. | | |
| T1-32 | N.D | huIgG1 | N.B. | | | N.B. | | |
| T1-33 | 1 | huIgG1 | P.F. | | | 3.73E−08 | 5.46E+05 | 2.04E−02 |
| T1-34 | 1 | huIgG1 | 4.26E−09 | 1.08E+05 | 4.58E−04 | 8.29E−09 | 7.75E+04 | 6.42E−04 |
| T1-35 | 2 | huIgG1 | P.F. | | | 1.56E−08 | 1.21E+05 | 1.88E−03 |
| T1-36 | 2 | huIgG1 | 7.37E−09 | 3.96E+05 | 2.92E−03 | 2.20E−08 | 1.06E+05 | 2.33E−03 |
| T1-37 | 1 | huIgG1 | P.F. | | | 5.73E−08 | 2.85E+05 | 1.64E−02 |
| T1-38 | 2 | huIgG1 | 1.49E−08 | 4.47E+05 | 6.67E−03 | 5.71E−08 | 9.73E+04 | 5.56E−03 |
| T1-39 | 1 | huIgG1 | P.F. | | | 4.97E−08 | 2.24E+05 | 1.11E−02 |
| T1-40 | 2 | huIgG1 | P.F. | | | 2.19E−08 | 8.37E+04 | 1.83E−03 |
| T1-41 | 1 | huIgG1 | 8.76E−09 | 5.97E+05 | 5.23E−03 | 1.63E−08 | 3.43E+05 | 5.58E−03 |
| T1-42 | 1 | huIgG1 | 1.68E−08 | 6.44E+05 | 1.08E−02 | 4.63E−08 | 3.14E+05 | 1.46E−02 |
| T1-43 | 2 | huIgG1 | 1.07E−08 | 1.29E+05 | 1.38E−03 | 1.22E−08 | 8.25E+04 | 1.00E−03 |
| T1-44 | 2 | huIgG1 | 2.96E−08 | 2.14E+05 | 6.33E−03 | 2.80E−08 | 1.37E+05 | 3.84E−03 |
| T1-45 | 2 | huIgG1 | 9.06E−09 | 1.61E+05 | 1.46E−03 | 1.07E−08 | 9.21E+04 | 9.81E−04 |
| T1-46 | 2 | huIgG1 | 1.08E−08 | 1.33E+05 | 1.43E−03 | 1.37E−08 | 8.23E+04 | 1.13E−03 |
| T1-47 | 2 | huIgG1 | P.F. | | | 3.81E−08 | 7.12E+04 | 2.71E−03 |
| T1-48 | 2 | huIgG1 | 3.41E−08 | 1.31E+05 | 4.46E−03 | 6.00E−08 | 8.82E+04 | 5.29E−03 |
| T1-49 | 2 | huIgG1 | 5.39E−09 | 1.54E+05 | 8.28E−04 | 9.46E−09 | 8.96E+04 | 8.48E−04 |
| T1-50 | 2 | huIgG1 | 2.80E−08 | 1.40E+05 | 3.91E−03 | 3.28E−08 | 1.53E+05 | 5.02E−03 |
| T1-51 | 1 | huIgG1 | P.F. | | | P.F. | | |
| T1-52 | 1 | huIgG1 | P.F. | | | 5.66E−08 | 4.23E+05 | 2.40E−02 |
| T1-53 | 2 | huIgG1 | 1.41E−08 | 1.24E+05 | 1.75E−03 | 1.91E−08 | 8.16E+04 | 1.56E−03 |
| T1-54 | 1 | huIgG1 | P.F. | | | P.F. | | |
| T1-55 | 2 | huIgG1 | 3.10E−08 | 1.05E+05 | 3.26E−03 | 8.86E−08 | 6.44E+04 | 5.71E−03 |
| T1-56 | 1 | huIgG1 | P.F. | | | 1.40E−08 | 9.98E+05 | 1.40E−02 |
| T1-57 | 1 | huIgG1 | P.F. | | | P.F. | | |
| T1-58 | 2 | huIgG1 | 2.26E−08 | 2.27E+05 | 5.14E−03 | 2.51E−08 | 1.49E+05 | 3.74E−03 |
| T1-59 | 2 | huIgG1 | 2.07E−08 | 2.25E+05 | 4.66E−03 | 2.32E−08 | 1.30E+05 | 3.01E−03 |
| T1-60 | 2 | huIgG1 | 2.35E−08 | 2.51E+05 | 5.88E−03 | 2.77E−08 | 1.21E+05 | 3.35E−03 |
| T1-61 | 2 | huIgG1 | 1.11E−07 | 6.77E+04 | 7.51E−03 | 3.68E−08 | 1.96E+05 | 7.23E−03 |
| T1-62 | 2 | huIgG1 | P.F. | | | P.F. | | |
| T1-63 | 2 | huIgG1 | P.F. | | | 2.99E−08 | 2.21E+05 | 6.61E−03 |
| T1-64 | 2 | huIgG1 | P.F. | | | 2.16E−07 | 6.31E+04 | 1.36E−02 |
| T1-65 | 2 | huIgG1 | P.F. | | | 2.71E−07 | 1.05E+05 | 2.85E−02 |
| T1-66 | 2 | huIgG1 | 1.18E−08 | 3.43E+05 | 4.05E−03 | 3.70E−08 | 9.74E+04 | 3.60E−03 |
| T1-67 | 1 | huIgG1 | 8.11E−08 | 3.30E+05 | 2.67E−02 | P.F. | | |
| T1-68 | 1 | huIgG1 | P.F. | | | 3.82E−08 | 5.08E+05 | 1.94E−02 |
| T1-69 | 1 | huIgG1 | 2.61E−08 | 3.35E+05 | 8.75E−03 | 3.47E−08 | 2.82E+05 | 9.77E−03 |

TABLE 1A-continued biochemical characterization

| Ab ID | Ab Bin | Isotype | Fab KD Human TREM1-Fc (M) Monovalent | kon (1/Ms) | koff (1/s) | IgG $K_D$ (M) monovalent | kon (1/Ms) | koff (1/s) |
|---|---|---|---|---|---|---|---|---|
| T1-70 | 1 | huIgG1 | P.F. | | | P.F. | | |
| T1-71 | 3 | huIgG1 | 2.23E−08 | 1.23E+06 | 2.74E−02 | 2.18E−08 | 8.54E+05 | 1.86E−02 |
| T1-72 | 1 | huIgG1 | P.F. | | | P.F. | | |
| T1-73 | 1 | huIgG1 | P.F. | | | P.F. | | |
| T1-74 | 1 | huIgG1 | P.F. | | | 1.35E−08 | 1.01E+06 | 1.36E−02 |
| T1-75 | 1 | huIgG1 | P.F. | | | P.F. | | |
| T1-76 | 1 | huIgG1 | 2.93E−08 | 7.42E+05 | 2.17E−02 | 3.94E−08 | 5.83E+05 | 2.30E−02 |
| T1-77 | 1 | huIgG1 | P.F. | | | P.F. | | |
| T1-78 | 2 | huIgG1 | 3.61E−08 | 2.77E+05 | 1.00E−02 | 4.64E−08 | 1.60E+05 | 7.40E−03 |
| T1-79 | 2 | huIgG1 | P.F. | | | 4.00E−08 | 1.19E+05 | 4.78E−03 |
| T1-80 | 1 | huIgG1 | P.F. | | | N.B. | | |

TABLE IB

Biological Functions

| Ab ID | Activate TREM1-dependent Gene expression Plate Bound | Activate TREM1-dependent Gene expression Solution | Receptor Down Regulation-Monocytes | Block Ligand Binding | Block Ligand-induced Gene expression | Enhance Ligand-induced Gene expression | Induction of Respiratory burst (reactive oxygen species | Release of DNA to the extra cellular mileu | Promote survival of neutrophiles in the presence of PGN-BS |
|---|---|---|---|---|---|---|---|---|---|
| T1-1 | +++ | +/− | + | ++ | − | − | | | |
| T1-2 | +++ | + | ++ | +++ | − | − | | | |
| T1-3 | +++ | − | + | ++ | ++ | − | | | |
| T1-4 | +++ | − | ++ | +++ | + | − | | | |
| T1-5 | +++ | +/− | + | ++ | − | − | | | |
| T1-6 | +++ | +/− | + | ++ | − | − | | | |
| T1-7 | +++ | +/− | + | ++ | + | − | | | |
| T1-8 | +++ | +/− | + | + | − | − | +++ | | |
| T1-9 | +++ | +/− | + | + | − | − | | | |
| T1-10 | +++ | − | + | + | − | + | +++ | | |
| T1-11 | +++ | +/− | + | ++ | − | − | | | |
| T1-12 | + | + | ++ | +++ | + | − | ++ | | |
| T1-13 | + | − | + | + | − | − | | | |
| T1-14 | +++ | ++ | + | ++ | − | − | | | |
| T1-15 | +++ | ++ | ++ | +++ | − | − | | | |
| T1-16 | + | ++ | + | + | − | + | | | |
| T1-17 | + | − | + | + | − | − | | | |
| T1-18 | + | + | ++ | +++ | − | − | ++ | | |
| T1-19 | + | ++ | + | ++ | − | − | ++ | | |
| T1-20 | ++ | ++ | ++ | + | − | − | + | | |
| T1-21 | + | − | + | + | − | − | ++ | | |
| T1-22 | +++ | +/++ | +++ | +++ | ++/+++ | − | ++ | | |
| T1-23 | ++ | + | ++ | +++ | + | − | | | |
| T1-24 | +++ | ++ | +++ | +++ | + | − | | | |
| T1-25 | ++ | +++ | ++ | +++ | − | − | | | |
| T1-26 | N.A. | N.A. | N.A. | N.A. | N.A. | N.A. | | | |
| T1-27 | N.A. | N.A. | N.A. | N.A. | N.A. | N.A. | | | |
| T1-28 | N.A. | N.A. | N.A. | N.A. | N.A. | N.A. | | | |
| T1-29 | N.A. | N.A. | N.A. | N.A. | N.A. | N.A. | | | |
| T1-30 | N.A. | N.A. | N.A. | N.A. | N.A. | N.A. | | | |
| T1-31 | N.A. | N.A. | N.A. | N.A. | N.A. | N.A. | | | |
| T1-32 | N.A. | N.A. | N.A. | N.A. | N.A. | N.A. | | | |
| T1-33 | +++ | + | +++ | +++ | ++ | − | +++ | | |
| T1-34 | +++ | +/− | ++ | +++ | +++ | − | ++ | +++ | +++ |
| T1-35 | +++ | + | + | + | + | − | | | |
| T1-36 | +++ | +/− | + | + | + | − | | | |
| T1-37 | +++ | + | + | + | + | − | | | |
| T1-38 | +++ | − | + | + | + | − | | | |
| T1-39 | +++ | +/− | ++ | +++ | +++ | − | +++ | +++ | |
| T1-40 | +++ | +/− | + | +++ | ++/+++ | − | ++ | +++ | |
| T1-41 | +++ | +/− | +++ | +++ | ++ | − | ++ | | |
| T1-42 | +++ | +/− | +++ | +++ | ++ | − | | | |
| T1-43 | +++ | +/− | + | + | − | − | ++ | | |
| T1-44 | ++ | +/− | + | + | − | − | | | |
| T1-45 | +++ | +/− | ++ | + | − | − | | | |

TABLE IB-continued

Biological Functions

| Ab ID | Activate TREM1-dependent Gene expression Plate Bound | Activate TREM1-dependent Gene expression Solution | Receptor Down Regulation-Monocytes | Block Ligand Binding | Block Ligand-induced Gene expression | Enhance Ligand-induced Gene expression | Induction of Respiratory burst (reactive oxygen species | Release of DNA to the extra cellular mileu | Promote survival of neutrophiles in the presence of PGN-BS |
|---|---|---|---|---|---|---|---|---|---|
| T1-46 | +++ | − | ++ | + | − | − | | | |
| T1-47 | +++ | − | + | ++ | ++ | − | | | |
| T1-48 | +++ | +/− | ++ | + | − | − | | | |
| T1-49 | +++ | − | + | + | + | − | | | |
| T1-50 | +++ | − | + | + | − | − | | | |
| T1-51 | +++ | + | +++ | +++ | ++/+++ | − | +++ | +++ | |
| T1-52 | +++ | ++ | +++ | +++ | ++ | − | ++ | +++ | |
| T1-53 | +++ | − | + | + | − | ++ | ++ | | |
| T1-54 | +++ | +++ | +++ | +++ | − | − | | | |
| T1-55 | +++ | − | + | + | + | − | ++ | | |
| T1-56 | +++ | +++ | +++ | +++ | − | − | ++ | + | |
| T1-57 | +++ | ++ | +++ | +++ | + | − | +++ | +++ | |
| T1-58 | +++ | − | + | ++ | ++ | − | | | |
| T1-59 | +++ | − | ++ | ++ | ++ | − | | | |
| T1-60 | +++ | − | + | ++ | ++ | − | | | |
| T1-61 | +++ | − | + | +++ | +++ | − | | | |
| T1-62 | +++ | ++ | + | ++ | − | +++ | ++ | ++ | − |
| T1-63 | ++ | − | +++ | ++ | − | +++ | +++ | | + |
| T1-64 | +++ | + | + | +++ | + | − | | | |
| T1-65 | ++ | − | + | + | − | − | | | |
| T1-66 | +++ | − | + | ++ | ++ | − | | | |
| T1-67 | +++ | +++ | +++ | +++ | + | − | | | |
| T1-68 | +++ | ++ | +++ | +++ | ++ | − | | | |
| T1-69 | +++ | + | +++ | +++ | ++ | − | ++ | + | |
| T1-70 | +++ | ++ | +++ | +++ | ++ | − | | | |
| T1-71 | +++ | ++ | +++ | +++ | + | − | +++ | +++ | +++ |
| T1-72 | ++ | +++ | +++ | +++ | − | − | ++ | | |
| T1-73 | +++ | +++ | +++ | +++ | − | − | | | |
| T1-74 | +++ | ++ | + | +++ | ++ | − | | | |
| T1-75 | +++ | ++ | +++ | +++ | + | − | +++ | | |
| T1-76 | +++ | +++ | +++ | +++ | − | − | +++ | +++ | +++ |
| T1-77 | + | + | +++ | +++ | ++ | − | ++ | +++ | |
| T1-78 | +++ | ++ | ++ | ++ | + | − | ++ | | |
| T1-79 | +++ | +/− | + | ++ | ++ | − | ++ | | |
| T1-80 | + | − | + | ++ | + | − | ++ | | |

Antibody Heavy Chain and Light Chain Variable Domain Sequences

Using standard techniques, the amino acid sequences encoding the light chain variable and the heavy chain variable domains of the generated antibodies were determined. The EU or Kabat light chain HVR sequences of the antibodies are set forth in Table 2-5. The EU or Kabat light chain HVR sequences of the antibodies are set forth in Table 2. The EU or Kabat heavy chain HVR sequences of the antibodies are set forth in Table 3. The EU or Kabat light chain framework (FR) sequences of the antibodies are set forth in Table 4. The EU or Kabat heavy chain framework (FR) sequences of the antibodies are set forth in Table 5.

TABLE 2

EU or Kabat light chain HVR sequences of anti-TREM1 antibodies

| Ab ID | HVR L1 | HVR L2 | HVR L3 |
|---|---|---|---|
| TI-1 | QASQDISNYLN (SEQ ID NO: 9) | DASNLET (SEQ ID NO: 28) | QQVYVLPFT (SEQ ID NO: 41) |
| TI-2 | RASQSVSSSYLA (SEQ ID NO: 10) | GASSRAT (SEQ ID NO: 29) | QQYLGFPPT (SEQ ID NO: 42) |
| TI-3 | KSSQSVLYSSNNKNYLA (SEQ ID NO: 11) | WASTRES (SEQ ID NO: 30) | QQSFLTPWT (SEQ ID NO: 43) |

TABLE 2 -continued

EU or Kabat light chain HVR sequences of anti-TREM1 antibodies

| Ab ID | HVR L1 | HVR L2 | HVR L3 |
| --- | --- | --- | --- |
| TI-4 | RASQSVSSNLA (SEQ ID NO: 12) | GASTRAT (SEQ ID NO: 31) | QQFNNHPIT (SEQ ID NO: 44) |
| TI-5 | RSSQSLLHSNGYNYLD (SEQ ID NO: 13) | LGSNRAS (SEQ ID NO: 32) | VQARQTPLT (SEQ ID NO: 45) |
| TI-6 | RSSQSLLHSNGYNYLD (SEQ ID NO: 13) | LGSNRAS (SEQ ID NO: 32) | MQARDAPWT (SEQ ID NO: 46) |
| TI-7 | KSSQSVLFSSNNKNYLA (SEQ ID NO: 14) | WASTRES (SEQ ID NO: 30) | QQLASYPYT (SEQ ID NO: 47) |
| TI-8 | RSSQSLLHSNGYNYLD (SEQ ID NO: 13) | LGSNRAS (SEQ ID NO: 32) | MQARQTPFT (SEQ ID NO: 48) |
| TI-9 | RSSQSLLHSNGYNYLD (SEQ ID NO: 13) | LGSNRAS (SEQ ID NO: 32) | MQARQAPWT (SEQ ID NO: 49) |
| TI-10 | RSSQSLLHSNGYNYLD (SEQ ID NO: 13) | LGSNRAS (SEQ ID NO: 32) | MQARQVPPWT (SEQ ID NO: 50) |
| TI-11 | RSSQSLLHSNGYNYLD (SEQ ID NO: 13) | LGSNRAS (SEQ ID NO: 32) | MQARQAFT (SEQ ID NO: 51) |
| TI-12 | RASQSVSSYLA (SEQ ID NO: 15) | DASNRAT (SEQ ID NO: 33) | QQYTSWPLT (SEQ ID NO: 52) |
| TI-13 | RASQSVSSSFLA (SEQ ID NO: 16) | GASSRAT (SEQ ID NO: 29) | QQLDSHPPT (SEQ ID NO: 53) |
| TI-14 | KSSQSVLYSSNNKNYLA (SEQ ID NO: 11) | WASTRES (SEQ ID NO: 30) | QQYDVDPLT (SEQ ID NO: 54) |
| TI-15 | RASQSVSSSYLA (SEQ ID NO: 10) | GASSRAT (SEQ ID NO: 29) | QQAFISPPT (SEQ ID NO: 55) |
| TI-16 | RASQGISSWLA (SEQ ID NO: 17) | AASSLQS (SEQ ID NO: 34) | QQADTLPIT (SEQ ID NO: 56) |
| TI-17 | QASQDISNYLN (SEQ ID NO: 9) | DASNLAT (SEQ ID NO: 35) | QQSDIHPRT (SEQ ID NO: 57) |
| TI-18 | RASQSISSWLA (SEQ ID NO: 18) | KASSLES (SEQ ID NO: 36) | QQDSIYPIT (SEQ ID NO: 58) |
| TI-19 | RASQGISSWLA (SEQ ID NO: 17) | AASNLQS (SEQ ID NO: 37) | QQANSFPLT (SEQ ID NO: 59) |
| TI-20 | RASQSISSWLA (SEQ ID NO: 18) | KASSLES (SEQ ID NO: 36) | QQYKSFSPFT (SEQ ID NO: 60) |
| TI-21 | RASQSISSFLN (SEQ ID NO: 19) | AASSLQS (SEQ ID NO: 34) | QQSYSDLT (SEQ ID NO: 61) |
| TI-22 | RASQSVSSSYLA (SEQ ID NO: 10) | GASSRAT (SEQ ID NO: 29) | QQYLIPPIT (SEQ ID NO: 62) |
| TI-23 | RASQSIGSWLA (SEQ ID NO: 20) | KASSLES (SEQ ID NO: 36) | QQHQSFSPT (SEQ ID NO: 63) |
| TI-24 | RASQSISSWLA (SEQ ID NO: 18) | KASSLES (SEQ ID NO: 36) | QQDSIYPIT (SEQ ID NO: 58) |
| TI-25 | RASQSVSSYLA (SEQ ID NO: 15) | DASNRAT (SEQ ID NO: 33) | QQRSVLPLT (SEQ ID NO: 64) |
| TI-26 | RASQSISSYLN (SEQ ID NO: 21) | AASSLQS (SEQ ID NO: 34) | QQIFSTPLT (SEQ ID NO: 65) |
| TI-27 | RASQSISSYLN (SEQ ID NO: 21) | AASSLQS (SEQ ID NO: 34) | QQSFYDPIT (SEQ ID NO: 66) |
| TI-28 | RASQSVGSNLA (SEQ ID NO: 22) | GASTRAT (SEQ ID NO: 31) | QQYLYFPLT (SEQ ID NO: 67) |

TABLE 2 -continued

EU or Kabat light chain HVR sequences of anti-TREM1 antibodies

| Ab ID | HVR L1 | HVR L2 | HVR L3 |
|---|---|---|---|
| TI-29 | RASQSVSSYLA (SEQ ID NO: 15) | DASNRAT (SEQ ID NO: 33) | QQGVNYPFT (SEQ ID NO: 68) |
| TI-30 | RASQGISSWLA (SEQ ID NO: 17) | AASSLQS (SEQ ID NO: 34) | QQVISFPT (SEQ ID NO: 69) |
| TI-31 | QASQDISNYLN (SEQ ID NO: 9) | DASNLET (SEQ ID NO: 28) | QQYDDFPPIT (SEQ ID NO: 70) |
| TI-32 | RASQSISRYLN (SEQ ID NO: 23) | AASSLQS (SEQ ID NO: 34) | QQSLDLPFT (SEQ ID NO: 71) |
| TI-33 | RASQGISSWLA (SEQ ID NO: 17) | AASSLQS (SEQ ID NO: 34) | QQINDHPFT (SEQ ID NO: 72) |
| TI-34 | RASQSINSWLA (SEQ ID NO: 24) | DASSLES (SEQ ID NO: 38) | QQYGPYPYT (SEQ ID NO: 73) |
| TI-35 | KSSQSVLYSSNNKNYLA (SEQ ID NO: 11) | WASTRES (SEQ ID NO: 30) | QQSHSTPLT (SEQ ID NO: 74) |
| TI-36 | KSSQSVLYSSNNKNYLA (SEQ ID NO: 11) | WASTRES (SEQ ID NO: 30) | QQLASQPPT (SEQ ID NO: 75) |
| TI-37 | RASQSVSSNLA (SEQ ID NO: 12) | GASTRAT (SEQ ID NO: 31) | QQYAYWPLT (SEQ ID NO: 76) |
| TI-38 | KSSQSVLFSSNNKNYLA (SEQ ID NO: 14) | WASTRES (SEQ ID NO: 30) | QQDFSLPYT (SEQ ID NO: 77) |
| TI-39 | RASQDISSWLA (SEQ ID NO: 25) | AASSLQS (SEQ ID NO: 34) | QQSLTHPT (SEQ ID NO: 78) |
| TI-40 | KSSQSVLFSSNNKNYLA (SEQ ID NO: 14) | WASTRES (SEQ ID NO: 30) | QQYDLLPYT (SEQ ID NO: 79) |
| TI-41 | RASQDISSWLA (SEQ ID NO: 25) | AASSLQS (SEQ ID NO: 34) | QQAVIHPPYT (SEQ ID NO: 80) |
| TI-42 | RASQSVSSNLA (SEQ ID NO: 12) | GASTRAT (SEQ ID NO: 31) | QQYNVHPPRT (SEQ ID NO: 81) |
| TI-43 | RSSQSLLHSNGYNYLD (SEQ ID NO: 13) | LGSNRAS (SEQ ID NO: 32) | MQSRNAPWT (SEQ ID NO: 82) |
| TI-44 | RSSQSLLHSNGYNYLD (SEQ ID NO: 13) | LGSNRAS (SEQ ID NO: 32) | MQARHGFT (SEQ ID NO: 83) |
| TI-45 | RSSQSLLHSNGYNYLD (SEQ ID NO: 13) | LGSNRAS (SEQ ID NO: 32) | MQAREVPFT (SEQ ID NO: 84) |
| TI-46 | RSSQSLLHSNGYNYLD (SEQ ID NO: 13) | LGSNRAS (SEQ ID NO: 32) | MQARHVPPLT (SEQ ID NO: 85) |
| TI-47 | KSSQSVLFSSNNKNYLA (SEQ ID NO: 14) | WASTRES (SEQ ID NO: 30) | QQHDSAPYT (SEQ ID NO: 86) |
| TI-48 | RSSQSLLHSNGYNYLD (SEQ ID NO: 13) | LGSHRAS (SEQ ID NO: 39) | MQGRQVPFT (SEQ ID NO: 87) |
| TI-49 | RSSQSLLHSNGYNYLD (SEQ ID NO: 13) | LGSNRAS (SEQ ID NO: 32) | MQARGTPWT (SEQ ID NO: 88) |
| TI-50 | RSSQSLLHSNGYNYLD (SEQ ID NO: 13) | LGSNRAS (SEQ ID NO: 32) | MQSRRAPPWT (SEQ ID NO: 89) |
| TI-51 | RASQSISSWLA (SEQ ID NO: 18) | KASSLES (SEQ ID NO: 36) | QQFQSYPFT (SEQ ID NO: 90) |
| TI-52 | RASQSISSWLA (SEQ ID NO: 18) | KASSLES (SEQ ID NO: 36) | QQSSADSPFT (SEQ ID NO: 91) |
| TI-53 | RSSQSLLHSNGYNYLD (SEQ ID NO: 13) | LGSNRAS (SEQ ID NO: 32) | MQARQLPWT (SEQ ID NO: 92) |

TABLE 2 -continued

EU or Kabat light chain HVR sequences of anti-TREM1 antibodies

| Ab ID | HVR L1 | HVR L2 | HVR L3 |
|---|---|---|---|
| TI-54 | RASQSVSSYLA (SEQ ID NO: 15) | DSSNRAT (SEQ ID NO: 40) | QQHDVVVPIT (SEQ ID NO: 93) |
| TI-55 | RSSQSLLHSNGYNYLD (SEQ ID NO: 13) | LGSNRAS (SEQ ID NO: 32) | MQTRHTPT (SEQ ID NO: 94) |
| TI-56 | RSSQSLLHSNGYNYLD (SEQ ID NO: 13) | LGSNRAS (SEQ ID NO: 32) | MQDFARPPT (SEQ ID NO: 95) |
| TI-57 | RASQGIDSWLA (SEQ ID NO: 26) | AASSLQS (SEQ ID NO: 34) | QQRAVFPPT (SEQ ID NO: 96) |
| TI-58 | KSSQSVLFSSNNKNYLA (SEQ ID NO: 14) | WASTRES (SEQ ID NO: 30) | QQDATGIT (SEQ ID NO: 97) |
| TI-59 | KSSQSVLYSSNNKNYLA (SEQ ID NO: 11) | WASTRES (SEQ ID NO: 30) | QQLASFPWT (SEQ ID NO: 98) |
| TI-60 | KSSQSVLFSSNNKNYLA (SEQ ID NO: 14) | WASTRES (SEQ ID NO: 30) | QQLAFTPWT (SEQ ID NO: 99) |
| TI-61 | KSSQSVLYSSNNKNYLA (SEQ ID NO: 11) | WASTRES (SEQ ID NO: 30) | QQDHSFIT (SEQ ID NO: 100) |
| TI-62 | RASQSVSSSYLA (SEQ ID NO: 10) | GASSRAT (SEQ ID NO: 29) | QQDVSDFT (SEQ ID NO: 101) |
| TI-63 | RASQSISRYLN (SEQ ID NO: 23) | AASSLQS (SEQ ID NO: 34) | QQLYHAPPIT (SEQ ID NO: 102) |
| TI-64 | KSSQSVLFSSNNKNYLA (SEQ ID NO: 14) | WASTRES (SEQ ID NO: 30) | QQYDSLPFT (SEQ ID NO: 103) |
| TI-65 | KSSQSVLYSSNNKNYLA (SEQ ID NO: 11) | WASTRES (SEQ ID NO: 30) | QQVYLFPWT (SEQ ID NO: 104) |
| TI-66 | KSSQSVLFSSNNKNYLA (SEQ ID NO: 14) | WASTRES (SEQ ID NO: 30) | QQFFLAPPT (SEQ ID NO: 105) |
| TI-67 | RASQSVSSSFLA (SEQ ID NO: 16) | GASSRAT (SEQ ID NO: 29) | QQAVSLPWT (SEQ ID NO: 106) |
| TI-68 | RASQSVSSYLA (SEQ ID NO: 15) | DASNRAT (SEQ ID NO: 33) | QQFDNLPYT (SEQ ID NO: 107) |
| TI-69 | RASQGISSWLA (SEQ ID NO: 17) | AASNLQS (SEQ ID NO: 37) | QQATAHPPT (SEQ ID NO: 108) |
| TI-70 | RASQDISSWLA (SEQ ID NO: 25) | AASSLQS (SEQ ID NO: 34) | QQAVSHPLT (SEQ ID NO: 109) |
| TI-71 | RASQGIDSWLA (SEQ ID NO: 26) | AASSLQS (SEQ ID NO: 34) | QQATSLPLT (SEQ ID NO: 110) |
| TI-72 | RSSQSLLHRNGYNYLD (SEQ ID NO: 27) | LGSNRAS (SEQ ID NO: 32) | MQRLQAWT (SEQ ID NO: 111) |
| TI-73 | RASQSISSWLA (SEQ ID NO: 18) | KASSLES (SEQ ID NO: 36) | QQYRTYPT (SEQ ID NO: 112) |
| TI-74 | RASQSISSWLA (SEQ ID NO: 18) | KASSLES (SEQ ID NO: 36) | QQHSLLSIT (SEQ ID NO: 113) |
| TI-75 | RASQSVSSYLA (SEQ ID NO: 15) | DASNRAT (SEQ ID NO: 33) | QHYNLWRT (SEQ ID NO: 114) |
| TI-76 | RASQSISSWLA (SEQ ID NO: 18) | DASSLES (SEQ ID NO: 38) | QQHSTYSWT (SEQ ID NO: 115) |
| TI-77 | RASQSVGSNLA (SEQ ID NO: 22) | GASTRAT (SEQ ID NO: 31) | QQHDVVPYT (SEQ ID NO: 116) |
| TI-78 | KSSQSVLFSSNNKNYLA (SEQ ID NO: 14) | WASTRES (SEQ ID NO: 30) | QQYFSTPPT (SEQ ID NO: 117) |

TABLE 2 -continued

EU or Kabat light chain HVR sequences of anti-TREM1 antibodies

| Ab ID | HVR L1 | HVR L2 | HVR L3 |
|---|---|---|---|
| TI-79 | KSSQSVLYSSNNKNYLA (SEQ ID NO: 11) | WASTRES (SEQ ID NO: 30) | QQYALTPYT (SEQ ID NO: 118) |
| TI-80 | RASQSVGSNLA (SEQ ID NO: 22) | GASTRAT (SEQ ID NO: 31) | QQDHDRPLT (SEQ ID NO: 119) |

TABLE 3

EU or Kabat heavy chain HVR sequences of anti-TREM1 antibodies

| Ab ID | HVR L1 | HVR H2 | HVR H3 |
|---|---|---|---|
| TI-1 | GTFSSYAIS (SEQ ID NO: 120) | GIIPIFGTANYAQKFQG (SEQ ID NO: 144) | ARGQGSDHYYYGMDV (SEQ ID NO: 173) |
| TI-2 | GTFSSYAIS (SEQ ID NO: 120) | GIIPIFGTANYAQKFQG (SEQ ID NO: 144) | AREGGPRGASFNWFDP (SEQ ID NO: 174) |
| TI-3 | GTFSSYAIS (SEQ ID NO: 120) | GIIPIFGTANYAQKFQG (SEQ ID NO: 144) | ARDVGSMYFDI (SEQ ID NO: 175) |
| TI-4 | GTFSSYAIS (SEQ ID NO: 120) | GIIPIFGTANYAQKFQG (SEQ ID NO: 144) | ARHYYYGYAYFDL (SEQ ID NO: 176) |
| TI-5 | YTFTSYYMH (SEQ ID NO: 121) | VINPSGGSTSYAQKFQG (SEQ ID NO: 145) | ARESDGIDSYFDY (SEQ ID NO: 177) |
| TI-6 | YTFTSYYMH (SEQ ID NO: 121) | VINPSGGSTSYAQKFQG (SEQ ID NO: 145) | ARESGHSYVSSFDP (SEQ ID NO: 178) |
| TI-7 | YTFTSYYMH (SEQ ID NO: 121) | IINPSGGSTSYAQKFQG (SEQ ID NO: 146) | ARGLIYGDAFDY (SEQ ID NO: 179) |
| TI-8 | YTFTSYYMH (SEQ ID NO: 121) | IINPSGGSTSYAQKFQG (SEQ ID NO: 146) | AREVSMTAASLDV (SEQ ID NO: 180) |
| TI-9 | YTFTSYYMH (SEQ ID NO: 121) | IINPSGGSTSYAQKFQG (SEQ ID NO: 146) | AREAGYDISSAFDI (SEQ ID NO: 181) |
| TI-10 | YTFTSYYMH (SEQ ID NO: 121) | IINPSGGSTSYAQKFQG (SEQ ID NO: 146) | AREGSGSWETLDV (SEQ ID NO: 182) |
| TI-11 | GSISSSSYYWG (SEQ ID NO: 122) | SIYYSGSTYYNPSLKS (SEQ ID NO: 147) | ARSGEYGFDL (SEQ ID NO: 183) |
| TI-12 | GSISSSSYYWG (SEQ ID NO: 122) | SIYYSGSTYYNPSLKS (SEQ ID NO: 147) | ARGGGYPWEAFDY (SEQ ID NO: 184) |
| TI-13 | FTFSSYSMN (SEQ ID NO: 123) | SISSSSNYIYYADSVKG (SEQ ID NO: 148) | ARGRYRRTGSLDV (SEQ ID NO: 185) |
| TI-14 | FTFSSYGMH (SEQ ID NO: 124) | VISYDGSNKYYADSVKG (SEQ ID NO: 149) | ARRSSGDYLDV (SEQ ID NO: 186) |
| TI-15 | FTFSSYSMN (SEQ ID NO: 123) | SISSSSYIYYADSVKG (SEQ ID NO: 150) | ARRGGSYDAFQH (SEQ ID NO: 187) |
| TI-16 | FTFDDYAMH (SEQ ID NO: 125) | GISWNSGSIGYADSVKG (SEQ ID NO: 151) | AKGPRMSGWWAD (SEQ ID NO: 188) |
| TI-17 | GSISSYYWS (SEQ ID NO: 126) | SIYYSGSTNYNPSLKS (SEQ ID NO: 152) | ARGAPGGRHNWFDP (SEQ ID NO: 189) |
| TI-18 | FTFDDYAMH (SEQ ID NO: 125) | GISWNSGDIGYADSVKG (SEQ ID NO: 153) | AKGPRMVTHLDV (SEQ ID NO: 190) |
| TI-19 | FTFSDHHMD (SEQ ID NO: 127) | RTRNKANSYTTEYAASVKG (SEQ ID NO: 154) | ARGPLGYKL (SEQ ID NO: 191) |
| TI-20 | FTFSSYWMS (SEQ ID NO: 128) | NIKQDGSEKYYVDSVKG (SEQ ID NO: 155) | ARDAPQLGLDV (SEQ ID NO: 192) |

TABLE 3 -continued

EU or Kabat heavy chain HVR sequences of anti-TREM1 antibodies

| Ab ID | HVR L1 | HVR H2 | HVR H3 |
| --- | --- | --- | --- |
| TI-21 | FTFSSYSMN (SEQ ID NO: 123) | YISSSSSTIYYADSVKG (SEQ ID NO: 156) | ARGGPLGYGDYKGMDV (SEQ ID NO: 193) |
| TI-22 | GSISSYYWS (SEQ ID NO: 126) | HIYYSGSTNYNPSLKS (SEQ ID NO: 157) | ARDAGRYYGSSSSWYFDL (SEQ ID NO: 194) |
| TI-23 | FTFDDYAMH (SEQ ID NO: 125) | GITWNSGSIGYADSVKG (SEQ ID NO: 158) | AKGPRLLSALDV (SEQ ID NO: 195) |
| TI-24 | FTFDDYAMH (SEQ ID NO: 125) | GITWNSGSIGYADSVKG (SEQ ID NO: 158) | AKGPRLLSALDV (SEQ ID NO: 195) |
| TI-25 | FTFDDYAMH (SEQ ID NO: 125) | GISWNSGSIGYADSVKG (SEQ ID NO: 151) | AKGGSRYSHFDY (SEQ ID NO: 196) |
| TI-26 | YTFTSYYIH (SEQ ID NO: 129) | IINPSGGSTSYAQKFQG (SEQ ID NO: 146) | ARDSAQETYYYGMDV (SEQ ID NO: 197) |
| TI-27 | GSISSGGYYWS (SEQ ID NO: 130) | YIYYSGSTYYNPSLKS (SEQ ID NO: 159) | ARDSSIAGRATLSFDY (SEQ ID NO: 198) |
| TI-28 | FTFSSYSMN (SEQ ID NO: 123) | SISSSSNYIYYADSVKG (SEQ ID NO: 148) | ARGPSQYYYDSSAIEAFDI (SEQ ID NO: 199) |
| TI-29 | GSISSSSYYWG (SEQ ID NO: 122) | SIYYSGSTYYNPSLKS (SEQ ID NO: 147) | ARDGGGTAQADGAYYYGMDV (SEQ ID NO: 200) |
| TI-30 | GSISSSSYYWG (SEQ ID NO: 122) | SIYYSGSTYYNPSLKS (SEQ ID NO: 147) | ARGRKAAAGIDEAEYFQH (SEQ ID NO: 201) |
| TI-31 | GSISSSSYYWG (SEQ ID NO: 122) | SIYYSGSTYYNPSLKS (SEQ ID NO: 147) | ARDRRMWDPYGMDV (SEQ ID NO: 202) |
| TI-32 | GSISSSSYYWG (SEQ ID NO: 122) | SIYYSGSTYYNPSLKS (SEQ ID NO: 147) | ARDAPAVVGESPAFDI (SEQ ID NO: 203) |
| TI-33 | FTFSNYGMH (SEQ ID NO: 131) | VIWYDGSNKYYADSVKG (SEQ ID NO: 160) | AKGSTHRGSAYGMDV (SEQ ID NO: 204) |
| TI-34 | FTFSSYSMN (SEQ ID NO: 123) | SISSSSNYIYYADSVKG (SEQ ID NO: 148) | ARRPDDRRGLFQH (SEQ ID NO: 205) |
| TI-35 | FTFSSYGMH (SEQ ID NO: 124) | VISYDGSNKYYADSVKG (SEQ ID NO: 149) | ARPDYYSSRGVFDI (SEQ ID NO: 206) |
| TI-36 | FTFSSYGMH (SEQ ID NO: 124) | VISYDGSNKYYADSVKG (SEQ ID NO: 149) | ARPDYYSSRGVFDI (SEQ ID NO: 206) |
| TI-37 | FTFSSYGMH (SEQ ID NO: 124) | LIWYDGSNKYYADSVKG (SEQ ID NO: 161) | AKGDYLDPLFDY (SEQ ID NO: 207) |
| TI-38 | LTFSSYGMH (SEQ ID NO: 132) | VISYDGSNKYYADSVKG (SEQ ID NO: 149) | ARERGTYYYASGWAN (SEQ ID NO: 208) |
| TI-39 | FTFSSYSMN (SEQ ID NO: 123) | SISSSSNYIYYADSVKG (SEQ ID NO: 148) | ARRGGSSSTGLLY (SEQ ID NO: 209) |
| TI-40 | FTFSSYSMN (SEQ ID NO: 123) | SISSSSYIYYADSVKG (SEQ ID NO: 150) | ARTRIDDSFDI (SEQ ID NO: 210) |
| TI-41 | FTFSTYAMS (SEQ ID NO: 133) | AISGSGGSTYYADSVKG (SEQ ID NO: 162) | AKSKHSTTSLDV (SEQ ID NO: 211) |
| TI-42 | FTFSSYGMH (SEQ ID NO: 124) | VIWYDGSNKGYADSVKG (SEQ ID NO: 163) | ARELMVTSGGWLYGMDV (SEQ ID NO: 212) |
| TI-43 | YTFTSYYMH (SEQ ID NO: 121) | IINPSGGSTSYAQKFQG (SEQ ID NO: 146) | AREAGNYYDIESAFDI (SEQ ID NO: 213) |
| TI-44 | YTFTSYYMH (SEQ ID NO: 121) | VINPSGGSTSYAQKFQG (SEQ ID NO: 145) | AREGSGYDESMDV (SEQ ID NO: 214) |
| TI-45 | YTFTSYYMH (SEQ ID NO: 121) | VINPSGGSTSYAQKFQG (SEQ ID NO: 145) | AREGSGYDESMDV (SEQ ID NO: 214) |

TABLE 3 -continued

EU or Kabat heavy chain HVR sequences of anti-TREM1 antibodies

| Ab ID | HVR L1 | HVR H2 | HVR H3 |
|---|---|---|---|
| TI-46 | YTFTSYYMH (SEQ ID NO: 121) | VINPSGGSTSYAQKFQG (SEQ ID NO: 145) | AREGSGYDESMDV (SEQ ID NO: 214) |
| TI-47 | GTFSNYAIS (SEQ ID NO: 134) | GIIPIFGTANYAQKFQG (SEQ ID NO: 144) | ARGRGIAFDI (SEQ ID NO: 215) |
| TI-48 | YTFTSYYMH (SEQ ID NO: 121) | VINPGGGSTSYAQKFQG (SEQ ID NO: 164) | AREAGQTSSALDV (SEQ ID NO: 216) |
| TI-49 | YTFTSYYMH (SEQ ID NO: 121) | IINPSGGSTSYAQKFQG (SEQ ID NO: 146) | AREAGSWLISTAFDI (SEQ ID NO: 217) |
| TI-50 | YTFTSYYMH (SEQ ID NO: 121) | IINPGGGSTSYAQKFQG (SEQ ID NO: 165) | AREAGTMSSAFDI (SEQ ID NO: 218) |
| TI-51 | GTFSSYAIS (SEQ ID NO: 120) | SIIPIFGTANYAQKFQG (SEQ ID NO: 166) | ARSGGYSSSWYGTGYDY (SEQ ID NO: 219) |
| TI-52 | GTFSSYAIS (SEQ ID NO: 120) | SIIPIFGTANYAQKFQG (SEQ ID NO: 166) | ARDRGQYSSSWYGRMDV (SEQ ID NO: 220) |
| TI-53 | YTFTSYYIH (SEQ ID NO: 129) | IINPSGGSTSYAQKFQG (SEQ ID NO: 146) | ARESGYHVSTAFDI (SEQ ID NO: 221) |
| TI-54 | GTFSSYAIS (SEQ ID NO: 120) | GIIPIFGTANYAQKFQG (SEQ ID NO: 144) | ARHWYALGSFDI (SEQ ID NO: 222) |
| TI-55 | YTFTSYYMH (SEQ ID NO: 121) | VINPSGGSTSYAQKFQG (SEQ ID NO: 145) | ARGADYYAGFDY (SEQ ID NO: 223) |
| TI-56 | FTFDDYAMH (SEQ ID NO: 125) | GISWNSGSIGYADSVKG (SEQ ID NO: 151) | AKGPRLLGYFDL (SEQ ID NO: 224) |
| TI-57 | FTFDDYAMH (SEQ ID NO: 125) | GITWNSGSIGYADSVKG (SEQ ID NO: 158) | AKGPRYSKPYFDY (SEQ ID NO: 225) |
| TI-58 | GSISSSSYYWG (SEQ ID NO: 122) | SIYYSGSTYYNPSLKS (SEQ ID NO: 147) | ARQEYGDGYFDL (SEQ ID NO: 226) |
| TI-59 | YSISSGYYWA (SEQ ID NO: 135) | SIYHSGSTYYNPSLKS (SEQ ID NO: 167) | ARDLGGYEGAFDP (SEQ ID NO: 227) |
| TI-60 | YSISSGYYWA (SEQ ID NO: 135) | SIYHSGSTYYNPSLKS (SEQ ID NO: 167) | ARDLGGYEGAFDP (SEQ ID NO: 227) |
| TI-61 | YSISSGYYWG (SEQ ID NO: 136) | SIYHSGSTYYNPSLKS (SEQ ID NO: 167) | ARHDDYLSSFDP (SEQ ID NO: 228) |
| TI-62 | GSISSGGYYWS (SEQ ID NO: 130) | YIYYSGSTYYNPSLKS (SEQ ID NO: 159) | ARGPSWIDV (SEQ ID NO: 229) |
| TI-63 | YSISSGYYWG (SEQ ID NO: 136) | SIYHSGNTYYNPSLKS (SEQ ID NO: 168) | ARELYAYSSPMFYGMDV (SEQ ID NO: 230) |
| TI-64 | GSISSSSYYWG (SEQ ID NO: 122) | SISYSGSTYYNPSLKS (SEQ ID NO: 169) | ARYYSPYGMDV (SEQ ID NO: 231) |
| TI-65 | GSISSSDYYWG (SEQ ID NO: 137) | SIYYSGSTYYNPSLKS (SEQ ID NO: 147) | ARDSGQYTGSLDV (SEQ ID NO: 232) |
| TI-66 | YTFTGYYMH (SEQ ID NO: 138) | WINPNSGGTKYAQKFQG (SEQ ID NO: 170) | ARERHSSLGYAY (SEQ ID NO: 233) |
| TI-67 | YTFTSYGIH (SEQ ID NO: 139) | WISAYNGNTNYAQKLQG (SEQ ID NO: 171) | ARGRPSSSWGNWFDP (SEQ ID NO: 234) |
| TI-68 | YSFTTYWIG (SEQ ID NO: 140) | IIYPGDSDTRYSPSFQG (SEQ ID NO: 172) | ARGSPWDGRLFDI (SEQ ID NO: 235) |
| TI-69 | YTFTSYGIS (SEQ ID NO: 141) | WISAYNGNTNYAQKLQG (SEQ ID NO: 171) | ARGAGMYDGSPLGMDV (SEQ ID NO: 236) |
| TI-70 | YTFTSYGIH (SEQ ID NO: 139) | WISAYNGNTNYAQKLQG (SEQ ID NO: 171) | ARAGTIYGRLDL (SEQ ID NO: 237) |

TABLE 3 -continued

EU or Kabat heavy chain HVR sequences of anti-TREM1 antibodies

| Ab ID | HVR L1 | HVR H2 | HVR H3 |
|---|---|---|---|
| TI-71 | FTFGDYAMH (SEQ ID NO: 142) | GISWNSGSIGYADSVKG (SEQ ID NO: 151) | AKGPRRTSHLDI (SEQ ID NO: 238) |
| TI-72 | FTFDDYAMH (SEQ ID NO: 125) | GISWNSGDIGYADSVKG (SEQ ID NO: 153) | AKGPRMTHSYFDL (SEQ ID NO: 239) |
| TI-73 | FTFDDYAMH (SEQ ID NO: 125) | GISWNSGSIGYADSVKG (SEQ ID NO: 151) | AKAPRMYGYFDL (SEQ ID NO: 240) |
| TI-74 | FTFDDYAMH (SEQ ID NO: 125) | GISWNSGSIGYADSVKG (SEQ ID NO: 151) | AKGPRTRGYFDL (SEQ ID NO: 241) |
| TI-75 | FTFDDYAMH (SEQ ID NO: 125) | GISWNSGDIGYADSVKG (SEQ ID NO: 153) | AKAPRTRWTYFDY (SEQ ID NO: 242) |
| TI-76 | FTFSSYAMS (SEQ ID NO: 143) | AISGSGGSTYYADSVKG (SEQ ID NO: 162) | ARARRGALAGMDV (SEQ ID NO: 243) |
| TI-77 | YSISSGYYWA (SEQ ID NO: 135) | SIYHSGSTYYNPSLKS (SEQ ID NO: 167) | ARGGPYPWSGWFDP (SEQ ID NO: 244) |
| TI-78 | GSISSSSYYWG (SEQ ID NO: 122) | SIYYSGSTYYNPSLKS (SEQ ID NO: 147) | ARDLGQYEGYFDL (SEQ ID NO: 245) |
| TI-79 | GSISSSSYYWG (SEQ ID NO: 122) | SIYYSGSTYYNPSLKS (SEQ ID NO: 147) | ARLGDGYRIWADY (SEQ ID NO: 246) |
| TI-80 | FTFSSYGMH (SEQ ID NO: 124) | LIWYDGSNKYYADSVKG (SEQ ID NO: 161) | ARELIVGATGGLTYYYGMDV (SEQ ID NO: 247) |

TABLE 4

EU or Kabat light chain Framework sequences of anti-TREM1 antibodies

| Ab ID | VL FR1 | VL FR2 | VL F3 | VL FR4 |
|---|---|---|---|---|
| TI-1 | DIQMTQSPSSLSASVGDRVTITC (SEQ ID NO: 248) | WYQQKPGKAPKLLIY (SEQ ID NO: 260) | GVPSRFSGSGSGTDFTFTISSLQPEDIATYYC (SEQ ID NO: 267) | FGGGTKVEIK (SEQ ID NO: 276) |
| TI-2 | EIVLTQSPGTLSLSPGERATLSC (SEQ ID NO: 249) | WYQQKPGQAPRLLIY (SEQ ID NO: 261) | GIPDRFSGSGSGTDFTLTISRLEPEDFAVYYC (SEQ ID NO: 268) | FGGGTKVEIK (SEQ ID NO: 276) |
| TI-3 | DIVMTQSPDSLAVSLGERATINC (SEQ ID NO: 250) | WYQQKPGQPPKLLIY (SEQ ID NO: 262) | GVPDRFSGSGSGTDFTLTISSLQAEDVAVYYC (SEQ ID NO: 269) | FGGGTKVEIK (SEQ ID NO: 276) |
| TI-4 | EIVMTQSPATLSVSPGERATLSC (SEQ ID NO: 251) | WYQQKPGQAPRLLIY (SEQ ID NO: 261) | GIPARFSGSGSGTEFTLTISSLQSEDFAVYYC (SEQ ID NO: 270) | FGGGTKVEIK (SEQ ID NO: 276) |
| TI-5 | DIVMTQSPLSLPVTPGEPASISC (SEQ ID NO: 252) | WYLQKPGQSPQLLIY (SEQ ID NO: 263) | GVPDRFSGSGSGTDFTLKISRVEAEDVGVYYC (SEQ ID NO: 271) | FGGGTKVEIK (SEQ ID NO: 276) |
| TI-6 | DIVMTQSPLSLPVTPGEPASISC (SEQ ID NO: 252) | WYLQKPGQSPQLLIY (SEQ ID NO: 263) | GVPDRFSGSGSGTDFTLKISRVEAEDVGVYYC (SEQ ID NO: 271) | FGGGTKVEIK (SEQ ID NO: 276) |
| TI-7 | DIVMTQSPDSLAVSLGERATINC (SEQ ID NO: 250) | WYQQKPGQPPKLLIY (SEQ ID NO: 262) | GVPDRFSGSGSGTDFTLTISSLQAEDVAVYYC (SEQ ID NO: 269) | FGGGTKVEIK (SEQ ID NO: 276) |
| TI-8 | DIVMTQSPLSLPVTPGEPASISC (SEQ ID NO: 252) | WYLQKPGQSPQLLIY (SEQ ID NO: 263) | GVPDRFSGSGSGTDFTLKISRVEAEDVGVYYC (SEQ ID NO: 271) | FGGGTKVEIK (SEQ ID NO: 276) |
| TI-9 | DIVMTQSPLSLPVTPGEPASISC (SEQ ID NO: 252) | WYLQKPGQSPQLLIY (SEQ ID NO: 263) | GVPDRFSGSGSGTDFTLKISRVEAEDVGVYYC (SEQ ID NO: 271) | FGGGTKVEIK (SEQ ID NO: 276) |

TABLE 4-continued

EU or Kabat light chain Framework sequences of anti-TREM1 antibodies

| Ab ID | VL FR1 | VL FR2 | VL F3 | VL FR4 |
|---|---|---|---|---|
| TI-10 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-11 | DIVMTQSPLSLPVTPG EPASISC (SEQ ID NO: 252) | WYLQKPGQSPQLL IF (SEQ ID NO: 264) | GVPDRFSGSGSGTDFTL KISRVEAEDVGVYYC (SEQ ID NO: 271) | FGGGTKVEIK (SEQ ID NO: 276) |
| TI-12 | EIVLTQSPATLSLSPGE RATLSC (SEQ ID NO: 253) | WYQQKPGQAPRL LIY (SEQ ID NO: 261) | GIPARFSGSGSGTDFTLTI SSLEPEDFAVYYC (SEQ ID NO: 272) | FGGGTKVEIK (SEQ ID NO: 276) |
| TI-13 | EIVLTQSPGTLSLSPGE RATLSC (SEQ ID NO: 249) | WYQQKPGQAPRL LIY (SEQ ID NO: 261) | GIPDRFSGSGSGTDFTLTI SRLEPEDFAVYYC (SEQ ID NO: 268) | FGGGTKVEIK (SEQ ID NO: 276) |
| TI-14 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-15 | EIVLTQSPGTLSLSPGE RATLSC (SEQ ID NO: 249) | WYQQKPGQAPRL LIY (SEQ ID NO: 261) | GIPDRFSGSGSGTDFTLTI SRLEPEDFAVYYC (SEQ ID NO: 268) | FGGGTKVEIK (SEQ ID NO: 276) |
| TI-16 | DIQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-17 | DIQMTQSPSSLSASVG DRVTITC (SEQ ID NO: 248) | WYQQKPGKAPKL LIY (SEQ ID NO: 260) | GVPSRFSGSGSGTDFTFT ISSLQPEDIATYYC (SEQ ID NO: 267) | FGGGTKVEIK (SEQ ID NO: 276) |
| TI-18 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-19 | DIQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-20 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-21 | DIQLTQSPSSLSASVGD RVTITC (SEQ ID NO: 256) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-22 | EIVLTQSPGTLSLSPGE RATLSC (SEQ ID NO: 249) | WYQQKPGQAPRL LIY (SEQ ID NO: 261) | GIPDRFSGSGSGTDFTLTI SRLEPEDFAVYYC (SEQ ID NO: 268) | FGGGTKVEIK (SEQ ID NO: 276) |
| TI-23 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-24 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-25 | EIVLTQSPATLSLSPGE RATLSC (SEQ ID NO: 253) | WYQQKPGQAPRL LIY (SEQ ID NO: 261) | GIPARFSGSGSGTDFTLTI SSLEPEDFAVYYC (SEQ ID NO: 272) | FGGGTKVEIK (SEQ ID NO: 276) |
| TI-26 | DIQMTQSPSSLSASVG DRVTITC (SEQ ID NO: 248) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-27 | DIQMTQSPSSLSASVG DRVTITC (SEQ ID NO: 248) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-28 | EIVLTQSPATLSVSPGE RATLSC (SEQ ID NO: 257) | WYQQKPGQAPRL LIY (SEQ ID NO: 261) | GIPARFSGSGSGTEFTLTI SSLQSEDFAVYYC (SEQ ID NO: 270) | FGGGTKVEIK (SEQ ID NO: 276) |

TABLE 4-continued

EU or Kabat light chain Framework sequences of anti-TREM1 antibodies

| Ab ID | VL FR1 | VL FR2 | VL F3 | VL FR4 |
|---|---|---|---|---|
| TI-29 | EIVLTQSPATLSLSPGE RATLSC (SEQ ID NO: 253) | WYQQKPGQAPRL LIY (SEQ ID NO: 261) | GIPARFSGSGSGTDFTLTI SSLEPEDFAVYYC (SEQ ID NO: 272) | FGGGTKVEIK (SEQ ID NO: 276) |
| TI-30 | D IQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-31 | DIQMTQSPSSLSASVG DRVTITC (SEQ ID NO: 248) | WYQQKPGKAPKL LIY (SEQ ID NO: 260) | GVPSRFSGSGSGTDFTFT ISSLQPEDIATYYC (SEQ ID NO: 267) | FGGGTKVEIK (SEQ ID NO: 276) |
| TI-32 | DIQMTQSPSSLSASVG DRVTITC (SEQ ID NO: 248) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-33 | DIQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-34 | DIQMTQSPSTLSASVG DRVTITC (SEQ ID NO: 255) | WYQQKPGKAPKL LIS (SEQ ID NO: 265) | GVPSRFSGSGSGIEFTLT ISSLQPDDFATYYC (SEQ ID NO: 274) | FGGGTKVEIK (SEQ ID NO: 276) |
| TI-35 | DIVMTQSPDSLAVSLG ERATINC (SEQ ID NO: 250) | WYQQKPGQPPKLGVPDRF LIY (SEQ ID NO: 262) | SGSGSGTDFTLT ISSLQAEDVAVYYC (SEQ ID NO: 269) | FGGGTKVEIK (SEQ ID NO: 276) |
| TI-36 | DIVMTQSPDSLAVSLG ERATINC (SEQ ID NO: 250) | WYQQKPGQPPKLGVPDRF LIY (SEQ ID NO: 262) | SGSGSGTDFTLT ISSLQAEDVAVYYC (SEQ ID NO: 269) | FGGGTKVEIK (SEQ ID NO: 276) |
| TI-37 | EIVMTQSPATLSVSPG ERATLSC (SEQ ID NO: 251) | WYQQKPGQAPRL LIY (SEQ ID NO: 261) | GIPARFSGSGSGTEFTLTI SSLQSEDFAVYYC (SEQ ID NO: 270) | FGGGTKVEIK (SEQ ID NO: 276) |
| TI-38 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-39 | DIQLTQSPSSVSASVG DRVTITC (SEQ ID NO: 258) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-40 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-41 | DIQLTQSPSSVSASVG DRVTITC (SEQ ID NO: 258) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-42 | EIVMTQSPATLSVSPG ERATLSC (SEQ ID NO: 251) | WYQQKPGQAPRL LIY (SEQ ID NO: 261) | GIPARFSGSGSGTEFTLTI SSLQSEDFAVYYC (SEQ ID NO: 270) | FGGGTKVEIK (SEQ ID NO: 276) |
| TI-43 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-44 | DIVMTQSPLSLPVTPG EPASISC (SEQ ID NO: 252) | WYLQKPGQSPQV LIY (SEQ ID NO: 266) | GVPDRFSGSGSGTDFTL KISRVEAEDVGVYYC (SEQ ID NO: 271) | FGGGTKVEIK (SEQ ID NO: 276) |
| TI-45 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-46 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-47 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |

TABLE 4 -continued

EU or Kabat light chain Framework sequences of anti-TREM1 antibodies

| Ab ID | VL FR1 | VL FR2 | VL F3 | VL FR4 |
|---|---|---|---|---|
| TI-48 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-49 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-50 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-51 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-52 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-53 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-54 | EIVMTQSPATLSLSPGE RATLSC (SEQ ID NO: 259) | WYQQKPGQAPRL LIY (SEQ ID NO: 261) | GIPARFSGSGSGTDFTLTI SSLEPEDFAVYYC (SEQ ID NO: 272) | FGGGTKVEIK (SEQ ID NO: 276) |
| TI-55 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-56 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-57 | DIQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-58 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-59 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-60 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-61 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-62 | EIVLTQSPGTLSLSPGE RATLSC (SEQ ID NO: 249) | WYQQKPGQAPRL LIY (SEQ ID NO: 261) | GIPDRFSGSGSGTDFTLTI SRLEPEDFAVYYC (SEQ ID NO: 268) | FGGGTKVEIK (SEQ ID NO: 276) |
| TI-63 | DIQMTQSPSSLSASVG DRVTITC (SEQ ID NO: 248) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-64 | DIVMTQSPDSLAVSLG ERATINC (SEQ ID NO: 250) | WYQQKPGQPPKL LIY (SEQ ID NO: 262) | GVPDRFSGSGSGTDFTLT ISSLEPEDVAVYYC (SEQ ID NO: 275) | FGGGTKVEIK (SEQ ID NO: 276) |
| TI-65 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-66 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |

TABLE 4 -continued

EU or Kabat light chain Framework sequences of anti-TREM1 antibodies

| Ab ID | VL FR1 | VL FR2 | VL F3 | VL FR4 |
|-------|--------|--------|-------|--------|
| TI-67 | EIVLTQSPGTLSLSPGE RATLSC (SEQ ID NO: 249) | WYQQKPGQAPRL LIY (SEQ ID NO: 261) | GIPDRFSGSGSGTDFTLTI SRLEPEDFAVYYC (SEQ ID NO: 268) | FGGGTKVEIK (SEQ ID NO: 276) |
| TI-68 | EIVLTQSPATLSLSPGE RATLSC (SEQ ID NO: 253) | WYQQKPGQAPRL LIY (SEQ ID NO: 261) | GIPARFSGSGSGTDFTLTI SSLEPEDFAVYYC (SEQ ID NO: 272) | FGGGTKVEIK (SEQ ID NO: 276) |
| TI-69 | DIQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-70 | DIQLTQSPSSVSASVG DRVTITC (SEQ ID NO: 258) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-71 | DIQMTQSPSSVSASVG DRVTITC (SEQ ID NO: 254) | WYQQKPGKAPKL LIY (SEQ ID NO: 260) | GVPSRFSGSGSGTDFTLT ISSLQPEDFATYYC (SEQ ID NO: 273) | FGGGTKVEIK (SEQ ID NO: 276) |
| TI-72 | DIVMTQSPLSLPVTPG EPASISC (SEQ ID NO: 252) | WYLQKPGQSPQLL IY (SEQ ID NO: 263) | GVPDRFSGSGSGTDFTL KISRVEAEDVGVYYC (SEQ ID NO: 271) | FGGGTKVEIK (SEQ ID NO: 276) |
| TI-73 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-74 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-75 | EIVLTQSPATLSLSPGE RATLSC (SEQ ID NO: 253) | WYQQKPGQAPRL LIY (SEQ ID NO: 261) | GIPARFSGSGSGTDFTLTI SSLEPEDFAVYYC (SEQ ID NO: 272) | FGGGTKVEIK (SEQ ID NO: 276) |
| TI-76 | DIQMTQSPSTLSASVG DRVTITC (SEQ ID NO: 255) | WYQQKPGKAPKL LIY (SEQ ID NO: 260) | GVPSRFSGSGSGIEFTLT ISSLQPDDFATYYC (SEQ ID NO: 274) | FGGGTKVEIK (SEQ ID NO: 276) |
| TI-77 | EIVMTQSPATLSVSPG ERATLSC (SEQ ID NO: 251) | WYQQKPGQAPRL LIY (SEQ ID NO: 261) | GIPARFSGSGSGTEFTLTI SSLQSEDFAVYYC (SEQ ID NO: 270) | FGGGTKVEIK (SEQ ID NO: 276) |
| TI-78 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-79 | DIVMTQSPDSLAVSLG ERATINC (SEQ ID NO: 250) | WYQQKPGQPPKL LIY (SEQ ID NO: 262) | GVPDRFSGSGSGTDFTLT ISSLQAEDVAVYYC (SEQ ID NO: 269) | FGGGTKVEIK (SEQ ID NO: 276) |
| TI-80 | EIVMTQSPATLSVSPG ERATLSC (SEQ ID NO: 251) | WYQQKPGQAPRL LIY (SEQ ID NO: 261) | GIPARFSGSGSGTEFTLTI SSLQSEDFAVYYC (SEQ ID NO: 270) | FGGGTKVEIK (SEQ ID NO: 276) |

TABLE 5

EU or Kabat heavy chain Framework sequences of anti-TREM1 antibodies

| Ab ID | VH FR1 | VH FR2 | VH F3 | VH FR4 |
|-------|--------|--------|-------|--------|
| TI-1 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTTVTVS S (SEQ ID NO: 309) |
| TI-2 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTLVTVS S (SEQ ID NO: 310) |
| TI-3 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTMVTVS S (SEQ ID NO: 311) |

TABLE 5 -continued

EU or Kabat heavy chain Framework sequences of anti-TREM1 antibodies

| Ab ID | VH FR1 | VH FR2 | VH F3 | VH FR4 |
|---|---|---|---|---|
| TI-4 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGRGTLVTVSS (SEQ ID NO: 312) |
| TI-5 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTLVTVS S (SEQ ID NO: 310) |
| TI-6 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTLVTVS S (SEQ ID NO: 310) |
| TI-7 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTLVTVS S (SEQ ID NO: 310) |
| TI-8 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-9 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-10 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-11 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGRGTLVTVS S (SEQ ID NO: 312) |
| TI-12 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGKGTTVTVS S (SEQ ID NO: 313) |
| TI-13 | EVQLVESGGGLVKPG GSLRLSCAASG (SEQ ID NO: 280) | WVRQAPGKGLEW VS (SEQ ID NO: 292) | RFTISRDNAKNSLYLQM NSLRAEDTAVYYC (SEQ ID NO: 300) | WGQGTMVTVS S (SEQ ID NO: 311) |
| TI-14 | QVQLVESGGGVVQP GRSLRLSCAASG (SEQ ID NO: 281) | WVRQAPGKGLEW VA (SEQ ID NO: 293) | RFTISRDNSKNTLYLQM NSLRAEDTAVYYC (SEQ ID NO: 301) | WGQGTMVTVS S (SEQ ID NO: 311) |
| TI-15 | EVQLVESGGGLVKPG GSLRLSCAASG (SEQ ID NO: 280) | WVRQAPGKGLEW VS (SEQ ID NO: 292) | RFTISRDNAKNSLYLQM NSLRAEDTAVYYC (SEQ ID NO: 300) | WGQGTLVTVS S (SEQ ID NO: 310) |
| TI-16 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGQGTLVTVS S (SEQ ID NO: 310) |
| TI-17 | QVQLQESGPGLVKPS ETLSLTCTVSG (SEQ ID NO: 283) | WIRQPPGKGLEWI G (SEQ ID NO: 291) | RVTISVDTSKNQFSLKLS SVTAADTAVYYC (SEQ ID NO: 299) | WGQGTLVTVS S (SEQ ID NO: 310) |
| TI-18 | EVQLVESGGGLVQPG RSLRLSCAASG (SEQ ID NO: 282) | WVRQAPGKGLEW VS (SEQ ID NO: 292) | RFTISRDNAKNTLYLQM NSLRAEDTALYYC (SEQ ID NO: 303) | WGQGTMVTVS S (SEQ ID NO: 311) |
| TI-19 | EVQLVESGGGLVQPG GSLRLSCAASG (SEQ ID NO: 284) | WVRQAPGKGLEW VG (SEQ ID NO: 294) | RFTISRDDSKNSLYLQM NSLKTEDTAVYYC (SEQ ID NO: 304) | WGQGTLVTVS S (SEQ ID NO: 310) |
| TI-20 | EVQLVESGGGLVQPG GSLRLSCAASG (SEQ ID NO: 284) | WVRQAPGKGLEW VA (SEQ ID NO: 293) | RFTISRDNAKNSLYLQM NSLRAEDTAVYYC (SEQ ID NO: 300) | WGQGTMVTVS S (SEQ ID NO: 311) |
| TI-21 | EVQLVESGGGLVQPG GSLRLSCAASG (SEQ ID NO: 284) | WVRQAPGKGLEW VS (SEQ ID NO: 292) | RFTISRDNAKNSLYLQM NSLRAEDTAVYYC (SEQ ID NO: 300) | WGQGTTVTVS S (SEQ ID NO: 309) |
| TI-22 | QVQLQESGPGLVKPS ETLSLTCTVSG (SEQ ID NO: 283) | WIRQPPGKGLEWI G (SEQ ID NO: 291) | RVTISVDTSKNQFSLKLS SVTAADTAVYYC (SEQ ID NO: 299) | WGRGTLVTVS S (SEQ ID NO: 312) |

TABLE 5 -continued

EU or Kabat heavy chain Framework sequences of anti-TREM1 antibodies

| Ab ID | VH FR1 | VH FR2 | VH F3 | VH FR4 |
|---|---|---|---|---|
| TI-23 | EVQLVESGGGLVQPGRSLRLSCAASG (SEQ ID NO: 282) | WVRQAPGKGLEWVS (SEQ ID NO: 292) | RFTISRDNAKNSLYLQMNSLRAEDTALYYC (SEQ ID NO: 302) | WGQGTMVTVSS (SEQ ID NO: 311) |
| TI-24 | EVQLVESGGGLVQPGRSLRLSCAASG (SEQ ID NO: 282) | WVRQAPGKGLEWVS (SEQ ID NO: 292) | RFTISRDNAKNSLYLQMNSLRAEDTALYYC (SEQ ID NO: 302) | WGQGTMVTVSS (SEQ ID NO: 311) |
| TI-25 | EVQLVESGGGLVQPGRSLRLSCAASG (SEQ ID NO: 282) | WVRQAPGKGLEWVS (SEQ ID NO: 292) | RFTISRDNAKNSLYLQMNSLRAEDTALYYC (SEQ ID NO: 302) | WGQGTLVTVSS (SEQ ID NO: 310) |
| TI-26 | QVQLVQSGAEVKKPGASVKVSCKASG (SEQ ID NO: 278) | WVRQAPGQGLEWMG (SEQ ID NO: 290) | RVTMTRDTSTSTVYMELSSLRSEDTAVYYC (SEQ ID NO: 298) | WGQGTTVTVSS (SEQ ID NO: 309) |
| TI-27 | QVQLQESGPGLVKPSQTLSLTCTVSG (SEQ ID NO: 285) | WIRQHPGKGLEWIG (SEQ ID NO: 295) | RVTISVDTSKNQFSLKLSSVTAADTAVYYC (SEQ ID NO: 299) | WGQGTLVTVSS (SEQ ID NO: 310) |
| TI-28 | EVQLVESGGGLVKPGGSLRLSCAASG (SEQ ID NO: 280) | WVRQAPGKGLEWVS (SEQ ID NO: 292) | RFTISRDNAKNSLYLQMNSLRAEDTAVYYC (SEQ ID NO: 300) | WGQGTMVTVSS (SEQ ID NO: 311) |
| TI-29 | QLQLQESGPGLVKPSETLSLTCTVSG (SEQ ID NO: 279) | WIRQPPGKGLEWIG (SEQ ID NO: 291) | RVTISVDTSKNQFSLKLSSVTAADTAVYYC (SEQ ID NO: 299) | WGQGTTVTVSS (SEQ ID NO: 309) |
| TI-30 | QLQLQESGPGLVKPSETLSLTCTVSG (SEQ ID NO: 279) | WIRQPPGKGLEWIG (SEQ ID NO: 291) | RVTISVDTSKNQFSLKLSSVTAADTAVYYC (SEQ ID NO: 299) | WGQGTLVTVSS (SEQ ID NO: 310) |
| TI-31 | QLQLQESGPGLVKPSETLSLTCTVSG (SEQ ID NO: 279) | WIRQPPGKGLEWIG (SEQ ID NO: 291) | RVTISVDTSKNQFSLKLSSVTAADTAVYYC (SEQ ID NO: 299) | WGQGTTVTVSS (SEQ ID NO: 309) |
| TI-32 | QLQLQESGPGLVKPSETLSLTCTVSG (SEQ ID NO: 279) | WIRQPPGKGLEWIG (SEQ ID NO: 291) | RVTISVDTSKNQFSLKLSSVTAADTAVYYC (SEQ ID NO: 299) | WGQGTMVTVSS (SEQ ID NO: 311) |
| TI-33 | QVQLVESGGGVVQPGRSLRLSCAASG (SEQ ID NO: 281) | WVRQAPGKGLEWVA (SEQ ID NO: 293) | RFTISRDNSKNTLYLQMNSLRAEDTAVYYC (SEQ ID NO: 301) | WGQGTTVTVSS (SEQ ID NO: 309) |
| TI-34 | EVQLVESGGGLVKPGGSLRLSCAASG (SEQ ID NO: 280) | WVRQAPGKGLEWVS (SEQ ID NO: 292) | RFTISRDNAKNSLYLQMNSLKAEDTAVYYC (SEQ ID NO: 305) | WGQGTLVTVSS (SEQ ID NO: 310) |
| TI-35 | QVQLVESGGGVVQPGRSLRLSCAASG (SEQ ID NO: 281) | WVRQAPGKGLEWVA (SEQ ID NO: 293) | RFTISRDNSKNTLYLQMNSLRAEDTAVYYC (SEQ ID NO: 301) | WGQGTMVTVSS (SEQ ID NO: 311) |
| TI-36 | QVQLVESGGGVVQPGRSLRLSCAASG (SEQ ID NO: 281) | WVRQAPGKGLEWVA (SEQ ID NO: 293) | RFTISRDNSKNTLYLQMNSLRAEDTAVYYC (SEQ ID NO: 301) | WGQGTMVTVSS (SEQ ID NO: 311) |
| TI-37 | QVQLVESGGGVVQPGRSLRLSCAASG (SEQ ID NO: 281) | WVRQAPGKGLEWVA (SEQ ID NO: 293) | RFTISRDNSKNTLYLQMNSLRAEDTAVYYC (SEQ ID NO: 301) | WGQGTLVTVSS (SEQ ID NO: 310) |
| TI-38 | QVQLVESGGGVVQPGRSLRLSCAASG (SEQ ID NO: 281) | WVRQAPGKGLEWVA (SEQ ID NO: 293) | RFTISRDNSKNTLYLQMNSLRAEDTAVYYC (SEQ ID NO: 301) | WGQGTLVTVSS (SEQ ID NO: 310) |
| TI-39 | EVQLVESGGGLVKPGGSLRLSCAASG (SEQ ID NO: 280) | WVRQAPGKGLEWVS (SEQ ID NO: 292) | RFTISRDNAKNSLYLQMNSLRAEDTAVYYC (SEQ ID NO: 300) | WGQGTLVTVSS (SEQ ID NO: 310) |
| TI-40 | EVQLVESGGGLVKPGGSLRLSCAASG (SEQ ID NO: 280) | WVRQAPGKGLEWVS (SEQ ID NO: 292) | RFTISRDNAKNSLYLQMNSLRAEDTAVYYC (SEQ ID NO: 300) | WGQGTMVTVSS (SEQ ID NO: 311) |
| TI-41 | EVQLLESGGGLVQPGGSLRLSCAASG (SEQ ID NO: 286) | WVRQAPGKGLEWVS (SEQ ID NO: 292) | RFTISRDNSKNTLYLQMNSLRAEDTAVYYC (SEQ ID NO: 301) | WGQGTMVTVSS (SEQ ID NO: 311) |

TABLE 5 -continued

EU or Kabat heavy chain Framework sequences of anti-TREM1 antibodies

| Ab ID | VH FR1 | VH FR2 | VH F3 | VH FR4 |
| --- | --- | --- | --- | --- |
| TI-42 | QVQLVESGGGVVQP GRSLRLSCAASG (SEQ ID NO: 281) | WVRQAPGKGLEW VA (SEQ ID NO: 293) | RFTISRDNSKNTLYLQM NSLRAEDTAVYYC (SEQ ID NO: 301) | WGQGTTVTVS S (SEQ ID NO: 309) |
| TI-43 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-44 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTTVTVS S (SEQ ID NO: 309) |
| TI-45 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTTVTVS S (SEQ ID NO: 309) |
| TI-46 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTTVTVS S (SEQ ID NO: 309) |
| TI-47 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTMVTVS S (SEQ ID NO: 311) |
| TI-48 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-49 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-50 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-51 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTLVTVS S (SEQ ID NO: 310) |
| TI-52 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTTVTVS S (SEQ ID NO: 309) |
| TI-53 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTMVTVS S (SEQ ID NO: 311) |
| TI-54 | QVQLVQSGAEVKKP GSSVKVSCKASG (SEQ ID NO: 277) | WVRQAPGQGLEW MG (SEQ ID NO: 290) | RVTITADESTSTAYMELS SLRSEDTAVYYC (SEQ ID NO: 297) | WGQGTMVTVS S (SEQ ID NO: 311) |
| TI-55 | QVQLVQSGAEVKKP GASVKVSCKASG (SEQ ID NO: 278) | WVRQAPGQGLEW MG (SEQ ID NO: 290) | RVTMTRDTSTSTVYMEL SSLRSEDTAVYYC (SEQ ID NO: 298) | WGQGTLVTVS S (SEQ ID NO: 310) |
| TI-56 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGRGTLVTVSS (SEQ ID NO: 312) |
| TI-57 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGQGTLVTVS S (SEQ ID NO: 310) |
| TI-58 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGRGTLVTVS S (SEQ ID NO: 312) |
| TI-59 | QVQLQESGPGLVKPS ETLSLTCAVSG (SEQ ID NO: 287) | WIRQPPGKGLEWI G (SEQ ID NO: 291) | RVTISVDTSKNQFSLKLS SVTAADTAVYYC (SEQ ID NO: 299) | WGQGTLVTVS S (SEQ ID NO: 310) |
| TI-60 | QVQLQESGPGLVKPS ETLSLTCAVSG (SEQ ID NO: 287) | WIRQPPGKGLEWI G (SEQ ID NO: 291) | RVTISVDTSKNQFSLKLS SVTAADTAVYYC (SEQ ID NO: 299) | WGQGTLVTVS S (SEQ ID NO: 310) |

TABLE 5 -continued

EU or Kabat heavy chain Framework sequences of anti-TREM1 antibodies

| Ab ID | VH FR1 | VH FR2 | VH F3 | VH FR4 |
|---|---|---|---|---|
| TI-61 | QVQLQESGPGLVKPS ETLSLTCAVSG (SEQ ID NO: 287) | WIRQPPGKGLEWI G (SEQ ID NO: 291) | RVTISVDTSKNQFSLKLS SVTAADTAVYYC (SEQ ID NO: 299) | WGQGTLVTVS S (SEQ ID NO: 310) |
| TI-62 | QVQLQESGPGLVKPS QTLSLTCTVSG (SEQ ID NO: 285) | WIRQHPGKGLEWI G (SEQ ID NO: 295) | RVTISVDTSKNQFSLKLS SVTAADTAVYYC (SEQ ID NO: 299) | WGQGTMVTVS S (SEQ ID NO: 311) |
| TI-63 | QVQLQESGPGLVKPS ETLSLTCAVSG (SEQ ID NO: 287) | WIRQPPGKGLEWI G (SEQ ID NO: 291) | RVTISVDTSKNQFSLKLS SVTAADTAVYYC (SEQ ID NO: 299) | S (SEQ ID NO: 314) |
| TI-64 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGQGTTVTVS S (SEQ ID NO: 309) |
| TI-65 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGQGTMVTVS S (SEQ ID NO: 311) |
| TI-66 | QVQLVQSGAEVKKP GASVKVSCKASG (SEQ ID NO: 278) | WVRQAPGQGLEW MG (SEQ ID NO: 290) | RVTMTRDTSISTAYMEL SRLRSDDTAVYYC (SEQ ID NO: 306) | WGQGTLVTVS S (SEQ ID NO: 310) |
| TI-67 | QVQLVQSGAEVKKP GASVKVSCKASG (SEQ ID NO: 278) | WVRQAPGQGLEW MG (SEQ ID NO: 290) | RVTMTTDTSTSTAYMEL RSLRSDDTAVYYC (SEQ ID NO: 307) | WGQGTTVTVS S (SEQ ID NO: 309) |
| TI-68 | EVQLVQSGAEVKKPG ESLKISCKGSG (SEQ ID NO: 288) | WVRQMPGKGLE WMG (SEQ ID NO: 296) | QVTISADKSISTAYLQWS SLKASDTAMYYC (SEQ ID NO: 308) | WGQGTMVTVS S (SEQ ID NO: 311) |
| TI-69 | QVQLVQSGAEVKKP GASVKVSCKASG (SEQ ID NO: 278) | WVRQAPGQGLEW MG (SEQ ID NO: 290) | RVTMTTDTSTSTAYMEL RSLRSDDTAVYYC (SEQ ID NO: 307) | WGQGTTVTVS S (SEQ ID NO: 309) |
| TI-70 | QVQLVQSGAEVKKP GASVKVSCKASG (SEQ ID NO: 278) | WVRQAPGQGLEW MG (SEQ ID NO: 290) | RVTMTTDTSTSTAYMEL RSLRSDDTAVYYC (SEQ ID NO: 307) | WGRGTLVTVSS (SEQ ID NO: 312) |
| TI-71 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGQGTMVTVS S (SEQ ID NO: 311) |
| TI-72 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGRGTLVTVSS (SEQ ID NO: 312) |
| TI-73 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGRGTSVTVSS (SEQ ID NO: 315) |
| TI-74 | EVQLVESGGGLVQPG RSLRLSCAASG (SEQ ID NO: 282) | WVRQAPGKGLEW VS (SEQ ID NO: 292) | RFTISRDNAKNSLYLQM NSLRAEDTALYYC (SEQ ID NO: 302) | WGRGTLVTVSS (SEQ ID NO: 312) |
| TI-75 | QVQLVESGGGLVQPG RSLRLSCAASG (SEQ ID NO: 289) | WVRQAPGKGLEW VS (SEQ ID NO: 292) | RFTISRDNAKNSLYLQM NSLRAEDTALYYC (SEQ ID NO: 302) | WGQGTLVTVS S (SEQ ID NO: 310) |
| TI-76 | EVQLLESGGGLVQPG GSLRLSCAASG (SEQ ID NO: 286) | WVRQAPGKGLEW VS (SEQ ID NO: 292) | RFTISRDNSKNTLYLQM NSLRAEDTAVYYC (SEQ ID NO: 301) | WGQGTTVTVS S (SEQ ID NO: 309) |
| TI-77 | QVQLQESGPGLVKPS ETLSLTCAVSG (SEQ ID NO: 287) | WIRQPPGKGLEWI G (SEQ ID NO: 291) | RVTISVDTSKNQFSLKLS SVTAADTAVYYC (SEQ ID NO: 299) | WGQGTLVTVS S (SEQ ID NO: 310) |
| TI-78 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGRGTLVTVSS (SEQ ID NO: 312) |
| TI-79 | QLQLQESGPGLVKPS ETLSLTCTVSG (SEQ ID NO: 279) | WIRQPPGKGLEWI G (SEQ ID NO: 291) | RVTISVDTSKNQFSLKLS SVTAADTAVYYC (SEQ ID NO: 299) | WGQGTLVTVS S (SEQ ID NO: 310) |

TABLE 5 -continued

EU or Kabat heavy chain Framework sequences of anti-TREM1 antibodies

| Ab ID | VH FR1 | VH FR2 | VH F3 | VH FR4 |
|---|---|---|---|---|
| TI-80 | QVQLVESGGGVVQP GRSLRLSCAASG (SEQ ID NO: 281) | WVRQAPGKGLEW VA (SEQ ID NO: 293) | RFTISRDNSKNTLYLQM NSLRAEDTAVYYC (SEQ ID NO: 301) | WGQGTTVTVS S (SEQ ID NO: 309) |

Characterization of TREM1 Antibody Binding

Initial characterization of TREM1 antibodies involved determining their ability to bind TREM1 expressed on monocytes and other primary human or mouse immune cells. Cells were harvested, plated at $10^5$/ml in a 96 well plate, washed, and incubated in 100 ul PBS containing 10-50 ug/ml Mab and Fc blocking reagent for 1 hour in ice. Cells were then washed twice and incubated in 100 ul PBS containing 5 ug/ml PE-conjugated secondary antibody for 30 minutes in ice. Cells were washed twice in cold PBS and acquired on a BD FACS Canto. Data analysis and calculation of mean fluorescence intensity (MFI) values or positive cells was performed with FlowJo (TreeStar) software version 10.0.7.

Figure 4A:
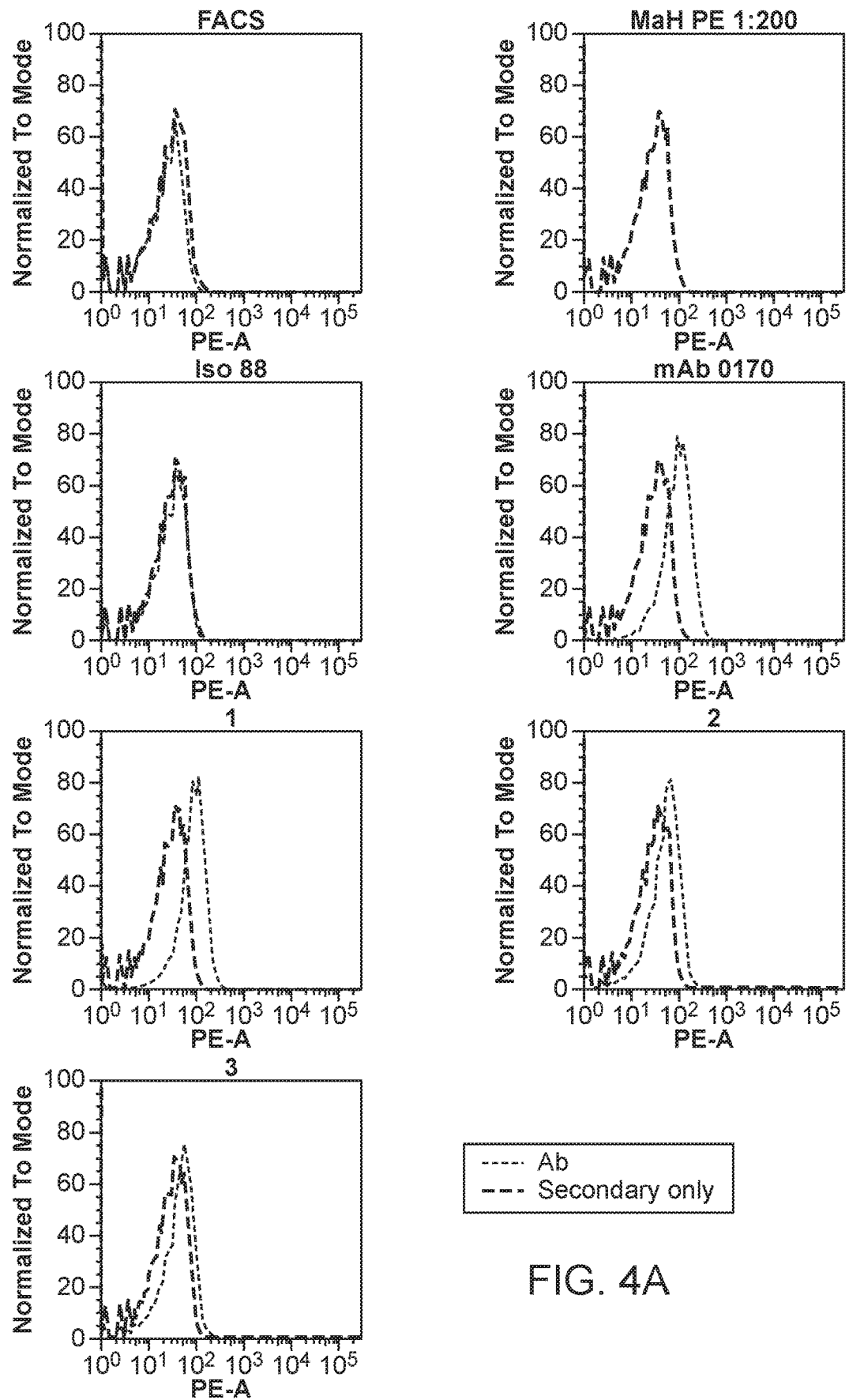
FIG. 4A shows FACS histograms of TREM1 antibodies T1-1 through T1-80 binding to primary human neutrophils. Antibody ISO88 represents a negative isotype control and MAB0170 represents a positive control. Shaded histograms represent the cells stained with anti-human Fc secondary antibody only. Black outlined histograms represent the TREM1 positive cell population.
Figure 4B:
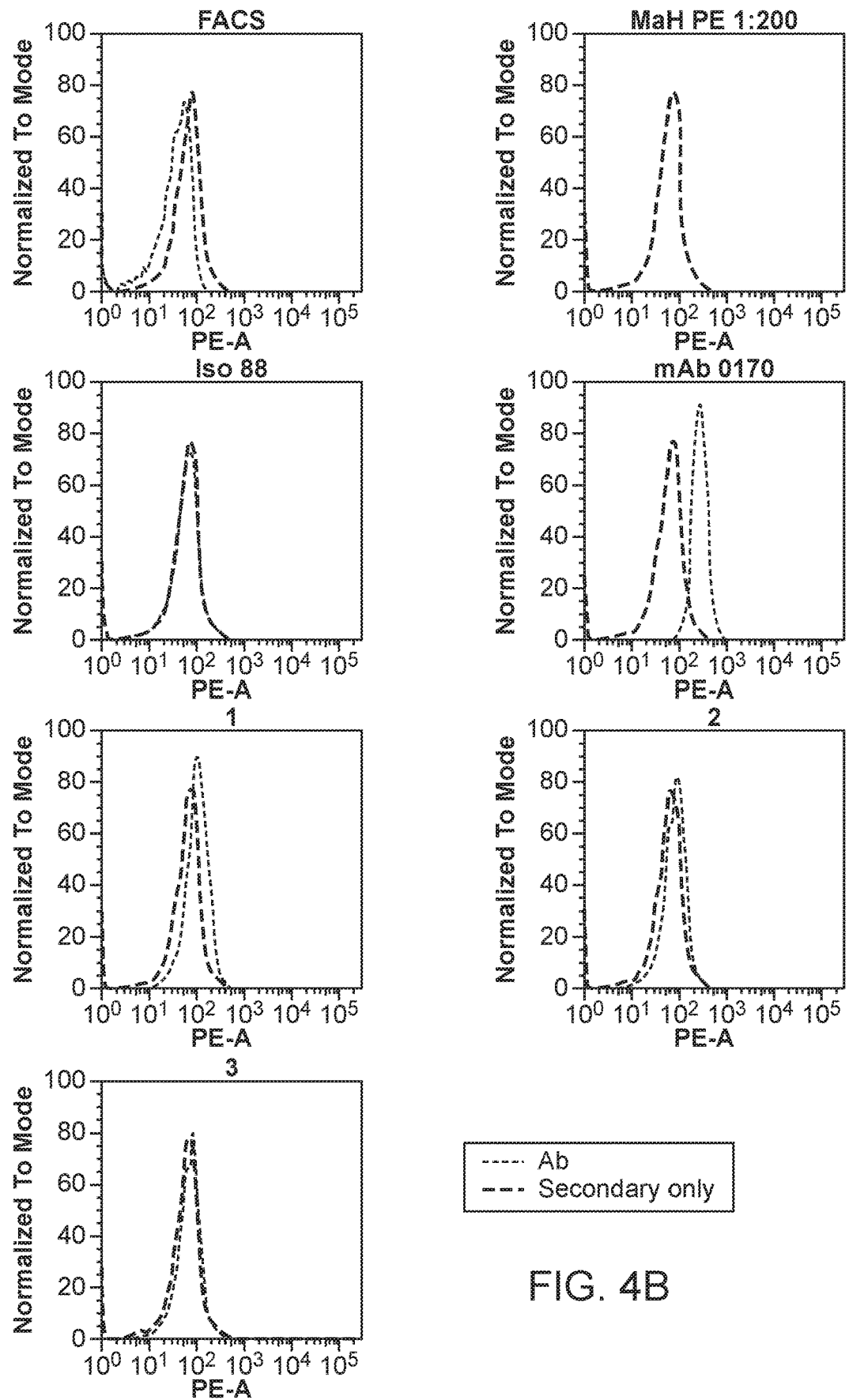
FIG. 4B shows FACS histograms of TREM1 antibodies T1-1 through T1-80 binding to primary human monocytes. Shaded histograms show binding of the isotype antibody negative control. Black outlined histograms represent binding of the TREM1 antibodies.
Figure 5B:
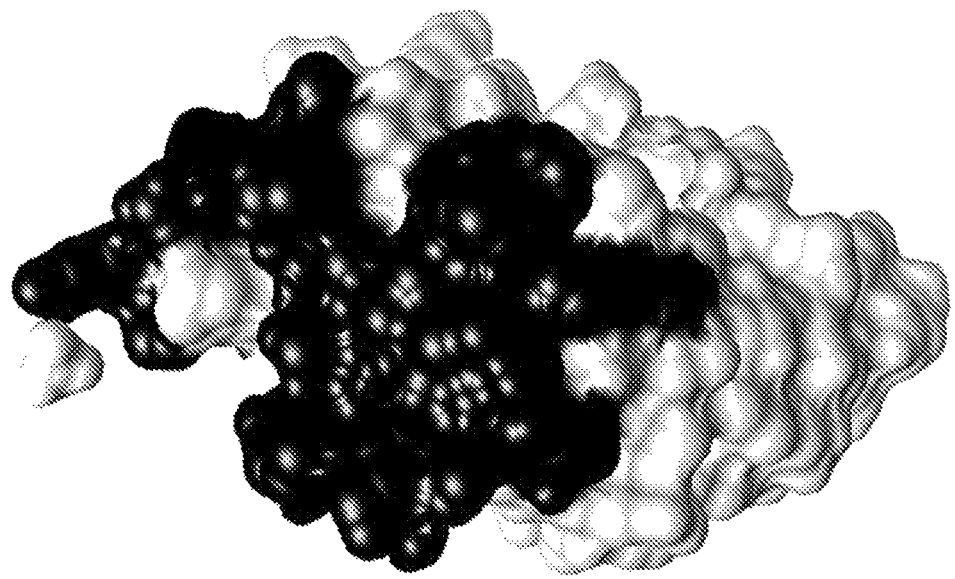
FIGS. 5A-5D show a structural map of human TREM1 (PDB 1Q8M) highlighting defined epitopes for the indicated anti-TREM1 antibodies.
Figure 5A:
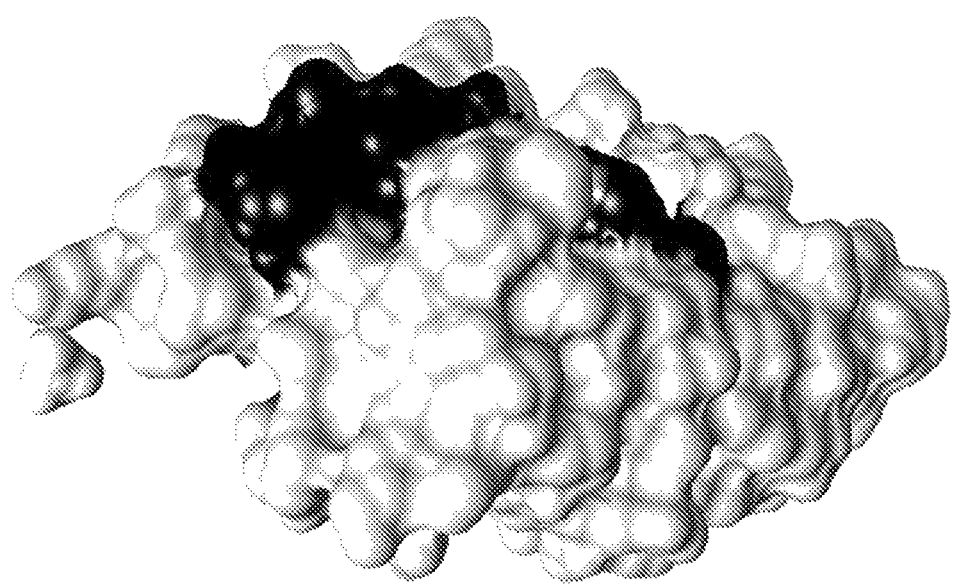
Figure 5D:
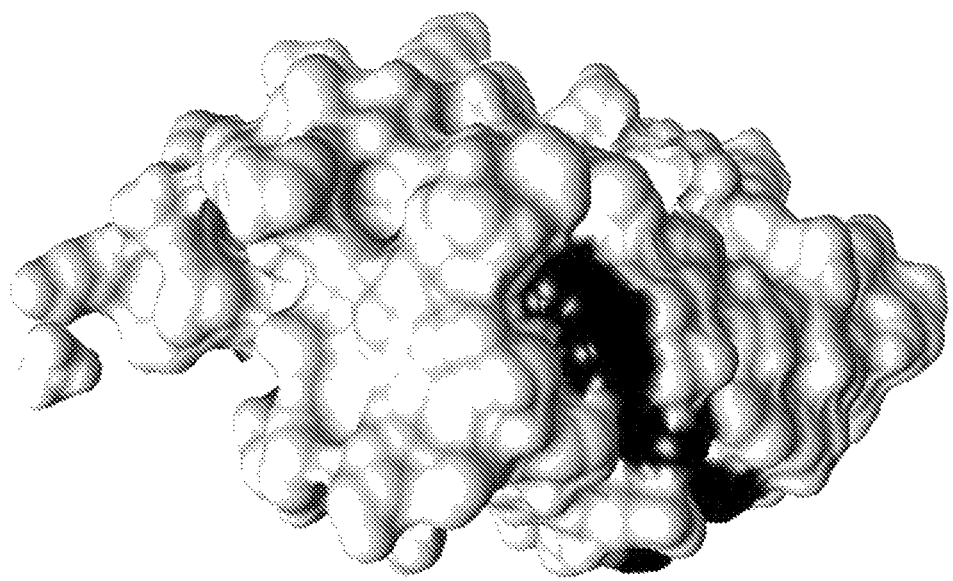
Figure 5C:
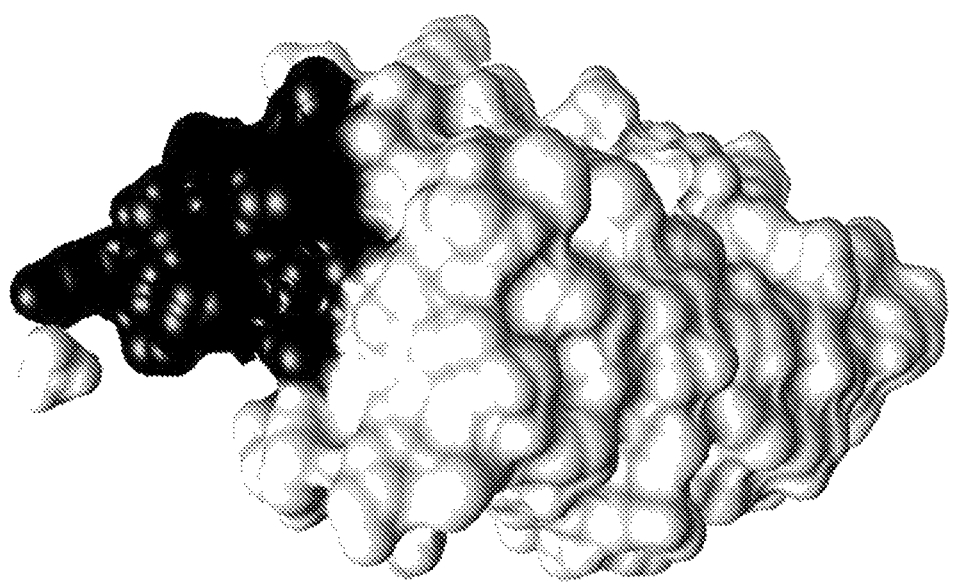

Antibodies T1-63 and T1-71, for example, demonstrated binding to a rodent cell line (CHO-huT1) expressing recombinant human TREM1, as indicated by positive TREM1 antibody staining detected via FACS analysis (black outlined histograms) (FIG. 3A). The negative isotype control (antibody ISO88) did not demonstrate binding. Antibodies T1-63 and T1-71 also demonstrated partial/weak binding to CHO cells highly overexpressing recombinant mouse TREM1 (CHO-mT1) (FIG. 3B). Likewise, antibodies T1-63 and T1-71, for example, demonstrated binding to both primary human neutrophils (FIG. 4A) and primary human monocytes (FIG. 4B).

Mean fluorescent intensity (MFI) values for cell lines bound by TREM1 antibodies are listed in Table 6. Binding is compared to the parental cell line (CHO parental) and to CHO cells that overexpress human TREM1 (CHO-hT1) and to CHO cells that overexpress mouse TREM1. TREM1 antibodies were also tested for cross-reactivity to TREM2. Binding is compared to the parental cell line (BWZ parental) and to BWZ cells that overexpress human TREM2 and to BWZ cells that overexpress mouse TREM2. Additionally, the table also summarizes binding to primary human neutrophils (hNeut). The results in Table 6 in indicate that antibodies all antibodies tested bind specifically to cell lines overexpressing human TREM1 on the cell membrane, but not to control cell lines that do not express human TREM1. With few exceptions, such as T1-26, T1-27, and T1-34, TREM1 antibodies primarily bound human TREM1 and not mouse TREM1. Importantly, none of the TREM1 antibodies bound to cell lines overexpressing human or mouse TREM2, confirming the specificity of the interaction. Surprisingly, the positive control antibody, MAB0170, which binds human TREM1 with high affinity, did demonstrate cross-reactivity to human and mouse TREM2. The antibodies also bind to human primary neutrophils. Binding to human primary cells is specific, as it is not detected with the isotype control antibodies huIgG1.

TABLE 6

TREM1 antibody binding to human cells expressing human or mouse TREM1

| Ab ID | Cell binding CHO Human TREM1 (FOB Fold Over Background) | Cell binding CHO Mouse TREM1 (FOB Fold Over Background) | Cell binding BWZ Human TREM2 (FOB Fold Over Background) | Cell binding BWZ Mouse TREM2 (FOB Fold Over Background) | Cell binding Human Neutrophils (FOB Fold Over Background) |
|---|---|---|---|---|---|
| T1-1 | 351.7 | 0.4 | 1.3 | 1.5 | 4.4 |
| T1-2 | 313.8 | 0.3 | 0.9 | 1.7 | 2.5 |
| T1-3 | 414.9 | 0.4 | 0.6 | 1.0 | 2.1 |
| T1-4 | 508.7 | 0.4 | 0.7 | 1.3 | 2.2 |
| T1-5 | 495.2 | 0.3 | 1.2 | 1.4 | 3.7 |
| T1-6 | 409.1 | 0.4 | 0.4 | 0.7 | 2.7 |
| T1-7 | 451.8 | 0.8 | 1.1 | 1.1 | 2.6 |
| T1-8 | 454.6 | 0.7 | 1.9 | 1.2 | 1.6 |
| T1-9 | 311.8 | 0.7 | 0.7 | 1.5 | 1.7 |
| T1-10 | 525.7 | 0.8 | 0.9 | 1.0 | 2.9 |
| T1-11 | 414.5 | 0.7 | 0.7 | 1.1 | 2.3 |
| T1-12 | 503.3 | 0.5 | 0.6 | 1.0 | 3.2 |
| T1-13 | 288.2 | 0.5 | 0.7 | 1.2 | 1.5 |
| T1-14 | 418.4 | 0.8 | 0.7 | 1.4 | 2.3 |
| T1-15 | 496.6 | 1.4 | 0.9 | 1.4 | 1.7 |
| T1-16 | 298.2 | 1.0 | 0.7 | 1.2 | 1.6 |
| T1-17 | 263.5 | 0.7 | 0.7 | 1.2 | 1.3 |
| T1-18 | 456.7 | 0.8 | 0.5 | 0.9 | 2.0 |
| T1-19 | 419.6 | 0.9 | 0.5 | 0.8 | 1.4 |
| T1-20 | 408.2 | 0.7 | 0.6 | 1.0 | 1.3 |
| T1-21 | 231.4 | 0.5 | 0.5 | 0.9 | 1.2 |
| T1-22 | 586.0 | 1.3 | 0.8 | 1.6 | 5.3 |
| T1-23 | 447.8 | 1.0 | 1.0 | 1.2 | 2.6 |
| T1-24 | 489.0 | 1.3 | 1.4 | 1.2 | 6.9 |
| T1-25 | 451.7 | 0.9 | 0.7 | 1.3 | 2.6 |
| T1-26 | 126.8 | 417.1 | 0.8 | 1.2 | 1.4 |

TABLE 6-continued

TREM1 antibody binding to human cells expressing human or mouse TREM1

| Ab ID | Cell binding CHO Human TREM1 (FOB Fold Over Background) | Cell binding CHO Mouse TREM1 (FOB Fold Over Background) | Cell binding BWZ Human TREM2 (FOB Fold Over Background) | Cell binding BWZ Mouse TREM2 (FOB Fold Over Background) | Cell binding Human Neutrophils (FOB Fold Over Background) |
|---|---|---|---|---|---|
| T1-27 | 362.2 | 522.9 | 0.8 | 1.2 | 1.4 |
| T1-28 | 16.6 | 408.1 | 0.6 | 1.1 | 1.0 |
| T1-29 | 7.9 | 401.0 | 0.7 | 1.2 | 1.1 |
| T1-30 | 19.4 | 453.2 | 0.5 | 0.8 | 1.1 |
| T1-31 | 14.4 | 447.0 | 0.5 | 0.9 | 1.1 |
| T1-32 | 27.2 | 380.1 | 0.9 | 1.2 | 1.0 |
| T1-33 | 463.8 | 22.5 | 0.8 | 1.9 | 3.3 |
| T1-34 | 511.3 | 158.7 | 0.8 | 1.3 | 3.6 |
| T1-35 | 435.1 | 37.0 | 0.7 | 1.1 | 2.3 |
| T1-36 | 452.8 | 59.1 | 0.8 | 1.1 | 2.8 |
| T1-37 | 322.9 | 39.2 | 0.7 | 0.9 | 2.2 |
| T1-38 | 387.7 | 22.9 | 0.5 | 0.8 | 2.1 |
| T1-39 | 440.6 | 54.3 | 0.8 | 1.2 | 2.4 |
| T1-40 | 458.2 | 51.0 | 0.7 | 1.1 | 3.5 |
| T1-41 | 445.4 | 0.6 | 1.0 | 1.6 | 2.6 |
| T1-42 | 397.0 | 11.4 | 0.9 | 1.4 | 3.3 |
| T1-43 | 455.7 | 7.6 | 0.9 | 1.5 | 2.3 |
| T1-44 | 431.0 | 8.0 | 0.9 | 1.2 | 3.1 |
| T1-45 | 445.5 | 0.8 | 1.0 | 1.2 | 5.4 |
| T1-46 | 491.3 | 2.6 | 0.9 | 1.0 | 5.9 |
| T1-47 | 395.4 | 3.7 | 0.7 | 1.0 | 2.3 |
| T1-48 | 291.2 | 8.4 | 1.2 | 1.0 | 4.0 |
| T1-49 | 504.3 | 16.3 | 2.5 | 0.9 | 4.9 |
| T1-50 | 420.8 | 2.6 | 1.2 | 1.3 | 2.7 |
| T1-51 | 499.8 | 4.1 | 0.9 | 1.1 | 2.4 |
| T1-52 | 475.3 | 3.2 | 1.0 | 1.2 | 4.2 |
| T1-53 | 459.1 | 2.0 | 0.9 | 1.2 | 2.3 |
| T1-54 | 437.9 | 3.1 | 1.1 | 1.2 | 3.8 |
| T1-55 | 420.4 | 3.3 | 1.1 | 1.1 | 2.0 |
| T1-56 | 431.5 | 1.1 | 1.2 | 1.3 | 6.8 |
| T1-57 | 456.5 | 1.7 | 0.9 | 1.3 | 4.4 |
| T1-58 | 418.0 | 1.6 | 1.0 | 1.2 | 2.6 |
| T1-59 | 432.5 | 1.5 | 0.9 | 1.2 | 5.3 |
| T1-60 | 398.4 | 1.0 | 0.8 | 1.1 | 2.8 |
| T1-61 | 433.2 | 2.4 | 0.9 | 1.1 | 5.7 |
| T1-62 | 363.8 | 1.9 | 1.4 | 0.9 | 2.1 |
| T1-63 | 501.8 | 1.5 | 1.1 | 1.2 | 8.7 |
| T1-64 | 410.0 | 0.7 | 1.0 | 1.2 | 4.7 |
| T1-65 | 400.2 | 1.4 | 1.0 | 1.4 | 2.2 |
| T1-66 | 506.8 | 1.5 | 0.9 | 1.1 | 2.7 |
| T1-67 | 475.1 | 1.0 | 0.9 | 0.9 | 4.4 |
| T1-68 | 410.9 | 1.0 | 0.9 | 1.1 | 2.2 |
| T1-69 | 463.6 | 1.5 | 0.9 | 0.9 | 5.5 |
| T1-70 | 404.8 | 1.2 | 0.9 | 0.9 | 2.2 |
| T1-71 | 507.3 | 1.2 | 1.1 | 1.0 | 6.3 |
| T1-72 | 504.0 | 1.2 | 1.3 | 1.3 | 5.2 |
| T1-73 | 478.6 | 1.2 | 1.0 | 0.9 | 3.7 |
| T1-74 | 498.8 | 1.9 | 0.7 | 0.9 | 3.9 |
| T1-75 | 428.4 | 1.1 | 1.0 | 1.1 | 3.0 |
| T1-76 | 516.3 | 1.0 | 0.9 | 1.2 | 3.2 |
| T1-77 | 444.0 | 0.8 | 0.9 | 1.1 | 2.4 |
| T1-78 | 405.3 | 1.1 | 1.2 | 1.2 | 6.2 |
| T1-79 | 425.8 | 1.1 | 1.8 | 1.2 | 4.5 |
| T1-80 | 345.8 | 1.2 | 1.0 | 0.9 | 1.7 |
| MAB0170 | 447.4 | 0.1 | 6.5 | 49.0 | 4.5 |
| huIgG1 | 0.1 | 0.1 | 1.0 | 0.9 | 1.0 |

Example 2: Epitope Mapping of TREM1 Antibodies

TREM1 antibodies were tested for their ability to bind 15-mer or 25-mer peptides spanning the entire human TREM1 (SEQ ID NO: 1).

Methodology

Linear 15-mer peptides were synthesized based on the sequence of human TREM1 (SEQ ID NO: 1), with a 14 residue overlap. In addition, linear 25-mer peptides were synthesized based on sequence of human TREM1 (SEQ ID NO: 1) or mouse TREM1 (SEQ ID NO: 2) with a single residue shift. The binding of TREM1 antibodies to each of the synthesized peptides was tested in an ELISA based method. In this assay, the peptide arrays were incubated with primary antibody solution (overnight at 4° C.). After washing, the peptide arrays were incubated with a 1/1000 dilution of an antibody peroxidase conjugate (SBA, cat. nr. 2010-05) for one hour at 25° C. After washing, the peroxidase substrate 2,2'-azino-di-3-ethylbenzthiazoline sulfonate (ABTS) and 2 µl/ml of 3% $H_2O_2$ were added. After one hour, the color development was measured. The color development was quantified with a charge coupled device (CCD) camera and an image processing system.

Alternatively, to reconstruct epitopes of the target molecule, libraries of looped and combinatorial peptides were synthesized. An amino functionalized polypropylene support was obtained by grafting with a proprietary hydrophilic polymer formulation, followed by reaction with t-butyloxy-carbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using Pepscan's proprietary Chemically Linked Peptides on Scaffolds (CLIPS) technology. CLIPS technology allows to structure peptides into single loops and double-loops. CLIPS templates are coupled to cysteine residues. The side-chains of multiple cysteines in the peptides are coupled to one or two CLIPS templates. For example, a 0.5 mM solution of the mP2 CLIPS (2,6-bis(bromomethyl)pyridine) is dissolved in ammonium bicarbonate (20 mM, pH 7.8)/acetonitrile (1:3 (v/v)). This solution is added onto the peptide arrays. The CLIPS template will bind to side-chains of two cysteines as present in the solid-phase bound peptides of the peptide-arrays (455 wells plate with 3 µl wells). The peptide arrays are gently shaken in the solution for 30 to 60 minutes while completely covered in solution. Finally, the peptide arrays are washed extensively with excess of $H_2O$ and sonicated in disrupt-buffer containing 1% SDS/0.1% β-mercaptoethanol in PBS (pH 7.2) at 70° C. for 30 minutes, followed by sonication in $H_2O$ for another 45 minutes. The T3 CLIPS (2,4,6-tris(bromomethyl)pyridine) carrying peptides were made in a similar way but now with three cysteines.

Looped peptides: constrained peptides of length 17. Positions 2-16 are 15-mers derived from the target sequence. Native Cys residues are protected by acetamidomethyl group (ACM). Positions 1 and 17 are Cys that are linked by mP2 CLIPS moieties. Combinatorial peptides (discontinuous mimics): constrained peptides of length 33. Positions 2-16 and 18-32 are 15-mer peptides derived from the target sequence with native Cys residues protected by ACM. Positions 1, 17 and 33 are Cys that are linked by T3 CLIPS moieties.

The binding of antibody to each of the synthesized peptides is tested in a PEPSCAN-based ELISA. The peptide arrays are incubated with test antibody solution composed of the experimentally optimized concentration of the test antibody and blocking solution (for example 4% horse serum, 5% ovalbumin (w/v) in PBS/1% Tween80). The peptide arrays are incubated with the test antibody solution overnight at 4° C. After extensive washing with washing buffer (1×PBS, 0.05% Tween80), the peptide arrays are incubated with a 1/1000 dilution of an appropriate antibody peroxidase conjugate for one hour at 25° C. After washing with the washing buffer, the peroxidase substrate 2,2'-azino-di-3-ethylbenzthiazoline sulfonate (ABTS) and 2 µl/ml of 3% $H_2O_2$ are added. After one hour, the color development is measured. The color development is quantified with a charge coupled device (CCD)—camera and an image processing system.

Alternatively a mass spectrometry method is used to identify conformational epitopes. In order to determine the key residues of conformational epitopes on the TREM1 protein that anti-TREM1 antibodies bind to with high resolution, antibody/antigen complexes are incubated with deuterated cross-linkers and subjected to multi-enzymatic proteolytic cleavage. After enrichment of the cross-linked peptides, the samples are analyzed by high resolution mass spectrometry (nLC-Orbitrap MS) and the data generated is analyzed using XQuest software. Specifically, TREM1 ECD/antibody complexes are generated by mixing equimolar solutions of TREM1 antigen and antibody (4 µM in 5 µl each). One µl of the mixture obtained is mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample is spotted on a MALDI plate (SCOUT 384). After crystallization at room temperature, the plate is introduced in aMALDI mass spectrometer and analyzed immediately. The analysis is repeated in triplicate. Peaks representing monomeric antibody, the antigen, and antibody and antigen/antibody complexes are detected at the predicted molecular weights.

It is then determined whether the epitope in conformational binding competes with unstructured C1q peptides generated by proteolysis. Specifically, to determine if TREM1 ECD/antibody complexes can compete with linear peptides, the TREM1 ECD antigen is digested with immobilized pepsin. 25 µl of the antigen with a concentration of 10 µM are mixed with immobilized pepsin 5 µM and incubate at room temperature for 30 minutes. After the incubation time, the sample are centrifuged and the supernatant is pipetted. The completion of the proteolysis is controlled by High-Mass MALDI mass spectrometry in linear mode. The pepsin proteolysis is optimized in order to obtain a large amount of peptide in the 1000-3500 Da range. Next, 5 µl of the antigen peptides generated by proteolysis are mixed with 5 µl of antibodies (8 µM) and incubated at 37° C. for 6 hours. After incubation of the antibodies with the TREM1 antigen peptides, 5 µl of the mixture is mixed with 5 µl of the intact TREM1 antigen (4 µM) so the final mix contains 2 µM/2 µM/2.5 µM of TREM1/antibody/TREM1 antigen peptides. The MALDI ToF MS analysis is performed using CovalX's HM3 interaction module with a standard nitrogen laser and focusing on different mass ranges from 0 to 2000 kDa. For the analysis, the following parameters are applied for the mass spectrometer: Linear and Positive mode; Ion Source 1: 20 kV; Ion Source 2: 17 kV; Pulse Ion Extraction: 400 ns; for HM3: Gain Voltage: 3.14 kV; Gain Voltage: 3.14 kV; Acceleration Voltage: 20 kV. To calibrate the instrument, an external calibration with clusters of Insulin, BSA and IgG is being applied. For each sample, 3 spots are analyzed (300 laser shots per spots). Presented spectrum corresponds to the sum of 300 laser shots. The MS data are analyzed using the Complex Tracker analysis software version 2.0 (CovalX Inc). To identify the conformational epitopes for TREM1 binding to antibodies, using chemical cross-linking, High-Mass MALDI mass spectrometry and nLCOrbitrap mass spectrometry the interaction interface between the antigen and antibodies the following procedure is followed. 5 µl of the sample antigen (concentration 4 µM) is mixed with 5 µl of the sample antibody (Concentration 4 µM) in order to obtain an antibody/antigen mix with final concentration 2 µM/2 µM. The mixture is incubated at 37° C. for 180 minutes. In a first step, 1 mg of DiSuccinimidylSuberate H12 (DSS-H12) cross-linker is mixed with 1 mg of DiSuccinimidylSuberate D12 (DSS-D12) cross-linker. The 2 mg prepared were mixed with 1 ml of DMF in order to obtain a 2 mg/ml solution of DSS H12/D12. 10 µl of the antibody/antigen mix prepared previously were mixed with 1 µl of the solution of cross-linker d0/d12 prepared (2 mg/ml). The solution is incubated 180 minutes at room temperature in order to achieve the cross-linking reaction.

In order to facilitate the proteolysis, it is necessary to reduce the disulfide bonds present in the protein. The cross-linked samples are mixed with 20 μl of ammonium bicarbonate (25 mM, pH 8.3). After mixing 2.5 μl of DTT (500 mM) is added to the solution. The mixture is then incubated 1 hour at 55° C. After incubation, 2.5 μl of iodioacetamide (1 M) is added before 1 hour of incubation at room temperature in a dark room. After incubation, the solution is diluted ⅕ by adding 120 μl of the buffer used for the proteolysis. 145 μl of the reduced/alkyled cross-linked sample is mixed with 2 μl of trypsin (Sigma, T6567). The proteolytic mixture is incubated overnight at 37° C. For a-chymotrypsin proteolysis, the buffer of proteolysis is Tris-HCL 100 mM, CaCl2 10 mM, pH7.8. The 145 μl of the reduced/alkyled cross-linked complex is mixed with 2 μl of α-chymotrypsin 200 μM and incubated overnight at 30° C. For this analysis, an nLC in combination with Orbitrap mass spectrometry is used. The cross-linker peptides are analyzed using Xquest version 2.0 and stavrox software. The peptides and cross-linked amino acids are then identified.

Results

The TREM1 binding region was determined for 9 anti-TREM1 antibodies. The binding regions within human TREM1 are listed in Table 7.

TABLE 7

TREM1 antibody binding region to human TREM1

| Antibody | Human TREM1 binding region | Amino acid region of SEQ ID NO: 1 |
|---|---|---|
| T1-53 | $^{45}$LEKFASSQKA$^{54}$, | 45-54, 70-79, |
| T1-63 | $^{70}$TERPSKNSHP$^{79}$, | 89-97, and |
|  | $^{89}$DYHDHGLLR$^{97}$, and | 119-125 |
|  | $^{119}$PKEPHML$^{125}$ |  |
| T1-34 | $^{83}$GRIILEDY$^{90}$ and | 83-90 and |
| T1-39 | $^{191}$NLTNVTDIIRV$^{201}$ | 191-201 |
| T1-62 |  |  |
| T1-71 |  |  |
| T1-76 |  |  |
| T1-10 | $^{45}$LEKFASSQKA$^{54}$ and | 45-54 and |
| T1-61 | $^{116}$YQPPKEPHML$^{125}$ | 116-125 |

As indicated in Table 7, antibodies T1-53 and T1-63 showed robust binding for several peptides within the extracellular IgV domain of human TREM1. As indicated in Table 6, the peptides recognized by antibodies T1-53 and T1-63 correspond to amino acid residues 45-54, 70-79, 89-97, and 119-125 of SEQ ID NO: 1 and have the amino acid sequences of: $^{45}$LEKFASSQKA$^{54}$, $^{70}$TERPSKNSHP$^{79}$, $^{89}$DYHDHGLLR$^{97}$, and $^{119}$PKEPHML$^{125}$.

As indicated in Table 7, antibodies T1-34, -39, -62, -71, and -76 showed robust binding exclusively for two peptides within the extracellular IgV domain of human TREM1. As indicated in Table 7, the peptides recognized by antibody T1-34, -39, -62, -71, and -76 corresponds to amino acid residues 83-90 and 191-201 of SEQ ID NO: 1 and have the amino acid sequences of: $^{83}$GRIILEDY$^{90}$ and $^{191}$NLTNVTDIIRV$^{201}$.

As indicated in Table 7, antibodies T1-10 and T1-61 showed robust binding exclusively for two peptides within the extracellular IgV domain of human TREM1. As indicated in Table 7, the human TREM1 peptides recognized by antibodies T1-10 and T1-61 correspond to amino acid residues 45-54 and 116-125 of SEQ ID NO: 1 and has the amino acid sequence of: $^{45}$LEKFASSQKA$^{54}$ and $^{116}$YQPPKEPHML$^{125}$.

FIG. 5 maps peptides bound by anti-TREM1 antibodies on a crystal structure of human TREM1 (pdb 1Q8M). The surface area highlighted in black represents the predicted epitope for the indicated antibody. For comparison, FIG. 5A maps the epitope for MAB0170, a positive control antibody for human TREM1. The epitope for MAB0170, defined through hydrogen-deuterium exchange as opposed to binding to peptide arrays, correspond to amino acid residues 38-48 of SEQ ID NO: 1 and has the amino acid sequence $^{38}$DVKCDYTLEKF$^{48}$. FIG. 5B maps the epitopes for T1-53 and T1-63 with the amino acid regions 45-54, 70-79, 89-97, and 119-125 highlighted in black. FIG. 5C maps the epitopes for T1-10 and T1-61 with the amino acid regions 45-54 and 116-125 highlighted in black. FIG. 5D maps a single epitope for T1-34, -39, -62, -71, and -76 with the amino acid regions 83-90 highlighted in black. The second epitope identified for this set of antibodies correspond to amino acid residues 191-201, which lie on a membrane-proximal region of the protein not resolved by the crystal structure.

Example 3: TREM1 Antibodies Induce Syk Phosphorylation

Spleen tyrosine kinase (Syk) is an intracellular signaling molecule that functions downstream of TREM1 by phosphorylating several substrates, thereby facilitating the formation of a signaling complex leading to cellular activation and inflammatory processes. The ability of agonist TREM1 antibodies to induce Syk activation was determined by culturing mouse macrophages and measuring the phosphorylation state of Syk protein in cell extracts.

Bone marrow-derived macrophages (BMDM) from wild-type (WT) mice, from TREM1 knockout (KO) mice, and from mice that lack expression of functional Fc receptor common gamma chain gene (FcgR KO; REF: Takai T 1994. Cell 76(3):519-29) were starved for 4 hours in 1% serum RPMI and then removed from tissue culture dishes with PBS-EDTA, washed with PBS, and counted. The cells were coated with full-length TREM1 antibodies or with control antibodies (10A9 or huIgG1 isotype control) for 15 minutes on ice. After washing with cold PBS, cells were incubated at 37° C. for the indicated period of time in the presence of goat anti-human IgG. After stimulation, cells were lysed with lysis buffer (1% v/v NP-40%, 50 Mm Tris-HCl (pH 8.0), 150 mM NaCl, 1 mM EDTA, 1.5 mM MgCl$_2$, 10% glycerol, plus protease and phosphatase inhibitors) followed by centrifugation at 16,000 g for 10 min at 4° C. to remove insoluble materials. Lysates were then immunoprecipitated with anti-Syk antibody (N-19 for BMDM or 4D10 for human DCs, Santa Cruz Biotechnology). Precipitated proteins were fractionated by SDS-PAGE, transferred to PVDF membranes and probed with anti-phosphotyrosine antibody (4G10, Millipore). To confirm that all substrates were adequately immunoprecipitated, immunoblots were reprobed with anti-Syk antibody (Abcam, for BMDM) or anti-Syk (Novus Biological, for human DCs). Visualization was performed with the enhanced chemiluminescence (ECL) system (GE healthcare), as described (e.g., Peng et al., (2010) Sci Signal., 3(122): ra38).

Example 4: TREM1 Antibodies Induce Syk Phosphorylation when Clustered by Adjacent Cells that Expresses Fc Gamma Receptors Activation of spleen tyrosine kinase (Syk) is facilitated by crosslinking two or more TREM1 receptors with antibodies, thereby facilitating the formation of a signaling complex leading to cellular activation and inflammatory processes. In vivo cross-linking is mediated by adjacent cells that express high affinity Fc receptors (FcR), such as B cells and other leukocytes (White A L Cancer Immunol Immunother (2013) 62:941-948; Wilson N S 2011, Cancer Cell 19, 101-113; Bartholomaeus P J Immunol 2014; 192:2091-2098).

The ability of Fc receptors to induce activation of Syk through antibody clustering was determined by culturing mouse macrophages in the presence of cells expressing Fc receptors and measuring the phosphorylation state of Syk protein in cell extracts. Bone marrow-derived macrophages (BMDM) from wild-type (WT) mice and from TREM1 knockout (KO) mice were starved for 4 hours in 1% serum RPMI and then removed from tissue culture dishes with PBS-EDTA, washed with PBS, and counted. The cells were coated with full-length TREM1 antibodies, or control antibodies (10A9 or huIgG1 isotype control) for 15 minutes on ice. After washing with cold PBS, cells were incubated for 5 minutes at 37° C. with glutaraldehyde-fixed cells that express Fc receptors and that were previously prepared as follows. Briefly, Fc receptors expressing cells were either B cells isolated from mouse spleens using MACS microbeads (CD19+ B-cell isolation kit Miltenyi Biotec) according to the manufacturer's protocol or alternatively the P815 cell line that overexpresses FcR2b and FcR3. $2 \times 10^6$ cells/ml cells were fixed with 0.05% glutaraldehyde for 1 minute at room temperature, the reaction was stopped with 1 μM Glycine and cells were then washed extensively with PBS. After stimulation, cells were lysed with lysis buffer (1% v/v NP-40%, 50 Mm Tris-HCl (pH 8.0), 150 mM NaCl, 1 mM EDTA, 1.5 mM $MgCl_2$, 10% glycerol, plus protease and phosphatase inhibitors) followed by centrifugation at 16,000 g for 10 min at 4° C. to remove insoluble materials. Lysates were then immunoprecipitated with anti-Syk antibody (N-19 for BMDM or 4D10 for human DCs, Santa Cruz Biotechnology). Precipitated proteins were fractionated by SDS-PAGE, transferred to PVDF membranes and probed with anti-phosphotyrosine antibody (4G10, Millipore). To confirm that all substrates were adequately immunoprecipitated, immunoblots were reprobed with anti-Syk antibody (Abcam, for BMDM) or anti-Syk (Novus Biological, for human DCs). Visualization was performed with the enhanced chemiluminescence (ECL) system (GE healthcare), as described (e.g., Peng et al., (2010) Sci Signal., 3(122): ra38).

Example 5: TREM1 Antibodies Block Ligand Binding

Figures 6A, 6B:
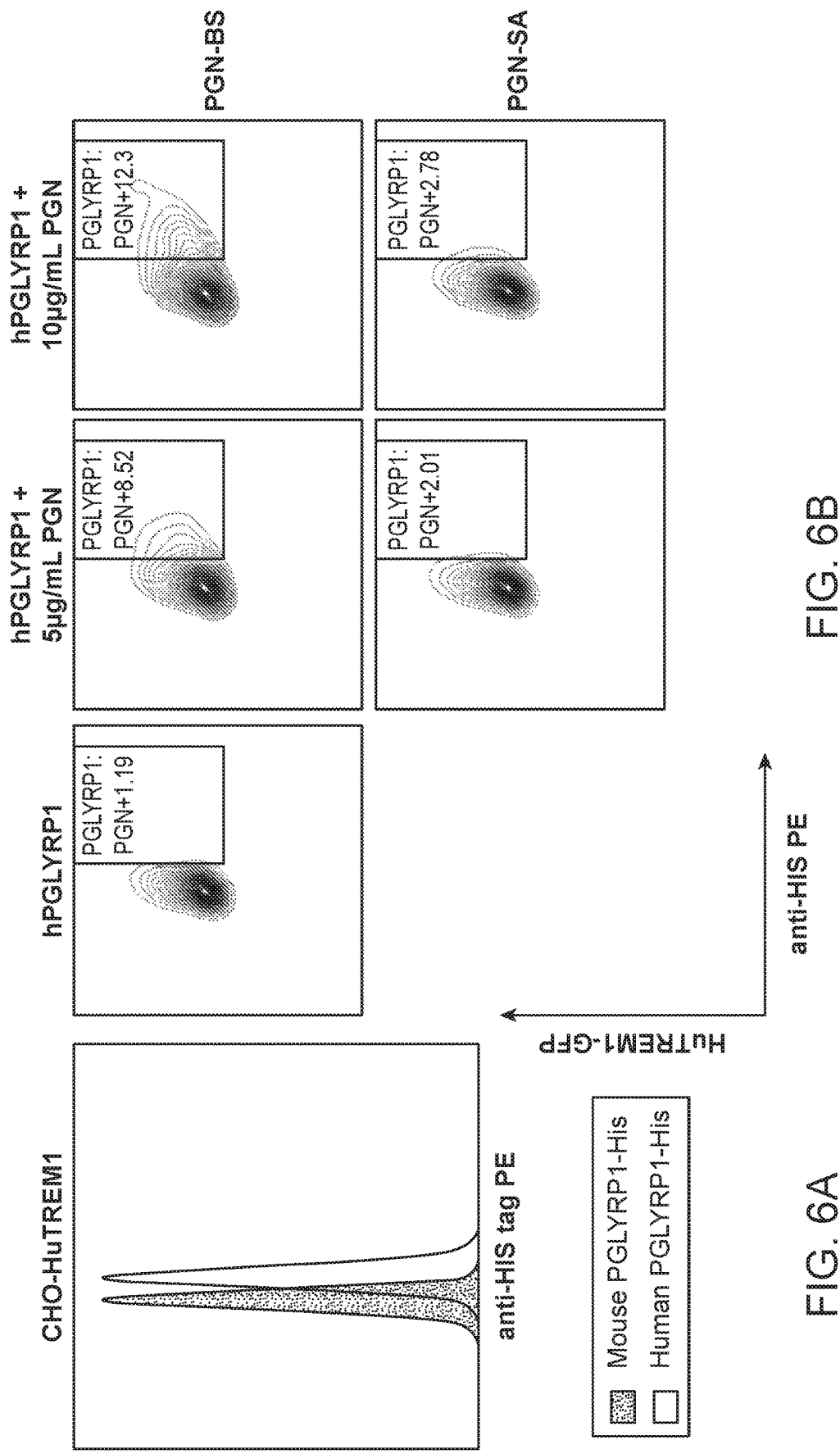
FIG. 6A shows FACS histograms of recombinant, His-tagged human PGLYRP1 binding to CHO cells expressing human TREM1 (CHO-huTREM1). PGLYRP1 was detected with PE-labeled anti-HIS tag secondary antibody. As a negative control (shaded histogram), mouse PGLYRP1 was added to CHO-huTREM1 cells.
FIG. 6B shows contour plots of human PGLYRP1 complexed with peptidoglycan isolated from Bacillus subtilis (PGN-BS) or Staphylococcus aureus (PGN-SA) binding to CHO-huTREM1. Gates show percentage of huPGLYRP1-high CHO-huTREM1 population indicating increased avidity for receptor binding in the context of ligand complexes with PGN-BS. Ligand complexes with PGN-SA do not increase the percentage of huPGLYRP1-high CHO-huTREM1 population.
Figure 6C:
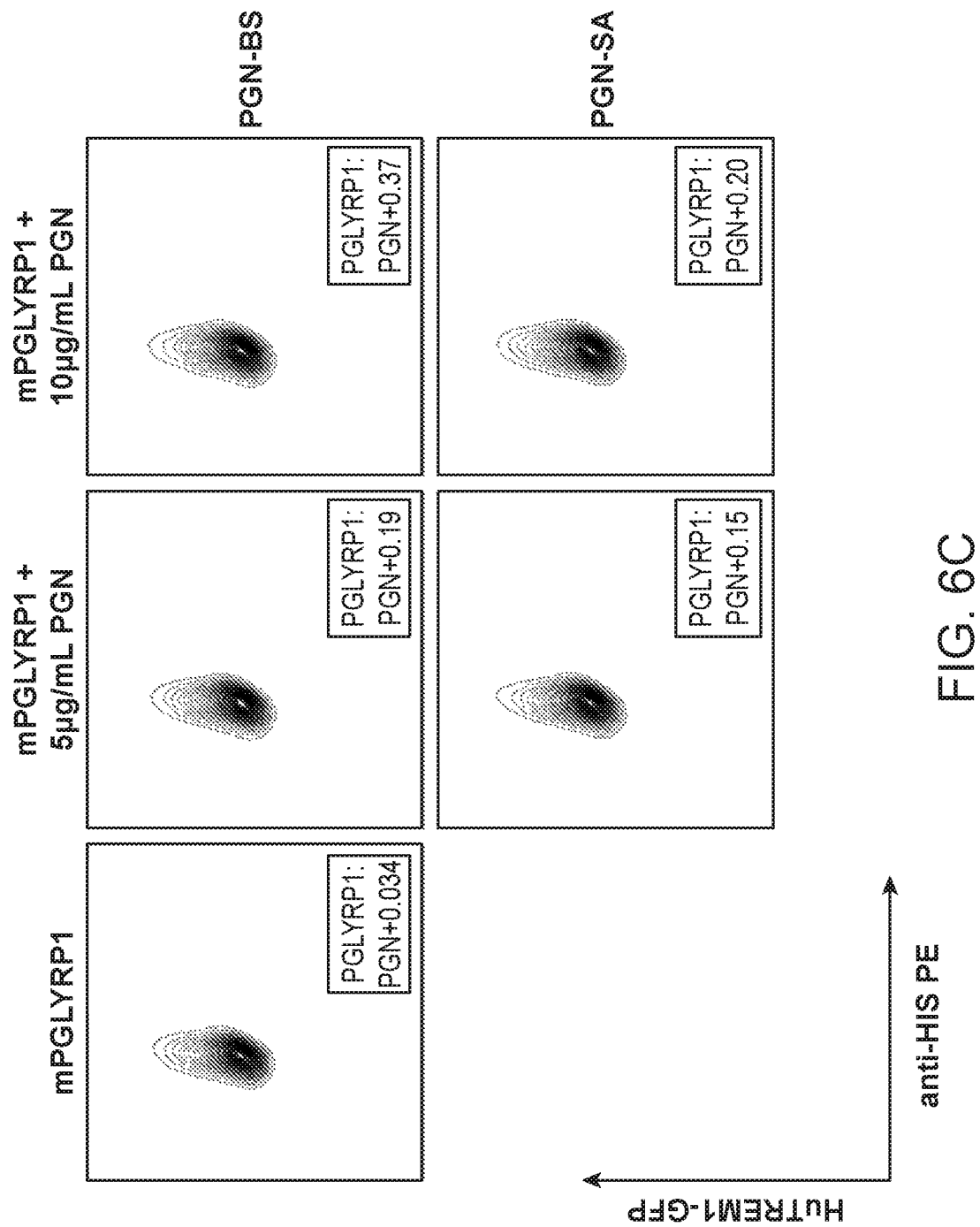
FIG. 6C shows contour plots of mouse PGLYRP1 complexed with peptidoglycan isolated from Bacillus subtilis (PGN-BS) or Staphylococcus aureus (PGN-SA) binding to CHO-huTREM1. Gates show percentage of mPGLYRP1-high CHO-huTREM1 population.

Published reports demonstrate that neutrophils exposed to Toll-like receptor (TLR) ligands reveal an endogenous ligand for TREM1 on their cell surface. For example, peritoneal neutrophils drawn from mice suffering from cecal ligation and puncture-induced peritonitis, but not neutrophils from naïve mice, bind to soluble fragments of recombinant mouse TREM1. Similarly, human neutrophils stimulated with TLR ligands activate reporter cells overexpressing human TREM1. Recently, human peptidoglycan recognition protein-1 (hPGLYRP1) was identified as a TREM1 ligand from human neutrophils stimulated with peptidoglycan, a major structural component of the cell wall of Gram-positive bacteria. Human PGLYRP1 belongs to a family of four conserved peptidoglycan-binding proteins that function as secreted pattern recognition receptors involved in the innate immune response against bacterial infection. Among the PGLYRP family, PGLYRP1 is uniquely expressed in neutrophil granules. To verify the interaction between human TREM1 and hPGLYRP1, CHO cells expressing human TREM1 (CHO-huTREM1) were incubated with either 180 nM of recombinant, His-tagged human PGLYRP1 or mouse PGLYRP1 on ice for 30 minutes. Subsequently, cells were washed and stained with a PE-labeled anti-HIS tag secondary monoclonal antibody on ice for 15 minutes. Ligand binding was assessed by flow cytometry. As shown in FIG. 6A, CHO-huTREM1 cells only stained with the secondary antibody in the presence of hPGLYRP1 demonstrating that human, but not mouse, PGLYRP1 binds human TREM1. Despite the high concentration of ligand, the shift in fluorescence intensity was narrow suggesting a low affinity interaction between ligand and receptor. To increase the avidity of this interaction, soluble TREM1 ligand complexes were formed by mixing 180 nM of hPGLYRP1 with increasing concentrations of peptidoglycan derived from either *Bacillus subtilis* (PGN-BS) or *Staphylococcus aureus* (PGN-SA). As shown in FIG. 6B, only soluble complexes consisting of hPGLYRP1 and PGN-BS, but not hPGLYRP1 and PGN-SA, increased the shift in fluorescence intensity in CHO-huTREM1 stained with secondary antibody. Importantly, FIG. 6C shows that neither PGN-BS nor PGN-SA augmented binding of mouse PGLYRP1 to human TREM1 expressed on CHO cells. Thus, soluble TREM1 ligand complexes comprised of recombinant hPGLYRP1 and PGN-BS form higher-order structures capable of avid binding to human TREM1.

Figure 6D:
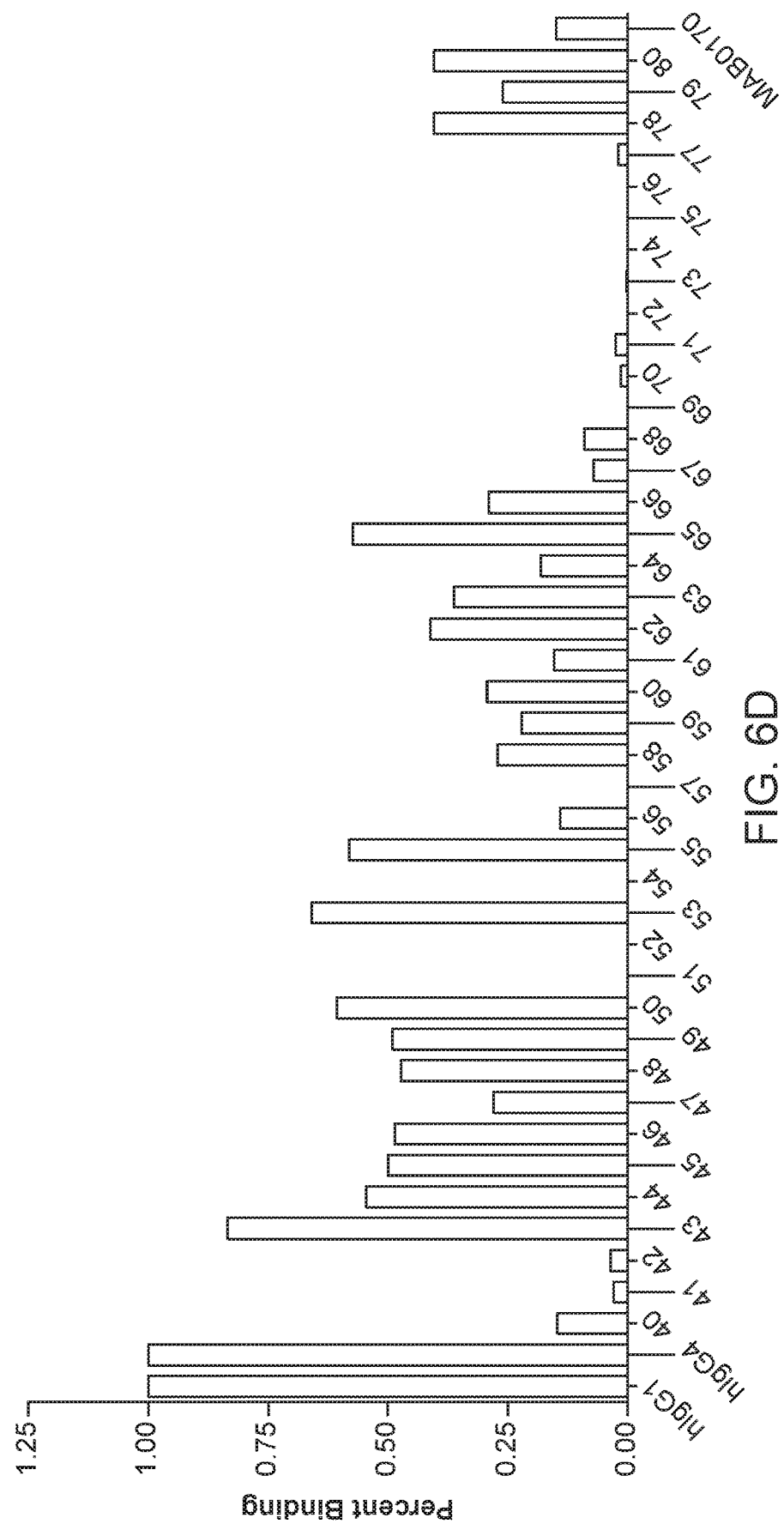
FIG. 6D shows blockade of soluble TREM1 ligand complex binding to CHO-huTREM1 cells by anti-TREM1 antibodies T1-40 through T1-80. TREM1 ligand consists of 50 nM of recombinant His-tagged human PGLYRP1 complexed with 10 µg/mL PGN-B S. TREM1 ligand binding to CHO-huTREM1 cells was detected with anti-HIS tag PE secondary antibody. Antibodies huIgG1 and huIgG4 represent the isotype negative controls, and Mab0170 represents positive control. Results are representative of the entire set of TREM1 antibodies available and are depicted as percent of ligand binding by dividing MFI value of samples treated with anti-TREM1 antibodies by the MFI value of samples treated with isotype controls.

The ability of TREM1 antibodies to block ligand binding to human TREM1 was determined by incubating CHO-huTREM1 cells with 10 μg/mL of soluble, full-length anti-TREM1 antibodies or isotype control for 30 minutes on ice. Subsequently, cells were washed and incubated on ice for 30 minutes with soluble TREM1 ligand complex consisting of 50 nM of recombinant, His-tagged hPGLYRP1 and 10 μg/mL of PGN-BS. Cells were then washed and stained with a PE-labeled anti-HIS tag secondary monoclonal antibody on ice for 15 minutes. Ligand binding was assessed by flow cytometry. As shown in FIG. 6D, all TREM1 antibodies at least partially reduced ligand binding to TREM1-expressing cells. However, as a general observation anti-TREM1 antibodies from the Bin 1 category blocked ligand binding to a greater extent than anti-TREM1 antibodies from the Bin 2 category. For example, the anti-TREM1 antibodies from the Bin 1 category, T1-41, -42, -51, -52, -56, -57, -67, -68, -69, -70, -71, -72, -73, -74, -75, -76, and -77, blocked ligand binding ≥85%. In contrast, the anti-TREM1 antibodies from the Bin 2 category, T1-40, -44, -45, -46, -47, -48, -49, -58, -59, -60, -61, -62, -63, -64, -65, -66, -78, and -79, blocked ligand binding ≥50%.

Example 6: Plate-Bound TREM1 Antibodies Induce TREM1-Dependent Genes

Figure 7:
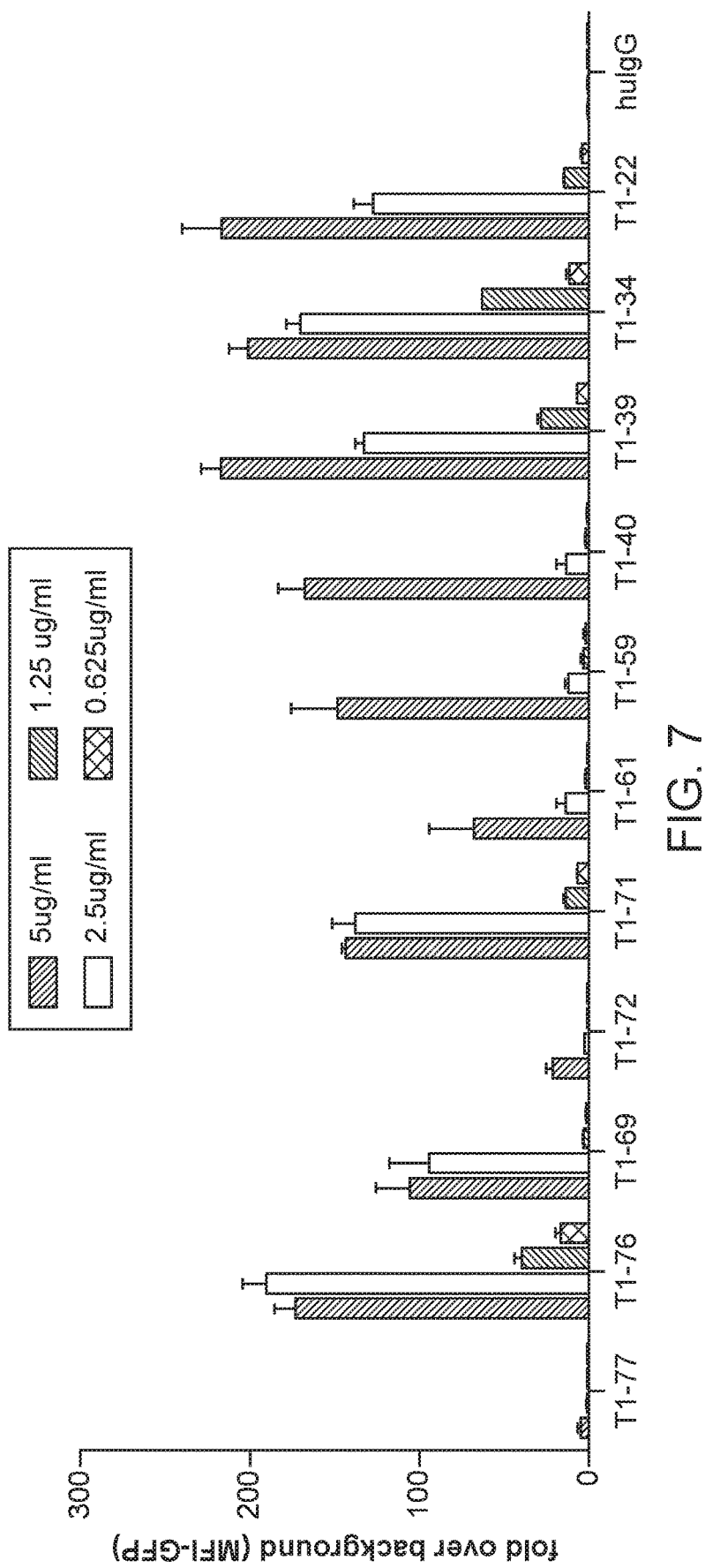
FIG. 7 shows induction of human TREM1-dependent GFP reporter in a cell-based assay. Cells were either treated with decreasing concentration of plate-bound, full-length human IgG1 isotype control or anti-TREM1 antibodies T1-77, -76, -69, -72, -71, -61, -59, -40, -39, -34, and -22. Results are expressed as fold over background. The background level is set to 1 on y-axis. Antibody huIgG1 is the isotype negative control.

The ability of plate-bound full-length anti-TREM1 antibodies to activate mouse or human TREM1-dependent genes was evaluated using a luciferase or GFP reporter gene under the control of an NFAT (nuclear factor of activated T-cells) promoter. The cell line BW5147.G.1.4 (ATCC® TIB48™), derived from mouse thymus lymphoma T lymphocytes, was infected with human or mouse TREM1 and DAP12, and with Cignal Lenti NFAT-luciferase virus (Qiagen). Alternatively the BW5147.G.1.4 cell line was infected with a human TREM1/CD3 zeta chain fusion protein, and with Cignal Lenti NFAT-GFP virus (Qiagen). PMA (0.05 ug/ml) and ionomycin (0.25 uM) were added to reporter cells as a positive control for NFAT signaling. Anti-TREM1 and isotype control antibodies were dissolved in PBS, plated on tissue culture plates at a concentration range of 0.625-10 ug/ml and incubated overnight at 4° C. to allow the antibodies to adsorb to the plate. After washing the plates, cells were seeded on plate-bound antibodies and incubated overnight at 37° C. GFP induction was analyzed by flow cytometry. Reporter cells do not display tonic TREM1-dependent signaling compared to the parental reporter cells (lacking TREM1-expression) in the absence of exogenous stimulation indicating the absence of an endogenous ligand or spontaneous receptor aggregation. As shown in FIG. 7A, anti-TREM1 antibodies T1-76, -69, -72, -71, -61, -59, -40, -39, -34, and -22 increased GFP expression in a dose-dependent manner in reporter cells expressing human TREM1, as compared to the isotype control (huIgG1), indicating that the antibodies were able to induce TREM1-dependent gene transcription. Additionally, certain anti-TREM1 antibodies, T1-77 and -72 for example, did not induce a significant amount of GFP expression in a plate-bound format.

Example 7: Soluble TREM1 Antibodies Induce TREM1-Dependent Fenes

The ability of soluble full-length anti-TREM1 antibodies to activate mouse or human TREM1-dependent genes was evaluated using a luciferase or GFP reporter gene under the control of an NFAT (nuclear factor of activated T-cells) promoter. The cell line BW5147.G.1.4 (ATCC® TIB48™), derived from mouse thymus lymphoma T lymphocytes, was infected with human or mouse TREM1 and DAP12, and with Cignal Lenti NFAT-luciferase virus (Qiagen). Alternatively the BW5147.G.1.4 cell line was infected with a human TREM1/CD3 zeta chain fusion protein, and with Cignal Lenti NFAT-GFP virus (Qiagen). To test NFAT-dependent GFP induction, these reporter cells were treated with PMA (0.05 ug/ml) and ionomycin (0.25 uM). To test TREM1 activation, reporter cells were incubated together with soluble anti-TREM1 or isotype control antibodies overnight at 37° C. and GFP induction was analyzed by flow cytometry. The reporter cells do not display tonic TREM1-dependent signaling compared to the parental reporter cells (lacking TREM1-expression) in the absence of exogenous stimulation indicating the absence of an endogenous ligand or spontaneous receptor aggregation.

As shown in FIG. 8A, soluble full-length anti-TREM1 antibodies T1-77, -78, -12, -51, -16, and -22 weakly increased GFP expression in reporter cells expressing human TREM1, whereas T1-52 and -62 increased GFP expression -3-fold, as compared to the isotype control (huIgG1), indicating that the antibodies are agonist able to induce TREM1-dependent gene transcription to varying degrees in solution. In contrast, soluble, full-length anti-TREM1 antibodies T1-79, -80, -40, -63, and -39 did not increase GFP expression in cells expressing human TREM1, as compared to the isotype control. The dotted line in FIG. 8A indicates the levels of TREM1 activity without stimulation.

As shown in FIG. 8B, anti-TREM1 antibodies T1-67, -70, -71, -72, -73, -74, -75, and -76 increased GFP expression ≥3-fold in cells expressing human TREM1, as compared to the isotype control (huIgG1), indicating that the antibodies are strong agonist antibodies that are able to induce TREM1-dependent gene transcription. In contrast, soluble full-length anti-TREM1 antibodies, such as T1-65 and -66, did not increase GFP expression in cells expressing human TREM1, as compared to the isotype control. The dotted line in FIG. 8B indicates the levels of TREM1 activity without stimulation.

Figure 8C:
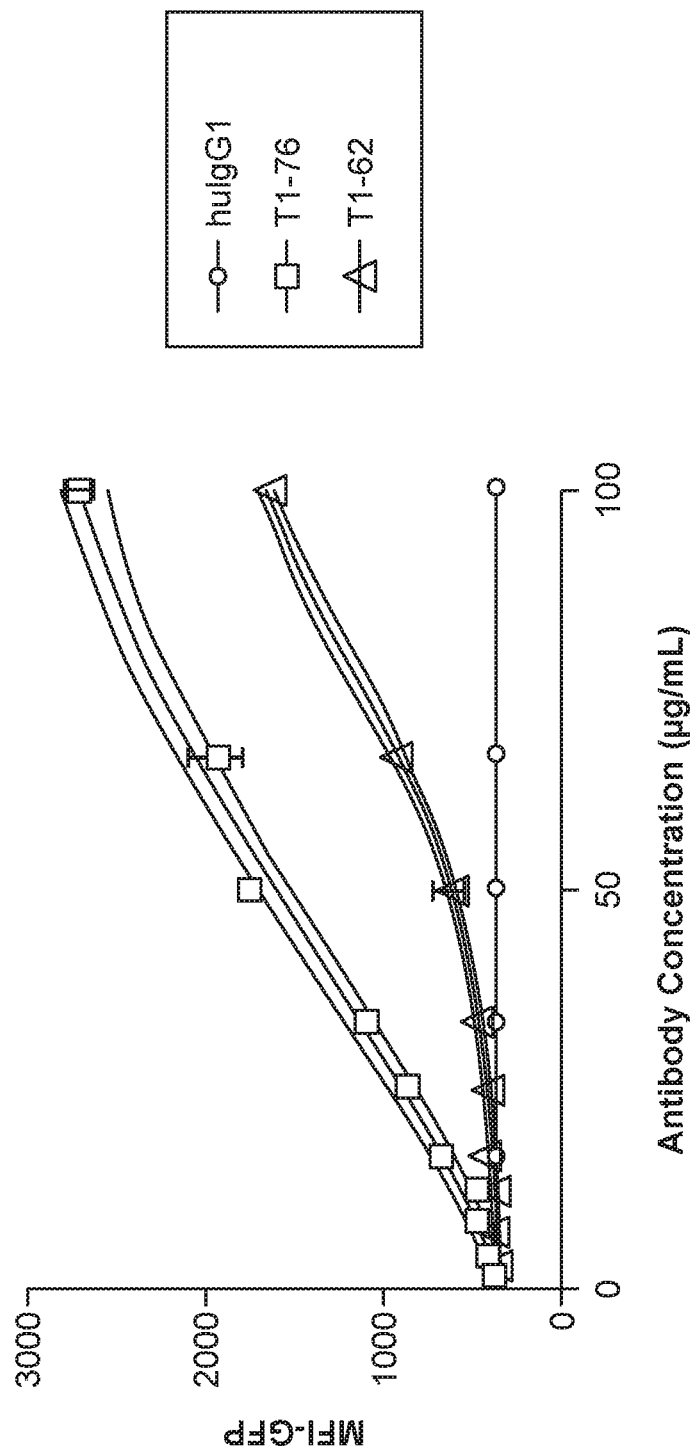
FIG. 8C shows a dose-response curve of GFP expression induced by increasing concentrations of soluble full-length antibodies, T1-62 and T1-76, or the isotype control in a cell-based assay.

FIG. 8C shows a dose response curve of GFP expression induced by weak or strong agonistic TREM1 antibodies. Increasing concentrations of soluble full-length anti-TREM1 antibodies, T1-62 and -76, were added to reporter cells overnight at 37° C. Flow cytometric analysis of GFP expression demonstrates that the effect on gene expression is dose dependent.

Taken together with the results in FIGS. 7A and 7B, the results in FIG. 8A-8C indicate that soluble agonist anti-TREM1 antibodies can induce gene expression to an extent that is similar to soluble human PGLYRP1 complexed with PGN-BS, which is believed to be a natural ligand of TREM1.

Example 8: Analysis of the Ability of Soluble TREM1 Antibodies to Enhance or Inhibit the Activity of Natural Ligands of TREM1

The ability of soluble full-length anti-TREM1 antibodies to enhance or inhibit the activity of natural ligands of mouse or human TREM1 was evaluated using a luciferase or GFP reporter gene under the control of an NFAT (nuclear factor of activated T-cells) promoter to measure activation of gene expression. The cell line BW5147.G.1.4 (ATCC® TIB48™), derived from mouse thymus lymphoma T lymphocytes, was infected with human or mouse TREM1 and DAP12, and with Cignal Lenti NFAT-luciferase virus (Qiagen). Alternatively the BW5147.G.1.4 cell line was infected with a human TREM1/CD3 zeta chain fusion protein, and with Cignal Lenti NFAT-GFP virus (Qiagen). Cells were incubated overnight at 37° C. with soluble anti-TREM1 or isotype control antibodies together with soluble TREM1 ligand complex consisting of 50 nM of recombinant human PGLYRP1 and 10 µg/mL PGN-BS. GFP expression was analyzed by flow cytometry.

As shown in FIG. 9A, the soluble full-length anti-TREM1 antibodies T1-77, -78, -79, -80, -12, -40, -51, -52, -22, and -39 decreased the magnitude of ligand-mediated human TREM1 activation, as compared to cells treated with TREM1 ligand and the isotype control (huIgG1). Though T1-77, -78, -12, -51, and -22 may weakly activate TREM1 gene expression in these reporter cells in the absence of ligand (as shown previously), their principal effect is to block ligand-induced signaling. In contrast, the soluble full-length antibodies T1-62 and T1-63 enhanced GFP expression in reporter cells when cultured with soluble TREM1 ligand complex. As shown in FIG. 9B, titrating the soluble full-length anti-TREM1 antibodies T1-62 and T1-63 to the lowest concentration of 2 µg/mL enhanced ligand-induced GFP expression in reporter cells even though the antibodies alone did not induce GFP. At higher concentrations, soluble full-length T1-62 potently activated TREM1 irrespective of ligand; whereas at higher concentrations, T1-63 had no significant effect on ligand-induced TREM1 signaling. These results indicate that antibodies T1-62 and T1-63 were able to enhance TREM1-dependent gene transcription induced by recombinant human PGLYRP-1, which is believed to be a natural ligand of TREM1.

Figure 9C:
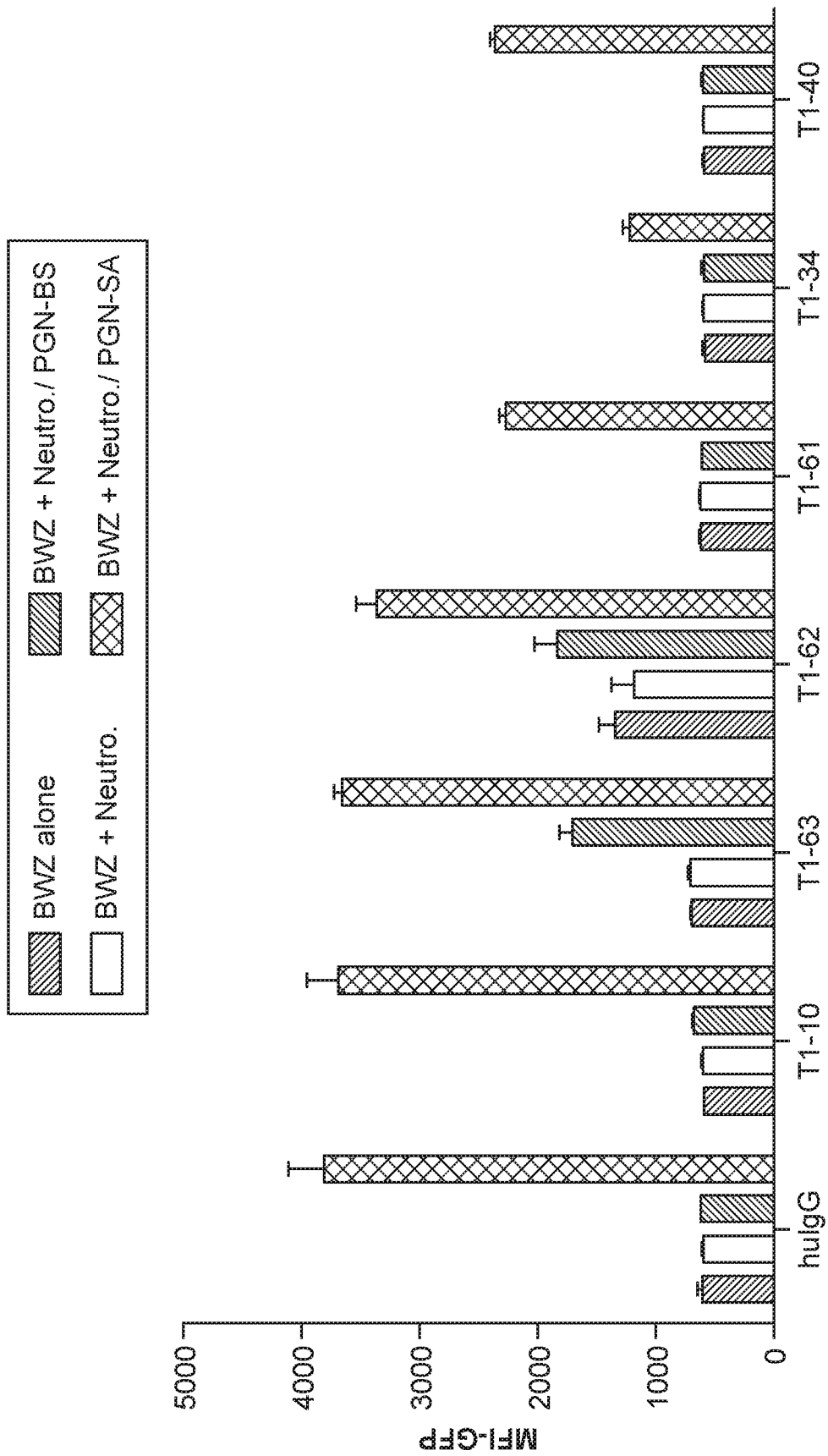
FIG. 9C shows the capacity of agonistic and antagonistic TREM1 antibodies to either enhance or inhibit TREM1 ligand-induced GFP expression in reporter cell-based assays. TREM1 ligand was sourced by stimulating primary human neutrophils with 10 μg/mL of PGN-BS or PGN-SA and subsequently co-culturing BWZ reporter cells in the presence or absence of the anti-TREM1 antibodies T1-10, -63, -62, -61, -34, and -40. 'No Ab' samples represent reporter cells not treated with antibodies, whereas 'huIgG' samples represent reporter cells treated with human IgG1 isotype negative control.
Figure 9D:
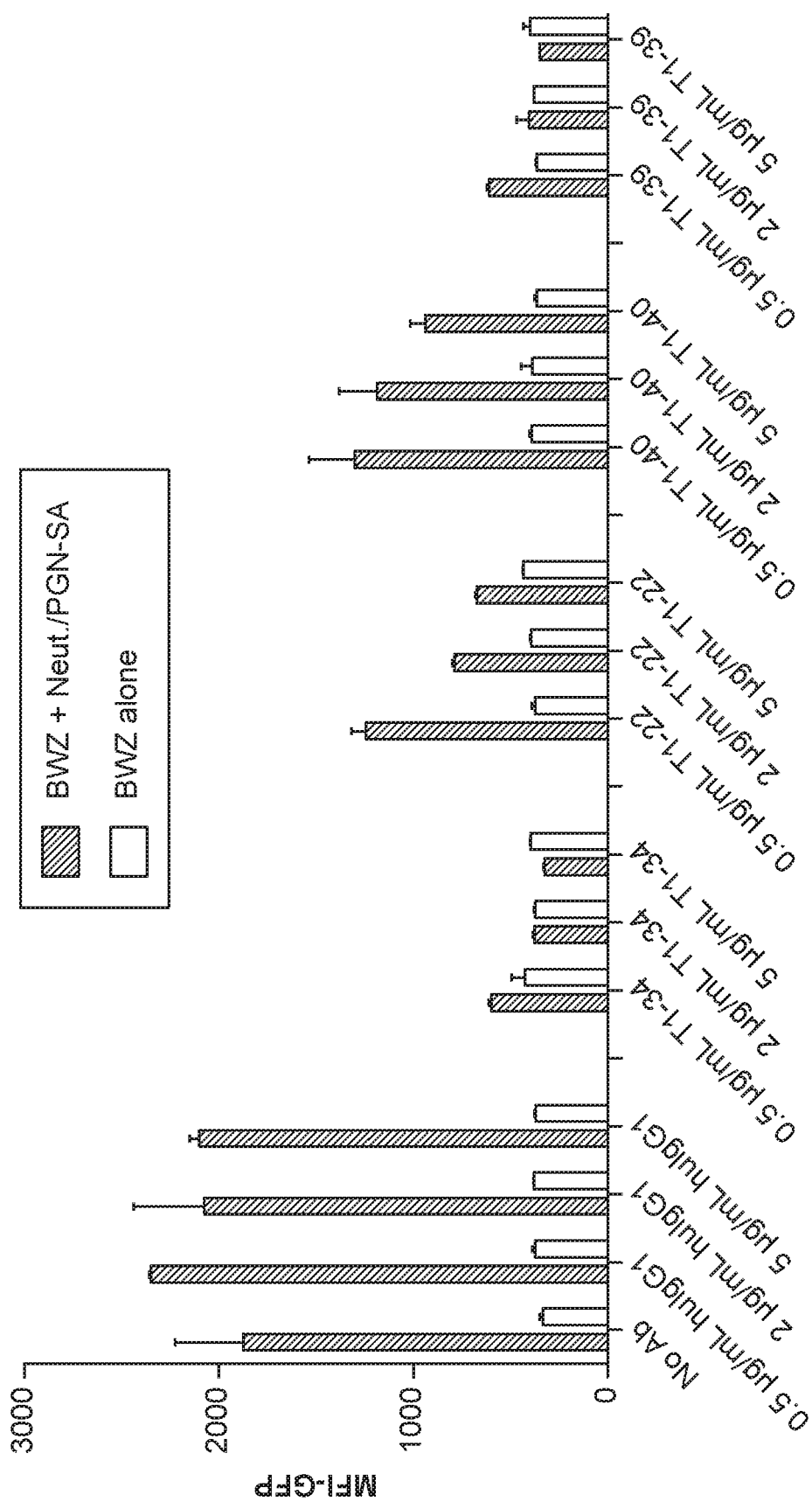
FIG. 9D shows the capacity of antagonistic TREM1 antibodies to inhibit TREM1 ligand-induced GFP expression in reporter cell-based assays. Stimulating primary human neutrophils with 10 μg/mL PGN-SA provided a natural source of TREM1 ligand, which was subsequently co-cultured with BWZ reporter cells with increasing concentrations of the anti-TREM1 antibodies T1-34, -22, -40, and -39. Results are depicted as absolute MFI values.

As shown in FIGS. 9C and 9D, human TREM1:NFAT-GFP reporter cells are also activated by human neutrophils stimulated with PGN-SA, but not untreated neutrophils, demonstrating that activated neutrophils may be a natural source of TREM1 ligand. In FIG. 9C, the soluble full-length anti-TREM1 antibodies T1-34, -61, and -40 blocked ligand-induced GFP expression in reporter cells co-cultured with PGN-SA-treated neutrophils, as compared to reporter cells co-cultured with PGN-SA-treated neutrophils and the isotype control (huIgG1). In contrast, the soluble full-length anti-TREM1 antibodies T1-10, T1-63, and T1-62 had no significant effect on ligand-induced GFP expression on reporter cells co-cultured with PGN-SA-treated neutrophils, as compared to reporter cells co-cultured with PGN-SA-treated neutrophils and the isotype control (huIgG1). As opposed to PGN-SA-treated neutrophils, PGN-BS-treated neutrophils did not induce GFP expression in human TREM1:NFAT-GFP reporter cells. However, in the presence of T1-62 and T1-63, PGN-BS-treated neutrophils activated TREM1, as compared to reporter cells co-cultured with PGN-BS-treated neutrophils and the isotype control (huIgG1). Importantly, T1-63 and -62 did not enhance GFP expression in reporter cells co-cultured with untreated neutrophils indicating that these antibodies (T1-62 and -63) were able to enhance TREM1-dependent gene transcription induced by natural ligands expressed from activated primary neutrophils.

FIG. 9D shows that increasing concentrations of the soluble anti-TREM1 antibodies T1-34, -22, -40, and -39 inhibit ligand-induced GFP expression in reporter cells co-cultured with PGN-SA-treated human primary neutrophils, as compared to reporter cells co-cultured with PGN-SA-treated neutrophils and increasing concentrations of the isotype control (huIgG1). Thus, these antibodies were able to antagonize TREM1-dependent gene transcription induced by natural ligands expressed from activated primary neutrophils.

These results, together with the results in FIG. 7A-B and FIG. 8A-C, demonstrate that certain agonistic anti-TREM1 antibodies identified herein synergize with natural ligands of TREM1, such as recombinant human PGLYRP-1 and ligands expressed on activated neutrophils, to enhance TREM1-dependent gene transcription, as the increased level in TREM1-dependent gene transcription induced by the combination of agonistic anti-TREM1 antibodies and TREM1 ligand was greater than the cumulative level in TREM1-dependent gene transcription that would be expected when the levels induced by the anti-TREM1 antibody alone and TREM1 ligand alone are added together.

Example 9: TREM1 Antibodies Induce Respiratory Burst in Immune Cells

The agonistic function of TREM1 antibodies was evaluated in primary human innate immune cells (e.g., monocytes and neutrophils).

Anti-TREM1 and isotype control antibodies were dissolved in PBS, plated on tissue culture-treated 96-well plates at a concentration of 10 μg/ml and incubated overnight at 4° C. to allow the antibodies to adsorb to the plate. After washing the plates, primary monocytes obtained from peripheral blood mononuclear cells were seeded on plate-bound antibodies. To detect the production of reactive oxygen species (ROS), cells were labeled with 2 μM of the fluorescent dye, CM-H2DCFDA. Following 1 hour of antibody-mediated stimulation in the presence of CM-H2DCFDA at 37° C., the relative fluorescence units in cells were measured at excitation wavelength 495 nm and emission wavelength 530 nm. Specific fluorescence index of stimulated cells was obtained by subtraction of background fluorescence of labeled cells incubated in medium alone and/or with plate-bound isotype control antibody (huIgG1). Plates were read with a BioTek Synergy™ Microplate Reader using GEN5™ 2.04 software.

Figure 10A:
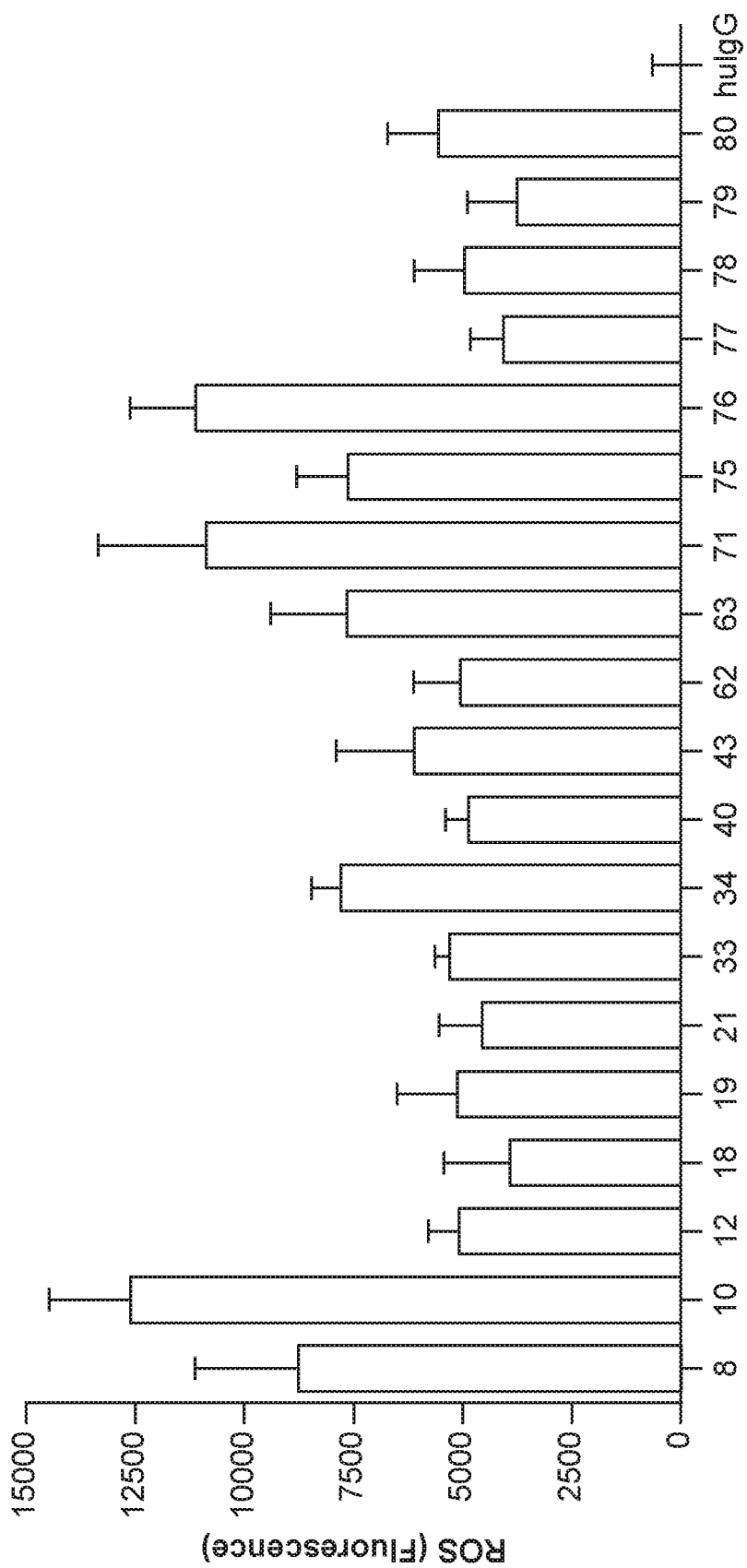
FIG. 10A shows TREM1-mediated respiratory burst from primary human monocytes. Cells were stimulated with plate-bound, full-length human IgG1 isotype control or the anti-TREM1 antibodies T1-8, -10, -12, -18, -19, 21, -33, -34, 40, -43, -62, -63, -71, -75, -76, -77, -78, -79, and -80. Antibody huIgG1 is the isotype negative control.

When primary human monocytes were stimulated with plate-bound, cross-linking anti-TREM1 antibodies, the results in FIG. 10A indicate that all antibodies tested induced respiratory burst to varying degrees, as compared to cells stimulated with the isotype control (huIgG). Furthermore, plate-bound antibodies that poorly activated TREM1 in previous assays performed with human TREM1:NFAT-GFP reporter cells, for example T1-12, -18, -19, -21, and -77, also weakly stimulated ROS production in monocytes. By contrast, the plate-bound antibodies T1-10, -71, and -76 induced the highest levels of ROS in monocytes, which correlate with their ability to induce GFP in reporter cells.

To ascertain if FcγRs expressed on monocytes obscure TREM1-mediated ROS production by plate-bound full-length anti-TREM1 antibodies, we generated Fab fragments of these antibodies and the isotype control. Fab fragments were plated on tissue culture-treated 96-well plates at a concentration of 10 μg/ml and incubated overnight at 4° C. to allow adsorption to the plate. After washing the plates, primary monocytes obtained from peripheral blood mononuclear cells were seeded on plate-bound Fab fragments. To detect the production of reactive oxygen species (ROS), cells were labeled with 2 μM of the fluorescent dye, CM-H2DCFDA. Following 1 hour of Fab-mediated stimulation in the presence of CM-H2DCFDA at 37° C., the relative fluorescence units in cells were measured at excitation wavelength 495 nm and emission wavelength 530 nm. Specific fluorescence index of stimulated cells was obtained by subtraction of background fluorescence of labeled cells incubated in medium alone and/or with plate-bound isotype control Fab. Plates were read with a BioTek Synergy™ Microplate Reader using GEN5™ 2.04 software.

Figure 10B:
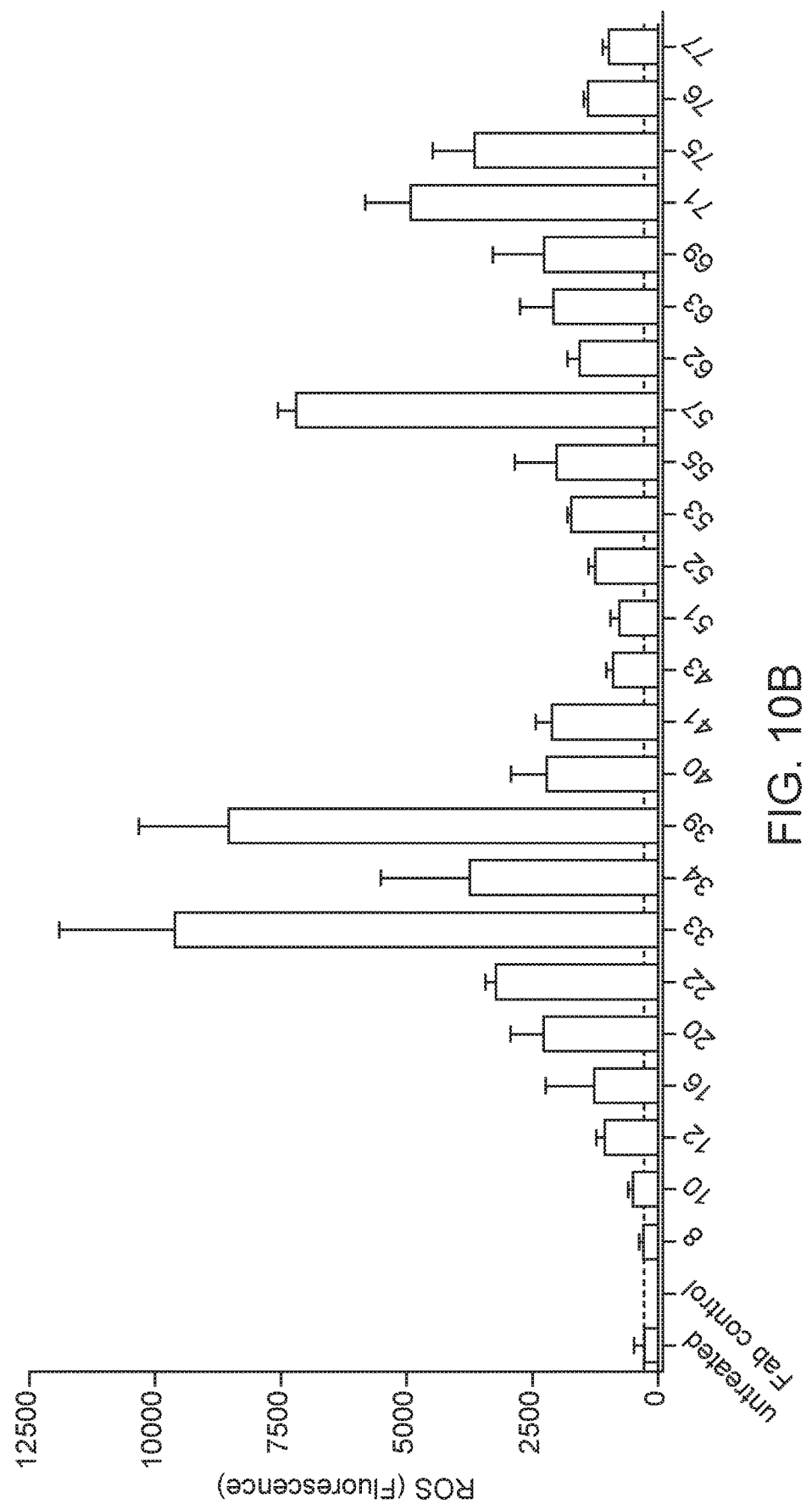
FIG. 10B shows TREM1-mediated respiratory burst from primary human monocytes. Cells were left untreated or stimulated with plate-bound Fab fragments of human IgG1 isotype control or Fab fragments of the anti-TREM1 antibodies T1-8, -10, -12, -16, -20, 22, -33, -34, -39, -40, -41, -43, -51, -52, -53, -55, -57, -62, -63, -69, -71, -75, -76, and -77.

In FIG. 10B, as a general observation, ROS production in monocytes stimulated with plate-bound Fab fragments appear lower than plate-bound full-length antibodies indicating a partial contribution of FcγRs in this assay. Nevertheless, Fab fragments from certain clones, for example T1-33, -39, -57, and -71, still induce robust respiratory burst demonstrating that TREM1 activation alone is sufficient for ROS production. As in the full-length format, Fab fragments of T1-12 and T1-77 also weakly induce ROS in monocytes.

In FIG. 10C, primary human neutrophils were stimulated with 20 μg/mL of soluble full-length anti-TREM1 antibodies or human IgG1 isotype control and labeled with 2 μM CM-H2DCFDA for 1 hour at 37° C. to monitor TREM1-mediated ROS production. The TREM1 antibodies T1-62, -71, -76, and -57 proved highly agonistic in solution consistent with observations of TREM1 activation made with reporter cells. In contrast, the TREM1 antibodies T1-63, -40, -34, -22, -61, -59, and -79 weakly activated TREM1-mediated respiratory burst while in solution, which was also consistent with assays performed with reporter cells. Contrary to their weak agonistic activity with reporter cells, the TREM1 antibodies T1-77, -39, and -51 strongly stimulated ROS production in neutrophils.

Figure 10D:
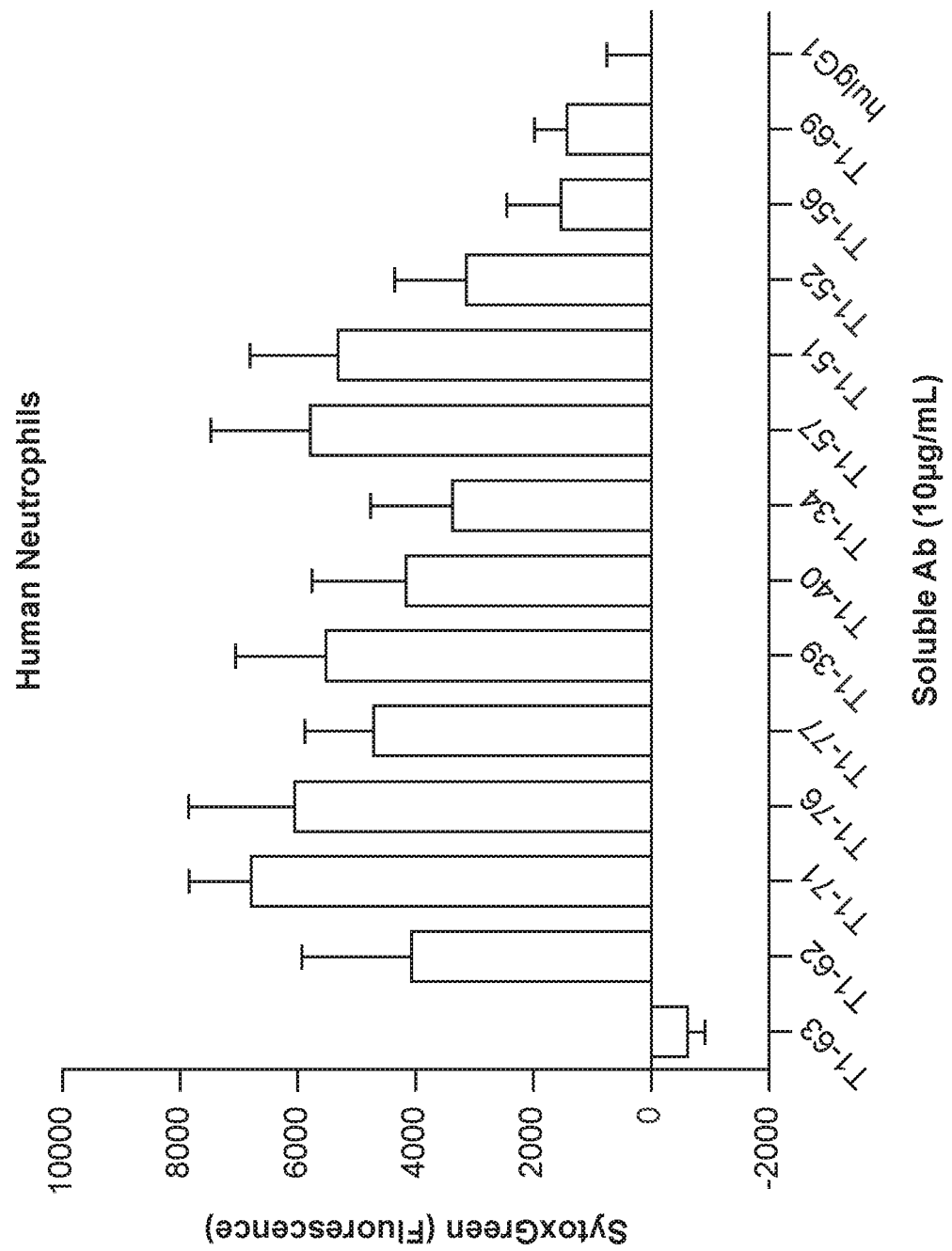
FIG. 10D shows TREM1-mediated release of cell-free, extracellular DNA from primary human neutrophils. Cells were stimulated with soluble, full-length human IgG1 isotype control or the anti-TREM1 antibodies, T1-63, -62, -71, -76, -77, -39, -40, -34, -57, -52, -56, and -69. Extracellular DNA was detected by staining supernatants with 5 μM of the fluorescent indicator, Sytox Green.

Neutrophils undergo a unique form of cell death, termed netosis, characterized by the extrusion of nuclear DNA to the extracellular space to form web-like traps called NETs (neutrophil extracellular traps). Substantial evidence in the literature has established that ROS production from activated neutrophils stimulates NET formation. In FIG. 10D, cells were incubated overnight at 37° C. with 20 μg/mL of soluble full-length anti-TREM1 antibodies or the human IgG1 isotype control. Extracellular DNA released from neutrophils was detected by adding 5 μM of Sytox Green, a membrane-impermeable fluorescent DNA intercalating agent. The relative fluorescence units in supernatants were measured at excitation wavelength 490 nm and emission wavelength 525 nm. Specific fluorescence index of stimulated cells was obtained by subtraction of background fluorescence of labeled cells incubated in medium alone and/or with isotype control. Plates were read with a BioTek Synergy™ Microplate Reader using GEN5™ 2.04 software. The results demonstrate that agonistic TREM1 antibodies capable of inducing ROS production in solution, for example T1-62, -71, -76, -77, -57, and -51, also increase the amount of cell-free, extracellular DNA released from primary human neutrophils. In contrast, neutrophils incubated with T1-63, which does not activate TREM1 in solution, failed to release extracellular DNA. Overall, the results presented in FIG. 10A-D establish that agonistic TREM1 antibodies act on primary human cells to activate TREM1-mediated processes such as ROS production and NET formation. Importantly, TREM1 antibodies are not dependent on adsorption onto tissue culture plates to cluster surface receptors for activity but rather retain agonistic properties in solution.

Example 10: TREM1 Antibodies Decrease Cell Surface Levels of TREM1

It is believed that antibodies that target certain ITIM/ITAM receptors expressed on the surface of immune cells can reduce the surface levels of the receptor on monocytes, macrophages, dendritic cells, neutrophils, and/or microglia.

The ability of anti-TREM1 antibodies to reduce cell surface expression of TREM1 on human primary monocytes (huMono) and neutrophils was evaluated. Human monocytes or neutrophils were cultured in 96-well tissue culture plates either alone or in the presence 10 µg/ml of soluble anti-TREM1 antibodies or isotype control antibodies. The following day, huMono or neutrophils were analyzed by FACS for TREM1 expression on the cell surface. TREM1 expression was detected using either a commercial anti-human TREM1 antibody (Biolegend, Trem-26) or fluorophore-conjugated Mab0170.

Figure 11A:
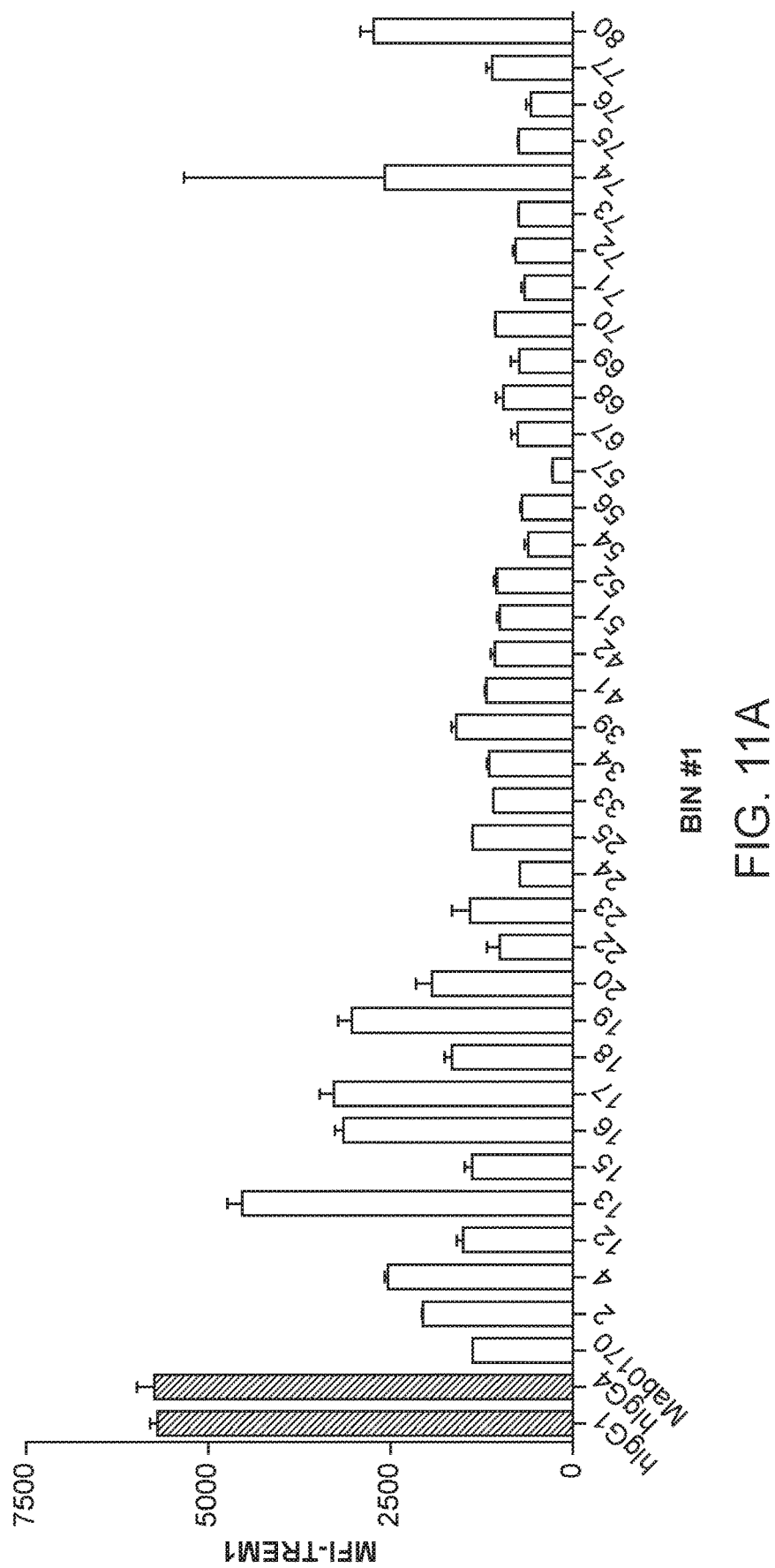
FIG. 11A shows TREM1 receptor down regulation in primary human monocytes in response to antibody stimulation. Cells were either treated with soluble full-length isotype controls or soluble full-length anti-TREM1 antibodies from the Bin 1 category and subsequently stained a commercially available bin 2 anti-TREM1 APC antibody (TREM-26, Biolegend).
Figure 11B:
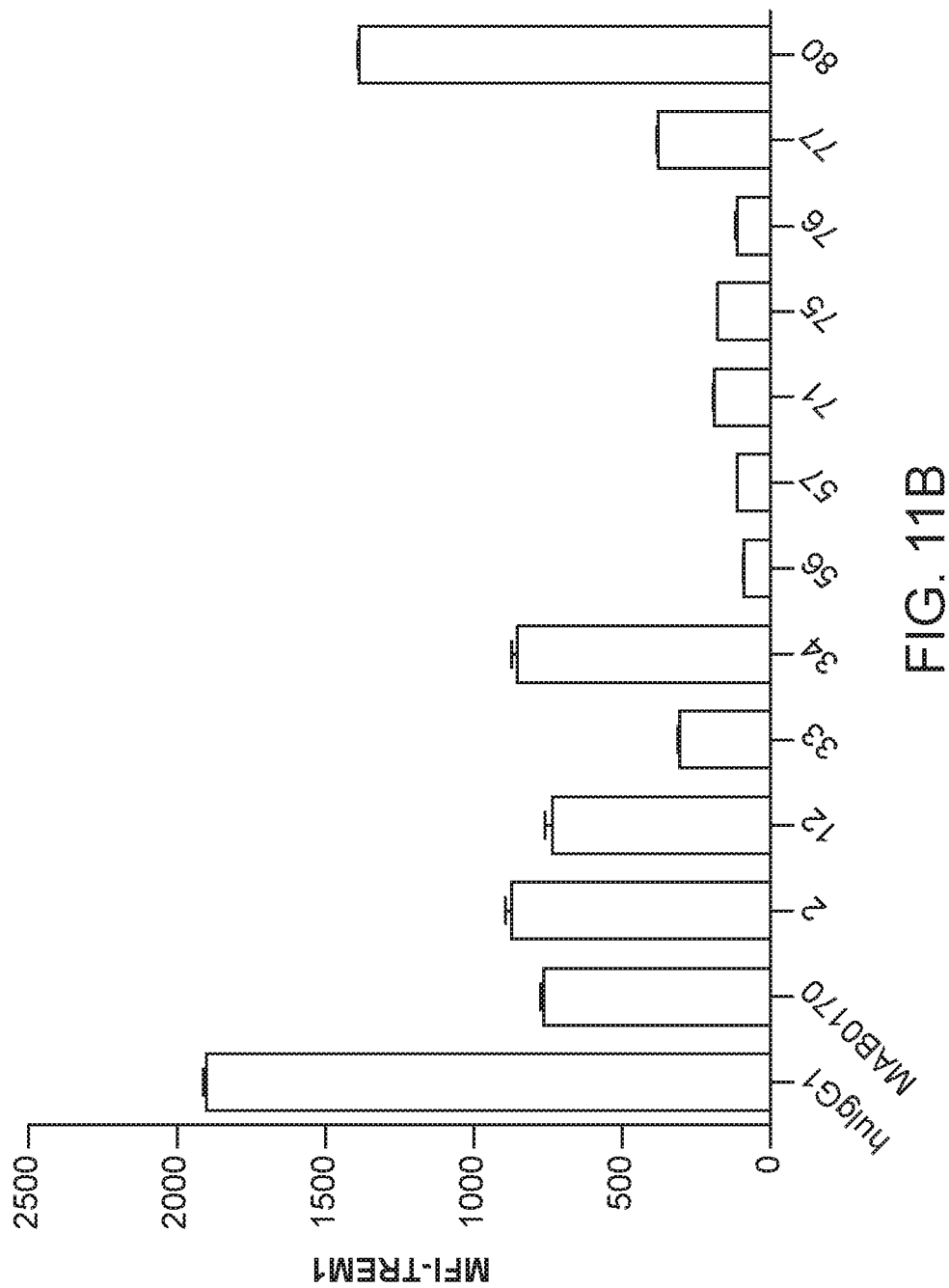
FIG. 11B shows TREM1 receptor down regulation in primary neutrophils in response to antibody stimulation. Cells were either treated with soluble full-length isotype control or soluble full-length Bin 1 anti-TREM1 antibodies T1-2, -12, -33, -34, -56, -57, -71, -75, -76, -77, and -80. Antibody huIgG1 represents the isotype negative control, and Mab0170 represents the positive control.

As shown in FIG. 11A, most soluble full-length anti-TREM1 antibodies from the Bin 1 category reduced cell surface levels of TREM1 by ≥70% on primary huMono, as compared to cells treated with isotype controls (hIgG1 and hIgG4). Similarly, FIG. 11B demonstrates that the soluble full-length anti-TREM1 antibodies from the Bin 1 category T1-2, -12, -33, -34, -56, -57, -71, -75, -76, and -77 reduced cell surface levels of TREM1 by ≥65% in primary human neutrophils, as compared to cells treated with isotype control (hIgG1).

Figure 11C:
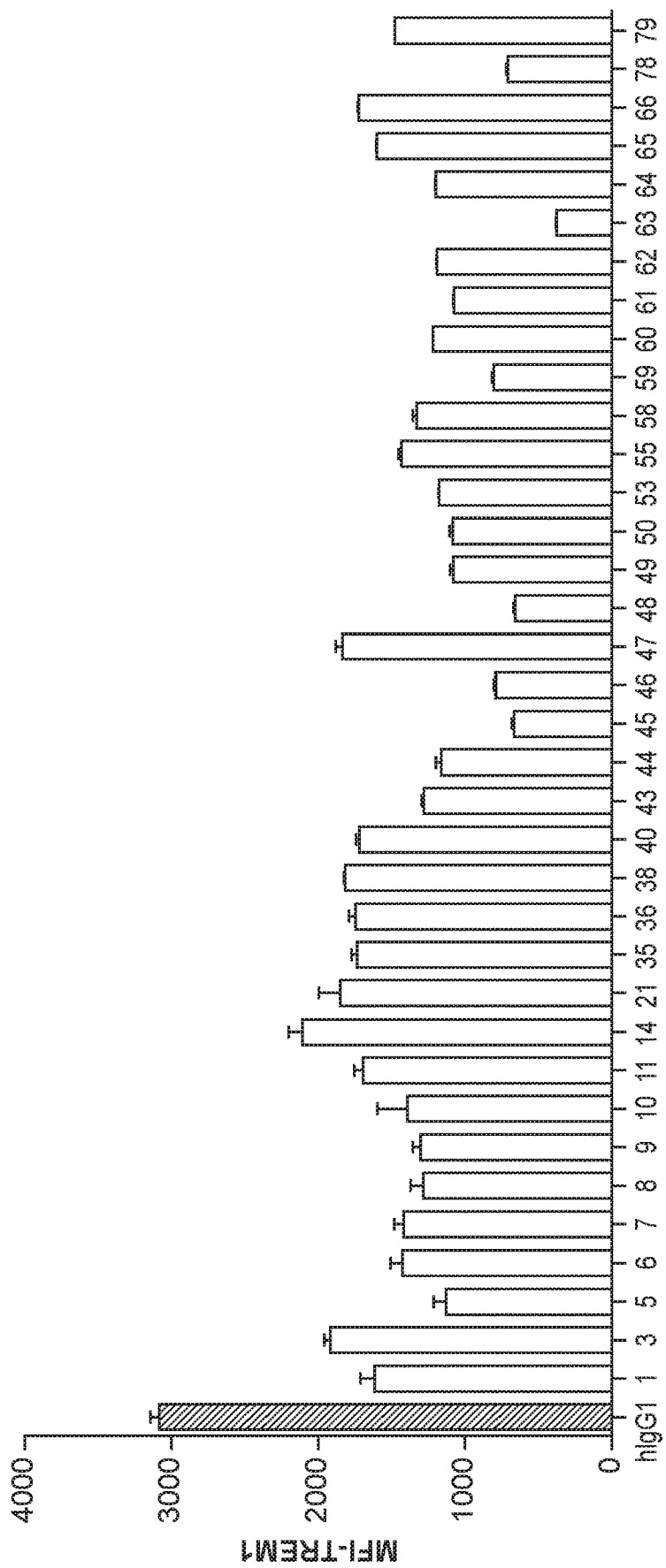
FIG. 11C shows TREM1 receptor down regulation in primary monocytes treated with Bin 2 antibodies and subsequently stained with fluorophore-conjugated Bin 1 antibody, Mab0170. Antibodies huIgG1 and huIgG4 represent isotype negative controls. Results are expressed as absolute median fluorescent intensity (MFI) values.

FIG. 11C demonstrates that most soluble full-length anti-TREM1 antibodies from the Bin 2 category reduced cell surface levels of TREM1 by ≥50%, as compared to cells treated with isotype control (hIgG). As a general observation, soluble full-length anti-TREM1 antibodies from Bin 1 downregulated cell surface expression of TREM1 to a greater extent than soluble full-length anti-TREM1 antibodies from Bin 2.

Example 11: TREM1 Ligand Increases Surivival of Immune Cells

In Vitro Cell Survival

Naïve mice with genetic deficiency in TREM1 reveal no intrinsic predisposition for reduced cell survival within the myeloid compartment compared to wild type mice. However, under inflammatory conditions, several studies demonstrate that TREM1-knockout mice present with decreased neutrophilic infiltration into affected tissues. These observations suggest that TREM1 may function in either the migratory capacity of neutrophils or their survival during inflammation. To evaluate the ability of TREM1 ligand to affect immune cell survival in vitro, primary human monocytes or neutrophils were cultured for 20 hours at 37° C. in the presence or absence of human PGLYRP1, PGN-BS, soluble TREM1 ligand complex, or LPS. Cell viability was determined by quantitation of ATP, an indicator of metabolic activity, using a luciferase-based assay kit (CellTiter-Glo; Promega) according to the manufacturer's instructions. Luminescence was measured with a BioTek Synergy™ Microplate Reader using GEN5™ 2.04 software.

As shown in FIG. 12A, stimulating primary human monocytes with TLR ligands, such as PGN-BS (10 µg/ml) or LPS (1 µg/ml), increased metabolically active cells ~3-fold relative to untreated cells indicative of improved cell survival. Similarly, treating monocytes with human PGLYRP1 (10 µg/ml) or soluble TREM1 ligand complex consisting of hPGLYRP1/PGN-BS also enhanced metabolically active cells ~3-fold relative to untreated cells. As shown in FIG. 12B, stimulating primary human neutrophils with TLR ligands yielded contrasting results. Whereas LPS (1 µg/ml) treatment increased metabolically active cells ~1.5-fold relative to untreated cells, PGN-BS (10 µg/ml) treatment decreased metabolically active cells ~55% relative to untreated cells. In contrast to PGN-BS, stimulating neutrophils with human PGLYRP1 alone (10 µg/ml) increased metabolically active cells ~1.5-fold relative to untreated cells. When PGLYRP1 and PGN-BS are combined to form a soluble TREM1 ligand complex, PGLYRP1 partially reverses the PGN-BS-mediated phenotype since there is only a 22% decrease in metabolically active cells relative to untreated cells. Thus, TREM1 ligation appears to inhbit PGN-induced neutrophilic cell death.

Figure 12C:
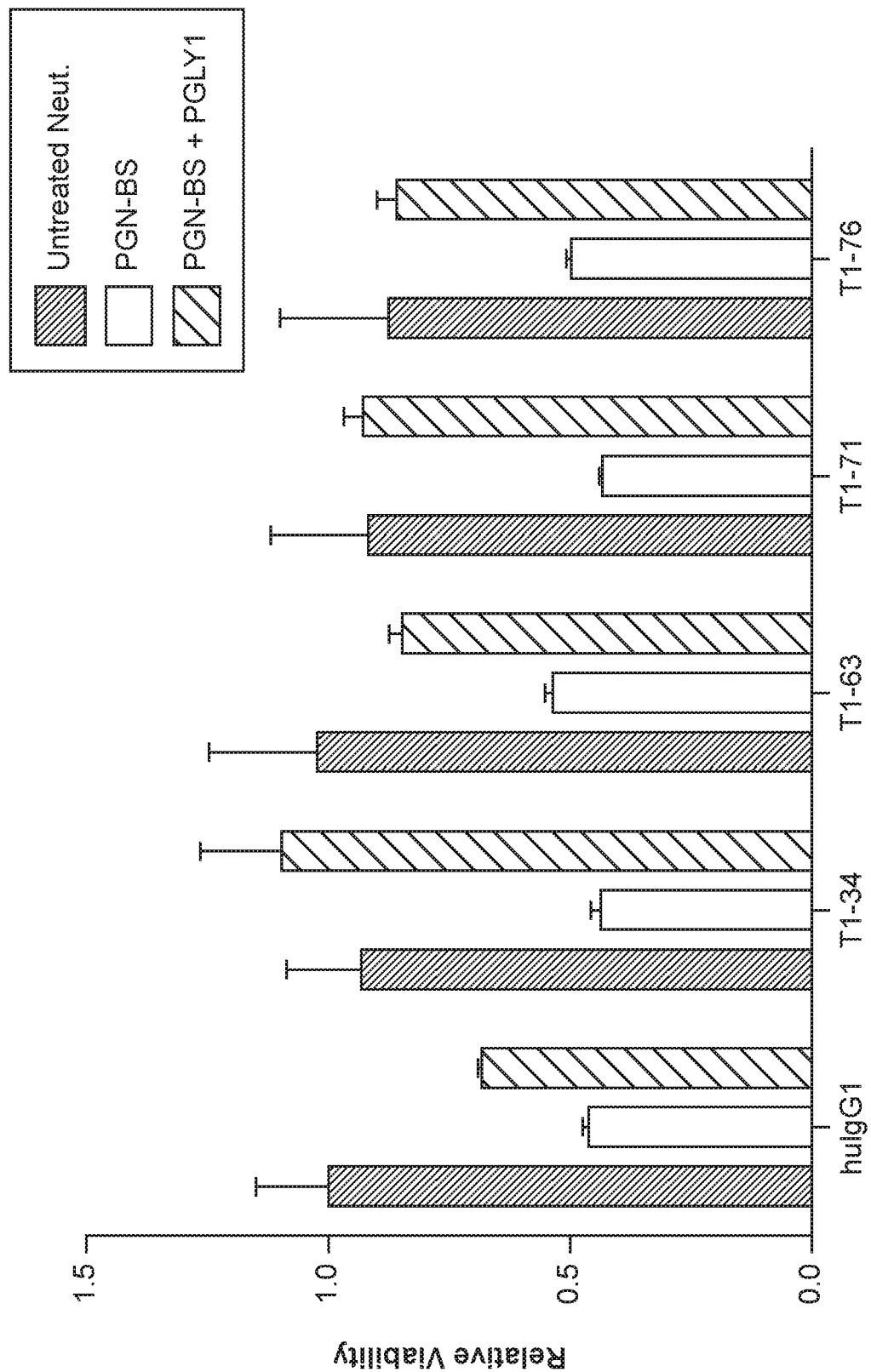
FIG. 12C shows the ability of anti-TREM1 antibodies to enhance the relative viability of primary human neutrophils cultured for 20 hours with soluble TREM1 ligand complex. Cells were treated with either human isotype control (huIgG1) or TREM1 antibodies, T1-34, -63, -71, and -76, in the presence of 10 μg/mL PGN-BS or soluble TREM1 ligand complex (500 nM PGLYRP1+10 μg/mL PGN-BS) or left untreated. Cell viability was determined by quantitation of ATP using a luciferase-based assay kit (CellTiter-Glo; Promega) according to the manufacturer's instructions.

To evaluate the ability of anti-TREM1 antibodies to synergize with ligand to increase the proportion of metabolically active neutrophils, cells were cultured with either 10 µg/ml of PGN-BS or 500 nM of hPGLYRP1 complexed with 10 µg/ml of PGN-BS in the presence of the anti-TREM1 antibodies T1-34, -63, -71, and -76 or the isotype control, human IgG1 (huIgG1). After incubating for 20 hours at 37° C., cell viability was determined by quantitation of ATP using a luciferase-based assay kit (CellTiter-Glo; Promega) according to the manufacturer's instructions. As shown in FIG. 12C, treating primary human neutrophils with PGN-BS decreased metabolic activity ~55% relative to untreated neutrophils in the presence of huIgG1 or anti-TREM1 antibodies. Adding PGLYRP1 with PGN-BS in the context of a soluble ligand complex increased neutrophil viability ~33% in the presence of the isotype control relative to PGN-BS alone. However, treating neutrophils with ligand complex in the presence of TREM1 antibodies, T1-34 and T1-71, increased cell viability ~60% and ~50%, respectively, relative to PGN-BS stimulation alone. The TREM1 antibodies, T1-63 and T1-76, exhibited more modest activity by increasing viability 40-45% in the presence of ligand complex relative to neutrophils treated with PGN-BS alone. Thus, TREM1 antibodies act with ligand to inhibit peptidoglycan-induced neutrophilic cell death.

Example 11: Summary of TREM1 Agonistic Antibodies that Induce Gene Expression or Enhance Gene Expression Induced by Natural Ligands Anti-TREM1 antibodies demonstrated agonistic or antagonistic activity, either in solution or following antibody clustering (i.e., by plate binding), in modulating TREM1- dependent gene expression in cells expressing human TREM1 (Table 1B), as measured by a luciferase reporter gene. A subset of TREM1 antibodies displays agonistic activity when plate-bound. Another subset of TREM1 antibodies displays agonistic activity when in solution. A third subset of TREM1 antibodies displays antagonistic effects of soluble non-cross-linked antibodies.

Example 12: Analysis of the Effect of TREM1 Antibodies in Increasing Recruitment of Immune Cells In Vivo The ability of TREM1 antibodies to modulate the recruitment of inflammatory cells (neutrophil granulocytes, monocytes, and macrophages) in the peritoneal cavity (PEC) of C57Bl6 mice after intraperitoneal (IP) administration of either antibody alone or in combination with LPS was evaluated. Briefly, mice receive first an IP injection of 40 mg/kg anti-TREM1 antibody or isotype control antibody mIgG1 (clone MOPC-21, Bioxcell). 14 hours later, mice receive an IP injection of 4 mg/kg LPS, or PBS as a control. 6 hours after LPS or PBS injection, cells were harvested from the PEC as described (see, e.g., Gawish R et al, 2014 *FASEB J*) and analyzed by FACS. For FACS analysis, PEC cells were incubated with anti-CD11b-Pacific Blue, anti-CD11c PeCy7, anti-MCH-II-APCCy7, anti-Gr1-FITC, anti-Ly6G-PE and a viability die (Life Technologies, Cat #L34957) for 1 hour on ice, then washed twice with cold FACS buffer. 4% PFA-fixed samples were then acquired. Data were acquired on a BD FACS CANTO II cytometer (Becton Dickinson) and analyzed with FlowJo software.

Example 13: TREM1 Antibodies Increase the Level of Soluble TREM1 in Mice

It is believed that the extracellular portion of TREM1 can be shedded into a soluble form (sTREM1), and thus can be detected in the plasma and cerebrospinal fluid (CSF). It is also believed that in individuals with Alzheimer's disease or frontotemporal dementia the amount of sTREM1 in the CSF is reduced compared to healthy control individuals.

To determine the effect of anti-TREM1 antibodies on the blood serum levels of sTREM1 in mice, the amount of sTREM1 present in the blood of mice was measured at 2, 4, 8 and 15 days after the injection of soluble anti-TREM1 antibody. Serum levels of sTREM1 were measured using a standard ELISA method. Briefly, Immulon ELISA 96-well plates were coated overnight at 4° C. with 100 µl of capture anti-TREM1 antibody at 2 µg/ml. The next morning plates were washed three times with 200 µl wash buffer (PBS+ 0.05% Tween-20). Then plates were blocked by addition of 300 µl binding buffer (PBS+1% BSA) for 1 hr at room temperature on orbital shaker. Subsequently serum samples (1:12 dilution) and standards (recombinant mouse TREM1, R&D Systems) were added in 100 µl binding buffer, and plates were incubated at room temperature for 1 hr. Then plates were washed three times with 200 µl wash buffer. The detection biotinylated rat anti-TREM1 (R&D Systems, biotinylated with micro-NHS-Peg4-Biotinylation kit from Life Technologies Pierce) was added at 1:10,000 in 100 µl binding buffer and incubated for 1h at room temperature on orbital shaker. Then plates were washed three times with 200 µl wash buffer. 100 µl Streptavidin-HRP (R&D Systems) at 1:200 in binding buffer was added to the plates and incubated for 20 min on orbital shaker. Then plates were washed three times with 200 µl wash buffer and 100 □l MB substrate (Life Technologies Pierce) was added and incubated on plate shaker until color developed. The reaction was stopped by addition of 50 □l sulfuric acid, and color was quantified using a Biotek Synergy H1 plate reader.

To determine the amount of anti-TREM1 antibodies present in the blood serum of mice at 2, 4, 8 and 15 days after injection of anti-TREM1 antibody, a standard ELISA method was utilized. Briefly, ELISA plates coated with 0.1 ug/well recombinant mouse TREM1 protein at 100 µL/well in carbonate coating buffer (pH 9.6) overnight at 4° C. Plates were then washed and blocked with 3% skim milk powder in PBS for 1 hour at room temperature and then washed. Mouse blood serum samples were titrated in PBS-Tween, added to the plate at 100 µL/well, and incubated for 1 hour at 37° C. with shaking. Anti-TREM1 antibodies were detected using a Goat anti-mouse IgG1-HRP secondary and developed with TMB substrate. A defined amount of anti-TREM1 antibody was spiked in the blood serum of a naïve mouse and titrated to obtain a calibration curve.

Example 15: Analysis of the Effect of Anti-TREM1 Antibodies in Mouse Models of Alzheimer's Disease Inflammatory Genes The ability of anti-TREM1 antibodies to modulate the expression of inflammatory genes in different regions of the brain of APPPS1 mice was evaluated after intracranial (IC) administration of anti-TREM1 antibody. APPPS1 mice contain human transgenes for both APP bearing the Swedish mutation (K670N, M671L) and PSEN1 containing an L166P mutation, both under the control of the Thy1 promoter. Five mice per group received an IC injection of 2 ul of a 1 mg/ml solution of anti-TREM1 antibody or isotype control antibody mIgG1 (clone MOPC-21, Bioxcell) as described (Wilcock D M, et al., (2003) *J Neurosci* 23:3745; Wilcock D M, et al., (2004) *Neurobiol Dis* 15:11; Sudduth et al., (2013) J. Neurosc, 33, 9684. Specifically, on the day of surgery mice were weighed, anesthetized with isoflurane, and placed in a stereotaxic apparatus (51733D digital dual manipulator mouse stereotaxic frame; Stoelting). A midsagittal incision was made to expose the cranium and four burr holes were drilled with a dental drill mounted in the stereotaxic frame over the frontal cortex and hippocampus to the following coordinates: frontal cortex, anteroposterior, +1.7 mm, lateral ±2.0 mm; hippocampus, anteroposterior -2.7 mm; lateral, ±2.5 mm, all taken from bregma. A 26 gauge needle attached to a 10 ml Hamilton syringe (Hamilton) containing the solution to be injected was lowered 3.0 mm ventral to bregma, and a 2 µl injection was made over a 2 min period. The incision was cleaned and closed with surgical staples. Three days post-injection, mice were perfused with saline and the right hemisphere of the brains was dissected into frontal cortex, hippocampus, rest of brain, and flash frozen. RNA was extracted from left hippocampus using the Trizol Plus RNA Purification System (Ambion, Invitrogen) according to the manufacturer's instructions. RNA was quantified using the BioSpec Nano spectrophotometer (Shimadzu) and cDNA was reverse transcribed using the cDNA High Capacity kit (Applied Biosystems) according to the manufacturer's instructions. Real-time PCR was performed using the 384-well microfluidic card custom TaqMan® assays containing TaqMan® gene expression probes for genes of interest IL-1b, IL-6, TNFa, IL-12, YM-1, IL-1Ra, MRC1, IL-10, CD86, FCGR1B, and TGFb (Applied Biosystems, Invitrogen). All gene expression data was normalized to 18S rRNA expression. Fold change was determined using ΔCT-method. Data are presented as mean±SEM. Statistical analysis is performed using the JMP statistical analysis program (SAS). Statistical significance was assigned where the p value was lower than 0.05. One-way ANOVA and two-way ANOVA were used, where appropriate, to detect treatment differences and differences within treatment groups along the time course.

Amyloid Beta Peptide

The ability of anti-TREM1 antibodies to reduce the amount of amyloid beta (Abeta) peptide in different regions of the brain of APPPS1 mice was evaluated after intracranial (IC) administration of anti-TREM1 antibody. Five mice per group received an IC injection of 2 ul of a 1 mg/ml solution of anti-TREM1 antibody or isotype control antibody mIgG1 (clone MOPC-21, Bioxcell). For the quantification of Abeta peptide, three days pot injection, after injection with a lethal dose of pentobarbital, mice were perfused intracardially with 25 ml of normal saline. Brains were rapidly removed and bisected in the mid-sagittal plane. The left half was immersion fixed in freshly prepared 4% paraformaldehyde. The right half was dissected with the frontal cortex and hippocampus being isolated, flash frozen in liquid nitrogen, and stored at −80° C. The left hemibrain was passed through a series of 10, 20, and 30% sucrose solutions as cryoprotection and 25 μm frozen horizontal sections were collected using a sliding microtome and stored floating in PBS containing sodium azide at 4° C. Sections spaced 300 μm spanning the estimated injection site were initially mounted and stained by cresyl violet to identify the injection site. For all subsequent histology and immunohistochemistry six sections spanning the injection site, spaced 100 μm apart were selected and analyzed. Free-floating immunohistochemistry for Abeta (rabbit polyclonal antibody Aβ1-16; Invitrogen) was performed. The percent area occupied by positive stain was calculated using Nikon elements BR software.

FAD Mouse Alzheimer's Disease Model

To evaluate the ability of anti-TREM1 antibodies to delay, prevent, or reverse the development of Alzheimer's disease (AD), 5×FAD mice are used. 5×FAD mice overexpress mutant human APP (695) with the Swedish (K670N, M671L), Florida (1716V), and London (V717I) familial Alzheimer's disease (FAD) mutations, along with human PS1 harboring two FAD mutations, M146L and L286V. Both transgenes are regulated by the mouse Thy1 promoter to drive over expression on the brain and recapitulate major features of AD. Mice are treated weekly with 50 mg/kg anti-TREM1 antibody or with isotype control antibody mIgG1 (clone MOPC-21, Bioxcell) starting from 14 weeks of age. Mice are tested for Abeta plaque load with immunohistochemistry and by ELISA of tissue extracts. Mice are further tested for the number of microglia in the brain, and for reduction in cognitive deficit using Morris Water maze, a spatial learning and memory task, Radial Arm Water Maze, a spatial learning and memory task, Y Maze (quantifies spontaneous alternation as a measure of spatial cognition), novelty preference in in an open field, operant learning to assess learning and memory, and fear conditioning (mouse-biology.org website; Wang et al., (2015) Cell. pii: S0092-8674(15)00127-0).

Tg2576 Mouse Alzheimer's Disease Nodel

To evaluate the ability of anti-TREM1 antibodies to delay, prevent, or reverse the development of Alzheimer's disease (AD), Tg2576 mice are used. Tg2576 mice overexpress a mutant form of APP (isoform 695) bearing the Swedish mutation (KM670/671NL). Mice are treated weekly with 50 mg/Kg anti-TREM1 antibody or with isotype control antibody mIgG1 (clone MOPC-21, Bioxcell) starting from 98-99 weeks of age. Mice are tested for Abeta plaque load with immunohistochemistry and by ELISA of tissue extracts. Mice are further tested for the number of microglia in the brain, and for reduction in cognitive deficit using Morris Water maze, a spatial learning and memory task, Radial Arm Water Maze, a spatial learning and memory task, Y Maze (quantifies spontaneous alternation as a measure of spatial cognition), novelty preference in in an open field, operant learning to assess learning and memory, and fear conditioning (mousebiology.org website; Wang et al., (2015) Cell. pii: S0092-8674(15)00127-0).

Example 16: TREM1 Expression in the Tumor Microenvironment

Groups of 3 C57Bl6 or BALB/c mice (females, 8 weeks old) were challenged subcutaneously with $1\times10^6$ MC38 or CT26 colon carcinoma cells, or EMT-6 murine mammary carcinoma cells, suspended in 100 ul PBS. Animals are anesthetized with isoflurane prior to implant. When the tumors reached a size of 700-1000 mm$^3$, tumors were explanted to analyze TREM1 expression in the tumor microenvironment by FACS. As a comparison, the spleen of the tumor baring mice or control spleen of naïve mice were also analyzed. For expression analysis by FACS, tumor and spleens were incubated in PBS containing 1 mg/ml collagenase and then processed thorugh a cell strained to obtain a single cell suspension. Cells were then incubated with anti-CD45-PerCp-Cy7, anti-CD11b-PerCP-Cy5.5, anti-CD3-PC, anti-Gr1-FITC, anti-NK1.1-PE, anti-TREM1-APC antibodies and a viability die (Life Technologies, Cat #L34957) for 30 min on ice, then washed twice with cold FACS buffer. 4% PFA-fixed samples were then acquired. Data were acquired on a BD FACS CANTO II cytometer (Becton Dickinson) and analyzed with FlowJo software.

Figure 13:
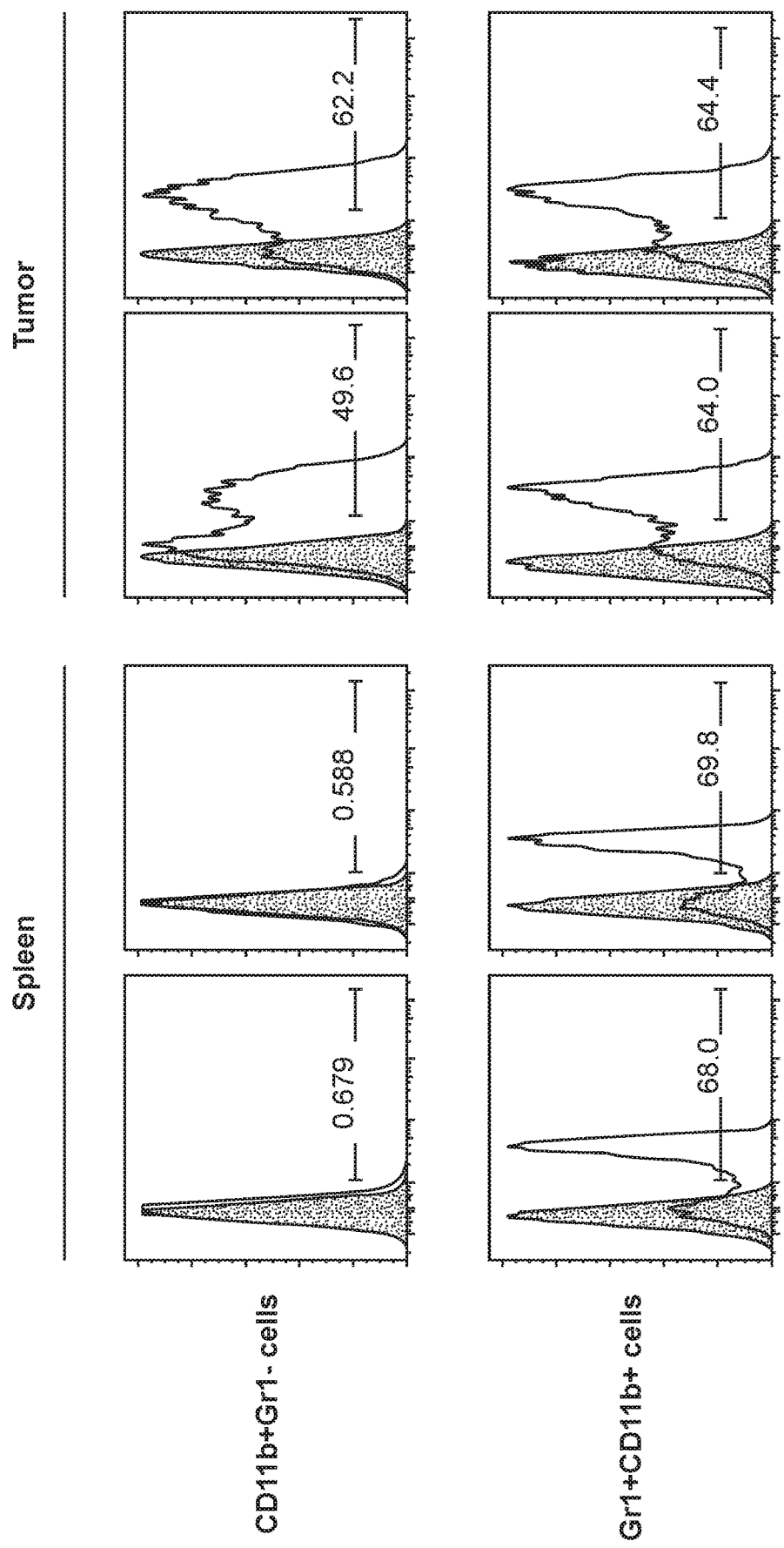
FIG. 13 shows TREM1 expression on the indicated immune cell populations present in the spleen (SPL) or in the tumor (Tum) of naïve mice or mice bearing the EMT-6 tumors.

As shown in FIG. 13, TREM1 was found highly upregulated in 50-60% of the CD11b+Gr1− cells in the EMT-6 tumor but not in the spleen. CD11b+Gr1+ MDSC cells express high levels of TREM1 both in the tumor and in the spleen.

As summarized in Table 8, TREM1 was found expressed on the cell surface in ~10-60% of CD45+CD3−CD11b+ Gr1− myeloid cells (which include macrophages, monocytes, and dendritic cells) and in ~40-70% of CD45+CD3− CD11b+Gr1+ myeloid derived suppressor cells (MDSC) that infiltrate MC38, CT26 and EMT6 tumors. TREM1 was not found expressed in CD11b+Gr1− cells in the spleen of tumor bearing mice or naïve mice. These results indicate that Bl6, MC38, CT26, and EMT-6 tumors stimulate cell surface expression of TREM1 in a subset of myeloid cells and MDSC.

TABLE 8

TREM1 expression in tumor microenvironment

| Markers | Cell Type | B16 | Madison | CT26 | EMT-6 | MC38 |
|---|---|---|---|---|---|---|
| CD45 + CD3+ NK1.1− | T cells | neg | neg | neg | neg | neg |
| CD45 + CD3− NK1.1− CD11b + Gr1− | Myeloid cells | % positive minimal increase in Tumor compared to spleen (from 0% to ~10%) | % positive minimal increase in Tumor compared to spleen (from 0% to ~10%) | % positive minimal increase in Tumor compared to spleen (from 0% to ~10-20%) | % positive increases in Tumor compared to spleen (from 0% to ~50-60%) | % positive increases in Tumor compared to spleen (from 10% to ~50-60%) |
| CD45 + CD3− NK1.1− CD11b + Gr1+ | MDSC | % positive similar in Tumor compared to spleen (~40-70%) | % positive similar in Tumor compared to spleen (~30-40%) | % positive similar in Tumor compared to spleen (~30-40%) | % positive similar in Tumor compared to spleen (~60-70%) | % positive similar in Tumor compared to spleen (~20-70%) |
| CD45 + CD3− NK1.1− CD11c+ | DCs | neg | neg (low in tumor?) | neg (low in tumor?) | n.d. | % positive similar in Tumor compared to spleen (~from 0 to 60-70%) |
| CD45− | Tumor/ Vasculature | neg | neg | neg | neg | n.d. |

Example 17: Analysis of Tumor Growth in TREM1-Deficient Mice

Groups of TREM1 wild-type (WT, n=11) and TREM1 knock-out (KO, n=14) mice (sex and age-matched littermates, 10 weeks old (+/−2 weeks)) were challenged subcutaneously with $1 \times 10^6$ MC38 colon carcinoma tumor cells suspended in 100 ul PBS. Mice were anesthetized with isoflurane prior to implant. Tumor growth was monitored with a caliper biweekly to measure tumor growth starting at day 5. The endpoint of the experiment is a tumor volume of 2000 mm$^3$ or 60 days. Tumor size over time (expressed as volume, mm$^3$) is the outcome measure.

Example 18: Analysis of the Anti-Cancer Effect of TREM1 Antibodies in a Mouse Model of Breast Cancer Groups of 10 BALB/c mice mice at 8 weeks (+/−2 weeks) of age are challenged subcutaneously with $5 \times 10^6$ EMT-6 tumor cells suspended in 100 ul PBS. Animals are anesthetized with isoflurane prior to implant. Starting at day 2, groups of mice are injected IP at day 1, 4, 8, 15, and 22 with 40 mg/kg of anti-TREM1 antibodies. Tumor growth is monitored with a caliper biweekly to measure tumor growth starting at day 4. The endpoint of the experiment is a tumor volume of 2000 mm$^3$ or 60 days. Tumor growth and % survival are the outcome measures. Reduced tumor take and growth rate, reduced number of tumor infiltrating immune suppressor macrophages, and increased effector T cell influx into the tumor indicate the anti-cancer effects of blocking anti-TREM1 antibodies.

Example 19: Analysis of Additive Anti-Tumor Effect of Combination Therapy That Combines TREM1 Antibodies with Antibodies Against Inhibitory Checkpoint Proteins or Inhibitory Cytokines/Chemokines and Their Receptors in a Mouse Model of Breast Cancer Groups of 10 BALB/c mice mice at 8 weeks (+/−2 weeks) of age are challenged subcutaneously with $5 \times 10^6$ EMT-6 tumor cells suspended in 100 ul PBS. Animals are anesthetized with isoflurane prior to implant. Starting at day 2, groups of mice are injected IP at day 1, 4, 8, 15, and 22 with 40 mg/kg of anti-TREM1 antibodies alone or in combination with antibodies against checkpoint proteins (e.g., anti-PDL1 mAb clone 10F.9G2 and/or anti-CTLA-4 mAb clone 9H10) at day 8 and 11. Treatment groups include anti-TREM1; anti-CTLA-4; anti-TREM1+anti-CTLA-4 and isotype control. Tumor growth is monitored with a caliper biweekly to measure tumor growth starting at day 4. The endpoint of the experiment is a tumor volume of 2000 mm$^3$ or 60 days. Tumor growth and % survival are the outcome measures. A decrease in tumor growth and an increase in percent survival with combination therapy indicate that anti-TREM1 antibodies have additive or synergistic therapeutic effects with anti-checkpoint antibodies. Antagonistic antibodies against checkpoint molecules include antibodies against PDL1, PDL2, PD1, CTLA-4, B7-H3, B7-H4, HVEM, BTLA, KIR, GAL9, TIM3, A2AR, LAG-3, and phosphatidylserine (PS). Antagonist antibodies against inhibitory cytokines include antibodies against CCL2, CSF-1, and IL-2.

Example 20: Analysis of Additive Anti-Tumor Effect of Combination Therapy That Combines TREM1 Antibodies with Antibodies that Activate Stimulatory Checkpoint Proteins Groups of 15 C57Bl6/NTac mice at 8 weeks (+/−2 weeks) of age are challenged subcutaneously with tumor cells as described in Example 19. Animals are anesthetized with isoflurane prior to implant. Starting at day 2, mice are injected intraperitoneally every 3 days for 4 doses with 200 ug anti-TREM1 antibodies alone or in combination with agonistic antibodies that activate stimulatory checkpoint proteins (e.g., OX40 or ICOS mAb) at day 3, 6, and 9. Tumor growth is monitored with a caliper biweekly to measure tumor growth starting at day 4. The endpoint of the experiment is a tumor volume of 2000 mm$^3$ or 60 days. Tumor growth and percent survival are the outcome measures. A decrease in tumor growth and an increase in percent survival with combination therapy indicate that anti-TREM1 antibodies have additive or synergistic therapeutic effects with stimulatory checkpoint antibodies. Stimulatory checkpoint antibodies include agonistic/stimulatory antibodies against CD28, ICOS, CD137, CD27, CD40, and GITR.

Example 21: Analysis of Additive Anti-Tumor Effect of Combination Therapy That Combines TREM1 Antibodies with Stimulatory Sytokines Groups of 15 C57Bl6/NTac mice at 8 weeks (+/−2 weeks) of age are challenged subcutaneously with tumor cells as described in Example 19. Animals are anesthetized with isoflurane prior to implant. Starting at day 2, mice are injected intraperitoneally every 3 days for 4 doses with 200 ug anti-TREM1 antibodies alone or in combination with stimulatory cytokines (e.g., IL-12, IFN-a). Tumor growth is monitored with a caliper biweekly to measure tumor growth starting at day 4. The endpoint of the experiment is a tumor volume of 2000 mm$^3$ or 60 days. Tumor growth and percent survival are the outcome measures. A decrease in tumor growth and an increase in percent survival with combination therapy indicate that anti-TREM1 antibodies have additive or synergistic therapeutic effects with immune-stimulatory cytokines. Stimulatory cytokines include IFN-a/b, IL-2, IL-12, IL-18, GM-CSF, and G-CSF.

Example 22: Characterization of the Therapeutic Use of Agonistic TREM1 and/or TREM1 Bispecific Antibodies in a Model of Inflammatory Diseases The therapeutic utility of agonistic anti-TREM1, and/or TREM1 bispecific antibodies is tested in a model of inflammatory diseases. For example rheumatoid arthritis or in an established model of another inflammatory disease (Mizoguchi (2012) Prog Mol Biol Transl Sci., 105:263-320; and Asquith et al., (2009) Eur J Immunol. 39:2040-4).

Example 23: In Vivo Protection from EAE and Cuprizone in a Whole Animal

Adult 7-9 week-old female C57BL/6 mice (obtained from Charles River Laboratories) are injected in the tail base bilaterally with 200 µl of an innoculum containing 100 µg of myelin oligodendrocyte glycoprotein peptide 35-55 (amino acids MEVGWYRSPFSRVVHLYRNGK (SEQ ID NO: 497); Seqlab) and 1 mg of *Mycobacterium tuberculosis* H37 Ra (Difco) in incomplete Freund adjuvant (Difco). Pertussis toxin (200 ng; List Bio-logical Laboratories) is injected at day 0 and at day 2 after immunization. Clinical signs are scored as follows: 0, no clinical signs; 1, complete limp tail; 2, complete limp tail and abnormal gait; 3, one hind-limb paraparesis; 4, complete hindlimb paraparesis; and 5, fore- and hind-limb paralysis or moribund. Only mice having disease onset (clinical score of 1 or more) at day 14 are used for experiments. Agonistic anti-TREM1, and/or TREM1 bispecific antibodies are injected intraperitoneally or intravenously in EAE-diseased mice at the day of the first clinical symptoms or at any other desired time (PLoS Med (2007) 4(4): e124).

Young or aged wild-type (WT) mice are fed a standard diet (Harlan) containing 0.2% cuprizone (CPZ) powdered oxalic bis(cyclohexylidenehydrazide) (Sigma-Aldrich) for 4, 6 or 12 weeks. For Histological and immunohistochemical analyses brains are removed after mouse perfusion with 4% paraformaldehyde (PFA), fixed in 4% PFA for 24 h, followed by immersion in 30% sucrose for 24-48 h. To evaluate myelin integrity and damage, as well as cell proliferation and inflammation sections or mouse brain are stained with anti-MBP (1:100; Abcam, ab7349), -dMBP (1:2000; Millipore, ab5864), -β APP (1:100; Invitrogen, 51-2700), -SMI-31 (1:1000; Covance, smi-31R), -Iba1 (1:600; Wako, 019-19741), -BrdU (1:250; Abcam, 7E5893), -GFAP (1:200; Invitrogen, 13-0300), -iNOS (1:100; BD Pharmingen, 610329), -LPL (1:400, from Dr. G. Olivecrona) and -MHC II (1:100; BD Pharmingen, 553549). For behavioral effects of the antibodies, mice are analyzed for locomotor activity using transparent polystyrene enclosures and computerized photobeam instrumentation. General activity variables (total ambulations, vertical rearings), along with indices of emotionality including time spent, distance traveled and entries, are analyzed. A battery of sensorimotor tests is performed to assess balance (ledge and platform), strength (inverted screen), coordination (pole and inclined screens) and initiation of movement (walking initiation). Motor coordination and balance are studied using a rotarod protocol (Cantoni et al., Acta Neuropathol (2015)129(3): 429-47).

Example 24: Characterization of the Therapeutic Use of Agonistic TREM1 and/or TREM1 Bispecific Antibodies in Established Animal Models of Traumatic Brain Injury The therapeutic utility of agonistic anti-TREM1, and/or TREM1 bispecific antibodies is tested in established animal models of traumatic brain injury (Tanaka, Y et al. (2013) Neuroscience 231 49-60). For example, a model of traumatic brain injury that induces the activation of microglia and astrocytes is used. Eight or nine week-old male C57BL/6J WT mice or progranulin heterozygous mice are used (purchased from Charles River Laboratories or Jackson Laboratories). Mice are anesthetized by intraperitoneal administration of xylazine hydrochloride (8 mg/kg) and chloral hydrate (300 mg/kg) dissolved in sterile saline, and subsequently placed in a stereotaxic apparatus (Narishige, Tokyo, Japan). An incision is made in the scalp and the cranium is exposed. The periosteum is cleaned from the skull, a hole is drilled over the right cerebral hemisphere with a dental drill, and the duramater is removed with a needle tip. A stainless steel cannula, with a 0.5 mm outer diameter, is used to make a longitudinal stab wound in the right hemisphere. The cannula is positioned at 1.3 mm lateral to the midline, and 1 mm posterior to bregma, and introduced into the brain until the tip reaches a depth of 2 mm. The cannula is then shifted 2 mm caudally (bregma 3 mm), and then shifts back 2 mm rostrally to its initial position. Finally, the cannula is removed from the brain, and the scalp wound is sutured.

Alternatively, a modified weight-drop device is used (Chen, Y., et al., (1996) J. Neurotrauma 13, 557-568). Specifically, following isoflurane anesthesia, a midline longitudinal incision is made and the skull exposed. A Teflontipped cone (2-mm diameter) is placed 1-2 mm lateral to the midline in the midcoronal plane. The head is manually held in place, and a 95-g weight is dropped on the cone from a prefixed height, resulting in a focal injury to the left hemisphere. After recovery from anesthesia, the mice are returned to their home cages with postoperative care and free access to food and water. Sham controls received anesthesia and skin incision only. Mice are treated with TREM1 antibodies delivered by Intraperitoneal injection at a volume of 250 ul/mouse (calculated as 100 ul/10 gr Body weight) at concentration of antibodies ranging from 4 mg/ml to 0.5 mg/ml. Control IgG antibody is injected at a concentration of 4 mg/ml. Antibodies are injected at days −3 to the traumatic brain injury and then at days 1, 7, 14, 21, 28. Neurological score (NSS) is evaluated 1 hour after TBI (to define, and ensure similar severity of injury in all groups) and then at 24 hour, and days 3, 5, 7, and once weekly till the end of the follow-up (4 weeks). Cognitive functions are being tested at days 4, 16, 32 after injury) using the novel object recognition test.

The Neurological Severity Score (NSS), is performed as described (Beni-Adani, L. et al., (2001) J. Neurotrauma 25, 324-333; Tsenter, J. et al., (2008). J. Neurotrauma 25, 324-333). Specifically, NSS consists of 10 individual tasks, including open-field performance, beam walk, balance, and hemiparesis evaluations, which reflect motor function, alertness, and behavior. One point is given for failure to perform a task and 0 for success. The NSS at 1 h post-trauma reflects the initial severity of injury. Thus, the extent of recovery (delta NSS) is calculated as the difference between the initial NSS score at 1 h postinjury and at any subsequent time point.

The novel object recognition test (NORT) is a sensitive and reproducible test for measuring cognitive abnormalities in TBI. Mice are placed for 1 h habituation period in an open glass aquarium-like transparent box, each at a time, in a sound-isolated room. On the following day they are re-introduced in the box for 5 min with two identical clean plaster objects, placed in two different corners of the box to measure baseline activity. Four hours later, one of the objects is replaced with a new one of the same size and texture, and the mice were re-introduced for additional 5 min into the same cage to test for novel object recognition. The time spent by the mouse in object exploration was recorded manually by an operator blinded to the different treatments. The cumulative time spent at each of the objects was recorded. Exploration of an object is defined as directing the nose to the object at a distance of 2 cm and/or touching it with the nose. The percentage of the total exploration time that the animal spent investigating the new object out of total exploration time is the measure of recognition memory. At baseline, the mouse spent about equal times at both objects since both are novel for him. At test, the cognitively healthy mice will identify the new object as "new", remembering the old one, and therefore will spend more time exploring the new object (~70-75% of the time). TBI leads to impaired memory, thus shorter (than normal) percent of the time exploring the new object. Some spontaneous recovery from TBI does occur, and could lead to TBI mice spending 60-65% of the time at the novel object. For statistical analyses, commercially available computer software (SigmaStat 2.03, Systat Software, San Jose, CA, USA) can be used. Treatments are the independent variables and the outcomes of the TBI parameters are the dependent variables. Significance for NSS and NORT experimental series are tested using two-way ANOVA for repeated measures, and post hoc Fisher's PLSD test. Data are expressed as mean±s.e.m.

Example 25: Characterization of Therapeutic Use of Agonistic TREM1 and/or TREM1 Bispecific Antibodies in a Model of Neuro-Inflammation and Neuron Loss Following Toxin-Induced Injury The therapeutic utility of agonistic anti-TREM1, and/or TREM1 bispecific antibodies is tested in a model of neuro-inflammation and neuron loss following toxin-induced injury (Martens, L H et al., (2012) The Journal of Clinical Investigation, 122, 3955). Three-month-old mice are treated with 4 intraperitoneal injections of MPTP (1-methyl-4-phenyl-1,2,3,6-tetrahydropyridine) per day for 2 days (4 µg/g body weight) (Sigma-Aldrich) or PBS. Mice are treated with agonistic anti-TREM1, and/or TREM1 bispecific antibodies according to standard protocols and then analyzed using Stereological counting to quantify dopamine neurons and microglia in the substantia nigra pars compacta (SNpc), as described.

Example 26: Enhancement of the Ability of BMDCs to Induce Antigen-Specific T-Cell Proliferation By Agonistic and/or Bispecific TREM1 Antibodies It is believed that agonistic anti-TREM1, and/or TREM1 bispecific antibodies may increase ability of bone marrow-derived dendritic cells (BMDC) to express the markers CD83 and CD86 and then to induce antigen-specific T-cell proliferation. To determine if TREM1 antibodies induce expression of the cell surface markers CD83 and CD86 on dendritic cells, antibodies are plated overnight at 4° C. in 12 well plates at 2 or 5 µg/ml in PBS. Wells are washed 3× with PBS the next day and day 5 immature human DCs are harvested and plated at 1 million cells per well and incubated at 37 C., 5% $CO_2$ in the absence of cytokine. FACS analysis of CD86, CD83 and CD11c (BD Biosciences) is performed on a BD FACS Canto 48 hours later. Data analysis was performed with FlowJo (TreeStar) software version 10.0.7. Alternatively, day 5 immature human dendritic cells are plated at 100,000 cells per well in a U-bottom non-TC treated 96 well plate in media without cytokine. Antibodies are added at 5 µg/ml with or without LPS-removed anti-human secondary antibody (Jackson ImmunoResearch) at 20 µg/ml. FACS analysis for CD86, CD83, and CD11c (BD Biosciences) is performed 48 hrs post antibody addition as previously described. Ovalbumin (OVA)-specific T-cell response induced by BMDCs can be determined by CFSE dilution. BMDCs are isolated by MACS after 6 days of culture and plated at $1\times10^4$ cells per well of a round bottom 96 well plate with OVA (2 or 0.5 mg/mL) and CpG DNA (100 or 25 nM) in the presence of GM-CSF (10 ng/mL) for 4 h. CD4 T-cells from the spleen and lymph nodes of OT-II transgenic mice are isolated by using Dynal Mouse CD4 Negative Isolation Kit (Invitrogen) and stained with CFSE (final 0.8 mM). After 4 h of DC culture, $1\times10^5$ CFSE-labeled CD4 OT-II T-cells are added into each well and incubated for 72 h. After culturing, cells are stained with an anti-CD4 monoclonal antibody and flow cytometry is performed to detect CFSE dilution of gated CD4 OT-II T-cells. Data analysis to calculate the percentage of divided and division index is performed by Flowjo software (Treestar) (Eur. J. Immunol. 2012. 42: 176-185).

Alternatively, Day 5 immature dendritic cells (CD14⁻CD11c⁺LIN⁻) are plated in 12 well dishes coated the previous day with 2 µg/ml antibody. Plates are washed 3 times with PBS before addition of T cells. CD4⁺ T cells from nonautologous donors were isolated and labeled with CFSE before addition to DCs in ratio of 1:10. CD3/CD28 Dynal beads serve as a positive control. Day 5 post co-culture cells are analyzed by flow cytometry on a BD FACSCanto II for CFSE dilution. Percent CFSE$^{hi}$ compared to CFSE$^{lo}$ cells are calculated for each condition with FlowJo (TreeStar).

Example 27: TREM1 Antibodies Induce the Expression of CD83 and CD86 on Human Dendritic Cells (Dcs) and Induce T Cell Proliferation To evaluate the ability of anti-TREM1 antibodies to modify expression of CD83 and CD86, both plate-bound and soluble antibodies were incubated with dendritic cells (DCs), and the expression of CD83, CD86, CCR7, and phosphorylated ERK were measured. To evaluate the ability of anti-TREM1 antibodies to modulate T cell proliferation, DCs were incubated with T cells and anti-TREM1 antibodies, and the level of T cell proliferation is measured. Antibodies are plated overnight at 4 C. in 12 well plates at 2 or 5 ug/ml in PBS. Wells were washed 3× with PBS the next day. On day 5, immature human DCs are harvested and plated at 1 million cells per well and incubated at 37 C., 5% CO$_2$ in the absence of cytokine. FACS analysis of CD86, CD83, CD11c, HLA-DR, and LIN (BD Biosciences) are performed on a BD FACS Canto 48 hours later. Data analysis is performed with FlowJo (TreeStar) software version 10.0.7. Levels of CD83, CD86, and CCR7 are evaluated for CD11c+HLA-DR+LIN– cell populations. For intracellular ERK phosphorylation, cells are fixed with 1% formaldehyde, permeabilized with cytofix/cytoperm kit (BD), and intracellular Erk phopshorylation is determined with flow cytometry after staining with PE-ERK antibody (BD).

Alternatively, Day 5 immature human dendritic cells are plated at 100,000 cells per well in a U-bottom non-TC treated 96 well plate in media without cytokine. Antibodies are added at 5 ug/ml with or without LPS-removed anti-human secondary (Jackson ImmunoResearch) at 20 ug/ml. FACS analysis for CD86, CD83, CD11c, HLA-DR, and LIN (BD Biosciences) is performed 48 hrs post antibody addition as previously described. Additionally, Day 5 immature dendritic cells (CD14⁻CD11c⁺LIN⁻) are plated in 12 well dishes coated the previous day with 2 ug/ml antibody. Plates are washed 3 times with PBS before addition of T cells. CD4⁺ T cells from non-autologous donors were isolated and labeled with CFSE before addition to DCs in ratio of 1:10, 1:50, or 1:250. CD3/CD28 Dynal beads serve as a positive control. Day 5 post co-culture cells are analyzed by flow cytometry on a BD FACSCanto II for CFSE dilution. Percent CFSE$^{hi}$ compared to CFSE$^{lo}$ cells are calculated for each condition with FlowJo (TreeStar).

Example 28: Normalization and Increase of Toll-Like Receptor (TLR) Responses in Macrophages by Agonistic and/or Bispecific TREM1, Antibodies To evaluate the ability of anti-TREM1 antibodies to modify TLR response, Bone marrow-derived macrophages (BMDM) or primary peritoneal macrophage responses are altered to TLR signaling by deficiency of TREM1 (Turnbull, I R et al., J Immunol 2006; 177:3520-3524). It is believed that agonistic anti-TREM1, and/or TREM1 bispecific antibodies may increase or normalize TLR responses in macrophages. To elicit primary macrophages, mice are treated with 1.5 ml of 2% thioglycollate medium by intraperitoneal injection, and cells are then isolated by peritoneal lavage. To generate BMDM, total bone marrow is cultured in DMEM supplemented with 10% bovine calf serum, 5% horse serum, and 6 ng/ml recombinant human CSF-1 (R&D Systems). Cells are cultured for 5-6 days, and adherent cells are detached with 1m MEDTA in PBS. Cells are stained with commercially available antibodies: anti-CD11b, anti-CD40, anti-GR1 (BD Pharmingen), and F4/80 (Caltag Laboratories). BMDM are re-plated and allowed to adhere for 4 h at 37° C., and then TLR agonists, such as LPS (*Salmonella abortus equi*), zymosan (*Saccharomyces cerevisiae*), and CpG 1826 DNA (purchased from e.g., Sigma-Aldrich) are added. Cell culture supernatant is collected 24 h after stimulation and the levels of IFN-a4, IFN-b, IL-6, IL-12 p70, and TNF Cytokine concentrations in the culture supernatants are determined using mouse IFN-a4, IFN-b, IL-6, IL-12 p70, TNF, and IL-10 ELISA kits (eBioscience) and VeriKine Mouse IFN-b ELISA kit (PBL interferon source) according to manufacturer's protocol. Alternatively Cytometric Bead Array for human or mouse cytokines (BD Biosciences), or a V-PLEX Human or mouse Cytokine system with the Meso scale discovery System can be used. Alternatively, to analyze cytokines secretion BM derived macrophages of the indicated genotype are harvested at day 5 and plated on 96-well plate at 10⁵ cells/well. Cells are then stimulated with the indicated concentration of LPS or zymosan. 24 hours later, cell culture supernatants are harvested and analyzed by FACS for the presence of inflammatory cytokines (IL-12, IL-10, IFN-γ, TNFa, IL-6, MCP-1) using a Cytometric Bead Array kit (BD, following manufacturer's instructions). Cells are also analyzed by FACS to assess viability (DAPI) and expression of surface markers (CD11b, CD86).

Example 29: TREM1 Increases Secretion of Inflammatory Cytokines from Macrophages Bone marrow-derived macrophages (BMDM) or primary peritoneal macrophage responses possess altered TLR signaling when deficient in TREM1 (Turnbull, I R et al., J Immunol 2006; 177:3520-3524). In order to determine whether TREM1 antibodies induce changes in inflammatory cytokine production, mouse wild-type (WT) and TREM1 KO mice (KO) or TREM1 Hetrozygous (HETS), are cultured with the antibodies alone or with the antibodies in cobinations with non-saturating levels of TLR stimulators and the level of cytokines are measured after 24-48 h. To generate BMDM, total bone marrow from wild-type (WT), was cultured in RPMI supplemented with 10% bovine calf serum, 5% horse serum, and 50 ng/ml recombinant mouse CSF-1 (R&D Systems). Cells are cultured for 5 days, and adherent cells are detached with 1 mM EDTA in PBS. BMDM are plated on 96-well plates at 10⁵ cells/well and allowed to adhere for 4 h at 37° C. Cells are then exposed to antibodies alone, stimulated with TLR agonists LPS (*Salmonella abortus equi*) or zymosan (*Saccharomyces cerevisiae*) at concentrations ranging from 0.01-100 ng/ml (LPS) or 0.01-100 □g/ml (zymosan) alone or stimulated with LPS or zymosan in combination with TREM1 antibodies. Alternatively, macrophages isolated from WT and KO mice are cultured in the presence of 10 ng/ml of the cytokine IL-4 or 50 ng/ml of IFN-□□ with or without TREM1 antibodies. Cell culture supernatant was collected 24 or 48 h after stimulation and the levels of TNFa, IL-6, IL-10, and MCP-1 cytokines were measured by using Cytometric Bead Array Mouse Inflamation Kit (BD) according to manufacturer's protocol.

Example 30: Inhibition of the Anti-Inflammatory Cytokine IL-10 in Bone Marrow-Derived Myeloid Precursor Cells by Agonistic and/or Bispecific TREM1 Antibodies It is believed that bone marrow-derived myeloid precursor cells may show a decrease in the anti-inflammatory cytokine IL-10 following treatment with agonistic anti-TREM1, and/or TREM1 bispecific antibodies and stimulation with 100 ng/ml LPS (Sigma), by co-culturing with apoptotic cells, or by a similar stimulus. Isolation of bone marrow-derived myeloid precursor cells is performed as follows. Bone marrow cells are isolated from adult 6-8 week-old female C57BL/6 mice (Charles River, Sulzfeld, Germany) and from TREM1 deficient mice (KOMP repository) from the medullary cavities of the tibia and femur of the hind limbs. Removal of erythrocytes is performed by lysis with hypotonic solution. Cells are cultured in DMEM medium (Invitrogen) containing 10% fetal calf serum (Pan Biotech) and 10 ng/ml of GM-CSF (R&D Systems) in 75 cm$^2$ culture flasks (Greiner Bio-One). After 24 h, non-adherent cells are collected and re-seeded in fresh 75 cm$^2$ culture flasks. Medium is changed after 5 d and cells are cultured for an additional 10-11 d. Cells are cultured in the presence or absence of TREM1 antibodies, supernatant is collected after 24 h, and the level of IL-10 released from the cells is determined by IL-10 ELISA according to manufacturer's instructions (QuantikineM mouse IL-10, R&D Systems) (JEM (2005), 201; 647-657; and PLoS Medicine (2004), 4|Issue 4|e124).

Example 31: Induction of Phagocytosis in Cells From the Myeloid Lineage by Agonistic and/or Bispecific TREM1 Antibodies It is believed that agonistic anti-TREM1 and/or TREM1 bispecific antibodies may induce phagocytosis of apoptotic neurons, nerve tissue debris, non-nerve tissue debris, bacteria, other foreign bodies, and disease-causing proteins, optionally, such as A beta peptide, alpha synuclain protein, Tau protein, TDP-43 protein, prion protein, huntingtin protein, RAN, translation products antigene, including the DiPeptide Repeats, (DPRs peptides) composed of glycine-alanine (GA), glycine-proline (GP), glycine-arginine (GR), proline-alanine (PA), or proline-arginine (PR) in cells from the myeloid lineage, such as monocytes, Dendritic cells macrophages and microglia. The bispecific antibodies may be antibodies that recognize the TREM1 antigen and a second antigen that includes, without limitation, A beta peptide, antigen or an alpha synuclain protein antigene or, Tau protein antigene or, TDP-43 protein antigene or, prion protein antigene or, huntingtin protein antigene, or RAN, translation Products antigene, including the DiPeptide Repeats, (DPRs peptides) composed of glycine-alanine (GA), glycine-proline (GP), glycine-arginine (GR), proline-alanine (PA), or proline-arginine (PR). Monocytes are isolated from peripheral blood that is collected from adult C57BL/6 mice. Hypotonic lysis buffer depletes erythrocytes. Cells are plated on culture dishes in RPMI medium (Invitrogen) containing 10% fetal calf serum (Pan Biotech). Cells are cultured for several hours at 37° C. in 10% $CO_2$. After trypsinization, adherent cells are collected and used for phagocytosis experiments.

Microglial cells are prepared from the brains of post-natal day 3 to 5 (P3 to P5) C57BL/6 mice. In brief, meninges are removed mechanically, and the cells are dissociated by trituration and cultured in basal medium (BME; GIBCO BRL) supplemented with 10% FCS (PAN Biotech GmbH), 1% glucose (Sigma-Aldrich), 1% L-glutamine (GIBCO BRL), and 1% penicillin/streptomycin (GIBCO BRL), for 14 d to form a confluent glial monolayer. To collect microglial cells, the cultures are shaken on a rotary shaker (200 rpm) for 2 h. The attached astrocytes are used for immunohistochemistry. The detached microglial cells are seeded in normal culture dishes for 1 h, and then all non-adherent cells are removed and discarded. Purity of the isolated microglial cells is about 95% as determined by flow cytometry analysis with antibody directed against CD11b (BD Biosciences). Microglial cells are cultured in basal medium as previously described (Hickman S E et al., J Neurosci. 2008 Aug. 13; 28(33):8354-60; and Microglia Methods and Protocols Vol. 1041). Oligodendrocytes (i.e., neurons) and neuron-enriched cells are prepared from the brain of C57BL/6 mouse embryos (E15-16). In brief, brain tissue is isolated and mechanically dispersed and seeded in culture dishes pre-coated with 0.01 mg/ml poly-L-ornithin (Sigma-Aldrich) and 10 µg/ml laminin (Sigma-Aldrich). Cells are cultured in neuronal condition medium (BME; GIBCO BRL) supplemented with 2% B-27 supplement (GIBCO BRL), 1% glucose (Sigma-Aldrich), and 1% FCS (PAN Biotech GmbH). Cells are cultured for 5-10 d to obtain morphologically mature oligodendrocytes.

To conduct phagocytosis assays microglia, macrophages or dendritic cells are cultured with apoptotic neurons, nerve tissue debris, non-nerve tissue debris, bacteria, other foreign bodies, and disease-causing proteins. Neurons are cultured for 5-10 d, and okadaic acid is then added at the final concentration of 30 nM for 3 h to induce apoptosis. Neuronal cell membranes are labeled with CellTracker CM-DiI membrane dye (Molecular Probes). After incubation, apoptotic neurons or other targets of phagocytosis are washed two times and added to the transduced microglial culture at an effector/target ratio of 1:20. At 1 and 24 h after addition of apoptotic neurons, the number of microglia having phagocytosed neuronal cell membranes is counted under a confocal fluorescence microscope (Leica). Apoptotic cells are counted in three different areas at a magnification of 60. The amount of phagocytosis is confirmed by flow cytometry. Moreover, 24, 48, or 72 h after the addition of apoptotic neurons, cells are collected and used for RT-PCR of cytokines. To conduct microsphere bead or bacterial phagocytosis assay, microglia, macrophages or dendritic cells are treated with anti-TREM1 agonistic antibodies. After 24 h, 1.00 µm of red fluorescent microsphere beads (Fluoresbrite Polychromatic Red Mi-crospheres; Polysciences Inc.) or, fluorescent labeled bacteria are added for 1 h. Phagocytosis of microsphere beads or, fluorescent labeled bacteria, by microglia is analyzed by fluorescence microscopy. Furthermore, microglia are collected from the culture plates and analyzed by flow cytometry. The percentage of microglia having phagocytosed beads is determined. To conduct amyloid phagocytosis assay, HiLyteFluor™ 647 (Anaspec)-Abeta-(1-40) is resuspended in Tris/EDTA (pH 8.2) at 20 mM and then incubated in the dark for 3 d at 37° C. to promote aggregation. Microglial, macrophages or dendritic cells are pretreated in low serum (0.5% FBS supplemented with insulin), LPS (50 ng/ml), IFNc (100 units/ml), and anti-TREM1 agonistic antibodies for 24 h prior to the addition of aggregated fluorescently labeled a beta peptide. Amyloid phagocytosis and surface expression of TREM1 are determined by flow cytometric analysis 5 h post-addition of 100 nM aggregated HiLyteFluor™ 647-Ab-(1-40) (ASN NEURO (2010) 2(3): 157-170). Phagocytosis of other disease-causing proteins is conducted in a similar manner.

Example 32: Induction of CCR7 and Migration Toward CCL19 and CCL21 in Microglia, Macrophages, and Dendritic Cells by Agonistic TREM1, or TREM1 Bispecific Antibodies It is believed that anti-TREM1, and/or TREM1/bispecific antibodies may induce CCR7 and migration toward CCL19 and CCL21 in microglial cells, macrophages, and dendritic cells. Microglial, macrophages or dendritic cells are either cultured with agonistic anti-TREM1, and/or TREM1/ DAP12 bispecific antibodies, or with a control antibody. Cells are collected after 72 h, immuno-labeled with CCR7 specific anti-bodies, and analyzed by flow cytometry. To determine any functional consequences of increased CCR7 expression, a chemotaxis assay is performed. Microglia, macrophages or dendritic cells are stimulated via TREM1 with the agonistic anti-TREM1, and/or TREM1/DAP12 bispecific antibodies and placed in a two-chamber system. The number of microglial cells migrating toward the chemokine ligands CCL19 and CCL21 is quantified (JEM (2005), 201, 647-657). For the chemotaxis assay, microglial, macrophages or dendritic cells are exposed to the agonistic anti-TREM1 or TREM1/bispecific antibodies and treated with 1 µg/ml LPS. Microglia, macrophages or dendritic cells are transferred into the upper chamber of a transwell system (3 µm pore filter; Millipore) containing 450 µl medium with 100 ng/ml CCL19 or CCL21 (both from PeproTech) in the lower chamber. After a 1 h incubation period, the number of microglial macrophages or dendritic cells that have migrated to the lower chamber is counted in three independent areas by microscopy (JEM (2005), 201, 647-657).

Example 33: Induction of F-Actin in Microglia, Macrophages, and Dendritic Cells by Agonistic TREM1, and/or TREM1 Bispecific Antibodies It is believed that agonistic anti-TREM1, or TREM1 bispecific antibodies may induce F-actin in microglial cells, macrophages, and dendritic cells. Microglia, macrophages or dendritic cells and other cells of interest that are transduced with TREM1 or that express TREM1 are added to culture plates and then exposed to agonistic anti-TREM1, and/or TREM1 bispecific antibodies, or a control antibody. Cells are fixed, blocked, and then stained with Alexa Fluor 546-conjugated phalloidin (Molecular Probes) after 1 h and F-actin is labeled with a fluorescence dye. Images are collected by confocal laser scanning microscopy with a 40× objective lens (Leica). (JEM (2005), 201, 647-657).

Example 34: Induction of Osteoclast Production and Increased Rate of Osteoclastogenesis by Agonistic TREM1, DAP12, and/or TREM1/DAP12 Bispecific Antibodies It is believed that agonistic anti-TREM1 and/or TREM1 bispecific antibodies may induce osteoclast production and increase the rate of osteoclastogenesis. RAW264.7 cells that make osteoclasts or bone marrow-derived monocyte/macrophage (BMM) precursor cells are maintained in RPMI-1640 medium (Mediatech), or another appropriate medium, supplemented with 10% FBS (Atlantic Biologics, Atlanta, GA, USA) and penicillin-streptomycin-glutamine (Mediatech). TREM1B cDNA with a FLAG epitope added to the N terminus is inserted into the retroviral vector pMXpie upstream of an IRES, followed by an eGFP cDNA sequence. Cells are transfected with pMXpie-FLAG TREM1B, using Fugene 6 (Roche) according to manufacturer's protocol. Cells are selected in puromycin (Sigma) at 2 µg/ml. Stable puromycin-resistant clones are screened for anti-FLAG M2 monoclonal antibody (Sigma) binding by using flow cytometry, and then subcloned and maintained on puromycin selection media.

RAW264.7 cells expressing TREM1B are seeded in 96-well plates with 3000 cells/well in alpha-MEM medium supplemented with 10% FBS, penicillin-streptomycin-glutamine, 50 ng/ml RANKL, and 20 ng/ml M-CSF. The medium is changed every 3 days, exposed to anti-TREM1 agonistic antibodies and the number of multinucleated (at least three nuclei) TRACP$^+$ osteoclasts are counted and scored by light microscopy. To determine complexity and size, osteoclasts are counted by number of nuclei (>10 or 3-10 nuclei). The surface area of osteoclasts is also measured by using Image J software (NIH). In addition, expression levels of osteoclasts genes are determined. Total RNA is extracted from osteoclastogenic cultures at different time points using TRIzol reagent (Invitrogen). After first-strand cDNA synthesis using a SuperScript III kit (Invitrogen), real-time quantitative PCR reactions are performed for Nfatc1, Acp5, Ctsk, Calcr, and Ccnd1. Relative quantification of target mRNA expression is calculated and normalized to the expression of cyclophilin and expressed as (mRNA of the target gene/mRNA of cyclophilin) $3\times10^6$. (J. OF BONE AND MINERAL RESEARCH (2006), 21, 237-245; *J Immunol* 2012; 188:2612-2621).

Alternatively, BMM cells are seeded onto the plates in triplicate wells and treated with RANKL, M-CSF, and with an anti-TREM1, and/or TREM1 bispecific antibody, or an isotype-matched control monoclonal antibody. The medium is changed every 3 days until large multinucleated cells are visible. After 3 to 5 days in culture, cells are fixed with 3.7% formaldehyde in PBS for 10 min. Plates are then washed twice in PBS, incubated for 30 s in a solution of 50% acetone and 50% ethanol, and washed with PBS. Cells are stained for tartrate-resistant acid phosphatase (TRAP) with a kit from Sigma (product 435). Multinucleated (more than two nuclei), TRAP-positive cells are then counted by light microscopy, as described (e.g., Peng et al., (2010) Sci Signal., 3(122): ra38).

Example 35: Characterization of the Therapeutic Use of Agonistic TREM1 and/or TREM1 Bispecific Antibodies in Animal Models of Aging, Seizures, Spinal Cord Injury, Retinal Dystrophy, Frontotemporal Dementia, and Alzheimer's Disease The therapeutic utility of agonistic anti-TREM1, and/or TREM1 bispecific antibodies is tested in animal models for aging, seizures, spinal cord injury, retinal dystrophy, frontotemporal dementia, Huntington disease, Parkinson's disease amyotrophic lateral sclerosis and Alzheimer's disease, as previously described (e.g., Beattie, M S et al., (2002) Neuron 36, 375-386; Volosin, M et al., (2006) J. Neurosci. 26, 7756-7766; Nykjaer, A et al., (2005) Curr. Opin. Neurobiol. 15, 49-57; Jansen, P et al., (2007) Nat. Neurosci. 10, 1449-1457; Volosin, M et al., (2008) J. Neurosci. 28, 9870-9879; Fahnestock, M et al., (2001) Mol. Cell Neurosci. 18, 210-220; Nakamura, K et al., (2007) Cell Death. Differ. 14, 1552-1554; Yune, T et al., (2007) Brain Res. 1183, 32-42; Wei, Y et al., (2007) Neurosci. Lett. 429, 169-174; Provenzano, M J et al., (2008) Laryngoscope 118, 87-93; Nykjaer, A et al., (2004) Nature 427, 843-848; Harrington, A W et al., (2004) Proc. Natl. Acad. Sci. U.S.A. 101, 6226-6230; Teng, H K et al., (2005) J. Neurosci. 25, 5455-5463; Jansen, P et al., (2007) Nat. Neurosci. 10, 1449-1457; Volosin, M et al., (2008) J. Neurosci. 28, 9870-9879; Fan, Y J et al., (2008) Eur. J. Neurosci. 27, 2380-2390; Al-Shawi, R et al., (2008) Eur. J. Neurosci. 27, 2103-2114; and Yano, H et al., (2009) J. Neurosci. 29, 14790-14802).

Example 36: Characterization of the Therapeutic Use of Agonistic TREM1 and/or TREM1 Bispecific Antibodies in Models of Atherosclerosis The therapeutic utility of agonistic anti-TREM1 and/or TREM1 bispecific antibodies is tested in models of atherosclerosis, as previously described (e.g., Lance, A et al., (2011) Diabetes, 60, 2285; and Kjolby, M et al., (2012) Cell Metabolism 12, 213-223).

Example 37: Characterization of the Therapeutic Use of Agonistic TREM1 and/or TREM1 Bispecific Antibodies in a Model of Infection The therapeutic utility of agonistic anti-TREM1 and/or TREM1 bispecific antibodies is tested in a model of infection. For example, *Listeria monocytogenes* or other infection in normal mice or progranulin heterozygous mice can be used, as previously described (e.g., Yin, F et al., (2009) J. Exp. Med, 207, 117-128).

Example 38: Screening for Anti-TREM1 and/or TREM1 Bispecific Antibodies That Induce Phosphorylation of TREM1, DAP12, Syk, ERK, and AKT, Which Indicate Activation of the PI3K Pathway Cells (J774, RAW 264.7, BMM cells, or osteoclasts) are removed from tissue culture dishes with PBS-EDTA, washed with PBS, and counted. J774 ($40 \times 10^6$) or RAW 264.7 cells ($10 \times 10^6$ BMM or osteoclasts) are incubated with an anti-TREM1 and/or TREM1 bispecific antibody or with an isotype-matched control antibody at 1 µg/$10^6$ cells for 20 min on ice or under other conditions. Cells are lysed in ice-cold radioimmunoprecipitation assay (RIPA) buffer for 20 min followed by centrifugation at 16,000 g for 10 min at 4° C. to remove insoluble materials. The resulting supernatant is subjected to immunoprecipitation reactions with the indicated antibodies (DAP12, ERK, or AKT) and protein A- or protein G-agarose (Sigma). The beads are extensively washed with RIPA buffer and the proteins are separated by SDS-polyacrylamide gel electrophoresis (SDS-PAGE). The proteins are then transferred to nitrocellulose membranes by Western blotting, incubated with the appropriate antibodies (antibodies that specifically recognize the phosphorylated form of DAP12, ERK, or AKT) and visualized with the enhanced chemiluminescence (ECL) system (Pierce), as described (e.g., Peng et al., (2010) Sci Signal., 3(122): ra38).

Example 39: Screening for Anti-TREM1, and/or TREM1 Bispecific Antibodies that Induce Calcium Flux BMM cells are washed twice with HEPES-containing buffer [20 mM HEPES (pH 7.3), 120 mM NaCl, 1 mM CaCl, 1 mM MgCl, 5 mM KCl, glucose (1 mg/ml), bovine serum albumin (1 mg/ml)] followed by incubation in 0.05% Pluronic F-127 (Invitrogen) and 1 µM Indo-1 AM (Invitrogen) for 20 min at 37° C. Cells are washed twice with HEPES buffer and are then stimulated with an anti-TREM1 and/or TREM1 bispecific antibody (16 µg/ml) or with a control antibody (16 µg/ml) and monitored by spectrophotometer (PTL Photon Technology International). The Indo-1 fluorescence emission is converted to calcium ($Ca^{2+}$) according to manufacturer's instructions (e.g., Peng et al., (2010) Sci Signal., 3(122): ra38).

Example 40: Screening for Anti-TREM1 and/or TREM1 Bispecific Antibodies that Promote Survival of Osteoclasts and/or Microglia Murine Bone Marrow precursors are obtained by flushing tibial and femoral marrow cells with cold PBS. After one wash with PBS, erythrocytes are lysed using ACK Lysing Buffer (Lonza), washed twice with PBS and suspended at $0.5 \times 10^6$ cells/ml in complete RPMI media (10% FCS, Pen/Strep, Gln, neAA) with the indicated amounts of 50 ng/ml M-CSF to make macrophages or 10 ng/ml GM-CSF. For M2-type macrophages, 10 ng/ml IL-4 is added to the cultured cells. For M1-type macrophages, 50 ng/ml IFN-γ is added. In some experiment LPS or zymosan is added to the cell culture at day 5, at a concentration of 1 µg/ml-0.01 ng/ml. Recombinant cytokines were purchased by Peprotech. To analyze viability of BM derived macrophages, cells of the indicated genotype are prepared as above and cultured in graded concentrations of MCSF. Cells are either plated at $10^5$/200 µl in a 96-well plate (for viability analysis using a luciferase based-assay) or at $0.5 \times 10^6$/1 ml in a 6-well plate (for Tripan Blue exclusion cell count) in non-tissue culture treated plates. Media containing fresh M-CSF is added at day 3. At the indicated time points cells are gently detached from the plates with 3 mM EDTA and counted using a Burker chamber. In some experiments cells are also stained for FACS analysis using CD11b antibody and DAPI. Alternatively, cells are directly incubated with ToxGlo reagent (Promega) and luciferase activity is determined. In some experiments MCSF is withdrawn or not from the culture media at day 5 and cell viability is analyzed 36 hours later by FACS. Mature osteoclast cell cultures are differentiated in 24-well dishes with RANKL and M-CSF. After 4 days, complete medium is substituted with serum-free medium to induce apoptosis. Cells are treated with RANKL, PBS, and an anti-TREM1 and/or TREM1 bispecific antibody, or an isotype-matched control antibody, during the overnight serum starvation. Cells are fixed in 1% paraformaldehyde and stained with a TUNEL-based kit (Millipore Corporation) according to manufacturer's instructions. Apoptotic nuclei are counted with a Nikon TE2000-E microscope with 20× magnification. Results are expressed as the percentage of apoptotic cells relative to the total number of cells in six randomly selected fields of the two wells, as described (e.g., Peng et al., (2010) Sci Signal., 3(122): ra38). Similar assays are performed with primary microglial cells.

Example 41: TREM1 Increases the Survival of Macrophages and Dendritic Cells

To evaluate the role of TREM1 in cell survival, wild-type (WT), TREM1 knock-out (KO), and TREM1 heterozygous (Het) macrophages and dendritic cells are cultured in the presence of TREM1 antibodies or fragment thereof and cell viability is determined.

Murine bone marrow precursor cells from TREM1 WT, Het, and KO mice are obtained by flushing tibial and femoral marrow cells with cold PBS. After one wash with PBS, erythrocytes are lysed using ACK Lysing Buffer (Lonza), washed twice with PBS and suspended at $0.5 \times 10^6$ cells/ml in complete RPMI media (10% FCS, Pen/Strep, Gln, neAA) with the indicated amounts of 50 ng/ml M-CSF to produce macrophages, or 10 ng/ml GM-CSF to produce dendritic cells. For M2-type macrophages, 10 ng/ml IL-4 is added to the cultured cells. For M1-type macrophages, 50 ng/ml IFN-γ is added. In some experiments LPS or zymosan is added to the cell culture at day 5 at a concentration range of 1 μg/ml-0.01 ng/ml. Recombinant cytokines are purchased from Peprotech. To analyze viability of bone marrow-derived macrophages, cells are prepared as above and cultured in MCSF. Cells are either plated at $10^5/200$ μl in a 96-well plate (for viability analysis using a luciferase based-assay) or at $0.5 \times 10^6/1$ ml in a 6-well plate (for Tripan Blue exclusion cell count) in non-tissue culture treated plates. Media containing fresh M-CSF is added at day 3. At indicated time points cells are gently detached from the plates with 3 mM EDTA and counted using a Burker chamber. For FACS analysis of live cells, macrophages are cultured either in 50 ng/ml MCSF for 6 days (+MCSF) or in 50 ng/ml MCSF for 4 days before MCSF is removed for an additional 36 hrs (−MCSF). Cells are stained using CD11b antibody and DAPI. For luciferase viability assays, cell viability is measured at day 5 of culture in graded concentrations of growth factors GMCSF (dendritic cells), MCSF (M1 macrophages), or MCSF+IL-4 (M2 macrophages). Cells are directly incubated with ToxGlo reagent (Promega) and luciferase activity (luminescence) is determined. For FACS analysis of viable macrophages cultured in the presence of inflammatory mediators IFN-γ, LPS, or zymosan, cells are collected at day 5 and stained using CD11b antibody and DAPI. All experiments are conducted in the presence or absence of TREM1 antibodies or control antibodies or fragments thereof. Alternatively, WT mice are injected with 40 mg/kg or another dose of TREM1 or control antibodies intraperitonially (IP) followed by IP injections of 2-4 mg/kg LPS 12-24 h latter. Cells are collected from the abdominal cavity 6 hours later and analyzed by FACS using the following markers; CD11b-PB; CD11c Pecy7; APCcy7; Gr1 FITC; Ly6G PE; Amcyan live/dead cells.

Example 42: Screening for Anti-TREM1 and/or TREM1 Bispecific Antibodies that Normalize TREM1/TYROBP-Dependent Changes in Gene Expression within the Immune/Microglia Regulatory Module Microglial cells derived from mouse embryonic stem cells are genetically modified by lentiviral vectors to overexpress either full-length or a truncated version of Tyrobp that lacks both intracellular immunoreceptor tyrosine-based activation motif (ITAM) motifs. Microglia cells are also derived from mouse embryonic stem cells that are heterozygous for TREM1. To assess the genome-wide gene-expression changes in response to the perturbation of Tyrobp or TREM1, gene-expression data is derived from the RNA sequencing of mouse microglial macrophages or dendritic cells overexpressing: (1) vehicle, (2) full-length Tyrobp, or (3) dominant-negative truncated Tyrobp; or (4) overexpressing a knockdown construct for TREM1, such as SiRNA and cells which are heterozygous for TREM1 as well as from cells derived from TREM1 deficient mouse. Approximately 2,638 and 3,415 differentially expressed genes for the overexpression of full-length Tyrobp and truncated Tyrob are identified, respectively (Zhang et al., (2013) Cell 153, 707-720). Approximately 99% of the differentially expressed genes from the microglia overexpressing intact Tyrobp are downregulated compared to the control vehicle. For example, 658 genes, related to the vacuole/autophagy, as well as genes involved with RNA metabolism and cell-cycle mitosis are downregulated by active Tyrobp, but upregulated in cells expressing dominant-negative truncated Tyrobp. Conversely, some 2,856 genes for the vacuole/autophagy pathway and for mitochondrion are selectively upregulated in microglia expressing the dominant-negative truncated Tyrobp. Agonistic anti-TREM1, and/or TREM1 bispecific antibodies are screened for their ability to elicit gene expression profiles similar to that observed in normal microglial cells and in microglial cells overexpressing intact Tyrobp in cells that express dominant-negative truncated Tyrobp (Zhang et al., (2013) Cell 153, 707-720), in cells that express the knockdown construct for TREM1, or in cells that are heterozygous for TREM1. Antibodies that are capable of changing the gene expression network are selected.

Example 43: Analysis of the Anti-Cancer Effect of TREM1 Antibodies

Groups of 10 C57Bl6/NTac mice at 8 weeks (+/−2 weeks) of age are challenged subcutaneously with tumor cells (e.g. $1 \times 10^5$ to $1 \times 10^6$ MC38, Lewis Lung, or B16 cells) suspended in 100 ul PBS. Animals are anesthetized with isoflurane prior to implant. Starting at day 2, groups of mice are injected intraperitoneally every 3 days for 4 doses with 200 ug of each of antagonistic anti-TREM1 antibodies, such as those described in Examples 38 and 40. Tumor growth is monitored with a caliper biweekly to measure tumor growth starting at day 4. The endpoint of the experiment is a tumor volume of 2000 mm³ or 60 days. Tumor growth and percent survival are the outcome measures. Reduced tumor take and growth rate, reduced number of tumor infiltrating immune suppressor macrophages, and increased effector T cell influx into the tumor indicate the anti-cancer effects of blocking anti-TREM1 antibodies.

Example 44: Analysis of Additive Anti-Tumor Effect of Combination Therapy that Combines TREM1 Antibodies with Antibodies Against Inhibitory Checkpoint Proteins or Inhibitory Cytokines/Chemokines and their Receptors Groups of 15 C57Bl6/NTac mice at 8 weeks (+/−2 weeks) of age are challenged subcutaneously with tumor cells. Animals are anesthetized with isoflurane prior to implant. Starting at day 2, mice are injected i.p. every 3 days for 4 doses with 200 ug anti-TREM1 antibodies alone or in combination with antibodies against checkpoint proteins (e.g. anti-PDL1 mAb clone 10F.9G2 and/or anti-CTLA-4 mAb clone UC10-4F10-11) at day 3, 6, and 9. Treatment groups include anti-TREM1; anti-CTLA-4; anti-PDL1; anti-TREM1+anti-CTLA-4; anti-TREM1+anti-PDL1; and isotype control. Tumor growth is monitored with a caliper biweekly to measure tumor growth starting at day 4. The endpoint of the experiment is a tumor volume of 2000 mm³ or 60 days. Tumor growth and % survival are the outcome measures. A decrease in tumor growth and an increase in % survival with combination therapy indicate that anti-TREM1 antibodies have additive or synergistic therapeutic effects with anti-checkpoint antibodies. Antagonistic antibodies against checkpoint molecules include antibodies against PDL1, PDL2, PD1, CTLA-4, B7-H3, B7-H4, HVEM, BTLA, KIR, GAL9, TIM3, A2AR, LAG-3, and phosphatidylserine (PS). Antagonist antibodies against inhibitory cytokines include antibodies against CCL2, CSF-1, and IL-2.

Example 45: Analysis of Additive Anti-Tumor Effect of Combination Therapy that Combines TREM1 Antibodies with Antibodies that Activate Stimulatory Checkpoint Proteins Groups of 15 C57Bl6/NTac mice at 8 weeks (+/−2 weeks) of age are challenged subcutaneously with tumor cells. Animals are anesthetized with isoflurane prior to implant. Starting at day 2, mice are injected intraperitoneally every 3 days for 4 doses with 200 ug anti-TREM1 antibodies alone or in combination with agonistic antibodies that activate stimulatory checkpoint proteins (e.g., OX40 or ICOS mAb) at day 3, 6, and 9. Tumor growth is monitored with a caliper biweekly to measure tumor growth starting at day 4. The endpoint of the experiment is a tumor volume of 2000 mm$^3$ or 60 days. Tumor growth and percent survival are the outcome measures. A decrease in tumor growth and an increase in % survival with combination therapy indicate that anti-TREM1 antibodies have additive or synergistic therapeutic effects with stimulatory checkpoint antibodies. Stimulatory checkpoint antibodies include agonistic/stimulatory antibodies against CD28, ICOS, CD137, CD27, CD40, and GITR.

Example 46: Analysis of Anti-Stroke Effect of TREM1 Antibodies

Transient occlusion of the middle cerebral artery (MCAO)—a model that closely resembles human stroke is used to induce cerebral infarction in mice. Monofilament (70SPRe, Doccol Corp, USA) is introduced into the internal carotid artery through an incision of the right common carotid artery. The middle cerebral artery is occluded for 30 minutes with a range of reperfusion times (6 h, 12 h, 24 h, 2 d, 7 d and 28 d). The effect of surgery is controlled using sham animals at 12 h and at 7 d. Sham animals undergo the same surgical procedure without occlusion of the middle cerebral artery. MCAO animals treated with agonistic anti-TREM1 antibodies or control antibodies are tested for infarct volumetry, acute inflammatory response (12 h reperfusion), transcription of pro-inflammatory cytokines TNFa, IL-1a, and IL-1b, microglial activity (CD68, Iba1), transcription of chemokines CCL2 (MCP1), CCL3 (MIP1a and the chemokine receptor CX3CR1 and invasion of CD3-positive T-cells (Sieber et al. (2013) PLoS ONE 8(1): e52982. doi: 10.1371/journal.pone.0052982.).

Example 47: Analysis of Anti-Alzheimer's Disease Effect of Anti-TREM1 Antibodies To evaluate the ability of anti-TREM1 antibodies to delay, prevent, or reverse the development of Alzheimer's disease (AD), 5×FAD mice are used. 5×FAD mice overexpress mutant human APP (695) with the Swedish (K670N, M671L), Florida (I716V), and London (V717I) familial Alzheimer's disease (FAD) mutations, along with human PS1 harboring two FAD mutations, M146L and L286V. Both transgenes are regulated by the mouse Thy1 promoter to drive over expression on the brain and recapitulate major features of AD. Mice treated with the agonistic anti-TREM1 antibodies or with control antibodies are tested for A beta plaque load with immunohistochemistry and by ELISA of tissue extracts. They are further tested for the number of microglia in the brain, and for reduction in cognitive deficit using Morris Water maze, a spatial learning and memory task, Radial Arm Water Maze, a spatial learning and memory task, Y Maze (quantifies spontaneous alternation as a measure of spatial cognition), novelty preference in in an open field, operant learning to assess learning and memory, and fear conditioning (mousebiology.org website, Wang et al., (2015) Cell, pii: S0092-8674(15)00127-0).

Example 48: Analysis of the Protective Effect of TREM1 Antibodies in Respiratory Tract Infections To evaluate the ability of TREM1 antibodies to delay, prevent, or treat bacterial respiratory tract infections, a preclinical mouse model involving challenge of C57Bl6 mice with *Streptococcus pneumoniae* is used. This model involves intranasal (i.n.) administration of 105 CFU *S. pneumoniae* serotype 3 (ATCC 6303) as described (see, e.g., Sharif O et al, 2014 *PLoS Pathog.* 2014 June; 10(6): e1004167; and Schabbauer G et al, 2010 *J Immunol* 185: 468-476). In this model ~90% WT C57Bl6 mice succumb to infection within 6 days post infection. Ten to fifteen mice/group are challenged with *S. pneumoniae* and concomitantly are treated with antagonist anti-TREM1 antibodies every other day starting from day 0. The first dose of anti-TREM1 antibodies is administered 3 hours prior to challenge with *S. pneumonia*. Mice are monitored daily for 15 days to check for death events. % of mice surviving bacteria challenge is determined. In separate experiments, count of bacterial load and cytokine expression in the blood and in the lungs is also determined. 24 or 48 hours after infection blood is collected in EDTA-containing tubes and plated on agar plates to enumerate bacterial CFU in the plasma. Plasma is stored at −20° C. for cytokine analysis by ELISA. Lungs are harvested, homogenized and plated on agar plates to enumerate bacterial CFU, or incubated for 30 min in lysis buffer and supernatants analyzed for cytokine measurements. In separate experiments, lungs are collected 40 hours post bacterial infection, fixed in 10% formalin, and embedded in paraffin for H&E pathology analysis.

Example 49: Analysis of the Protective Effect of TREM1 Antibodies in Sepsis

To evaluate the ability of TREM1 antibodies to delay, prevent, or treat sepsis, a preclinical mouse model involving systemic challenge of C57Bl6 mice with LPS is used. This model involves intraperitoneal (i.p.) administration of 37 mg/ml LPS as described (see, e.g., Gawish R et al, 2014 *FASEB J*). In this model >95% WT C57Bl6 mice succumb infection within 40 hours post LPS injection. Cohorts of mice are challenged with LPS and concomitantly are treated with antagonist anti-TREM1 antibodies every day starting from day 0. The first dose of anti-TREM1 antibodies is administered 3 hours prior to challenge with LPS. Mice are monitored every ~4 hours during daytime, to check for death events. Percentage of mice surviving LPS challenge is determined.

In separate experiments, peritoneal lavage fluid (PLF) is collected. Supernatants are stored at −20° C. for cytokine analysis by ELISA; pelleted cells are counted to quantify inflammatory cells recruited in the peritoneal cavity. Similar studies can be conducted to test the efficacy of TREM1 antibodies in other models of infection (see, e.g., Sun et al., (2013) *Invest Ophthalmol Vis Sci.* 17; 54(5):3451-62).

Example 50: Analysis of the Protective Effect of TREM1 Antibodies in Acute and Chronic Colitis To evaluate the ability of anti-TREM1 antibodies to delay, prevent, or treat colitis, preclinical mouse models of acute or chronic colitis are used. For DSS-induced colitis, mice receive 3% DSS in drinking water ad libitum for 8 days. For TNBS-induced colitis, mice are anesthetized and treated with an intra-rectal injection of 3 mg TNBS in 20% ethanol (vol/vol) or vehicle alone as a control. For the chronic colitis model, all mice are treated with 3 cycles of 2% DSS for 5 days, followed by a 10-day recovery period. For all models, weight loss, stool consistency, and presence of fecal occult blood are monitored daily and used to calculate the disease activity index, as described (see, e.g., Correale C, 2013, *Gastroenterology*, February 2013, pp. 346-356.03). Cohorts of mice are treated with antagonist anti-TREM1 antibodies every day starting from day 0 and subjected to DSS or TNBS administration. Mice are monitored every day, to check for weight loss, stool consistency, and presence of fecal occult blood were monitored daily and used to calculate the disease activity index, as described (see, e.g., S. Vetrano, *Gastroenterology*, 135 (2008), pp. 173-1.84). In separate experiments, endoscopic and histological images of mucosal damage are collected to evaluate inflammatory cell infiltration and mucosal damage. Similar studies can be conducted to test the benefit of TREM1 antibodies in other models of autoimmunity including Crohn's disease, inflammatory bowel disease, and ulcerative colitis (see, e.g., Low et al., (2013) *Drug Des Devel Ther.;* 7: 1341-1357; and Sollid et al., (2008) *PLoS Med* 5(9): e198).

Example 51: Analysis of the Protective Effect of Agonist TREM1 in Wound Healing

To evaluate the ability of anti-TREM1 antibodies to increase colonic wound repair following injury, a mouse model of biopsy injury in the colon is used. In this model, the endoscope with outer operating sheath is inserted to the mid-descending colon and the mucosa is surveyed to the ano-rectal junction. Then, a single full thickness area of the entire mucosa and submucosa is removed with flexible biopsy forceps with a diameter of 3 French, avoiding penetration of the muscularis propria. Each mouse is biopsy injured at 3-5 sites along the dorsal side of the colon (see, e.g., Seno H, 2008, *Proc Natl Acad Sci USA.* 2009 Jan. 6; 106(1): 256-261). Cohorts of mice are treated with agonist anti-TREM1 antibodies 2 or 3 days after biopsy injury. Mice are monitored every day for 15 days, to check for weight loss and wound healing by measuring the surface area of lesions.

Example 52: Analysis of the Protective Effect of TREM1 Antibodies in Retinal Degeneration AMD is a degenerative disease of the outer retina. It is thought that inflammation, particularly inflammatory cytokines and macrophages, contribute to AMD disease progression. The presence of macrophages in the proximity of AMD lesions is documented, in the drusen, Bruch's membrane, choroid and retina. Macrophages release tissue factor (TF) and vascular endothelial growth factor (VEGF), which triggers the expansion of new blood vessels formation in patients showing choroidal neovasulcarization. The type of macrophage present in the macular choroid changes with age, displaying elevated levels of M2 macrophages in older eyes compared to younger eyes. However, advanced AMD maculae had higher M1 to M2 rations compared to normal autopsied eyes of similar age. (see, e.g., Cao X et al, (2011), *Pathol Int* 61(9): pp528-35). This suggests a link between classical M1 macrophage activation in the eye in the late onset of AMD progression. Retinal microglia cells are tissue-resident macrophages that are also normally present in the inner retina. In the event of damage, microglia can be activated and act as mediator of inflammation. Activated microglia has been detected in the AMD tissue samples and has been proposed as one potential contributor of inflammatory processed that lead to AMD pathogenesis (Gupta et al., (2003) *Exp Eye Res.,* 76(4):463-71.). The ability of antagonist TREM1 antibodies to prevent, delay, or reverse AMD is tested in one or more of AMD models (see, e.g., Pennesi et al., (2012) *Mol Aspects Med.;* 33(4): 487-509). Overall inflammatory macrophages (either M1 and/or activated microglia) are documented to correlate with AMD disease progression and therefore represent a therapeutic target for antagonist TREM1 antibodies. Similar therapeutic benefit can be achieved in glaucoma and genetic forms or retinal degeneration such as retinitis pigmentosa.

The ability of TREM1 antibodies to prevent, delay, or reverse retinal ganglion cell degeneration in glaucoma is tested in a glaucoma model (see, e.g., El-Danaf et al., (2015). *J Neurosci.* 11; 35(6):2329-43). Likewise, the therapeutic benefit of TREM1 antibodies in genetically induced retinal degeneration and retinitis pigmentosa is tested as described in Chang et al., (2002) Vision Res.; 42(4):517-25, and in "Retinal Degeneration Rat Model Resource Availability of P23H and S334ter Mutant Rhodopsin Transgenic Rats and RCS Inbred and RCS Congenic Strains of Rats," M M LaVail, Jun. 30, 2011.

Example 53: Analysis of the Protective Effect of TREM1 Antibodies in Adipogenesis and Diet-Induced Obesity To test the effect of TREM1 antibodies in adipogenesis and obesity, a mouse model of high-fat diet (HFD) is used (see, e.g., Park et al., (2015) *Diabetes.* 64(1):117-27).

Example 54: Analysis of the Protective Effect of TREM1 Antibodies in Malaria

TREM1 expression in the nonparenchymal liver cells closely correlates with resistance to liver stage infection with the maliaria agent *Plasmodium berghei* (Gonçalves et al., (2013) *Proc Natl Acad Sci* 26; 110(48):19531-6). Without wishing to be bound to theory, it is believed that TREM1 antibodies increase resistence to liver stage infection with *P. berghei*. The ability of TREM1 antibodies to increase resistance to malaria infection is tested as diescribed in Gonçalves et al., (2013) *Proc Natl Acad Sci* 26; 110(48):19531-6. Briefly, GFP-expressing *P. berghei* ANKA sporozoites are obtained by dissection of infected salivary glands from *Anopheles stephensi* mosquitoes. Sporozoite suspensions in RPMI medium are injected i.v. in 100 μL of inocula containing $10^4$ sporozoites per mouse. Livers are collected at 40 h after injection or survival, and parasitemia is followed for 28 days. For experimental cerebral malaria scoring, neurologic symptoms are monitored from day 5 after injection.

Example 55: Analysis of the Protective Effect of TREM1 Antibodies in Osteoporosis Bone is a dynamic organ constantly remodeled to support calcium homeostasis and structural needs. The osteoclast is the cell responsible for removing both the organic and inorganic components of bone. The osteoclast is derived from hematopoietic progenitors in the macrophage lineage and differentiates in response to the tumor necrosis factor family cytokine receptor activators of NFκB ligand. Osteoclasts, the only bone-resorbing cells, are central to the pathogenesis of osteoporosis and osteopetrosis (Novack et al., (2008) *Annual Rev Pathol.,* 3:457-84). Osteoporosis is a progressive bone disease that is characterized by a decrease in bone mass and density which can lead to an increased risk of fracture. It is mostly manifested in the first years following menopause, when bone turnover is accelerated, with increased activity of both osteoclasts and osteoblasts. Owing to an imbalance in the processes of resorption and synthesis, however, the net effect is bone loss, which is largely trabecular. Thus, the most prevalent sites of fracture in osteoporosis are the wrist, femoral neck, and vertebral bodies, in which the trabecular structure is key to overall bone strength. Accelerated osteoclast differentiation and increased bone resorption capacity, resulting in osteoporosis have been described in animal models lacking the expression of TREM1 (Otero et al (2012) *J. Immunol.* 188, 2612-2621). Reduced osteoclast function results in osteopetrosis, with increased bone mass and elimination of bone marrow space, as observed in animal models lacking DAP12 ITAM signaling adapter and resulting in a significant defect in differentiation of osteoclast-like cells (Koga, et al., (2004) *Nature* 428: 758-763). Without wishing to be bound by theory, it is believed that administering an anti-TREM1 antibody of the present disclosure can prevent, reduce the risk of, and/or treat osteoporosis. In some embodiments, administering an agonist anti-TREM1 antibody may induce one or more TREM1 activities in an individual having osteopetrosis (e.g., DAP12 phosphorylation, Syk activation, and accelerated differentiation into osteoclasts) (Peng et al (2010). *Sci Signal.* 2010 18; 3 122; and Humphrey et al., (2006) *J Bone Miner Res.,* 21 (2): 237-45).

Example 56: Identification of Tumor Types in Humans Most Likely to Respond to Anti-TREM1 Antibodies TREM1 is expressed on tumor-infiltrating myeloid cells in human cancers; modulating TREM1 activity is expected to have more of an impact in some tumor types than others. To identify the tumor types where anti-TREM1 antibodies are most likely to have an impact on disease, more than 8000 primary human tumor samples across 21 tumor types within the TCGA database were interrogated for an association between TREM1 expression, as measured by RNAseq, and patient survival. The association between expression and survival was evaluated by the Cox proportional hazards model in R, correcting for gender, age, and tumor grade.

Significant associations between high TREM1 expression and poor patient prognosis, after Bonferroni multiple testing corrections, were observed in cervical cancer (CESC, nominal p=1.8E-3, corrected p=3.8E-2), liver cancer (LIHC, nominal p=3.7E-5, corrected p=7.7E-4), and low grade glioma (LGG, nominal p=1.3E-5, corrected p=2.7E-4). Association was also observed for squamous non-small cell lung cancer (LUSC, nominal p=3.6E-3, corrected p=7.6E-2). Examples of significant associations are shown in FIG. 17 where High and Low TTREM1 expression were defined as the TREM1 expression level in the top and bottom 20% of samples within a given tumor type. In one analysis, association was also observed with glioma and glioblastoma when grouped together and renal clear cell carcinoma, renal papillary cell carcinoma, and chromophobe renal cell carcinoma, when grouped together; and nominal associations between high TREM1 expression and poor patient survival were found in pancreatic cancer and renal clear cell carcinoma.

REFERENCES

Adib-Conquy, M., M. Monchi, C. Goulenok, I. Laurent, M. Thuong, J.-M. Cavaillon and C. Adrie (2007). "INCREASED PLASMA LEVELS OF SOLUBLE TRIGGERING RECEPTOR EXPRESSED ON MYELOID CELLS 1 AND PROCALCITONIN AFTER CARDIAC SURGERY AND CARDIAC ARREST WITHOUT INFECTION." *Shock* 28(4): 406-410.

Allcock, R. J. N., A. D. Barrow, S. Forbes, S. Beck and J. Trowsdale (2003). "The human TREM gene cluster at 6p21.1 encodes both activating and inhibitory single IgV domain receptors and includes NKp44." *European Journal of Immunology* 33(2): 567-577.

Arts, R. J., L. A. Joosten, C. A. Dinarello, B. J. Kullberg, J. W. van der Meer and M. G. Netea (2011). "TREM-1 interaction with the LPS/TLR4 receptor complex." *Eur Cytokine Netw* 22(1): 11-14.

Arts, R. J. W., L. A. B. Joosten, J. W. M. van der Meer and M. G. Netea (2012). "TREM-1: intracellular signaling pathways and interaction with pattern recognition receptors." *Journal of Leukocyte Biology* 93(2): 209-215.

Barletta, K. E., R. E. Cagnina, M. D. Burdick, J. Linden and B. Mehrad (2012). "Adenosine A2B Receptor Deficiency Promotes Host Defenses against Gram-Negative Bacterial Pneumonia." *American Journal of Respiratory and Critical Care Medicine* 186(10): 1044-1050.

Borrello, M. G., D. Degl'Innocenti and M. A. Pierotti (2008). "Inflammation and cancer: The oncogene-driven connection." *Cancer Letters* 267(2): 262-270.

Bosco, M. C., D. Pierobon, F. Blengio, F. Raggi, C. Vanni, M. Gattorno, A. Eva, F. Novelli, P. Cappello, M. Giovarelli and L. Varesio (2010). "Hypoxia modulates the gene expression profile of immunoregulatory receptors in human mature dendritic cells: identification of TREM-1 as a novel hypoxic marker in vitro and in vivo." *Blood* 117(9): 2625-2639.

Bouchon, A., J. Dietrich and M. Colonna (2000). "Cutting edge: inflammatory responses can be triggered by TREM-1, a novel receptor expressed on neutrophils and monocytes." *J Immunol* 164(10): 4991-4995.

Bouchon, A., F. Facchetti, M. A. Weigand and M. Colonna (2001). *Nature* 410(6832): 1103-1107.

Collins, C. E., D. T. La, H. T. Yang, F. Massin, S. Gibot, G. Faure and W. Stohl (2008). "Elevated synovial expression of triggering receptor expressed on myeloid cells 1 in patients with septic arthritis or rheumatoid arthritis." *Annals of the Rheumatic Diseases* 68(11): 1768-1774.

El Mezayen, R., M. El Gazzar, M. C. Seeds, C. E. McCall, S. C. Dreskin and M. R. Nicolls (2007). "Endogenous signals released from necrotic cells augment inflammatory responses to bacterial endotoxin." *Immunology Letters* 111(1): 36-44.

Ford, J. W. and D. W. McVicar (2009). "TREM and TREM-like receptors in inflammation and disease." *Current Opinion in Immunology* 21(1): 38-46.

Gibot, S. (2004). "Plasma Level of a Triggering Receptor Expressed on Myeloid Cells-1: Its Diagnostic Accuracy in Patients with Suspected Sepsis." *Annals of Internal Medicine* 141(1): 9.

Gibot, S. (2004). "A Soluble Form of the Triggering Receptor Expressed on Myeloid Cells-1 Modulates the Inflammatory Response in Murine Sepsis." *Journal of Experimental Medicine* 200(11): 1419-1426.

Gibot, S., C. Alauzet, F. Massin, N. Sennoune, Gilbert C. Faure, M. C. Béné, A. Lozniewski, P. E. Bollaert and B. Lévy (2006). "Modulation of the Triggering Receptor Expressed on Myeloid Cells-1 Pathway during Pneumonia in Rats." *The Journal of Infectious Diseases* 194(7): 975-983.

Gibot, S., C. Buonsanti, F. Massin, M. Romano, M. N. Kolopp-Sarda, F. Benigni, G. C. Faure, M. C. Bene, P. Panina-Bordignon, N. Passini and B. Levy (2006). "Modulation of the triggering receptor expressed on the myeloid cell type 1 pathway in murine septic shock." *Infect Immun* 74(5): 2823-2830.

Gibot, S., F. Massin, M. Marcou, V. Taylor, R. Stidwill, P. Wilson, M. Singer and G. Bellingan (2007). "TREM-1 promotes survival during septic shock in mice." *European Journal of Immunology* 37(2): 456-466.

Haselmayer, P., L. Grosse-Hovest, P. von Landenberg, H. Schild and M. P. Radsak (2007). "TREM-1 ligand expression on platelets enhances neutrophil activation." *Blood* 110(3): 1029-1035.

Ho, C.-C., W.-Y. Liao, C.-Y. Wang, Y.-H. Lu, H.-Y. Huang, H.-Y. Chen, W.-K. Chan, H.-W. Chen and P.-C. Yang (2008). "TREM-1 Expression in Tumor-associated Macrophages and Clinical Outcome in Lung Cancer." *Am J Respir Crit Care Med* 177(7): 763-770.

Klesney-Tait, J., K. Keck, X. Li, S. Gilfillan, K. Otero, S. Baruah, D. K. Meyerholz, S. M. Varga, C. J. Knudson, T. O. Moninger, J. Moreland, J. Zabner and M. Colonna (2012). "Transepithelial migration of neutrophils into the lung requires TREM-1." *Journal of Clinical Investigation* 123(1): 138-149.

Klesney-Tait, J., I. R. Turnbull and M. Colonna (2006). "The TREM receptor family and signal integration." *Nat Immunol* 7(12): 1266-1273.

Kuraishy, A., M. Karin and Sergei I. Grivennikov (2011). "Tumor Promotion via Injury- and Death-Induced Inflammation." *Immunity* 35(4): 467-477.

Lin, Y. T., K. Y. Tseng, Y. C. Yeh, F. C. Yang, C. P. Fung and N. J. Chen (2014). "TREM-1 promotes survival during Klebsiella pneumoniae liver abscess in mice." *Infect Immun* 82(3): 1335-1342.

Murakami, Y., T. Akahoshi, I. Hayashi, H. Endo, S. Kawai, M. Inoue, H. Kondo and H. Kitasato (2006). "Induction of triggering receptor expressed on myeloid cells 1 in murine resident peritoneal macrophages by monosodium urate monohydrate crystals." *Arthritis & Rheumatism* 54(2): 455-462.

Radsak, M. P., H. R. Salih, H. G. Rammensee and H. Schild (2004). "Triggering Receptor Expressed on Myeloid Cells-1 in Neutrophil Inflammatory Responses: Differential Regulation of Activation and Survival." *The Journal of Immunology* 172(8): 4956-4963.

Radsak, M. P., C. Taube, P. Haselmayer, S. Tenzer, H. R. Salih, R. Wiewrodt, R. Buhl and H. Schild (2007). "Soluble Triggering Receptor Expressed on Myeloid Cells 1 Is Released in Patients with Stable Chronic Obstructive Pulmonary Disease." *Clinical and Developmental Immunology* 2007: 1-7.

Read, C. B., J. L. Kuijper, S. A. Hjorth, M. D. Heipel, X. Tang, A. J. Fleetwood, J. L. Dantzler, S. N. Grell, J. Kastrup, C. Wang, C. S. Brandt, A. J. Hansen, N. R. Wagtmann, W. Xu and V. W. Stennicke (2015). "Cutting Edge: identification of neutrophil PGLYRP1 as a ligand for TREM-1." *J Immunol* 194(4): 1417-1421.

Saurer, L., S. Rihs, M. Birrer, N. Saxer-Seculic, M. Radsak and C. Mueller (2012). "Elevated levels of serum-soluble triggering receptor expressed on myeloid cells-1 in patients with IBD do not correlate with intestinal TREM-1 mRNA expression and endoscopic disease activity." *Journal of Crohn's and Colitis* 6(9): 913-923.

Schenk, M., A. Bouchon, F. Seibold and C. Mueller (2007). "TREM-1-expressing intestinal macrophages crucially amplify chronic inflammation in experimental colitis and inflammatory bowel diseases." *Journal of Clinical Investigation* 117(10): 3097-3106.

Trinchieri, G. (2011). "Innate inflammation and cancer: Is it time for cancer prevention?" *F1000 Med Rep* 3.

Trinchieri, G. (2012). "Cancer and Inflammation: An Old Intuition with Rapidly Evolving New Concepts *." *Annual Review of Immunology* 30(1): 677-706.

Weber, B., L. Saurer, M. Schenk, N. Dickgreber and C. Mueller (2011). "CX3CR1 defines functionally distinct intestinal mononuclear phagocyte subsets which maintain their respective functions during homeostatic and inflammatory conditions." *European Journal of Immunology* 41(3): 773-779.

Weber, B., S. Schuster, D. Zysset, S. Rihs, N. Dickgreber, C. Schurch, C. Riether, M. Siegrist, C. Schneider, H. Pawelski, U. Gurzeler, P. Ziltener, V. Genitsch, F. Tacchini-Cottier, A. Ochsenbein, W. Hofstetter, M. Kopf, T. Kaufmann, A. Oxenius, W. Reith, L. Saurer and C. Mueller (2014). "TREM-1 deficiency can attenuate disease severity without affecting pathogen clearance." *PLoS Pathog* 10(1): e1003900.

Wu, J., J. Li, R. Salcedo, N. F. Mivechi, G. Trinchieri and A. Horuzsko (2012). "The proinflammatory myeloid cell receptor TREM-1 controls Kupffer cell activation and development of hepatocellular carcinoma." *Cancer Res* 72(16): 3977-3986.

Wu, J., J. Li, R. Salcedo, N. F. Mivechi, G. Trinchieri and A. Horuzsko (2012). "The Proinflammatory Myeloid Cell Receptor TREM-1 Controls Kupffer Cell Activation and Development of Hepatocellular Carcinoma." *Cancer Research* 72(16): 3977-3986.

Yuan, Z., H. J. Mehta, K. Mohammed, N. Nasreen, R. Roman, M. Brantly and R. T. Sadikot (2014). "TREM-1 is induced in tumor associated macrophages by cyclooxygenase pathway in human non-small cell lung cancer." *PLoS One* 9(5): e94241.

Zanzinger, K., C. Schellack, N. Nausch and A. Cerwenka (2009). "Regulation of triggering receptor expressed on myeloid cells 1 expression on mouse inflammatory monocytes." *Immunology* 128(2): 185-195.

| ANTIBODY VARIABLE REGION SEQUENCES |
|---|

Ligh chain variable region sequences

TI-1 (ADI-19067) light chain variable region
(SEQ ID NO: 316)
DIQMTQSPSSLSASVGDRVTITCQASQDISNYLNWYQQKPGKAPKLLIYDASNLETGVPSRFSGSGSG

TDFTFTISSLQPEDIATYYCQQVYVLPFTFGGGTKVEIK

TI-2 (ADI-19068) light chain variable region
(SEQ ID NO: 317)
EIVLTQSPGTLSLSPGERATLSCRASQSVSSSYLAWYQQKPGQAPRLLIYGASSRATGIPDRFSGSGS

GTDFTLTISRLEPEDFAVYYCQQYLGFPPTFGGGTKVEIK

TI-3 (ADI-19069) light chain variable region
(SEQ ID NO: 318)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQSFLTPWTFGGGTKVEIK

TI-4 (ADI-19070) light chain variable region
(SEQ ID NO: 319)
EIVMTQSPATLSVSPGERATLSCRASQSVSSNLAWYQQKPGQAPRLLIYGASTRATGIPARFSGSGSG

TEFTLTISSLQSEDFAVYYCQQFNNHPITFGGGTKVEIK

TI-5 (ADI-19071) light chain variable region
(SEQ ID NO: 320)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCVQARQTPLTFGGGTKVEIK

TI-6 (ADI-19072) light chain variable region
(SEQ ID NO: 321)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQARDAPWTFGGGTKVEIK

TI-7 (ADI-19073) light chain variable region
(SEQ ID NO: 322)
DIVMTQSPDSLAVSLGERATINCKSSQSVLFSSNNKNYLAWYQQKPGQPPKLLIYWASTRESGVPDRF

SGSGSGTDFTLTISSLQAEDVAVYYCQQLASYPYTFGGGTKVEIK

TI-8 (ADI-19074) light chain variable region
(SEQ ID NO: 323)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQARQTPFTFGGGTKVEIK

TI-9 (ADI-19076) light chain variable region
(SEQ ID NO: 324)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQARQAPWTFGGGTKVEIK

TI-10 (ADI-19077) light chain variable region
(SEQ ID NO: 325)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQARQVPPWTFGGGTKVEIK

TI-11 (ADI-19078) light chain variable region
(SEQ ID NO: 326)
DIVMTQSPLSLPVTPGEPASISCRSSQSLLHSNGYNYLDWYLQKPGQSPQLLIFLGSNRASGVPDRFS

GSGSGTDFTLKISRVEAEDVGVYYCMQARQAFTFGGGTKVEIK

TI-12 (ADI-19079) light chain variable region
(SEQ ID NO: 327)
EIVLTQSPATLSLSPGERATLSCRASQSVSSYLAWYQQKPGQAPRLLIYDASNRATGIPARFSGSGSG

TDFTLTISSLEPEDFAVYYCQQYTSWPLTFGGGTKVEIK

TI-13 (ADI-19080) light chain variable region
(SEQ ID NO: 328)
EIVLTQSPGTLSLSPGERATLSCRASQSVSSSFLAWYQQKPGQAPRLLIYGASSRATGIPDRFSGSGS

GTDFTLTISRLEPEDFAVYYCQQLDSHPPTFGGGTKVEIK

ANTIBODY VARIABLE REGION SEQUENCES

TI-14 (ADI-19081) light chain variable region
(SEQ ID NO: 329)
DIVMTQSPDSLAVSLGERATINCKSSQSVLYSSNNKNYLAWYQQKPGQPPKLLIYWASTRESGVPDRF
SGSGSGTDFTLTISSLQAEDVAVYYCQQYDVDPLTFGGGTKVEIK TI-15 (ADI-19082) light chain variable region
(SEQ ID NO: 330)
EIVLTQSPGTLSLSPGERATLSCRASQSVSSSYLAWYQQKPGQAPRLLIYGASSRATGIPDRFSGSGS
GTDFTLTISRLEPEDFAVYYCQQAFISPPTFGGGTKVEIK TI-16 (ADI-19083) light chain variable region
(SEQ ID NO: 331)
DIQMTQSPSSVSASVGDRVTITCRASQGISSWLAWYQQKPGKAPKLLIYAASSLQSGVPSRFSGSGSG
TDFTLTISSLQPEDFATYYCQQADTLPITFGGGTKVEIK TI-17 (ADI-19084) light chain variable region
(SEQ ID NO: 332)
DIQMTQSPSSLSASVGDRVTITCQASQDISNYLNWYQQKPGKAPKLLIYDASNLATGVPSRFSGSGSG
TDFTFTISSLQPEDIATYYCQQSDIHPRTFGGGTKVEIK TI-18 (ADI-19085) light chain variable region
(SEQ ID NO: 333)
DIQMTQSPSTLSASVGDRVTITCRASQSISSWLAWYQQKPGKAPKLLIYKASSLESGVPSRFSGSGSG
TEFTLTISSLQPDDFATYYCQQDSIYPITFGGGTKVEIK TI-19 (ADI-19086) light chain variable region
(SEQ ID NO: 334)
DIQMTQSPSSVSASVGDRVTITCRASQGISSWLAWYQQKPGKAPKLLIYAASNLQSGVPSRFSGSGSG
TDFTLTISSLQPEDFATYYCQQANSFPLTFGGGTKVEIK TI-20 (ADI-19087) light chain variable region
(SEQ ID NO: 335)
DIQMTQSPSTLSASVGDRVTITCRASQSISSWLAWYQQKPGKAPKLLIYKASSLESGVPSRFSGSGSG
TEFTLTISSLQPDDFATYYCQQYKSFSPFTFGGGTKVEIK TI-21 (ADI-19088) light chain variable region
(SEQ ID NO: 336)
DIQLTQSPSSLSASVGDRVTITCRASQSISSFLNWYQQKPGKAPKLLIYAASSLQSGVPSRFSGSGSG
TDFTLTISSLQPEDFATYYCQQSYSDLTFGGGTKVEIK TI-22 (ADI-19089) light chain variable region
(SEQ ID NO: 337)
EIVLTQSPGTLSLSPGERATLSCRASQSVSSSYLAWYQQKPGQAPRLLIYGASSRATGIPDRFSGSGS
GTDFTLTISRLEPEDFAVYYCQQYLIPPITFGGGTKVEIK TI-23 (ADI-19090) light chain variable region
(SEQ ID NO: 338)
DIQMTQSPSTLSASVGDRVTITCRASQSIGSWLAWYQQKPGKAPKLLIYKASSLESGVPSRFSGSGSG
TEFTLTISSLQPDDFATYYCQQHQSFSPTFGGGTKVEIK TI-24 (ADI-19150) light chain variable region
(SEQ ID NO: 339)
DIQMTQSPSTLSASVGDRVTITCRASQSISSWLAWYQQKPGKAPKLLIYKASSLESGVPSRFSGSGSG
TEFTLTISSLQPDDFATYYCQQDSIYPITFGGGTKVEIK TI-25 (ADI-19092) light chain variable region
(SEQ ID NO: 340)
EIVLTQSPATLSLSPGERATLSCRASQSVSSYLAWYQQKPGQAPRLLIYDASNRATGIPARFSGSGSG
TDFTLTISSLEPEDFAVYYCQQRSVLPLTFGGGTKVEIK

| ANTIBODY VARIABLE REGION SEQUENCES |
|---|

TI-26 (ADI-19097) light chain variable region
(SEQ ID NO: 341)
DIQMTQSPSSLSASVGDRVTITCRASQSISSYLNWYQQKPGKAPKLLIYAASSLQSGVPSRFSGSGSG

TDFTLTISSLQPEDFATYYCQQIFSTPLTFGGGTKVEIK

TI-27 (ADI-19098) light chain variable region
(SEQ ID NO: 342)
DIQMTQSPSSLSASVGDRVTITCRASQSISSYLNWYQQKPGKAPKLLIYAASSLQSGVPSRFSGSGSG

TDFTLTISSLQPEDFATYYCQQSFYDPITFGGGTKVEIK

TI-28 (ADI-19101) light chain variable region
(SEQ ID NO: 343)
EIVLTQSPATLSVSPGERATLSCRASQSVGSNLAWYQQKPGQAPRLLIYGASTRATGIPARFSGSGSG

TEFTLTISSLQSEDFAVYYCQQYLYFPLTFGGGTKVEIK

TI-29 (ADI-19102) light chain variable region
(SEQ ID NO: 344)
EIVLTQSPATLSLSPGERATLSCRASQSVSSYLAWYQQKPGQAPRLLIYDASNRATGIPARFSGSGSG

TDFTLTISSLEPEDFAVYYCQQGVNYPFTFGGGTKVEIK

TI-30 (ADI-19103) light chain variable region
(SEQ ID NO: 345)
DIQMTQSPSSVSASVGDRVTITCRASQGISSWLAWYQQKPGKAPKLLIYAASSLQSGVPSRFSGSGSG

TDFTLTISSLQPEDFATYYCQQVISFPTFGGGTKVEIK

TI-31 (ADI-19104) light chain variable region
(SEQ ID NO: 346)
DIQMTQSPSSLSASVGDRVTITCQASQDISNYLNWYQQKPGKAPKLLIYDASNLETGVPSRFSGSGSG

TDFTFTISSLQPEDIATYYCQQYDDFPPITFGGGTKVEIK

TI-32 (ADI-19105) light chain variable region
(SEQ ID NO: 347)
DIQMTQSPSSLSASVGDRVTITCRASQSISRYLNWYQQKPGKAPKLLIYAASSLQSGVPSRFSGSGSG

TDFTLTISSLQPEDFATYYCQQSLDLPFTFGGGTKVEIK

TI-33 (ADI-19107) light chain variable region
(SEQ ID NO: 348)
DIQMTQSPSSVSASVGDRVTITCRASQGISSWLAWYQQKPGKAPKLLIYAASSLQSGVPSRFSGSGSG

TDFTLTISSLQPEDFATYYCQQINDHPFTFGGGTKVEIK

TI-34 (ADI-19108) light chain variable region
(SEQ ID NO: 349)
DIQMTQSPSTLSASVGDRVTITCRASQSINSWLAWYQQKPGKAPKLLISDASSLESGVPSRFSGSGSG

TEFTLTISSLQPDDFATYYCQQYGPYPYTFGGGTKVEIK

TI-35 (ADI-19109) light chain variable region
(SEQ ID NO: 350)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQSHSTPLTFGGGTKVEIK

TI-36 (ADI-19110) light chain variable region
(SEQ ID NO: 351)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQLASQPPTFGGGTKVEIK

TI-37 (ADI-19111) light chain variable region
(SEQ ID NO: 352)
EIVMTQSPATLSVSPGERATLSCRASQSVSSNLAWYQQKPGQAPRLLIYGASTRATGIPARFSGSGSG

TEFTLTISSLQSEDFAVYYCQQYAYWPLTFGGGTKVEIK

ANTIBODY VARIABLE REGION SEQUENCES

TI-38 (ADI-19112) light chain variable region
(SEQ ID NO: 353)
DIVMTQSPDSLAVSLGERATINCKSSQSVLFSSNNKNYLAWYQQKPGQPPKLLIYWASTRESGVPDRF
SGSGSGTDFTLTISSLQAEDVAVYYCQQDFSLPYTFGGGTKVEIK TI-39 (ADI-19113) light chain variable region
(SEQ ID NO: 354)
DIQLTQSPSSVSASVGDRVTITCRASQDISSWLAWYQQKPGKAPKLLIYAASSLQSGVPSRFSGSGSG
TDFTLTISSLQPEDFATYYCQQSLTHPTFGGGTKVEIK TI-40 (ADI-19114) light chain variable region
(SEQ ID NO: 355)
DIVMTQSPDSLAVSLGERATINCKSSQSVLFSSNNKNYLAWYQQKPGQPPKLLIYWASTRESGVPDRF
SGSGSGTDFTLTISSLQAEDVAVYYCQQYDLLPYTFGGGTKVEIK TI-41 (ADI-19115) light chain variable region
(SEQ ID NO: 356)
DIQLTQSPSSVSASVGDRVTITCRASQDISSWLAWYQQKPGKAPKLLIYAASSLQSGVPSRFSGSGSG
TDFTLTISSLQPEDFATYYCQQAVIHPPYTFGGGTKVEIK TI-42 (ADI-19116) light chain variable region
(SEQ ID NO: 357)
EIVMTQSPATLSVSPGERATLSCRASQSVSSNLAWYQQKPGQAPRLLIYGASTRATGIPARFSGSGSG
TEFTLTISSLQSEDFAVYYCQQYNVHPPRTFGGGTKVEIK TI-43 (ADI-19117) light chain variable region
(SEQ ID NO: 358)
DIVMTQSPLSLPVTPGEPASISCRSSQSLLHSNGYNYLDWYLQKPGQSPQLLIYLGSNRASGVPDRFS
GSGSGTDFTLKISRVEAEDVGVYYCMQSRNAPWTFGGGTKVEIK TI-44 (ADI-19119) light chain variable region
(SEQ ID NO: 359)
DIVMTQSPLSLPVTPGEPASISCRSSQSLLHSNGYNYLDWYLQKPGQSPQVLIYLGSNRASGVPDRFS
GSGSGTDFTLKISRVEAEDVGVYYCMQARHGFTFGGGTKVEIK TI-45 (ADI-19123) light chain variable region
(SEQ ID NO: 360)
DIVMTQSPLSLPVTPGEPASISCRSSQSLLHSNGYNYLDWYLQKPGQSPQLLIYLGSNRASGVPDRFS
GSGSGTDFTLKISRVEAEDVGVYYCMQAREVPFTFGGGTKVEIK TI-46 (ADI-19124) light chain variable region
(SEQ ID NO: 361)
DIVMTQSPLSLPVTPGEPASISCRSSQSLLHSNGYNYLDWYLQKPGQSPQLLIYLGSNRASGVPDRFS
GSGSGTDFTLKISRVEAEDVGVYYCMQARHVPPLTFGGGTKVEIK TI-47 (ADI-19120) light chain variable region
(SEQ ID NO: 362)
DIVMTQSPDSLAVSLGERATINCKSSQSVLFSSNNKNYLAWYQQKPGQPPKLLIYWASTRESGVPDRF
SGSGSGTDFTLTISSLQAEDVAVYYCQQHDSAPYTFGGGTKVEIK TI-48 (ADI-19121) light chain variable region
(SEQ ID NO: 363)
DIVMTQSPLSLPVTPGEPASISCRSSQSLLHSNGYNYLDWYLQKPGQSPQLLIYLGSHRASGVPDRFS
GSGSGTDFTLKISRVEAEDVGVYYCMQGRQVPFTFGGGTKVEIK TI-49 (ADI-19122) light chain variable region
(SEQ ID NO: 364)
DIVMTQSPLSLPVTPGEPASISCRSSQSLLHSNGYNYLDWYLQKPGQSPQLLIYLGSNRASGVPDRFS
GSGSGTDFTLKISRVEAEDVGVYYCMQARGTPWTFGGGTKVEIK

ANTIBODY VARIABLE REGION SEQUENCES

TI-50 (ADI-19125) light chain variable region
(SEQ ID NO: 365)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQSRRAPPWTFGGGTKVEIK

TI-51 (ADI-19126) light chain variable region
(SEQ ID NO: 366)
DIQMTQSPSTLSASVGDRVTITCRASQSISSWLAWYQQKPGKAPKLLIYKASSLESGVPSRFSGSGSG

TEFTLTISSLQPDDFATYYCQQFQSYPFTFGGGTKVEIK

TI-52 (ADI-19127) light chain variable region
(SEQ ID NO: 367)
DIQMTQSPSTLSASVGDRVTITCRASQSISSWLAWYQQKPGKAPKLLIYKASSLESGVPSRFSGSGSG

TEFTLTISSLQPDDFATYYCQQSSADSPFTFGGGTKVEIK

TI-53 (ADI-19128) light chain variable region
(SEQ ID NO: 368)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQARQLPWTFGGGTKVEIK

TI-54 (ADI-19129) light chain variable region
(SEQ ID NO: 369)
EIVMTQSPATLSLSPGERATLSCRASQSVSSYLAWYQQKPGQAPRLLIYDSSNRATGIPARFSGSGSG

TDFTLTISSLEPEDFAVYYCQQHDVWPITFGGGTKVEIK

TI-55 (ADI-19130) light chain variable region
(SEQ ID NO: 370)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQTRHTPTFGGGTKVEIK

TI-56 (ADI-19131) light chain variable region
(SEQ ID NO: 371)
DIVMTQSPLSLPVTPGEPASISCRSSQSLLHSNGYNYLDWYLQKPGQSPQLLIYLGSNRASGVPDRFS

GSGSGTDFTLKISRVEAEDVGVYYCMQDFARPPTFGGGTKVEIK

TI-57 (ADI-19132) light chain variable region
(SEQ ID NO: 372)
DIQMTQSPSSVSASVGDRVTITCRASQGIDSWLAWYQQKPGKAPKLLIYAASSLQSGVPSRFSGSGSG

TDFTLTISSLQPEDFATYYCQQRAVFPPTFGGGTKVEIK

TI-58 (ADI-19133) light chain variable region
(SEQ ID NO: 373)
DIVMTQSPDSLAVSLGERATINCKSSQSVLFSSNNKNYLAWYQQKPGQPPKLLIYWASTRESGVPDRF

SGSGSGTDFTLTISSLQAEDVAVYYCQQDATGITFGGGTKVEIK

TI-59 (ADI-19135) light chain variable region
(SEQ ID NO: 374)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQLASFPWTFGGGTKVEIK

TI-60 (ADI-19136) light chain variable region
(SEQ ID NO: 375)
DIVMTQSPDSLAVSLGERATINCKSSQSVLFSSNNKNYLAWYQQKPGQPPKLLIYWASTRESGVPDRF

SGSGSGTDFTLTISSLQAEDVAVYYCQQLAFTPWTFGGGTKVEIK

TI-61 (ADI-19137) light chain variable region
(SEQ ID NO: 376)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQDHSFITFGGGTKVEIK

ANTIBODY VARIABLE REGION SEQUENCES

TI-62 (ADI-19138) light chain variable region
(SEQ ID NO: 377)
EIVLTQSPGTLSLSPGERATLSCRASQSVSSSYLAWYQQKPGQAPRLLIYGASSRATGIPDRFSGSGS
GTDFTLTISRLEPEDFAVYYCQQDVSDFTFGGGTKVEIK TI-63 (ADI-19139) light chain variable region
(SEQ ID NO: 378)
DIQMTQSPSSLSASVGDRVTITCRASQSISRYLNWYQQKPGKAPKLLIYAASSLQSGVPSRFSGSGSG
TDFTLTISSLQPEDFATYYCQQLYHAPPITFGGGTKVEIK TI-64 (ADI-19140) light chain variable region
(SEQ ID NO: 379)
DIVMTQSPDSLAVSLGERATINCKSSQSVLFSSNNKNYLAWYQQKPGQPPKLLIYWASTRESGVPDRF
SGSGSGTDFTLTISSLEPEDVAVYYCQQYDSLPFTFGGGTKVEIK TI-65 (ADI-19141) light chain variable region
(SEQ ID NO: 380)
DIVMTQSPDSLAVSLGERATINCKSSQSVLYSSNNKNYLAWYQQKPGQPPKLLIYWASTRESGVPDRF
SGSGSGTDFTLTISSLQAEDVAVYYCQQVYLFPWTFGGGTKVEIK TI-66 (ADI-19142) light chain variable region
(SEQ ID NO: 381)
DIVMTQSPDSLAVSLGERATINCKSSQSVLFSSNNKNYLAWYQQKPGQPPKLLIYWASTRESGVPDRF
SGSGSGTDFTLTISSLQAEDVAVYYCQQFFLAPPTFGGGTKVEIK TI-67 (ADI-19143) light chain variable region
(SEQ ID NO: 382)
EIVLTQSPGTLSLSPGERATLSCRASQSVSSSFLAWYQQKPGQAPRLLIYGASSRATGIPDRFSGSGS
GTDFTLTISRLEPEDFAVYYCQQAVSLPWTFGGGTKVEIK TI-68 (ADI-19144) light chain variable region
(SEQ ID NO: 383)
EIVLTQSPATLSLSPGERATLSCRASQSVSSYLAWYQQKPGQAPRLLIYDASNRATGIPARFSGSGSG
TDFTLTISSLEPEDFAVYYCQQFDNLPYTFGGGTKVEIK TI-69 (ADI-19145) light chain variable region
(SEQ ID NO: 384)
DIQMTQSPSSVSASVGDRVTITCRASQGISSWLAWYQQKPGKAPKLLIYAASNLQSGVPSRFSGSGSG
TDFTLTISSLQPEDFATYYCQQATAHPPTFGGGTKVEIK TI-70 (ADI-19146) light chain variable region
(SEQ ID NO: 385)
DIQLTQSPSSVSASVGDRVTITCRASQDISSWLAWYQQKPGKAPKLLIYAASSLQSGVPSRFSGSGSG
TDFTLTISSLQPEDFATYYCQQAVSHPLTFGGGTKVEIK TI-71 (ADI-19147) light chain variable region
(SEQ ID NO: 386)
DIQMTQSPSSVSASVGDRVTITCRASQGIDSWLAWYQQKPGKAPKLLIYAASSLQSGVPSRFSGSGSG
TDFTLTISSLQPEDFATYYCQQATSLPLTFGGGTKVEIK TI-72 (ADI-19148) light chain variable region
(SEQ ID NO: 387)
DIVMTQSPLSLPVTPGEPASISCRSSQSLLHRNGYNYLDWYLQKPGQSPQLLIYLGSNRASGVPDRFS
GSGSGTDFTLKISRVEAEDVGVYYCMQRLQAWTFGGGTKVEIK TI-73 (ADI-19149) light chain variable region
(SEQ ID NO: 388)
DIQMTQSPSTLSASVGDRVTITCRASQSISSWLAWYQQKPGKAPKLLIYKASSLESGVPSRFSGSGSG
TEFTLTISSLQPDDFATYYCQQYRTYPTFGGGTKVEIK

| ANTIBODY VARIABLE REGION SEQUENCES |
| --- |

TI-74 (ADI-19151) light chain variable region
(SEQ ID NO: 389)
DIQMTQSPSTLSASVGDRVTITCRASQSISSWLAWYQQKPGKAPKLLIYKASSLESGVPSRFSGSGSG

TEFTLTISSLQPDDFATYYCQQHSLLSITFGGGTKVEIK

TI-75 (ADI-19152) light chain variable region
(SEQ ID NO: 390)
EIVLTQSPATLSLSPGERATLSCRASQSVSSYLAWYQQKPGQAPRLLIYDASNRATGIPARFSGSGSG

TDFTLTISSLEPEDFAVYYCQHYNLWRTFGGGTKVEIK

TI-76 (ADI-19153) light chain variable region
(SEQ ID NO: 391)
DIQMTQSPSTLSASVGDRVTITCRASQSISSWLAWYQQKPGKAPKLLIYDASSLESGVPSRFSGSGSG

TEFTLTISSLQPDDFATYYCQQHSTYSWTFGGGTKVEIK

TI-77 (ADI-19154) light chain variable region
(SEQ ID NO: 392)
EIVMTQSPATLSVSPGERATLSCRASQSVGSNLAWYQQKPGQAPRLLIYGASTRATGIPARFSGSGSG

TEFTLTISSLQSEDFAVYYCQQHDVWPYTFGGGTKVEIK

TI-78 (ADI-19155) light chain variable region
(SEQ ID NO: 393)
DIVMTQSPDSLAVSLGERATINCKSSQSVLFSSNNKNYLAWYQQKPGQPPKLLIYWASTRESGVPDRF

SGSGSGTDFTLTISSLQAEDVAVYYCQQYFSTPPTFGGGTKVEIK

TI-79 (ADI-19156) light chain variable region
(SEQ ID NO: 394)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQYALTPYTFGGGTKVEIK

TI-80 (ADI-19159) light chain variable region
(SEQ ID NO: 395)
EIVMTQSPATLSVSPGERATLSCRASQSVGSNLAWYQQKPGQAPRLLIYGASTRATGIPARFSGSGSG

TEFTLTISSLQSEDFAVYYCQQDHDRPLTFGGGTKVEIK

| Heavy chain variable region sequences |
| --- |

TI-1 (ADI-19067) heavy chain variable region
(SEQ ID NO: 396)
QVQLVQSGAEVKKPGSSVKVSCKASGGTFSSYAISWVRQAPGQGLEWMGGIIPIFGTANYAQKFQGRV

TITADESTSTAYMELSSLRSEDTAVYYCARGQGSDHYYYGMDVWGQGTTVTVSS

TI-2 (ADI-19068) heavy chain variable region
(SEQ ID NO: 397)
QVQLVQSGAEVKKPGSSVKVSCKASGGTFSSYAISWVRQAPGQGLEWMGGIIPIFGTANYAQKFQGRV

TITADESTSTAYMELSSLRSEDTAVYYCAREGGPRGASFNWFDPWGQGTLVTVSS

TI-3 (ADI-19069) heavy chain variable region
(SEQ ID NO: 398)
QVQLVQSGAEVKKPGSSVKVSCKASGGTFSSYAISWVRQAPGQGLEWMGGIIPIFGTANYAQKFQGRV

TITADESTSTAYMELSSLRSEDTAVYYCARDVGSMYFDIWGQGTMVTVSS

TI-4 (ADI-19070) heavy chain variable region
(SEQ ID NO: 399)
QVQLVQSGAEVKKPGSSVKVSCKASGGTFSSYAISWVRQAPGQGLEWMGGIIPIFGTANYAQKFQGRV

TITADESTSTAYMELSSLRSEDTAVYYCARHYYYGYAYFDLWGRGTLVTVSS

TI-5 (ADI-19071) heavy chain variable region
(SEQ ID NO: 400)
QVQLVQSGAEVKKPGASVKVSCKASGYTFTSYYMHWVRQAPGQGLEWMGVINPSGGSTSYAQKFQGRV

TMTRDTSTSTVYMELSSLRSEDTAVYYCARESDGIDSYFDYWGQGTLVTVSS

ANTIBODY VARIABLE REGION SEQUENCES

TI-6 (ADI-19072) heavy chain variable region
(SEQ ID NO: 401)
QVQLVQSGAEVKKPGASVKVSCKASGYTFTSYYMHWVRQAPGQGLEWMGVINPSGGSTSYAQKFQGRV

TMTRDTSTSTVYMELSSLRSEDTAVYYCARESGHSYVSSFDPWGQGTLVTVSS

TI-7 (ADI-19073) heavy chain variable region
(SEQ ID NO: 402)
QVQLVQSGAEVKKPGASVKVSCKASGYTFTSYYMHWVRQAPGQGLEWMGIINPSGGSTSYAQKFQGRV

TMTRDTSTSTVYMELSSLRSEDTAVYYCARGLIYGDAFDYWGQGTLVTVSS

TI-8 (ADI-19074) heavy chain variable region
(SEQ ID NO: 403)
QVQLVQSGAEVKKPGASVKVSCKASGYTFTSYYMHWVRQAPGQGLEWMGIINPSGGSTSYAQKFQGRV

TMTRDTSTSTVYMELSSLRSEDTAVYYCAREVSMTAASLDVWGQGTMVTVSS

TI-9 (ADI-19076) heavy chain variable region
(SEQ ID NO: 404)
QVQLVQSGAEVKKPGASVKVSCKASGYTFTSYYMHWVRQAPGQGLEWMGIINPSGGSTSYAQKFQGRV

TMTRDTSTSTVYMELSSLRSEDTAVYYCAREAGYDISSAFDIWGQGTMVTVSS

TI-10 (ADI-19077) heavy chain variable region
(SEQ ID NO: 405)
QVQLVQSGAEVKKPGASVKVSCKASGYTFTSYYMHWVRQAPGQGLEWMGIINPSGGSTSYAQKFQGRV

TMTRDTSTSTVYMELSSLRSEDTAVYYCAREGSGSWETLDVWGQGTMVTVSS

TI-11 (ADI-19078) heavy chain variable region
(SEQ ID NO: 406)
QLQLQESGPGLVKPSETLSLTCTVSGGSISSSSYYWGWIRQPPGKGLEWIGSIYYSGSTYYNPSLKSR

VTISVDTSKNQFSLKLSSVTAADTAVYYCARSGEYGFDLWGRGTLVTVSS

TI-12 (ADI-19079) heavy chain variable region
(SEQ ID NO: 407)
QLQLQESGPGLVKPSETLSLTCTVSGGSISSSSYYWGWIRQPPGKGLEWIGSIYYSGSTYYNPSLKSR

VTISVDTSKNQFSLKLSSVTAADTAVYYCARGGGYPWEAFDYWGKGTTVTVSS

TI-13 (ADI-19080) heavy chain variable region
(SEQ ID NO: 408)
EVQLVESGGGLVKPGGSLRLSCAASGFTFSSYSMNWVRQAPGKGLEWVSSISSSSNYIYYADSVKGRF

TISRDNAKNSLYLQMNSLRAEDTAVYYCARGRYRRTGSLDVWGQGTMVTVSS

TI-14 (ADI-19081) heavy chain variable region
(SEQ ID NO: 409)
QVQLVESGGGVVQPGRSLRLSCAASGFTFSSYGMHWVRQAPGKGLEWVAVISYDGSNKYYADSVKGRF

TISRDNSKNTLYLQMNSLRAEDTAVYYCARRSSGDYLDVWGQGTMVTVSS

TI-15 (ADI-19082) heavy chain variable region
(SEQ ID NO: 410)
EVQLVESGGGLVKPGGSLRLSCAASGFTFSSYSMNWVRQAPGKGLEWVSSISSSSSYIYYADSVKGRF

TISRDNAKNSLYLQMNSLRAEDTAVYYCARRGGSYDAFQHWGQGTLVTVSS

TI-16 (ADI-19083) heavy chain variable region
(SEQ ID NO: 411)
EVQLVESGGGLVQPGRSLRLSCAASGFTFDDYAMHWVRQAPGKGLEWVSGISWNSGSIGYADSVKGRF

TISRDNAKNSLYLQMNSLRAEDTALYYCAKGPRMSGWWADWGQGTLVTVSS

TI-17 (ADI-19084) heavy chain variable region
(SEQ ID NO: 412)
QVQLQESGPGLVKPSETLSLTCTVSGGSISSYYWSWIRQPPGKGLEWIGSIYYSGSTNYNPSLKSRVT

ISVDTSKNQFSLKLSSVTAADTAVYYCARGAPGGRHNWFDPWGQGTLVTVSS

ANTIBODY VARIABLE REGION SEQUENCES

TI-18 (ADI-19085) heavy chain variable region
(SEQ ID NO: 413)
EVQLVESGGGLVQPGRSLRLSCAASGFTFDDYAMHWVRQAPGKGLEWVSGISWNSGDIGYADSVKGRF
TISRDNAKNTLYLQMNSLRAEDTALYYCAKGPRMVTHLDVWGQGTMVTVSS TI-19 (ADI-19086) heavy chain variable region
(SEQ ID NO: 414)
EVQLVESGGGLVQPGGSLRLSCAASGFTFSDHHMDWVRQAPGKGLEWVGRTRNKANSYTTEYAASVKG
RFTISRDDSKNSLYLQMNSLKTEDTAVYYCARGPLGYKLWGQGTLVTVSS TI-20 (ADI-19087) heavy chain variable region
(SEQ ID NO: 415)
EVQLVESGGGLVQPGGSLRLSCAASGFTFSSYWMSWVRQAPGKGLEWVANIKQDGSEKYYVDSVKGRF
TISRDNAKNSLYLQMNSLRAEDTAVYYCARDAPQLGLDVWGQGTMVTVSS TI-21 (ADI-19088) heavy chain variable region
(SEQ ID NO: 416)
EVQLVESGGGLVQPGGSLRLSCAASGFTFSSYSMNWVRQAPGKGLEWVSYISSSSSTIYYADSVKGRF
TISRDNAKNSLYLQMNSLRAEDTAVYYCARGGPLGYGDYKGMDVWGQGTTVTVSS TI-22 (ADI-19089) heavy chain variable region
(SEQ ID NO: 417)
QVQLQESGPGLVKPSETLSLTCTVSGGSISSYYWSWIRQPPGKGLEWIGHIYYSGSTNYNPSLKSRVT
ISVDTSKNQFSLKLSSVTAADTAVYYCARDAGRYYGSSSSWYFDLWGRGTLVTVSS TI-23 (ADI-19090) heavy chain variable region
(SEQ ID NO: 418)
EVQLVESGGGLVQPGRSLRLSCAASGFTFDDYAMHWVRQAPGKGLEWVSGITWNSGSIGYADSVKGRF
TISRDNAKNSLYLQMNSLRAEDTALYYCAKGPRLLSALDVWGQGTMVTVSS TI-24 (ADI-19150) heavy chain variable region
(SEQ ID NO: 419)
EVQLVESGGGLVQPGRSLRLSCAASGFTFDDYAMHWVRQAPGKGLEWVSGITWNSGSIGYADSVKGRF
TISRDNAKNSLYLQMNSLRAEDTALYYCAKGPRLLSALDVWGQGTMVTVSS TI-25 (ADI-19092) heavy chain variable region
(SEQ ID NO: 420)
EVQLVESGGGLVQPGRSLRLSCAASGFTFDDYAMHWVRQAPGKGLEWVSGISWNSGSIGYADSVKGRF
TISRDNAKNSLYLQMNSLRAEDTALYYCAKGGSRYSHFDYWGQGTLVTVSS TI-26 (ADI-19097) heavy chain variable region
(SEQ ID NO: 421)
QVQLVQSGAEVKKPGASVKVSCKASGYTFTSYYIHWVRQAPGQGLEWMGIINPSGGSTSYAQKFQGRV
TMTRDTSTSTVYMELSSLRSEDTAVYYCARDSAQETYYYGMDVWGQGTTVTVSS TI-27 (ADI-19098) heavy chain variable region
(SEQ ID NO: 422)
QVQLQESGPGLVKPSQTLSLTCTVSGGSISSGGYYWSWIRQHPGKGLEWIGYIYYSGSTYYNPSLKSR
VTISVDTSKNQFSLKLSSVTAADTAVYYCARDSSIAGRATLSFDYWGQGTLVTVSS TI-28 (ADI-19101) heavy chain variable region
(SEQ ID NO: 423)
EVQLVESGGGLVKPGGSLRLSCAASGFTFSSYSMNWVRQAPGKGLEWVSSISSSSNYIYYADSVKGRF
TISRDNAKNSLYLQMNSLRAEDTAVYYCARGPSQYYYDSSAIEAFDIWGQGTMVTVSS TI-29 (ADI-19102) heavy chain variable region
(SEQ ID NO: 424)
QLQLQESGPGLVKPSETLSLTCTVSGGSISSSSYYWGWIRQPPGKGLEWIGSIYYSGSTYYNPSLKSR
VTISVDTSKNQFSLKLSSVTAADTAVYYCARDGGGTAQADGAYYYGMDVWGQGTTVTVSS -continued

ANTIBODY VARIABLE REGION SEQUENCES

TI-30 (ADI-19103) heavy chain variable region
(SEQ ID NO: 425)
QLQLQESGPGLVKPSETLSLTCTVSGGSISSSSYYWGWIRQPPGKGLEWIGSIYYSGSTYYNPSLKSR

VTISVDTSKNQFSLKLSSVTAADTAVYYCARGRKAAAGIDEAEYFQHWGQGTLVTVSS

TI-31 (ADI-19104) heavy chain variable region
(SEQ ID NO: 426)
QLQLQESGPGLVKPSETLSLTCTVSGGSISSSSYYWGWIRQPPGKGLEWIGSIYYSGSTYYNPSLKSR

VTISVDTSKNQFSLKLSSVTAADTAVYYCARDRRMWDPYGMDVWGQGTTVTVSS

TI-32 (ADI-19105) heavy chain variable region
(SEQ ID NO: 427)
QLQLQESGPGLVKPSETLSLTCTVSGGSISSSSYYWGWIRQFPGKGLEWIGSIYYSGSTYYNPSLKSR

VTISVDTSKNQFSLKLSSVTAADTAVYYCARDAPAVVGESPAFDIWGQGTMVTVSS

TI-33 (ADI-19107) heavy chain variable region
(SEQ ID NO: 428)
QVQLVESGGGVVQPGRSLRLSCAASGFTFSNYGMHWVRQAPGKGLEWVAVIWYDGSNKYYADSVKGRF

TISRDNSKNTLYLQMNSLRAEDTAVYYCAKGSTHRGSAYGMDVWGQGTTVTVSS

TI-34 (ADI-19108) heavy chain variable region
(SEQ ID NO: 429)
EVQLVESGGGLVKPGGSLRLSCAASGFTFSSYSMNWVRQAPGKGLEWVSSISSSSNYIYYADSVKGRF

TISRDNAKNSLYLQMNSLKAEDTAVYYCARRPDDRRGLFQHWGQGTLVTVSS

TI-35 (ADI-19109) heavy chain variable region
(SEQ ID NO: 430)
QVQLVESGGGVVQPGRSLRLSCAASGFTFSSYGMHWVRQAPGKGLEWVAVISYDGSNKYYADSVKGRF

TISRDNSKNTLYLQMNSLRAEDTAVYYCARPDYYSSRGVFDIWGQGTMVTVSS

TI-36 (ADI-19110) heavy chain variable region
(SEQ ID NO: 431)
QVQLVESGGGVVQPGRSLRLSCAASGFTFSSYGMHWVRQAPGKGLEWVAVISYDGSNKYYADSVKGRF

TISRDNSKNTLYLQMNSLRAEDTAVYYCARPDYYSSRGVFDIWGQGTMVTVSS

TI-37 (ADI-19111) heavy chain variable region
(SEQ ID NO: 432)
QVQLVESGGGVVQPGRSLRLSCAASGFTFSSYGMHWVRQAPGKGLEWVALIWYDGSNKYYADSVKGRF

TISRDNSKNTLYLQMNSLRAEDTAVYYCAKGDYLDPLFDYWGQGTLVTVSS

TI-38 (ADI-19112) heavy chain variable region
(SEQ ID NO: 433)
QVQLVESGGGVVQPGRSLRLSCAASGLTFSSYGMHWVRQAPGKGLEWVAVISYDGSNKYYADSVKGRF

TISRDNSKNTLYLQMNSLRAEDTAVYYCARERGTYYYASGWANWGQGTLVTVSS

TI-39 (ADI-19113) heavy chain variable region
(SEQ ID NO: 434)
EVQLVESGGGLVKPGGSLRLSCAASGFTFSSYSMNWVRQAPGKGLEWVSSISSSSNYIYYADSVKGRF

TISRDNAKNSLYLQMNSLRAEDTAVYYCARRGGSSSTGLLYWGQGTLVTVSS

TI-40 (ADI-19114) heavy chain variable region
(SEQ ID NO: 435)
EVQLVESGGGLVKPGGSLRLSCAASGFTFSSYSMNWVRQAPGKGLEWVSSISSSSSYIYYADSVKGRF

TISRDNAKNSLYLQMNSLRAEDTAVYYCARTRIDDSFDIWGQGTMVTVSS

TI-41 (ADI-19115) heavy chain variable region
(SEQ ID NO: 436)
EVQLLESGGGLVQPGGSLRLSCAASGFTFSTYAMSWVRQAPGKGLEWVSAISGSGGSTYYADSVKGRF

TISRDNSKNTLYLQMNSLRAEDTAVYYCAKSKHSTTSLDVWGQGTMVTVSS

ANTIBODY VARIABLE REGION SEQUENCES

TI-42 (ADI-19116) heavy chain variable region
(SEQ ID NO: 437)
QVQLVESGGGVVQPGRSLRLSCAASGFTFSSYGMHWVRQAPGKGLEWVAVIWYDGSNKGYADSVKGRF

TISRDNSKNTLYLQMNSLRAEDTAVYYCARELMVTSGGWLYGMDVWGQGTTVTVSS

TI-43 (ADI-19117) heavy chain variable region
(SEQ ID NO: 438)
QVQLVQSGAEVKKPGASVKVSCKASGYTFTSYYMHWVRQAPGQGLEWMGIINPSGGSTSYAQKFQGRV

TMTRDTSTSTVYMELSSLRSEDTAVYYCAREAGNYYDIESAFDIWGQGTMVTVSS

TI-44 (ADI-19119) heavy chain variable region
(SEQ ID NO: 439)
QVQLVQSGAEVKKPGASVKVSCKASGYTFTSYYMHWVRQAPGQGLEWMGVINPSGGSTSYAQKFQGRV

TMTRDTSTSTVYMELSSLRSEDTAVYYCAREGSGYDESMDVWGQGTTVTVSS

TI-45 (ADI-19123) heavy chain variable region
(SEQ ID NO: 440)
QVQLVQSGAEVKKPGASVKVSCKASGYTFTSYYMHWVRQAPGQGLEWMGVINPSGGSTSYAQKFQGRV

TMTRDTSTSTVYMELSSLRSEDTAVYYCAREGSGYDESMDVWGQGTTVTVSS

TI-46 (ADI-19124) heavy chain variable region
(SEQ ID NO: 441)
QVQLVQSGAEVKKPGASVKVSCKASGYTFTSYYMHWVRQAPGQGLEWMGVINPSGGSTSYAQKFQGRV

TMTRDTSTSTVYMELSSLRSEDTAVYYCAREGSGYDESMDVWGQGTTVTVSS

TI-47 (ADI-19120) heavy chain variable region
(SEQ ID NO: 442)
QVQLVQSGAEVKKPGSSVKVSCKASGGTFSNYAISWVRQAPGQGLEWMGGIIPIFGTANYAQKFQGRV

TITADESTSTAYMELSSLRSEDTAVYYCARGRGIAFDIWGQGTMVTVSS

TI-48 (ADI-19121) heavy chain variable region
(SEQ ID NO: 443)
QVQLVQSGAEVKKPGASVKVSCKASGYTFTSYYMHWVRQAPGQGLEWMGVINPGGGSTSYAQKFQGRV

TMTRDTSTSTVYMELSSLRSEDTAVYYCAREAGQTSSALDVWGQGTMVTVSS

TI-49 (ADI-19122) heavy chain variable region
(SEQ ID NO: 444)
QVQLVQSGAEVKKPGASVKVSCKASGYTFTSYYMHWVRQAPGQGLEWMGIINPSGGSTSYAQKFQGRV

TMTRDTSTSTVYMELSSLRSEDTAVYYCAREAGSWLISTAFDIWGQGTMVTVSS

TI-50 (ADI-19125) heavy chain variable region
(SEQ ID NO: 445)
QVQLVQSGAEVKKPGASVKVSCKASGYTFTSYYMHWVRQAPGQGLEWMGIINPGGGSTSYAQKFQGRV

TMTRDTSTSTVYMELSSLRSEDTAVYYCAREAGTMSSAFDIWGQGTMVTVSS

TI-51 (ADI-19126) heavy chain variable region
(SEQ ID NO: 446)
QVQLVQSGAEVKKPGSSVKVSCKASGGTFSSYAISWVRQAPGQGLEWMGSIIPIFGTANYAQKFQGRV

TITADESTSTAYMELSSLRSEDTAVYYCARSGGYSSSWYGTGYDYWGQGTLVTVSS

TI-52 (ADI-19127) heavy chain variable region
(SEQ ID NO: 447)
QVQLVQSGAEVKKPGSSVKVSCKASGGTFSSYAISWVRQAPGQGLEWMGSIIPIFGTANYAQKFQGRV

TITADESTSTAYMELSSLRSEDTAVYYCARDRGQYSSSWYGRMDVWGQGTTVTVSS

TI-53 (ADI-19128) heavy chain variable region
(SEQ ID NO: 448)
QVQLVQSGAEVKKPGASVKVSCKASGYTFTSYYIHWVRQAPGQGLEWMGIINPSGGSTSYAQKFQGRV

TMTRDTSTSTVYMELSSLRSEDTAVYYCARESGYHVSTAFDIWGQGTMVTVSS

ANTIBODY VARIABLE REGION SEQUENCES

TI-54 (ADI-19129) heavy chain variable region
(SEQ ID NO: 449)
QVQLVQSGAEVKKPGSSVKVSCKASGGTFSSYAISWVRQAPGQGLEWMGGIIPIFGTANYAQKFQGRV

TITADESTSTAYMELSSLRSEDTAVYYCARHWYALGSFDIWGQGTMVTVSS

TI-55 (ADI-19130) heavy chain variable region
(SEQ ID NO: 450)
QVQLVQSGAEVKKPGASVKVSCKASGYTFTSYYMHWVRQAPGQGLEWMGVINPSGGSTSYAQKFQGRV

TMTRDTSTSTVYMELSSLRSEDTAVYYCARGADYYAGFDYWGQGTLVTVSS

TI-56 (ADI-19131) heavy chain variable region
(SEQ ID NO: 451)
EVQLVESGGGLVQPGRSLRLSCAASGFTFDDYAMHWVRQAPGKGLEWVSGISWNSGSIGYADSVKGRF

TISRDNAKNSLYLQMNSLRAEDTALYYCAKGPRLLGYFDLWGRGTLVTVSS

TI-57 (ADI-19132) heavy chain variable region
(SEQ ID NO: 452)
EVQLVESGGGLVQPGRSLRLSCAASGFTFDDYAMHWVRQAPGKGLEWVSGITWNSGSIGYADSVKGRF

TISRDNAKNSLYLQMNSLRAEDTALYYCAKGPRYSKPYFDYWGQGTLVTVSS

TI-58 (ADI-19133) heavy chain variable region
(SEQ ID NO: 453)
QLQLQESGPGLVKPSETLSLTCTVSGGSISSSSYYWGWIRQFPGKGLEWIGSIYYSGSTYYNPSLKSR

VTISVDTSKNQFSLKLSSVTAADTAVYYCARQEYGDGYFDLWGRGTLVTVSS

TI-59 (ADI-19135) heavy chain variable region
(SEQ ID NO: 454)
QVQLQESGPGLVKPSETLSLTCAVSGYSISSGYYWAWIRQPPGKGLEWIGSIYHSGSTYYNTSLKSRV

TISVDTSKNQFSLKLSSVTAADTAVYYCARDLGGYEGAFDPWGQGTLVTVSS

TI-60 (ADI-19136) heavy chain variable region
(SEQ ID NO: 455)
QVQLQESGPGLVKPSETLSLTCAVSGYSISSGYYWAWIRQPPGKGLEWIGSIYHSGSTYYNTSLKSRV

TISVDTSKNQFSLKLSSVTAADTAVYYCARDLGGYEGAFDPWGQGTLVTVSS

TI-61 (ADI-19137) heavy chain variable region
(SEQ ID NO: 456)
QVQLQESGPGLVKPSETLSLTCAVSGYSISSGYYWGWIRQPPGKGLEWIGSIYHSGSTYYMPSLKSRV

TISVDTSKNQFSLKLSSVTAADTAVYYCARHDDYLSSFDPWGQGTLVTVSS

TI-62 (ADI-19138) heavy chain variable region
(SEQ ID NO: 457)
QVQLQESGPGLVKPSQTLSLTCTVSGGSISSGGYYWSWIRQHPGKGLEWIGYIYYSGSTYYNPSLKSR

VTISVDTSKNQFSLKLSSVTAADTAVYYCARGPSWIDVWGQGTMVTVSS

TI-63 (ADI-19139) heavy chain variable region
(SEQ ID NO: 458)
QVQLQESGPGLVKPSETLSLTCAVSGYSISSGYYWGWIRQPPGKGLEWIGSIYHSGNTYYMPSLKSRV

TISVDTSKNQFSLKLSSVTAADTAVYYCARELYAYSSPMFYGMDVWGRGTTVTVSS

TI-64 (ADI-19140) heavy chain variable region
(SEQ ID NO: 459)
QLQLQESGPGLVKPSETLSLTCTVSGGSISSSSYYWGWIRQPPGKGLEWIGSISYSGSTYYNPSLKSR

VTISVDTSKNQFSLKLSSVTAADTAVYYCARYYSPYGMDVWGQGTTVTVSS

TI-65 (ADI-19141) heavy chain variable region
(SEQ ID NO: 460)
QLQLQESGPGLVKPSETLSLTCTVSGGSISSSDYYWGWIRQPPGKGLEWIGSIYYSGSTYYNPSLKSR

VTISVDTSKNQFSLKLSSVTAADTAVYYCARDSGQYTGSLDVWGQGTMVTVSS

ANTIBODY VARIABLE REGION SEQUENCES

TI-66 (ADI-19142) heavy chain variable region
(SEQ ID NO: 461)
QVQLVQSGAEVKKPGASVKVSCKASGYTFTGYYMHWVRQAPGQGLEWMGWINPNSGGTKYAQKFQGRV

TMTRDTSISTAYMELSRLRSDDTAVYYCARERHSSLGYAYWGQGTLVTVSS

TI-67 (ADI-19143) heavy chain variable region
(SEQ ID NO: 462)
QVQLVQSGAEVKKPGASVKVSCKASGYTFTSYGIHWVRQAPGQGLEWMGWISAYNGNTNYAQKLQGRV

TMTTDTSTSTAYMELRSLRSDDTAVYYCARGRPSSSWGNWFDPWGQGTTVTVSS

TI-68 (ADI-19144) heavy chain variable region
(SEQ ID NO: 463)
EVQLVQSGAEVKKPGESLKISCKGSGYSFTTYWIGWVRQMPGKGLEWMGIIYPGDSDTRYSPSFQGQV

TISADKSISTAYLQWSSLKASDTAMYYCARGSPWDGRLFDIWGQGTMVTVSS

TI-69 (ADI-19145) heavy chain variable region
(SEQ ID NO: 464)
QVQLVQSGAEVKKPGASVKVSCKASGYTFTSYGISWVRQAPGQGLEWMGWISAYNGNTNYAQKLQGRV

TMTTDTSTSTAYMELRSLRSDDTAVYYCARGAGMYDGSPLGMDVWGQGTTVTVSS

TI-70 (ADI-19146) heavy chain variable region
(SEQ ID NO: 465)
QVQLVQSGAEVKKPGASVKVSCKASGYTFTSYGIHWVRQAPGQGLEWMGWISAYNGNTNYAQKLQGRV

TMTTDTSTSTAYMELRSLRSDDTAVYYCARAGTIYGRLDLWGRGTLVTVSS

TI-71 (ADI-19147) heavy chain variable region
(SEQ ID NO: 466)
EVQLVESGGGLVQPGRSLRLSCAASGFTFGDYAMHWVRQAPGKGLEWVSGISWNSGSIGYADSVKGRF

TISRDNAKNSLYLQMNSLRAEDTALYYCAKGPRRTSHLDIWGQGTMVTVSS

TI-72 (ADI-19148) heavy chain variable region
(SEQ ID NO: 467)
EVQLVESGGGLVQPGRSLRLSCAASGFTFDDYAMHWVRQAPGKGLEWVSGISWNSGDIGYADSVKGRF

TISRDNAKNSLYLQMNSLRAEDTALYYCAKGPRMTHSYFDLWGRGTLVTVSS

TI-73 (ADI-19149) heavy chain variable region
(SEQ ID NO: 468)
EVQLVESGGGLVQPGRSLRLSCAASGFTFDDYAMHWVRQAPGKGLEWVSGISWNSGSIGYADSVKGRF

TISRDNAKNSLYLQMNSLRAEDTALYYCAKAPRMYGYFDLWGRGTSVTVSS

TI-74 (ADI-19151) heavy chain variable region
(SEQ ID NO: 469)
EVQLVESGGGLVQPGRSLRLSCAASGFTFDDYAMHWVRQAPGKGLEWVSGISWNSGSIGYADSVKGRF

TISRDNAKNSLYLQMNSLRAEDTALYYCAKGPRTRGYFDLWGRGTLVTVSS

TI-75 (ADI-19152) heavy chain variable region
(SEQ ID NO: 470)
QVQLVESGGGLVQPGRSLRLSCAASGFTFDDYAMHWVRQAPGKGLEWVSGISWNSGDIGYADSVKGRF

TISRDNAKNSLYLQMNSLRAEDTALYYCAKAPRTRWTYFDYWGQGTLVTVSS

TI-76 (ADI-19153) heavy chain variable region
(SEQ ID NO: 471)
EVQLLESGGGLVQPGGSLRLSCAASGFTFSSYAMSWVRQAPGKGLEWVSAISGSGGSTYYADSVKGRF

TISRDNSKNTLYLQMNSLRAEDTAVYYCARARRGALAGMDVWGQGTTVTVSS

TI-77 (ADI-19154) heavy chain variable region
(SEQ ID NO: 472)
QVQLQESGPGLVKPSETLSLTCAVSGYSISSGYYWAWIRQPPGKGLEWIGSIYHSGSTYYNTSLKSRV

TISVDTSKNQFSLKLSSVTAADTAVYYCARGGPYPWSGWFDPWGQGTLVTVSS

ANTIBODY VARIABLE REGION SEQUENCES

TI-78 (ADI-19155) heavy chain variable region
(SEQ ID NO: 473)
QLQLQESGPGLVKPSETLSLTCTVSGGSISSSSYYWGWIRQPPGKGLEWIGSIYYSGSTYYNPSLKSR

VTISVDTSKNQFSLKLSSVTAADTAVYYCARDLGQYEGYFDLWGRGTLVTVSS

TI-79 (ADI-19156) heavy chain variable region
(SEQ ID NO: 474)
QLQLQESGPGLVKPSETLSLTCTVSGGSISSSSYYWGWIRQPPGKGLEWIGSIYYSGSTYYNPSLKSR

VTISVDTSKNQFSLKLSSVTAADTAVYYCARLGDGYRIWADYWGQGTLVTVSS

TI-80 (ADI-19159) heavy chain variable region
(SEQ ID NO: 475)
QVQLVESGGGVVQPGRSLRLSCAASGFTFSSYGMHWVRQAPGKGLEWVALIWYDGSNKYYADSVKGRF

TISRDNSKNTLYLQMNSLRAEDTAVYYCARELIVGATGGLTYYYGMDVWGQGTTVTVSS

Illustrative TREM1 protein sequences:

mouse TREM1 protein (Uniprot Accession No. Q9JKE2; SEQ ID NO: 2)
MRKAGLWGLLCVFFVSEVKAAIVLEEERYDLVEGQTLTVKCPFNIMKYANSQKAWQRLPDGKEPLTLV

VTQRPFTRPSEVHMGKFTLKHDPSEAMLQVQMTDLQVTDSGLYRCVIYHPPNDPVVLFHPVRLVVTKG

SSDVFTPVIIPITRLTERPILITTKYSPSDTTTTRSLPKPTAVVSSPGLGVTIINGTDADSVSTSSVT

ISVICGLLSKSLVFIILFIVTKRTFG rat TREM1 protein (Uniprot Accession No. D4ABU7; SEQ ID NO: 3)
MRKAGLWGLLLVFFVSEVKAAIVPEEERYDLVEGQTLTVNCPFNIMKYARSRKAWQRLSAGKEPLTLV

VTERSSTTSSEVRVGKYTLKDDPTEAMLFVQMTDLQVTDSGLYRCVIYHPPNDPVLLFHPVRLVVTKG

SSGVSVPDIIPTTKPTEVPVLITTKHSTPTRSLPKSTAVVSSPDPGVTINNGTDPTSVSTYNVVVPVV

CGLLIKTLIFFVLFVVTKRSFG

Rhesus monkey TREM1 protein (Uniprot Accession No. F6TBB4; SEQ ID NO: 4)
MRKTRLWGLLWMLFVSELRATTELTEEKYEYKEGQTLEVKCDYALEKYANSRKAWQKMEGKMPKILAK

TERPSENSHPVQVGRITLEDYPDHGLLQVQMTNLQVEDSGLYQCVIYQHPKESHVLFNPICLVVTKGS

SGTPGSSENSTQNVYRTPSTTAKALGPRYTSPRTVTQAPPESTVVVSTPGPGPLPFFPSPCAERM bovine TREM1 protein (Uniprot Accession No. Q6QUN5; SEQ ID NO: 5)
MRKAGVWGLLWMLFIEEIQAAAEVFEEKCTLAEGQTLKVSCPTNTNIYSNSQKAWQRLKDNGEVQTLA

ITEGSSQVRVGKYFLEDIPSEGMLQIQMANLQVEDSGLYRCVILGPSDPIILFHPVRLVVTKNSLGTP

ASDEYPCQVSVQNPTPLPVTTKLRPRPRPRPKPVTQPIPTSADRLSSPGFTVTPTNVTHVNRAPGISI

IIPAACGLLSKTLVFIGLFAVTHRSFAS equine TREM1 protein (Uniprot Accession No. F6PSF7; SEQ ID NO: 6)
MRKAKLWGLLGMLFVSELQAAAGQAEEKKILTEGETLNYHCVYTRKHSQSQKAWQRVMDGGKAETLAF

TEKTSKNSQELGGRYFLEDNTTQGAVHVRMTNVQMSDSGLYRCVIYPILSNPEVLESLRLVVTKGDTV

SLGSSPSDSPSPDKNPPRDKAQTTTFPPATKAPVTQPPPKSTAGVSRPGLEVNPTHVTDVTRISVFSI

VIPVACALVTKSLVLTVLFAVTQKSFGS pig TREM1 protein (Uniprot Accession No. R4SEY7; SEQ ID NO: 7)
MRSARLGRLLWMLFITEIQAATELPEEKYILAEGETLNVNCPVTVGVYSNSRKAWQKLNRNGKFQTLA

ITERVSGQVSKVQVGKIFLTDEPSEGMLHVQMTNVQAEDSGLYRCVIYQPPKDPIILFYPVRLVVTNY

SSGTPASAETPTQSCSPTTTLPPTTTTNRHRPRPRTVRTVTQFLTDFTTSLSSPGLKVTLTNVTDITR

DTEISLILPAVCGLLSKSLVFIVLFVVTRMSFTP

Illustrative TREM1 protein sequences:

dog TREM1 protein (Uniprot Accession No. E2RP37; SEQ ID NO: 8)
MRKARLWELLWLLFISELQATTEPDEIKYVLAEGGTLNMKCTTSWKYTYSQKAWQKLMDREKPLTLI
FTENVSGDTSQVQRGRYFLEDIPSEAILNVQMTNLQVEDSGLYQCVIYHPQKNPDILYPRVRLVVTKG
ITASDKSPTQNLAQISTHPPTTTKAQSTLLASPRTVTQLPPKSTADTSSPDFGVNITNVTNVTSYGFR
FSVINIVILVLCGFLSKSLVFTVLIAVTQRSFGP Chimpanzee TREM1 protein (Uniprot Accession No. H2QSZ3; SEQ ID NO: 561)
MRKTRLWGLLWMLFVSELRAATKLTEEKYELKEGQTLDVKCDYTLEKFASSQKAWQIIRDGEMPKTLA
CTERPSENSHPVQVGRIILEDYHDHGLLRVRMVNLQVEDSGLYQCVIYQPPKEPHILFDRIRLVVTKG
FSGTPGSNENSTQNVYKIPPTTTKALHPLYTSPRTVTQAPPKSTADVSTPDSEINLTNVTDIIRVPVF
NIVILLAGGFLSKSLVFSVLFAVTLRSFVP

What is claimed is:

1. An isolated antibody that binds to a TREM1 protein, comprising a heavy chain and a light chain, wherein the light chain comprises a hypervariable region L1 (HVR-L1) comprising the amino acid sequence of SEQ ID NO: 10, an HVR-L2 comprising the amino acid sequence of SEQ ID NO: 29, and an HVR-L3 comprising the amino acid sequence of SEQ ID NO: 101, and wherein the heavy chain comprises an HVR-H1 comprising the amino acid sequence of SEQ ID NO: 130, an HVR-H2 comprising the amino acid sequence of SEQ ID NO: 159, and an HVR-H3 comprising the amino acid sequence of SEQ ID NO: 229.

2. The isolated antibody of claim 1, wherein the antibody comprises a heavy chain variable region comprising the amino acid sequence of SEQ ID NO: 457.

3. The isolated antibody of claim 1, wherein the antibody comprises a light chain variable region comprising the amino acid sequence of SEQ ID NO: 377.

4. The isolated antibody of claim 1, wherein the antibody comprises a heavy chain variable region comprising the amino acid sequence of SEQ ID NO: 457 and a light chain variable region comprising the amino acid sequence of SEQ ID NO: 377.

5. The isolated antibody of claim 1, wherein the antibody enhances one or more TREM1 activities induced by binding of one or more TREM1 ligands to the TREM1 protein, as compared to the one or more TREM1 activities induced by binding of the one or more TREM1 ligands to the TREM1 protein in the absence of the isolated antibody.

6. The isolated antibody of claim 5, wherein the one or more TREM1 activities are selected from the group consisting of:
   a) TREM1 binding to DAP12;
   b) TREM1 phosphorylation;
   c) DAP12 phosphorylation; and
   d) induction of respiratory burst in immune cells.

7. The isolated antibody of claim 5, wherein the antibody enhances TREM1-dependent gene transcription induced by binding of one or more TREM1 ligands to the TREM1 protein.

8. The isolated antibody of claim 7, wherein the one or more TREM1 ligands are selected from PGLYRP1 and a natural ligand expressed on activated neutrophils.

9. The isolated antibody of claim 1, wherein the antibody binds to the TREM1 IgV domain.

10. The isolated antibody of claim 1, wherein the antibody binds to amino acids 83-90 and 191-201 of SEQ ID NO: 1.

11. The isolated antibody of claim 1, wherein the antibody competes with one or more TREM1 ligands for binding to the TREM1 protein.

12. The isolated antibody of claim 1, wherein the antibody enhances one or more TREM1 activities induced by binding of one or more TREM1 ligands to the TREM1 protein in vitro on dendritic cells, bone marrow-derived dendritic cells, monocytes, microglia, macrophages, neutrophils, NK cells, osteoclasts, Langerhans cells of skin, Kupffer cells, or cell lines, as compared to the one or more TREM1 activities induced by binding of the one or more TREM1 ligands to the TREM1 protein in the absence of the isolated antibody.

13. The isolated antibody of claim 1, wherein the antibody decreases levels of TREM1 on one or more cells.

14. The isolated antibody of claim 13, wherein the antibody decreases levels of TREM1 in vitro on dendritic cells, bone marrow-derived dendritic cells, monocytes, microglia, macrophages, neutrophils, NK cells, osteoclasts, Langerhans cells of skin, Kupffer cells, or cell lines.

15. The isolated antibody of claim 1, wherein the antibody is an IgG1, IgG2, IgG3, or IgG4 isotype.

16. The isolated antibody of claim 15, wherein the antibody binds an inhibitory Fc receptor.

17. The isolated antibody of claim 16, wherein the inhibitory Fc receptor is inhibitory Fc-gamma receptor IIB (FcγIIB).

18. The isolated antibody of claim 15, wherein the isolated antibody is a human IgG1 isotype.

19. The isolated antibody of claim 18, wherein the isolated antibody comprises one or more amino acid substitutions in the Fc region selected from N297A, D265A, D270A, L234A, L235A, G237A, C226S, C229S, E233P, L234V, L234F, L235E, P331S, S267E, L328F, A330L, M252Y, S254T, T256E, L328E, P238D, S267E, L328F, E233D, G237D, H268D, P271G, A330R, and any combination thereof, or comprises a G236 deletion in the Fc region, wherein the numbering of the residues is according to EU numbering.

20. The isolated antibody of claim 15, wherein the isolated antibody:
   (a) has a hybrid IgG1/IgG2 isotype comprising a human IgG1 constant region modified to replace the IgG1 heavy chain constant domain 1 (CH1) and hinge region with the human IgG2 CH1 and hinge region, optionally wherein the IgG2 isotype CH1 and hinge region comprises the amino acid sequence of ASTKGPSVFP LAPCSRSTSE STAALGCL VK DYFPEPVTVS WNSGAL TSGVHTFPA VLQSS GL YSLSSVVT VPSSNFGTQT YTCNVDHKPS NTKVDKTVERKCCVECPPCP (SEQ ID NO: 476), and optionally wherein the antibody Fc region comprises a S267E amino acid substitution, a L328F amino acid substitution, or both, and/or a N297A or N297Q amino acid substitution, wherein the numbering of the residues is according to EU numbering;
   (b) has an IgG2 isotype and comprises one or more amino acid substitutions in the Fc region selected from P238S, V234A, G237A, H268A, H268Q, V309L, A330S, P331S, C214S, C232S, C233S, S267E, L328F, M252Y, S254T, T256E, H268E, N297A, N297Q, A330L, and any combination thereof, wherein the numbering of the residues is according to EU numbering;
   (c) has a human IgG4 isotype and comprises one or more amino acid substitutions in the Fc region selected from L235A, G237A, S228P, L236E, S267E, E318A, L328F, M252Y, S254T, T256E, E233P, F234V, L234A/ F234A, S228P, S241P, L248E, T394D, N297A, N297Q, L235E, and any combination thereof, wherein the numbering of the residues is according to EU numbering; or
   (d) has a hybrid IgG2/4 isotype, and optionally wherein the antibody comprises an amino acid sequence comprising amino acids 118 to 260 of human IgG2 and amino acids 261 to 447 of human IgG4, wherein the numbering of the residues is according to EU numbering.

21. An isolated antibody that binds to TREM1 produced by the method comprising culturing a host cell comprising a vector comprising a nucleic acid sequence encoding the antibody of claim 1 so that the antibody is produced.

22. A pharmaceutical composition comprising the antibody of claim 1 and a pharmaceutically acceptable carrier.

* * * * *

```
                            SEQUENCE LISTING

Sequence total quantity: 561
SEQ ID NO: 1               moltype = AA   length = 234
FEATURE                    Location/Qualifiers
source                     1..234
                           mol_type = protein
                           organism = Homo sapiens
SEQUENCE: 1
MRKTRLWGLL WMLFVSELRA ATKLTEEKYE LKEGQTLDVK CDYTLEKFAS SQKAWQIIRD  60
GEMPKTLACT ERPSKNSHPV QVGRIILEDY HDHGLLRVRM VNLQVEDSGL YQCVIYQPPK  120
EPHMLFDRIR LVVTKGFSGT PGSNENSTQN VYKIPPTTTK ALCPLYTSPR TVQAPPKST   180
ADVSTPDSEI NLTNVTDIIR VPVFNIVILL AGGFLSKSLV FSVLFAVTLR SFVP        234

SEQ ID NO: 2               moltype = AA   length = 230
FEATURE                    Location/Qualifiers
source                     1..230
                           mol_type = protein
                           organism = Mus musculus
SEQUENCE: 2
MRKAGLWGLL CVFFVSEVKA AIVLEEERYD LVEGQTLTVK CPFNIMKYAN SQKAWQRLPD  60
GKEPLTLVVT QRPFTRPSEV HMGKFTLKHD PSEAMLQVQM TDLQVTDSGL YRCVIYHPPN  120
DPVVLFHPVR LVVTKGSSDV FTPVIIPITR LTERPILITT KYSPSDTTTT RSLPKPTAVV  180
SSPGLGVTII NGTDADSVST SSVTISVICG LLSKSLVFII LFIVTKRTFG             230

SEQ ID NO: 3               moltype = AA   length = 226
FEATURE                    Location/Qualifiers
source                     1..226
                           mol_type = protein
                           organism = Rattus norvegicus
SEQUENCE: 3
MRKAGLWGLL LVFFVSEVKA AIVPEEERYD LVEGQTLTVN CPFNIMKYAR SRKAWQRLSA  60
GKEPLTLVVT ERSSTTSSEV RVGKYTLKDD PTEAMLQVQM TDLQVTDSGL YRCVIYHPPN  120
DPVLLFHPVR LVVTKGSSGV SVPDIIPTTK PTEVPVLITT KHSTPTRSLP KSTAVVSSPD  180
PGVTINNGTD PTSVSTYNVV VPVVCGLLIK TLIFFVLFVV TKRSFG                 226

SEQ ID NO: 4               moltype = AA   length = 201
FEATURE                    Location/Qualifiers
source                     1..201
                           mol_type = protein
                           organism = Macaca mulatta
SEQUENCE: 4
MRKTRLWGLL WMLFVSELRA TTELTEEKYE YKEGQTLEVK CDYALEKYAN SRKAWQKMEG  60
KMPKILAKTE RPSENSHPVQ VGRITLEDYP DHGLLQVQMT NLQVEDSGLY QCVIYQHPKE  120
SHVLFNPICL VVTKGSSGTP GSSENSTQNV YRTPSTTAKA LGPRYTSPRT VTQAPPESTV  180
VVSTPGPGPL PFFPSPCAER M                                            201

SEQ ID NO: 5               moltype = AA   length = 232
FEATURE                    Location/Qualifiers
source                     1..232
                           mol_type = protein
                           organism = Bos taurus
SEQUENCE: 5
MRKAGVWGLL WMLFIEEIQA AAEVFEEKCT LAEGQTLKVS CPTNTNIYSN SQKAWQRLKD  60
```

```
NGEVQTLAIT EGSSQVRVGK YFLEDIPSEG MLQIQMANLQ VEDSGLYRCV ILGPSDPIIL    120
FHPVRLVVTK NSLGTPASDE YPCQVSVQNP TPLPVTTKLR PRPRPRPKPV TQPIPTSADR    180
LSSPGFTVTP TNVTHVNRAP GISIIIPAAC GLLSKTLVFI GLFAVTHRSF AS            232

SEQ ID NO: 6            moltype = AA  length = 232
FEATURE                 Location/Qualifiers
source                  1..232
                        mol_type = protein
                        organism = Equus caballus
SEQUENCE: 6
MRKAKLWGLL GMLFVSELQA AAGQAEEKKI LTEGETLNYH CVYTRKHSQS QKAWQRVMDG    60
GKAETLAFTE KTSKNSQELG GRYFLEDNTT QGAVHVRMTN VQMSDSGLYR CVIYPILSNP   120
EVLESLRLVV TKGDTVSLGS SPSDSPSPDK NPPRDKAQTT TFPPATKAPV TQPPPKSTAG   180
VSRPGLEVNP THVTDVTRIS VFSIVIPVAC ALVTKSLVLT VLFAVTQKSF GS           232

SEQ ID NO: 7            moltype = AA  length = 238
FEATURE                 Location/Qualifiers
source                  1..238
                        mol_type = protein
                        organism = Sus scrofa
SEQUENCE: 7
MRSARLGRLL WMLFITEIQA ATELPEEKYI LAEGETLNVN CPVTGVYSN SRKAWQKLNR     60
NGKFQTLAIT ERVSGQVSKV QVGKIFLTDE PSEGMLHVQM TNVQAEDSGL YRCVIYQPPK   120
DPIILFYPVR LVVTNYSSGT PASAETPTQS CSPTTTLPPT TTTNRHRPRP RTVRTVTQFL   180
TDFTTSLSSP GLKVTLTNVT DITRDTEISL ILPAVCGLLS KSLVFIVLFV VTRMSFTP     238

SEQ ID NO: 8            moltype = AA  length = 238
FEATURE                 Location/Qualifiers
source                  1..238
                        mol_type = protein
                        organism = Canis lupus
SEQUENCE: 8
MRKARLWELL WLLFISELQA TTEPDEIKYV LAEGGTLNMK CTTSTWKYTY SQKAWQKLMD    60
REKPLTLIFT ENVSGDTSQV QRGRYFLEDI PSEAILNVQM TNLQVEDSGL YQCVIYHPQK   120
NPDILYPRVR LVVTKGITAS DKSPTQNLAQ ISTHPPTTTK AQSTLLASPR TVTQLPPKST   180
ADTSSPDFGV NITNVTNVTS YGFRFSVINI VILVLCGFLS KSLVFTVLIA VTQRSFGP     238

SEQ ID NO: 9            moltype = AA  length = 11
FEATURE                 Location/Qualifiers
REGION                  1..11
                        note = Synthetic
source                  1..11
                        mol_type = protein
                        organism = synthetic construct
SEQUENCE: 9
QASQDISNYL N                                                         11

SEQ ID NO: 10           moltype = AA  length = 12
FEATURE                 Location/Qualifiers
REGION                  1..12
                        note = Synthetic
source                  1..12
                        mol_type = protein
                        organism = synthetic construct
SEQUENCE: 10
RASQSVSSSY LA                                                        12

SEQ ID NO: 11           moltype = AA  length = 17
FEATURE                 Location/Qualifiers
REGION                  1..17
                        note = Synthetic
source                  1..17
                        mol_type = protein
                        organism = synthetic construct
SEQUENCE: 11
KSSQSVLYSS NNKNYLA                                                   17

SEQ ID NO: 12           moltype = AA  length = 11
FEATURE                 Location/Qualifiers
REGION                  1..11
                        note = Synthetic
source                  1..11
                        mol_type = protein
                        organism = synthetic construct
SEQUENCE: 12
RASQSVSSNL A                                                         11

SEQ ID NO: 13           moltype = AA  length = 16
FEATURE                 Location/Qualifiers
```

```
REGION                    1..16
                          note = Synthetic
source                    1..16
                          mol_type = protein
                          organism = synthetic construct
SEQUENCE: 13
RSSQSLLHSN GYNYLD                                                      16

SEQ ID NO: 14             moltype = AA  length = 17
FEATURE                   Location/Qualifiers
REGION                    1..17
                          note = Synthetic
source                    1..17
                          mol_type = protein
                          organism = synthetic construct
SEQUENCE: 14
KSSQSVLFSS NNKNYLA                                                     17

SEQ ID NO: 15             moltype = AA  length = 11
FEATURE                   Location/Qualifiers
REGION                    1..11
                          note = Synthetic
source                    1..11
                          mol_type = protein
                          organism = synthetic construct
SEQUENCE: 15
RASQSVSSYL A                                                           11

SEQ ID NO: 16             moltype = AA  length = 12
FEATURE                   Location/Qualifiers
REGION                    1..12
                          note = Synthetic
source                    1..12
                          mol_type = protein
                          organism = synthetic construct
SEQUENCE: 16
RASQSVSSSF LA                                                          12

SEQ ID NO: 17             moltype = AA  length = 11
FEATURE                   Location/Qualifiers
REGION                    1..11
                          note = Synthetic
source                    1..11
                          mol_type = protein
                          organism = synthetic construct
SEQUENCE: 17
RASQGISSWL A                                                           11

SEQ ID NO: 18             moltype = AA  length = 11
FEATURE                   Location/Qualifiers
REGION                    1..11
                          note = Synthetic
source                    1..11
                          mol_type = protein
                          organism = synthetic construct
SEQUENCE: 18
RASQSISSWL A                                                           11

SEQ ID NO: 19             moltype = AA  length = 11
FEATURE                   Location/Qualifiers
REGION                    1..11
                          note = Synthetic
source                    1..11
                          mol_type = protein
                          organism = synthetic construct
SEQUENCE: 19
RASQSISSFL N                                                           11

SEQ ID NO: 20             moltype = AA  length = 11
FEATURE                   Location/Qualifiers
REGION                    1..11
                          note = Synthetic
source                    1..11
                          mol_type = protein
                          organism = synthetic construct
SEQUENCE: 20
RASQSIGSWL A                                                           11

SEQ ID NO: 21             moltype = AA  length = 11
```

```
FEATURE               Location/Qualifiers
REGION                1..11
                      note = Synthetic
source                1..11
                      mol_type = protein
                      organism = synthetic construct
SEQUENCE: 21
RASQSISSYL N                                                                    11

SEQ ID NO: 22         moltype = AA  length = 11
FEATURE               Location/Qualifiers
REGION                1..11
                      note = Synthetic
source                1..11
                      mol_type = protein
                      organism = synthetic construct
SEQUENCE: 22
RASQSVGSNL A                                                                    11

SEQ ID NO: 23         moltype = AA  length = 11
FEATURE               Location/Qualifiers
REGION                1..11
                      note = Synthetic
source                1..11
                      mol_type = protein
                      organism = synthetic construct
SEQUENCE: 23
RASQSISRYL N                                                                    11

SEQ ID NO: 24         moltype = AA  length = 11
FEATURE               Location/Qualifiers
REGION                1..11
                      note = Synthetic
source                1..11
                      mol_type = protein
                      organism = synthetic construct
SEQUENCE: 24
RASQSINSWL A                                                                    11

SEQ ID NO: 25         moltype = AA  length = 11
FEATURE               Location/Qualifiers
REGION                1..11
                      note = Synthetic
source                1..11
                      mol_type = protein
                      organism = synthetic construct
SEQUENCE: 25
RASQDISSWL A                                                                    11

SEQ ID NO: 26         moltype = AA  length = 11
FEATURE               Location/Qualifiers
REGION                1..11
                      note = Synthetic
source                1..11
                      mol_type = protein
                      organism = synthetic construct
SEQUENCE: 26
RASQGIDSWL A                                                                    11

SEQ ID NO: 27         moltype = AA  length = 16
FEATURE               Location/Qualifiers
REGION                1..16
                      note = Synthetic
source                1..16
                      mol_type = protein
                      organism = synthetic construct
SEQUENCE: 27
RSSQSLLHRN GYNYLD                                                               16

SEQ ID NO: 28         moltype = AA  length = 7
FEATURE               Location/Qualifiers
REGION                1..7
                      note = Synthetic
source                1..7
                      mol_type = protein
                      organism = synthetic construct
SEQUENCE: 28
DASNLET                                                                          7
```

```
SEQ ID NO: 29          moltype = AA  length = 7
FEATURE                Location/Qualifiers
REGION                 1..7
                       note = Synthetic
source                 1..7
                       mol_type = protein
                       organism = synthetic construct
SEQUENCE: 29
GASSRAT                                                                    7

SEQ ID NO: 30          moltype = AA  length = 7
FEATURE                Location/Qualifiers
REGION                 1..7
                       note = Synthetic
source                 1..7
                       mol_type = protein
                       organism = synthetic construct
SEQUENCE: 30
WASTRES                                                                    7

SEQ ID NO: 31          moltype = AA  length = 7
FEATURE                Location/Qualifiers
REGION                 1..7
                       note = Synthetic
source                 1..7
                       mol_type = protein
                       organism = synthetic construct
SEQUENCE: 31
GASTRAT                                                                    7

SEQ ID NO: 32          moltype = AA  length = 7
FEATURE                Location/Qualifiers
REGION                 1..7
                       note = Synthetic
source                 1..7
                       mol_type = protein
                       organism = synthetic construct
SEQUENCE: 32
LGSNRAS                                                                    7

SEQ ID NO: 33          moltype = AA  length = 7
FEATURE                Location/Qualifiers
REGION                 1..7
                       note = Synthetic
source                 1..7
                       mol_type = protein
                       organism = synthetic construct
SEQUENCE: 33
DASNRAT                                                                    7

SEQ ID NO: 34          moltype = AA  length = 7
FEATURE                Location/Qualifiers
REGION                 1..7
                       note = Synthetic
source                 1..7
                       mol_type = protein
                       organism = synthetic construct
SEQUENCE: 34
AASSLQS                                                                    7

SEQ ID NO: 35          moltype = AA  length = 7
FEATURE                Location/Qualifiers
REGION                 1..7
                       note = Synthetic
source                 1..7
                       mol_type = protein
                       organism = synthetic construct
SEQUENCE: 35
DASNLAT                                                                    7

SEQ ID NO: 36          moltype = AA  length = 7
FEATURE                Location/Qualifiers
REGION                 1..7
                       note = Synthetic
source                 1..7
                       mol_type = protein
                       organism = synthetic construct
SEQUENCE: 36
KASSLES                                                                    7
```

```
SEQ ID NO: 37           moltype = AA   length = 7
FEATURE                 Location/Qualifiers
REGION                  1..7
                        note = Synthetic
source                  1..7
                        mol_type = protein
                        organism = synthetic construct
SEQUENCE: 37
AASNLQS                                                                    7

SEQ ID NO: 38           moltype = AA   length = 7
FEATURE                 Location/Qualifiers
REGION                  1..7
                        note = Synthetic
source                  1..7
                        mol_type = protein
                        organism = synthetic construct
SEQUENCE: 38
DASSLES                                                                    7

SEQ ID NO: 39           moltype = AA   length = 7
FEATURE                 Location/Qualifiers
REGION                  1..7
                        note = Synthetic
source                  1..7
                        mol_type = protein
                        organism = synthetic construct
SEQUENCE: 39
LGSHRAS                                                                    7

SEQ ID NO: 40           moltype = AA   length = 7
FEATURE                 Location/Qualifiers
REGION                  1..7
                        note = Synthetic
source                  1..7
                        mol_type = protein
                        organism = synthetic construct
SEQUENCE: 40
DSSNRAT                                                                    7

SEQ ID NO: 41           moltype = AA   length = 9
FEATURE                 Location/Qualifiers
REGION                  1..9
                        note = Synthetic
source                  1..9
                        mol_type = protein
                        organism = synthetic construct
SEQUENCE: 41
QQVYVLPFT                                                                  9

SEQ ID NO: 42           moltype = AA   length = 9
FEATURE                 Location/Qualifiers
REGION                  1..9
                        note = Synthetic
source                  1..9
                        mol_type = protein
                        organism = synthetic construct
SEQUENCE: 42
QQYLGFPPT                                                                  9

SEQ ID NO: 43           moltype = AA   length = 9
FEATURE                 Location/Qualifiers
REGION                  1..9
                        note = Synthetic
source                  1..9
                        mol_type = protein
                        organism = synthetic construct
SEQUENCE: 43
QQSFLTPWT                                                                  9

SEQ ID NO: 44           moltype = AA   length = 9
FEATURE                 Location/Qualifiers
REGION                  1..9
                        note = Synthetic
source                  1..9
                        mol_type = protein
                        organism = synthetic construct
SEQUENCE: 44
```

```
QQFNNHPIT                                                                              9

SEQ ID NO: 45           moltype = AA  length = 9
FEATURE                 Location/Qualifiers
REGION                  1..9
                        note = Synthetic
source                  1..9
                        mol_type = protein
                        organism = synthetic construct
SEQUENCE: 45
VQARQTPLT                                                                              9

SEQ ID NO: 46           moltype = AA  length = 9
FEATURE                 Location/Qualifiers
REGION                  1..9
                        note = Synthetic
source                  1..9
                        mol_type = protein
                        organism = synthetic construct
SEQUENCE: 46
MQARDAPWT                                                                              9

SEQ ID NO: 47           moltype = AA  length = 9
FEATURE                 Location/Qualifiers
REGION                  1..9
                        note = Synthetic
source                  1..9
                        mol_type = protein
                        organism = synthetic construct
SEQUENCE: 47
QQLASYPYT                                                                              9

SEQ ID NO: 48           moltype = AA  length = 9
FEATURE                 Location/Qualifiers
REGION                  1..9
                        note = Synthetic
source                  1..9
                        mol_type = protein
                        organism = synthetic construct
SEQUENCE: 48
MQARQTPFT                                                                              9

SEQ ID NO: 49           moltype = AA  length = 9
FEATURE                 Location/Qualifiers
REGION                  1..9
                        note = Synthetic
source                  1..9
                        mol_type = protein
                        organism = synthetic construct
SEQUENCE: 49
MQARQAPWT                                                                              9

SEQ ID NO: 50           moltype = AA  length = 10
FEATURE                 Location/Qualifiers
REGION                  1..10
                        note = Synthetic
source                  1..10
                        mol_type = protein
                        organism = synthetic construct
SEQUENCE: 50
MQARQVPPWT                                                                            10

SEQ ID NO: 51           moltype = AA  length = 8
FEATURE                 Location/Qualifiers
REGION                  1..8
                        note = Synthetic
source                  1..8
                        mol_type = protein
                        organism = synthetic construct
SEQUENCE: 51
MQARQAFT                                                                               8

SEQ ID NO: 52           moltype = AA  length = 9
FEATURE                 Location/Qualifiers
REGION                  1..9
                        note = Synthetic
source                  1..9
                        mol_type = protein
                        organism = synthetic construct
```

```
SEQUENCE: 52
QQYTSWPLT                                                                   9

SEQ ID NO: 53          moltype = AA  length = 9
FEATURE                Location/Qualifiers
REGION                 1..9
                       note = Synthetic
source                 1..9
                       mol_type = protein
                       organism = synthetic construct
SEQUENCE: 53
QQLDSHPPT                                                                   9

SEQ ID NO: 54          moltype = AA  length = 9
FEATURE                Location/Qualifiers
REGION                 1..9
                       note = Synthetic
source                 1..9
                       mol_type = protein
                       organism = synthetic construct
SEQUENCE: 54
QQYDVDPLT                                                                   9

SEQ ID NO: 55          moltype = AA  length = 9
FEATURE                Location/Qualifiers
REGION                 1..9
                       note = Synthetic
source                 1..9
                       mol_type = protein
                       organism = synthetic construct
SEQUENCE: 55
QQAFISPPT                                                                   9

SEQ ID NO: 56          moltype = AA  length = 9
FEATURE                Location/Qualifiers
REGION                 1..9
                       note = Synthetic
source                 1..9
                       mol_type = protein
                       organism = synthetic construct
SEQUENCE: 56
QQADTLPIT                                                                   9

SEQ ID NO: 57          moltype = AA  length = 9
FEATURE                Location/Qualifiers
REGION                 1..9
                       note = Synthetic
source                 1..9
                       mol_type = protein
                       organism = synthetic construct
SEQUENCE: 57
QQSDIHPRT                                                                   9

SEQ ID NO: 58          moltype = AA  length = 9
FEATURE                Location/Qualifiers
REGION                 1..9
                       note = Synthetic
source                 1..9
                       mol_type = protein
                       organism = synthetic construct
SEQUENCE: 58
QQDSIYPIT                                                                   9

SEQ ID NO: 59          moltype = AA  length = 9
FEATURE                Location/Qualifiers
REGION                 1..9
                       note = Synthetic
source                 1..9
                       mol_type = protein
                       organism = synthetic construct
SEQUENCE: 59
QQANSFPLT                                                                   9

SEQ ID NO: 60          moltype = AA  length = 10
FEATURE                Location/Qualifiers
REGION                 1..10
                       note = Synthetic
source                 1..10
                       mol_type = protein
```

```
                              organism = synthetic construct
SEQUENCE: 60
QQYKSFSPFT                                                                      10

SEQ ID NO: 61           moltype = AA  length = 8
FEATURE                 Location/Qualifiers
REGION                  1..8
                        note = Synthetic
source                  1..8
                        mol_type = protein
                        organism = synthetic construct
SEQUENCE: 61
QQSYSDLT                                                                         8

SEQ ID NO: 62           moltype = AA  length = 9
FEATURE                 Location/Qualifiers
REGION                  1..9
                        note = Synthetic
source                  1..9
                        mol_type = protein
                        organism = synthetic construct
SEQUENCE: 62
QQYLIPPIT                                                                        9

SEQ ID NO: 63           moltype = AA  length = 9
FEATURE                 Location/Qualifiers
REGION                  1..9
                        note = Synthetic
source                  1..9
                        mol_type = protein
                        organism = synthetic construct
SEQUENCE: 63
QQHQSFSPT                                                                        9

SEQ ID NO: 64           moltype = AA  length = 9
FEATURE                 Location/Qualifiers
REGION                  1..9
                        note = Synthetic
source                  1..9
                        mol_type = protein
                        organism = synthetic construct
SEQUENCE: 64
QQRSVLPLT                                                                        9

SEQ ID NO: 65           moltype = AA  length = 9
FEATURE                 Location/Qualifiers
REGION                  1..9
                        note = Synthetic
source                  1..9
                        mol_type = protein
                        organism = synthetic construct
SEQUENCE: 65
QQIFSTPLT                                                                        9

SEQ ID NO: 66           moltype = AA  length = 9
FEATURE                 Location/Qualifiers
REGION                  1..9
                        note = Synthetic
source                  1..9
                        mol_type = protein
                        organism = synthetic construct
SEQUENCE: 66
QQSFYDPIT                                                                        9

SEQ ID NO: 67           moltype = AA  length = 9
FEATURE                 Location/Qualifiers
REGION                  1..9
                        note = Synthetic
source                  1..9
                        mol_type = protein
                        organism = synthetic construct
SEQUENCE: 67
QQYLYFPLT                                                                        9

SEQ ID NO: 68           moltype = AA  length = 9
FEATURE                 Location/Qualifiers
REGION                  1..9
                        note = Synthetic
source                  1..9
```

```
                        mol_type = protein
                        organism = synthetic construct
SEQUENCE: 68
QQGVNYPFT                                                                     9

SEQ ID NO: 69           moltype = AA  length = 8
FEATURE                 Location/Qualifiers
REGION                  1..8
                        note = Synthetic
source                  1..8
                        mol_type = protein
                        organism = synthetic construct
SEQUENCE: 69
QQVISFPT                                                                      8

SEQ ID NO: 70           moltype = AA  length = 10
FEATURE                 Location/Qualifiers
REGION                  1..10
                        note = Synthetic
source                  1..10
                        mol_type = protein
                        organism = synthetic construct
SEQUENCE: 70
QQYDDFPPIT                                                                   10

SEQ ID NO: 71           moltype = AA  length = 9
FEATURE                 Location/Qualifiers
REGION                  1..9
                        note = Synthetic
source                  1..9
                        mol_type = protein
                        organism = synthetic construct
SEQUENCE: 71
QQSLDLPFT                                                                     9

SEQ ID NO: 72           moltype = AA  length = 9
FEATURE                 Location/Qualifiers
REGION                  1..9
                        note = Synthetic
source                  1..9
                        mol_type = protein
                        organism = synthetic construct
SEQUENCE: 72
QQINDHPFT                                                                     9

SEQ ID NO: 73           moltype = AA  length = 9
FEATURE                 Location/Qualifiers
REGION                  1..9
                        note = Synthetic
source                  1..9
                        mol_type = protein
                        organism = synthetic construct
SEQUENCE: 73
QQYGPYPYT                                                                     9

SEQ ID NO: 74           moltype = AA  length = 9
FEATURE                 Location/Qualifiers
REGION                  1..9
                        note = Synthetic
source                  1..9
                        mol_type = protein
                        organism = synthetic construct
SEQUENCE: 74
QQSHSTPLT                                                                     9

SEQ ID NO: 75           moltype = AA  length = 9
FEATURE                 Location/Qualifiers
REGION                  1..9
                        note = Synthetic
source                  1..9
                        mol_type = protein
                        organism = synthetic construct
SEQUENCE: 75
QQLASQPPT                                                                     9

SEQ ID NO: 76           moltype = AA  length = 9
FEATURE                 Location/Qualifiers
REGION                  1..9
                        note = Synthetic
```

```
                           -continued source                1..9
                      mol_type = protein
                      organism = synthetic construct
SEQUENCE: 76
QQYAYWPLT                                                              9

SEQ ID NO: 77         moltype = AA   length = 9
FEATURE               Location/Qualifiers
REGION                1..9
                      note = Synthetic
source                1..9
                      mol_type = protein
                      organism = synthetic construct
SEQUENCE: 77
QQDFSLPYT                                                              9

SEQ ID NO: 78         moltype = AA   length = 8
FEATURE               Location/Qualifiers
REGION                1..8
                      note = Synthetic
source                1..8
                      mol_type = protein
                      organism = synthetic construct
SEQUENCE: 78
QQSLTHPT                                                               8

SEQ ID NO: 79         moltype = AA   length = 9
FEATURE               Location/Qualifiers
REGION                1..9
                      note = Synthetic
source                1..9
                      mol_type = protein
                      organism = synthetic construct
SEQUENCE: 79
QQYDLLPYT                                                              9

SEQ ID NO: 80         moltype = AA   length = 10
FEATURE               Location/Qualifiers
REGION                1..10
                      note = Synthetic
source                1..10
                      mol_type = protein
                      organism = synthetic construct
SEQUENCE: 80
QQAVIHPPYT                                                            10

SEQ ID NO: 81         moltype = AA   length = 10
FEATURE               Location/Qualifiers
REGION                1..10
                      note = Synthetic
source                1..10
                      mol_type = protein
                      organism = synthetic construct
SEQUENCE: 81
QQYNVHPPRT                                                            10

SEQ ID NO: 82         moltype = AA   length = 9
FEATURE               Location/Qualifiers
REGION                1..9
                      note = Synthetic
source                1..9
                      mol_type = protein
                      organism = synthetic construct
SEQUENCE: 82
MQSRNAPWT                                                              9

SEQ ID NO: 83         moltype = AA   length = 8
FEATURE               Location/Qualifiers
REGION                1..8
                      note = Synthetic
source                1..8
                      mol_type = protein
                      organism = synthetic construct
SEQUENCE: 83
MQARHGFT                                                               8

SEQ ID NO: 84         moltype = AA   length = 9
FEATURE               Location/Qualifiers
REGION                1..9
```

```
                    note = Synthetic
source              1..9
                    mol_type = protein
                    organism = synthetic construct
SEQUENCE: 84
MQAREVPFT                                                                    9

SEQ ID NO: 85       moltype = AA   length = 10
FEATURE             Location/Qualifiers
REGION              1..10
                    note = Synthetic
source              1..10
                    mol_type = protein
                    organism = synthetic construct
SEQUENCE: 85
MQARHVPPLT                                                                   10

SEQ ID NO: 86       moltype = AA   length = 9
FEATURE             Location/Qualifiers
REGION              1..9
                    note = Synthetic
source              1..9
                    mol_type = protein
                    organism = synthetic construct
SEQUENCE: 86
QQHDSAPYT                                                                    9

SEQ ID NO: 87       moltype = AA   length = 9
FEATURE             Location/Qualifiers
REGION              1..9
                    note = Synthetic
source              1..9
                    mol_type = protein
                    organism = synthetic construct
SEQUENCE: 87
MQGRQVPFT                                                                    9

SEQ ID NO: 88       moltype = AA   length = 9
FEATURE             Location/Qualifiers
REGION              1..9
                    note = Synthetic
source              1..9
                    mol_type = protein
                    organism = synthetic construct
SEQUENCE: 88
MQARGTPWT                                                                    9

SEQ ID NO: 89       moltype = AA   length = 10
FEATURE             Location/Qualifiers
REGION              1..10
                    note = Synthetic
source              1..10
                    mol_type = protein
                    organism = synthetic construct
SEQUENCE: 89
MQSRRAPPWT                                                                   10

SEQ ID NO: 90       moltype = AA   length = 9
FEATURE             Location/Qualifiers
REGION              1..9
                    note = Synthetic
source              1..9
                    mol_type = protein
                    organism = synthetic construct
SEQUENCE: 90
QQFQSYPFT                                                                    9

SEQ ID NO: 91       moltype = AA   length = 10
FEATURE             Location/Qualifiers
REGION              1..10
                    note = Synthetic
source              1..10
                    mol_type = protein
                    organism = synthetic construct
SEQUENCE: 91
QQSSADSPFT                                                                   10

SEQ ID NO: 92       moltype = AA   length = 9
FEATURE             Location/Qualifiers
```

-continued

```
REGION                  1..9
                        note = Synthetic
source                  1..9
                        mol_type = protein
                        organism = synthetic construct
SEQUENCE: 92
MQARQLPWT                                                                  9

SEQ ID NO: 93           moltype = AA  length = 9
FEATURE                 Location/Qualifiers
REGION                  1..9
                        note = Synthetic
source                  1..9
                        mol_type = protein
                        organism = synthetic construct
SEQUENCE: 93
QQHDVWPIT                                                                  9

SEQ ID NO: 94           moltype = AA  length = 8
FEATURE                 Location/Qualifiers
REGION                  1..8
                        note = Synthetic
source                  1..8
                        mol_type = protein
                        organism = synthetic construct
SEQUENCE: 94
MQTRHTPT                                                                   8

SEQ ID NO: 95           moltype = AA  length = 9
FEATURE                 Location/Qualifiers
REGION                  1..9
                        note = Synthetic
source                  1..9
                        mol_type = protein
                        organism = synthetic construct
SEQUENCE: 95
MQDFARPPT                                                                  9

SEQ ID NO: 96           moltype = AA  length = 9
FEATURE                 Location/Qualifiers
REGION                  1..9
                        note = Synthetic
source                  1..9
                        mol_type = protein
                        organism = synthetic construct
SEQUENCE: 96
QQRAVFPPT                                                                  9

SEQ ID NO: 97           moltype = AA  length = 8
FEATURE                 Location/Qualifiers
REGION                  1..8
                        note = Synthetic
source                  1..8
                        mol_type = protein
                        organism = synthetic construct
SEQUENCE: 97
QQDATGIT                                                                   8

SEQ ID NO: 98           moltype = AA  length = 9
FEATURE                 Location/Qualifiers
REGION                  1..9
                        note = Synthetic
source                  1..9
                        mol_type = protein
                        organism = synthetic construct
SEQUENCE: 98
QQLASFPWT                                                                  9

SEQ ID NO: 99           moltype = AA  length = 9
FEATURE                 Location/Qualifiers
REGION                  1..9
                        note = Synthetic
source                  1..9
                        mol_type = protein
                        organism = synthetic construct
SEQUENCE: 99
QQLAFTPWT                                                                  9

SEQ ID NO: 100          moltype = AA  length = 8
```

```
FEATURE                 Location/Qualifiers
REGION                  1..8
                        note = Synthetic
source                  1..8
                        mol_type = protein
                        organism = synthetic construct
SEQUENCE: 100
QQDHSFIT                                                                         8

SEQ ID NO: 101          moltype = AA  length = 8
FEATURE                 Location/Qualifiers
REGION                  1..8
                        note = Synthetic
source                  1..8
                        mol_type = protein
                        organism = synthetic construct
SEQUENCE: 101
QQDVSDFT                                                                         8

SEQ ID NO: 102          moltype = AA  length = 10
FEATURE                 Location/Qualifiers
REGION                  1..10
                        note = Synthetic
source                  1..10
                        mol_type = protein
                        organism = synthetic construct
SEQUENCE: 102
QQLYHAPPIT                                                                      10

SEQ ID NO: 103          moltype = AA  length = 9
FEATURE                 Location/Qualifiers
REGION                  1..9
                        note = Synthetic
source                  1..9
                        mol_type = protein
                        organism = synthetic construct
SEQUENCE: 103
QQYDSLPFT                                                                        9

SEQ ID NO: 104          moltype = AA  length = 9
FEATURE                 Location/Qualifiers
REGION                  1..9
                        note = Synthetic
source                  1..9
                        mol_type = protein
                        organism = synthetic construct
SEQUENCE: 104
QQVYLFPWT                                                                        9

SEQ ID NO: 105          moltype = AA  length = 9
FEATURE                 Location/Qualifiers
REGION                  1..9
                        note = Synthetic
source                  1..9
                        mol_type = protein
                        organism = synthetic construct
SEQUENCE: 105
QQFFLAPPT                                                                        9

SEQ ID NO: 106          moltype = AA  length = 9
FEATURE                 Location/Qualifiers
REGION                  1..9
                        note = Synthetic
source                  1..9
                        mol_type = protein
                        organism = synthetic construct
SEQUENCE: 106
QQAVSLPWT                                                                        9

SEQ ID NO: 107          moltype = AA  length = 9
FEATURE                 Location/Qualifiers
REGION                  1..9
                        note = Synthetic
source                  1..9
                        mol_type = protein
                        organism = synthetic construct
SEQUENCE: 107
QQFDNLPYT                                                                        9
```

| | | |
|---|---|---|
| SEQ ID NO: 108<br>FEATURE<br>REGION<br><br>source<br><br><br><br>SEQUENCE: 108<br>QQATAHPPT | moltype = AA   length = 9<br>Location/Qualifiers<br>1..9<br>note = Synthetic<br>1..9<br>mol_type = protein<br>organism = synthetic construct<br><br> | <br><br><br><br><br><br><br><br>9 |
| SEQ ID NO: 109<br>FEATURE<br>REGION<br><br>source<br><br><br><br>SEQUENCE: 109<br>QQAVSHPLT | moltype = AA   length = 9<br>Location/Qualifiers<br>1..9<br>note = Synthetic<br>1..9<br>mol_type = protein<br>organism = synthetic construct<br><br> | <br><br><br><br><br><br><br><br>9 |
| SEQ ID NO: 110<br>FEATURE<br>REGION<br><br>source<br><br><br><br>SEQUENCE: 110<br>QQATSLPLT | moltype = AA   length = 9<br>Location/Qualifiers<br>1..9<br>note = Synthetic<br>1..9<br>mol_type = protein<br>organism = synthetic construct<br><br> | <br><br><br><br><br><br><br><br>9 |
| SEQ ID NO: 111<br>FEATURE<br>REGION<br><br>source<br><br><br><br>SEQUENCE: 111<br>MQRLQAWT | moltype = AA   length = 8<br>Location/Qualifiers<br>1..8<br>note = Synthetic<br>1..8<br>mol_type = protein<br>organism = synthetic construct<br><br> | <br><br><br><br><br><br><br><br>8 |
| SEQ ID NO: 112<br>FEATURE<br>REGION<br><br>source<br><br><br><br>SEQUENCE: 112<br>QQYRTYPT | moltype = AA   length = 8<br>Location/Qualifiers<br>1..8<br>note = Synthetic<br>1..8<br>mol_type = protein<br>organism = synthetic construct<br><br> | <br><br><br><br><br><br><br><br>8 |
| SEQ ID NO: 113<br>FEATURE<br>REGION<br><br>source<br><br><br><br>SEQUENCE: 113<br>QQHSLLSIT | moltype = AA   length = 9<br>Location/Qualifiers<br>1..9<br>note = Synthetic<br>1..9<br>mol_type = protein<br>organism = synthetic construct<br><br> | <br><br><br><br><br><br><br><br>9 |
| SEQ ID NO: 114<br>FEATURE<br>REGION<br><br>source<br><br><br><br>SEQUENCE: 114<br>QHYNLWRT | moltype = AA   length = 8<br>Location/Qualifiers<br>1..8<br>note = Synthetic<br>1..8<br>mol_type = protein<br>organism = synthetic construct<br><br> | <br><br><br><br><br><br><br><br>8 |
| SEQ ID NO: 115<br>FEATURE<br>REGION<br><br>source<br><br><br><br>SEQUENCE: 115<br>QQHSTYSWT | moltype = AA   length = 9<br>Location/Qualifiers<br>1..9<br>note = Synthetic<br>1..9<br>mol_type = protein<br>organism = synthetic construct<br><br> | <br><br><br><br><br><br><br><br>9 |

```
SEQ ID NO: 116         moltype = AA   length = 9
FEATURE                Location/Qualifiers
REGION                 1..9
                       note = Synthetic
source                 1..9
                       mol_type = protein
                       organism = synthetic construct
SEQUENCE: 116
QQHDVWPYT                                                                  9

SEQ ID NO: 117         moltype = AA   length = 9
FEATURE                Location/Qualifiers
REGION                 1..9
                       note = Synthetic
source                 1..9
                       mol_type = protein
                       organism = synthetic construct
SEQUENCE: 117
QQYFSTPPT                                                                  9

SEQ ID NO: 118         moltype = AA   length = 9
FEATURE                Location/Qualifiers
REGION                 1..9
                       note = Synthetic
source                 1..9
                       mol_type = protein
                       organism = synthetic construct
SEQUENCE: 118
QQYALTPYT                                                                  9

SEQ ID NO: 119         moltype = AA   length = 9
FEATURE                Location/Qualifiers
REGION                 1..9
                       note = Synthetic
source                 1..9
                       mol_type = protein
                       organism = synthetic construct
SEQUENCE: 119
QQDHDRPLT                                                                  9

SEQ ID NO: 120         moltype = AA   length = 9
FEATURE                Location/Qualifiers
REGION                 1..9
                       note = Synthetic
source                 1..9
                       mol_type = protein
                       organism = synthetic construct
SEQUENCE: 120
GTFSSYAIS                                                                  9

SEQ ID NO: 121         moltype = AA   length = 9
FEATURE                Location/Qualifiers
REGION                 1..9
                       note = Synthetic
source                 1..9
                       mol_type = protein
                       organism = synthetic construct
SEQUENCE: 121
YTFTSYYMH                                                                  9

SEQ ID NO: 122         moltype = AA   length = 11
FEATURE                Location/Qualifiers
REGION                 1..11
                       note = Synthetic
source                 1..11
                       mol_type = protein
                       organism = synthetic construct
SEQUENCE: 122
GSISSSSYYW G                                                              11

SEQ ID NO: 123         moltype = AA   length = 9
FEATURE                Location/Qualifiers
REGION                 1..9
                       note = Synthetic
source                 1..9
                       mol_type = protein
                       organism = synthetic construct
SEQUENCE: 123
```

```
FTFSSYSMN                                                                               9

SEQ ID NO: 124          moltype = AA   length = 9
FEATURE                 Location/Qualifiers
REGION                  1..9
                        note = Synthetic
source                  1..9
                        mol_type = protein
                        organism = synthetic construct
SEQUENCE: 124
FTFSSYGMH                                                                               9

SEQ ID NO: 125          moltype = AA   length = 9
FEATURE                 Location/Qualifiers
REGION                  1..9
                        note = Synthetic
source                  1..9
                        mol_type = protein
                        organism = synthetic construct
SEQUENCE: 125
FTFDDYAMH                                                                               9

SEQ ID NO: 126          moltype = AA   length = 9
FEATURE                 Location/Qualifiers
REGION                  1..9
                        note = Synthetic
source                  1..9
                        mol_type = protein
                        organism = synthetic construct
SEQUENCE: 126
GSISSYYWS                                                                               9

SEQ ID NO: 127          moltype = AA   length = 9
FEATURE                 Location/Qualifiers
REGION                  1..9
                        note = Synthetic
source                  1..9
                        mol_type = protein
                        organism = synthetic construct
SEQUENCE: 127
FTFSDHHMD                                                                               9

SEQ ID NO: 128          moltype = AA   length = 9
FEATURE                 Location/Qualifiers
REGION                  1..9
                        note = Synthetic
source                  1..9
                        mol_type = protein
                        organism = synthetic construct
SEQUENCE: 128
FTFSSYWMS                                                                               9

SEQ ID NO: 129          moltype = AA   length = 9
FEATURE                 Location/Qualifiers
REGION                  1..9
                        note = Synthetic
source                  1..9
                        mol_type = protein
                        organism = synthetic construct
SEQUENCE: 129
YTFTSYYIH                                                                               9

SEQ ID NO: 130          moltype = AA   length = 11
FEATURE                 Location/Qualifiers
REGION                  1..11
                        note = Synthetic
source                  1..11
                        mol_type = protein
                        organism = synthetic construct
SEQUENCE: 130
GSISSGGYYW S                                                                           11

SEQ ID NO: 131          moltype = AA   length = 9
FEATURE                 Location/Qualifiers
REGION                  1..9
                        note = Synthetic
source                  1..9
                        mol_type = protein
                        organism = synthetic construct
```

```
SEQUENCE: 131
FTFSNYGMH                                                                    9

SEQ ID NO: 132          moltype = AA  length = 9
FEATURE                 Location/Qualifiers
REGION                  1..9
                        note = Synthetic
source                  1..9
                        mol_type = protein
                        organism = synthetic construct
SEQUENCE: 132
LTFSSYGMH                                                                    9

SEQ ID NO: 133          moltype = AA  length = 9
FEATURE                 Location/Qualifiers
REGION                  1..9
                        note = Synthetic
source                  1..9
                        mol_type = protein
                        organism = synthetic construct
SEQUENCE: 133
FTFSTYAMS                                                                    9

SEQ ID NO: 134          moltype = AA  length = 9
FEATURE                 Location/Qualifiers
REGION                  1..9
                        note = Synthetic
source                  1..9
                        mol_type = protein
                        organism = synthetic construct
SEQUENCE: 134
GTFSNYAIS                                                                    9

SEQ ID NO: 135          moltype = AA  length = 10
FEATURE                 Location/Qualifiers
REGION                  1..10
                        note = Synthetic
source                  1..10
                        mol_type = protein
                        organism = synthetic construct
SEQUENCE: 135
YSISSGYYWA                                                                  10

SEQ ID NO: 136          moltype = AA  length = 10
FEATURE                 Location/Qualifiers
REGION                  1..10
                        note = Synthetic
source                  1..10
                        mol_type = protein
                        organism = synthetic construct
SEQUENCE: 136
YSISSGYYWG                                                                  10

SEQ ID NO: 137          moltype = AA  length = 11
FEATURE                 Location/Qualifiers
REGION                  1..11
                        note = Synthetic
source                  1..11
                        mol_type = protein
                        organism = synthetic construct
SEQUENCE: 137
GSISSSDYYW G                                                                11

SEQ ID NO: 138          moltype = AA  length = 9
FEATURE                 Location/Qualifiers
REGION                  1..9
                        note = Synthetic
source                  1..9
                        mol_type = protein
                        organism = synthetic construct
SEQUENCE: 138
YTFTGYYMH                                                                    9

SEQ ID NO: 139          moltype = AA  length = 9
FEATURE                 Location/Qualifiers
REGION                  1..9
                        note = Synthetic
source                  1..9
                        mol_type = protein
```

```
                        organism = synthetic construct
SEQUENCE: 139
YTFTSYGIH                                                                       9

SEQ ID NO: 140          moltype = AA  length = 9
FEATURE                 Location/Qualifiers
REGION                  1..9
                        note = Synthetic
source                  1..9
                        mol_type = protein
                        organism = synthetic construct
SEQUENCE: 140
YSFTTYWIG                                                                       9

SEQ ID NO: 141          moltype = AA  length = 9
FEATURE                 Location/Qualifiers
REGION                  1..9
                        note = Synthetic
source                  1..9
                        mol_type = protein
                        organism = synthetic construct
SEQUENCE: 141
YTFTSYGIS                                                                       9

SEQ ID NO: 142          moltype = AA  length = 9
FEATURE                 Location/Qualifiers
REGION                  1..9
                        note = Synthetic
source                  1..9
                        mol_type = protein
                        organism = synthetic construct
SEQUENCE: 142
FTFGDYAMH                                                                       9

SEQ ID NO: 143          moltype = AA  length = 9
FEATURE                 Location/Qualifiers
REGION                  1..9
                        note = Synthetic
source                  1..9
                        mol_type = protein
                        organism = synthetic construct
SEQUENCE: 143
FTFSSYAMS                                                                       9

SEQ ID NO: 144          moltype = AA  length = 17
FEATURE                 Location/Qualifiers
REGION                  1..17
                        note = Synthetic
source                  1..17
                        mol_type = protein
                        organism = synthetic construct
SEQUENCE: 144
GIIPIFGTAN YAQKFQG                                                             17

SEQ ID NO: 145          moltype = AA  length = 17
FEATURE                 Location/Qualifiers
REGION                  1..17
                        note = Synthetic
source                  1..17
                        mol_type = protein
                        organism = synthetic construct
SEQUENCE: 145
VINPSGGSTS YAQKFQG                                                             17

SEQ ID NO: 146          moltype = AA  length = 17
FEATURE                 Location/Qualifiers
REGION                  1..17
                        note = Synthetic
source                  1..17
                        mol_type = protein
                        organism = synthetic construct
SEQUENCE: 146
IINPSGGSTS YAQKFQG                                                             17

SEQ ID NO: 147          moltype = AA  length = 16
FEATURE                 Location/Qualifiers
REGION                  1..16
                        note = Synthetic
source                  1..16
```

```
                        mol_type = protein
                        organism = synthetic construct
SEQUENCE: 147
SIYYSGSTYY NPSLKS                                                     16

SEQ ID NO: 148          moltype = AA  length = 17
FEATURE                 Location/Qualifiers
REGION                  1..17
                        note = Synthetic
source                  1..17
                        mol_type = protein
                        organism = synthetic construct
SEQUENCE: 148
SISSSSNYIY YADSVKG                                                    17

SEQ ID NO: 149          moltype = AA  length = 17
FEATURE                 Location/Qualifiers
REGION                  1..17
                        note = Synthetic
source                  1..17
                        mol_type = protein
                        organism = synthetic construct
SEQUENCE: 149
VISYDGSNKY YADSVKG                                                    17

SEQ ID NO: 150          moltype = AA  length = 17
FEATURE                 Location/Qualifiers
REGION                  1..17
                        note = Synthetic
source                  1..17
                        mol_type = protein
                        organism = synthetic construct
SEQUENCE: 150
SISSSSSYIY YADSVKG                                                    17

SEQ ID NO: 151          moltype = AA  length = 17
FEATURE                 Location/Qualifiers
REGION                  1..17
                        note = Synthetic
source                  1..17
                        mol_type = protein
                        organism = synthetic construct
SEQUENCE: 151
GISWNSGSIG YADSVKG                                                    17

SEQ ID NO: 152          moltype = AA  length = 16
FEATURE                 Location/Qualifiers
REGION                  1..16
                        note = Synthetic
source                  1..16
                        mol_type = protein
                        organism = synthetic construct
SEQUENCE: 152
SIYYSGSTNY NPSLKS                                                     16

SEQ ID NO: 153          moltype = AA  length = 17
FEATURE                 Location/Qualifiers
REGION                  1..17
                        note = Synthetic
source                  1..17
                        mol_type = protein
                        organism = synthetic construct
SEQUENCE: 153
GISWNSGDIG YADSVKG                                                    17

SEQ ID NO: 154          moltype = AA  length = 19
FEATURE                 Location/Qualifiers
REGION                  1..19
                        note = Synthetic
source                  1..19
                        mol_type = protein
                        organism = synthetic construct
SEQUENCE: 154
RTRNKANSYT TEYAASVKG                                                  19

SEQ ID NO: 155          moltype = AA  length = 17
FEATURE                 Location/Qualifiers
REGION                  1..17
                        note = Synthetic
```

```
source                    1..17
                          mol_type = protein
                          organism = synthetic construct
SEQUENCE: 155
NIKQDGSEKY YVDSVKG                                                      17

SEQ ID NO: 156            moltype = AA  length = 17
FEATURE                   Location/Qualifiers
REGION                    1..17
                          note = Synthetic
source                    1..17
                          mol_type = protein
                          organism = synthetic construct
SEQUENCE: 156
YISSSSSTIY YADSVKG                                                      17

SEQ ID NO: 157            moltype = AA  length = 16
FEATURE                   Location/Qualifiers
REGION                    1..16
                          note = Synthetic
source                    1..16
                          mol_type = protein
                          organism = synthetic construct
SEQUENCE: 157
HIYYSGSTNY NPSLKS                                                       16

SEQ ID NO: 158            moltype = AA  length = 17
FEATURE                   Location/Qualifiers
REGION                    1..17
                          note = Synthetic
source                    1..17
                          mol_type = protein
                          organism = synthetic construct
SEQUENCE: 158
GITWNSGSIG YADSVKG                                                      17

SEQ ID NO: 159            moltype = AA  length = 16
FEATURE                   Location/Qualifiers
REGION                    1..16
                          note = Synthetic
source                    1..16
                          mol_type = protein
                          organism = synthetic construct
SEQUENCE: 159
YIYYSGSTYY NPSLKS                                                       16

SEQ ID NO: 160            moltype = AA  length = 17
FEATURE                   Location/Qualifiers
REGION                    1..17
                          note = Synthetic
source                    1..17
                          mol_type = protein
                          organism = synthetic construct
SEQUENCE: 160
VIWYDGSNKY YADSVKG                                                      17

SEQ ID NO: 161            moltype = AA  length = 17
FEATURE                   Location/Qualifiers
REGION                    1..17
                          note = Synthetic
source                    1..17
                          mol_type = protein
                          organism = synthetic construct
SEQUENCE: 161
LIWYDGSNKY YADSVKG                                                      17

SEQ ID NO: 162            moltype = AA  length = 17
FEATURE                   Location/Qualifiers
REGION                    1..17
                          note = Synthetic
source                    1..17
                          mol_type = protein
                          organism = synthetic construct
SEQUENCE: 162
AISGSGGSTY YADSVKG                                                      17

SEQ ID NO: 163            moltype = AA  length = 17
FEATURE                   Location/Qualifiers
REGION                    1..17
```

```
                        note = Synthetic
source                  1..17
                        mol_type = protein
                        organism = synthetic construct
SEQUENCE: 163
VIWYDGSNKG YADSVKG                                                    17

SEQ ID NO: 164          moltype = AA  length = 17
FEATURE                 Location/Qualifiers
REGION                  1..17
                        note = Synthetic
source                  1..17
                        mol_type = protein
                        organism = synthetic construct
SEQUENCE: 164
VINPGGGSTS YAQKFQG                                                    17

SEQ ID NO: 165          moltype = AA  length = 17
FEATURE                 Location/Qualifiers
REGION                  1..17
                        note = Synthetic
source                  1..17
                        mol_type = protein
                        organism = synthetic construct
SEQUENCE: 165
IINPGGGSTS YAQKFQG                                                    17

SEQ ID NO: 166          moltype = AA  length = 17
FEATURE                 Location/Qualifiers
REGION                  1..17
                        note = Synthetic
source                  1..17
                        mol_type = protein
                        organism = synthetic construct
SEQUENCE: 166
SIIPIFGTAN YAQKFQG                                                    17

SEQ ID NO: 167          moltype = AA  length = 16
FEATURE                 Location/Qualifiers
REGION                  1..16
                        note = Synthetic
source                  1..16
                        mol_type = protein
                        organism = synthetic construct
SEQUENCE: 167
SIYHSGSTYY NPSLKS                                                     16

SEQ ID NO: 168          moltype = AA  length = 16
FEATURE                 Location/Qualifiers
REGION                  1..16
                        note = Synthetic
source                  1..16
                        mol_type = protein
                        organism = synthetic construct
SEQUENCE: 168
SIYHSGNTYY NPSLKS                                                     16

SEQ ID NO: 169          moltype = AA  length = 16
FEATURE                 Location/Qualifiers
REGION                  1..16
                        note = Synthetic
source                  1..16
                        mol_type = protein
                        organism = synthetic construct
SEQUENCE: 169
SISYSGSTYY NPSLKS                                                     16

SEQ ID NO: 170          moltype = AA  length = 17
FEATURE                 Location/Qualifiers
REGION                  1..17
                        note = Synthetic
source                  1..17
                        mol_type = protein
                        organism = synthetic construct
SEQUENCE: 170
WINPNSGGTK YAQKFQG                                                    17

SEQ ID NO: 171          moltype = AA  length = 17
FEATURE                 Location/Qualifiers
```

```
REGION                          1..17
                                note = Synthetic
source                          1..17
                                mol_type = protein
                                organism = synthetic construct
SEQUENCE: 171
WISAYNGNTN YAQKLQG                                                              17

SEQ ID NO: 172                  moltype = AA  length = 17
FEATURE                         Location/Qualifiers
REGION                          1..17
                                note = Synthetic
source                          1..17
                                mol_type = protein
                                organism = synthetic construct
SEQUENCE: 172
IIYPGDSDTR YSPSFQG                                                              17

SEQ ID NO: 173                  moltype = AA  length = 15
FEATURE                         Location/Qualifiers
REGION                          1..15
                                note = Synthetic
source                          1..15
                                mol_type = protein
                                organism = synthetic construct
SEQUENCE: 173
ARGQGSDHYY YGMDV                                                                15

SEQ ID NO: 174                  moltype = AA  length = 16
FEATURE                         Location/Qualifiers
REGION                          1..16
                                note = Synthetic
source                          1..16
                                mol_type = protein
                                organism = synthetic construct
SEQUENCE: 174
AREGGPRGAS FNWFDP                                                               16

SEQ ID NO: 175                  moltype = AA  length = 11
FEATURE                         Location/Qualifiers
REGION                          1..11
                                note = Synthetic
source                          1..11
                                mol_type = protein
                                organism = synthetic construct
SEQUENCE: 175
ARDVGSMYFD I                                                                    11

SEQ ID NO: 176                  moltype = AA  length = 13
FEATURE                         Location/Qualifiers
REGION                          1..13
                                note = Synthetic
source                          1..13
                                mol_type = protein
                                organism = synthetic construct
SEQUENCE: 176
ARHYYYGYAY FDL                                                                  13

SEQ ID NO: 177                  moltype = AA  length = 13
FEATURE                         Location/Qualifiers
REGION                          1..13
                                note = Synthetic
source                          1..13
                                mol_type = protein
                                organism = synthetic construct
SEQUENCE: 177
ARESDGIDSY FDY                                                                  13

SEQ ID NO: 178                  moltype = AA  length = 14
FEATURE                         Location/Qualifiers
REGION                          1..14
                                note = Synthetic
source                          1..14
                                mol_type = protein
                                organism = synthetic construct
SEQUENCE: 178
ARESGHSYVS SFDP                                                                 14

SEQ ID NO: 179                  moltype = AA  length = 12
```

```
FEATURE              Location/Qualifiers
REGION               1..12
                     note = Synthetic
source               1..12
                     mol_type = protein
                     organism = synthetic construct
SEQUENCE: 179
ARGLIYGDAF DY                                                            12

SEQ ID NO: 180       moltype = AA  length = 13
FEATURE              Location/Qualifiers
REGION               1..13
                     note = Synthetic
source               1..13
                     mol_type = protein
                     organism = synthetic construct
SEQUENCE: 180
AREVSMTAAS LDV                                                           13

SEQ ID NO: 181       moltype = AA  length = 14
FEATURE              Location/Qualifiers
REGION               1..14
                     note = Synthetic
source               1..14
                     mol_type = protein
                     organism = synthetic construct
SEQUENCE: 181
AREAGYDISS AFDI                                                          14

SEQ ID NO: 182       moltype = AA  length = 13
FEATURE              Location/Qualifiers
REGION               1..13
                     note = Synthetic
source               1..13
                     mol_type = protein
                     organism = synthetic construct
SEQUENCE: 182
AREGSGSWET LDV                                                           13

SEQ ID NO: 183       moltype = AA  length = 10
FEATURE              Location/Qualifiers
REGION               1..10
                     note = Synthetic
source               1..10
                     mol_type = protein
                     organism = synthetic construct
SEQUENCE: 183
ARSGEYGFDL                                                               10

SEQ ID NO: 184       moltype = AA  length = 13
FEATURE              Location/Qualifiers
REGION               1..13
                     note = Synthetic
source               1..13
                     mol_type = protein
                     organism = synthetic construct
SEQUENCE: 184
ARGGYPWEA FDY                                                            13

SEQ ID NO: 185       moltype = AA  length = 13
FEATURE              Location/Qualifiers
REGION               1..13
                     note = Synthetic
source               1..13
                     mol_type = protein
                     organism = synthetic construct
SEQUENCE: 185
ARGRYRRTGS LDV                                                           13

SEQ ID NO: 186       moltype = AA  length = 11
FEATURE              Location/Qualifiers
REGION               1..11
                     note = Synthetic
source               1..11
                     mol_type = protein
                     organism = synthetic construct
SEQUENCE: 186
ARRSSGDYLD V                                                             11
```

```
SEQ ID NO: 187          moltype = AA   length = 12
FEATURE                 Location/Qualifiers
REGION                  1..12
                        note = Synthetic
source                  1..12
                        mol_type = protein
                        organism = synthetic construct
SEQUENCE: 187
ARRGGSYDAF QH                                                              12

SEQ ID NO: 188          moltype = AA   length = 12
FEATURE                 Location/Qualifiers
REGION                  1..12
                        note = Synthetic
source                  1..12
                        mol_type = protein
                        organism = synthetic construct
SEQUENCE: 188
AKGPRMSGWW AD                                                              12

SEQ ID NO: 189          moltype = AA   length = 14
FEATURE                 Location/Qualifiers
REGION                  1..14
                        note = Synthetic
source                  1..14
                        mol_type = protein
                        organism = synthetic construct
SEQUENCE: 189
ARGAPGGRHN WFDP                                                            14

SEQ ID NO: 190          moltype = AA   length = 12
FEATURE                 Location/Qualifiers
REGION                  1..12
                        note = Synthetic
source                  1..12
                        mol_type = protein
                        organism = synthetic construct
SEQUENCE: 190
AKGPRMVTHL DV                                                              12

SEQ ID NO: 191          moltype = AA   length = 9
FEATURE                 Location/Qualifiers
REGION                  1..9
                        note = Synthetic
source                  1..9
                        mol_type = protein
                        organism = synthetic construct
SEQUENCE: 191
ARGPLGYKL                                                                   9

SEQ ID NO: 192          moltype = AA   length = 11
FEATURE                 Location/Qualifiers
REGION                  1..11
                        note = Synthetic
source                  1..11
                        mol_type = protein
                        organism = synthetic construct
SEQUENCE: 192
ARDAPQLGLD V                                                               11

SEQ ID NO: 193          moltype = AA   length = 16
FEATURE                 Location/Qualifiers
REGION                  1..16
                        note = Synthetic
source                  1..16
                        mol_type = protein
                        organism = synthetic construct
SEQUENCE: 193
ARGGPLGYGD YKGMDV                                                          16

SEQ ID NO: 194          moltype = AA   length = 18
FEATURE                 Location/Qualifiers
REGION                  1..18
                        note = Synthetic
source                  1..18
                        mol_type = protein
                        organism = synthetic construct
SEQUENCE: 194
ARDAGRYYGS SSSWYFDL                                                        18
```

| SEQ ID NO: 195 | moltype = AA   length = 12 | |
| --- | --- | --- |
| FEATURE | Location/Qualifiers | |
| REGION | 1..12 | |
| | note = Synthetic | |
| source | 1..12 | |
| | mol_type = protein | |
| | organism = synthetic construct | |
| SEQUENCE: 195 | | |
| AKGPRLLSAL DV | | 12 |

| SEQ ID NO: 196 | moltype = AA   length = 12 | |
| --- | --- | --- |
| FEATURE | Location/Qualifiers | |
| REGION | 1..12 | |
| | note = Synthetic | |
| source | 1..12 | |
| | mol_type = protein | |
| | organism = synthetic construct | |
| SEQUENCE: 196 | | |
| AKGGSRYSHF DY | | 12 |

| SEQ ID NO: 197 | moltype = AA   length = 15 | |
| --- | --- | --- |
| FEATURE | Location/Qualifiers | |
| REGION | 1..15 | |
| | note = Synthetic | |
| source | 1..15 | |
| | mol_type = protein | |
| | organism = synthetic construct | |
| SEQUENCE: 197 | | |
| ARDSAQETYY YGMDV | | 15 |

| SEQ ID NO: 198 | moltype = AA   length = 16 | |
| --- | --- | --- |
| FEATURE | Location/Qualifiers | |
| REGION | 1..16 | |
| | note = Synthetic | |
| source | 1..16 | |
| | mol_type = protein | |
| | organism = synthetic construct | |
| SEQUENCE: 198 | | |
| ARDSSIAGRA TLSFDY | | 16 |

| SEQ ID NO: 199 | moltype = AA   length = 19 | |
| --- | --- | --- |
| FEATURE | Location/Qualifiers | |
| REGION | 1..19 | |
| | note = Synthetic | |
| source | 1..19 | |
| | mol_type = protein | |
| | organism = synthetic construct | |
| SEQUENCE: 199 | | |
| ARGPSQYYYD SSAIEAFDI | | 19 |

| SEQ ID NO: 200 | moltype = AA   length = 20 | |
| --- | --- | --- |
| FEATURE | Location/Qualifiers | |
| REGION | 1..20 | |
| | note = Synthetic | |
| source | 1..20 | |
| | mol_type = protein | |
| | organism = synthetic construct | |
| SEQUENCE: 200 | | |
| ARDGGGTAQA DGAYYYGMDV | | 20 |

| SEQ ID NO: 201 | moltype = AA   length = 18 | |
| --- | --- | --- |
| FEATURE | Location/Qualifiers | |
| REGION | 1..18 | |
| | note = Synthetic | |
| source | 1..18 | |
| | mol_type = protein | |
| | organism = synthetic construct | |
| SEQUENCE: 201 | | |
| ARGRKAAAGI DEAEYFQH | | 18 |

| SEQ ID NO: 202 | moltype = AA   length = 14 | |
| --- | --- | --- |
| FEATURE | Location/Qualifiers | |
| REGION | 1..14 | |
| | note = Synthetic | |
| source | 1..14 | |
| | mol_type = protein | |
| | organism = synthetic construct | |
| SEQUENCE: 202 | | |

```
ARDRRMWDPY GMDV                                                         14

SEQ ID NO: 203          moltype = AA   length = 16
FEATURE                 Location/Qualifiers
REGION                  1..16
                        note = Synthetic
source                  1..16
                        mol_type = protein
                        organism = synthetic construct
SEQUENCE: 203
ARDAPAVVGE SPAFDI                                                       16

SEQ ID NO: 204          moltype = AA   length = 15
FEATURE                 Location/Qualifiers
REGION                  1..15
                        note = Synthetic
source                  1..15
                        mol_type = protein
                        organism = synthetic construct
SEQUENCE: 204
AKGSTHRGSA YGMDV                                                        15

SEQ ID NO: 205          moltype = AA   length = 13
FEATURE                 Location/Qualifiers
REGION                  1..13
                        note = Synthetic
source                  1..13
                        mol_type = protein
                        organism = synthetic construct
SEQUENCE: 205
ARRPDDRRGL FQH                                                          13

SEQ ID NO: 206          moltype = AA   length = 14
FEATURE                 Location/Qualifiers
REGION                  1..14
                        note = Synthetic
source                  1..14
                        mol_type = protein
                        organism = synthetic construct
SEQUENCE: 206
ARPDYYSSRG VFDI                                                         14

SEQ ID NO: 207          moltype = AA   length = 12
FEATURE                 Location/Qualifiers
REGION                  1..12
                        note = Synthetic
source                  1..12
                        mol_type = protein
                        organism = synthetic construct
SEQUENCE: 207
AKGDYLDPLF DY                                                           12

SEQ ID NO: 208          moltype = AA   length = 15
FEATURE                 Location/Qualifiers
REGION                  1..15
                        note = Synthetic
source                  1..15
                        mol_type = protein
                        organism = synthetic construct
SEQUENCE: 208
ARERGTYYYA SGWAN                                                        15

SEQ ID NO: 209          moltype = AA   length = 13
FEATURE                 Location/Qualifiers
REGION                  1..13
                        note = Synthetic
source                  1..13
                        mol_type = protein
                        organism = synthetic construct
SEQUENCE: 209
ARRGGSSSTG LLY                                                          13

SEQ ID NO: 210          moltype = AA   length = 11
FEATURE                 Location/Qualifiers
REGION                  1..11
                        note = Synthetic
source                  1..11
                        mol_type = protein
                        organism = synthetic construct
```

```
SEQUENCE: 210
ARTRIDDSFD I                                                                11

SEQ ID NO: 211          moltype = AA  length = 12
FEATURE                 Location/Qualifiers
REGION                  1..12
                        note = Synthetic
source                  1..12
                        mol_type = protein
                        organism = synthetic construct
SEQUENCE: 211
AKSKHSTTSL DV                                                               12

SEQ ID NO: 212          moltype = AA  length = 17
FEATURE                 Location/Qualifiers
REGION                  1..17
                        note = Synthetic
source                  1..17
                        mol_type = protein
                        organism = synthetic construct
SEQUENCE: 212
ARELMVTSGG WLYGMDV                                                          17

SEQ ID NO: 213          moltype = AA  length = 16
FEATURE                 Location/Qualifiers
REGION                  1..16
                        note = Synthetic
source                  1..16
                        mol_type = protein
                        organism = synthetic construct
SEQUENCE: 213
AREAGNYYDI ESAFDI                                                           16

SEQ ID NO: 214          moltype = AA  length = 13
FEATURE                 Location/Qualifiers
REGION                  1..13
                        note = Synthetic
source                  1..13
                        mol_type = protein
                        organism = synthetic construct
SEQUENCE: 214
AREGSGYDES MDV                                                              13

SEQ ID NO: 215          moltype = AA  length = 10
FEATURE                 Location/Qualifiers
REGION                  1..10
                        note = Synthetic
source                  1..10
                        mol_type = protein
                        organism = synthetic construct
SEQUENCE: 215
ARGRGIAFDI                                                                  10

SEQ ID NO: 216          moltype = AA  length = 13
FEATURE                 Location/Qualifiers
REGION                  1..13
                        note = Synthetic
source                  1..13
                        mol_type = protein
                        organism = synthetic construct
SEQUENCE: 216
AREAGQTSSA LDV                                                              13

SEQ ID NO: 217          moltype = AA  length = 15
FEATURE                 Location/Qualifiers
REGION                  1..15
                        note = Synthetic
source                  1..15
                        mol_type = protein
                        organism = synthetic construct
SEQUENCE: 217
AREAGSWLIS TAFDI                                                            15

SEQ ID NO: 218          moltype = AA  length = 13
FEATURE                 Location/Qualifiers
REGION                  1..13
                        note = Synthetic
source                  1..13
                        mol_type = protein
```

```
                                          -continued organism = synthetic construct
SEQUENCE: 218
AREAGTMSSA FDI                                                              13

SEQ ID NO: 219        moltype = AA   length = 17
FEATURE               Location/Qualifiers
REGION                1..17
                      note = Synthetic
source                1..17
                      mol_type = protein
                      organism = synthetic construct
SEQUENCE: 219
ARSGGYSSSW YGTGYDY                                                          17

SEQ ID NO: 220        moltype = AA   length = 17
FEATURE               Location/Qualifiers
REGION                1..17
                      note = Synthetic
source                1..17
                      mol_type = protein
                      organism = synthetic construct
SEQUENCE: 220
ARDRGQYSSS WYGRMDV                                                          17

SEQ ID NO: 221        moltype = AA   length = 14
FEATURE               Location/Qualifiers
REGION                1..14
                      note = Synthetic
source                1..14
                      mol_type = protein
                      organism = synthetic construct
SEQUENCE: 221
ARESGYHVST AFDI                                                             14

SEQ ID NO: 222        moltype = AA   length = 12
FEATURE               Location/Qualifiers
REGION                1..12
                      note = Synthetic
source                1..12
                      mol_type = protein
                      organism = synthetic construct
SEQUENCE: 222
ARHWYALGSF DI                                                               12

SEQ ID NO: 223        moltype = AA   length = 12
FEATURE               Location/Qualifiers
REGION                1..12
                      note = Synthetic
source                1..12
                      mol_type = protein
                      organism = synthetic construct
SEQUENCE: 223
ARGADYYAGF DY                                                               12

SEQ ID NO: 224        moltype = AA   length = 12
FEATURE               Location/Qualifiers
REGION                1..12
                      note = Synthetic
source                1..12
                      mol_type = protein
                      organism = synthetic construct
SEQUENCE: 224
AKGPRLLGYF DL                                                               12

SEQ ID NO: 225        moltype = AA   length = 13
FEATURE               Location/Qualifiers
REGION                1..13
                      note = Synthetic
source                1..13
                      mol_type = protein
                      organism = synthetic construct
SEQUENCE: 225
AKGPRYSKPY FDY                                                              13

SEQ ID NO: 226        moltype = AA   length = 12
FEATURE               Location/Qualifiers
REGION                1..12
                      note = Synthetic
source                1..12
```

```
                           mol_type = protein
                           organism = synthetic construct
SEQUENCE: 226
ARQEYGDGYF DL                                                          12

SEQ ID NO: 227             moltype = AA   length = 13
FEATURE                    Location/Qualifiers
REGION                     1..13
                           note = Synthetic
source                     1..13
                           mol_type = protein
                           organism = synthetic construct
SEQUENCE: 227
ARDLGGYEGA FDP                                                         13

SEQ ID NO: 228             moltype = AA   length = 12
FEATURE                    Location/Qualifiers
REGION                     1..12
                           note = Synthetic
source                     1..12
                           mol_type = protein
                           organism = synthetic construct
SEQUENCE: 228
ARHDDYLSSF DP                                                          12

SEQ ID NO: 229             moltype = AA   length = 9
FEATURE                    Location/Qualifiers
REGION                     1..9
                           note = Synthetic
source                     1..9
                           mol_type = protein
                           organism = synthetic construct
SEQUENCE: 229
ARGPSWIDV                                                              9

SEQ ID NO: 230             moltype = AA   length = 17
FEATURE                    Location/Qualifiers
REGION                     1..17
                           note = Synthetic
source                     1..17
                           mol_type = protein
                           organism = synthetic construct
SEQUENCE: 230
ARELYAYSSP MFYGMDV                                                     17

SEQ ID NO: 231             moltype = AA   length = 11
FEATURE                    Location/Qualifiers
REGION                     1..11
                           note = Synthetic
source                     1..11
                           mol_type = protein
                           organism = synthetic construct
SEQUENCE: 231
ARYYSPYGMD V                                                           11

SEQ ID NO: 232             moltype = AA   length = 13
FEATURE                    Location/Qualifiers
REGION                     1..13
                           note = Synthetic
source                     1..13
                           mol_type = protein
                           organism = synthetic construct
SEQUENCE: 232
ARDSGQYTGS LDV                                                         13

SEQ ID NO: 233             moltype = AA   length = 12
FEATURE                    Location/Qualifiers
REGION                     1..12
                           note = Synthetic
source                     1..12
                           mol_type = protein
                           organism = synthetic construct
SEQUENCE: 233
ARERHSSLGY AY                                                          12

SEQ ID NO: 234             moltype = AA   length = 15
FEATURE                    Location/Qualifiers
REGION                     1..15
                           note = Synthetic
```

```
source                   1..15
                         mol_type = protein
                         organism = synthetic construct
SEQUENCE: 234
ARGRPSSSWG NWFDP                                                          15

SEQ ID NO: 235           moltype = AA   length = 13
FEATURE                  Location/Qualifiers
REGION                   1..13
                         note = Synthetic
source                   1..13
                         mol_type = protein
                         organism = synthetic construct
SEQUENCE: 235
ARGSPWDGRL FDI                                                            13

SEQ ID NO: 236           moltype = AA   length = 16
FEATURE                  Location/Qualifiers
REGION                   1..16
                         note = Synthetic
source                   1..16
                         mol_type = protein
                         organism = synthetic construct
SEQUENCE: 236
ARGAGMYDGS PLGMDV                                                         16

SEQ ID NO: 237           moltype = AA   length = 12
FEATURE                  Location/Qualifiers
REGION                   1..12
                         note = Synthetic
source                   1..12
                         mol_type = protein
                         organism = synthetic construct
SEQUENCE: 237
ARAGTIYGRL DL                                                             12

SEQ ID NO: 238           moltype = AA   length = 12
FEATURE                  Location/Qualifiers
REGION                   1..12
                         note = Synthetic
source                   1..12
                         mol_type = protein
                         organism = synthetic construct
SEQUENCE: 238
AKGPRRTSHL DI                                                             12

SEQ ID NO: 239           moltype = AA   length = 13
FEATURE                  Location/Qualifiers
REGION                   1..13
                         note = Synthetic
source                   1..13
                         mol_type = protein
                         organism = synthetic construct
SEQUENCE: 239
AKGPRMTHSY FDL                                                            13

SEQ ID NO: 240           moltype = AA   length = 12
FEATURE                  Location/Qualifiers
REGION                   1..12
                         note = Synthetic
source                   1..12
                         mol_type = protein
                         organism = synthetic construct
SEQUENCE: 240
AKAPRMYGYF DL                                                             12

SEQ ID NO: 241           moltype = AA   length = 12
FEATURE                  Location/Qualifiers
REGION                   1..12
                         note = Synthetic
source                   1..12
                         mol_type = protein
                         organism = synthetic construct
SEQUENCE: 241
AKGPRTRGYF DL                                                             12

SEQ ID NO: 242           moltype = AA   length = 13
FEATURE                  Location/Qualifiers
REGION                   1..13
```

```
                              note = Synthetic
source                        1..13
                              mol_type = protein
                              organism = synthetic construct
SEQUENCE: 242
AKAPRTRWTY FDY                                                              13

SEQ ID NO: 243                moltype = AA  length = 13
FEATURE                       Location/Qualifiers
REGION                        1..13
                              note = Synthetic
source                        1..13
                              mol_type = protein
                              organism = synthetic construct
SEQUENCE: 243
ARARRGALAG MDV                                                              13

SEQ ID NO: 244                moltype = AA  length = 14
FEATURE                       Location/Qualifiers
REGION                        1..14
                              note = Synthetic
source                        1..14
                              mol_type = protein
                              organism = synthetic construct
SEQUENCE: 244
ARGGPYPWSG WFDP                                                             14

SEQ ID NO: 245                moltype = AA  length = 13
FEATURE                       Location/Qualifiers
REGION                        1..13
                              note = Synthetic
source                        1..13
                              mol_type = protein
                              organism = synthetic construct
SEQUENCE: 245
ARDLGQYEGY FDL                                                              13

SEQ ID NO: 246                moltype = AA  length = 13
FEATURE                       Location/Qualifiers
REGION                        1..13
                              note = Synthetic
source                        1..13
                              mol_type = protein
                              organism = synthetic construct
SEQUENCE: 246
ARLGDGYRIW ADY                                                              13

SEQ ID NO: 247                moltype = AA  length = 20
FEATURE                       Location/Qualifiers
REGION                        1..20
                              note = Synthetic
source                        1..20
                              mol_type = protein
                              organism = synthetic construct
SEQUENCE: 247
ARELIVGATG GLTYYYGMDV                                                       20

SEQ ID NO: 248                moltype = AA  length = 23
FEATURE                       Location/Qualifiers
REGION                        1..23
                              note = Synthetic
source                        1..23
                              mol_type = protein
                              organism = synthetic construct
SEQUENCE: 248
DIQMTQSPSS LSASVGDRVT ITC                                                   23

SEQ ID NO: 249                moltype = AA  length = 23
FEATURE                       Location/Qualifiers
REGION                        1..23
                              note = Synthetic
source                        1..23
                              mol_type = protein
                              organism = synthetic construct
SEQUENCE: 249
EIVLTQSPGT LSLSPGERAT LSC                                                   23

SEQ ID NO: 250                moltype = AA  length = 23
FEATURE                       Location/Qualifiers
```

```
REGION                  1..23
                        note = Synthetic
source                  1..23
                        mol_type = protein
                        organism = synthetic construct
SEQUENCE: 250
DIVMTQSPDS LAVSLGERAT INC                                              23

SEQ ID NO: 251          moltype = AA  length = 23
FEATURE                 Location/Qualifiers
REGION                  1..23
                        note = Synthetic
source                  1..23
                        mol_type = protein
                        organism = synthetic construct
SEQUENCE: 251
EIVMTQSPAT LSVSPGERAT LSC                                              23

SEQ ID NO: 252          moltype = AA  length = 23
FEATURE                 Location/Qualifiers
REGION                  1..23
                        note = Synthetic
source                  1..23
                        mol_type = protein
                        organism = synthetic construct
SEQUENCE: 252
DIVMTQSPLS LPVTPGEPAS ISC                                              23

SEQ ID NO: 253          moltype = AA  length = 23
FEATURE                 Location/Qualifiers
REGION                  1..23
                        note = Synthetic
source                  1..23
                        mol_type = protein
                        organism = synthetic construct
SEQUENCE: 253
EIVLTQSPAT LSLSPGERAT LSC                                              23

SEQ ID NO: 254          moltype = AA  length = 23
FEATURE                 Location/Qualifiers
REGION                  1..23
                        note = Synthetic
source                  1..23
                        mol_type = protein
                        organism = synthetic construct
SEQUENCE: 254
DIQMTQSPSS VSASVGDRVT ITC                                              23

SEQ ID NO: 255          moltype = AA  length = 23
FEATURE                 Location/Qualifiers
REGION                  1..23
                        note = Synthetic
source                  1..23
                        mol_type = protein
                        organism = synthetic construct
SEQUENCE: 255
DIQMTQSPST LSASVGDRVT ITC                                              23

SEQ ID NO: 256          moltype = AA  length = 23
FEATURE                 Location/Qualifiers
REGION                  1..23
                        note = Synthetic
source                  1..23
                        mol_type = protein
                        organism = synthetic construct
SEQUENCE: 256
DIQLTQSPSS LSASVGDRVT ITC                                              23

SEQ ID NO: 257          moltype = AA  length = 23
FEATURE                 Location/Qualifiers
REGION                  1..23
                        note = Synthetic
source                  1..23
                        mol_type = protein
                        organism = synthetic construct
SEQUENCE: 257
EIVLTQSPAT LSVSPGERAT LSC                                              23

SEQ ID NO: 258          moltype = AA  length = 23
```

```
FEATURE              Location/Qualifiers
REGION               1..23
                     note = Synthetic
source               1..23
                     mol_type = protein
                     organism = synthetic construct
SEQUENCE: 258
DIQLTQSPSS VSASVGDRVT ITC                                             23

SEQ ID NO: 259       moltype = AA  length = 23
FEATURE              Location/Qualifiers
REGION               1..23
                     note = Synthetic
source               1..23
                     mol_type = protein
                     organism = synthetic construct
SEQUENCE: 259
EIVMTQSPAT LSLSPGERAT LSC                                             23

SEQ ID NO: 260       moltype = AA  length = 15
FEATURE              Location/Qualifiers
REGION               1..15
                     note = Synthetic
source               1..15
                     mol_type = protein
                     organism = synthetic construct
SEQUENCE: 260
WYQQKPGKAP KLLIY                                                      15

SEQ ID NO: 261       moltype = AA  length = 15
FEATURE              Location/Qualifiers
REGION               1..15
                     note = Synthetic
source               1..15
                     mol_type = protein
                     organism = synthetic construct
SEQUENCE: 261
WYQQKPGQAP RLLIY                                                      15

SEQ ID NO: 262       moltype = AA  length = 15
FEATURE              Location/Qualifiers
REGION               1..15
                     note = Synthetic
source               1..15
                     mol_type = protein
                     organism = synthetic construct
SEQUENCE: 262
WYQQKPGQPP KLLIY                                                      15

SEQ ID NO: 263       moltype = AA  length = 15
FEATURE              Location/Qualifiers
REGION               1..15
                     note = Synthetic
source               1..15
                     mol_type = protein
                     organism = synthetic construct
SEQUENCE: 263
WYLQKPGQSP QLLIY                                                      15

SEQ ID NO: 264       moltype = AA  length = 15
FEATURE              Location/Qualifiers
REGION               1..15
                     note = Synthetic
source               1..15
                     mol_type = protein
                     organism = synthetic construct
SEQUENCE: 264
WYLQKPGQSP QLLIF                                                      15

SEQ ID NO: 265       moltype = AA  length = 15
FEATURE              Location/Qualifiers
REGION               1..15
                     note = Synthetic
source               1..15
                     mol_type = protein
                     organism = synthetic construct
SEQUENCE: 265
WYQQKPGKAP KLLIS                                                      15
```

| | | |
|---|---|---|
| SEQ ID NO: 266 | moltype = AA length = 15 | |
| FEATURE | Location/Qualifiers | |
| REGION | 1..15 | |
| | note = Synthetic | |
| source | 1..15 | |
| | mol_type = protein | |
| | organism = synthetic construct | |
| SEQUENCE: 266 | | |
| WYLQKPGQSP QVLIY | | 15 |
| | | |
| SEQ ID NO: 267 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 267 | | |
| GVPSRFSGSG SGTDFTFTIS SLQPEDIATY YC | | 32 |
| | | |
| SEQ ID NO: 268 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 268 | | |
| GIPDRFSGSG SGTDFTLTIS RLEPEDFAVY YC | | 32 |
| | | |
| SEQ ID NO: 269 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 269 | | |
| GVPDRFSGSG SGTDFTLTIS SLQAEDVAVY YC | | 32 |
| | | |
| SEQ ID NO: 270 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 270 | | |
| GIPARFSGSG SGTEFTLTIS SLQSEDFAVY YC | | 32 |
| | | |
| SEQ ID NO: 271 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 271 | | |
| GVPDRFSGSG SGTDFTLKIS RVEAEDVGVY YC | | 32 |
| | | |
| SEQ ID NO: 272 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 272 | | |
| GIPARFSGSG SGTDFTLTIS SLEPEDFAVY YC | | 32 |
| | | |
| SEQ ID NO: 273 | moltype = AA length = 32 | |
| FEATURE | Location/Qualifiers | |
| REGION | 1..32 | |
| | note = Synthetic | |
| source | 1..32 | |
| | mol_type = protein | |
| | organism = synthetic construct | |
| SEQUENCE: 273 | | |
| GVPSRFSGSG SGTDFTLTIS SLQPEDFATY YC | | 32 |

```
SEQ ID NO: 274         moltype = AA   length = 32
FEATURE                Location/Qualifiers
REGION                 1..32
                       note = Synthetic
source                 1..32
                       mol_type = protein
                       organism = synthetic construct
SEQUENCE: 274
GVPSRFSGSG SGTEFTLTIS SLQPDDFATY YC                                    32

SEQ ID NO: 275         moltype = AA   length = 32
FEATURE                Location/Qualifiers
REGION                 1..32
                       note = Synthetic
source                 1..32
                       mol_type = protein
                       organism = synthetic construct
SEQUENCE: 275
GVPDRFSGSG SGTDFTLTIS SLEPEDVAVY YC                                    32

SEQ ID NO: 276         moltype = AA   length = 10
FEATURE                Location/Qualifiers
REGION                 1..10
                       note = Synthetic
source                 1..10
                       mol_type = protein
                       organism = synthetic construct
SEQUENCE: 276
FGGGTKVEIK                                                             10

SEQ ID NO: 277         moltype = AA   length = 26
FEATURE                Location/Qualifiers
REGION                 1..26
                       note = Synthetic
source                 1..26
                       mol_type = protein
                       organism = synthetic construct
SEQUENCE: 277
QVQLVQSGAE VKKPGSSVKV SCKASG                                           26

SEQ ID NO: 278         moltype = AA   length = 26
FEATURE                Location/Qualifiers
REGION                 1..26
                       note = Synthetic
source                 1..26
                       mol_type = protein
                       organism = synthetic construct
SEQUENCE: 278
QVQLVQSGAE VKKPGASVKV SCKASG                                           26

SEQ ID NO: 279         moltype = AA   length = 26
FEATURE                Location/Qualifiers
REGION                 1..26
                       note = Synthetic
source                 1..26
                       mol_type = protein
                       organism = synthetic construct
SEQUENCE: 279
QLQLQESGPG LVKPSETLSL TCTVSG                                           26

SEQ ID NO: 280         moltype = AA   length = 26
FEATURE                Location/Qualifiers
REGION                 1..26
                       note = Synthetic
source                 1..26
                       mol_type = protein
                       organism = synthetic construct
SEQUENCE: 280
EVQLVESGGG LVKPGGSLRL SCAASG                                           26

SEQ ID NO: 281         moltype = AA   length = 26
FEATURE                Location/Qualifiers
REGION                 1..26
                       note = Synthetic
source                 1..26
                       mol_type = protein
                       organism = synthetic construct
SEQUENCE: 281
```

```
QVQLVESGGG VVQPGRSLRL SCAASG                                           26

SEQ ID NO: 282          moltype = AA  length = 26
FEATURE                 Location/Qualifiers
REGION                  1..26
                        note = Synthetic
source                  1..26
                        mol_type = protein
                        organism = synthetic construct
SEQUENCE: 282
EVQLVESGGG LVQPGRSLRL SCAASG                                           26

SEQ ID NO: 283          moltype = AA  length = 26
FEATURE                 Location/Qualifiers
REGION                  1..26
                        note = Synthetic
source                  1..26
                        mol_type = protein
                        organism = synthetic construct
SEQUENCE: 283
QVQLQESGPG LVKPSETLSL TCTVSG                                           26

SEQ ID NO: 284          moltype = AA  length = 26
FEATURE                 Location/Qualifiers
REGION                  1..26
                        note = Synthetic
source                  1..26
                        mol_type = protein
                        organism = synthetic construct
SEQUENCE: 284
EVQLVESGGG LVQPGGSLRL SCAASG                                           26

SEQ ID NO: 285          moltype = AA  length = 26
FEATURE                 Location/Qualifiers
REGION                  1..26
                        note = Synthetic
source                  1..26
                        mol_type = protein
                        organism = synthetic construct
SEQUENCE: 285
QVQLQESGPG LVKPSQTLSL TCTVSG                                           26

SEQ ID NO: 286          moltype = AA  length = 26
FEATURE                 Location/Qualifiers
REGION                  1..26
                        note = Synthetic
source                  1..26
                        mol_type = protein
                        organism = synthetic construct
SEQUENCE: 286
EVQLLESGGG LVQPGGSLRL SCAASG                                           26

SEQ ID NO: 287          moltype = AA  length = 26
FEATURE                 Location/Qualifiers
REGION                  1..26
                        note = Synthetic
source                  1..26
                        mol_type = protein
                        organism = synthetic construct
SEQUENCE: 287
QVQLQESGPG LVKPSETLSL TCAVSG                                           26

SEQ ID NO: 288          moltype = AA  length = 26
FEATURE                 Location/Qualifiers
REGION                  1..26
                        note = Synthetic
source                  1..26
                        mol_type = protein
                        organism = synthetic construct
SEQUENCE: 288
EVQLVQSGAE VKKPGESLKI SCKGSG                                           26

SEQ ID NO: 289          moltype = AA  length = 26
FEATURE                 Location/Qualifiers
REGION                  1..26
                        note = Synthetic
source                  1..26
                        mol_type = protein
                        organism = synthetic construct
```

```
SEQUENCE: 289
QVQLVESGGG LVQPGRSLRL SCAASG                                          26

SEQ ID NO: 290         moltype = AA  length = 14
FEATURE                Location/Qualifiers
REGION                 1..14
                       note = Synthetic
source                 1..14
                       mol_type = protein
                       organism = synthetic construct
SEQUENCE: 290
WVRQAPGQGL EWMG                                                       14

SEQ ID NO: 291         moltype = AA  length = 14
FEATURE                Location/Qualifiers
REGION                 1..14
                       note = Synthetic
source                 1..14
                       mol_type = protein
                       organism = synthetic construct
SEQUENCE: 291
WIRQPPGKGL EWIG                                                       14

SEQ ID NO: 292         moltype = AA  length = 14
FEATURE                Location/Qualifiers
REGION                 1..14
                       note = Synthetic
source                 1..14
                       mol_type = protein
                       organism = synthetic construct
SEQUENCE: 292
WVRQAPGKGL EWVS                                                       14

SEQ ID NO: 293         moltype = AA  length = 14
FEATURE                Location/Qualifiers
REGION                 1..14
                       note = Synthetic
source                 1..14
                       mol_type = protein
                       organism = synthetic construct
SEQUENCE: 293
WVRQAPGKGL EWVA                                                       14

SEQ ID NO: 294         moltype = AA  length = 14
FEATURE                Location/Qualifiers
REGION                 1..14
                       note = Synthetic
source                 1..14
                       mol_type = protein
                       organism = synthetic construct
SEQUENCE: 294
WVRQAPGKGL EWVG                                                       14

SEQ ID NO: 295         moltype = AA  length = 14
FEATURE                Location/Qualifiers
REGION                 1..14
                       note = Synthetic
source                 1..14
                       mol_type = protein
                       organism = synthetic construct
SEQUENCE: 295
WIRQHPGKGL EWIG                                                       14

SEQ ID NO: 296         moltype = AA  length = 14
FEATURE                Location/Qualifiers
REGION                 1..14
                       note = Synthetic
source                 1..14
                       mol_type = protein
                       organism = synthetic construct
SEQUENCE: 296
WVRQMPGKGL EWMG                                                       14

SEQ ID NO: 297         moltype = AA  length = 30
FEATURE                Location/Qualifiers
REGION                 1..30
                       note = Synthetic
source                 1..30
                       mol_type = protein
```

```
                                  organism = synthetic construct
SEQUENCE: 297
RVTITADEST STAYMELSSL RSEDTAVYYC                                              30

SEQ ID NO: 298           moltype = AA  length = 30
FEATURE                  Location/Qualifiers
REGION                   1..30
                         note = Synthetic
source                   1..30
                         mol_type = protein
                         organism = synthetic construct
SEQUENCE: 298
RVTMTRDTST STVYMELSSL RSEDTAVYYC                                              30

SEQ ID NO: 299           moltype = AA  length = 30
FEATURE                  Location/Qualifiers
REGION                   1..30
                         note = Synthetic
source                   1..30
                         mol_type = protein
                         organism = synthetic construct
SEQUENCE: 299
RVTISVDTSK NQFSLKLSSV TAADTAVYYC                                              30

SEQ ID NO: 300           moltype = AA  length = 30
FEATURE                  Location/Qualifiers
REGION                   1..30
                         note = Synthetic
source                   1..30
                         mol_type = protein
                         organism = synthetic construct
SEQUENCE: 300
RFTISRDNAK NSLYLQMNSL RAEDTAVYYC                                              30

SEQ ID NO: 301           moltype = AA  length = 30
FEATURE                  Location/Qualifiers
REGION                   1..30
                         note = Synthetic
source                   1..30
                         mol_type = protein
                         organism = synthetic construct
SEQUENCE: 301
RFTISRDNSK NTLYLQMNSL RAEDTAVYYC                                              30

SEQ ID NO: 302           moltype = AA  length = 30
FEATURE                  Location/Qualifiers
REGION                   1..30
                         note = Synthetic
source                   1..30
                         mol_type = protein
                         organism = synthetic construct
SEQUENCE: 302
RFTISRDNAK NSLYLQMNSL RAEDTALYYC                                              30

SEQ ID NO: 303           moltype = AA  length = 30
FEATURE                  Location/Qualifiers
REGION                   1..30
                         note = Synthetic
source                   1..30
                         mol_type = protein
                         organism = synthetic construct
SEQUENCE: 303
RFTISRDNAK NTLYLQMNSL RAEDTALYYC                                              30

SEQ ID NO: 304           moltype = AA  length = 30
FEATURE                  Location/Qualifiers
REGION                   1..30
                         note = Synthetic
source                   1..30
                         mol_type = protein
                         organism = synthetic construct
SEQUENCE: 304
RFTISRDDSK NSLYLQMNSL KTEDTAVYYC                                              30

SEQ ID NO: 305           moltype = AA  length = 30
FEATURE                  Location/Qualifiers
REGION                   1..30
                         note = Synthetic
source                   1..30
```

```
                        mol_type = protein
                        organism = synthetic construct
SEQUENCE: 305
RFTISRDNAK NSLYLQMNSL KAEDTAVYYC                                    30

SEQ ID NO: 306          moltype = AA  length = 30
FEATURE                 Location/Qualifiers
REGION                  1..30
                        note = Synthetic
source                  1..30
                        mol_type = protein
                        organism = synthetic construct
SEQUENCE: 306
RVTMTRDTSI STAYMELSRL RSDDTAVYYC                                    30

SEQ ID NO: 307          moltype = AA  length = 30
FEATURE                 Location/Qualifiers
REGION                  1..30
                        note = Synthetic
source                  1..30
                        mol_type = protein
                        organism = synthetic construct
SEQUENCE: 307
RVTMTTDTST STAYMELRSL RSDDTAVYYC                                    30

SEQ ID NO: 308          moltype = AA  length = 30
FEATURE                 Location/Qualifiers
REGION                  1..30
                        note = Synthetic
source                  1..30
                        mol_type = protein
                        organism = synthetic construct
SEQUENCE: 308
QVTISADKSI STAYLQWSSL KASDTAMYYC                                    30

SEQ ID NO: 309          moltype = AA  length = 11
FEATURE                 Location/Qualifiers
REGION                  1..11
                        note = Synthetic
source                  1..11
                        mol_type = protein
                        organism = synthetic construct
SEQUENCE: 309
WGQGTTVTVS S                                                        11

SEQ ID NO: 310          moltype = AA  length = 11
FEATURE                 Location/Qualifiers
REGION                  1..11
                        note = Synthetic
source                  1..11
                        mol_type = protein
                        organism = synthetic construct
SEQUENCE: 310
WGQGTLVTVS S                                                        11

SEQ ID NO: 311          moltype = AA  length = 11
FEATURE                 Location/Qualifiers
REGION                  1..11
                        note = Synthetic
source                  1..11
                        mol_type = protein
                        organism = synthetic construct
SEQUENCE: 311
WGQGTMVTVS S                                                        11

SEQ ID NO: 312          moltype = AA  length = 11
FEATURE                 Location/Qualifiers
REGION                  1..11
                        note = Synthetic
source                  1..11
                        mol_type = protein
                        organism = synthetic construct
SEQUENCE: 312
WGRGTLVTVS S                                                        11

SEQ ID NO: 313          moltype = AA  length = 11
FEATURE                 Location/Qualifiers
REGION                  1..11
                        note = Synthetic
```

```
source                  1..11
                        mol_type = protein
                        organism = synthetic construct
SEQUENCE: 313
WGKGTTVTVS S                                                                11

SEQ ID NO: 314          moltype = AA   length = 11
FEATURE                 Location/Qualifiers
REGION                  1..11
                        note = Synthetic
source                  1..11
                        mol_type = protein
                        organism = synthetic construct
SEQUENCE: 314
WGRGTTVTVS S                                                                11

SEQ ID NO: 315          moltype = AA   length = 11
FEATURE                 Location/Qualifiers
REGION                  1..11
                        note = Synthetic
source                  1..11
                        mol_type = protein
                        organism = synthetic construct
SEQUENCE: 315
WGRGTSVTVS S                                                                11

SEQ ID NO: 316          moltype = AA   length = 107
FEATURE                 Location/Qualifiers
REGION                  1..107
                        note = Synthetic
source                  1..107
                        mol_type = protein
                        organism = synthetic construct
SEQUENCE: 316
DIQMTQSPSS LSASVGDRVT ITCQASQDIS NYLNWYQQKP GKAPKLLIYD ASNLETGVPS            60
RFSGSGSGTD FTFTISSLQP EDIATYYCQQ VYVLPFTFGG GTKVEIK                         107

SEQ ID NO: 317          moltype = AA   length = 108
FEATURE                 Location/Qualifiers
REGION                  1..108
                        note = Synthetic
source                  1..108
                        mol_type = protein
                        organism = synthetic construct
SEQUENCE: 317
EIVLTQSPGT LSLSPGERAT LSCRASQSVS SSYLAWYQQK PGQAPRLLIY GASSRATGIP            60
DRFSGSGSGT DFTLTISRLE PEDFAVYYCQ QYLGFPPTFG GGTKVEIK                        108

SEQ ID NO: 318          moltype = AA   length = 113
FEATURE                 Location/Qualifiers
REGION                  1..113
                        note = Synthetic
source                  1..113
                        mol_type = protein
                        organism = synthetic construct
SEQUENCE: 318
DIVMTQSPDS LAVSLGERAT INCKSSQSVL YSSNNKNYLA WYQQKPGQPP KLLIYWASTR            60
ESGVPDRFSG SGSGTDFTLT ISSLQAEDVA VYYCQQSFLT PWTFGGGTKV EIK                  113

SEQ ID NO: 319          moltype = AA   length = 107
FEATURE                 Location/Qualifiers
REGION                  1..107
                        note = Synthetic
source                  1..107
                        mol_type = protein
                        organism = synthetic construct
SEQUENCE: 319
EIVMTQSPAT LSVSPGERAT LSCRASQSVS SNLAWYQQKP GQAPRLLIYG ASTRATGIPA            60
RFSGSGSGTE FTLTISSLQS EDFAVYYCQQ FNNHPITFGG GTKVEIK                         107

SEQ ID NO: 320          moltype = AA   length = 112
FEATURE                 Location/Qualifiers
REGION                  1..112
                        note = Synthetic
source                  1..112
                        mol_type = protein
                        organism = synthetic construct
SEQUENCE: 320
DIVMTQSPLS LPVTPGEPAS ISCRSSQSLL HSNGYNYLDW YLQKPGQSPQ LLIYLGSNRA            60
```

```
SGVPDRFSGS GSGTDFTLKI SRVEAEDVGV YYCVQARQTP LTFGGGTKVE IK            112

SEQ ID NO: 321          moltype = AA   length = 112
FEATURE                 Location/Qualifiers
REGION                  1..112
                        note = Synthetic
source                  1..112
                        mol_type = protein
                        organism = synthetic construct
SEQUENCE: 321
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQARDAP WTFGGGTKVE IK            112

SEQ ID NO: 322          moltype = AA   length = 113
FEATURE                 Location/Qualifiers
REGION                  1..113
                        note = Synthetic
source                  1..113
                        mol_type = protein
                        organism = synthetic construct
SEQUENCE: 322
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQLASY PYTFGGGTKV EIK           113

SEQ ID NO: 323          moltype = AA   length = 112
FEATURE                 Location/Qualifiers
REGION                  1..112
                        note = Synthetic
source                  1..112
                        mol_type = protein
                        organism = synthetic construct
SEQUENCE: 323
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQARQTP FTFGGGTKVE IK            112

SEQ ID NO: 324          moltype = AA   length = 112
FEATURE                 Location/Qualifiers
REGION                  1..112
                        note = Synthetic
source                  1..112
                        mol_type = protein
                        organism = synthetic construct
SEQUENCE: 324
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQARQAP WTFGGGTKVE IK            112

SEQ ID NO: 325          moltype = AA   length = 113
FEATURE                 Location/Qualifiers
REGION                  1..113
                        note = Synthetic
source                  1..113
                        mol_type = protein
                        organism = synthetic construct
SEQUENCE: 325
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQARQVP PWTFGGGTKV EIK           113

SEQ ID NO: 326          moltype = AA   length = 111
FEATURE                 Location/Qualifiers
REGION                  1..111
                        note = Synthetic
source                  1..111
                        mol_type = protein
                        organism = synthetic construct
SEQUENCE: 326
DIVMTQSPLS LPVTPGEPAS ISCRSSQSLL HSNGYNYLDW YLQKPGQSPQ LLIFLGSNRA    60
SGVPDRFSGS GSGTDFTLKI SRVEAEDVGV YYCMQARQAF TFGGGTKVEI K             111

SEQ ID NO: 327          moltype = AA   length = 107
FEATURE                 Location/Qualifiers
REGION                  1..107
                        note = Synthetic
source                  1..107
                        mol_type = protein
                        organism = synthetic construct
SEQUENCE: 327
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ YTSWPLTFGG GTKVEIK                  107
```

| SEQ ID NO: 328 | moltype = AA length = 108 |
|---|---|
| FEATURE | Location/Qualifiers |
| REGION | 1..108 |
| | note = Synthetic |
| source | 1..108 |
| | mol_type = protein |
| | organism = synthetic construct |

SEQUENCE: 328
EIVLTQSPGT LSLSPGERAT LSCRASQSVS SSFLAWYQQK PGQAPRLLIY GASSRATGIP     60
DRFSGSGSGT DFTLTISRLE PEDFAVYYCQ QLDSHPPTFG GGTKVEIK                108

| SEQ ID NO: 329 | moltype = AA length = 113 |
|---|---|
| FEATURE | Location/Qualifiers |
| REGION | 1..113 |
| | note = Synthetic |
| source | 1..113 |
| | mol_type = protein |
| | organism = synthetic construct |

SEQUENCE: 329
DIVMTQSPDS LAVSLGERAT INCKSSQSVL YSSNNKNYLA WYQQKPGQPP KLLIYWASTR     60
ESGVPDRFSG SGSGTDFTLT ISSLQAEDVA VYYCQQYDVD PLTFGGGTKV EIK          113

| SEQ ID NO: 330 | moltype = AA length = 108 |
|---|---|
| FEATURE | Location/Qualifiers |
| REGION | 1..108 |
| | note = Synthetic |
| source | 1..108 |
| | mol_type = protein |
| | organism = synthetic construct |

SEQUENCE: 330
EIVLTQSPGT LSLSPGERAT LSCRASQSVS SSYLAWYQQK PGQAPRLLIY GASSRATGIP     60
DRFSGSGSGT DFTLTISRLE PEDFAVYYCQ QAFISPPTFG GGTKVEIK                108

| SEQ ID NO: 331 | moltype = AA length = 107 |
|---|---|
| FEATURE | Location/Qualifiers |
| REGION | 1..107 |
| | note = Synthetic |
| source | 1..107 |
| | mol_type = protein |
| | organism = synthetic construct |

SEQUENCE: 331
DIQMTQSPSS VSASVGDRVT ITCRASQGIS SWLAWYQQKP GKAPKLLIYA ASSLQSGVPS     60
RFSGSGSGTD FTLTISSLQP EDFATYYCQQ ADTLPITFGG GTKVEIK                 107

| SEQ ID NO: 332 | moltype = AA length = 107 |
|---|---|
| FEATURE | Location/Qualifiers |
| REGION | 1..107 |
| | note = Synthetic |
| source | 1..107 |
| | mol_type = protein |
| | organism = synthetic construct |

SEQUENCE: 332
DIQMTQSPSS LSASVGDRVT ITCQASQDIS NYLNWYQQKP GKAPKLLIYD ASNLATGVPS     60
RFSGSGSGTD FTFTISSLQP EDIATYYCQQ SDIHPRTFGG GTKVEIK                 107

| SEQ ID NO: 333 | moltype = AA length = 107 |
|---|---|
| FEATURE | Location/Qualifiers |
| REGION | 1..107 |
| | note = Synthetic |
| source | 1..107 |
| | mol_type = protein |
| | organism = synthetic construct |

SEQUENCE: 333
DIQMTQSPST LSASVGDRVT ITCRASQSIS SWLAWYQQKP GKAPKLLIYK ASSLESGVPS     60
RFSGSGSGTE FTLTISSLQP DDFATYYCQQ DSIYPITFGG GTKVEIK                 107

| SEQ ID NO: 334 | moltype = AA length = 107 |
|---|---|
| FEATURE | Location/Qualifiers |
| REGION | 1..107 |
| | note = Synthetic |
| source | 1..107 |
| | mol_type = protein |
| | organism = synthetic construct |

SEQUENCE: 334
DIQMTQSPSS VSASVGDRVT ITCRASQGIS SWLAWYQQKP GKAPKLLIYA ASNLQSGVPS     60
RFSGSGSGTD FTLTISSLQP EDFATYYCQQ ANSFPLTFGG GTKVEIK                 107

| SEQ ID NO: 335 | moltype = AA length = 108 |
|---|---|
| FEATURE | Location/Qualifiers |

```
                              -continued
REGION                   1..108
                         note = Synthetic
source                   1..108
                         mol_type = protein
                         organism = synthetic construct
SEQUENCE: 335
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YKSFSPFTFG GGTKVEIK                108

SEQ ID NO: 336           moltype = AA  length = 106
FEATURE                  Location/Qualifiers
REGION                   1..106
                         note = Synthetic
source                   1..106
                         mol_type = protein
                         organism = synthetic construct
SEQUENCE: 336
DIQLTQSPSS LSASVGDRVT ITCRASQSIS SFLNWYQQKP GKAPKLLIYA ASSLQSGVPS    60
RFSGSGSGTD FTLTISSLQP EDFATYYCQQ SYSDLTFGGG TKVEIK                  106

SEQ ID NO: 337           moltype = AA  length = 108
FEATURE                  Location/Qualifiers
REGION                   1..108
                         note = Synthetic
source                   1..108
                         mol_type = protein
                         organism = synthetic construct
SEQUENCE: 337
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYLIPPITFG GGTKVEIK                108

SEQ ID NO: 338           moltype = AA  length = 107
FEATURE                  Location/Qualifiers
REGION                   1..107
                         note = Synthetic
source                   1..107
                         mol_type = protein
                         organism = synthetic construct
SEQUENCE: 338
DIQMTQSPST LSASVGDRVT ITCRASQSIG SWLAWYQQKP GKAPKLLIYK ASSLESGVPS    60
RFSGSGSGTE FTLTISSLQP DDFATYYCQQ HQSFSPTFGG GTKVEIK                 107

SEQ ID NO: 339           moltype = AA  length = 107
FEATURE                  Location/Qualifiers
REGION                   1..107
                         note = Synthetic
source                   1..107
                         mol_type = protein
                         organism = synthetic construct
SEQUENCE: 339
DIQMTQSPST LSASVGDRVT ITCRASQSIS SWLAWYQQKP GKAPKLLIYK ASSLESGVPS    60
RFSGSGSGTE FTLTISSLQP DDFATYYCQQ DSIYPITFGG GTKVEIK                 107

SEQ ID NO: 340           moltype = AA  length = 107
FEATURE                  Location/Qualifiers
REGION                   1..107
                         note = Synthetic
source                   1..107
                         mol_type = protein
                         organism = synthetic construct
SEQUENCE: 340
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSVLPLTFGG GTKVEIK                 107

SEQ ID NO: 341           moltype = AA  length = 107
FEATURE                  Location/Qualifiers
REGION                   1..107
                         note = Synthetic
source                   1..107
                         mol_type = protein
                         organism = synthetic construct
SEQUENCE: 341
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ IFSTPLTFGG GTKVEIK                 107

SEQ ID NO: 342           moltype = AA  length = 107
FEATURE                  Location/Qualifiers
REGION                   1..107
                         note = Synthetic
```

```
source                    1..107
                          mol_type = protein
                          organism = synthetic construct
SEQUENCE: 342
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SFYDPITFGG GTKVEIK                 107

SEQ ID NO: 343            moltype = AA   length = 107
FEATURE                   Location/Qualifiers
REGION                    1..107
                          note = Synthetic
source                    1..107
                          mol_type = protein
                          organism = synthetic construct
SEQUENCE: 343
EIVLTQSPAT LSVSPGERAT LSCRASQSVG SNLAWYQQKP GQAPRLLIYG ASTRATGIPA    60
RFSGSGSGTE FTLTISSLQS EDFAVYYCQQ YLYFPLTFGG GTKVEIK                 107

SEQ ID NO: 344            moltype = AA   length = 107
FEATURE                   Location/Qualifiers
REGION                    1..107
                          note = Synthetic
source                    1..107
                          mol_type = protein
                          organism = synthetic construct
SEQUENCE: 344
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ GVNYPFTFGG GTKVEIK                 107

SEQ ID NO: 345            moltype = AA   length = 106
FEATURE                   Location/Qualifiers
REGION                    1..106
                          note = Synthetic
source                    1..106
                          mol_type = protein
                          organism = synthetic construct
SEQUENCE: 345
DIQMTQSPSS VSASVGDRVT ITCRASQGIS SWLAWYQQKP GKAPKLLIYA ASSLQSGVPS    60
RFSGSGSGTD FTLTISSLQP EDFATYYCQQ VISFPTFGGG TKVEIK                  106

SEQ ID NO: 346            moltype = AA   length = 108
FEATURE                   Location/Qualifiers
REGION                    1..108
                          note = Synthetic
source                    1..108
                          mol_type = protein
                          organism = synthetic construct
SEQUENCE: 346
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YDDFPPITFG GGTKVEIK                108

SEQ ID NO: 347            moltype = AA   length = 107
FEATURE                   Location/Qualifiers
REGION                    1..107
                          note = Synthetic
source                    1..107
                          mol_type = protein
                          organism = synthetic construct
SEQUENCE: 347
DIQMTQSPSS LSASVGDRVT ITCRASQSIS RYLNWYQQKP GKAPKLLIYA ASSLQSGVPS    60
RFSGSGSGTD FTLTISSLQP EDFATYYCQQ SLDLPFTFGG GTKVEIK                 107

SEQ ID NO: 348            moltype = AA   length = 107
FEATURE                   Location/Qualifiers
REGION                    1..107
                          note = Synthetic
source                    1..107
                          mol_type = protein
                          organism = synthetic construct
SEQUENCE: 348
DIQMTQSPSS VSASVGDRVT ITCRASQGIS SWLAWYQQKP GKAPKLLIYA ASSLQSGVPS    60
RFSGSGSGTD FTLTISSLQP EDFATYYCQQ INDHPFTFGG GTKVEIK                 107

SEQ ID NO: 349            moltype = AA   length = 107
FEATURE                   Location/Qualifiers
REGION                    1..107
                          note = Synthetic
source                    1..107
                          mol_type = protein
```

```
                        organism = synthetic construct
SEQUENCE: 349
DIQMTQSPST LSASVGDRVT ITCRASQSIN SWLAWYQQKP GKAPKLLISD ASSLESGVPS      60
RFSGSGSGTE FTLTISSLQP DDFATYYCQQ YGPYPYTFGG GTKVEIK                   107

SEQ ID NO: 350          moltype = AA   length = 113
FEATURE                 Location/Qualifiers
REGION                  1..113
                        note = Synthetic
source                  1..113
                        mol_type = protein
                        organism = synthetic construct
SEQUENCE: 350
DIVMTQSPDS LAVSLGERAT INCKSSQSVL YSSNNKNYLA WYQQKPGQPP KLLIYWASTR      60
ESGVPDRFSG SGSGTDFTLT ISSLQAEDVA VYYCQQSHST PLTFGGGTKV EIK            113

SEQ ID NO: 351          moltype = AA   length = 113
FEATURE                 Location/Qualifiers
REGION                  1..113
                        note = Synthetic
source                  1..113
                        mol_type = protein
                        organism = synthetic construct
SEQUENCE: 351
DIVMTQSPDS LAVSLGERAT INCKSSQSVL YSSNNKNYLA WYQQKPGQPP KLLIYWASTR      60
ESGVPDRFSG SGSGTDFTLT ISSLQAEDVA VYYCQQLASQ PPTFGGGTKV EIK            113

SEQ ID NO: 352          moltype = AA   length = 107
FEATURE                 Location/Qualifiers
REGION                  1..107
                        note = Synthetic
source                  1..107
                        mol_type = protein
                        organism = synthetic construct
SEQUENCE: 352
EIVMTQSPAT LSVSPGERAT LSCRASQSVS SNLAWYQQKP GQAPRLLIYG ASTRATGIPA      60
RFSGSGSGTE FTLTISSLQS EDFAVYYCQQ YAYWPLTFGG GTKVEIK                   107

SEQ ID NO: 353          moltype = AA   length = 113
FEATURE                 Location/Qualifiers
REGION                  1..113
                        note = Synthetic
source                  1..113
                        mol_type = protein
                        organism = synthetic construct
SEQUENCE: 353
DIVMTQSPDS LAVSLGERAT INCKSSQSVL FSSNNKNYLA WYQQKPGQPP KLLIYWASTR      60
ESGVPDRFSG SGSGTDFTLT ISSLQAEDVA VYYCQQDFSL PYTFGGGTKV EIK            113

SEQ ID NO: 354          moltype = AA   length = 106
FEATURE                 Location/Qualifiers
REGION                  1..106
                        note = Synthetic
source                  1..106
                        mol_type = protein
                        organism = synthetic construct
SEQUENCE: 354
DIQLTQSPSS VSASVGDRVT ITCRASQDIS SWLAWYQQKP GKAPKLLIYA ASSLQSGVPS      60
RFSGSGSGTD FTLTISSLQP EDFATYYCQQ SLTHPTFGGG TKVEIK                    106

SEQ ID NO: 355          moltype = AA   length = 113
FEATURE                 Location/Qualifiers
REGION                  1..113
                        note = Synthetic
source                  1..113
                        mol_type = protein
                        organism = synthetic construct
SEQUENCE: 355
DIVMTQSPDS LAVSLGERAT INCKSSQSVL FSSNNKNYLA WYQQKPGQPP KLLIYWASTR      60
ESGVPDRFSG SGSGTDFTLT ISSLQAEDVA VYYCQQYDLL PYTFGGGTKV EIK            113

SEQ ID NO: 356          moltype = AA   length = 108
FEATURE                 Location/Qualifiers
REGION                  1..108
                        note = Synthetic
source                  1..108
                        mol_type = protein
                        organism = synthetic construct
SEQUENCE: 356
```

```
DIQLTQSPSS VSASVGDRVT ITCRASQDIS SWLAWYQQKP GKAPKLLIYA ASSLQSGVPS    60
RFSGSGSGTD FTLTISSLQP EDFATYYCQQ AVIHPPYTFG GGTKVEIK               108

SEQ ID NO: 357          moltype = AA  length = 108
FEATURE                 Location/Qualifiers
REGION                  1..108
                        note = Synthetic
source                  1..108
                        mol_type = protein
                        organism = synthetic construct
SEQUENCE: 357
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNVHPPRTFG GGTKVEIK               108

SEQ ID NO: 358          moltype = AA  length = 112
FEATURE                 Location/Qualifiers
REGION                  1..112
                        note = Synthetic
source                  1..112
                        mol_type = protein
                        organism = synthetic construct
SEQUENCE: 358
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQSRNAP WTFGGGTKVE IK          112

SEQ ID NO: 359          moltype = AA  length = 111
FEATURE                 Location/Qualifiers
REGION                  1..111
                        note = Synthetic
source                  1..111
                        mol_type = protein
                        organism = synthetic construct
SEQUENCE: 359
DIVMTQSPLS LPVTPGEPAS ISCRSSQSLL HSNGYNYLDW YLQKPGQSPQ VLIYLGSNRA    60
SGVPDRFSGS GSGTDFTLKI SRVEAEDVGV YYCMQARHGF TFGGGTKVEI K           111

SEQ ID NO: 360          moltype = AA  length = 112
FEATURE                 Location/Qualifiers
REGION                  1..112
                        note = Synthetic
source                  1..112
                        mol_type = protein
                        organism = synthetic construct
SEQUENCE: 360
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQAREVP FTFGGGTKVE IK          112

SEQ ID NO: 361          moltype = AA  length = 113
FEATURE                 Location/Qualifiers
REGION                  1..113
                        note = Synthetic
source                  1..113
                        mol_type = protein
                        organism = synthetic construct
SEQUENCE: 361
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQARHVP PLTFGGGTKV EIK         113

SEQ ID NO: 362          moltype = AA  length = 113
FEATURE                 Location/Qualifiers
REGION                  1..113
                        note = Synthetic
source                  1..113
                        mol_type = protein
                        organism = synthetic construct
SEQUENCE: 362
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQHDSA PYTFGGGTKV EIK         113

SEQ ID NO: 363          moltype = AA  length = 112
FEATURE                 Location/Qualifiers
REGION                  1..112
                        note = Synthetic
source                  1..112
                        mol_type = protein
                        organism = synthetic construct
SEQUENCE: 363
DIVMTQSPLS LPVTPGEPAS ISCRSSQSLL HSNGYNYLDW YLQKPGQSPQ LLIYLGSHRA    60
SGVPDRFSGS GSGTDFTLKI SRVEAEDVGV YYCMQGRQVP FTFGGGTKVE IK          112
```

```
SEQ ID NO: 364          moltype = AA   length = 112
FEATURE                 Location/Qualifiers
REGION                  1..112
                        note = Synthetic
source                  1..112
                        mol_type = protein
                        organism = synthetic construct
SEQUENCE: 364
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQARGTP WTFGGGTKVE IK          112

SEQ ID NO: 365          moltype = AA   length = 113
FEATURE                 Location/Qualifiers
REGION                  1..113
                        note = Synthetic
source                  1..113
                        mol_type = protein
                        organism = synthetic construct
SEQUENCE: 365
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQSRRAP PWTFGGGTKV EIK         113

SEQ ID NO: 366          moltype = AA   length = 107
FEATURE                 Location/Qualifiers
REGION                  1..107
                        note = Synthetic
source                  1..107
                        mol_type = protein
                        organism = synthetic construct
SEQUENCE: 366
DIQMTQSPST LSASVGDRVT ITCRASQSIS SWLAWYQQKP GKAPKLLIYK ASSLESGVPS   60
RFSGSGSGTE FTLTISSLQP DDFATYYCQQ FQSYPFTFGG GTKVEIK                107

SEQ ID NO: 367          moltype = AA   length = 108
FEATURE                 Location/Qualifiers
REGION                  1..108
                        note = Synthetic
source                  1..108
                        mol_type = protein
                        organism = synthetic construct
SEQUENCE: 367
DIQMTQSPST LSASVGDRVT ITCRASQSIS SWLAWYQQKP GKAPKLLIYK ASSLESGVPS   60
RFSGSGSGTE FTLTISSLQP DDFATYYCQQ SSADSPFTFG GGTKVEIK               108

SEQ ID NO: 368          moltype = AA   length = 112
FEATURE                 Location/Qualifiers
REGION                  1..112
                        note = Synthetic
source                  1..112
                        mol_type = protein
                        organism = synthetic construct
SEQUENCE: 368
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQARQLP WTFGGGTKVE IK          112

SEQ ID NO: 369          moltype = AA   length = 107
FEATURE                 Location/Qualifiers
REGION                  1..107
                        note = Synthetic
source                  1..107
                        mol_type = protein
                        organism = synthetic construct
SEQUENCE: 369
EIVMTQSPAT LSLSPGERAT LSCRASQSVS SYLAWYQQKP GQAPRLLIYD SSNRATGIPA   60
RFSGSGSGTD FTLTISSLEP EDFAVYYCQQ HDVWPITFGG GTKVEIK                107

SEQ ID NO: 370          moltype = AA   length = 111
FEATURE                 Location/Qualifiers
REGION                  1..111
                        note = Synthetic
source                  1..111
                        mol_type = protein
                        organism = synthetic construct
SEQUENCE: 370
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQTRHTP TFGGGTKVEI K           111

SEQ ID NO: 371          moltype = AA   length = 112
```

```
FEATURE                 Location/Qualifiers
REGION                  1..112
                        note = Synthetic
source                  1..112
                        mol_type = protein
                        organism = synthetic construct
SEQUENCE: 371
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQDFARP PTFGGGTKVE IK           112

SEQ ID NO: 372          moltype = AA  length = 107
FEATURE                 Location/Qualifiers
REGION                  1..107
                        note = Synthetic
source                  1..107
                        mol_type = protein
                        organism = synthetic construct
SEQUENCE: 372
DIQMTQSPSS VSASVGDRVT ITCRASQGID SWLAWYQQKP GKAPKLLIYA ASSLQSGVPS    60
RFSGSGSGTD FTLTISSLQP EDFATYYCQQ RAVFPPTFGG GTKVEIK                 107

SEQ ID NO: 373          moltype = AA  length = 112
FEATURE                 Location/Qualifiers
REGION                  1..112
                        note = Synthetic
source                  1..112
                        mol_type = protein
                        organism = synthetic construct
SEQUENCE: 373
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQDATG ITFGGGTKVE IK           112

SEQ ID NO: 374          moltype = AA  length = 113
FEATURE                 Location/Qualifiers
REGION                  1..113
                        note = Synthetic
source                  1..113
                        mol_type = protein
                        organism = synthetic construct
SEQUENCE: 374
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQLASF PWTFGGGTKV EIK          113

SEQ ID NO: 375          moltype = AA  length = 113
FEATURE                 Location/Qualifiers
REGION                  1..113
                        note = Synthetic
source                  1..113
                        mol_type = protein
                        organism = synthetic construct
SEQUENCE: 375
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQLAFT PWTFGGGTKV EIK          113

SEQ ID NO: 376          moltype = AA  length = 112
FEATURE                 Location/Qualifiers
REGION                  1..112
                        note = Synthetic
source                  1..112
                        mol_type = protein
                        organism = synthetic construct
SEQUENCE: 376
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQDHSF ITFGGGTKVE IK           112

SEQ ID NO: 377          moltype = AA  length = 107
FEATURE                 Location/Qualifiers
REGION                  1..107
                        note = Synthetic
source                  1..107
                        mol_type = protein
                        organism = synthetic construct
SEQUENCE: 377
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QDVSDFTFGG GTKVEIK                 107

SEQ ID NO: 378          moltype = AA  length = 108
FEATURE                 Location/Qualifiers
REGION                  1..108
```

```
                           note = Synthetic
source                     1..108
                           mol_type = protein
                           organism = synthetic construct
SEQUENCE: 378
DIQMTQSPSS LSASVGDRVT ITCRASQSIS RYLNWYQQKP GKAPKLLIYA ASSLQSGVPS   60
RFSGSGSGTD FTLTISSLQP EDFATYYCQQ LYHAPPITFG GGTKVEIK               108

SEQ ID NO: 379             moltype = AA   length = 113
FEATURE                    Location/Qualifiers
REGION                     1..113
                           note = Synthetic
source                     1..113
                           mol_type = protein
                           organism = synthetic construct
SEQUENCE: 379
DIVMTQSPDS LAVSLGERAT INCKSSQSVL FSSNNKNYLA WYQQKPGQPP KLLIYWASTR   60
ESGVPDRFSG SGSGTDFTLT ISSLEPEDVA VYYCQQYDSL PFTFGGGTKV EIK         113

SEQ ID NO: 380             moltype = AA   length = 113
FEATURE                    Location/Qualifiers
REGION                     1..113
                           note = Synthetic
source                     1..113
                           mol_type = protein
                           organism = synthetic construct
SEQUENCE: 380
DIVMTQSPDS LAVSLGERAT INCKSSQSVL YSSNNKNYLA WYQQKPGQPP KLLIYWASTR   60
ESGVPDRFSG SGSGTDFTLT ISSLQAEDVA VYYCQQVYLF PWTFGGGTKV EIK         113

SEQ ID NO: 381             moltype = AA   length = 113
FEATURE                    Location/Qualifiers
REGION                     1..113
                           note = Synthetic
source                     1..113
                           mol_type = protein
                           organism = synthetic construct
SEQUENCE: 381
DIVMTQSPDS LAVSLGERAT INCKSSQSVL FSSNNKNYLA WYQQKPGQPP KLLIYWASTR   60
ESGVPDRFSG SGSGTDFTLT ISSLQAEDVA VYYCQQFFLA PPTFGGGTKV EIK         113

SEQ ID NO: 382             moltype = AA   length = 108
FEATURE                    Location/Qualifiers
REGION                     1..108
                           note = Synthetic
source                     1..108
                           mol_type = protein
                           organism = synthetic construct
SEQUENCE: 382
EIVLTQSPGT LSLSPGERAT LSCRASQSVS SSFLAWYQQK PGQAPRLLIY GASSRATGIP   60
DRFSGSGSGT DFTLTISRLE PEDFAVYYCQ QAVSLPWTFG GGTKVEIK               108

SEQ ID NO: 383             moltype = AA   length = 107
FEATURE                    Location/Qualifiers
REGION                     1..107
                           note = Synthetic
source                     1..107
                           mol_type = protein
                           organism = synthetic construct
SEQUENCE: 383
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ FDNLPYTFGG GTKVEIK                107

SEQ ID NO: 384             moltype = AA   length = 107
FEATURE                    Location/Qualifiers
REGION                     1..107
                           note = Synthetic
source                     1..107
                           mol_type = protein
                           organism = synthetic construct
SEQUENCE: 384
DIQMTQSPSS VSASVGDRVT ITCRASQGIS SWLAWYQQKP GKAPKLLIYA ASNLQSGVPS   60
RFSGSGSGTD FTLTISSLQP EDFATYYCQQ ATAHPPTFGG GTKVEIK                107

SEQ ID NO: 385             moltype = AA   length = 107
FEATURE                    Location/Qualifiers
REGION                     1..107
                           note = Synthetic
source                     1..107
```

```
                            mol_type = protein
                            organism = synthetic construct
SEQUENCE: 385
DIQLTQSPSS VSASVGDRVT ITCRASQDIS SWLAWYQQKP GKAPKLLIYA ASSLQSGVPS      60
RFSGSGSGTD FTLTISSLQP EDFATYYCQQ AVSHPLTFGG GTKVEIK                    107

SEQ ID NO: 386              moltype = AA   length = 107
FEATURE                     Location/Qualifiers
REGION                      1..107
                            note = Synthetic
source                      1..107
                            mol_type = protein
                            organism = synthetic construct
SEQUENCE: 386
DIQMTQSPSS VSASVGDRVT ITCRASQGID SWLAWYQQKP GKAPKLLIYA ASSLQSGVPS      60
RFSGSGSGTD FTLTISSLQP EDFATYYCQQ ATSLPLTFGG GTKVEIK                    107

SEQ ID NO: 387              moltype = AA   length = 111
FEATURE                     Location/Qualifiers
REGION                      1..111
                            note = Synthetic
source                      1..111
                            mol_type = protein
                            organism = synthetic construct
SEQUENCE: 387
DIVMTQSPLS LPVTPGEPAS ISCRSSQSLL HRNGYNYLDW YLQKPGQSPQ LLIYLGSNRA      60
SGVPDRFSGS GSGTDFTLKI SRVEAEDVGV YYCMQRLQAW TFGGGTKVEI K               111

SEQ ID NO: 388              moltype = AA   length = 106
FEATURE                     Location/Qualifiers
REGION                      1..106
                            note = Synthetic
source                      1..106
                            mol_type = protein
                            organism = synthetic construct
SEQUENCE: 388
DIQMTQSPST LSASVGDRVT ITCRASQSIS SWLAWYQQKP GKAPKLLIYK ASSLESGVPS      60
RFSGSGSGTE FTLTISSLQP DDFATYYCQQ YRTYPTFGGG TKVEIK                     106

SEQ ID NO: 389              moltype = AA   length = 107
FEATURE                     Location/Qualifiers
REGION                      1..107
                            note = Synthetic
source                      1..107
                            mol_type = protein
                            organism = synthetic construct
SEQUENCE: 389
DIQMTQSPST LSASVGDRVT ITCRASQSIS SWLAWYQQKP GKAPKLLIYK ASSLESGVPS      60
RFSGSGSGTE FTLTISSLQP DDFATYYCQQ HSLLSITFGG GTKVEIK                    107

SEQ ID NO: 390              moltype = AA   length = 106
FEATURE                     Location/Qualifiers
REGION                      1..106
                            note = Synthetic
source                      1..106
                            mol_type = protein
                            organism = synthetic construct
SEQUENCE: 390
EIVLTQSPAT LSLSPGERAT LSCRASQSVS SYLAWYQQKP GQAPRLLIYD ASNRATGIPA      60
RFSGSGSGTD FTLTISSLEP EDFAVYYCQH YNLWRTFGGG TKVEIK                     106

SEQ ID NO: 391              moltype = AA   length = 107
FEATURE                     Location/Qualifiers
REGION                      1..107
                            note = Synthetic
source                      1..107
                            mol_type = protein
                            organism = synthetic construct
SEQUENCE: 391
DIQMTQSPST LSASVGDRVT ITCRASQSIS SWLAWYQQKP GKAPKLLIYD ASSLESGVPS      60
RFSGSGSGTE FTLTISSLQP DDFATYYCQQ HSTYSWTFGG GTKVEIK                    107

SEQ ID NO: 392              moltype = AA   length = 107
FEATURE                     Location/Qualifiers
REGION                      1..107
                            note = Synthetic
source                      1..107
                            mol_type = protein
                            organism = synthetic construct
```

```
SEQUENCE: 392
EIVMTQSPAT LSVSPGERAT LSCRASQSVG SNLAWYQQKP GQAPRLLIYG ASTRATGIPA    60
RFSGSGSGTE FTLTISSLQS EDFAVYYCQQ HDVWPYTFGG GTKVEIK                107

SEQ ID NO: 393           moltype = AA   length = 113
FEATURE                  Location/Qualifiers
REGION                   1..113
                         note = Synthetic
source                   1..113
                         mol_type = protein
                         organism = synthetic construct
SEQUENCE: 393
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQYFST PPTFGGGTKV EIK          113

SEQ ID NO: 394           moltype = AA   length = 113
FEATURE                  Location/Qualifiers
REGION                   1..113
                         note = Synthetic
source                   1..113
                         mol_type = protein
                         organism = synthetic construct
SEQUENCE: 394
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQYALT PYTFGGGTKV EIK          113

SEQ ID NO: 395           moltype = AA   length = 107
FEATURE                  Location/Qualifiers
REGION                   1..107
                         note = Synthetic
source                   1..107
                         mol_type = protein
                         organism = synthetic construct
SEQUENCE: 395
EIVMTQSPAT LSVSPGERAT LSCRASQSVG SNLAWYQQKP GQAPRLLIYG ASTRATGIPA    60
RFSGSGSGTE FTLTISSLQS EDFAVYYCQQ DHDRPLTFGG GTKVEIK                107

SEQ ID NO: 396           moltype = AA   length = 122
FEATURE                  Location/Qualifiers
REGION                   1..122
                         note = Synthetic
source                   1..122
                         mol_type = protein
                         organism = synthetic construct
SEQUENCE: 396
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCARGQ GSDHYYYGMD VWGQGTTVTV   120
SS                                                                  122

SEQ ID NO: 397           moltype = AA   length = 123
FEATURE                  Location/Qualifiers
REGION                   1..123
                         note = Synthetic
source                   1..123
                         mol_type = protein
                         organism = synthetic construct
SEQUENCE: 397
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCAREG GPRGASFNWF DPWGQGTLVT   120
VSS                                                                 123

SEQ ID NO: 398           moltype = AA   length = 118
FEATURE                  Location/Qualifiers
REGION                   1..118
                         note = Synthetic
source                   1..118
                         mol_type = protein
                         organism = synthetic construct
SEQUENCE: 398
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCARDV GSMYFDIWGQ GTMVTVSS     118

SEQ ID NO: 399           moltype = AA   length = 120
FEATURE                  Location/Qualifiers
REGION                   1..120
                         note = Synthetic
source                   1..120
                         mol_type = protein
                         organism = synthetic construct
```

```
SEQUENCE: 399
QVQLVQSGAE VKKPGSSVKV SCKASGGTFS SYAISWVRQA PGQGLEWMGG IIPIFGTANY     60
AQKFQGRVTI TADESTSTAY MELSSLRSED TAVYYCARHY YYGYAYFDLW GRGTLVTVSS    120

SEQ ID NO: 400           moltype = AA   length = 120
FEATURE                  Location/Qualifiers
REGION                   1..120
                         note = Synthetic
source                   1..120
                         mol_type = protein
                         organism = synthetic construct
SEQUENCE: 400
QVQLVQSGAE VKKPGASVKV SCKASGYTFT SYYMHWVRQA PGQGLEWMGV INPSGGSTSY     60
AQKFQGRVTM TRDTSTSTVY MELSSLRSED TAVYYCARES DGIDSYFDYW GQGTLVTVSS    120

SEQ ID NO: 401           moltype = AA   length = 121
FEATURE                  Location/Qualifiers
REGION                   1..121
                         note = Synthetic
source                   1..121
                         mol_type = protein
                         organism = synthetic construct
SEQUENCE: 401
QVQLVQSGAE VKKPGASVKV SCKASGYTFT SYYMHWVRQA PGQGLEWMGV INPSGGSTSY     60
AQKFQGRVTM TRDTSTSTVY MELSSLRSED TAVYYCARES GHSYVSSFDP WGQGTLVTVS    120
S                                                                   121

SEQ ID NO: 402           moltype = AA   length = 119
FEATURE                  Location/Qualifiers
REGION                   1..119
                         note = Synthetic
source                   1..119
                         mol_type = protein
                         organism = synthetic construct
SEQUENCE: 402
QVQLVQSGAE VKKPGASVKV SCKASGYTFT SYYMHWVRQA PGQGLEWMGI INPSGGSTSY     60
AQKFQGRVTM TRDTSTSTVY MELSSLRSED TAVYYCARGL IYGDAFDYWG QGTLVTVSS     119

SEQ ID NO: 403           moltype = AA   length = 120
FEATURE                  Location/Qualifiers
REGION                   1..120
                         note = Synthetic
source                   1..120
                         mol_type = protein
                         organism = synthetic construct
SEQUENCE: 403
QVQLVQSGAE VKKPGASVKV SCKASGYTFT SYYMHWVRQA PGQGLEWMGI INPSGGSTSY     60
AQKFQGRVTM TRDTSTSTVY MELSSLRSED TAVYYCAREV SMTAASLDVW GQGTMVTVSS    120

SEQ ID NO: 404           moltype = AA   length = 121
FEATURE                  Location/Qualifiers
REGION                   1..121
                         note = Synthetic
source                   1..121
                         mol_type = protein
                         organism = synthetic construct
SEQUENCE: 404
QVQLVQSGAE VKKPGASVKV SCKASGYTFT SYYMHWVRQA PGQGLEWMGI INPSGGSTSY     60
AQKFQGRVTM TRDTSTSTVY MELSSLRSED TAVYYCAREA GYDISSAFDI WGQGTMVTVS    120
S                                                                   121

SEQ ID NO: 405           moltype = AA   length = 120
FEATURE                  Location/Qualifiers
REGION                   1..120
                         note = Synthetic
source                   1..120
                         mol_type = protein
                         organism = synthetic construct
SEQUENCE: 405
QVQLVQSGAE VKKPGASVKV SCKASGYTFT SYYMHWVRQA PGQGLEWMGI INPSGGSTSY     60
AQKFQGRVTM TRDTSTSTVY MELSSLRSED TAVYYCAREG SGSWETLDVW GQGTMVTVSS    120

SEQ ID NO: 406           moltype = AA   length = 118
FEATURE                  Location/Qualifiers
REGION                   1..118
                         note = Synthetic
source                   1..118
                         mol_type = protein
                         organism = synthetic construct
```

```
SEQUENCE: 406
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARS GEYGFDLWGR GTLVTVSS    118

SEQ ID NO: 407          moltype = AA   length = 121
FEATURE                 Location/Qualifiers
REGION                  1..121
                        note = Synthetic
source                  1..121
                        mol_type = protein
                        organism = synthetic construct
SEQUENCE: 407
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARG GGYPWEAFDY WGKGTTVTVS   120
S                                                                  121

SEQ ID NO: 408          moltype = AA   length = 120
FEATURE                 Location/Qualifiers
REGION                  1..120
                        note = Synthetic
source                  1..120
                        mol_type = protein
                        organism = synthetic construct
SEQUENCE: 408
EVQLVESGGG LVKPGGSLRL SCAASGFTFS SYSMNWVRQA PGKGLEWVSS ISSSSNYIYY    60
ADSVKGRFTI SRDNAKNSLY LQMNSLRAED TAVYYCARGR YRRTGSLDVW GQGTMVTVSS   120

SEQ ID NO: 409          moltype = AA   length = 118
FEATURE                 Location/Qualifiers
REGION                  1..118
                        note = Synthetic
source                  1..118
                        mol_type = protein
                        organism = synthetic construct
SEQUENCE: 409
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCARRS SGDYLDVWGQ GTMVTVSS    118

SEQ ID NO: 410          moltype = AA   length = 119
FEATURE                 Location/Qualifiers
REGION                  1..119
                        note = Synthetic
source                  1..119
                        mol_type = protein
                        organism = synthetic construct
SEQUENCE: 410
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCARRG GSYDAFQHWG QGTLVTVSS   119

SEQ ID NO: 411          moltype = AA   length = 119
FEATURE                 Location/Qualifiers
REGION                  1..119
                        note = Synthetic
source                  1..119
                        mol_type = protein
                        organism = synthetic construct
SEQUENCE: 411
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKGP RMSGWWADWG QGTLVTVSS   119

SEQ ID NO: 412          moltype = AA   length = 120
FEATURE                 Location/Qualifiers
REGION                  1..120
                        note = Synthetic
source                  1..120
                        mol_type = protein
                        organism = synthetic construct
SEQUENCE: 412
QVQLQESGPG LVKPSETLSL TCTVSGGSIS SYYWSWIRQP PGKGLEWIGS IYYSGSTNYN    60
PSLKSRVTIS VDTSKNQFSL KLSSVTAADT AVYYCARGAP GGRHNWFDPW GQGTLVTVSS  120

SEQ ID NO: 413          moltype = AA   length = 119
FEATURE                 Location/Qualifiers
REGION                  1..119
                        note = Synthetic
source                  1..119
                        mol_type = protein
                        organism = synthetic construct
SEQUENCE: 413
```

```
EVQLVESGGG LVQPGRSLRL SCAASGFTFD DYAMHWVRQA PGKGLEWVSG ISWNSGDIGY    60
ADSVKGRFTI SRDNAKNTLY LQMNSLRAED TALYYCAKGP RMVTHLDVWG QGTMVTVSS    119

SEQ ID NO: 414           moltype = AA  length = 118
FEATURE                  Location/Qualifiers
REGION                   1..118
                         note = Synthetic
source                   1..118
                         mol_type = protein
                         organism = synthetic construct
SEQUENCE: 414
EVQLVESGGG LVQPGGSLRL SCAASGFTFS DHHMDWVRQA PGKGLEWVGR TRNKANSYTT    60
EYAASVKGRF TISRDDSKNS LYLQMNSLKT EDTAVYYCAR GPLGYKLWGQ GTLVTVSS     118

SEQ ID NO: 415           moltype = AA  length = 118
FEATURE                  Location/Qualifiers
REGION                   1..118
                         note = Synthetic
source                   1..118
                         mol_type = protein
                         organism = synthetic construct
SEQUENCE: 415
EVQLVESGGG LVQPGGSLRL SCAASGFTFS SYWMSWVRQA PGKGLEWVAN IKQDGSEKYY    60
VDSVKGRFTI SRDNAKNSLY LQMNSLRAED TAVYYCARDA PQLGLDVWGQ GTMVTVSS     118

SEQ ID NO: 416           moltype = AA  length = 123
FEATURE                  Location/Qualifiers
REGION                   1..123
                         note = Synthetic
source                   1..123
                         mol_type = protein
                         organism = synthetic construct
SEQUENCE: 416
EVQLVESGGG LVQPGGSLRL SCAASGFTFS SYSMNWVRQA PGKGLEWVSY ISSSSSTIYY    60
ADSVKGRFTI SRDNAKNSLY LQMNSLRAED TAVYYCARGG PLGYGDYKGM DVWGQGTTVT   120
VSS                                                                 123

SEQ ID NO: 417           moltype = AA  length = 124
FEATURE                  Location/Qualifiers
REGION                   1..124
                         note = Synthetic
source                   1..124
                         mol_type = protein
                         organism = synthetic construct
SEQUENCE: 417
QVQLQESGPG LVKPSETLSL TCTVSGGSIS SYYWSWIRQP PGKGLEWIGH IYYSGSTNYN    60
PSLKSRVTIS VDTSKNQFSL KLSSVTAADT AVYYCARDAG RYYGSSSSWY FDLWGRGTLV   120
TVSS                                                                124

SEQ ID NO: 418           moltype = AA  length = 119
FEATURE                  Location/Qualifiers
REGION                   1..119
                         note = Synthetic
source                   1..119
                         mol_type = protein
                         organism = synthetic construct
SEQUENCE: 418
EVQLVESGGG LVQPGRSLRL SCAASGFTFD DYAMHWVRQA PGKGLEWVSG ITWNSGSIGY    60
ADSVKGRFTI SRDNAKNSLY LQMNSLRAED TALYYCAKGP RLLSALDVWG QGTMVTVSS   119

SEQ ID NO: 419           moltype = AA  length = 119
FEATURE                  Location/Qualifiers
REGION                   1..119
                         note = Synthetic
source                   1..119
                         mol_type = protein
                         organism = synthetic construct
SEQUENCE: 419
EVQLVESGGG LVQPGRSLRL SCAASGFTFD DYAMHWVRQA PGKGLEWVSG ITWNSGSIGY    60
ADSVKGRFTI SRDNAKNSLY LQMNSLRAED TALYYCAKGP RLLSALDVWG QGTMVTVSS   119

SEQ ID NO: 420           moltype = AA  length = 119
FEATURE                  Location/Qualifiers
REGION                   1..119
                         note = Synthetic
source                   1..119
                         mol_type = protein
                         organism = synthetic construct
SEQUENCE: 420
```

```
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKGG SRYSHFDYWG QGTLVTVSS    119

SEQ ID NO: 421          moltype = AA  length = 122
FEATURE                 Location/Qualifiers
REGION                  1..122
                        note = Synthetic
source                  1..122
                        mol_type = protein
                        organism = synthetic construct
SEQUENCE: 421
QVQLVQSGAE VKKPGASVKV SCKASGYTFT SYYIHWVRQA PGQGLEWMGI INPSGGSTSY    60
AQKFQGRVTM TRDTSTSTVY MELSSLRSED TAVYYCARDS AQETYYYGMD VWGQGTTVTV    120
SS                                                                   122

SEQ ID NO: 422          moltype = AA  length = 124
FEATURE                 Location/Qualifiers
REGION                  1..124
                        note = Synthetic
source                  1..124
                        mol_type = protein
                        organism = synthetic construct
SEQUENCE: 422
QVQLQESGPG LVKPSQTLSL TCTVSGGSIS SGGYYWSWIR QHPGKGLEWI GYIYYSGSTY    60
YNPSLKSRVT ISVDTSKNQF SLKLSSVTAA DTAVYYCARD SSIAGRATLS FDWGQGTLV     120
TVSS                                                                 124

SEQ ID NO: 423          moltype = AA  length = 126
FEATURE                 Location/Qualifiers
REGION                  1..126
                        note = Synthetic
source                  1..126
                        mol_type = protein
                        organism = synthetic construct
SEQUENCE: 423
EVQLVESGGG LVKPGGSLRL SCAASGFTFS SYSMNWVRQA PGKGLEWVSS ISSSSNYIYY    60
ADSVKGRFTI SRDNAKNSLY LQMNSLRAED TAVYYCARGP SQYYYDSSAI EAFDIWGQGT    120
MVTVSS                                                               126

SEQ ID NO: 424          moltype = AA  length = 128
FEATURE                 Location/Qualifiers
REGION                  1..128
                        note = Synthetic
source                  1..128
                        mol_type = protein
                        organism = synthetic construct
SEQUENCE: 424
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARD GGGTAQADGA YYYGMDVWGQ    120
GTTVTVSS                                                             128

SEQ ID NO: 425          moltype = AA  length = 126
FEATURE                 Location/Qualifiers
REGION                  1..126
                        note = Synthetic
source                  1..126
                        mol_type = protein
                        organism = synthetic construct
SEQUENCE: 425
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARG RKAAAGIDEA EYFQHWGQGT    120
LVTVSS                                                               126

SEQ ID NO: 426          moltype = AA  length = 122
FEATURE                 Location/Qualifiers
REGION                  1..122
                        note = Synthetic
source                  1..122
                        mol_type = protein
                        organism = synthetic construct
SEQUENCE: 426
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARD RRMWDPYGMD VWGQGTTVTV    120
SS                                                                   122

SEQ ID NO: 427          moltype = AA  length = 124
FEATURE                 Location/Qualifiers
REGION                  1..124
                        note = Synthetic
```

```
source                  1..124
                        mol_type = protein
                        organism = synthetic construct
SEQUENCE: 427
QLQLQESGPG LVKPSETLSL TCTVSGGSIS SSSYYWGWIR QPPGKGLEWI GSIYYSGSTY     60
YNPSLKSRVT ISVDTSKNQF SLKLSSVTAA DTAVYYCARD APAVVGESPA FDIWGQGTMV    120
TVSS                                                                 124

SEQ ID NO: 428          moltype = AA  length = 122
FEATURE                 Location/Qualifiers
REGION                  1..122
                        note = Synthetic
source                  1..122
                        mol_type = protein
                        organism = synthetic construct
SEQUENCE: 428
QVQLVESGGG VVQPGRSLRL SCAASGFTFS NYGMHWVRQA PGKGLEWVAV IWYDGSNKYY     60
ADSVKGRFTI SRDNSKNTLY LQMNSLRAED TAVYYCAKGS THRGSAYGMD VWGQGTTVTV    120
SS                                                                   122

SEQ ID NO: 429          moltype = AA  length = 120
FEATURE                 Location/Qualifiers
REGION                  1..120
                        note = Synthetic
source                  1..120
                        mol_type = protein
                        organism = synthetic construct
SEQUENCE: 429
EVQLVESGGG LVKPGGSLRL SCAASGFTFS SYSMNWVRQA PGKGLEWVSS ISSSSNYIYY     60
ADSVKGRFTI SRDNAKNSLY LQMNSLKAED TAVYYCARRP DDRRGLFQHW GQGTLVTVSS    120

SEQ ID NO: 430          moltype = AA  length = 121
FEATURE                 Location/Qualifiers
REGION                  1..121
                        note = Synthetic
source                  1..121
                        mol_type = protein
                        organism = synthetic construct
SEQUENCE: 430
QVQLVESGGG VVQPGRSLRL SCAASGFTFS SYGMHWVRQA PGKGLEWVAV ISYDGSNKYY     60
ADSVKGRFTI SRDNSKNTLY LQMNSLRAED TAVYYCARPD YYSSRGVFDI WGQGTMVTVS    120
S                                                                    121

SEQ ID NO: 431          moltype = AA  length = 121
FEATURE                 Location/Qualifiers
REGION                  1..121
                        note = Synthetic
source                  1..121
                        mol_type = protein
                        organism = synthetic construct
SEQUENCE: 431
QVQLVESGGG VVQPGRSLRL SCAASGFTFS SYGMHWVRQA PGKGLEWVAV ISYDGSNKYY     60
ADSVKGRFTI SRDNSKNTLY LQMNSLRAED TAVYYCARPD YYSSRGVFDI WGQGTMVTVS    120
S                                                                    121

SEQ ID NO: 432          moltype = AA  length = 119
FEATURE                 Location/Qualifiers
REGION                  1..119
                        note = Synthetic
source                  1..119
                        mol_type = protein
                        organism = synthetic construct
SEQUENCE: 432
QVQLVESGGG VVQPGRSLRL SCAASGFTFS SYGMHWVRQA PGKGLEWVAL IWYDGSNKYY     60
ADSVKGRFTI SRDNSKNTLY LQMNSLRAED TAVYYCAKGD YLDPLFDYWG QGTLVTVSS     119

SEQ ID NO: 433          moltype = AA  length = 122
FEATURE                 Location/Qualifiers
REGION                  1..122
                        note = Synthetic
source                  1..122
                        mol_type = protein
                        organism = synthetic construct
SEQUENCE: 433
QVQLVESGGG VVQPGRSLRL SCAASGLTFS SYGMHWVRQA PGKGLEWVAV ISYDGSNKYY     60
ADSVKGRFTI SRDNSKNTLY LQMNSLRAED TAVYYCARER GTYYYASGWA NWGQGTLVTV    120
SS                                                                   122

SEQ ID NO: 434          moltype = AA  length = 120
```

```
FEATURE                 Location/Qualifiers
REGION                  1..120
                        note = Synthetic
source                  1..120
                        mol_type = protein
                        organism = synthetic construct
SEQUENCE: 434
EVQLVESGGG LVKPGGSLRL SCAASGFTFS SYSMNWVRQA PGKGLEWVSS ISSSSNYIYY    60
ADSVKGRFTI SRDNAKNSLY LQMNSLRAED TAVYYCARRG GSSSTGLLYW GQGTLVTVSS   120

SEQ ID NO: 435          moltype = AA   length = 118
FEATURE                 Location/Qualifiers
REGION                  1..118
                        note = Synthetic
source                  1..118
                        mol_type = protein
                        organism = synthetic construct
SEQUENCE: 435
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCARTR IDDSFDIWGQ GTMVTVSS    118

SEQ ID NO: 436          moltype = AA   length = 119
FEATURE                 Location/Qualifiers
REGION                  1..119
                        note = Synthetic
source                  1..119
                        mol_type = protein
                        organism = synthetic construct
SEQUENCE: 436
EVQLLESGGG LVQPGGSLRL SCAASGFTFS TYAMSWVRQA PGKGLEWVSA ISGSGGSTYY    60
ADSVKGRFTI SRDNSKNTLY LQMNSLRAED TAVYYCAKSK HSTTSLDVWG QGTMVTVSS   119

SEQ ID NO: 437          moltype = AA   length = 124
FEATURE                 Location/Qualifiers
REGION                  1..124
                        note = Synthetic
source                  1..124
                        mol_type = protein
                        organism = synthetic construct
SEQUENCE: 437
QVQLVESGGG VVQPGRSLRL SCAASGFTFS SYGMHWVRQA PGKGLEWVAV IWYDGSNKGY    60
ADSVKGRFTI SRDNSKNTLY LQMNSLRAED TAVYYCAREL MVTSGGWLYG MDVWGQGTTV   120
TVSS                                                               124

SEQ ID NO: 438          moltype = AA   length = 123
FEATURE                 Location/Qualifiers
REGION                  1..123
                        note = Synthetic
source                  1..123
                        mol_type = protein
                        organism = synthetic construct
SEQUENCE: 438
QVQLVQSGAE VKKPGASVKV SCKASGYTFT SYYMHWVRQA PGQGLEWMGI INPSGGSTSY    60
AQKFQGRVTM TRDTSTSTVY MELSSLRSED TAVYYCAREA GNYYDIESAF DIWGQGTMVT   120
VSS                                                                123

SEQ ID NO: 439          moltype = AA   length = 120
FEATURE                 Location/Qualifiers
REGION                  1..120
                        note = Synthetic
source                  1..120
                        mol_type = protein
                        organism = synthetic construct
SEQUENCE: 439
QVQLVQSGAE VKKPGASVKV SCKASGYTFT SYYMHWVRQA PGQGLEWMGV INPSGGSTSY    60
AQKFQGRVTM TRDTSTSTVY MELSSLRSED TAVYYCAREG SGYDESMDVW GQGTTVTVSS   120

SEQ ID NO: 440          moltype = AA   length = 120
FEATURE                 Location/Qualifiers
REGION                  1..120
                        note = Synthetic
source                  1..120
                        mol_type = protein
                        organism = synthetic construct
SEQUENCE: 440
QVQLVQSGAE VKKPGASVKV SCKASGYTFT SYYMHWVRQA PGQGLEWMGV INPSGGSTSY    60
AQKFQGRVTM TRDTSTSTVY MELSSLRSED TAVYYCAREG SGYDESMDVW GQTTVTVSS   120

SEQ ID NO: 441          moltype = AA   length = 120
```

```
FEATURE                 Location/Qualifiers
REGION                  1..120
                        note = Synthetic
source                  1..120
                        mol_type = protein
                        organism = synthetic construct
SEQUENCE: 441
QVQLVQSGAE VKKPGASVKV SCKASGYTFT SYYMHWVRQA PGQGLEWMGV INPSGGSTSY    60
AQKFQGRVTM TRDTSTSTVY MELSSLRSED TAVYYCAREG SGYDESMDVW GQGTTVTVSS   120

SEQ ID NO: 442          moltype = AA  length = 117
FEATURE                 Location/Qualifiers
REGION                  1..117
                        note = Synthetic
source                  1..117
                        mol_type = protein
                        organism = synthetic construct
SEQUENCE: 442
QVQLVQSGAE VKKPGSSVKV SCKASGGTFS NYAISWVRQA PGQGLEWMGG IIPIFGTANY    60
AQKFQGRVTI TADESTSTAY MELSSLRSED TAVYYCARGR GIAFDIWGQG TMVTVSS      117

SEQ ID NO: 443          moltype = AA  length = 120
FEATURE                 Location/Qualifiers
REGION                  1..120
                        note = Synthetic
source                  1..120
                        mol_type = protein
                        organism = synthetic construct
SEQUENCE: 443
QVQLVQSGAE VKKPGASVKV SCKASGYTFT SYYMHWVRQA PGQGLEWMGV INPGGGSTSY    60
AQKFQGRVTM TRDTSTSTVY MELSSLRSED TAVYYCAREA GQTSSALDVW GQGTMVTVSS   120

SEQ ID NO: 444          moltype = AA  length = 122
FEATURE                 Location/Qualifiers
REGION                  1..122
                        note = Synthetic
source                  1..122
                        mol_type = protein
                        organism = synthetic construct
SEQUENCE: 444
QVQLVQSGAE VKKPGASVKV SCKASGYTFT SYYMHWVRQA PGQGLEWMGI INPSGGSTSY    60
AQKFQGRVTM TRDTSTSTVY MELSSLRSED TAVYYCAREA GSWLISTAFD IWGQGTMVTV   120
SS                                                                  122

SEQ ID NO: 445          moltype = AA  length = 120
FEATURE                 Location/Qualifiers
REGION                  1..120
                        note = Synthetic
source                  1..120
                        mol_type = protein
                        organism = synthetic construct
SEQUENCE: 445
QVQLVQSGAE VKKPGASVKV SCKASGYTFT SYYMHWVRQA PGQGLEWMGI INPGGGSTSY    60
AQKFQGRVTM TRDTSTSTVY MELSSLRSED TAVYYCAREA GTMSSAFDIW GQGTMVTVSS   120

SEQ ID NO: 446          moltype = AA  length = 124
FEATURE                 Location/Qualifiers
REGION                  1..124
                        note = Synthetic
source                  1..124
                        mol_type = protein
                        organism = synthetic construct
SEQUENCE: 446
QVQLVQSGAE VKKPGSSVKV SCKASGGTFS SYAISWVRQA PGQGLEWMGS IIPIFGTANY    60
AQKFQGRVTI TADESTSTAY MELSSLRSED TAVYYCARSG GYSSSWYGTG YDYWGQGTLV   120
TVSS                                                                124

SEQ ID NO: 447          moltype = AA  length = 124
FEATURE                 Location/Qualifiers
REGION                  1..124
                        note = Synthetic
source                  1..124
                        mol_type = protein
                        organism = synthetic construct
SEQUENCE: 447
QVQLVQSGAE VKKPGSSVKV SCKASGGTFS SYAISWVRQA PGQGLEWMGS IIPIFGTANY    60
AQKFQGRVTI TADESTSTAY MELSSLRSED TAVYYCARDR GQYSSSWYGR MDVWGQGTTV   120
TVSS                                                                124
```

```
SEQ ID NO: 448          moltype = AA  length = 121
FEATURE                 Location/Qualifiers
REGION                  1..121
                        note = Synthetic
source                  1..121
                        mol_type = protein
                        organism = synthetic construct
SEQUENCE: 448
QVQLVQSGAE VKKPGASVKV SCKASGYTFT SYYIHWVRQA PGQGLEWMGI INPSGGSTSY    60
AQKFQGRVTM TRDTSTSTVY MELSSLRSED TAVYYCARES GYHVSTAFDI WGQGTMVTVS   120
S                                                                  121

SEQ ID NO: 449          moltype = AA  length = 119
FEATURE                 Location/Qualifiers
REGION                  1..119
                        note = Synthetic
source                  1..119
                        mol_type = protein
                        organism = synthetic construct
SEQUENCE: 449
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCARHW YALGSFDIWG QGTMVTVSS    119

SEQ ID NO: 450          moltype = AA  length = 119
FEATURE                 Location/Qualifiers
REGION                  1..119
                        note = Synthetic
source                  1..119
                        mol_type = protein
                        organism = synthetic construct
SEQUENCE: 450
QVQLVQSGAE VKKPGASVKV SCKASGYTFT SYYMHWVRQA PGQGLEWMGV INPSGGSTSY    60
AQKFQGRVTM TRDTSTSTVY MELSSLRSED TAVYYCARGA DYYAGFDYWG QGTLVTVSS    119

SEQ ID NO: 451          moltype = AA  length = 119
FEATURE                 Location/Qualifiers
REGION                  1..119
                        note = Synthetic
source                  1..119
                        mol_type = protein
                        organism = synthetic construct
SEQUENCE: 451
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKGP RLLGYFDLWG RGTLVTVSS    119

SEQ ID NO: 452          moltype = AA  length = 120
FEATURE                 Location/Qualifiers
REGION                  1..120
                        note = Synthetic
source                  1..120
                        mol_type = protein
                        organism = synthetic construct
SEQUENCE: 452
EVQLVESGGG LVQPGRSLRL SCAASGFTFD DYAMHWVRQA PGKGLEWVSG ITWNSGSIGY    60
ADSVKGRFTI SRDNAKNSLY LQMNSLRAED TALYYCAKGP RYSKPYFDYW GQGTLVTVSS   120

SEQ ID NO: 453          moltype = AA  length = 120
FEATURE                 Location/Qualifiers
REGION                  1..120
                        note = Synthetic
source                  1..120
                        mol_type = protein
                        organism = synthetic construct
SEQUENCE: 453
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCARQ EYGDGYFDLW GRGTLVTVSS   120

SEQ ID NO: 454          moltype = AA  length = 120
FEATURE                 Location/Qualifiers
REGION                  1..120
                        note = Synthetic
source                  1..120
                        mol_type = protein
                        organism = synthetic construct
SEQUENCE: 454
QVQLQESGPG LVKPSETLSL TCAVSGYSIS SGYYWAWIRQ PPGKGLEWIG SIYHSGSTYY    60
NPSLKSRVTI SVDTSKNQFS LKLSSVTAAD TAVYYCARDL GGYEGAFDPW GQGTLVTVSS   120

SEQ ID NO: 455          moltype = AA  length = 120
```

```
FEATURE                 Location/Qualifiers
REGION                  1..120
                        note = Synthetic
source                  1..120
                        mol_type = protein
                        organism = synthetic construct
SEQUENCE: 455
QVQLQESGPG LVKPSETLSL TCAVSGYSIS SGYYWAWIRQ PPGKGLEWIG SIYHSGSTYY    60
NPSLKSRVTI SVDTSKNQFS LKLSSVTAAD TAVYYCARDL GGYEGAFDPW GQGTLVTVSS   120

SEQ ID NO: 456          moltype = AA  length = 119
FEATURE                 Location/Qualifiers
REGION                  1..119
                        note = Synthetic
source                  1..119
                        mol_type = protein
                        organism = synthetic construct
SEQUENCE: 456
QVQLQESGPG LVKPSETLSL TCAVSGYSIS SGYYWGWIRQ PPGKGLEWIG SIYHSGSTYY    60
NPSLKSRVTI SVDTSKNQFS LKLSSVTAAD TAVYYCARHD DYLSSFDPWG QGTLVTVSS    119

SEQ ID NO: 457          moltype = AA  length = 117
FEATURE                 Location/Qualifiers
REGION                  1..117
                        note = Synthetic
source                  1..117
                        mol_type = protein
                        organism = synthetic construct
SEQUENCE: 457
QVQLQESGPG LVKPSQTLSL TCTVSGGSIS SGGYYWSWIR QHPGKGLEWI GYIYYSGSTY    60
YNPSLKSRVT ISVDTSKNQF SLKLSSVTAA DTAVYYCARG PSWIDVWGQG TMVTVSS      117

SEQ ID NO: 458          moltype = AA  length = 124
FEATURE                 Location/Qualifiers
REGION                  1..124
                        note = Synthetic
source                  1..124
                        mol_type = protein
                        organism = synthetic construct
SEQUENCE: 458
QVQLQESGPG LVKPSETLSL TCAVSGYSIS SGYYWGWIRQ PPGKGLEWIG SIYHSGNTYY    60
NPSLKSRVTI SVDTSKNQFS LKLSSVTAAD TAVYYCAREL YAYSSPMFYG MDVWGRGTTV   120
TVSS                                                                124

SEQ ID NO: 459          moltype = AA  length = 119
FEATURE                 Location/Qualifiers
REGION                  1..119
                        note = Synthetic
source                  1..119
                        mol_type = protein
                        organism = synthetic construct
SEQUENCE: 459
QLQLQESGPG LVKPSETLSL TCTVSGGSIS SSSYYWGWIR QPPGKGLEWI GSISYSGSTY    60
YNPSLKSRVT ISVDTSKNQF SLKLSSVTAA DTAVYYCARY YSPYGMDVWG QGTTVTVSS    119

SEQ ID NO: 460          moltype = AA  length = 121
FEATURE                 Location/Qualifiers
REGION                  1..121
                        note = Synthetic
source                  1..121
                        mol_type = protein
                        organism = synthetic construct
SEQUENCE: 460
QLQLQESGPG LVKPSETLSL TCTVSGGSIS SSDYYWGWIR QPPGKGLEWI GSIYYSGSTY    60
YNPSLKSRVT ISVDTSKNQF SLKLSSVTAA DTAVYYCARD SGQYTGSLDV WGQGTMVTVS   120
S                                                                   121

SEQ ID NO: 461          moltype = AA  length = 119
FEATURE                 Location/Qualifiers
REGION                  1..119
                        note = Synthetic
source                  1..119
                        mol_type = protein
                        organism = synthetic construct
SEQUENCE: 461
QVQLVQSGAE VKKPGASVKV SCKASGYTFT GYYMHWVRQA PGQGLEWMGW INPNSGGTKY    60
AQKFQGRVTM TRDTSISTAY MELSRLRSDD TAVYYCARER HSSLGYAYWG QGTLVTVSS    119

SEQ ID NO: 462          moltype = AA  length = 122
```

```
FEATURE                 Location/Qualifiers
REGION                  1..122
                        note = Synthetic
source                  1..122
                        mol_type = protein
                        organism = synthetic construct
SEQUENCE: 462
QVQLVQSGAE VKKPGASVKV SCKASGYTFT SYGIHWVRQA PGQGLEWMGW ISAYNGNTNY    60
AQKLQGRVTM TTDTSTSTAY MELRSLRSDD TAVYYCARGR PSSSWGNWFD PWGQGTTVTV   120
SS                                                                 122

SEQ ID NO: 463          moltype = AA  length = 120
FEATURE                 Location/Qualifiers
REGION                  1..120
                        note = Synthetic
source                  1..120
                        mol_type = protein
                        organism = synthetic construct
SEQUENCE: 463
EVQLVQSGAE VKKPGESLKI SCKGSGYSFT TYWIGWVRQM PGKGLEWMGI IYPGDSDTRY    60
SPSFQGQVTI SADKSISTAY LQWSSLKASD TAMYYCARGS PWDGRLFDIW GQGTMVTVSS   120

SEQ ID NO: 464          moltype = AA  length = 123
FEATURE                 Location/Qualifiers
REGION                  1..123
                        note = Synthetic
source                  1..123
                        mol_type = protein
                        organism = synthetic construct
SEQUENCE: 464
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARGA GMYDGSPLGM DVWGQGTTVT   120
VSS                                                                123

SEQ ID NO: 465          moltype = AA  length = 119
FEATURE                 Location/Qualifiers
REGION                  1..119
                        note = Synthetic
source                  1..119
                        mol_type = protein
                        organism = synthetic construct
SEQUENCE: 465
QVQLVQSGAE VKKPGASVKV SCKASGYTFT SYGIHWVRQA PGQGLEWMGW ISAYNGNTNY    60
AQKLQGRVTM TTDTSTSTAY MELRSLRSDD TAVYYCARAG TIYGRLDLWG RGTLVTVSS    119

SEQ ID NO: 466          moltype = AA  length = 119
FEATURE                 Location/Qualifiers
REGION                  1..119
                        note = Synthetic
source                  1..119
                        mol_type = protein
                        organism = synthetic construct
SEQUENCE: 466
EVQLVESGGG LVQPGRSLRL SCAASGFTFG DYAMHWVRQA PGKGLEWVSG ISWNSGSIGY    60
ADSVKGRFTI SRDNAKNSLY LQMNSLRAED TALYYCAKGP RRTSHLDIWG QGTMVTVSS    119

SEQ ID NO: 467          moltype = AA  length = 120
FEATURE                 Location/Qualifiers
REGION                  1..120
                        note = Synthetic
source                  1..120
                        mol_type = protein
                        organism = synthetic construct
SEQUENCE: 467
EVQLVESGGG LVQPGRSLRL SCAASGFTFD DYAMHWVRQA PGKGLEWVSG ISWNSGDIGY    60
ADSVKGRFTI SRDNAKNSLY LQMNSLRAED TALYYCAKGP RMTHSYFDLW GRGTLVTVSS   120

SEQ ID NO: 468          moltype = AA  length = 119
FEATURE                 Location/Qualifiers
REGION                  1..119
                        note = Synthetic
source                  1..119
                        mol_type = protein
                        organism = synthetic construct
SEQUENCE: 468
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAKAP RMYGYFDLWG RGTSVTVSS    119

SEQ ID NO: 469          moltype = AA  length = 119
```

```
FEATURE                     Location/Qualifiers
REGION                      1..119
                            note = Synthetic
source                      1..119
                            mol_type = protein
                            organism = synthetic construct
SEQUENCE: 469
EVQLVESGGG LVQPGRSLRL SCAASGFTFD DYAMHWVRQA PGKGLEWVSG ISWNSGSIGY     60
ADSVKGRFTI SRDNAKNSLY LQMNSLRAED TALYYCAKGP RTRGYFDLWG RGTLVTVSS    119

SEQ ID NO: 470              moltype = AA  length = 120
FEATURE                     Location/Qualifiers
REGION                      1..120
                            note = Synthetic
source                      1..120
                            mol_type = protein
                            organism = synthetic construct
SEQUENCE: 470
QVQLVESGGG LVQPGRSLRL SCAASGFTFD DYAMHWVRQA PGKGLEWVSG ISWNSGDIGY     60
ADSVKGRFTI SRDNAKNSLY LQMNSLRAED TALYYCAKAP RTRWTYFDYW GQGTLVTVSS    120

SEQ ID NO: 471              moltype = AA  length = 120
FEATURE                     Location/Qualifiers
REGION                      1..120
                            note = Synthetic
source                      1..120
                            mol_type = protein
                            organism = synthetic construct
SEQUENCE: 471
EVQLLESGGG LVQPGGSLRL SCAASGFTFS SYAMSWVRQA PGKGLEWVSA ISGSGGSTYY     60
ADSVKGRFTI SRDNSKNTLY LQMNSLRAED TAVYYCARAR RGALAGMDVW GQGTTVTVSS    120

SEQ ID NO: 472              moltype = AA  length = 121
FEATURE                     Location/Qualifiers
REGION                      1..121
                            note = Synthetic
source                      1..121
                            mol_type = protein
                            organism = synthetic construct
SEQUENCE: 472
QVQLQESGPG LVKPSETLSL TCAVSGYSIS SGYYWAWIRQ PPGKGLEWIG SIYHSGSTYY     60
NPSLKSRVTI SVDTSKNQFS LKLSSVTAAD TAVYYCARGG PYPWSGWFDP WGQGTLVTVS    120
S                                                                    121

SEQ ID NO: 473              moltype = AA  length = 121
FEATURE                     Location/Qualifiers
REGION                      1..121
                            note = Synthetic
source                      1..121
                            mol_type = protein
                            organism = synthetic construct
SEQUENCE: 473
QLQLQESGPG LVKPSETLSL TCTVSGGSIS SSSYYWGWIR QPPGKGLEWI GSIYYSGSTY     60
YNPSLKSRVT ISVDTSKNQF SLKLSSVTAA DTAVYYCARD LGQYEGYFDL WGRGTLVTVS    120
S                                                                    121

SEQ ID NO: 474              moltype = AA  length = 121
FEATURE                     Location/Qualifiers
REGION                      1..121
                            note = Synthetic
source                      1..121
                            mol_type = protein
                            organism = synthetic construct
SEQUENCE: 474
QLQLQESGPG LVKPSETLSL TCTVSGGSIS SSSYYWGWIR QPPGKGLEWI GSIYYSGSTY     60
YNPSLKSRVT ISVDTSKNQF SLKLSSVTAA DTAVYYCARL GDGYRIWADY WGQGTLVTVS    120
S                                                                    121

SEQ ID NO: 475              moltype = AA  length = 127
FEATURE                     Location/Qualifiers
REGION                      1..127
                            note = Synthetic
source                      1..127
                            mol_type = protein
                            organism = synthetic construct
SEQUENCE: 475
QVQLVESGGG VVQPGRSLRL SCAASGFTFS SYGMHWVRQA PGKGLEWVAL IWYDGSNKYY     60
ADSVKGRFTI SRDNSKNTLY LQMNSLRAED TAVYYCAREL IVGATGGLTY YYGMDVWGQG    120
TTVTVSS                                                              127
```

```
SEQ ID NO: 476          moltype = AA   length = 110
FEATURE                 Location/Qualifiers
REGION                  1..110
                        note = Synthetic
source                  1..110
                        mol_type = protein
                        organism = synthetic construct
SEQUENCE: 476
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP              110

SEQ ID NO: 477          moltype = AA   length = 9
FEATURE                 Location/Qualifiers
REGION                  1..9
                        note = Synthetic
source                  1..9
                        mol_type = protein
                        organism = synthetic construct
SEQUENCE: 477
ARGPSWIDV                                                             9

SEQ ID NO: 478          moltype = AA   length = 8
FEATURE                 Location/Qualifiers
REGION                  1..8
                        note = Synthetic
source                  1..8
                        mol_type = protein
                        organism = synthetic construct
SEQUENCE: 478
SISSGYYW                                                              8

SEQ ID NO: 479          moltype = AA   length = 13
FEATURE                 Location/Qualifiers
REGION                  1..13
                        note = Synthetic
SITE                    4
                        note = misc_feature - X is S or Y
SITE                    7
                        note = misc_feature - Xaa can be any naturally occurring
                         amino acid
SITE                    10
                        note = misc_feature - Xaa can be any naturally occurring
                         amino acid
source                  1..13
                        mol_type = protein
                        organism = synthetic construct
SEQUENCE: 479
WIGXIYXSGX TYY                                                       13

SEQ ID NO: 480          moltype = AA   length = 17
FEATURE                 Location/Qualifiers
REGION                  1..17
                        note = Synthetic
source                  1..17
                        mol_type = protein
                        organism = synthetic construct
SEQUENCE: 480
ARELYAYSSP MFYGMDV                                                   17

SEQ ID NO: 481          moltype = AA   length = 17
FEATURE                 Location/Qualifiers
REGION                  1..17
                        note = Synthetic
source                  1..17
                        mol_type = protein
                        organism = synthetic construct
SEQUENCE: 481
ARELYAYSSP MFYGMDV                                                   17

SEQ ID NO: 482          moltype =    length =
SEQUENCE: 482
000

SEQ ID NO: 483          moltype = AA   length = 8
FEATURE                 Location/Qualifiers
REGION                  1..8
                        note = Synthetic
SITE                    5
```

```
                          note = misc_feature - X is G or A
source                    1..8
                          mol_type = protein
                          organism = synthetic construct
SEQUENCE: 483
LLIYXASS                                                                       8

SEQ ID NO: 484            moltype = AA  length = 4
FEATURE                   Location/Qualifiers
REGION                    1..4
                          note = Synthetic
source                    1..4
                          mol_type = protein
                          organism = synthetic construct
SEQUENCE: 484
LLIY                                                                           4

SEQ ID NO: 485            moltype = AA  length = 10
FEATURE                   Location/Qualifiers
REGION                    1..10
                          note = Synthetic
source                    1..10
                          mol_type = protein
                          organism = synthetic construct
SEQUENCE: 485
QQLYHAPPIT                                                                    10

SEQ ID NO: 486            moltype = AA  length = 13
FEATURE                   Location/Qualifiers
REGION                    1..13
                          note = Synthetic
source                    1..13
                          mol_type = protein
                          organism = synthetic construct
SEQUENCE: 486
ARRPDDRRGL FQH                                                                13

SEQ ID NO: 487            moltype = AA  length = 9
FEATURE                   Location/Qualifiers
REGION                    1..9
                          note = Synthetic
SITE                      5
                          note = misc_feature - X is S or T
source                    1..9
                          mol_type = protein
                          organism = synthetic construct
SEQUENCE: 487
FTFSXYSMN                                                                      9

SEQ ID NO: 488            moltype = AA  length = 14
FEATURE                   Location/Qualifiers
REGION                    1..14
                          note = Synthetic
SITE                      10
                          note = misc_feature - Xaa can be any naturally occurring
                           amino acid
source                    1..14
                          mol_type = protein
                          organism = synthetic construct
SEQUENCE: 488
WVSSISSSSX YIYY                                                               14

SEQ ID NO: 489            moltype = AA  length = 13
FEATURE                   Location/Qualifiers
REGION                    1..13
                          note = Synthetic
source                    1..13
                          mol_type = protein
                          organism = synthetic construct
SEQUENCE: 489
ARRGGSSSTG LLY                                                                13

SEQ ID NO: 490            moltype = AA  length = 11
FEATURE                   Location/Qualifiers
REGION                    1..11
                          note = Synthetic
source                    1..11
                          mol_type = protein
                          organism = synthetic construct
```

```
SEQUENCE: 490
ARTRIDDSFD I                                                        11

SEQ ID NO: 491          moltype = AA   length = 9
FEATURE                 Location/Qualifiers
REGION                  1..9
                        note = Synthetic
source                  1..9
                        mol_type = protein
                        organism = synthetic construct
SEQUENCE: 491
QQYGPYPYT                                                            9

SEQ ID NO: 492          moltype = AA   length = 8
FEATURE                 Location/Qualifiers
REGION                  1..8
                        note = Synthetic
SITE                    2
                        note = misc_feature - X is S or D
source                  1..8
                        mol_type = protein
                        organism = synthetic construct
SEQUENCE: 492
QXISSWLA                                                             8

SEQ ID NO: 493          moltype = AA   length = 11
FEATURE                 Location/Qualifiers
REGION                  1..11
                        note = Synthetic
SITE                    5
                        note = misc_feature - X is D or A
SITE                    10
                        note = misc_feature - X is E or Q
source                  1..11
                        mol_type = protein
                        organism = synthetic construct
SEQUENCE: 493
LLIYXASSLX S                                                        11

SEQ ID NO: 494          moltype = AA   length = 8
FEATURE                 Location/Qualifiers
REGION                  1..8
                        note = Synthetic
source                  1..8
                        mol_type = protein
                        organism = synthetic construct
SEQUENCE: 494
QQSLTHPT                                                             8

SEQ ID NO: 495          moltype = AA   length = 9
FEATURE                 Location/Qualifiers
REGION                  1..9
                        note = Synthetic
source                  1..9
                        mol_type = protein
                        organism = synthetic construct
SEQUENCE: 495
AAQDLLPYT                                                            9

SEQ ID NO: 496          moltype = AA   length = 13
FEATURE                 Location/Qualifiers
REGION                  1..13
                        note = Synthetic
source                  1..13
                        mol_type = protein
                        organism = synthetic construct
SEQUENCE: 496
ARRPDDRRGL FQH                                                      13

SEQ ID NO: 497          moltype = AA   length = 21
FEATURE                 Location/Qualifiers
REGION                  1..21
                        note = Synthetic
source                  1..21
                        mol_type = protein
                        organism = synthetic construct
SEQUENCE: 497
MEVGWYRSPF SRVVHLYRNG K                                             21
```

```
SEQ ID NO: 498            moltype = AA  length = 191
FEATURE                   Location/Qualifiers
source                    1..191
                          mol_type = protein
                          organism = Homo sapiens
SEQUENCE: 498
GQTLDVKCDY TLEKFASSQK AWQIIRDGEM PKTLACTERP SKNSHPVQVG RIILEDYHDH    60
GLLRVRMVNL QVEDSGLYQC VIYQPPKEPH MLFDRIRLVV TKGFSGTPGS NENSTQNVYK   120
IPPTTTKALC PLYTSPRTVT QAPPKSTADV STPDSEINLT NVTDIIRVPV FNIVILLAGG   180
FLSKSLVFSV L                                                       191

SEQ ID NO: 499            moltype = AA  length = 179
FEATURE                   Location/Qualifiers
source                    1..179
                          mol_type = protein
                          organism = Homo sapiens
SEQUENCE: 499
GQTLTVRCQY PPTGSLYEKK GWCKEASALV CIRLVTSSKP RTMAWTSRFT IWDDPDAGFF    60
TVTMTDLREE DSGHYWCRIY RPSDNSVSKS VRFYLVVSPA SASTQTSWTP RDLVSSQTQT   120
QSCVPPTAGA RQAPESPSTI PVPSQPQNST LRPGPAAPIA LVPVFCGLLV AKSLVLSAL    179

SEQ ID NO: 500            moltype = AA  length = 232
FEATURE                   Location/Qualifiers
source                    1..232
                          mol_type = protein
                          organism = Homo sapiens
SEQUENCE: 500
MRKTRLWGLL WMLFVSELRA ATKLTEEKYE LKEGQTLDVK CDYTLEKFAS SQKAWQIIRD    60
GEMPKTLACT ERPSKNSHPV QVGRIILEDY HDHGLLRVRM VNLQVEDSGL YQCVIYQPPK   120
EPHMLFDRIR LVVTKGFSGT PGSNENSTQN VYKIPPTTTK ALCPLYTSPR TVTQAPPKST   180
ADVSTPDSEI NLTNVTDIIR VPVFNIVILL AGGFLSKSLV FSVLFAVTLR SF           232

SEQ ID NO: 501            moltype = AA  length = 229
FEATURE                   Location/Qualifiers
source                    1..229
                          mol_type = protein
                          organism = Mus musculus
SEQUENCE: 501
MRKAGLWGLL CVFFVSEVKA AIVLEEERYD LVEGQTLTVK CPFNIMKYAN SQKAWQRLPD    60
GKEPLTVVT QRPFTRPSEV HMGKFTLKHD PSEAMLQVQM TDLQVTDSGL YRCVIYHPPN   120
DPVVLFHPVR LVVTKGSSDV FTPVIIPITR LTERPILITT KYSPSDTTTT RSLPKPTAVV   180
SSPGLGVTII NGTDADSVST SSVTISVICG LLSKSLVFII LFIVTKRTF               229

SEQ ID NO: 502            moltype = AA  length = 105
FEATURE                   Location/Qualifiers
source                    1..105
                          mol_type = protein
                          organism = Homo sapiens
SEQUENCE: 502
LLWMLFVSEL RAATKLTEEK YELKEGQTLD VKCDYTLEKF ASSQKAWQII RDGEMPKTLA    60
CTERPSKNSH PVQVGRIILE DYHDHGLLRV RMVNLQVEDS GLYQC                  105

SEQ ID NO: 503            moltype = AA  length = 105
FEATURE                   Location/Qualifiers
source                    1..105
                          mol_type = protein
                          organism = Homo sapiens
SEQUENCE: 503
LLILLFVTEL SGAHNTTVFQ GVAGQSLQVS CPYDSMKHWG RRKAWCRQLG EKGPCQRVVS    60
THNLWLLSFL RRWNGSTAIT DDTLGGTLTI TLRNLQPHDA GLYQC                  105

SEQ ID NO: 504            moltype = AA  length = 98
FEATURE                   Location/Qualifiers
REGION                    1..98
                          note = Synthetic
source                    1..98
                          mol_type = protein
                          organism = synthetic construct
SEQUENCE: 504
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCAR                           98

SEQ ID NO: 505            moltype = AA  length = 108
FEATURE                   Location/Qualifiers
REGION                    1..108
                          note = Synthetic
source                    1..108
                          mol_type = protein
                          organism = synthetic construct
```

```
SEQUENCE: 505
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCARRG GSYDAFQH              108

SEQ ID NO: 506          moltype = AA  length = 109
FEATURE                 Location/Qualifiers
REGION                  1..109
                        note = Synthetic
source                  1..109
                        mol_type = protein
                        organism = synthetic construct
SEQUENCE: 506
EVQLVESGGG LVKPGGSLRL SCAASGFTFS SYSMNWVRQA PGKGLEWVSS ISSSSNYIYY    60
ADSVKGRFTI SRDNAKNSLY LQMNSLRAED TAVYYCARRG GSSSTGLLY             109

SEQ ID NO: 507          moltype = AA  length = 109
FEATURE                 Location/Qualifiers
REGION                  1..109
                        note = Synthetic
source                  1..109
                        mol_type = protein
                        organism = synthetic construct
SEQUENCE: 507
EVQLVESGGG LVKPGGSLRL SCAASGFTFS SYSMNWVRQA PGKGLEWVSS ISSSSNYIYY    60
ADSVKGRFTI SRDNAKNSLY LQMNSLKAED TAVYYCARRP DDRRGLFQH             109

SEQ ID NO: 508          moltype = AA  length = 115
FEATURE                 Location/Qualifiers
REGION                  1..115
                        note = Synthetic
source                  1..115
                        mol_type = protein
                        organism = synthetic construct
SEQUENCE: 508
EVQLVESGGG LVKPGGSLRL SCAASGFTFS SYSMNWVRQA PGKGLEWVSS ISSSSNYIYY    60
ADSVKGRFTI SRDNAKNSLY LQMNSLRAED TAVYYCARGP SQYYYDSSAI EAFDI      115

SEQ ID NO: 509          moltype = AA  length = 109
FEATURE                 Location/Qualifiers
REGION                  1..109
                        note = Synthetic
source                  1..109
                        mol_type = protein
                        organism = synthetic construct
SEQUENCE: 509
EVQLVESGGG LVKPGGSLRL SCAASGFTFS SYSMNWVRQA PGKGLEWVSS ISSSSNYIYY    60
ADSVKGRFTI SRDNAKNSLY LQMNSLRAED TAVYYCARGR YRRTGSLDV             109

SEQ ID NO: 510          moltype = AA  length = 107
FEATURE                 Location/Qualifiers
REGION                  1..107
                        note = Synthetic
source                  1..107
                        mol_type = protein
                        organism = synthetic construct
SEQUENCE: 510
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCARTR IDDSFDI               107

SEQ ID NO: 511          moltype = AA  length = 98
FEATURE                 Location/Qualifiers
REGION                  1..98
                        note = Synthetic
source                  1..98
                        mol_type = protein
                        organism = synthetic construct
SEQUENCE: 511
QVQLQESGPG LVKPSETLSL TCAVSGYSIS SGYYWGWIRQ PPGKGLEWIG SIYHSGSTYY    60
NPSLKSRVTI SVDTSKNQFS LKLSSVTAAD TAVYYCAR                          98

SEQ ID NO: 512          moltype = AA  length = 113
FEATURE                 Location/Qualifiers
REGION                  1..113
                        note = Synthetic
source                  1..113
                        mol_type = protein
                        organism = synthetic construct
SEQUENCE: 512
QVQLQESGPG LVKPSETLSL TCAVSGYSIS SGYYWGWIRQ PPGKGLEWIG SIYHSGNTYY    60
```

```
NPSLKSRVTI SVDTSKNQFS LKLSSVTAAD TAVYYCAREL YAYSSPMFYG MDV          113

SEQ ID NO: 513            moltype = AA   length = 109
FEATURE                   Location/Qualifiers
REGION                    1..109
                          note = Synthetic
source                    1..109
                          mol_type = protein
                          organism = synthetic construct
SEQUENCE: 513
QVQLQESGPG LVKPSETLSL TCAVSGYSIS SGYYWAWIRQ PPGKGLEWIG SIYHSGSTYY    60
NPSLKSRVTI SVDTSKNQFS LKLSSVTAAD TAVYYCARDL GGYEGAFDP              109

SEQ ID NO: 514            moltype = AA   length = 109
FEATURE                   Location/Qualifiers
REGION                    1..109
                          note = Synthetic
source                    1..109
                          mol_type = protein
                          organism = synthetic construct
SEQUENCE: 514
QVQLQESGPG LVKPSETLSL TCAVSGYSIS SGYYWAWIRQ PPGKGLEWIG SIYHSGSTYY    60
NPSLKSRVTI SVDTSKNQFS LKLSSVTAAD TAVYYCARDL GGYEGAFDP              109

SEQ ID NO: 515            moltype = AA   length = 108
FEATURE                   Location/Qualifiers
REGION                    1..108
                          note = Synthetic
source                    1..108
                          mol_type = protein
                          organism = synthetic construct
SEQUENCE: 515
QVQLQESGPG LVKPSETLSL TCAVSGYSIS SGYYWGWIRQ PPGKGLEWIG SIYHSGSTYY    60
NPSLKSRVTI SVDTSKNQFS LKLSSVTAAD TAVYYCARHD DYLSSFDP               108

SEQ ID NO: 516            moltype = AA   length = 110
FEATURE                   Location/Qualifiers
REGION                    1..110
                          note = Synthetic
source                    1..110
                          mol_type = protein
                          organism = synthetic construct
SEQUENCE: 516
QVQLQESGPG LVKPSETLSL TCAVSGYSIS SGYYWAWIRQ PPGKGLEWIG SIYHSGSTYY    60
NPSLKSRVTI SVDTSKNQFS LKLSSVTAAD TAVYYCARGG PYPWSGWFDP             110

SEQ ID NO: 517            moltype = AA   length = 99
FEATURE                   Location/Qualifiers
REGION                    1..99
                          note = Synthetic
source                    1..99
                          mol_type = protein
                          organism = synthetic construct
SEQUENCE: 517
QVQLQESGPG LVKPSQTLSL TCTVSGGSIS SGGYYWSWIR QHPGKGLEWI GYIYYSGSTY    60
YNPSLKSLVT ISVDTSKNQF SLKLSSVTAA DTAVYYCAR                          99

SEQ ID NO: 518            moltype = AA   length = 113
FEATURE                   Location/Qualifiers
REGION                    1..113
                          note = Synthetic
source                    1..113
                          mol_type = protein
                          organism = synthetic construct
SEQUENCE: 518
QVQLQESGPG LVKPSQTLSL TCTVSGGSIS SGGYYWSWIR QHPGKGLEWI GYIYYSGSTY    60
YNPSLKSRVT ISVDTSKNQF SLKLSSVTAA DTAVYYCARD SSIAGRATLS FDY         113

SEQ ID NO: 519            moltype = AA   length = 106
FEATURE                   Location/Qualifiers
REGION                    1..106
                          note = Synthetic
source                    1..106
                          mol_type = protein
                          organism = synthetic construct
SEQUENCE: 519
QVQLQESGPG LVKPSQTLSL TCTVSGGSIS SGGYYWSWIR QHPGKGLEWI GYIYYSGSTY    60
YNPSLKSRVT ISVDTSKNQF SLKLSSVTAA DTAVYYCARG PSWIDV                 106
```

```
SEQ ID NO: 520          moltype = AA  length = 98
FEATURE                 Location/Qualifiers
REGION                  1..98
                        note = Synthetic
source                  1..98
                        mol_type = protein
                        organism = synthetic construct
SEQUENCE: 520
EVQLVESGGG LVQPGRSLRL SCAASGFTFD DYAMHWVRQA PGKGLEWVSG ISWNSGSIGY   60
ADSVKGRFTI SRDNAKNSLY LQMNSLRAED TALYYCAK                          98

SEQ ID NO: 521          moltype = AA  length = 108
FEATURE                 Location/Qualifiers
REGION                  1..108
                        note = Synthetic
source                  1..108
                        mol_type = protein
                        organism = synthetic construct
SEQUENCE: 521
EVQLVESGGG LVQPGRSLRL SCAASGFTFD DYAMHWVRQA PGKGLEWVSG ISWNSGSIGY   60
ADSVKGRFTI SRDNAKNSLY LQMNSLRAED TALYYCAKGG SRYSHFDY               108

SEQ ID NO: 522          moltype = AA  length = 108
FEATURE                 Location/Qualifiers
REGION                  1..108
                        note = Synthetic
source                  1..108
                        mol_type = protein
                        organism = synthetic construct
SEQUENCE: 522
EVQLVESGGG LVQPGRSLRL SCAASGFTFD DYAMHWVRQA PGKGLEWVSG ISWNSGDIGY   60
ADSVKGRFTI SRDNAKNTLY LQMNSLRAED TALYYCAKGP RMVTHLDV               108

SEQ ID NO: 523          moltype = AA  length = 108
FEATURE                 Location/Qualifiers
REGION                  1..108
                        note = Synthetic
source                  1..108
                        mol_type = protein
                        organism = synthetic construct
SEQUENCE: 523
EVQLVESGGG LVQPGRSLRL SCAASGFTFD DYAMHWVRQA PGKGLEWVSG ITWNSGSIGY   60
ADSVKGRFTI SRDNAKNSLY LQMNSLRAED TALYYCAKGP RLLSALDV               108

SEQ ID NO: 524          moltype = AA  length = 108
FEATURE                 Location/Qualifiers
REGION                  1..108
                        note = Synthetic
source                  1..108
                        mol_type = protein
                        organism = synthetic construct
SEQUENCE: 524
EVQLVESGGG LVQPGRSLRL SCAASGFTFD DYAMHWVRQA PGKGLEWVSG ITWNSGSIGY   60
ADSVKGRFTI SRDNAKNSLY LQMNSLRAED TALYYCAKGP RLLSALDV               108

SEQ ID NO: 525          moltype = AA  length = 108
FEATURE                 Location/Qualifiers
REGION                  1..108
                        note = Synthetic
source                  1..108
                        mol_type = protein
                        organism = synthetic construct
SEQUENCE: 525
EVQLVESGGG LVQPGRSLRL SCAASGFTFG DYAMHWVRQA PGKGLEWVSG ISWNSGSIGY   60
ADSVKGRFTI SRDNAKNSLY LQMNSLRAED TALYYCAKGP RRTSHLDI               108

SEQ ID NO: 526          moltype = AA  length = 109
FEATURE                 Location/Qualifiers
REGION                  1..109
                        note = Synthetic
source                  1..109
                        mol_type = protein
                        organism = synthetic construct
SEQUENCE: 526
QVQLVESGGG LVQPGRSLRL SCAASGFTFD DYAMHWVRQA PGKGLEWVSG ISWNSGDIGY   60
ADSVKGRFTI SRDNAKNSLY LQMNSLRAED TALYYCAKAP RTRWTYFDY              109

SEQ ID NO: 527          moltype = AA  length = 109
FEATURE                 Location/Qualifiers
```

```
REGION                  1..109
                        note = Synthetic
source                  1..109
                        mol_type = protein
                        organism = synthetic construct
SEQUENCE: 527
EVQLVESGGG LVQPGRSLRL SCAASGFTFD DYAMHWVRQA PGKGLEWVSG ITWNSGSIGY   60
ADSVKGRFTI SRDNAKNSLY LQMNSLRAED TALYYCAKGP RYSKPYFDY              109

SEQ ID NO: 528          moltype = AA  length = 108
FEATURE                 Location/Qualifiers
REGION                  1..108
                        note = Synthetic
source                  1..108
                        mol_type = protein
                        organism = synthetic construct
SEQUENCE: 528
EVQLVESGGG LVQPGRSLRL SCAASGFTFD DYAMHWVRQA PGKGLEWVSG ISWNSGSIGY   60
ADSVKGRFTI SRDNAKNSLY LQMNSLRAED TALYYCAKGP RMSGWWAD               108

SEQ ID NO: 529          moltype = AA  length = 109
FEATURE                 Location/Qualifiers
REGION                  1..109
                        note = Synthetic
source                  1..109
                        mol_type = protein
                        organism = synthetic construct
SEQUENCE: 529
EVQLVESGGG LVQPGRSLRL SCAASGFTFD DYAMHWVRQA PGKGLEWVSG ISWNSGDIGY   60
ADSVKGRFTI SRDNAKNSLY LQMNSLRAED TALYYCAKGP RMTHSYFDL              109

SEQ ID NO: 530          moltype = AA  length = 108
FEATURE                 Location/Qualifiers
REGION                  1..108
                        note = Synthetic
source                  1..108
                        mol_type = protein
                        organism = synthetic construct
SEQUENCE: 530
EVQLVESGGG LVQPGRSLRL SCAASGFTFD DYAMHWVRQA PGKGLEWVSG ISWNSGSIGY   60
ADSVKGRFTI SRDNAKNSLY LQMNSLRAED TALYYCAKGP RLLGYFDL                108

SEQ ID NO: 531          moltype = AA  length = 108
FEATURE                 Location/Qualifiers
REGION                  1..108
                        note = Synthetic
source                  1..108
                        mol_type = protein
                        organism = synthetic construct
SEQUENCE: 531
EVQLVESGGG LVQPGRSLRL SCAASGFTFD DYAMHWVRQA PGKGLEWVSG ISWNSGSIGY   60
ADSVKGRFTI SRDNAKNSLY LQMNSLRAED TALYYCAKGP RTRGYFDL                108

SEQ ID NO: 532          moltype = AA  length = 108
FEATURE                 Location/Qualifiers
REGION                  1..108
                        note = Synthetic
source                  1..108
                        mol_type = protein
                        organism = synthetic construct
SEQUENCE: 532
EVQLVESGGG LVQPGRSLRL SCAASGFTFD DYAMHWVRQA PGKGLEWVSG ISWNSGSIGY   60
ADSVKGRFTI SRDNAKNSLY LQMNSLRAED TALYYCAKAP RMYGYFDL                108

SEQ ID NO: 533          moltype = AA  length = 98
FEATURE                 Location/Qualifiers
REGION                  1..98
                        note = Synthetic
source                  1..98
                        mol_type = protein
                        organism = synthetic construct
SEQUENCE: 533
EVQLVQSGAE VKKPGESLKI SCKGSGYSFT SYWIGWVRQM PGKGLEWMGI IYPGDSDTRY   60
SPSFQGQVTI SADKSISTAY LQWSSLKASD TAMYYCAR                          98

SEQ ID NO: 534          moltype = AA  length = 98
FEATURE                 Location/Qualifiers
REGION                  1..98
                        note = Synthetic
```

```
source                  1..98
                        mol_type = protein
                        organism = synthetic construct
SEQUENCE: 534
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCAR                            98

SEQ ID NO: 535          moltype = AA  length = 98
FEATURE                 Location/Qualifiers
REGION                  1..98
                        note = Synthetic
source                  1..98
                        mol_type = protein
                        organism = synthetic construct
SEQUENCE: 535
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCAR                            98

SEQ ID NO: 536          moltype = AA  length = 98
FEATURE                 Location/Qualifiers
REGION                  1..98
                        note = Synthetic
source                  1..98
                        mol_type = protein
                        organism = synthetic construct
SEQUENCE: 536
QVQLVQSGAE VKKPGASVKV SCKASGYTFT GYYMHWVRQA PGQGLEWMGW INPNSGGTNY    60
AQKFQGRVTM TRDTSISTAY MELSRLRSDD TAVYYCAR                            98

SEQ ID NO: 537          moltype = AA  length = 98
FEATURE                 Location/Qualifiers
REGION                  1..98
                        note = Synthetic
source                  1..98
                        mol_type = protein
                        organism = synthetic construct
SEQUENCE: 537
QVQLVQSGAE VKKPGASVKV SCKASGYTFT SYYMHWVRQA PGQGLEWMGI INPSGGSTSY    60
AQKFQGRVTM TRDTSTSTVY MELSSLRSED TAVYYCAR                            98

SEQ ID NO: 538          moltype = AA  length = 98
FEATURE                 Location/Qualifiers
REGION                  1..98
                        note = Synthetic
source                  1..98
                        mol_type = protein
                        organism = synthetic construct
SEQUENCE: 538
QVQLQESGPG LVKPSETLSL TCAVSGYSIS SGYYWGWIRQ PPGKGLEWIG SIYHSGSTYY    60
NPSLKSRVTI SVDTSKNQFS LKLSSVTAAD TAVYYCAR                            98

SEQ ID NO: 539          moltype = AA  length = 97
FEATURE                 Location/Qualifiers
REGION                  1..97
                        note = Synthetic
source                  1..97
                        mol_type = protein
                        organism = synthetic construct
SEQUENCE: 539
QVQLQESGPG LVKPSETLSL TCTVSGGSIS SYYWSWIRQP PGKGLEWIGY IYYSGSTNYN    60
PSLKSRVTIS VDTSKNQFSL KLSSVTAADT AVYYCAR                             97

SEQ ID NO: 540          moltype = AA  length = 99
FEATURE                 Location/Qualifiers
REGION                  1..99
                        note = Synthetic
source                  1..99
                        mol_type = protein
                        organism = synthetic construct
SEQUENCE: 540
QVQLQESGPG LVKPSQTLSL TCTVSGGSIS SGGYYWSWIR QHPGKGLEWI GYIYYSGSTY    60
YNPSLKSLVT ISVDTSKNQF SLKLSSVTAA DTAVYYCAR                           99

SEQ ID NO: 541          moltype = AA  length = 99
FEATURE                 Location/Qualifiers
REGION                  1..99
                        note = Synthetic
source                  1..99
                        mol_type = protein
```

```
                        organism = synthetic construct
SEQUENCE: 541
QLQLQESGPG LVKPSETLSL TCTVSGGSIS SSSYYWGWIR QPPGKGLEWI GSIYYSGSTY    60
YNPSLKSRVT ISVDTSKNQF SLKLSSVTAA DTAVYYCAR                          99

SEQ ID NO: 542          moltype = AA   length = 100
FEATURE                 Location/Qualifiers
REGION                  1..100
                        note = Synthetic
source                  1..100
                        mol_type = protein
                        organism = synthetic construct
SEQUENCE: 542
EVQLVESGGG LVQPGGSLRL SCAASGFTFS DHYMDWVRQA PGKGLEWVGR TRNKANSYTT    60
EYAASVKGRF TISRDDSKNS LYLQMNSLKT EDTAVYYCAR                         100

SEQ ID NO: 543          moltype = AA   length = 98
FEATURE                 Location/Qualifiers
REGION                  1..98
                        note = Synthetic
source                  1..98
                        mol_type = protein
                        organism = synthetic construct
SEQUENCE: 543
EVQLVESGGG LVQPGGSLRL SCAASGFTFS SYWMSWVRQA PGKGLEWVAN IKQDGSEKYY    60
VDSVKGRFTI SRDNAKNSLY LQMNSLRAED TAVYYCAR                           98

SEQ ID NO: 544          moltype = AA   length = 98
FEATURE                 Location/Qualifiers
REGION                  1..98
                        note = Synthetic
source                  1..98
                        mol_type = protein
                        organism = synthetic construct
SEQUENCE: 544
QVQLVESGGG VVQPGRSLRL SCAASGFTFS SYGMHWVRQA PGKGLEWVAV IWYDGSNKYY    60
ADSVKGRFTI SRDNSKNTLY LQMNSLRAED TAVYYCAR                           98

SEQ ID NO: 545          moltype = AA   length = 98
FEATURE                 Location/Qualifiers
REGION                  1..98
                        note = Synthetic
source                  1..98
                        mol_type = protein
                        organism = synthetic construct
SEQUENCE: 545
QVQLVESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAR                           98

SEQ ID NO: 546          moltype = AA   length = 98
FEATURE                 Location/Qualifiers
REGION                  1..98
                        note = Synthetic
source                  1..98
                        mol_type = protein
                        organism = synthetic construct
SEQUENCE: 546
EVQLVESGGG LVQPGRSLRL SCAASGFTFD DYAMHWVRQA PGKGLEWVSG ISWNSGSIGY    60
ADSVKGRFTI SRDNAKNSLY LQMNSLRAED TALYYCAK                           98

SEQ ID NO: 547          moltype = AA   length = 98
FEATURE                 Location/Qualifiers
REGION                  1..98
                        note = Synthetic
source                  1..98
                        mol_type = protein
                        organism = synthetic construct
SEQUENCE: 547
EVQLVESGGG LVQPGGSLRL SCAASGFTFS SYSMNWVRQA PGKGLEWVSY ISSSSSTIYY    60
ADSVKGRFTI SRDNAKNSLY LQMNSLRAED TAVYYCAR                           98

SEQ ID NO: 548          moltype = AA   length = 98
FEATURE                 Location/Qualifiers
REGION                  1..98
                        note = Synthetic
source                  1..98
                        mol_type = protein
                        organism = synthetic construct
SEQUENCE: 548
```

```
EVQLVESGGG LVKPGGSLRL SCAASGFTFS SYSMNWVRQA PGKGLEWVSS ISSSSSYIYY    60
ADSVKGRFTI SRDNAKNSLY LQMNSLRAED TAVYYCAR                           98

SEQ ID NO: 549          moltype = AA  length = 98
FEATURE                 Location/Qualifiers
REGION                  1..98
                        note = Synthetic
source                  1..98
                        mol_type = protein
                        organism = synthetic construct
SEQUENCE: 549
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAK                           98

SEQ ID NO: 550          moltype = AA  length = 101
FEATURE                 Location/Qualifiers
REGION                  1..101
                        note = Synthetic
source                  1..101
                        mol_type = protein
                        organism = synthetic construct
SEQUENCE: 550
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTP P                      101

SEQ ID NO: 551          moltype = AA  length = 96
FEATURE                 Location/Qualifiers
REGION                  1..96
                        note = Synthetic
source                  1..96
                        mol_type = protein
                        organism = synthetic construct
SEQUENCE: 551
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YDNLPP                             96

SEQ ID NO: 552          moltype = AA  length = 96
FEATURE                 Location/Qualifiers
REGION                  1..96
                        note = Synthetic
source                  1..96
                        mol_type = protein
                        organism = synthetic construct
SEQUENCE: 552
DIQMTQSPST LSASVGDRVT ITCRASQSIS SWLAWYQQKP GKAPKLLIYD ASSLESGVPS    60
RFSGSGSGTE FTLTISSLQP DDFATYYCQQ YNSYSP                             96

SEQ ID NO: 553          moltype = AA  length = 96
FEATURE                 Location/Qualifiers
REGION                  1..96
                        note = Synthetic
source                  1..96
                        mol_type = protein
                        organism = synthetic construct
SEQUENCE: 553
DIQMTQSPST LSASVGDRVT ITCRASQSIS SWLAWYQQKP GKAPKLLIYK ASSLESGVPS    60
RFSGSGSGTE FTLTISSLQP DDFATYYCQQ YNSYSP                             96

SEQ ID NO: 554          moltype = AA  length = 96
FEATURE                 Location/Qualifiers
REGION                  1..96
                        note = Synthetic
source                  1..96
                        mol_type = protein
                        organism = synthetic construct
SEQUENCE: 554
DIQMTQSPSS VSASVGDRVT ITCRASQGIS SWLAWYQQKP GKAPKLLIYA ASSLQSGVPS    60
RFSGSGSGTD FTLTISSLQP EDFATYYCQQ ANSFPP                             96

SEQ ID NO: 555          moltype = AA  length = 96
FEATURE                 Location/Qualifiers
REGION                  1..96
                        note = Synthetic
source                  1..96
                        mol_type = protein
                        organism = synthetic construct
SEQUENCE: 555
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPP                             96
```

```
SEQ ID NO: 556           moltype = AA  length = 102
FEATURE                  Location/Qualifiers
REGION                   1..102
                         note = Synthetic
source                   1..102
                         mol_type = protein
                         organism = synthetic construct
SEQUENCE: 556
DIVMTQSPDS LAVSLGERAT INCKSSQSVL YSSNNKNYLA WYQQKPGQPP KLLIYWASTR   60
ESGVPDRFSG SGSGTDFTLT ISSLQAEDVA VYYCQQYYST PP                     102

SEQ ID NO: 557           moltype = AA  length = 97
FEATURE                  Location/Qualifiers
REGION                   1..97
                         note = Synthetic
source                   1..97
                         mol_type = protein
                         organism = synthetic construct
SEQUENCE: 557
EIVLTQSPGT LSLSPGERAT LSCRASQSVS SSYLAWYQQK PGQAPRLLIY GASSRATGIP   60
DRFSGSGSGT DFTLTISRLE PEDFAVYYCQ QYGSSPP                           97

SEQ ID NO: 558           moltype = AA  length = 96
FEATURE                  Location/Qualifiers
REGION                   1..96
                         note = Synthetic
source                   1..96
                         mol_type = protein
                         organism = synthetic construct
SEQUENCE: 558
EIVMTQSPAT LSVSPGERAT LSCRASQSVS SNLAWYQQKP GQAPRLLIYG ASTRATGIPA   60
RFSGSGSGTE FTLTISSLQS EDFAVYYCQQ YNNWPP                            96

SEQ ID NO: 559           moltype = AA  length = 96
FEATURE                  Location/Qualifiers
REGION                   1..96
                         note = Synthetic
source                   1..96
                         mol_type = protein
                         organism = synthetic construct
SEQUENCE: 559
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPP                            96

SEQ ID NO: 560           moltype = AA  length = 113
FEATURE                  Location/Qualifiers
source                   1..113
                         mol_type = protein
                         organism = Homo sapiens
SEQUENCE: 560
MGGLEPCSRL LLLPLLLAVS GLRPVQAQAQ SDCSCSTVSP GVLAGIVMGD LVLTVLIALA   60
VYFLGRLVPR GRGAAEAATR KQRITETESP YQELQGQRSD VYSDLNTQRP YYK          113

SEQ ID NO: 561           moltype = AA  length = 234
FEATURE                  Location/Qualifiers
source                   1..234
                         mol_type = protein
                         organism = Pan paniscus
SEQUENCE: 561
MRKTRLWGLL WMLFVSELRA ATKLTEEKYE LKEGQTLDVK CDYTLEKFAS SQKAWQIIRD   60
GEMPKTLACT ERPSENSHPV QVGRIILEDY HDHGLLRVRM VNLQVEDSGL YQCVIYQPPK  120
EPHILFDRIR LVVTKGFSGT PGSNENSTQN VYKIPPTTTK ALHPLYTSPR TVTQAPPKST  180
ADVSTPDSEI NLTNVTDIIR VPVFNIVILL AGGFLSKSLV FSVLFAVTLR SFVP        234
```